US012598458B2

(12) United States Patent
Forsell

(10) Patent No.: US 12,598,458 B2
(45) Date of Patent: Apr. 7, 2026

(54) METHODS AND DEVICES FOR SECURE COMMUNICATION WITH AND OPERATION OF AN IMPLANT

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 58 days.

(21) Appl. No.: 18/443,367

(22) Filed: Feb. 16, 2024

(65) Prior Publication Data

US 2024/0214798 A1 Jun. 27, 2024

Related U.S. Application Data

(63) Continuation-in-part of application No. PCT/EP2023/053882, filed on Feb. 16, 2023, and a continuation-in-part of application No. PCT/EP2022/073816, filed on Aug. 26, 2022.

(30) Foreign Application Priority Data

Aug. 30, 2021 (WO) ................. PCT/EP2021/073893
Feb. 18, 2022 (SE) .................................... 2250209-0

(51) Int. Cl.
| | |
|---|---|
| *H04W 12/06* | (2021.01) |
| *G16H 40/40* | (2018.01) |
| *G16H 40/67* | (2018.01) |
| *H04L 9/40* | (2022.01) |
| *H04W 12/033* | (2021.01) |
| *H04W 88/04* | (2009.01) |

(52) U.S. Cl.
CPC .......... *H04W 12/033* (2021.01); *G16H 40/67* (2018.01)

(58) Field of Classification Search
CPC ............................ H04W 12/033; G16H 40/67

USPC .......................................................... 713/153
See application file for complete search history.

(56) References Cited

U.S. PATENT DOCUMENTS

| | | | |
|---|---|---|---|
| 2005/0204134 A1* | 9/2005 | Von Arx | H04L 9/0891 |
| | | | 713/168 |
| 2005/0261934 A1* | 11/2005 | Thompson | G16H 40/40 |
| | | | 380/255 |
| 2005/0283198 A1 | 12/2005 | Haubrich et al. | |

(Continued)

FOREIGN PATENT DOCUMENTS

| | | |
|---|---|---|
| AU | 2009302943 B2 | 5/2016 |
| CA | 2957008 A1 | 2/2016 |

(Continued)

OTHER PUBLICATIONS

Christos Strydis; A System Architecture, Processor, and Communication Protocol for Secure Implants; ACM:2013; pp. 1-23.*

*Primary Examiner* — Monjur Rahim

(57) ABSTRACT

The present disclosure relates to an apparatus for powering an implant for a human patient and a method for powering an implant for a human patient. Wherein said apparatus comprises an implantable energy source for providing energy to the implant, an energy provider connected to the implantable energy source and connected to an energy consuming part of the implant, the energy provider being configured to store energy to provide a burst of energy to the energy consuming part, wherein the energy provider is configured to be charged by the implantable energy source and to provide the energy consuming part with electrical power during startup of the energy consuming part.

20 Claims, 125 Drawing Sheets

(56)  References Cited

U.S. PATENT DOCUMENTS

| | | | |
|---|---|---|---|
| 2005/0288739 A1 | 12/2005 | Hassler, Jr. et al. | |
| 2008/0288029 A1 | 11/2008 | Healy et al. | |
| 2009/0054937 A1 | 2/2009 | Severin et al. | |
| 2010/0114242 A1 | 5/2010 | Doerr et al. | |
| 2010/0211134 A1 | 8/2010 | Forsell | |
| 2010/0222848 A1 | 9/2010 | Forsell | |
| 2011/0193688 A1 | 8/2011 | Forsell | |
| 2011/0213621 A1* | 9/2011 | Dicks | G16H 15/00 |
| | | | 705/2 |
| 2013/0110008 A1 | 5/2013 | Bourget et al. | |
| 2014/0304773 A1 | 10/2014 | Woods et al. | |
| 2015/0089590 A1* | 3/2015 | Krishnan | A61N 1/37254 |
| | | | 607/59 |
| 2015/0207622 A1* | 7/2015 | Andersen | H04L 9/0816 |
| | | | 380/46 |
| 2016/0250490 A1* | 9/2016 | Hoffman | A61N 1/37254 |
| | | | 607/60 |
| 2017/0259072 A1* | 9/2017 | Newham | A61N 1/37276 |
| 2018/0182491 A1* | 6/2018 | Belliveau | A43B 3/34 |
| 2018/0243573 A1* | 8/2018 | Yoder | H04W 4/80 |
| 2020/0305000 A1* | 9/2020 | Obaidi | A61F 2/02 |
| 2020/0398062 A1 | 12/2020 | Ibarrola et al. | |
| 2020/0398063 A1* | 12/2020 | DeBates | A61N 1/37282 |
| 2022/0035900 A1* | 2/2022 | Flakne | A61N 1/37247 |

FOREIGN PATENT DOCUMENTS

| | | |
|---|---|---|
| EP | 2968740 A1 | 1/2016 |
| EP | 3391808 A1 | 10/2018 |
| WO | 2009097485 A1 | 8/2009 |
| WO | 2011022166 A1 | 2/2011 |
| WO | 2012170278 A2 | 12/2012 |
| WO | 2013055527 A1 | 4/2013 |
| WO | 2014113272 A2 | 7/2014 |
| WO | 2016004262 A1 | 1/2016 |
| WO | 2017160627 A2 | 9/2017 |

* cited by examiner 103
104
105
106
107
108

102

110 | 112 | 114
1091 | 1092

203
204
206
207
208

200

C1

200

102

C2

100

101

W1

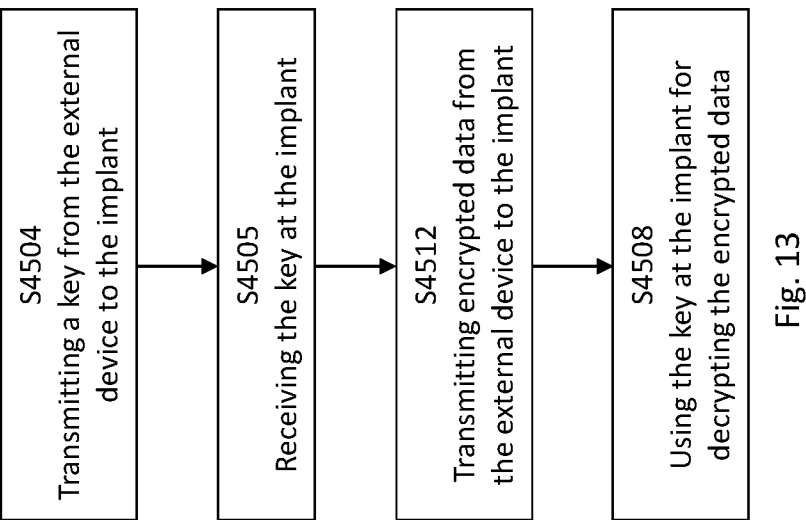

| S4504 Transmitting a key from the external device to the implant | → | S4505 Receiving the key at the implant | → | S4512 Transmitting encrypted data from the external device to the implant | → | S4508 Using the key at the implant for decrypting the encrypted data |

Fig. 13

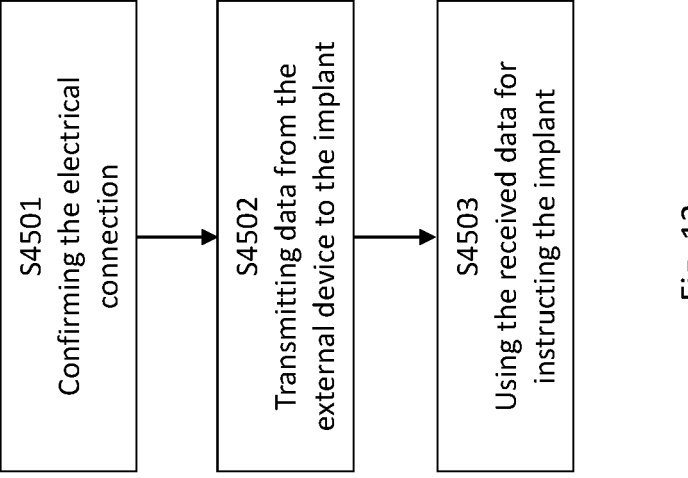

| S4501 Confirming the electrical connection | → | S4502 Transmitting data from the external device to the implant | → | S4503 Using the received data for instructing the implant |

Fig. 12

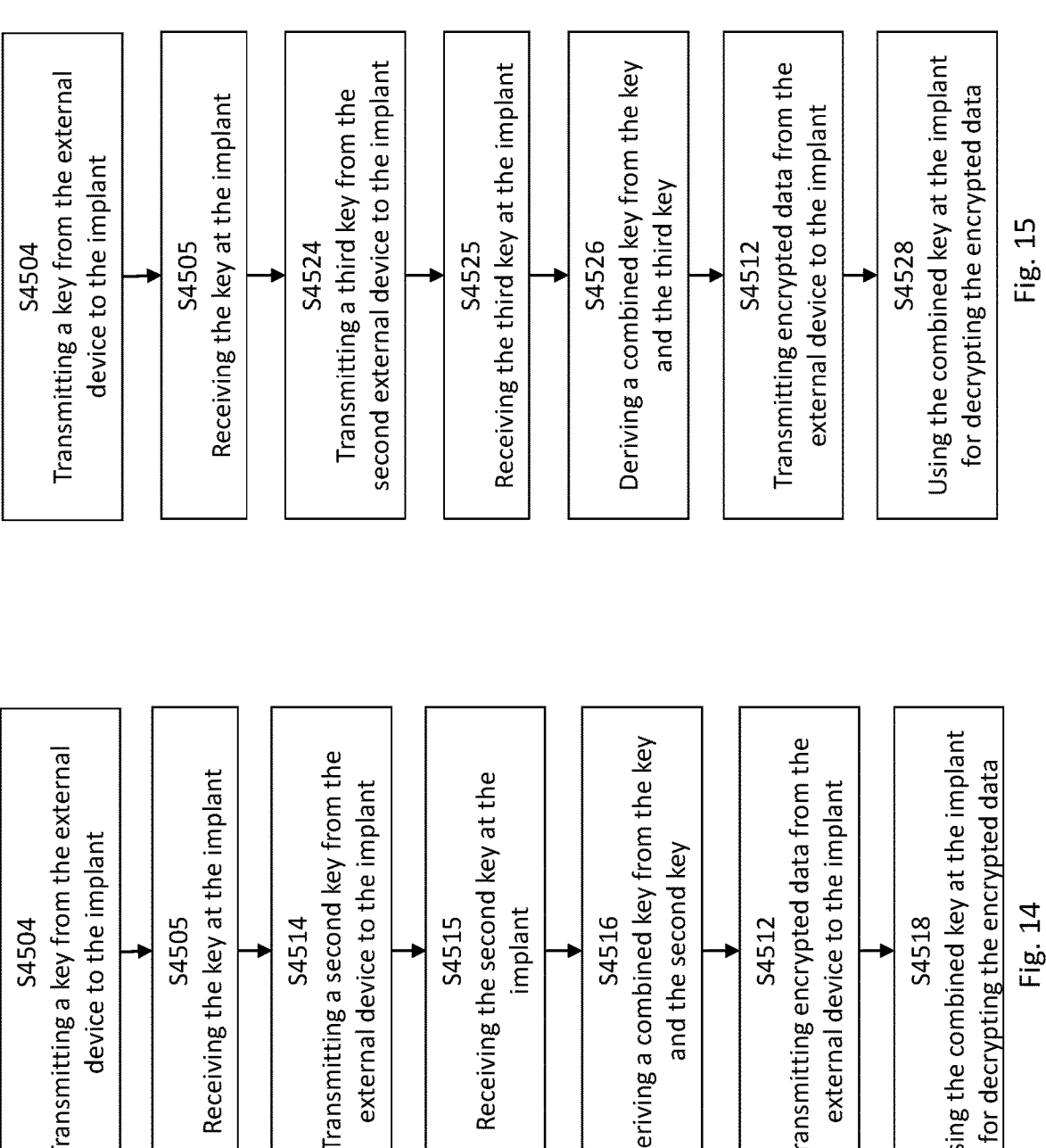

S4504
Transmitting a key from the external device to the implant

S4505
Receiving the key at the implant

S4524
Transmitting a third key from the second external device to the implant

S4525
Receiving the third key at the implant

S4526
Deriving a combined key from the key and the third key

S4512
Transmitting encrypted data from the external device to the implant

S4528
Using the combined key at the implant for decrypting the encrypted data

Fig. 15

S4504
Transmitting a key from the external device to the implant

S4505
Receiving the key at the implant

S4514
Transmitting a second key from the external device to the implant

S4515
Receiving the second key at the implant

S4516
Deriving a combined key from the key and the second key

S4512
Transmitting encrypted data from the external device to the implant

S4518
Using the combined key at the implant for decrypting the encrypted data

Fig. 14

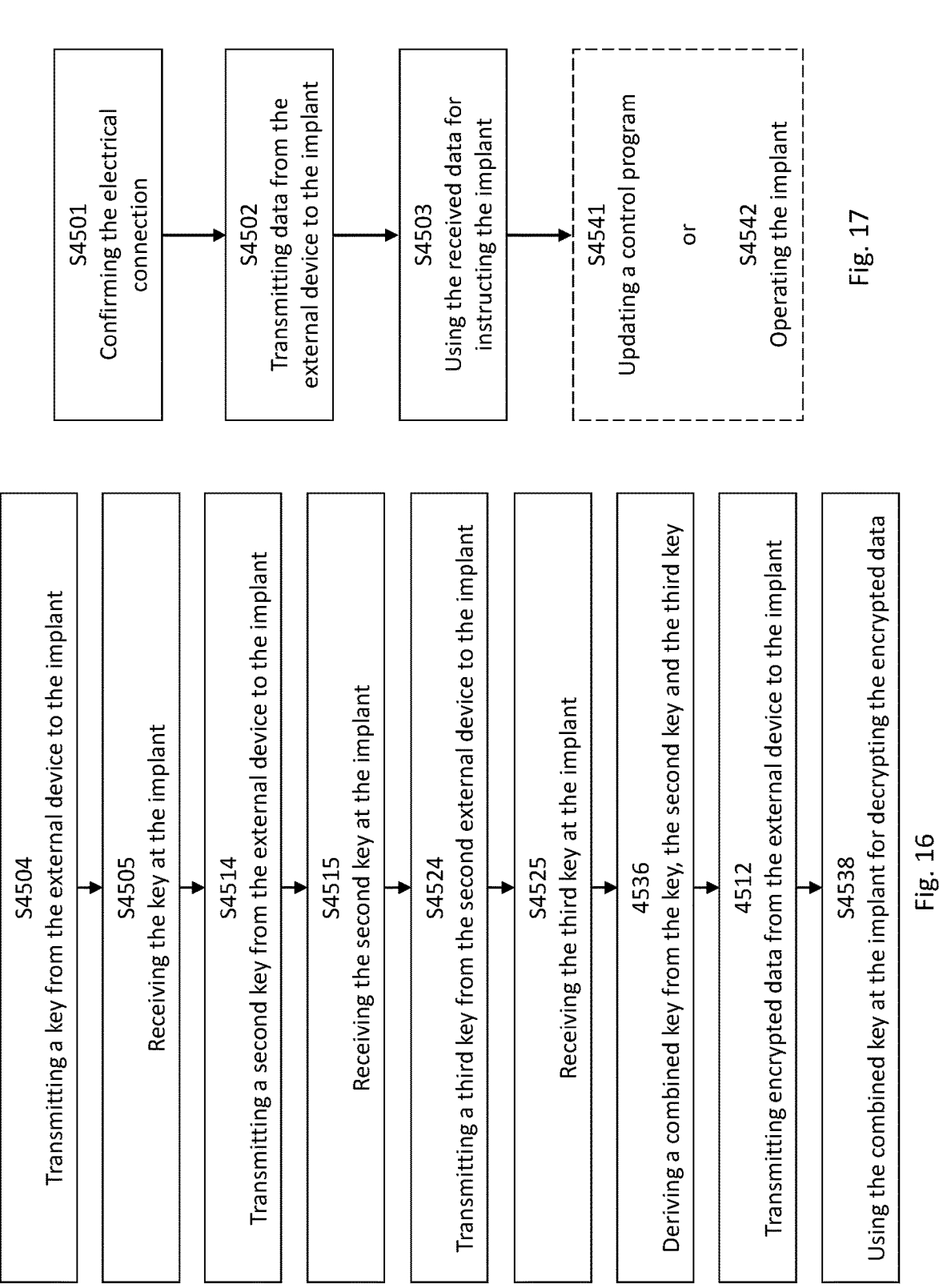

S4501
Confirming the electrical connection

S4502
Transmitting data from the external device to the implant

S4503
Using the received data for instructing the implant

S4541
Updating a control program or

S4542
Operating the implant

Fig. 17

S4504
Transmitting a key from the external device to the implant

S4505
Receiving the key at the implant

S4514
Transmitting a second key from the external device to the implant

S4515
Receiving the second key at the implant

S4524
Transmitting a third key from the second external device to the implant

S4525
Receiving the third key at the implant

4536
Deriving a combined key from the key, the second key and the third key

4512
Transmitting encrypted data from the external device to the implant

S4538
Using the combined key at the implant for decrypting the encrypted data

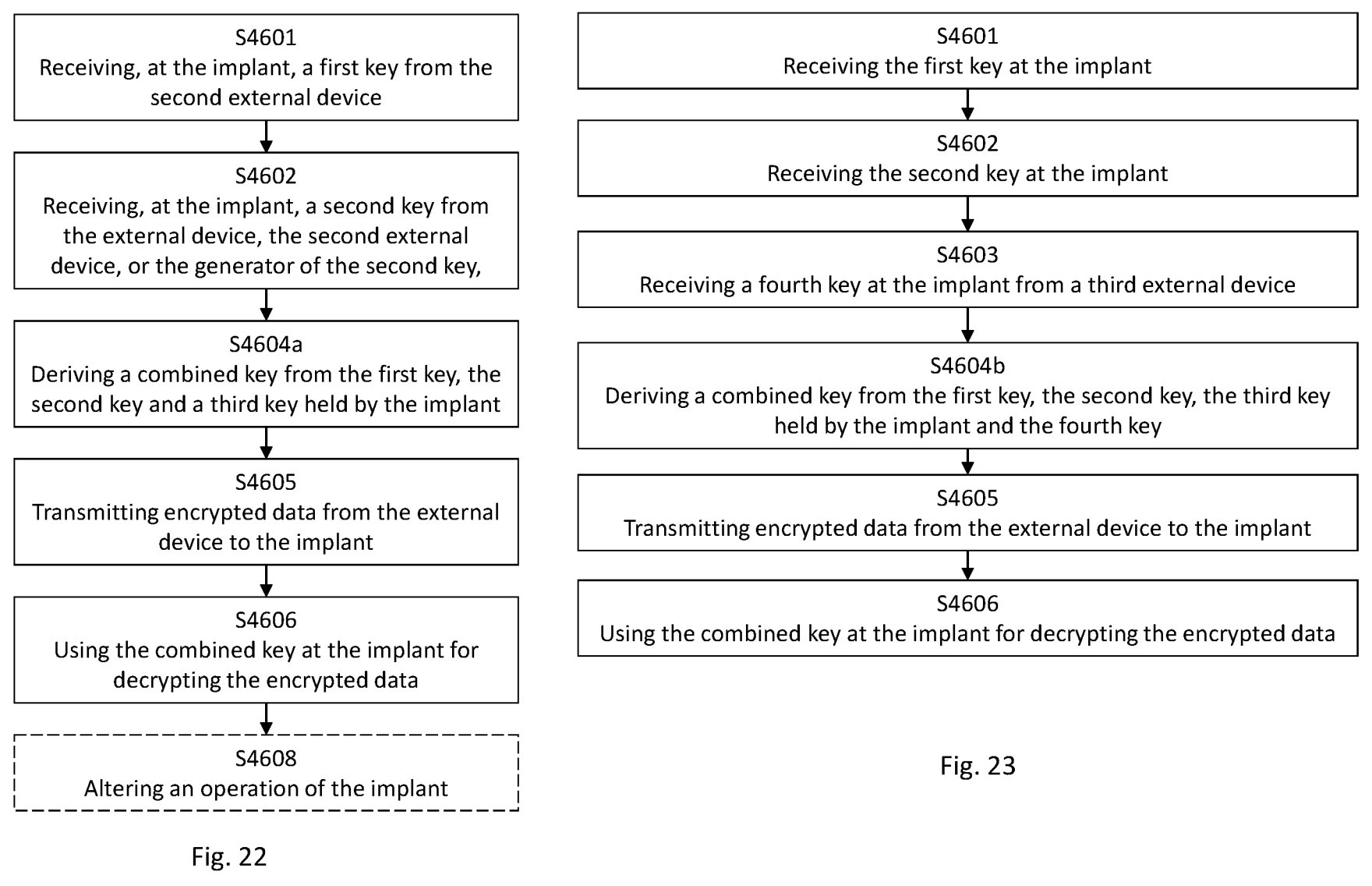

Receiving the first key at the implant

S4602

Receiving the second key at the implant

S4603

Receiving a fourth key at the implant from a third external device

S4604b

Deriving a combined key from the first key, the second key, the third key held by the implant and the fourth key

S4605

Transmitting encrypted data from the external device to the implant

S4606

Using the combined key at the implant for decrypting the encrypted data

Receiving, at the implant, a first key from the second external device

S4602

Receiving, at the implant, a second key from the external device, the second external device, or the generator of the second key, S4604a Deriving a combined key from the first key, the second key and a third key held by the implant

S4605

Transmitting encrypted data from the external device to the implant

S4606

Using the combined key at the implant for decrypting the encrypted data

S4608

Altering an operation of the implant

Fig. 22

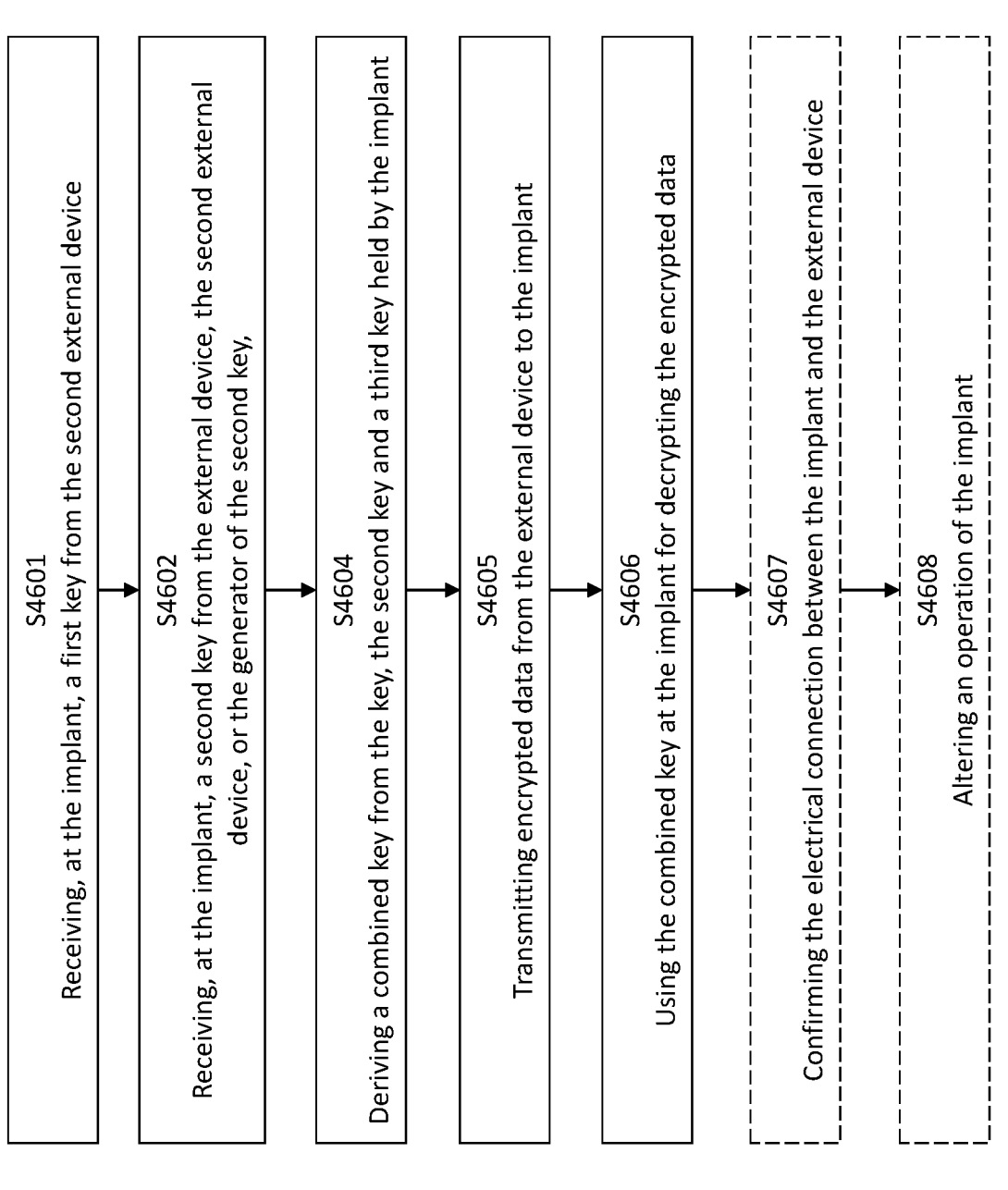

S4601
Receiving, at the implant, a first key from the second external device

S4602
Receiving, at the implant, a second key from the external device, the second external device, or the generator of the second key, S4604
Deriving a combined key from the key, the second key and a third key held by the implant S4605
Transmitting encrypted data from the external device to the implant S4606
Using the combined key at the implant for decrypting the encrypted data S4607
Confirming the electrical connection between the implant and the external device S4608
Altering an operation of the implant

Fig. 24

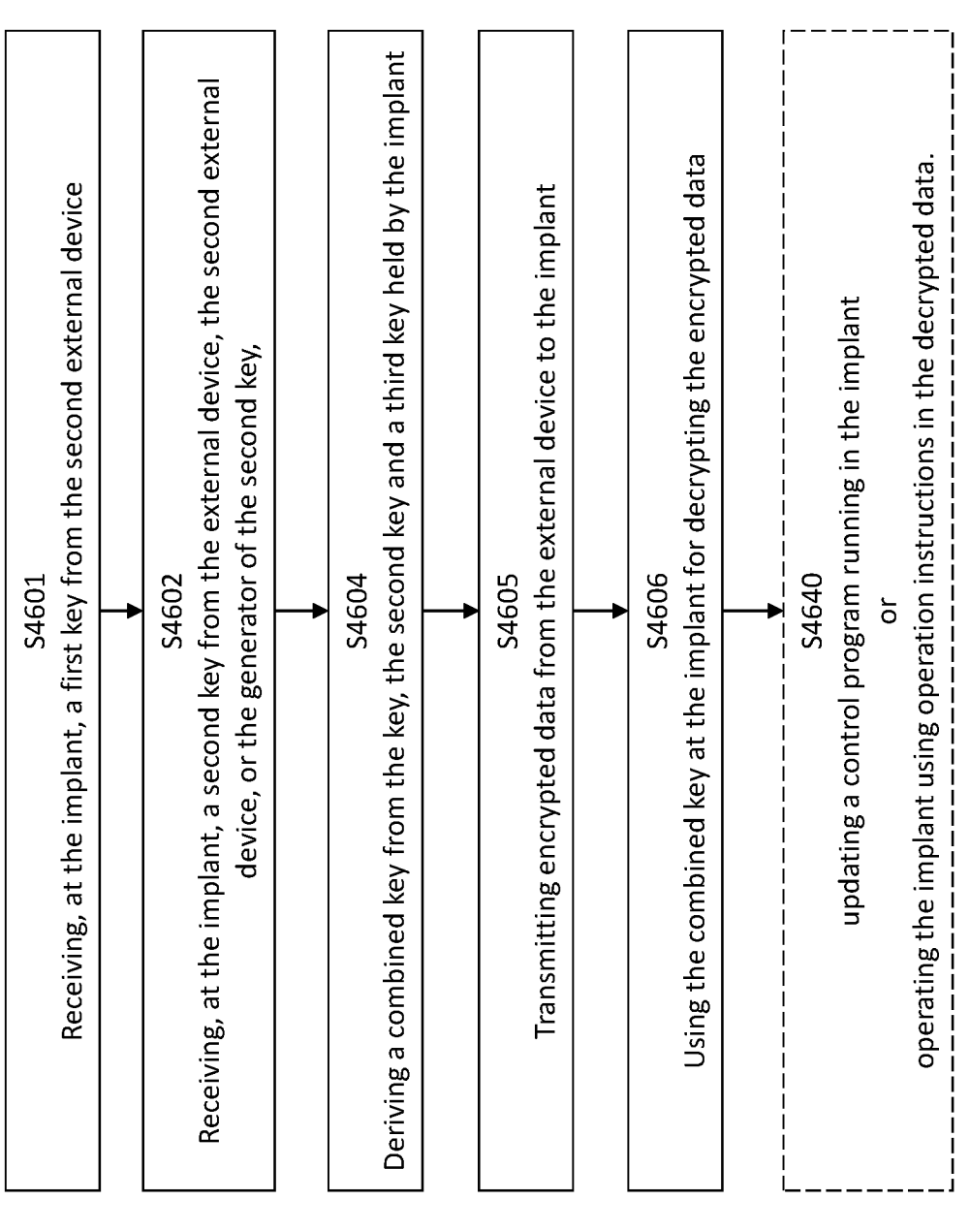

S4601
Receiving, at the implant, a first key from the second external device

S4602
Receiving, at the implant, a second key from the external device, the second external device, or the generator of the second key, S4604
Deriving a combined key from the key, the second key and a third key held by the implant S4605
Transmitting encrypted data from the external device to the implant S4606
Using the combined key at the implant for decrypting the encrypted data S4640
updating a control program running in the implant
or
operating the implant using operation instructions in the decrypted data.

Fig. 26

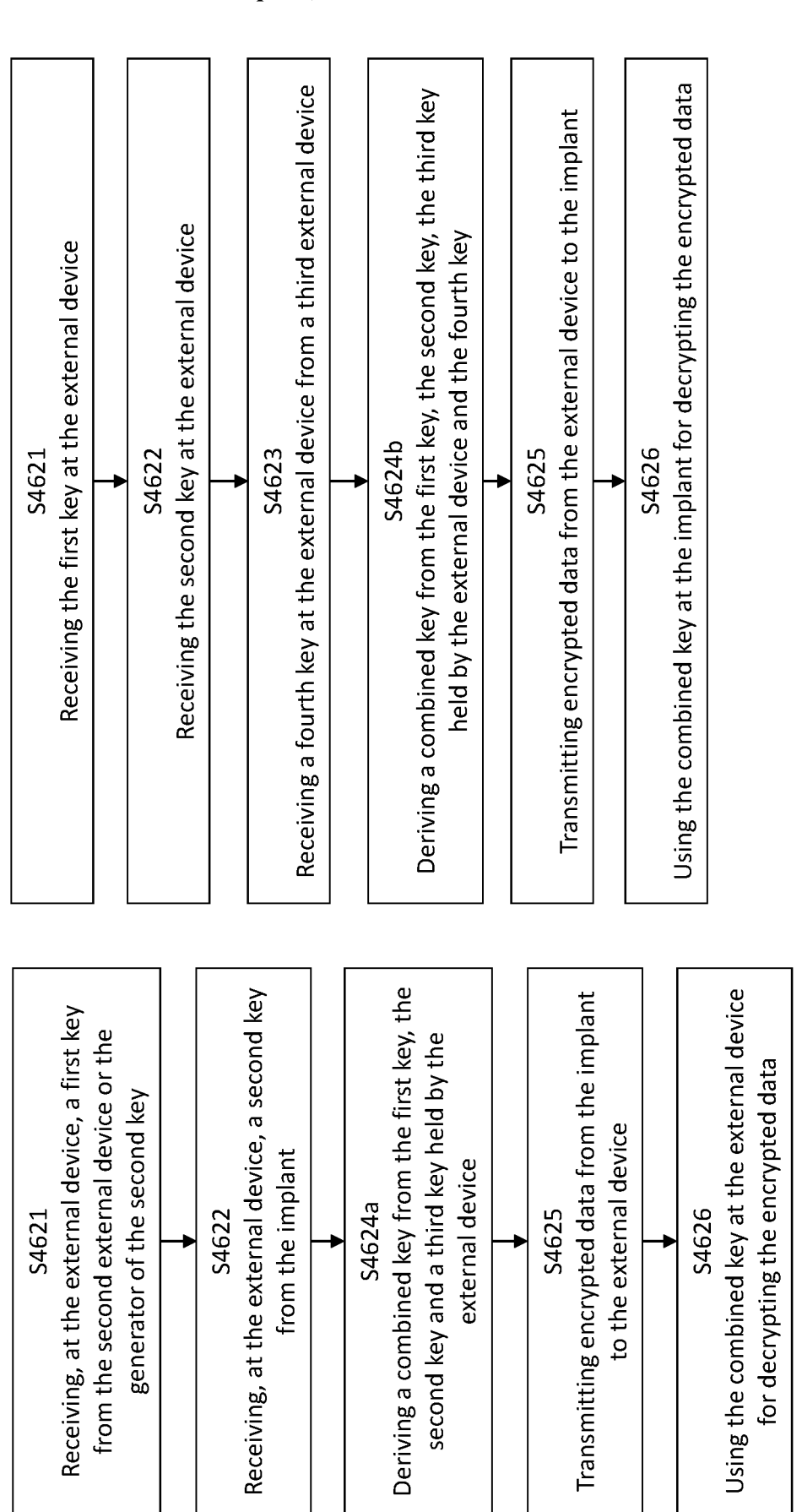

S4621
Receiving the first key at the external device

S4622
Receiving the second key at the external device

S4623
Receiving a fourth key at the external device from a third external device S4624b
Deriving a combined key from the first key, the second key, the third key held by the external device and the fourth key S4625
Transmitting encrypted data from the external device to the implant S4626
Using the combined key at the implant for decrypting the encrypted data

Fig. 28

S4621
Receiving, at the external device, a first key from the second external device or the generator of the second key S4622
Receiving, at the external device, a second key from the implant S4624a
Deriving a combined key from the first key, the second key and a third key held by the external device S4625
Transmitting encrypted data from the implant to the external device S4626
Using the combined key at the external device for decrypting the encrypted data

Fig. 27

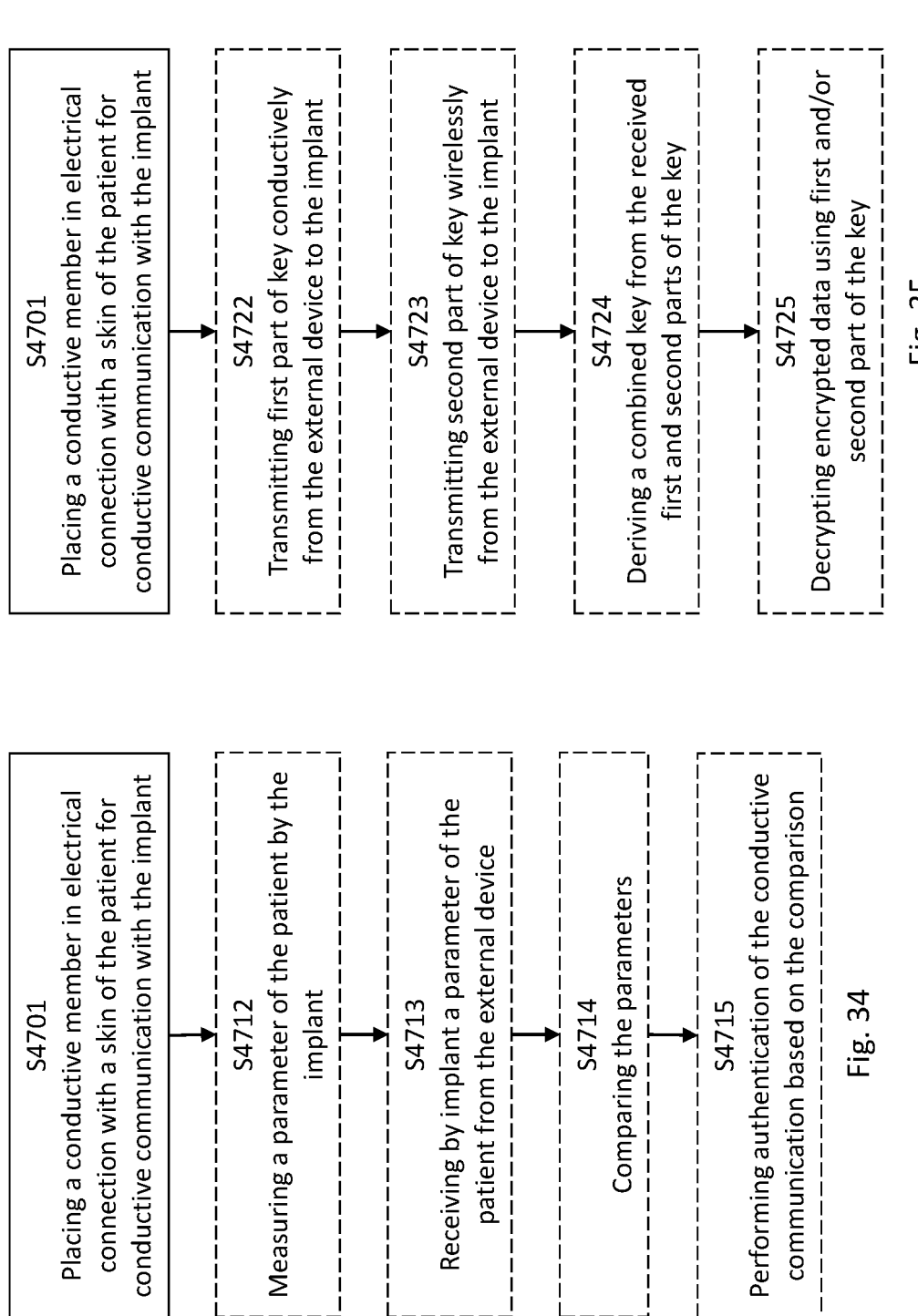

S4701
Placing a conductive member in electrical connection with a skin of the patient for conductive communication with the implant S4722
Transmitting first part of key conductively from the external device to the implant S4723
Transmitting second part of key wirelessly from the external device to the implant S4724
Deriving a combined key from the received first and second parts of the key S4725
Decrypting encrypted data using first and/or second part of the key

Fig. 35

S4701
Placing a conductive member in electrical connection with a skin of the patient for conductive communication with the implant S4712
Measuring a parameter of the patient by the implant S4713
Receiving by implant a parameter of the patient from the external device S4714
Comparing the parameters S4715
Performing authentication of the conductive communication based on the comparison

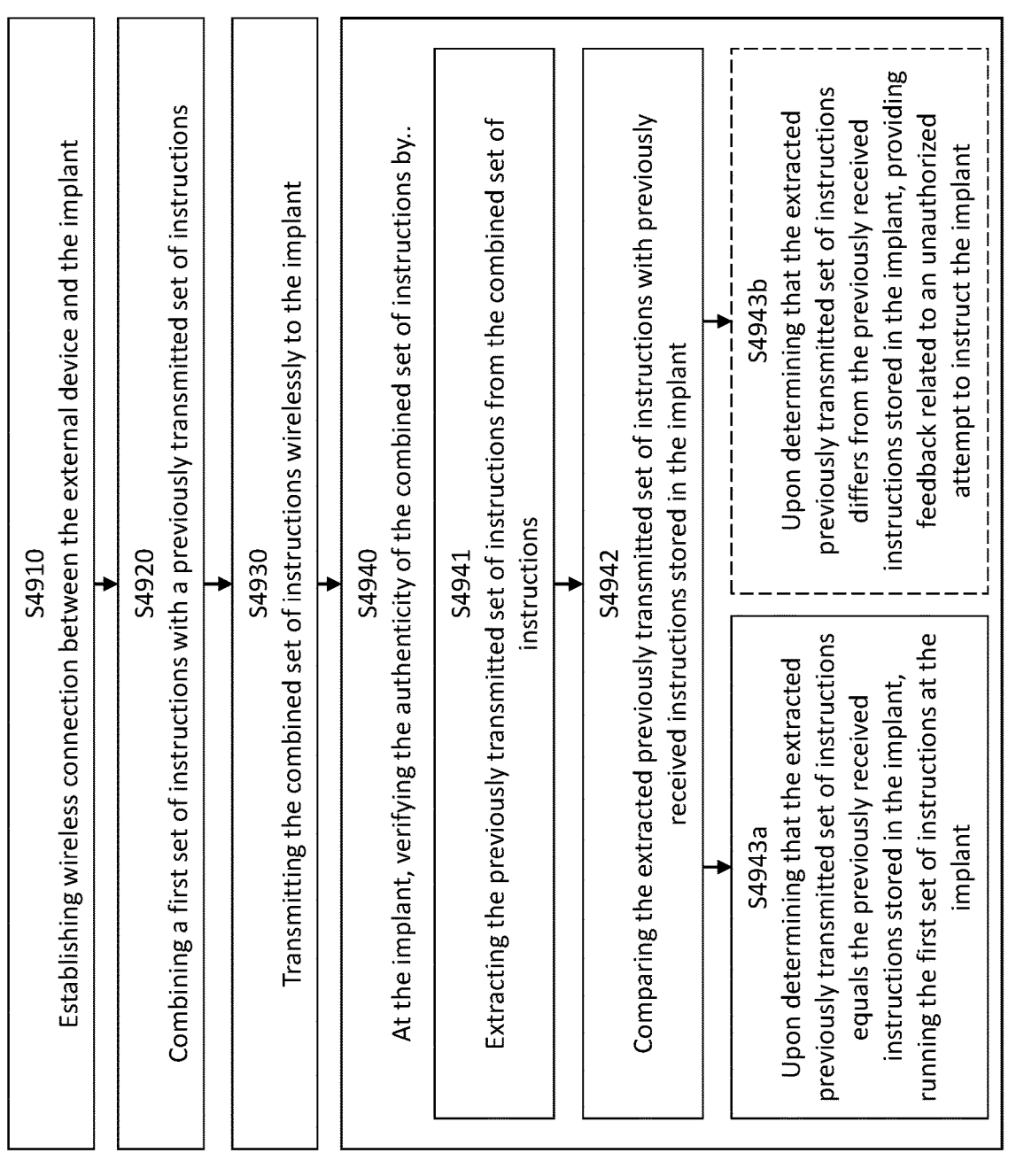

S4910
Establishing wireless connection between the external device and the implant S4920
Combining a first set of instructions with a previously transmitted set of instructions S4930
Transmitting the combined set of instructions wirelessly to the implant S4940
At the implant, verifying the authenticity of the combined set of instructions by..

S4941
Extracting the previously transmitted set of instructions from the combined set of instructions S4942
Comparing the extracted previously transmitted set of instructions with previously received instructions stored in the implant S4943a
Upon determining that the extracted previously transmitted set of instructions equals the previously received instructions stored in the implant, running the first set of instructions at the implant S4943b
Upon determining that the extracted previously transmitted set of instructions differs from the previously received instructions stored in the implant, providing feedback related to an unauthorized attempt to instruct the implant

Fig. 40

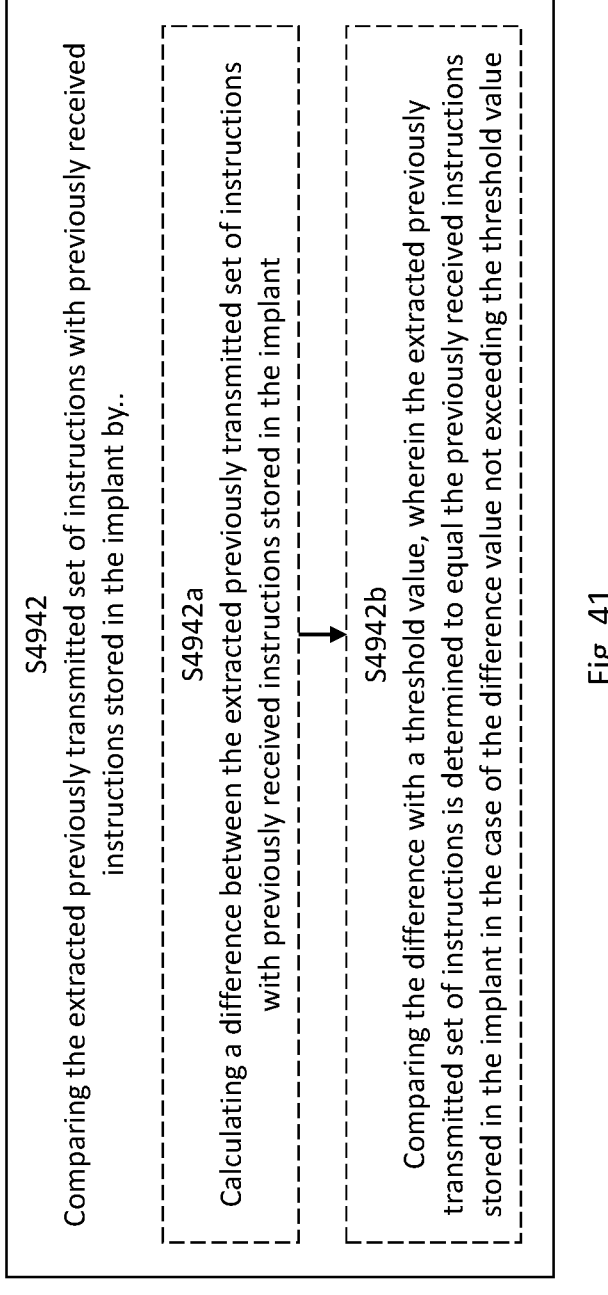

S4942

Comparing the extracted previously transmitted set of instructions with previously received instructions stored in the implant by..

S4942a

Calculating a difference between the extracted previously transmitted set of instructions with previously received instructions stored in the implant S4942b Comparing the difference with a threshold value, wherein the extracted previously transmitted set of instructions is determined to equal the previously received instructions stored in the implant in the case of the difference value not exceeding the threshold value

Fig. 41

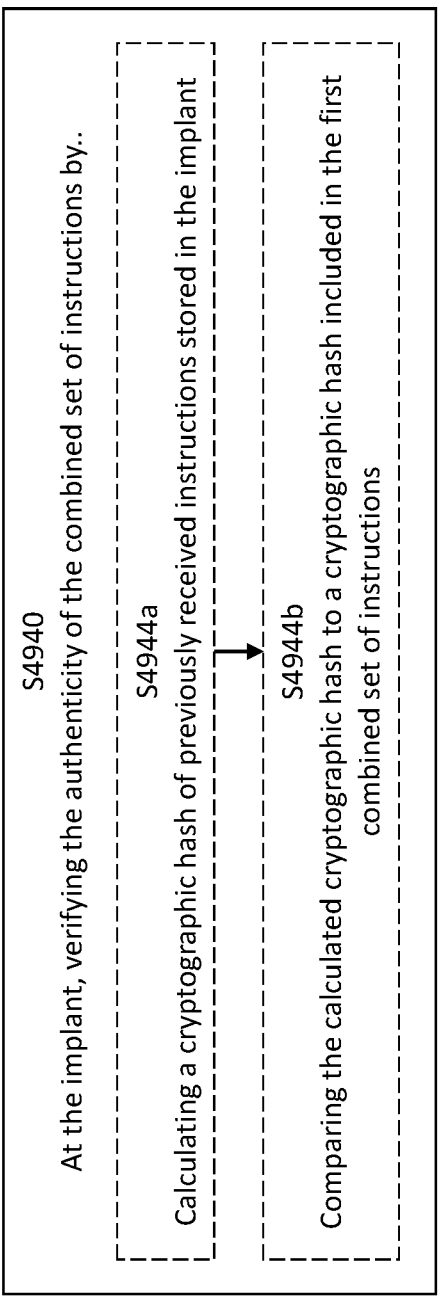

S4940

At the implant, verifying the authenticity of the combined set of instructions by..

S4944a

Calculating a cryptographic hash of previously received instructions stored in the implant S4944b Comparing the calculated cryptographic hash to a cryptographic hash included in the first combined set of instructions

Fig. 42

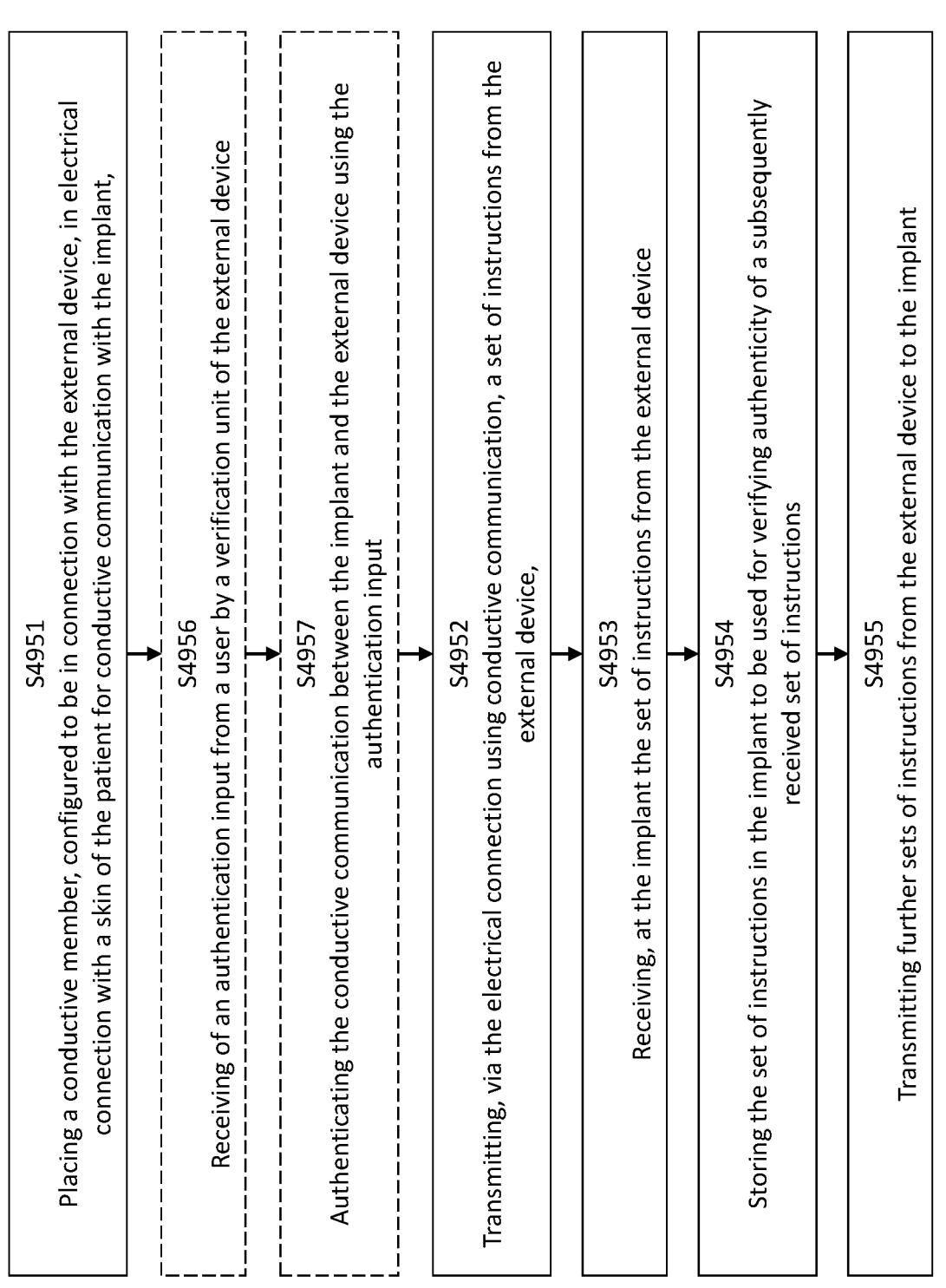

S4951

Placing a conductive member, configured to be in connection with the external device, in electrical connection with a skin of the patient for conductive communication with the implant,

S4956

Receiving of an authentication input from a user by a verification unit of the external device

S4957

Authenticating the conductive communication between the implant and the external device using the authentication input

S4952

Transmitting, via the electrical connection using conductive communication, a set of instructions from the external device,

S4953

Receiving, at the implant the set of instructions from the external device

S4954

Storing the set of instructions in the implant to be used for verifying authenticity of a subsequently received set of instructions

S4955

Transmitting further sets of instructions from the external device to the implant

Fig. 46

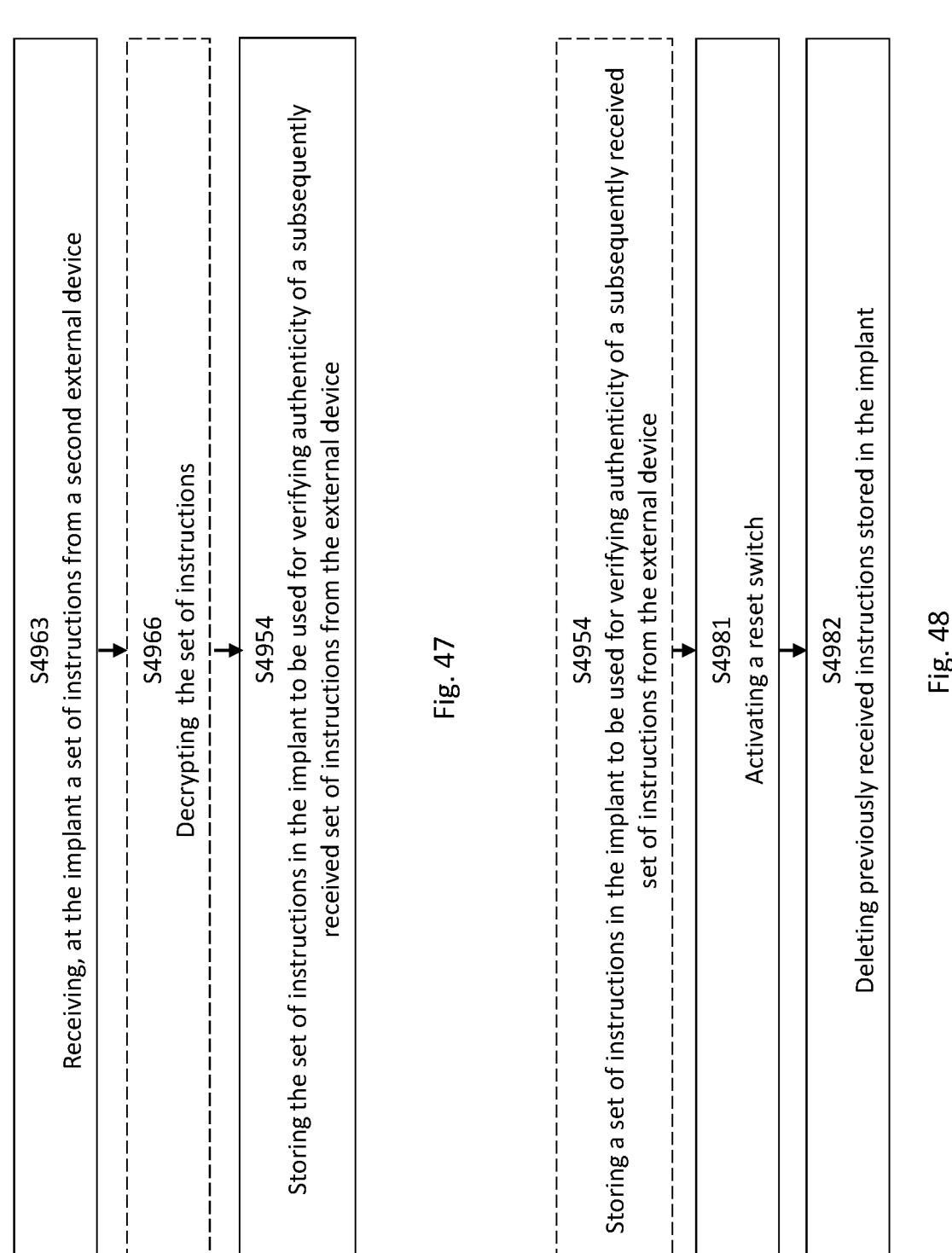

S4963
Receiving, at the implant a set of instructions from a second external device S4966
Decrypting the set of instructions S4954
Storing the set of instructions in the implant to be used for verifying authenticity of a subsequently received set of instructions from the external device

Fig. 47

S4954
Storing a set of instructions in the implant to be used for verifying authenticity of a subsequently received set of instructions from the external device S4981
Activating a reset switch S4982
Deleting previously received instructions stored in the implant

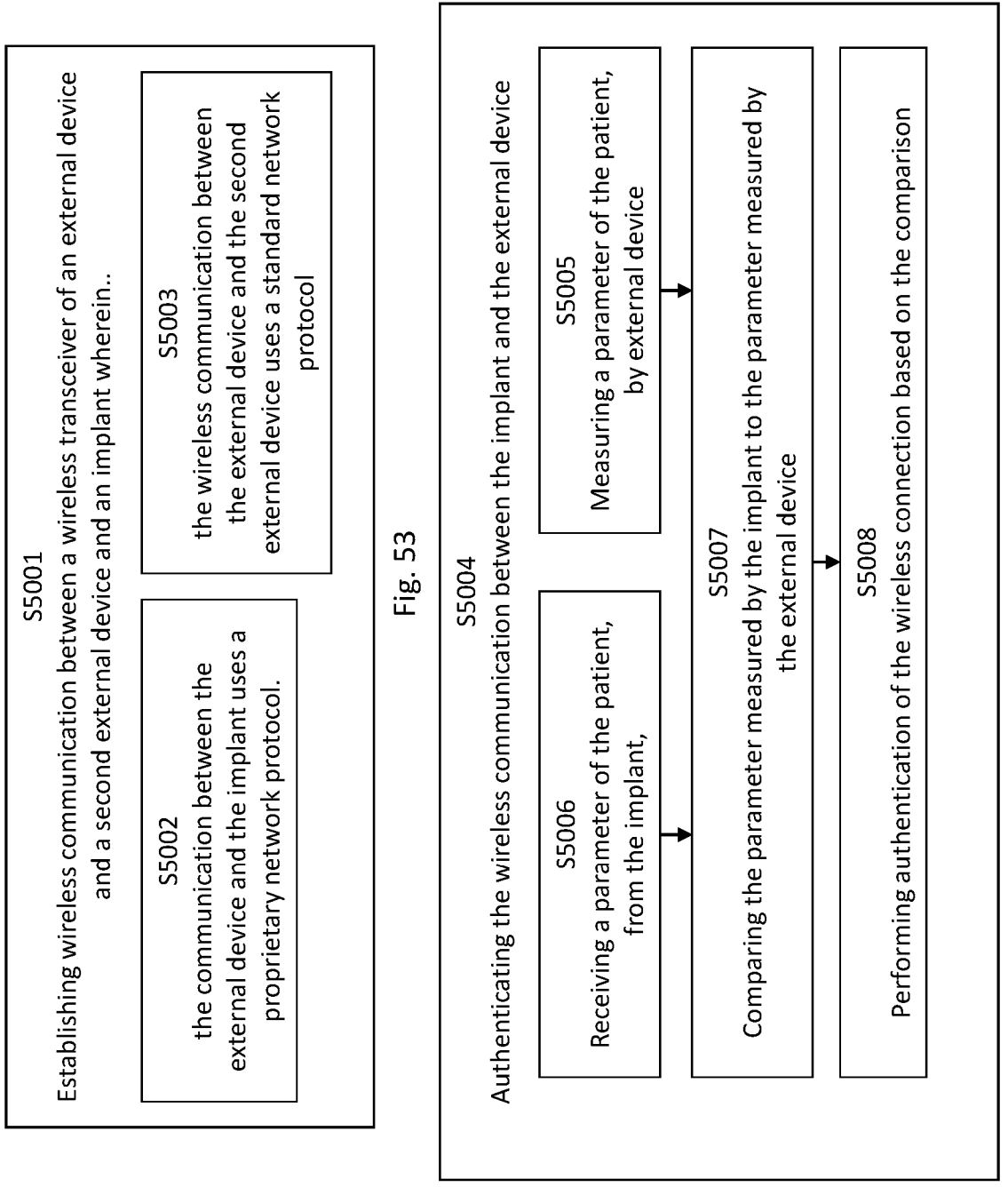

S5001

Establishing wireless communication between a wireless transceiver of an external device and a second external device and an implant wherein..

S5002 the communication between the external device and the implant uses a proprietary network protocol.

S5003 the wireless communication between the external device and the second external device uses a standard network protocol

Authenticating the wireless communication between the implant and the external device

S5005

Measuring a parameter of the patient, by external device

S5006

Receiving a parameter of the patient, from the implant,

S5007

Comparing the parameter measured by the implant to the parameter measured by the external device

S5008

Performing authentication of the wireless connection based on the comparison

Fig. 54

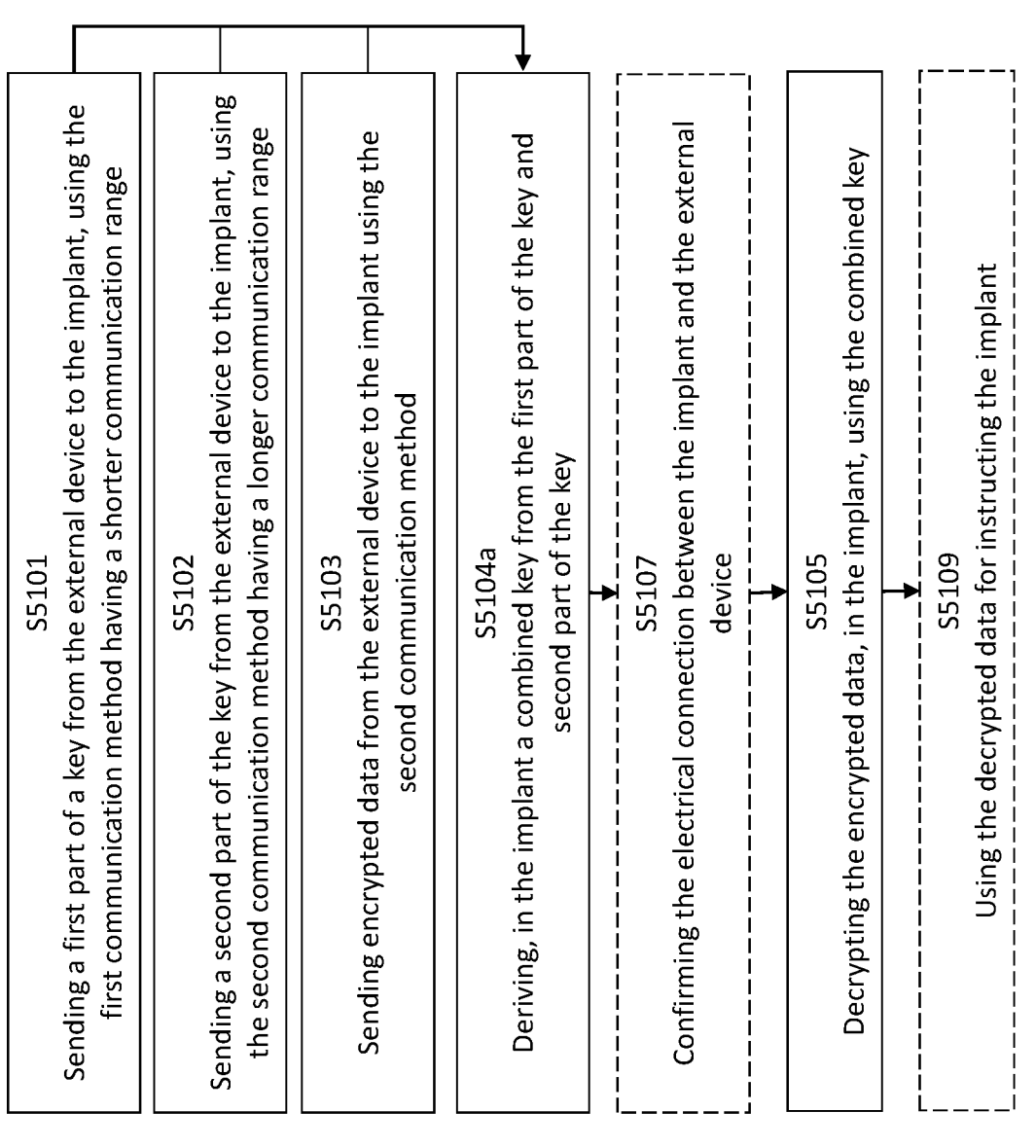

S5101

Sending a first part of a key from the external device to the implant, using the first communication method having a shorter communication range

S5102

Sending a second part of the key from the external device to the implant, using the second communication method having a longer communication range

S5103

Sending encrypted data from the external device to the implant using the second communication method S5104a Deriving, in the implant a combined key from the first part of the key and second part of the key

S5107

Confirming the electrical connection between the implant and the external device

S5105

Decrypting the encrypted data, in the implant, using the combined key

S5109

Using the decrypted data for instructing the implant

Fig. 56

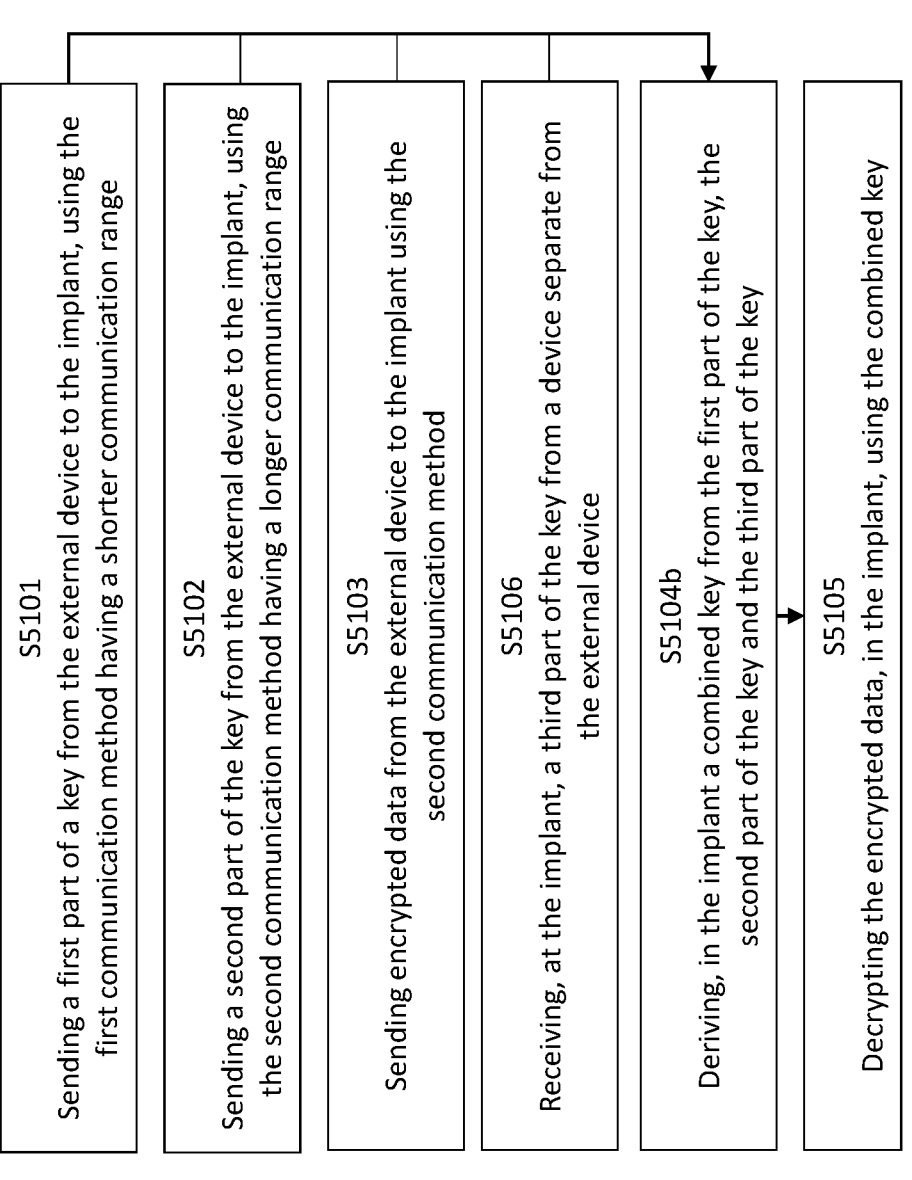

S5101
Sending a first part of a key from the external device to the implant, using the first communication method having a shorter communication range S5102
Sending a second part of the key from the external device to the implant, using the second communication method having a longer communication range S5103
Sending encrypted data from the external device to the implant using the second communication method S5106
Receiving, at the implant, a third part of the key from a device separate from the external device S5104b
Deriving, in the implant a combined key from the first part of the key, the second part of the key and the third part of the key S5105
Decrypting the encrypted data, in the implant, using the combined key

Fig. 57

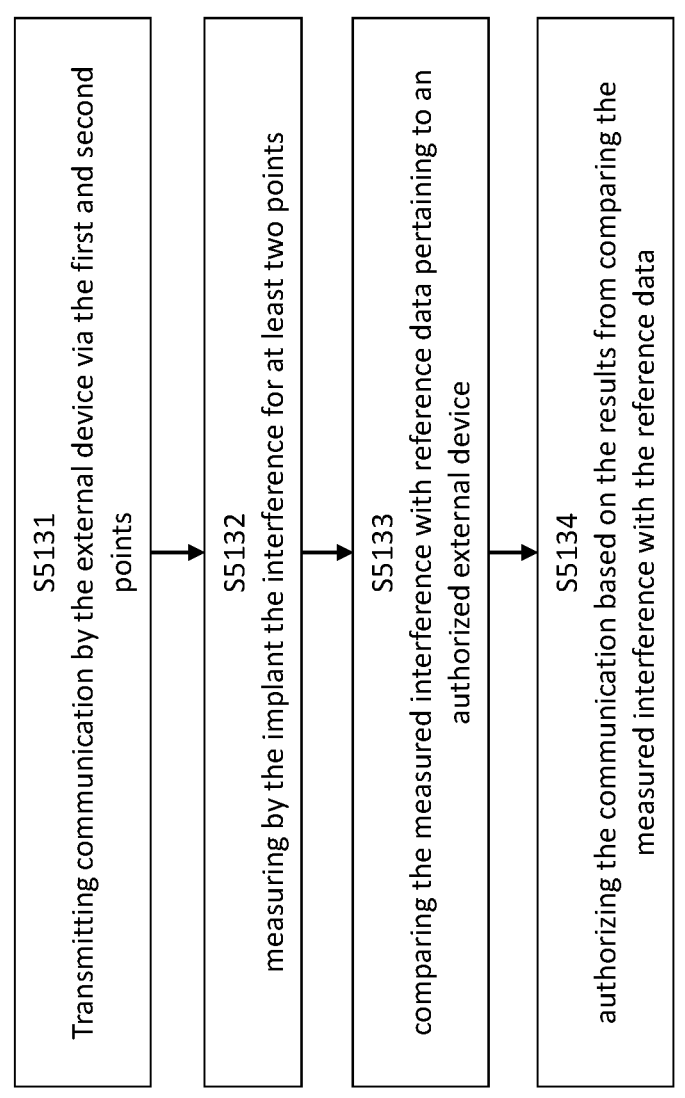

S5131
Transmitting communication by the external device via the first and second points S5132
measuring by the implant the interference for at least two points S5133
comparing the measured interference with reference data pertaining to an authorized external device S5134
authorizing the communication based on the results from comparing the measured interference with the reference data

Fig. 60

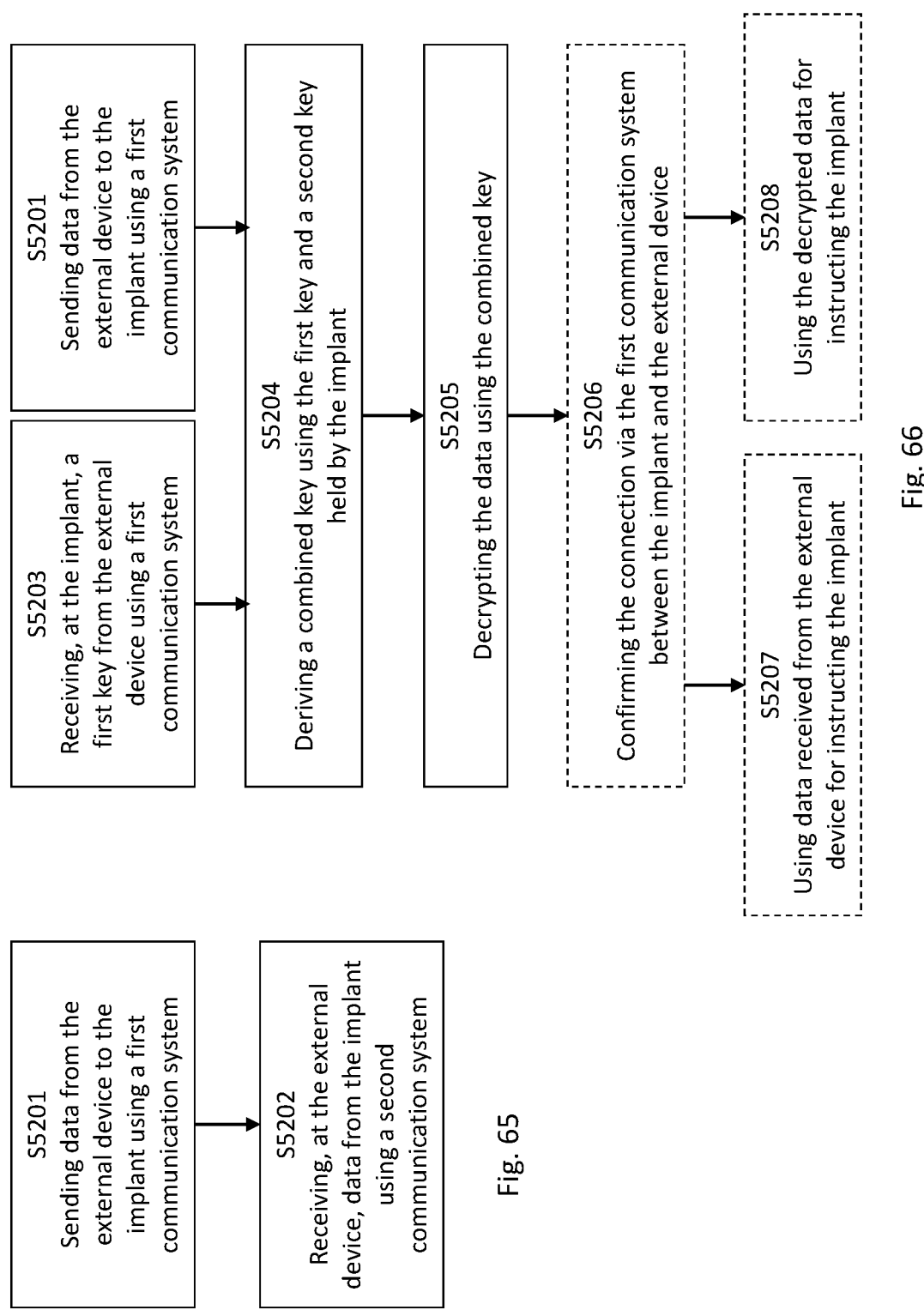

S5201
Sending data from the external device to the implant using a first communication system

S5203
Receiving, at the implant, a first key from the external device using a first communication system

S5204
Deriving a combined key using the first key and a second key held by the implant

S5205
Decrypting the data using the combined key

S5206
Confirming the connection via the first communication system between the implant and the external device

S5208
Using the decrypted data for instructing the implant

S5207
Using data received from the external device for instructing the implant

Fig. 66

S5201
Sending data from the external device to the implant using a first communication system

S5202
Receiving, at the external device, data from the implant using a second communication system

Fig. 65

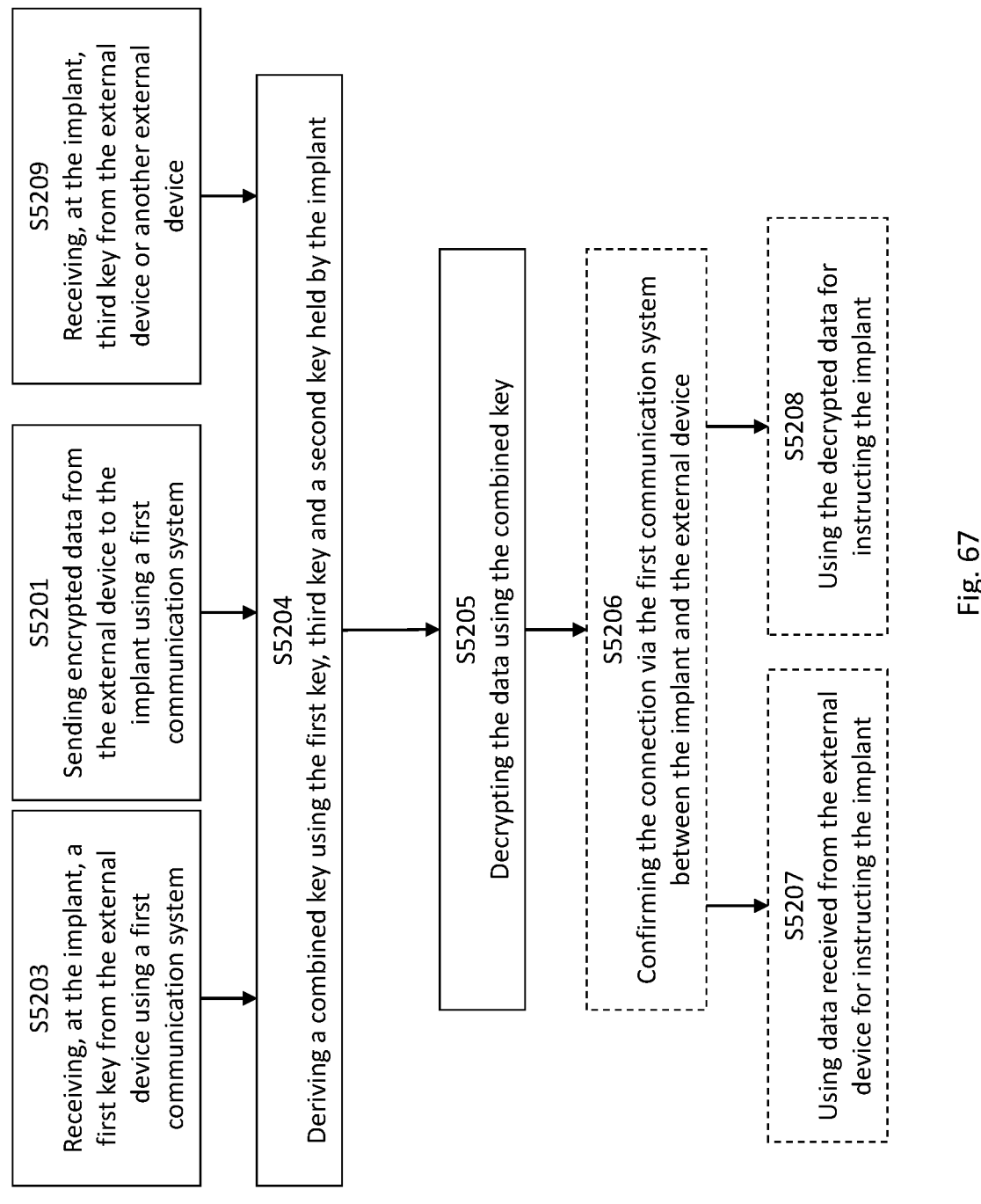

S5209
Receiving, at the implant, third key from the external device or another external device S5201
Sending encrypted data from the external device to the implant using a first communication system S5203
Receiving, at the implant, a first key from the external device using a first communication system S5204
Deriving a combined key using the first key, third key and a second key held by the implant S5205
Decrypting the data using the combined key S5206
Confirming the connection via the first communication system between the implant and the external device S5207
Using data received from the external device for instructing the implant S5208
Using the decrypted data for instructing the implant

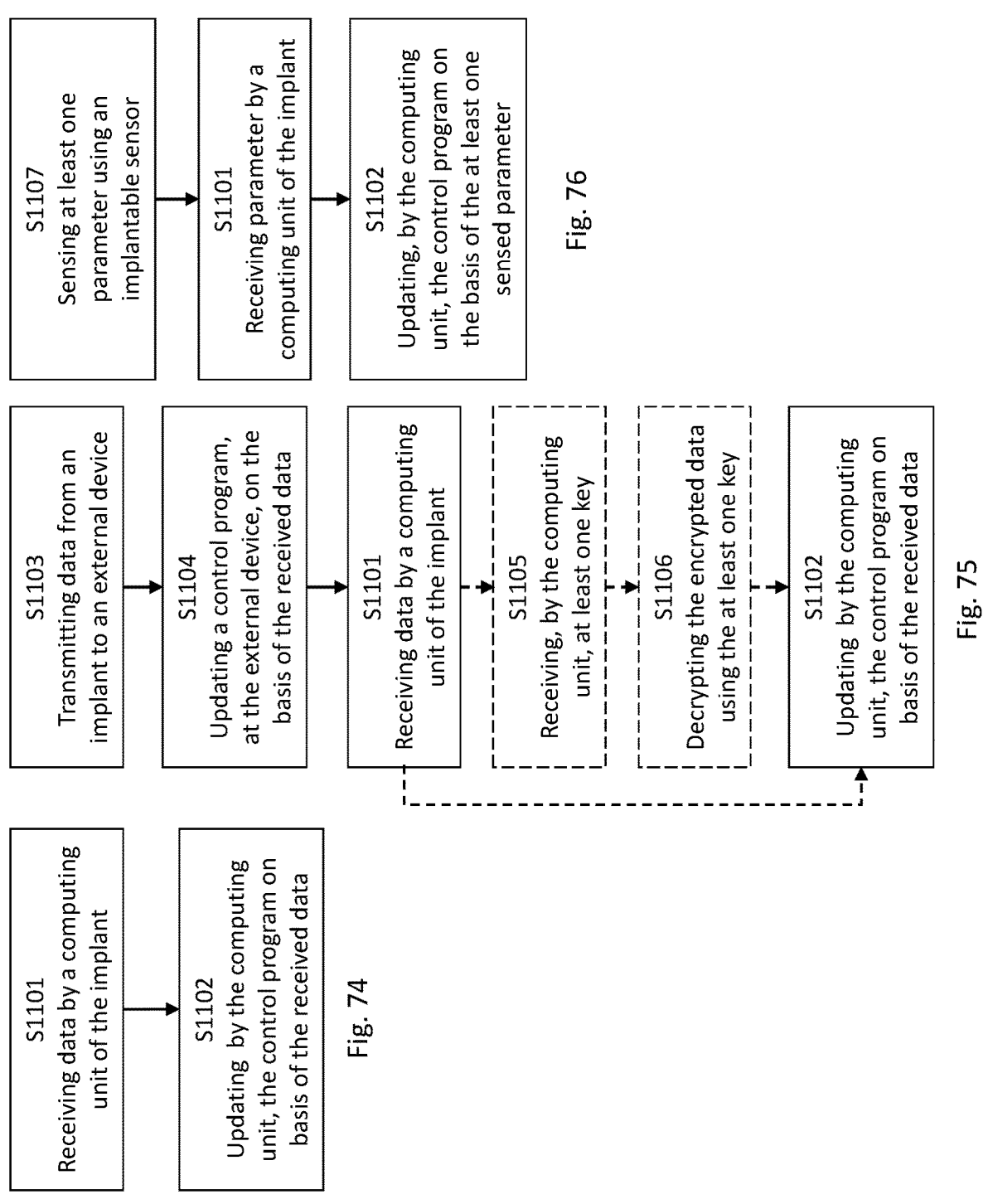

S1107
Sensing at least one parameter using an implantable sensor

S1101
Receiving parameter by a computing unit of the implant

S1102
Updating, by the computing unit, the control program on the basis of the at least one sensed parameter

Fig. 76

S1103
Transmitting data from an implant to an external device

S1104
Updating a control program, at the external device, on the basis of the received data S1101
Receiving data by a computing unit of the implant S1105
Receiving, by the computing unit, at least one key S1106
Decrypting the encrypted data using the at least one key S1102
Updating by the computing unit, the control program on basis of the received data

Fig. 75

S1101
Receiving data by a computing unit of the implant

S1102
Updating by the computing unit, the control program on basis of the received data

Fig. 74

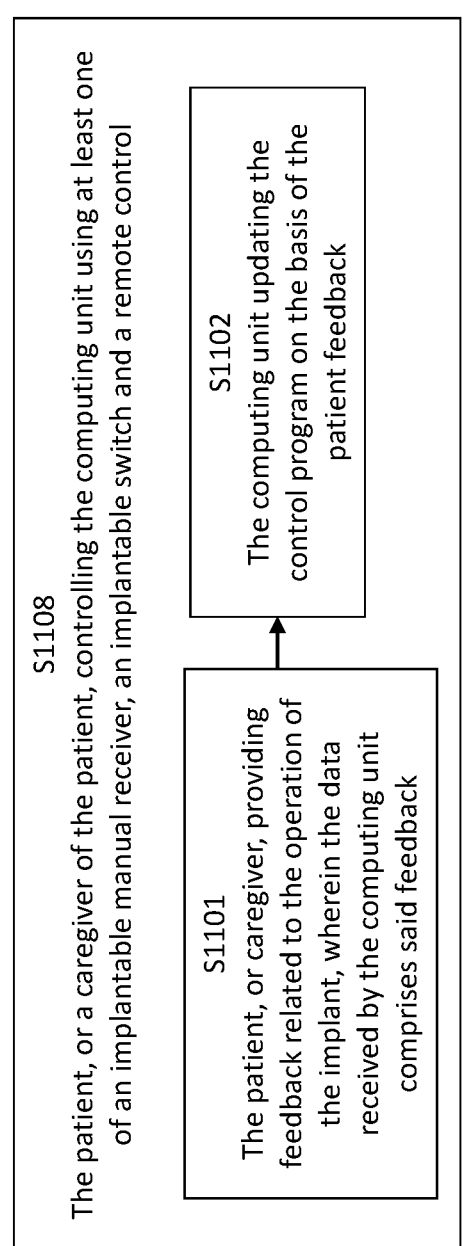

S1108

The patient, or a caregiver of the patient, controlling the computing unit using at least one of an implantable manual receiver, an implantable switch and a remote control

S1101

The patient, or caregiver, providing feedback related to the operation of the implant, wherein the data received by the computing unit comprises said feedback

S1102

The computing unit updating the control program on the basis of the patient feedback

Fig. 77

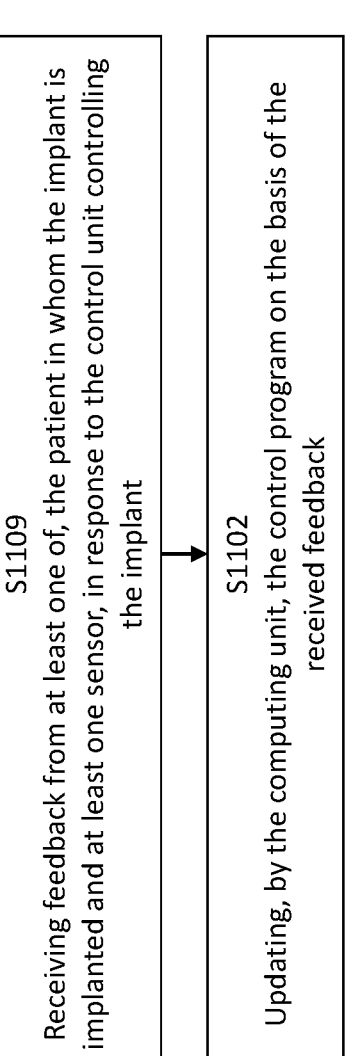

S1109

Receiving feedback from at least one of, the patient in whom the implant is implanted and at least one sensor, in response to the control unit controlling the implant

S1102

Updating, by the computing unit, the control program on the basis of the received feedback

Fig. 78

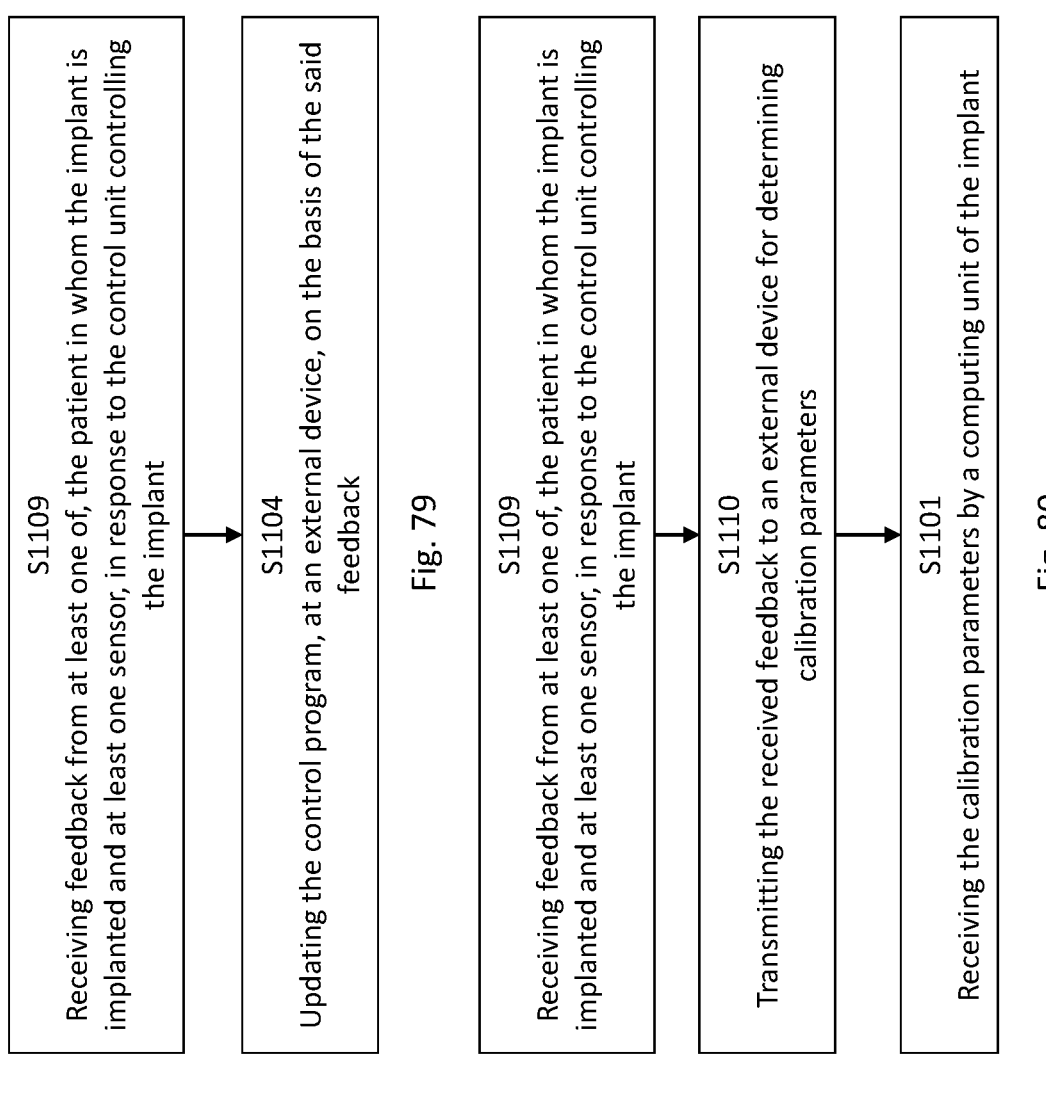

S1109
Receiving feedback from at least one of, the patient in whom the implant is implanted and at least one sensor, in response to the control unit controlling the implant S1104
Updating the control program, at an external device, on the basis of the said feedback

Fig. 79

S1109
Receiving feedback from at least one of, the patient in whom the implant is implanted and at least one sensor, in response to the control unit controlling the implant S1110
Transmitting the received feedback to an external device for determining calibration parameters S1101
Receiving the calibration parameters by a computing unit of the implant

Fig. 80

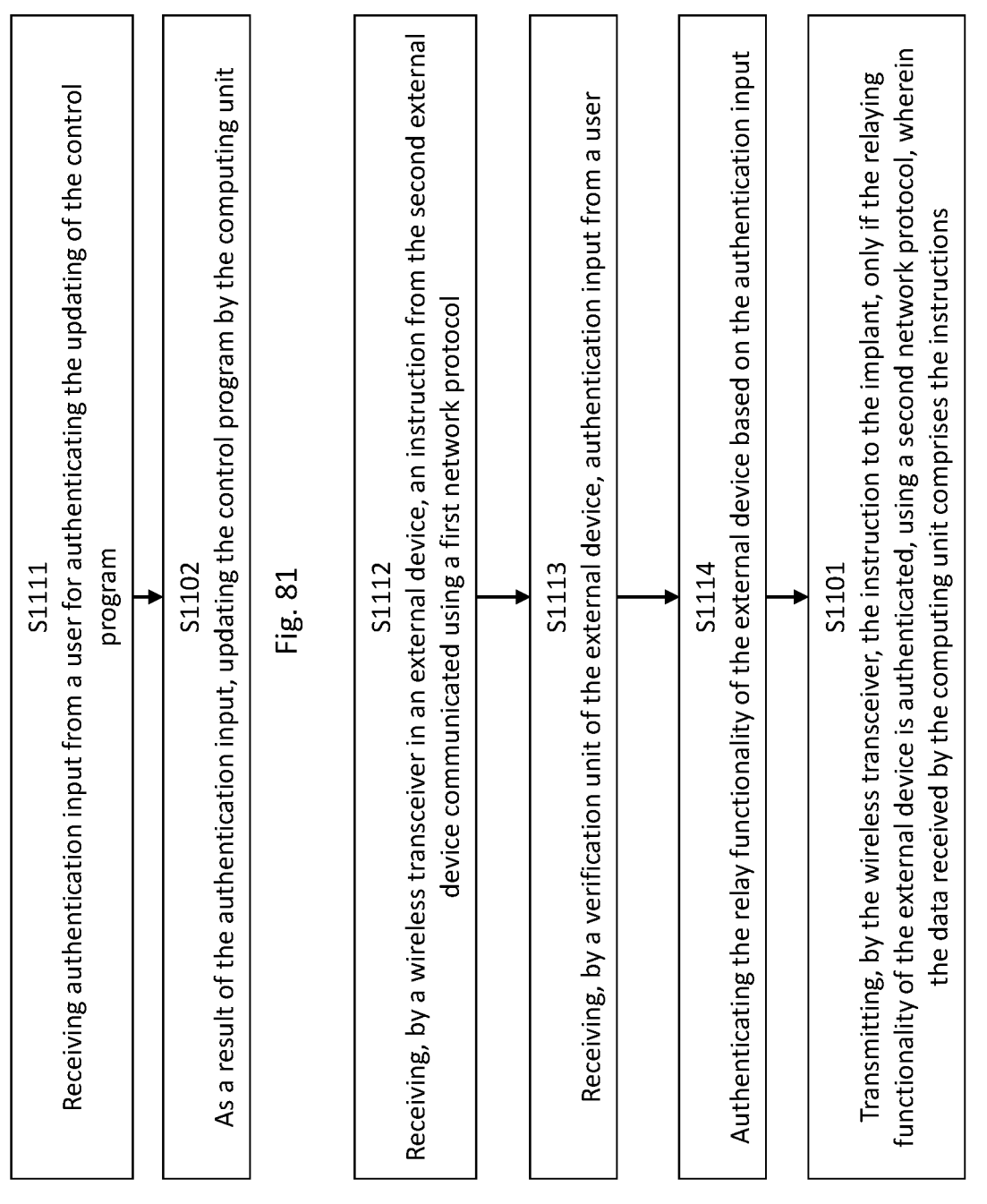

S1111

Receiving authentication input from a user for authenticating the updating of the control program

S1102

As a result of the authentication input, updating the control program by the computing unit

Receiving, by a wireless transceiver in an external device, an instruction from the second external device communicated using a first network protocol

S1113

Receiving, by a verification unit of the external device, authentication input from a user

S1114

Authenticating the relay functionality of the external device based on the authentication input

S1101

Transmitting, by the wireless transceiver, the instruction to the implant, only if the relaying functionality of the external device is authenticated, using a second network protocol, wherein the data received by the computing unit comprises the instructions

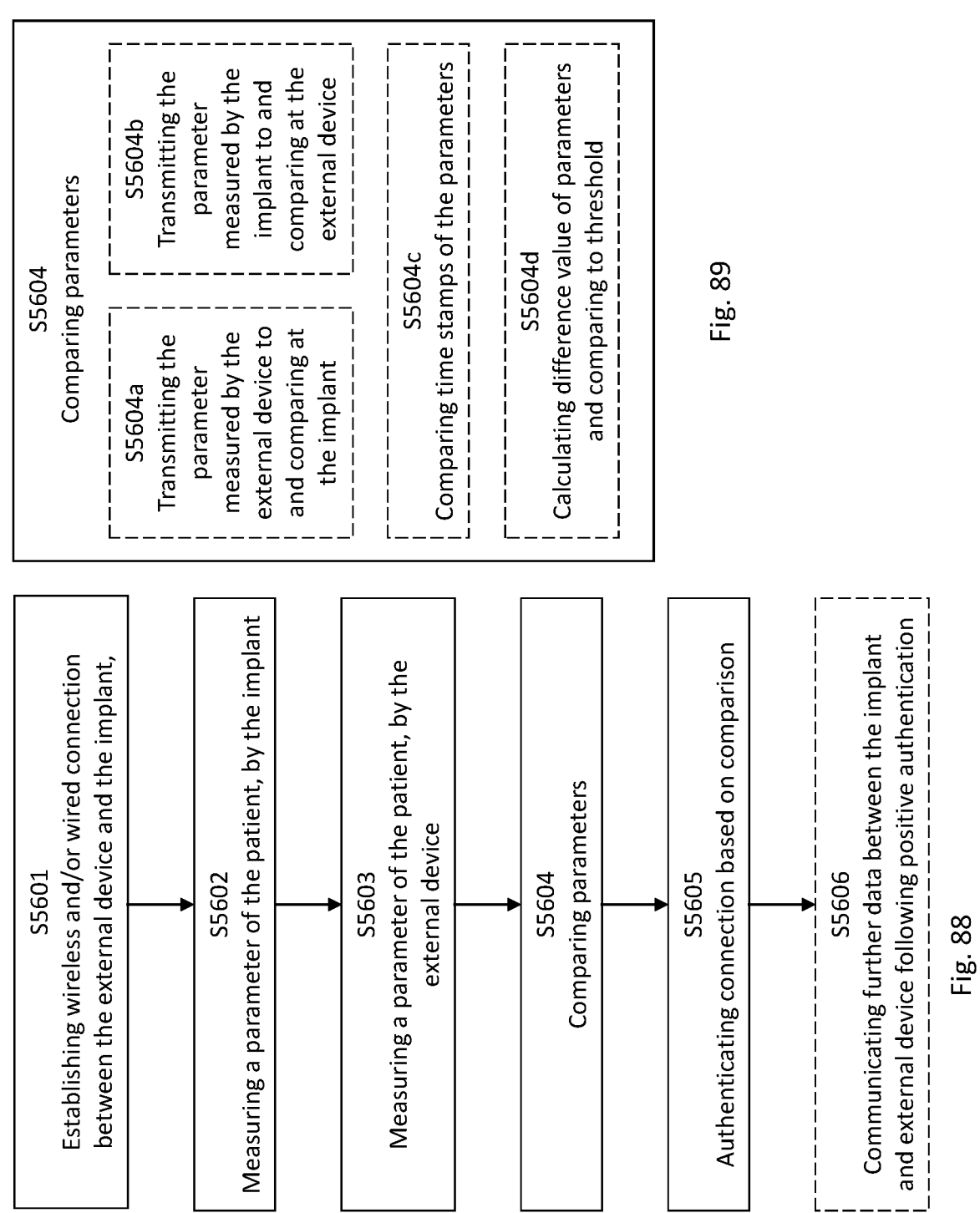

S5604
Comparing parameters

S5604a
Transmitting the parameter measured by the external device to and comparing at the implant S5604b
Transmitting the parameter measured by the implant to and comparing at the external device S5604c
Comparing time stamps of the parameters S5604d
Calculating difference value of parameters and comparing to threshold

Fig. 89

S5601
Establishing wireless and/or wired connection between the external device and the implant, S5602
Measuring a parameter of the patient, by the implant S5603
Measuring a parameter of the patient, by the external device S5604
Comparing parameters S5605
Authenticating connection based on comparison S5606
Communicating further data between the implant and external device following positive authentication

Fig. 88

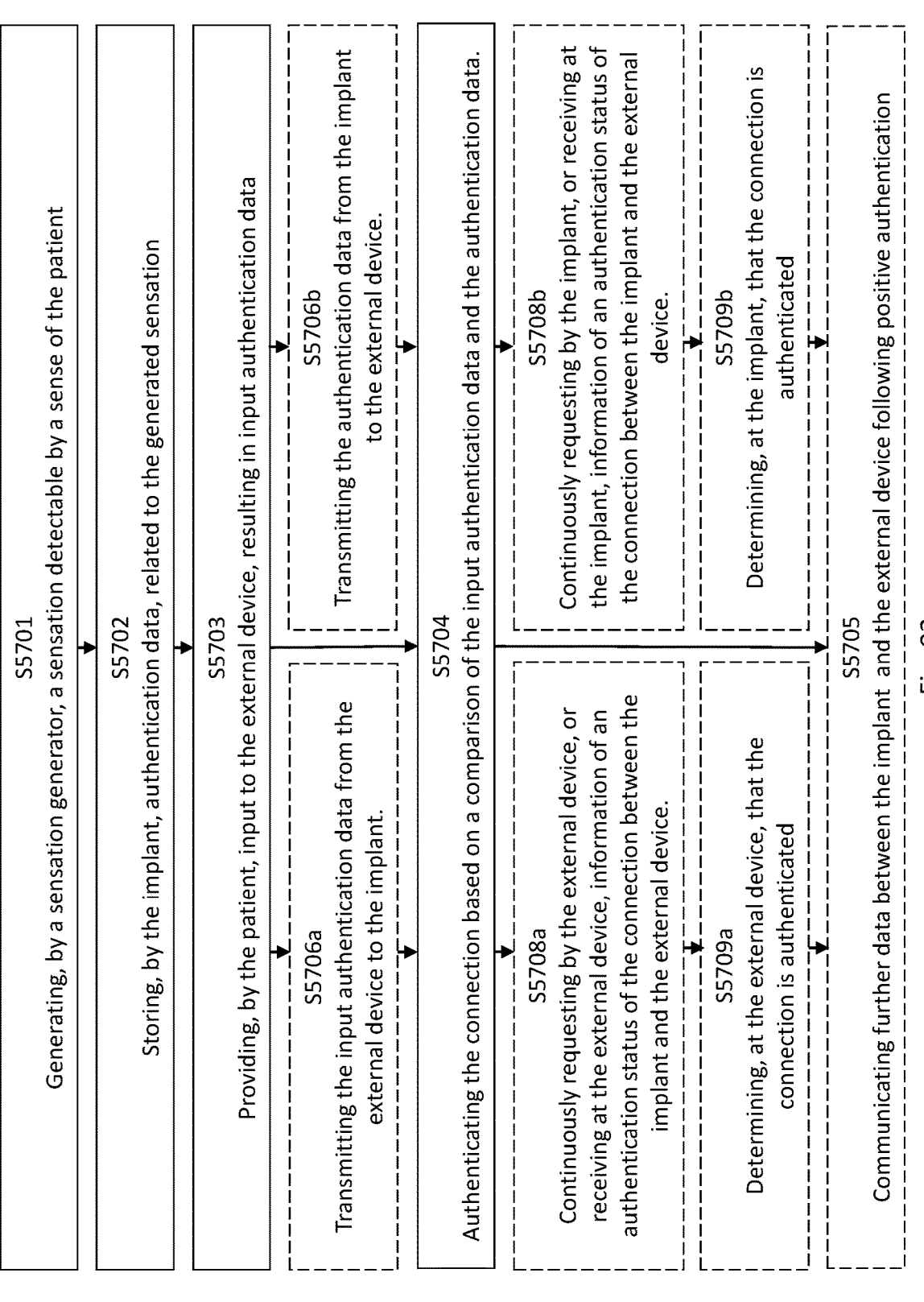

S5701
Generating, by a sensation generator, a sensation detectable by a sense of the patient S5702
Storing, by the implant, authentication data, related to the generated sensation S5703
Providing, by the patient, input to the external device, resulting in input authentication data S5706b
Transmitting the authentication data from the implant to the external device.

S5706a
Transmitting the input authentication data from the external device to the implant.

S5704
Authenticating the connection based on a comparison of the input authentication data and the authentication data.

S5708b
Continuously requesting by the implant, or receiving at the implant, information of an authentication status of the connection between the implant and the external device.

S5708a
Continuously requesting by the external device, or receiving at the external device, information of an authentication status of the connection between the implant and the external device.

S5709b
Determining, at the implant, that the connection is authenticated

S5709a
Determining, at the external device, that the connection is authenticated S5705
Communicating further data between the implant and the external device following positive authentication

*Fig.120*
*Fig.121*
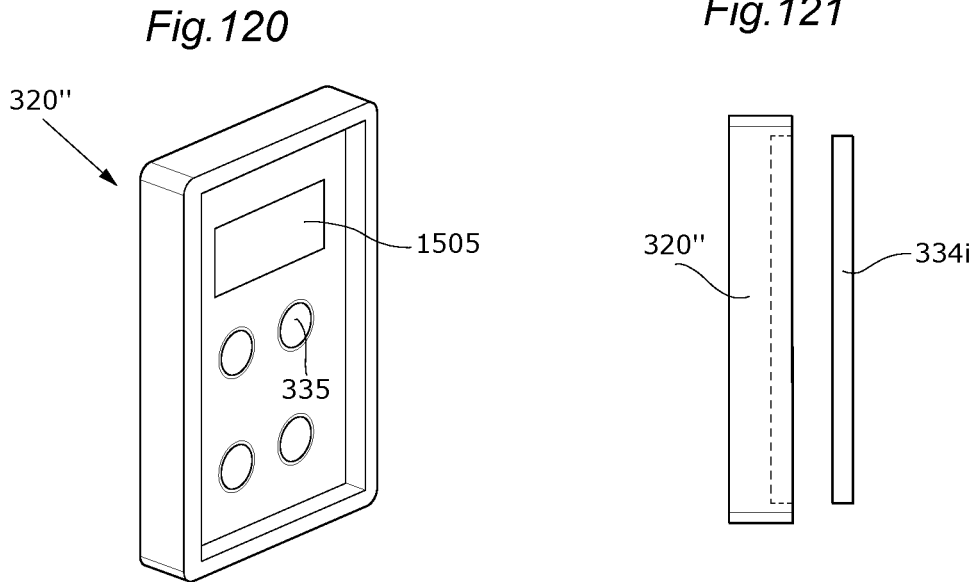
*Fig.122*
*Fig.123*
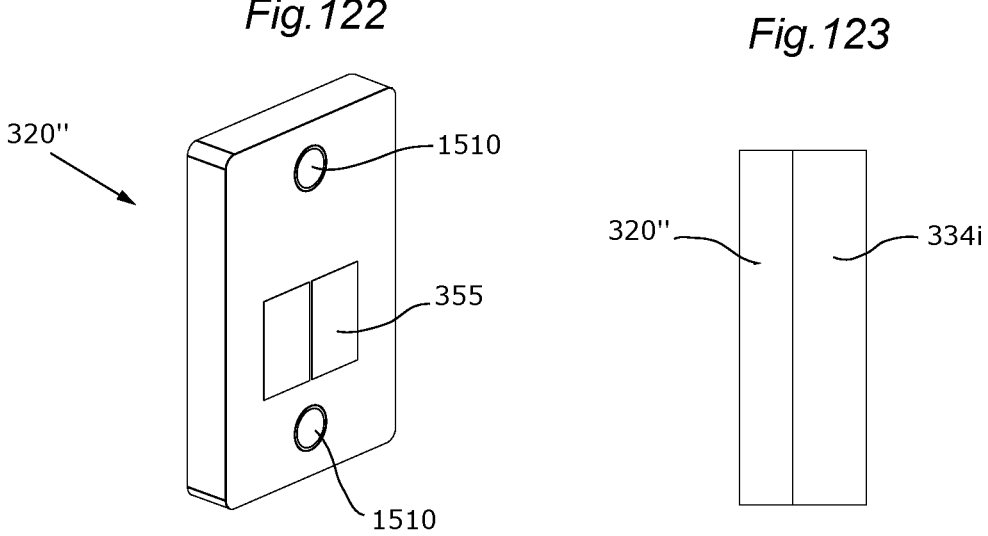

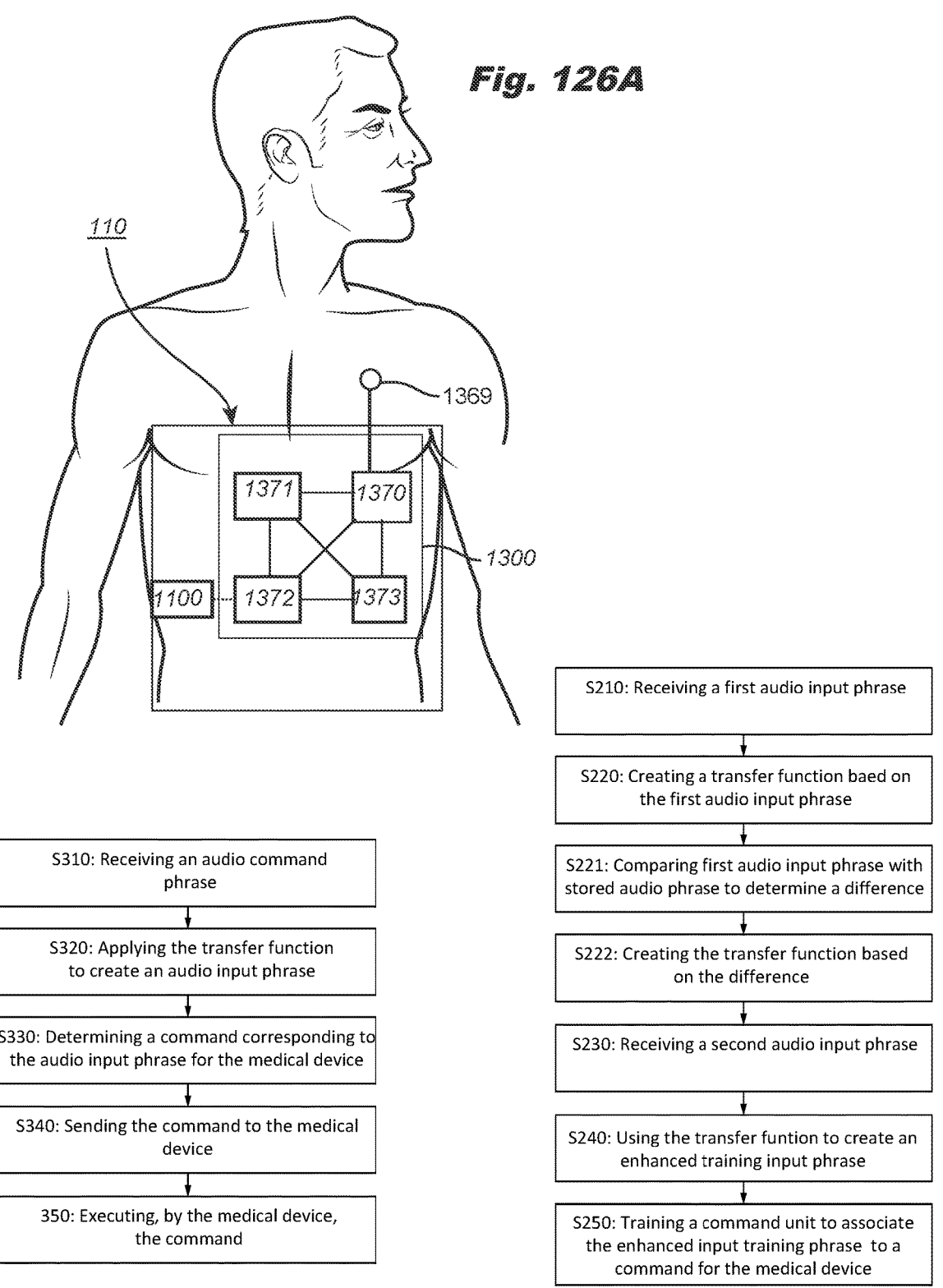

S310: Receiving an audio command
phrase

S320: Applying the transfer function
to create an audio input phrase

S330: Determining a command corresponding to
the audio input phrase for the medical device S340: Sending the command to the medical
device 350: Executing, by the medical device,
the command

*Fig. 126C*

S210: Receiving a first audio input phrase

S220: Creating a transfer function baed on
the first audio input phrase

S221: Comparing first audio input phrase with
stored audio phrase to determine a difference S222: Creating the transfer function based
on the difference S230: Receiving a second audio input phrase S240: Using the transfer funtion to create an
enhanced training input phrase S250: Training a command unit to associate
the enhanced input training phrase  to a
command for the medical device

*Fig. 126B*

METHODS AND DEVICES FOR SECURE COMMUNICATION WITH AND OPERATION OF AN IMPLANT

This application is a continuation in part of International Application No. PCT/EP2023/053882, filed Feb. 16, 2023, which designates the US and claims priority to Swedish Application No 2250209-0, filed Feb. 18, 2022 and to International Application No. PCT/EP2022/073816 filed Aug. 26, 2022, this application is also a continuation in part of International Application No. PCT/EP2022/073816, filed Aug. 26, 2022, which designates the US and claims priority to Swedish Application No 2250209-0, filed Feb. 18, 2022 and to International Application No. PCT/EP2021/073893 filed Aug. 30, 2021, the entire contents of each of which are hereby incorporated by reference.

TECHNICAL FIELD

This disclosure generally relates to an implant, and in particular to methods and devices which facilitate secure communication with and operation of the implant.

BACKGROUND

A medical implant is designed to be subcutaneously implanted in a patient's body. The new generation of implants is getting more advanced, and some implants may obtain, read and/or store data. This data can consist of various information, relating to for example different physiological parameters of the patient's body. For some implants, this data can be transferred via wires or wirelessly communicated to other external or internal devices. Some data may contain sensitive information and therefore require a reliable communication approach in order to avoid unauthorized recipients to gain access to it. Other sensitive data being transferred to and/or from the implant may contain information on program updates or control data for programs controlling the implant. Such data must also be protected to ensure that the implant is only controlled by authorized users.

There is thus a need for improvements within this context.

SUMMARY

In view of the above, it is thus an object of the present invention to overcome or at least mitigate the problems discussed above.

An external device configured for communication with the implantable medical device according to any of the embodiments herein, when implanted in a patient, is further provided. The external device comprises at least one first wireless transceiver configured for communication with the implantable medical device using a first network protocol, for determining a distance between the external device and the implantable medical device, and at least one second wireless transceiver configured for communication with the implantable medical device using a second network protocol, for transferring data between the external device and the implantable medical device.

According to one embodiment, the first wireless transceiver comprises an UWB transceiver.

According to one embodiment, the first wireless transceiver is configured for transcutaneous energy transfer for at least one of: powering an energy consuming component of the implantable medical device, and charging an implantable energy storage unit.

According to one embodiment, the second network protocol is a standard network protocol.

According to one embodiment, the second wireless transceiver comprises a Bluetooth transceiver.

According to one embodiment, the external device is further configured to communicate with a second external device using the at least one wireless transceiver.

According to one embodiment, the external device is configured for determining a distance between the external device and the implantable medical device by determining the RSSI.

According to one embodiment, the standard network protocol is one of, or a combination of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, a communication range of the first network protocol is less than a communication range of the second network protocol.

According to one embodiment, a frequency band of the first network protocol differs from a frequency band of the second network protocol.

According to one embodiment, the external device is configured to authenticate the implantable medical device if the determined distance between the external device and the implantable medical device is less than a predetermined threshold value. The external device may be configured to allow the transfer of data between the external device and the implantable medical device after the implantable medical device has been authenticated.

According to one embodiment, the external device is a wearable external device.

According to one embodiment, the external device is a handset.

An implantable medical device configured for communication with an external device according to one of the embodiments herein is further provided. The implantable medical device comprising at least one first wireless transceiver configured for communication with the external device using a first network protocol, for determining a distance between the external device and the implantable medical device, and at least one second wireless transceiver configured for communication with the external device using a second network protocol, for transferring data between the external device and the implantable medical device.

According to one embodiment, the first wireless transceiver comprises an UWB transceiver.

According to one embodiment, the first wireless transceiver is configured for transcutaneous energy transfer for at least one of: powering an energy consuming component of the implantable medical device, and charging an implantable energy storage unit.

According to one embodiment, the second network protocol is a standard network protocol.

According to one embodiment, the second wireless transceiver comprises a Bluetooth transceiver.

According to one embodiment, the implantable medical device is further configured to communicate with a second external device using said at least one wireless transceiver.

According to one embodiment, the implantable medical device is configured for determining a distance between the external device and the implantable medical device by determining the RSSI.

According to one embodiment, the standard network protocol is one of, or a combination of: Radio Frequency type protocol, RFID type protocol, WLAN type protocol,

US 12,598,458 B2

3

Bluetooth type protocol, BLE type protocol, NFC type protocol, 3G/4G/5G type protocol, and GSM type protocol.

The communication range of the first network protocol may be less than the communication range of the second network protocol.

The frequency band of the first network protocol may differ from a frequency band of the second network protocol.

According to one embodiment, the implantable medical device is configured to authenticate the external device if the determined distance between the external device and the implantable medical device is less than a predetermined threshold value.

According to one embodiment, the implantable medical device may be configured to allow the transfer of data between the implantable medical device and the external device after the external device has been authenticated.

An external device configured for communication with an implantable medical device according to any one of the embodiments disclosed herein is further provided. The external device comprising a wireless communication unit configured for wireless transmission of control commands to the implantable medical device and configured for wireless communication with a display device, and a computing unit configured for running a control software for creating the control commands for the operation of the implantable medical device. The computing unit may be configured to transmit a control interface to a display device configured to display the control interface to a user, receive user input from the display device, and transform the user input into the control commands for wireless transmission to the implantable medical device.

In one embodiment, the wireless communication unit comprises a wireless transceiver for wireless transmission of control commands to the implantable medical device, and wireless transmission of the control interface to the display device.

According to one embodiment, the wireless communication unit comprises a first wireless transceiver for wireless transmission of control commands to the implantable medical device, and a second wireless transceiver for wireless transmission of the control interface to the display device.

The wireless communication unit may in one embodiment be configured for wireless communication with the display device using a standard network protocol.

In one embodiment, the wireless communication unit is configured for wireless communication with the implantable medical device using a proprietary network protocol.

The wireless communication unit may comprise a Bluetooth transceiver, which may be comprised in one of the first and second wireless transceiver.

According to one embodiment, the wireless communication unit comprises a UWB transceiver, which may be comprised in one of the first and second wireless transceiver.

The wireless communication unit may comprise at least one first wireless transceiver configured for communication with the implantable medical device using a first network protocol, for determining a distance between the external device and the implantable medical device, and at least one second wireless transceiver configured for communication with the implantable medical device using a second network protocol, for transferring data between the external device and the implantable medical device.

According to one embodiment, the first wireless transceiver is configured for transcutaneous energy transfer for at least one of: powering an energy consuming component of the implantable medical device, and charging an implantable energy storage unit.

4

According to one embodiment, the standard network protocol is one of, or a combination of: Radio Frequency type protocol, RFID type protocol, WLAN type protocol, Bluetooth type protocol, BLE type protocol, NFC type protocol, 3G/4G/5G type protocol, and GSM type protocol.

The communication range of the first wireless transceiver may be less than a communication range of the second wireless transceiver The frequency band of the first network protocol may differ from a frequency band of the second network protocol.

According to one embodiment, the external device is configured to authenticate the implantable medical device if a distance between the external device and the implantable medical device is less than a predetermined threshold value.

According to one embodiment, the external device is configured to be authenticated by the implantable medical device if a distance between the external device and the implantable medical device is less than a predetermined threshold value.

According to one embodiment, the external device is configured to authenticate the display device if a distance between the external device and the display device is less than a predetermined threshold value.

According to one embodiment, the external device is configured to be authenticated by the implantable medical device if a distance between the external device and the display device is less than a predetermined threshold value.

The external device may be configured to allow the transfer of data between the external device and the implantable medical device, and/or the external device and the display device, on the basis of the authentication.

According to one embodiment, the computing unit is configured to encrypt at least one of the control interface and the control commands.

A display device for communication with an external device for communication with an implantable medical device is further provided. The display device comprises a wireless communication unit configured for wirelessly receiving an implant control interface from the external device and configured for wirelessly transmitting implant control user input to the external device. The display device further comprising a display for displaying the received implant control interface, and an input device for receiving implant control input from the user.

According to one embodiment, the display device further comprises an auxiliary wireless communication unit configured to be disabled to enable at least one of: wirelessly receiving the implant control interface from the external device, and wirelessly transmitting implant control user input to the external device.

According to one embodiment, the wireless communication unit is configured for wireless communication with the external device using a standard network protocol.

According to one embodiment, the wireless communication unit is configured for wireless communication with the external device using a proprietary network protocol.

According to one embodiment, the wireless communication unit comprises a Bluetooth transceiver.

According to one embodiment, the wireless communication unit comprises a UWB transceiver.

According to one embodiment, the standard network protocol is one of, or a combination of: Radio Frequency type protocol, RFID type protocol, WLAN type protocol, Bluetooth type protocol, BLE type protocol, NFC type protocol, 3G/4G/5G type protocol, and GSM type protocol.

The communication range of the wireless communication unit of the display device may be less than a communication range of the auxiliary wireless communication unit.

According to one embodiment, the display device is configured to authenticate the external device if a distance between the display device and the external device is less than a predetermined threshold value.

According to one embodiment, the display device is configured to be authenticated by the external device if a distance between the display device and the external device is less than a predetermined threshold value.

According to one embodiment, the display device is configured to allow the transfer of data between the display device and the external device on the basis of the authentication.

The display device may be a wearable external device or a handset.

A communication system for enabling communication between a display device and an implantable medical device is further provided. The communication system comprising a display device, a server, and an external device. The display device comprises a wireless communication unit configured for wirelessly receiving an implant control interface from the server, the implant control interface being provided by the external device, the wireless communication unit further being configured for wirelessly transmitting implant control user input to the server, destined for the external device, a display for displaying the received implant control interface, and an input device for receiving implant control input from the user. The server of the communication system comprises: a wireless communication unit configured for wirelessly receiving an implant control interface from the external device and wirelessly transmitting the implant control interface to the display device, the wireless communication unit further being configured for wirelessly receiving implant control user input from the display device and wirelessly transmitting the implant control user input to the external device. The external device of the communication system comprises a wireless communication unit configured for wireless transmission of control commands to the implantable medical device and configured for wireless communication with the server, and a computing unit configured for: running a control software for creating the control commands for the operation of the implantable medical device, transmit a control interface to the server, destined for the display device, receive implant control user input generated at the display device, from the server, and transform the user input into the control commands for wireless transmission to the implantable medical device.

According to one embodiment, the computing unit of the communication system is configured to encrypt at least one of the control interface and the control commands.

According to one embodiment, the display device is configured to encrypt the user input.

According to one embodiment, the server is configured to encrypt at least one of the user input received from the display device and the control interface received from the external device.

According to one embodiment, the computing unit is configured to encrypt the control interface and the display device is configured to decrypt the encrypted control interface.

According to one embodiment, the server is configured to act as a router, transferring the encrypted control interface from the external device to the display device without decryption.

A display device for communication with an external device for communication with an implantable medical device is further provided. The display device comprising a wireless communication unit, a display, and an input device for receiving implant control input from the user. The display device is configured to run a first application for wireless communication with a server, and to run a second application for wireless communication with the external device for transmission of the implant control input to the external device for the communication with the implantable medical device, wherein the second application is configured to be accessed through the first application. The display device may comprise a first log-in function and a second log-in function, and wherein the first log-in function gives the user access to the first application and wherein the first and second log-in function in combination gives the user access to the second application.

According to one embodiment, the first log-in is a PIN-based log-in.

According to one embodiment, at least one of the first and second log-in is a log-in based on a biometric input or a hardware key.

According to one embodiment, the display device further comprises an auxiliary wireless communication unit, and the auxiliary wireless communication unit is configured to be disabled to enable wireless communication with the external device.

According to one embodiment, the display device is configured to wirelessly receive an implant control interface from the external device to be displayed on the display.

According to one embodiment of the display device, the wireless communication unit is configured for wireless communication with the external device using a standard network protocol.

According to one embodiment of the display device, the wireless communication unit is configured for wireless communication with the external device using a proprietary network protocol.

According to one embodiment of the display device, the wireless communication unit is configured for wireless communication with the external device using a first network protocol and with the server using a second network protocol.

According to one embodiment of the display device, the wireless communication unit is configured for wireless communication with the external device using a first frequency band and with the server using a second frequency band.

According to one embodiment of the display device, the wireless communication unit comprises a Bluetooth transceiver.

According to one embodiment of the display device, the wireless communication unit comprises a UWB transceiver.

According to one embodiment, the standard network protocol is one of, or a combination of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the communication range of the wireless communication unit is less than a communication range of the auxiliary wireless communication unit.

According to one embodiment, the wireless communication unit comprises a first wireless transceiver for communication with the external device and a second wireless transceiver for communication with the server.

The second wireless transceiver may be configured to be disabled to enable wireless communication using the first wireless transceiver.

According to one embodiment, the display device is configured to authenticate the external device if a distance between the display device and the external device is less than a predetermined threshold value, and the display device is configured to be authenticated by the external device if a distance between the display device and the external device is less than a predetermined threshold value.

According to one embodiment, the display device is configured to allow the transfer of data between the display device and the external device on the basis of the authentication.

The display device may be a wearable external device or a handset.

According to one embodiment of the display device, the second application may be configured to receive data related to a parameter of the implanted medical device.

According to one embodiment, the second application is configured to receive data related to a sensor value received from the implanted medical device.

According to one embodiment, the second application is configured to receive data related to a parameter related to at least one of: a battery status, a temperature, a time, or an error.

According to one embodiment, the display device is configured to encrypt the user input.

According to one embodiment, the display is configured to encrypt the user input for decryption by the implantable medical device.

According to one embodiment, the display device is configured to decrypt the control interface received from the external device, for displaying the control interface on the display.

According to one embodiment, at least one of the first and second application is configured to receive data from an auxiliary external device and present the received data to the user.

At least one of the first and second application may be configured to receive data from an auxiliary external device comprising a scale for determining the weight of the user.

According to one embodiment, at least one of the first and second application may be configured to receive data related to the weight of the user from an auxiliary external device comprising a scale.

According to one embodiment, the display device is configured to: wirelessly transmit the data related to the weight of the user to the external device, or wirelessly transmit an instruction derived from the data related to the weight of the user, or wirelessly transmit an instruction derived from a combination of the data related to the weight of the user and the implant control input received from the user.

A communication system for enabling communication between a display device and an implantable medical device is further provided. The communication system comprises a display device, a server, and an external device. The display device comprises: a wireless communication unit configured for wirelessly receiving an implant control interface from the external device, the wireless communication unit further being configured for wirelessly transmitting implant control user input to the external device. The display device further comprises a display for displaying the received implant control interface, and an input device for receiving implant control input from the user, wherein the display device is configured to run a first application for wireless communication with the server, and to run a second application for wireless communication with the external device for transmission of the implant control input to the external device for the communication with the implantable medical device. The external device comprises a wireless communication unit configured for wireless transmission of control commands based on the implant control input to the implantable medical device and configured for wireless communication with the display device.

According to one embodiment, the display device comprises a first log-in function and a second log-in function, and wherein the first log-in function gives the user access to the first application and wherein the first and second log-in function in combination gives the user access to the second application.

The second application may be configured to receive data related to a parameter of the implanted medical device, and the second application may be configured to receive data related to a sensor value received from the implanted medical device.

According to one embodiment, the second application is configured to receive data related to a parameter related to at least one of: a battery status, a temperature, a time, or an error.

According to one embodiment, the display device is configured to encrypt the user input.

According to one embodiment, the display is configured to encrypt the user input for decryption by the implantable medical device.

According to one embodiment, the external device is configured to act as a router, transferring the encrypted user input from the display device to the implantable medical device without decryption.

According to one embodiment, the external device is configured to encrypt at least one of the control interface and the control commands.

According to one embodiment, the external device is configured to encrypt the control interface and wherein the display device is configured to decrypt the encrypted control interface.

A computer program product configured to run in a display device comprising a wireless communication unit, a display for displaying the received implant control interface, and an input device for receiving implant control input from a user is further provided. The computer program product comprising a first application for communication with a server, and a second application for communication with an external device for transmission of the implant control input to the external device for the communication with an implantable medical device, wherein the second application is configured to be accessed through the first application. The computer program product further comprises a first log-in function, and a second log-in function, wherein the first log-in function gives the user access to the first application and the first and second log-in function in combination gives the user access to the second application.

According to one embodiment of the computer program product, the second application is configured to receive data related to a parameter of the implanted medical device.

According to one embodiment of the computer program product, the second application is configured to receive data related to a sensor value received from the implanted medical device.

According to one embodiment of the computer program product, the second application is configured to receive data related to a parameter related to at least one of: a battery status, a temperature, a time, or an error.

A communication system for enabling communication between a display device, an external device, a server and an implantable medical device is further provided. The communication system comprising: a server, a display device, an external device, and an implantable medical device. The display device comprises: a wireless communication unit for wirelessly communicating with at least one of the external device and the server, a display, and an input device for receiving input from the user. The external device comprises: a wireless communication unit configured for wireless transmission of control commands to the implantable medical device and configured for wireless communication with at least one of the display device and the server. The server comprises: a wireless communication unit configured for wireless communication with at least one of the display device and the external device. The implantable medical device comprises: a wireless communication unit configured for wireless communication with the external device. The implantable medical device comprises an encryption unit which is configured to encrypt data destined for the server, transmit the data to the server via the external device, wherein the external device acts as a router transferring the data without full decryption, or the implantable medical device comprises an encryption unit and is configured to: encrypt data destined for the display device, transmit the data to the display device via the external device, wherein the external device acts as a router transferring the data without full decryption, or the server comprises an encryption unit and is configured to: encrypt data destined for the implantable medical device, transmit the data to the implantable medical device via the external device, wherein the external device acts as a router transferring the data without full decryption, or the server comprises an encryption unit and is configured to: encrypt data destined for the implantable medical device, transmit the data to the implantable medical device via the display device and the external device, wherein the display device and the external device acts as a router transferring the data without full decryption, or the display device comprises an encryption unit and is configured to: encrypt data destined for the implantable medical device, transmit the data to the implantable medical device via the external device, wherein the external device acts as a router transferring the data without full decryption, or the display device comprises an encryption unit and is configured to: encrypt data destined for the implantable medical device, transmit the data to the implantable medical device via the server and the external device, wherein the server and the external device acts as a router transferring the data without full decryption.

According to one embodiment, the display device is configured to wirelessly receive an implant control interface from the external device to be displayed on the display.

According to one embodiment of the communication system, at least two of: the wireless communication unit of the server, the wireless communication unit of the display device, the wireless communication unit of the external device, and the wireless communication unit of the implantable medical device—is configured for wireless communication using a standard network protocol.

According to one embodiment, the at least two of: the wireless communication unit of the server, the wireless communication unit of the display device, the wireless communication unit of the external device, and the wireless communication unit of the implantable medical device—is configured for wireless communication using a proprietary network protocol.

According to one embodiment, the wireless communication unit of the external device is configured to: use a first network protocol for communication with the implantable medical device and use a second network protocol for communication with the server, or use a first network protocol for communication with the implantable medical device and use a second network protocol for communication with the display device.

According to one embodiment, the wireless communication unit of the external device is configured to: use a first frequency band for communication with the implantable medical device and use a second frequency band for communication with the server, or use a first frequency band for communication with the implantable medical device and use a second frequency band for communication with the display device.

According to one embodiment, the wireless communication unit of the display device is configured to use a first network protocol for communication with the external device and use a second network protocol for communication with the server.

According to one embodiment, the wireless communication unit of the display device is configured to use a first frequency band for communication with the external device and use a second frequency band for communication with the server.

According to one embodiment, the wireless communication unit of the server is configured to use a first network protocol for communication with the external device and use a second network protocol for communication with the display device.

According to one embodiment, the wireless communication unit of the server is configured to use a first frequency band for communication with the external device and use a second frequency band for communication with the display device.

According to one embodiment, the wireless communication unit of at least one of the server, the display device, the external device, and the implantable medical device comprises a Bluetooth transceiver.

According to one embodiment, the wireless communication unit of at least one of the server, the display device, the external device, and the implantable medical device comprises a UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and a GSM type protocol.

According to one embodiment, the wireless communication unit of the external device comprises a first wireless transceiver for wireless communication with the implantable medical device, and a second wireless transceiver for wireless communication with the server, and wherein the second wireless transceiver has a longer effective range than the first wireless transceiver.

According to one embodiment, the wireless communication unit of the external device comprises a first wireless transceiver for wireless communication with the implantable medical device, and a second wireless transceiver for wireless communication with the display device, and wherein the second wireless transceiver has a longer effective range than the first wireless transceiver.

According to one embodiment, the wireless communication unit of the display device comprises a first wireless transceiver for wireless communication with the external device, and a second wireless transceiver for wireless communication with the server, and wherein the second wireless transceiver has a longer effective range than the first wireless transceiver.

According to one embodiment, the second wireless transceiver has an effective range being one of: 2 times, 4 times, 8 times 20 times, 50 times or 100 times longer than the first wireless transceiver.

According to one embodiment, the second wireless transceiver is configured to be disabled to enable wireless communication using the first wireless transceiver.

According to one embodiment, of the communication system, at least one of:

the display device is configured to authenticate the external device if a distance between the display device and the external device is less than a predetermined threshold value, the display device is configured to be authenticated by the external device if a distance between the display device and the external device is less than a predetermined threshold value, the display device is configured to authenticate the implantable medical device if a distance between the display device and the implantable medical device is less than a predetermined threshold value, the display device is configured to be authenticated by the implantable medical device if a distance between the display device and the implantable medical device is less than a predetermined threshold value, the external device is configured to authenticate the display device if a distance between the external device and the display device is less than a predetermined threshold value, the external device is configured to be authenticated by the display device if a distance between the external device and the display device is less than a predetermined threshold value, the external device is configured to authenticate the implantable medical device if a distance between the external device and the implantable medical device is less than a predetermined threshold value, and the external device is configured to be authenticated by the implantable medical device if a distance between the external device and the implantable medical device is less than a predetermined threshold value.

According to one embodiment of the communication system, the display device may be configured to allow the transfer of data between the display device and the external device on the basis of the authentication.

According to one embodiment of the communication system, the external device is configured to allow the transfer of data between the display device and the external device on the basis of the authentication.

According to one embodiment of the communication system, the external device is configured to allow the transfer of data between the external device and the implantable medical device on the basis of the authentication.

According to one embodiment of the communication system, the display device is a wearable external device or a handset.

According to one embodiment of the communication system, the data encrypted by the implantable medical device is related to at least one of: a battery status, a temperature, a time, or an error.

A server for use in the communication system according to any one of the embodiments above is further provided.

A display device for use in the communication system according to any one of the embodiments above is further provided.

An external device for use in the communication system according to any one of the embodiments above is further provided.

An implantable medical device for use in the communication system according to any one of the embodiments above is further provided.

Any embodiment, part of embodiment, method, or part of method may be combined in any applicable way.

According to one embodiment, the body engaging portion is a constriction device configured to constrict a luminary organ of a patient, and the body engaging portion may comprise an implantable constriction device.

According to one embodiment, the implantable constriction device comprises an implantable constriction device for constricting a luminary organ of the patient. The luminary organ could be an intestine of the patient, such as a colon or rectum of the patient or a region of a stoma of the patient.

According to one embodiment, the luminary organ could be a blood vessel of the patient. The implantable constriction device may be a device for constricting the venous blood flow leading from an erectile tissue for promoting the engorgement of the erectile tissue, or may be a device configured to constrict a portion of a blood vessel having an aneurysm.

According to one embodiment, the luminary organ could be the vas deference of the patient.

According to one embodiment, the body engaging portion could comprise an implantable element for actively emptying the urinary bladder of the patient, and the implantable element for actively emptying the urinary bladder of the patient could be configured to empty the bladder of the patient by compressing the urinary bladder from the outside thereof.

The implantable medical device/implant described and disclosed herein could comprises at least one of the following implantable components and/or functions:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 244SE Implantable Reset Switch—Implant Comprising a Reset Function—Embodiments of the Aspect 244SE of the Disclosure In a first part of aspect 244SE, an implant is provided. The implant comprises an internal computing unit configured to control a function of said implant. The internal computing unit comprises an internal memory configured to store: a first control program for controlling said function, and a second, updatable, control program for controlling said function of said implant. The implant comprises an internal communication unit comprising said internal computing unit and configured to communicate with an external device. The internal computing unit is configured to receive updates to the second control program via said internal communication unit. The implant further comprises a reset function of, connected to, or transmitted to said internal computing unit, said reset function being configured to make said internal computing unit switch from running said second control program to running said first control program.

According to some embodiments of the first part of the aspect 244SE, the reset function is configured to make said internal computing unit delete said second control program from said internal memory.

According to some embodiments of the first part of the aspect 244SE, the internal communication unit comprises an internal wireless transceiver for communicating wirelessly with said external device.

According to some embodiments of the first part of the aspect 244SE, the internal communication unit is configured to be in electrical connection with said external device and communicate with said external device using a body of a patient, in which the implant is implanted, as a conductor.

According to some embodiments of the first part of the aspect 244SE, the reset function is configured to be operated by palpating a skin of a patient in which the implant is implanted.

According to some embodiments of the first part of the aspect 244SE, the reset function is configured to be operated by penetration of a skin of a patient in which the implant is implanted.

According to some embodiments of the first part of the aspect 244SE, the reset function is configured to be operated by magnetic force from outside a body of a patient in which the implant is implanted.

According to some embodiments of the first part of the aspect 244SE, the reset function is configured to be operated by said magnetic force being applied for a duration of time exceeding 2 seconds.

According to some embodiments of the first part of the aspect 244SE, the reset function is configured to be operated by said magnetic force being applied for a duration of time exceeding 5 seconds.

According to some embodiments of the first part of the aspect 244SE, the reset function is configured to be operated by said magnetic force being applied for a duration of time exceeding 10 seconds.

According to some embodiments of the first part of the aspect 244SE, the implant further comprising a feedback unit configured to provide feedback related to said internal computing unit switching from running said second control program to running said first control program.

According to some embodiments of the first part of the aspect 244SE, the feedback unit is configured to provide visual feedback.

According to some embodiments of the first part of the aspect 244SE, the feedback unit is configured to provide audible feedback.

According to some embodiments of the first part of the aspect 244SE, the feedback unit is configured to provide tactile feedback.

According to some embodiments of the first part of the aspect 244SE, the feedback unit is configured to provide feedback in the form of a wireless signal.

According to some embodiments of the first part of the aspect 244SE, the internal memory is configured to store a third control program for controlling said function of said implant, wherein said internal computing unit is configured to update the second control program to the third control program.

According to some embodiments of the first part of the aspect 244SE, the implant has a first power supply for running the first control program, and a second power supply, different from the first power supply, for running the second control program.

According to some embodiments of the first part of the aspect 244SE, the first power supply comprises a first internal energy storage, and wherein the second power supply comprises a second internal energy storage.

According to some embodiments of the first part of the aspect 244SE, the first power supply comprises a first energy receiver, and wherein the second power supply comprises a second energy receiver.

According to some embodiments of the first part of the aspect 244SE, the first energy receiver is configured to receive energy via a RFID pulse.

According to some embodiments of the first part of the aspect 244SE, the implant further comprising a feedback unit, configured to provide feedback related to said internal computing unit switching from running said second control program to running said first control program, wherein said feedback pertains to an amount of energy received via the RFID pulse.

In a second part of the aspect 244SE, a method for switching between a first and a second control program for controlling a function of an implant is provided.

The implant comprising: an internal computing unit configured to control a function of said implant, said internal computing unit comprises an internal memory configured to store: a first control program for controlling said function, and a second, updatable, control program for controlling said function of said implant.

The implant further comprising an internal communication unit comprising said internal computing unit and configured to communicate with an external device, wherein said internal computing unit is configured to receive updates to the second control program via said internal communication unit, and a reset function of, or connected to said internal computing unit, said reset function being configured to make said internal computing unit switch from running said second control program to running said first control program.

The method comprising the steps of activating said reset function, and instructing, by the reset function, said internal computing unit to switch from running said second control program to running said first control program.

According to some embodiments of the second part of the aspect 244SE, the method further comprising the step of: deleting, by the internal computing unit, said second control program from said internal memory.

According to some embodiments of the second part of the aspect 244SE, the internal memory is configured to store a third control program for controlling said function of said implant, wherein said internal computing unit is configured to update the second control program to the third control program, the method further comprising the steps of: updating the second control program to the third control program.

According to some embodiments of the second part of the aspect 244SE, the method further comprising the step of switching, by the internal computing unit, from running said first control program to running said first second program after updating the second control program.

According to some embodiments of the second part of the aspect 244SE, the internal communication unit is configured to be in electrical connection with said external device, and communicate with said external device using a body of a patient in which the implant is implanted as a conductor, the method further comprising the steps of: communicating, from said external device, to the internal communication unit, an update of the second control program, switching, by the internal computing unit, from running said first control program to running said first second program after updating the second control program.

According to some embodiments of the second part of the aspect 244SE, the step of activating said reset function comprises: palpating a skin of a patient in which the implant is implanted.

According to some embodiments of the second part of the aspect 244SE, wherein the step of activating said reset function comprises penetration of a skin of a patient in which the implant is implanted.

According to some embodiments of the second part of the aspect 244SE, the step of activating said reset function comprises applying a magnetic force from outside a body of a patient in which the implant is implanted.

According to some embodiments of the second part of the aspect 244SE, the method further comprising the step of providing feedback, by a feedback unit of the implant, said feedback related to said internal computing unit switching from running said second control program to running said first control program.

According to some embodiments of the second part of the aspect 244SE, the implant has a first power supply for running the first control program, and a second power supply, different from the first power supply, for running the second control program, wherein the first power supply comprises a first energy receiver, and wherein the second power supply comprises a second energy receiver, the method further comprising the steps of: providing, by an energy transmitter of the external device, energy to the first energy receiver.

According to some embodiments of the second part of the aspect 244SE, the step of providing, by the energy transmitter of the external device, energy to the first energy receiver comprises providing energy using a RFID pulse.

According to some embodiments of the second part of the aspect 244SE, the implant has a feedback unit, configured to provide feedback related to said internal computing unit, the method further comprising: providing, by the feedback unit, feedback to the said energy transmitter, wherein said feedback pertains to an amount of energy received via the RFID pulse, and adjusting, by the energy transmitter, a parameter of a subsequent RFID pulse based on the feedback.

According to some embodiments of the second part of the aspect 244SE, the parameter of the subsequent RFID pulse comprises at least one an energy level, a pulse frequency, and a pulse amplitude.

The above method according to the aspect 244SE may be implemented in software, which may be a computer program product comprising a computer-readable storage medium with instructions adapted to carry out the method when executed by a device having processing capability. The device having processing capacity being a computing unit in an external device or in the implant.

According to some embodiments of the first part of the aspect 244SE the reset function is a reset switch.

According to some embodiments of the second part of the aspect 244SE the reset function is a reset switch.

According to some embodiments of the first part of the aspect 244SE the internal computing unit is further configured for receiving, from said external device, an update of the second control program, updating the second control program.

switching, by the internal computing unit, from running said first control program to running said second program after updating the second control program.

According to some embodiments of the first part of the aspect 244SE the reset function is triggered by an update of the first or second control program.

According to some embodiments of the first part of the aspect 244SE the reset function is triggered by a malfunction of the first or second control program.

According to some embodiments of the first part of the aspect 244SE the reset function is triggered by a malfunction of an active device of the implant.

According to some embodiments of the first part of the aspect 244SE said reset function is configured to be operated by NFC.

According to some embodiments of the first part of the aspect 244SE the reset function is configured to trigger implant diagnostics to be transmitted from the implant to the external device.

According to some embodiments of the first part of the aspect 244SE said reset function is configured to be operated by said magnetic force being applied at least two times.

According to some embodiments of the first part of the aspect 244SE the first energy receiver is configured to receive energy conductively or inductively.

According to some embodiments of the first part of the aspect 244SE the reset function is configured to be triggered if the first energy receiver is receiving energy.

According to some embodiments of the first part of the aspect 244SE the first control program is configured to be running, powered by conductively or inductively received energy.

According to some embodiments of the first part of the aspect 244SE said amount of energy received via the RFID pulse is encoded in a variable pulse feedback signal provided by the feedback unit.

According to some embodiments of the first part of the aspect 244SE the implant comprises at least one of:

a pacemaker unit or implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant an implant for adjusting or replacing any bone part of a body of the patient, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an active electrically controlled implant devoid of an electrical heart stimulation system, an active electrically controlled non-heart stimulation implant.

an implant adapted for electrical stimulation of muscles, a non-nerve stimulation system, an active non-stimulation implant, an implant for high current electrical stimulation defined as current above 1 mA or current above 5 mA, 10 mA, or 20 mA, an implant replacing an organ of the patient or part of an organ of the patient or the function thereof, a vascular treatment device, and an implant adapted to move fluid inside the body of the patient.

According to some embodiments of the first part of the aspect 244SE the implant comprises an internal control unit adapted to be involved in at least a part of the actions performed by the implant in at least a part of any one of the other embodiments of the aspect 244SE.

Aspect 245SE 2-Part Key—Encrypted Communication Between Implant and External Device—Embodiments of the Second Aspect of the Disclosure In a first part of aspect 245SE, a method of communication between an external device and an implant is provided. The method is performed when the implant is implanted in a patient and the external device positioned external to the body of the patient. The external device is adapted to be in electrical connection with the implant, using the body as a conductor. The implant and the external device each comprise a wireless transceiver. The method comprising, confirming the electrical connection between the implant and the external device, transmitting data from the external device to the implant wirelessly or through the electrical connection, and, as a result of the confirmation, using the received data for instructing the implant.

According to some embodiments of the first part of aspect 245SE, the step of transmitting data from the external device to the implant wirelessly comprises transmitting encrypted data wirelessly.

According to some embodiments of the first part of aspect 245SE, the method further comprising: transmitting a key from the external device to the implant using the electrical connection, receiving the key at the implant, and using the key for decrypting the encrypted data.

According to some embodiments of the first part of aspect 245SE, the method further comprising: transmitting a second key from the external device to the implant wirelessly, receiving the second key at the implant, deriving a combined key from the key and second key, and decrypting the encrypted data using the combined key.

According to some embodiments of the first part of aspect 245SE, the method further comprising: transmitting a third key from a second external device, separate from the external device, to the implant wirelessly, receiving the third key at the implant, deriving a combined key from the key and the third key, and decrypting the encrypted data using the combined key.

According to some embodiments of the first part of aspect 245SE, the method further comprising: transmitting a third key from a second external device, separate from the external device, to the implant wirelessly, receiving the third key at the implant, deriving a combined key from the key, the second key and the third key, and decrypting the encrypted data using the combined key.

According to some embodiments of the first part of aspect 245SE, the external device is a wearable external device.

According to some embodiments of the first part of aspect 245SE, the external device is a handset.

According to some embodiments of the first part of aspect 245SE, the second external device is a handset.

According to some embodiments of the first part of aspect 245SE, the second external device is a server.

According to some embodiments of the first part of aspect 245SE, the second external device is cloud based.

According to some embodiments of the first part of aspect 245SE, the step of transmitting a third key from a second external device, separate from the external device, to the implant wirelessly, comprises routing the third key through the external device.

According to some embodiments of the first part of aspect 245SE, the step of transmitting data comprises transmitting data comprising operation instructions to the implant.

According to some embodiments of the first part of aspect 245SE, the method further comprises using the received data to perform at least one of the steps of: updating a control program running in the implant, and operating the implant using the operation instructions.

According to some embodiments of the first part of aspect 245SE, the method further comprises placing a conductive member, configured to be in connection with the external device, in electrical connection with a skin of the patient for conductive communication with the implant.

According to some embodiments of the first part of aspect 245SE the step of transmitting data from the external device to the implant comprises: performing data transmission through the electrical connection involving at least one of transmitting: encrypted data, pulses, positive or negative transients, different frequencies, and using a capacitive coupling.

In a second part of aspect 245SE, an implant adapted for communication with an external device when implanted in a patient is provided. The implant comprises: a first internal transceiver configured to be in electrical connection with the external device, using the body as a conductor, a wireless receiver configured to receive wireless communication from the external device to receive data from the external device. The implant further comprises a computing unit configured to: confirm the electrical connection between the external device and the first internal transceiver and accept wireless communication from the external device on the basis of the confirmation.

According to some embodiments of the second part of aspect 245SE, the wireless receiver is configured to receive wireless communication comprising encrypted data, and wherein the computing unit is further configured to decrypt the encrypted data received wirelessly from the external device.

According to some embodiments of the second part of aspect 245SE, the first internal transceiver is further configured to receive a key from the external device, and wherein the computing unit is further configured to use the key for decrypting the encrypted data.

According to some embodiments of the second part of aspect 245SE, the wireless transceiver is further configured to receive a second key from the external device, and wherein the computing unit is further configured to derive a combined key from the key and the second key and use the derived combined key for decrypting the encrypted data.

According to some embodiments of the second part of aspect 245SE, the wireless transceiver is further configured to receive a third key from a second external device, and wherein the computing unit is further configured to derive a combined key from the key and the third key and use the derived combined key for decrypting the encrypted data.

According to some embodiments of the second part of aspect 245SE, the implant comprises a second wireless receiver for receiving wireless communication from a second external device.

According to some embodiments of the second part of aspect 245SE, the computing unit is further configured to use the received data to perform at least one of: update a control program running in the implant, and operate the implant using the operation instructions.

According to some embodiments of the second part of aspect 245SE the implant comprises at least one of:
  a pacemaker unit or implantable cardioverter defibrillators,
  an external heart compression device,
  an apparatus assisting the pump function of a heart of the patient,
  an operable artificial heart valve,
  an implantable drug delivery device,
  a hydraulic, mechanic, and/or electric constriction implant,
  an operable volume filling device,
  an operable gastric band,
  an operable implant for stretching the stomach wall of the patient,
  an operable cosmetic implant,
  an implant for adjusting or replacing any bone part of a body of the patient, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an active electrically controlled implant devoid of an electrical heart stimulation system, an active electrically controlled non-heart stimulation implant, an implant adapted for electrical stimulation of muscles, a non-nerve stimulation system, an active non-stimulation implant, an implant for high current electrical stimulation defined as current above 1 mA or current above 5 mA, 10 mA, or 20 mA, an implant replacing an organ of the patient or part of an organ of the patient or the function thereof, a vascular treatment device, and an implant adapted to move fluid inside the body of the patient.

According to some embodiments of the second part of aspect 245SE the implant comprises an internal control unit adapted to be involved in at least a part of the actions performed by the implant in at least a part of any one of the above embodiments of aspect 245SE.

In a third part of aspect 245SE, an external device adapted for communication with an implant when implanted in a patient is provided. The external device comprises: a first external transmitter configured to be in electrical connection with the implant, using the body as a conductor, and a wireless transmitter configured to transmit wireless communication to the implant.

According to some embodiments of the third part of aspect 245SE, the wireless transmitter is configured to transmit wireless communication comprising encrypted data.

According to some embodiments of the third part of aspect 245SE, the first external transmitter is further configured to transmit a key to the implant, the key being a key for decrypting the encrypted data.

According to some embodiments of the third part of aspect 245SE, the wireless transmitter is further configured to transmit a second key to the implant, the second key being configured to be used in combination with the key for decrypting the encrypted data.

According to some embodiments of the third part of aspect 245SE, the external device is further configured to receive secondary wireless communication from a second external device and transmit the secondary wireless communication to the implant.

According to some embodiments of the third part of aspect 245SE, the external device is a wearable external device.

According to some embodiments of the third part of aspect 245SE, the external device is a handset.

In a fourth part of aspect 245SE, there is provided a system comprising the implant and the external device of aspect 245SE.

According to some embodiments of the fourth part of aspect 245SE, wherein the implant is implanted in a patient, the system further comprising a conductive member configured to be in electrical connection with the external device, wherein the conductive member is configured to be placed in electrical connection with a skin of the patient for conductive communication with the implant.

In a fifth part of aspect 245SE, there is provided computer program product of, or adapted to be run on, an external device adapted for communication with an implant when implanted in a patient, the external device comprising:

a first external transmitter configured to be in electrical connection with the implant, using the body as a conductor.

wherein the computer program product is configured to cause a wireless transmitter to transmit wireless communication comprising encrypted data to the implant.

According to some embodiments of the fifth part of aspect 245SE the computer program product is configured to cause the wireless transmitter is to transmit wireless communication comprising encrypted data.

According to some embodiments of the fifth part of aspect 245SE the computer program product is configured to cause the first external transmitter to transmit a key to the implant, the key being a key for decrypting the encrypted data.

According to some embodiments of the fifth part of aspect 245SE the computer program product is configured to cause the wireless transmitter to transmit a second key to the implant, the second key being configured to be used in combination with the key for decrypting the encrypted data.

According to some embodiments of the fifth part of aspect 245SE the computer program product is configured to cause the external to receive secondary wireless communication from a second external device, and transmit data received in the secondary wireless communication to the implant.

In a fifth part of aspect 245SE, there is provided computer program product of, or adapted to be run on an implant, when implanted in a patient, adapted for communication with an external device, the implant comprising:

a first external transmitter configured to be in electrical connection with the implant, using the body as a conductor.

wherein the computer program product is configured to cause a wireless transmitter to transmit wireless communication to the external device.

Aspect 246SE 3-Part Key—Multi-Party Encrypted Communication Between Implant and External Device—Embodiments of Aspect 246SE of the Disclosure In first part of aspect 246SE, a method of communication between an external device and an implant is provided. In this method, the implant is implanted in a patient and the external device positioned external to the body of the patient, wherein the implant and the external device each comprise a wireless transceiver. The method comprising:

receiving, at the implant, a first key from an external device, receiving, at the implant, by a wireless transmission, a second key, the second key being generated by a second external device, separate from the external device or by a another external device being a generator of the second key on behalf of the second external device, the second key being received at the implant from anyone of, the external device, the second external device, and the generator of the second key, deriving a combined key by combining the first key and the second key with a third key held by the implant, transmitting, by a wireless transmission, encrypted data from the external device to the implant, and decrypting the encrypted data, in the implant, using the combined key.

According to some embodiments of the first part of aspect 246SE, the external device is adapted to be in electrical connection with the implant, using the body as a conductor, wherein the implant is receiving the first key using the electrical connection.

receiving, at the implant, a fourth key from a third external device, the third external device being separate from the external device, deriving a combined key by combining the first, second and fourth key with the third key held by the implant, and decrypting the encrypted data, in the implant, using the combined key.

According to some embodiments of the first part of aspect 246SE, the encrypted data originates from the second or third external device.

According to some embodiments of aspect 246SE, the method further comprises altering an operation of the implant comprises controlling or switching an active unit of the implant.

According to some embodiments of the first part of aspect 246SE, the method further comprises confirming the electrical connection between the implant and the external device, and as a result of the confirmation, altering an operation of the implant based on the decrypted data.

According to some embodiments of the first part of aspect 246SE, the confirmation of the electrical connection comprises:

measuring a parameter of the patient, by the implant, measuring the parameter of the patient, by the external device, comparing the parameter measured by the implant to the parameter measured by the external device, and authenticating the connection based on the comparison.

According to some embodiments of the first part of aspect 246SE, the method further comprises the steps of:

measuring a parameter of the patient, by the implant, measuring the parameter of the patient, by the external device, comparing the parameter measured by the implant to the parameter measured by the external device, authenticating the connection between the implant and the external device based on the comparison, as a result of the confirmation, altering an operation of the implant based on the decrypted data.

According to some embodiments of the first part of aspect 246SE, the external device is a wearable external device.

According to some embodiments of the first part of aspect 246SE, the external device is a handset.

According to some embodiments of the first part of aspect 246SE, the second and/or third external device is a handset.

According to some embodiments of the first part of aspect 246SE, the second and/or third external device is a server.

According to some embodiments of the first part of aspect 246SE, the second and/or third external device is cloud based.

According to some embodiments of the first part of aspect 246SE, the first key is routed through the external device from the second external device.

According to some embodiments of the first part of aspect 246SE, the fourth key is routed through the external device from the third external device.

According to some embodiments of the first part of aspect 246SE, the method further comprises at least one of the steps of:

based on the decrypted data, updating a control program running in the implant, and operating the implant using operation instructions in the decrypted data.

According to some embodiments of aspect 246SE, one or more of the first, second and third key comprises a biometric key.

In a second part of aspect 246SE, there is provided a method for encrypted communication between an external device and an implant, the method comprising:

receiving, at the external device, a first key, the first key being generated by a second external device, separate from the external device or by another external device being a generator of the second key on behalf of the second external device, the first key being received from anyone of the second external device and the generator of the second key, receiving, at the external device, a second key from the implant, deriving a combined key by combining the first key and the second key with a third key held by the external device, transmitting encrypted data from the implant to the external device, and decrypting the encrypted data, in the external device, using the combined key.

According to some embodiments of the second part of aspect 246SE, the method further comprises:

receiving, at the external device, a fourth key from a third external device, the third external device being separate from the external device, deriving a combined key by combining the first, second and fourth key with the third key held by the external device, and decrypting the encrypted data, in the external device, using the combined key.

According to some embodiments of the second part of aspect 246SE, the external device is a wearable external device.

According to some embodiments of the second part of aspect 246SE, the external device is a handset.

According to some embodiments of the second part of aspect 246SE, the second and/or third external device is a handset.

According to some embodiments of the second part of aspect 246SE, the second and/or third external device is a server.

According to some embodiments of the second part of aspect 246SE, the second and/or third external device is cloud based.

According to some embodiments of the second part of aspect 246SE, one or more of the first, second and third key comprises a biometric key.

According to some embodiments of the second part of aspect 246SE, the method further comprising authentication of the communication between the implant and the external device comprising the steps of:

measuring a parameter of the patient, by the implant, measuring the parameter of the patient, by the external device, comparing the parameter measured by the implant to the parameter measured by the external device, and authenticating the connection between the implant and the external device based on the comparison, as a result of authentication, decrypting the encrypted data, in the external device, using the combined key.

According to some embodiments of the first or second part of aspect 246SE, the method further comprises placing a conductive member, configured to be in connection with the external device, in electrical connection with a skin of the patient for conductive communication with the implant.

In a third part of aspect 246SE, there is provided an implant adapted for communication with an external device, when the implant is implanted in a patient, the implant comprising: a wireless transceiver configured to receive wireless communication, and configured for:

receiving a first key from the external device, receiving a second key, the second key being generated by a second external device, separate from the external device or by a another external device being a generator of the second key on behalf of the second external device, the second key being received at the implant from anyone of, the external device, the second external device, and the generator of the second key, from the external device, receiving encrypted data, The implant further comprising a computing unit configured for:

deriving a combined key by combining the first and second keys with a third key held by the implant, decrypting the encrypted data using the combined key.

According to some embodiments of the third part of aspect 246SE, the wireless transceiver is configured for:

receiving a fourth key from a third external device, wherein the computing unit is configured for:

deriving a combined key by combining the first, second and fourth key with the third key held by the implant, and decrypting the encrypted data using the combined key.

According to some embodiments of the third part of aspect 246SE, the computing unit is configured for altering an operation of the implant based on the decrypted data.

According to some embodiments of the third part of aspect 246SE, the computing unit is configured for controlling or switching an active unit of the implant.

According to some embodiments of the third part of aspect 246SE, the computing unit is configured for: confirming a connection between the implant and the external device, and as a result of the confirmation, altering an operation of the implant based on the decrypted data.

According to some embodiments of the third part of aspect 246SE, the confirmation of the electrical connection comprises:

measuring a parameter of the patient, by the implant, receiving a measured parameter of the patient, from the external device, comparing the parameter measured by the implant to the parameter measured by the external device, and performing confirmation of the connection based on the comparison.

According to some embodiments of the third part of aspect 246SE, the computing unit is configured for at least one of: based on the decrypted data, updating a control program running in the implant, and operating the implant using operation instructions in the decrypted data.

According to some embodiments of the third part of aspect 246SE, the third key comprises a biometric key.

In a fourth part of aspect 246SE, there is provided an external device adapted for communication with an implant, when the implant is implanted in a patient, the external device comprising a wireless transceiver configured to receive wireless communication, and configured for:

receiving a first key, the first key being generated by a second external device, separate from the external device or by another external device being a generator of the second key on behalf of the second external device, the first key being received from anyone of the second external device and the generator of the second key, receiving a second key from the implant, receiving encrypted data from the implant, The external device further comprises a computing unit configured for:

deriving a combined key by combining the first and second keys with a third key held by the external device, decrypting the encrypted data using the combined key.

According to some embodiments of the fourth part of aspect 246SE, the wireless transceiver is configured for:

receiving a fourth key from a third external device, wherein the computing unit is configured for:

deriving a combined key by combining the first, second and fourth key with the third key held by the external device, and decrypting the encrypted data using the combined key.

According to some embodiments of the fourth part of aspect 246SE, the external device is a wearable external device.

According to some embodiments of the fourth part of aspect 246SE, the external device is a handset.

According to some embodiments of the fourth part of aspect 246SE, the computing unit is configured to confirm the communication between the implant and the external device, wherein the confirmation comprises:

measuring a parameter of the patient, by the external device, receiving a measured parameter of the patient, from the implant, comparing the parameter measured by the implant to the parameter measured by the external device, performing confirmation of the connection based on the comparison, and as a result of the confirmation, decrypting the encrypted data, in the external device, using the combined key.

According to some embodiments of the fourth part of aspect 246SE, the third key comprises a biometric key.

In a fifth part of aspect 246SE, there is provided a system comprising an implant according to the third part of aspect 246SE and an external device according to the fourth part of aspect 246SE, wherein the implant is implanted in a patient, the system further comprising a conductive member configured to be in electrical connection with the external device, wherein the conductive member is configured to be placed in electrical connection with a skin of the patient for conductive communication with the implant.

In a sixth part of aspect 246SE, there is provided a computer program product comprising a computer-readable storage medium with instructions adapted to carry out the method the first or second part of aspect 246SE, and/or with instructions adapted to carry out anyone of the implant actions from of aspect 246SE, when executed by an external device having processing capability.

According to some embodiments of the first part of aspect 246SE the first key is received at the implant from the external device, by a wireless transmission.

According to some embodiments of the first part of aspect 246SE the first key is transmitted by the external device.

According to some embodiments of the third part of aspect 246SE the encrypted data is received from the external device or the second external device or another external device via the internet.

According to some embodiments of the third part of aspect 246SE the third external device is a server comprising a database, the database comprising data pertaining to control program updates and/or instructions.

According to some embodiments of the third part of aspect 246SE the database may communicate with a caregiver and/or the implant According to some embodiments of the third part of aspect 246SE the database may communicate with a caregiver and/or the implant via the external device.

According to some embodiments of the third part of aspect 246SE the implant comprises at least one of:

a pacemaker unit or implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant for adjusting or replacing any bone part of a body of the patient, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an active electrically controlled implant devoid of an electrical heart stimulation system, an active electrically controlled non-heart stimulation implant, an implant adapted for electrical stimulation of muscles, a non-nerve stimulation system, an active non-stimulation implant, an implant for high current electrical stimulation defined as current above 1 mA or current above 5 mA, 10 mA, or 20 mA, an implant replacing an organ of the patient or part of an organ of the patient or the function thereof, a vascular treatment device, and an implant adapted to move fluid inside the body of the patient.

In a seventh part of aspect 246SE, there is provided a computer program product of, or adapted to be run on, an external device adapted for communication with an implant, when the implant is implanted in a patient, the external device comprising:

a. a wireless transceiver configured to receive wireless communication, wherein the computer program product is configured to cause the wireless transceiver to:

i. receive a first key, the first key being generated by a second external device, separate from the external device or by another external device being a generator of the second key on behalf of the second external device, the first key being received from anyone of the second external device and the generator of the second key, ii. receive a second key from the implant, iii. receive encrypted data from the implant, b. a computing unit, wherein the computer program product is configured cause the computing unit to:

i. derive a combined key by combining the first and second keys with a third key held by the external device, ii. decrypt the encrypted data using the combined key.

According to some embodiments of the seventh part of aspect 246SE the computer program product is configured to cause the wireless transceiver to:

a. receive a fourth key from a third external device, wherein the computing unit is configured to:

b. derive a combined key by combining the first, second and fourth key with the third key held by the external device, and c. decrypt the encrypted data using the combined key.

According to some embodiments of the seventh part of aspect 246SE the computer program product is configured to cause the computing unit to confirm the communication between the implant and the external device, wherein the confirmation comprises:

a. measuring a parameter of the patient, by the external device, b. receiving a measured parameter of the patient, from the implant, c. comparing the parameter measured by the implant to the parameter measured by the external device, d. performing confirmation of the connection based on the comparison, and e. as a result of the confirmation, decrypting the encrypted data, in the external device, using the combined key.

According to some embodiments of the seventh part of aspect 246SE the third key comprises a biometric key.

In an eighth part of aspect 246SE, there is provided a computer program product adapted to be run on, an implant adapted for communication with an external device, when the implant is implanted in a patient, the implant comprising:

a. a wireless transceiver configured to receive wireless communication, wherein the computer program product is configured to cause the wireless transceiver to:
  i. receive a first key, the first key being generated by a second external device, separate from the external device or by another external device being a generator of the second key on behalf of the second external device, the first key being received from anyone of the second external device and the generator of the second key,
  ii. receive a second key from the external device,
  iii. receive encrypted data from the external device,
 b. a computing unit, wherein the software is configured to cause the computing unit to:
  i. derive a combined key by combining the first and second keys with a third key held by the implant,
  ii. decrypt the encrypted data using the combined key.

According to some embodiments of the eighth part of aspect 246SE the computer program product is configured to cause the wireless transceiver to:

a. receive a fourth key from a third external device, wherein the computing unit is configured to:
 b. derive a combined key by combining the first, second and fourth key with the third key held by the external device, and
 c. decrypt the encrypted data using the combined key.

According to some embodiments of the eighth part of aspect 246SE the computer program product is configured to cause the computing unit to confirm the communication between the implant and the external device, wherein the confirmation comprises:

a. measuring a parameter of the patient, by the external device,
 b. receiving a measured parameter of the patient, from the implant,
 c. comparing the parameter measured by the implant to the parameter measured by the external device,
 d. performing confirmation of the connection based on the comparison, and
 e. as a result of the confirmation, decrypting the encrypted data, in the external device, using the combined key.

According to some embodiments of the eighth part of aspect 246SE the third key comprises a biometric key.

In a ninth part of aspect 246SE, there is provided a computer program product comprising a computer-readable storage medium with instructions adapted to carry out the method of the aspect 244SE and/or with instructions adapted to carry out anyone of the implant actions of aspect 245SE, when executed by an implant having processing capability.

According to some embodiments of the second part of aspect 246SE, and/or with ability to use any of the methods of the first part of aspect 246SE, and/or with ability to communicate with an external device of the third part of aspect 246SE, and or with ability to use anyone of the computer program product of the sixth, eighth, or ninth parts of aspect 246SE.

In a tenth part of aspect 246SE, there is provided a method for communication between an external device and an implant, when the implant is implanted in a patient and the external device positioned external to the body of the patient, wherein the implant and the external device each comprise a wireless transceiver, the method comprising:

receiving, at the implant, a first key from an external device,
 deriving a combined key by combining the first key and a key held by the implant.
 transmitting, by a wireless or electrical transmission, encrypted data from the external device to the implant, and
 decrypting the encrypted data, in the implant, using the combined key.

Aspect 247SE Electrical Connection—Conductive Member in Electrical Connection with the External Device—Embodiments of Aspect 247SE of the Disclosure In a first part of aspect 247SE, a system for communication between an external device and an implant implanted in a patient is provided. The system comprises a conductive member configured to be in connection with the external device, the conductive member being configured to be placed in electrical connection with a skin of the patient for electrical or conductive communication with the implant.

According to some embodiments of the first part of aspect 247SE, the conductive member comprises a conductive interface for connecting the conductive member to the external device.

According to some embodiments of the first part of aspect 247SE, the external device is configured to transmit a conductive communication to the implant.

According to some embodiments of the first part of aspect 247SE, the implant is configured to transmit a conductive communication to the external device.

According to some embodiments of the first part of aspect 247SE, the external device and/or the conductive member comprises a verification unit configured to receive authentication input from a user, for authenticating the conductive communication between the implant and the external device.

According to some embodiments of the first part of aspect 247SE, the authentication input is a code.

According to some embodiments of the first part of aspect 247SE, the authentication input is based on a biometric technique selected from the list of: a fingerprint, a palm vein structure, image recognition, face recognition, iris recognition, a retinal scan, a hand geometry, and genome comparison.

According to some embodiments of the first part of aspect 247SE, the conductive member comprises a fingerprint reader, wherein the verification unit is configured to receive a fingerprint from the conductive member. Any other means for collecting biometric data is equally possible.

According to some embodiments of the first part of aspect 247SE, the implant comprises: a first sensor for measuring a parameter of the patient, by the implant, and an internal computing unit configured for:

receiving a parameter of the patient, from the external device,
 comparing the parameter measured by the implant to a parameter measured by the external device, and
 performing authentication of the conductive communication based on the comparison.

According to some embodiments of the first part of aspect 247SE, the implant being connected to a sensation generator, the implant being configured for:

storing authentication data, related to a sensation generated by the sensation generator, receiving input authentication data from the external device, and wherein the implant comprises an internal computing unit configured for:

comparing the authentication data to the input authentication data, and performing authentication of the conductive communication based on the comparison.

According to some embodiments of the first part of aspect 247SE, the external device is a handset or a wearable device.

According to some embodiments of the first part of aspect 247SE, the conductive communication comprises a key or a part of the key to be used for decrypting encrypted data received by the external device or the implant.

According to some embodiments of the first part of aspect 247SE, the external device is configured to transmit a first part of the key to the implant using the conductive communication, and to wirelessly transmit a second part of the key to the implant, wherein the implant is adapted to decrypt the encrypted data, using a combined key derived from the received first and second parts of the key.

According to some embodiments of the first part of aspect 247SE, the implant comprises an internal computing unit configured to operate the implant using operation instructions, wherein the conductive communication comprises instructions for operating the implant. In some embodiments, the operation of the implant is only conducted upon positive authentication of the conductive communication as described above.

According to some embodiments of the first part of aspect 247SE, the implant comprises an internal computing unit configured to update a control program running in the implant, wherein the conductive communication comprises instructions for updating the control program. In some embodiments, the updating of the control program of the implant is only conducted upon positive authentication of the conductive communication as described above.

According to some embodiments of the first part of aspect 247SE, the conductive communication comprises feedback parameters relating to functionality of the implant.

According to some embodiments of the first part of aspect 247SE, the implant comprises a sensor for sensing at least one physiological parameter of the patient, wherein the conductive communication comprises said at least one physiological parameter of the patient.

In a second part of aspect 247SE, a method for communication between an external device and an implant implanted in a patient is provided. The method comprises placing a conductive member, configured to be in connection with the external device, in electrical connection with a skin of the patient for conductive communication with the implant.

According to some embodiments of the second part of aspect 247SE, the conductive member comprises a conductive interface for connecting the conductive member to the external device.

According to some embodiments of the second part of aspect 247SE, the method comprises transmitting a conductive communication to the implant by the external device.

According to some embodiments of the second part of aspect 247SE, the method comprises transmitting a conductive communication to the external device by the implant.

According to some embodiments of the second part of aspect 247SE, the method comprises receiving of an authentication input from a user by a verification unit of the external device and authenticating the conductive communication between the implant and the external device using the authentication input.

According to some embodiments of the second part of aspect 247SE, the authentication input is a code.

According to some embodiments of the second part of aspect 247SE, the authentication input is based on a biometric technique selected from the list of: a fingerprint, a palm vein structure, image recognition, face recognition, iris recognition, a retinal scan, a hand geometry, and genome comparison.

According to some embodiments of the second part of aspect 247SE, the conductive member comprises a fingerprint reader, wherein the method comprises receiving a fingerprint from the conductive member by the verification unit.

According to some embodiments of the second part of aspect 247SE, the method comprises measuring a parameter of the patient by a sensor of the implant, receiving, by an internal computing unit of the implant, a parameter of the patient from the external device, comparing, by the internal computing unit of the implant, the parameter measured by the implant to the parameter measured by the external device, and performing, by the internal computing unit of the implant, authentication of the conductive communication based on the comparison.

According to some embodiments of the second part of aspect 247SE, the method comprises: generating, by a sensation generator, a sensation detectable by a sense of the patient, storing, by the implant, authentication data, related to the generated sensation, providing, by the patient, input to the external device, resulting in input authentication data, and authenticating the conductive communication based on a comparison of the input authentication data and the authentication data.

According to some embodiments of the second part of aspect 247SE, the external device is a handset or a wearable device.

According to some embodiments of the second part of aspect 247SE, the conductive communication comprises a key or a part of the key to be used for decrypting encrypted data received by the external device or the implant.

According to some embodiments of the second part of aspect 247SE, the method comprises: transmitting, by the external device, a first part of the key to the implant using the conductive communication, transmitting, by the external device, a second part of the key to the implant using a wireless connection, deriving a combined key from the received first and second parts of the key, and decrypting, by the implant, the encrypted data, using the combined key.

According to some embodiments of the second part of aspect 247SE, the method comprises operating the implant using operation instructions, by an internal computing unit of the implant, wherein the conductive communication comprises instructions for operating the implant.

According to some embodiments of the second part of aspect 247SE, the method comprises updating a control program running in the implant, by an internal computing unit of the implant, wherein the conductive communication comprises instructions for updating the control program.

According to some embodiments of the second part of aspect 247SE, the conductive communication comprises feedback parameters relating to functionality of the implant.

According to some embodiments of the second part of aspect 247SE, the method comprises sensing of at least one physiological parameter of the patient, by a sensor of the implant, wherein the conductive communication comprises said at least one physiological parameter of the patient.

In a third part of aspect 247SE, an implant implanted in a patient is provided. The implant comprises an internal computing unit configured to operate the implant based on an authentication input and/or using operating instructions, wherein the authentication input and/or the operating instructions are received by conductive communication with an external device.

According to some embodiments of the third part of aspect 247SE, the internal computing unit is further configured to update a control program running in the implant, wherein the conductive communication comprises instructions for updating the control program.

According to some embodiments of the third part of aspect 247SE, the implant further comprising a sensor for measuring a parameter of the patient and wherein the internal computing unit is further configured for:

receiving a parameter of the patient, from the external device, comparing the parameter measured by the implant to a parameter measured by the external device, performing authentication of the conductive communication based on the comparison; and upon an authenticated conductive communication, operating the implant using the operating instructions.

According to some embodiments of the third part of aspect 247SE, the implant being connected to a sensation generator, the implant being configured for:

storing authentication data, related to a sensation generated by the sensation generator, receiving input authentication data from the external device, and wherein the implant comprises an internal computing unit configured for:

comparing the authentication data to the input authentication data, and performing authentication of the conductive communication based on the comparison, upon an authenticated conductive communication, operating the implant using the operating instructions.

According to some embodiments of the third part of aspect 247SE, the implant further comprising a sensor for sensing at least one physiological parameter of the patient, wherein the conductive communication comprises said at least one physiological parameter of the patient.

In a fourth part of aspect 247SE, an external device adapted for communication with an implant, when the implant is implanted in a patient, is provided. The external device is configured to be placed in electrical connection with a conductive member, for conductive communication with the implant.

According to some embodiments of the fourth part of aspect 247SE, the external device comprises a conductive interface for connecting with the conductive member.

According to some embodiments of the fourth part of aspect 247SE, the external device being configured to transmit a conductive communication to the implant when in electrical connection with the conductive member.

According to some embodiments of the fourth part of aspect 247SE, the external device being configured to receive conductive communication from the implant when in electrical connection with the conductive member.

According to some embodiments of the fourth part of aspect 247SE, the external device comprising a verification unit configured to receive authentication input from a user, for authenticating the conductive communication between the implant and the external device.

According to some embodiments of the fourth part of aspect 247SE, the external device being a handset or a wearable device.

According to some embodiments of the fourth part of aspect 247SE, the conductive communication comprises a key or a part of the key to be used for decrypting encrypted data received by the external device or the implant.

According to some embodiments of the fourth part of aspect 247SE, the external device is configured to transmit a first part of the key to the implant using the conductive communication, and to wirelessly transmit a second part of the key to the implant, and to encrypt data to be sent to the implant such that it can be decrypted using a combined key derived from the first and second parts of the key.

According to some embodiments of the fourth part of aspect 247SE, the external device being configured to transmit instructions for updating a control program of the implant using the conductive communication.

According to some embodiments of the fourth part of aspect 247SE, the external device being configured to transmit operation instructions of the implant using the conductive communication.

In a fifth part of aspect 247SE, a conductive member configured to be in connection with an external device for communication between the external device and an implant implanted in a patient is provided. The conductive member being configured to be in electrical connection with a skin of the patient or any other part of a body of the patient.

According to some embodiments of the fifth part of aspect 247SE, the conductive member comprising a conductive interface for connecting the conductive member to the external device.

According to some embodiments of the fifth part of aspect 247SE, the conductive member comprising a fingerprint reader, wherein the conductive member is configured to transmit a fingerprint read by the fingerprint reader to the external device.

According to some embodiments of the fifth part of aspect 247SE, the conductive member being in the form of a case of the external device, the case comprising a capacitive area configured to be in electrical connection with a skin of the patient.

According to some embodiments of the fifth part of aspect 247SE, the external device is a mobile phone, wherein the conductive member is in the form of a mobile phone case.

According to some embodiments of the fifth part of aspect 247SE the conductive member is arranged as an arm or wrist band being integrally formed with, or connected to, the external device.

According to some embodiments of the first part of aspect 247SE the conductive member is configured to be in conductive or electrical connection with the external device.

According to some embodiments of the first part of aspect 247SE the conductive member is configured to be in wireless connection with the external device.

According to some embodiments of the first part of aspect 247SE the conductive member is configured to be a screen of the external device, the screen being configured to receive data using electric charge.

According to some embodiments of the first part of aspect 247SE wherein the conductive member comprises the verification unit.

According to some embodiments of the first part of aspect 247SE the external device comprises the verification unit.

According to some embodiments of the first part of aspect 247SE wherein the establishment of conductive communication is configured to authenticate or partially authenticate the conductive communication between the implant and the external device.

According to some embodiments the implant of the third part of aspect 247SE, and/or with ability to use any of the methods of the second part of aspect 247SE, and/or with ability to be part of any of the systems of the first part of aspect 247SE, and/or with ability to communicate via the conductive member according to any of the fifth part of aspect 247SE, and/or with ability to communicate with the external device of the fourth part of aspect 247SE, and/or with ability to use the computer program product of the sixth part of aspect 247SE, and/or with ability to use an internal control unit, wherein the implant comprises at least one of:

a pacemaker unit or implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant for adjusting or replacing any bone part of a body of the patient, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an active electrically controlled implant devoid of an electrical heart stimulation system, an active electrically controlled non-heart stimulation implant.

an implant adapted for electrical stimulation of muscles, a non-nerve stimulation system, an active non-stimulation implant, an implant for high current electrical stimulation defined as current above 1 mA or current above 5 mA, 10 mA, or 20 mA, an implant replacing an organ of the patient or part of an organ of the patient or the function thereof.

a vascular treatment device, and an implant adapted to move fluid inside the body of the patient.

According to some embodiments of the fourth part of aspect 247SE the external device is a smartwatch.

In a sixth part of aspect 247SE, there is provided computer program product of, or adapted to be run on, an external device adapted for communication with an implant, when the implant is implanted in a patient, wherein the external device is configured to be placed in electrical connection with a conductive member, wherein the computer program product is configured to cause the conductive member to have conductive communication with the implant.

According to some embodiments of the sixth part of aspect 247SE the computer program product is configured to cause the external device to transmit a conductive communication to the implant when in electrical connection with the conductive member.

According to some embodiments of the sixth part of aspect 247SE the computer program product is configured to cause the external device to receive conductive communication from the implant when in electrical connection with the conductive member.

According to some embodiments of the sixth part of aspect 247SE the computer program product is configured to cause a verification unit of the external device to receive authentication input from a user, for authenticating the conductive communication between the implant and the external device.

According to some embodiments of the sixth part of aspect 247SE the conductive communication comprises a key or a part of the key to be used for decrypting encrypted data received by the external device or the implant.

According to some embodiments of the sixth part of aspect 247SE the computer program product is configured to cause the external device to transmit a first part of the key to the implant using the conductive communication, and to wirelessly transmit a second part of the key to the implant, and to encrypt data to be sent to the implant such that it can be decrypted using a combined key derived from the first and second parts of the key.

According to some embodiments of the sixth part of aspect 247SE the computer program product is configured to cause the external device to transmit instructions for updating a control program of the implant using the conductive communication.

According to some embodiments of the sixth part of aspect 247SE the computer program product is configured to cause the external device to transmit operation instructions of the implant using the conductive communication.

In a seventh part of aspect 247SE, there is provided computer program product of, or adapted to be run on, an implant adapted for communication with an external device adapted to be placed in electrical connection with a conductive member, when the implant is implanted in a patient, wherein the computer program product used by a computing unit on the implant is configured to cause the implant to have communication with the conductive member using the body as a signal transmitter.

According to some embodiments of the seventh part of aspect 247SE the computer program product is configured to cause the implant to transmit a conductive communication to the external device when in electrical connection with the conductive member.

According to some embodiments of the seventh part of aspect 247SE the computer program product is configured to cause the implant to receive conductive communication from the external device when in electrical connection with the conductive member.

According to some embodiments of the seventh part of aspect 247SE the computer program product is configured to cause a verification unit of the implant to receive authentication input from a user, for authenticating the conductive communication between the implant and the external device.

According to some embodiments of the seventh part of aspect 247SE the conductive communication comprises a key or a part of the key to be used for decrypting encrypted data received by the implant.

According to some embodiments of the seventh part of aspect 247SE the computer program product is configured to receive from the external device a first part of the key to the implant using the conductive communication, and to receive wirelessly a second part of the key to the implant, and to encrypt data sent to the implant such that it can be decrypted using a combined key derived from the first and second parts of the key.

According to some embodiments of the seventh part of aspect 247SE the computer program product is configured to receive instructions for updating a control program at the implant from the external device using the conductive communication.

According to some embodiments of the seventh part of aspect 247SE the computer program product is configured to receive operation instructions at the implant from the external device using the conductive communication.

According to some embodiments of the first part of aspect 247SE the external device is configured to transmit a conductive communication to the implant.

According to some embodiments of the first part of aspect 247SE the implant is configured to transmit a conductive communication to the external device.

According to some embodiments of the first part of aspect 247SE the external device and/or the conductive member comprises a verification unit configured to receive authentication input from a user, for authenticating the conductive communication between the implant and the external device.

According to some embodiments of the first part of aspect 247SE the authentication input is a code.

According to some embodiments of the first part of aspect 247SE the authentication input is based on a biometric technique selected from the list of: a fingerprint, a palm vein structure, image recognition, face recognition, iris recognition, a retinal scan, a hand geometry, and genome comparison.

According to some embodiments of the first part of aspect 247SE the implant comprises:

a. a sensor for measuring a parameter of the patient, by the implant
b. an internal computing unit configured for:
   i. receiving a parameter of the patient, from the external device,
   ii. comparing the parameter measured by the implant to the parameter measured by the external device, and
   iii. performing authentication of the conductive communication based on the comparison According to some embodiments of the first part of aspect 247SE the implant being connected to a sensation generator, the implant being configured for:

a. storing authentication data, related to a sensation generated by the sensation generator,
b. receiving input authentication data from the external device, and wherein the implant comprises an internal computing unit configured for:
   i. comparing the authentication data to the input authentication data, and
   ii. performing authentication of the conductive communication based on the comparison.

According to some embodiments of the first part of aspect 247SE the external device is a handset or a wearable device.

According to some embodiments of the first part of aspect 247SE the conductive communication comprises a key or a part of the key to be used for decrypting encrypted data received by the external device or the implant.

According to some embodiments of the first part of aspect 247SE the external device is configured to transmit a first part of the key to the implant using the conductive communication, and to wirelessly transmit a second part of the key to the implant, wherein the implant is adapted to decrypt the encrypted data, using a combined key derived from the received first and second parts of the key.

According to some embodiments of the first part of aspect 247SE the implant comprises an internal computing unit configured to operate the implant using operation instructions, wherein the conductive communication comprises instructions for operating the implant.

According to some embodiments of the first part of aspect 247SE the implant comprises an internal computing unit configured to update a control program running in the implant, wherein the conductive communication comprises instructions for updating the control program.

According to some embodiments of the first part of aspect 247SE the conductive communication comprises feedback parameters relating to functionality of the implant.

According to some embodiments of the first part of aspect 247SE the implant comprises a sensor for sensing at least one physiological parameter of the patient, wherein the conductive communication comprises said at least one physiological parameter of the patient.

According to some embodiments, the implant according to the third part of aspect 247SE, and/or with ability to use any of the methods of the second part of aspect 247SE, and/or with ability to be part of any system of the first part of aspect 247SE, and/or with ability to communicate via the conductive member of the fifth part of aspect 247SE, and/or with ability to communicate with the external device of the fourth part of aspect 247SE, and/or with ability to use the computer program product of the sixth or seventh parts of aspect 247SE, comprising an internal control unit adapted to be involved in at least a part of the actions performed by the implant in at least a part of any one of the other embodiments.

Aspect 248SE Device Synchronization Sensation—Authenticating a Connection Between an Implant and the External Device by Generating Sensations—Embodiments of Aspect 248SE of the Disclosure In a first part of aspect 248SE, there is provided a method of authenticating a connection between an implant implanted in a patient, and an external device. The method comprising:

generating, by a sensation generator, a sensation detectable by a sense of the patient, storing, by the implant, authentication data, related to the generated sensation, providing, by the patient, input to the external device, resulting in input authentication data, and authenticating the connection based on an analysis of the input authentication data and the authentication data.

According to some embodiments of the first part of aspect 248SE the method further comprises the step of communicating further data between the implant and the external device following positive authentication.

According to some embodiments of the first part of aspect 248SE authentication data comprises a timestamp of the sensation and wherein the input authentication data comprises a timestamp of the input from the patient.

According to some embodiments of the first part of aspect 248SE authenticating the connection comprises: calculating a time difference between the timestamp of the sensation and the timestamp of the input from the patient, and upon determining that the time difference is less than a threshold, authenticating the connection According to some embodiments of the first part of aspect 248SE authentication data comprises a number of times that the sensation is generated by the sensation generator, and wherein the input authentication data comprises an input from the patient relating to a number of times the patient detected the sensation, wherein authenticating the connection comprises: upon determining that the number of times of the authentication data and the input authentication data are equal, authenticating the connection.

According to some embodiments of the first part of aspect 248SE the sensation comprises a plurality of sensation components.

According to some embodiments of the first part of aspect 248SE the sensation or sensation components comprise a vibration.

According to some embodiments of the first part of aspect 248SE the sensation or sensation components comprise a sound.

According to some embodiments of the first part of aspect 248SE the sensation or sensation components comprise a photonic signal.

According to some embodiments of the first part of aspect 248SE the sensation or sensation components comprise a light signal.

According to some embodiments of the first part of aspect 248SE the sensation or sensation components comprise an electric signal.

According to some embodiments of the first part of aspect 248SE the sensation or sensation components comprise a heat signal.

According to some embodiments of the first part of aspect 248SE the sensation generator is contained within the implant.

According to some embodiments of the first part of aspect 248SE the communication between the implant and the external device is a wireless communication.

According to some embodiments of the first part of aspect 248SE the communication between the implant and the external device is a conductive communication.

According to some embodiments of the first part of aspect 248SE the method further comprises the step of:

transmitting the input authentication data from the external device to the implant, wherein the analysis is performed by the implant.

According to some embodiments of the first part of aspect 248SE the method further comprises the step of:

transmitting the authentication data from the implant to the external device, wherein the analysis is performed by the external device.

According to some embodiments of the first part of aspect 248SE the implant comprises a motor for controlling a physical function in the body of the patient, wherein the motor being the sensation generator.

According to some embodiments of the first part of aspect 248SE the sensation is a vibration created by running the motor.

According to some embodiments of the first part of aspect 248SE the sensation is a sound created by running the motor.

According to some embodiments of the first part of aspect 248SE the analysis is performed by the implant, the method further comprising the step of:

continuously requesting by the external device, or receiving at the external device, information of an authentication status of the connection between the implant and the external device, and upon determining, at the external device, that the connection is authenticated, transmitting further data from the external device to the implant.

According to some embodiments of the first part of aspect 248SE the further data comprises at least one of:

data for updating a control program running in the implant, and operation instructions for operating the implant.

According to some embodiments of the first part of aspect 248SE the analysis is performed by the external device, the method further comprising the step of:

continuously requesting by the implant, or receiving at the implant, information of an authentication status of the connection between the implant and the external device, and upon determining, at the implant, that the connection is authenticated, transmitting further data from the implant to the external device.

According to some embodiments of the first part of aspect 248SE the further data comprises data sensed by a sensor connected to the implant.

In a second part of aspect 248SE, there is provided an implant, implanted in a patient, adapted for connection with an external device, the implant connected to a sensation generator, the implant being configured for: storing authentication data, related to a sensation generated by the sensation generator, receiving input authentication data from the external device, and wherein the implant comprises an internal computing unit configured for:

analyzing the authentication data and the input authentication data, and performing authentication of the connection based on the analysis.

According to some embodiments of the second part of aspect 248SE the implant is further configured for communicating further data to the external device following positive authentication.

According to some embodiments of the second part of aspect 248SE the authentication data comprises a timestamp of the sensation and wherein the input authentication data comprises a timestamp of the input from the patient.

According to some embodiments of the second part of aspect 248SE authenticating the connection comprises: calculating a time difference between the timestamp of the sensation and the timestamp of the input from the patient, and upon determining that the time difference is less than a threshold, authenticating the connection.

According to some embodiments of the second part of aspect 248SE the authentication data comprises a number of times that the sensation is generated by the sensation generator, and wherein the input authentication data comprises an input from the patient relating to a number of times the patient detected the sensation, wherein authenticating the connection comprises: upon determining that the number of times of the authentication data and the input authentication data are equal, authenticating the connection.

According to some embodiments of the second part of aspect 248SE the sensation generator is contained within the implant.

According to some embodiments of the second part of aspect 248SE the sensation generator is configured to create the sensation comprising a plurality of sensation components.

According to some embodiments of the second part of aspect 248SE the sensation generator is configured to create the sensation or sensation components by vibration of the sensation generator.

According to some embodiments of the second part of aspect 248SE the sensation generator is configured to create the sensation or sensation components by playing a sound.

According to some embodiments of the second part of aspect 248SE the sensation generator is configured to create the sensation or sensation components by providing a photonic signal.

According to some embodiments of the second part of aspect 248SE the sensation generator is configured to create the sensation or sensation components by providing a light signal.

According to some embodiments of the second part of aspect 248SE the sensation generator is configured to create the sensation or sensation components by providing an electric signal.

According to some embodiments of the second part of aspect 248SE the sensation generator is configured to create the sensation or sensation components by providing a heat signal.

According to some embodiments of the second part of aspect 248SE the communication between the implant and the external device is a wireless communication.

According to some embodiments of the second part of aspect 248SE the communication between the implant and the external device is a conductive communication.

According to some embodiments of the second part of aspect 248SE the implant comprises a motor for controlling a physical function in the body of the patient, wherein the motor being the sensation generator.

According to some embodiments of the second part of aspect 248SE the sensation is a vibration created by running the motor.

According to some embodiments of the second part of aspect 248SE the sensation is a sound created by running the motor.

In a third part of aspect 248SE, there is provided an external device, adapted for connection with an implant, implanted in a patient, the external device comprising:

an interface for receiving, by the patient, input to the external device, resulting in input authentication data, a receiver for receiving authentication data from the implant, the authentication data relating to a generated sensation of a sensation generator connected to the implant;

an external computing unit configured for:
i. analyzing the authentication data and the input authentication data, and
ii. performing authentication of the connection based on the analysis.

According to some embodiments of the third part of aspect 248SE the external device is further configured for communicating further data to the implant following positive authentication.

According to some embodiments of the third part of aspect 248SE the authentication data comprises a timestamp and wherein the input authentication data comprises a timestamp of the input from the patient.

According to some embodiments of the third part of aspect 248SE authenticating the connection comprises: calculating a time difference between the timestamp of the authentication data and the timestamp of the input from the patient, and upon determining that the time difference is less than a threshold, authenticating the connection.

According to some embodiments of the third part of aspect 248SE the authentication data comprises a number of times that the sensation is generated by the sensation generator, and wherein the input authentication data comprises an input from the patient relating to a number of times the patient detected the sensation, wherein authenticating the connection comprises: upon determining that the number of times of the authentication data and the input authentication data are equal, authenticating the connection.

According to some embodiments of the third part of aspect 248SE the communication between the implant and the external device is a wireless communication.

According to some embodiments of the third part of aspect 248SE the communication between the implant and the external device is a conductive communication.

According to some embodiments of the third part of aspect 248SE the external device further comprises a conductive member configured to be in electrical connection with the external device, wherein the conductive member is configured to be placed in electrical connection with a skin of the patient for conductive communication with the implant.

According to some embodiments of the first part of aspect 248SE the method further comprises transmitting further data between the implant and the external device, wherein the further data is used or acted upon, only after authentication of the connection is performed.

According to some embodiments of the second part of aspect 248SE the implant comprises at least one of:

a pacemaker unit or implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

In a fourth part of aspect 248SE there is provided a computer program product of, or adapted to be run on, an external device, adapted for connection with an implant, implanted in a patient, the external device comprising:

a. an interface for receiving, by the patient, input to the external device, resulting in input authentication data, b. a receiver for receiving authentication data from the implant, the authentication data relating to a generated sensation of a sensation generator being part of the implant or external device.

c. an external computing unit, wherein the computer program product is configured to cause the external computing unit to:

i. analyze the authentication data and the input authentication data, and ii. perform authentication of the connection based on the analysis.

According to some embodiments of the fourth part of aspect 248SE the computer program product is configured to cause the external device to communicate further data to the implant following positive authentication.

According to some embodiments of the fourth part of aspect 248SE the authentication data comprises a timestamp and wherein the input authentication data comprises a time-stamp of the input from the patient.

According to some embodiments of the fourth part of aspect 248SE authenticating the connection comprises: calculating a time difference between the timestamp of the authentication data and the timestamp of the input from the patient, and upon determining that the time difference is less than a threshold, authenticating the connection.

According to some embodiments of the fourth part of aspect 248SE the authentication data comprises a number of times that the sensation is generated by the sensation generator, and wherein the input authentication data comprises an input from the patient relating to a number of times the patient detected the sensation, wherein authenticating the connection comprises: upon determining that the number of times of the authentication data and the input authentication data are equal, authenticating the connection.

According to some embodiments of the fourth part of aspect 248SE the communication between the implant and the external device is a wireless communication.

According to some embodiments of the fourth part of aspect 248SE the communication between the implant and the external device is a conductive communication.

In a fifth part of aspect 248SE there is provided a computer program product adapted to be run on, an implant, implanted in a patient, adapted for connection with an external device, the implant comprising:

a. an interface for receiving, by the patient, input to the implant, resulting in input authentication data, b. a receiver for receiving authentication data from the external device, the authentication data relating to a generated sensation of a sensation generator of the implant or the external device, c. a computing unit.

wherein the computer program product is configured to cause the computing unit to:

i. analyze the authentication data and the input authentication data, and ii. perform authentication of the connection based on the analysis.

According to some embodiments of the fifth part of aspect 248SE the computer program product is configured to cause the implant to accept further communication with further data received by the implant following positive authentication.

According to some embodiments of the fifth part of aspect 248SE the authentication data comprises a timestamp and wherein the input authentication data comprises a timestamp of the input from the patient.

According to some embodiments of the fifth part of aspect 248SE authenticating the connection comprises: calculating a time difference between the timestamp of the authentication data and the timestamp of the input from the patient, and upon determining that the time difference is less than a threshold, authenticating the connection.

According to some embodiments of the fifth part of aspect 248SE the authentication data comprises a number of times that the sensation is generated by the sensation generator, and wherein the input authentication data comprises an input from the patient relating to a number of times the patient detected the sensation, wherein authenticating the connection comprises: upon determining that the number of times of the authentication data and the input authentication data are equal, authenticating the connection.

According to some embodiments of the fifth part of aspect 248SE the further communication between the implant and the external device is a wireless communication.

According to some embodiments of the fifth part of aspect 248SE the communication between the implant and the external device is a wireless communication.

According to some embodiments of the fifth part of aspect 248SE the communication between the implant and the external device is a conductive communication.

According to some embodiments of the fifth part of aspect 248SE the further communication between the implant and the external device is a wireless communication.

The implant according to the second part of aspect 248SE and/or with ability to use any of the methods of the first part of aspect 248SE, and/or with ability to perform the authentication process in any of third part of aspect 248SE and/or with ability to use any of the computer program products of the fourth part of aspect 248SE, may comprise an internal control unit adapted to be involved in at least a part of the actions performed by the implant in at least a part of any one of the embodiments of the above.

Aspect 249SE Prior Verified
Communication—Verifying Authenticity of
Instructions Sent from the External Device to the
Implant—Embodiments of Aspect 249SE of the
Disclosure In a first part of aspect 249SE, a method of communicating instructions from an external device to an implant implanted in a patient is provided. The method comprising establishing a connection between the external device and the implant, combining a first set of instructions with a previously transmitted set of instructions, forming a first combined set of instructions, transmitting the first combined set of instructions to the implant.

The method further comprising, at the implant, verifying the authenticity of the first combined set of instructions, by: extracting the previously transmitted set of instructions from the first combined set of instructions, comparing the extracted previously transmitted set of instructions with previously received instructions stored in the implant, and upon determining that the extracted previously transmitted set of instructions equals the previously received instructions stored in the implant, running the first set of instructions at the implant and storing the first combined set of instructions in the implant, to be used for verifying a subsequent received set of instructions.

According to some embodiments of the first part of aspect 249SE, step of verifying the authenticity of the first combined set of instructions further comprises upon determining that the extracted previously transmitted set of instructions differs from the previously received instructions stored in the implant, providing feedback related to an unauthorized attempt to instruct the implant.

According to some embodiments of the first part of aspect 249SE, the step of comparing the extracted previously transmitted set of instructions with previously received instructions stored in the implant comprises calculating a difference between the extracted previously transmitted set of instructions with the previously received instructions stored in the implant, and comparing the difference with a threshold value, wherein the extracted previously transmitted set of instructions is determined to equal the previously received instructions stored in the implant in the case of the difference value not exceeding the threshold value.

According to some embodiments of the first part of aspect 249SE, the combined set of instructions comprises the first set of instructions and a cryptographic hash of the previously transmitted set of instructions, wherein the method further comprises, at the implant, calculating a cryptographic hash of the previously received instructions stored in the implant and comparing the calculated cryptographic hash to the cryptographic hash included in the first combined set of instructions.

According to some embodiments of the first part of aspect 249SE, the method further comprises the steps of: combining a second set of instructions with the first combined set of instructions, forming a second combined set of instructions, wherein the second combined set of instructions comprises a cryptographic hash of the first combined set of instructions, and transmitting the second combined set of instructions to the implant. The authenticity of the second combined set of instructions is verified at the implant by calculating a cryptographic hash of the first combined set of instructions stored in the implant, and comparing the calculated cryptographic hash with the cryptographic hash included in the received second combined set of instructions. Upon determining that the calculated cryptographic hash of the first combined set of instructions equals the cryptographic hash included in the received second combined set, the second set of instructions is run at the implant, and the second combined set of instruction is stored in the implant, to be used for verifying a subsequent received set of instructions.

According to some embodiments of the first part of aspect 249SE, wherein the first combined set of instructions is transmitted to the implant using a proprietary network protocol.

According to some embodiments of the first part of aspect 249SE, the first combined set of instructions is transmitted to the implant using a standard network protocol.

In a second part of aspect 249SE, a method of communicating instructions from an external device to an implant implanted in a patient is provided. The method comprises the steps of: establishing a connection between the external device and the implant, confirming the connection between the implant and the external device, receiving a set of instructions from the external device, as a result of the confirmation, verifying the authenticity of the set of instructions and storing the set of instructions in the implant to be used for verifying authenticity of a subsequently received set of instructions, and transmitting further sets of instructions from the external device to the implant according any embodiment the first part of aspect 249SE.

According to some embodiments of the second part of aspect 249SE, the step of confirming the connection between the implant and the external device comprises: measuring a parameter of the patient, by implant, measuring a parameter of the patient, by external device, comparing the parameter measured by the implant to the parameter measured by the external device, and performing authentication of the connection based on the comparison.

According to some embodiments of the second part of aspect 249SE, the step of confirming the connection between the implant and the external device comprises: generating, by a sensation generator, a sensation detectable by a sense of the patient, by the implant, authentication data, related to the generated sensation, providing, by the patient, input to the external device, resulting in input authentication data, and authenticating the connection based on a comparison of the input authentication data and the authentication data.

In a third part of aspect 249SE, a method of communicating instructions from an external device to an implant implanted in a patient is provided. The method comprising: placing a conductive member, configured to be in connection with the external device, in electrical connection with a skin of the patient for conductive communication with the implant, transmitting, via the electrical connection using conductive communication, a set of instructions from the external device, receiving, at the implant the set of instructions from the external device, storing the set of instructions in the implant to be used for verifying authenticity of a subsequently received set of instructions, and transmitting further sets of instructions from the external device to the implant according any embodiment the first part of aspect 249SE.

According to some embodiments of the third part of aspect 249SE, the method further comprising: a, prior to transmitting, via the electrical connection using conductive communication, a set of instructions from the external device, receiving of an authentication input from a user by a verification unit of the external device, and authenticating the conductive communication between the implant and the external device using the authentication input, as a result of the authentication, transmitting, via the electrical connection using conductive communication, the set of instructions from the external device.

In a fourth part of aspect 249SE, a method of communicating instructions from an external device to an implant implanted in a patient is provided. The method comprises the steps of: receiving, at the implant a set of instructions from a second external device, storing the set of instructions in the implant to be used for verifying authenticity of a subsequently received set of instructions from the external device, and transmitting further sets of instructions from the external device to the implant according to any embodiment the first part of aspect 249SE.

According to some embodiments of the fourth part of aspect 249SE, the second external device transmits the set of instructions using a proprietary network protocol.

According to some embodiments of the fourth part of aspect 249SE, the set of instructions received by the implant from the second external device is encrypted, wherein the method further comprising decrypting the set of instructions and storing the decrypted set of instructions in the implant to be used for verifying authenticity of a subsequently received set of instructions from the external device.

According to some embodiments of either one of the first to fourth part of aspect 249SE, the implant comprises a reset switch, wherein the method further comprising comprises the steps of: activating said reset switch and deleting previously received instructions stored in the implant.

According to some embodiments of either one of the first to fourth part of aspect 249SE, the method further comprises: storing a set of instructions in the implant to be used for verifying authenticity of a subsequently received set of instructions from the external device using any one of the embodiments of the second to fourth part of aspect 249SE.

In a fifth part of aspect 249SE, an implant comprising a transceiver configured to establish a connection with an external device when the implant is implanted in a patient is provided. The implant further comprising a computing unit configured to verify the authenticity of instructions received at the transceiver by: extracting a previously transmitted set of instructions from a first combined set of instructions received by the transceiver, comparing the extracted previously transmitted set of instructions with previously received instructions stored in the implant, upon determining that the extracted previously transmitted set of instructions equals the previously received instructions stored in the implant, running the first set of instructions at the implant.

According to some embodiments of the fifth part of aspect 249SE, the computing unit is configured to: upon determining that the extracted previously transmitted set of instructions differs from the previously received instructions stored in the implant, provide feedback, via a feedback unit of the implant, related to an unauthorized attempt to instruct the implant.

According to some embodiments of the fifth part of aspect 249SE, computing unit is configured to compare the extracted previously transmitted set of instructions with previously received instructions stored in the implant by calculating a difference between the extracted previously transmitted set of instructions with previously received instructions stored in the implant, and compare the difference with a threshold value, wherein the extracted previously transmitted set of instructions is determined to equal the previously received instructions stored in the implant in the case of the difference value not exceeding the threshold value.

According to some embodiments of the fifth part of aspect 249SE, the first combined set of instructions comprises the first set of instructions and a cryptographic hash of the previously transmitted set of instructions, wherein the computing unit is configured to calculate a cryptographic hash of previously received instructions stored in the implant and compare the calculated cryptographic hash to the cryptographic hash included in the first combined set of instructions.

According to some embodiments of the fifth part of aspect 249SE, the computing unit is further configured to verify the authenticity of a second combined set of instructions, the second combined set of instructions comprising a cryptographic hash of the first combined set of instructions, the second combined set of instructions received at the transceiver by: extracting the first combined set of instructions from the second combined set of instructions, calculating a cryptographic hash of the first combined set of instructions and comparing the calculated cryptographic hash with the cryptographic hash included in the received second combined set of instructions, calculating a cryptographic hash of previously received instructions stored in the implant and comparing this to the cryptographic hash included in the extracted first combined set of instructions. Upon determining, by the computing unit, that the cryptographic hash of the first combined set of instructions equals the cryptographic hash included in the received second combined set, and that the cryptographic hash of previously received instructions stored in the implant equals the cryptographic hash included in the extracted first combined set of instructions, the second set of instructions is run at the implant.

According to some embodiments of the fifth part of aspect 249SE, the first combined set of instructions is received at the implant using a proprietary network protocol.

According to some embodiments of the fifth part of aspect 249SE, the first combined set of instructions is received at the implant using a standard network protocol.

In a sixth part of aspect 249SE, an implant comprising a transceiver configured to establish a connection with an external device when the implant is implanted in a patient is provided. The implant further comprising a computing unit configured to verify the authenticity of instructions received at the transceiver by:

a. establishing a connection with the external device, b. confirming the connection, c. receiving a set of instructions from the external device, d. as a result of the confirmation, verifying the authenticity of the set of instructions and storing the set of instructions in the implant to be used for verifying authenticity of a subsequently received set of instructions. The computing unit is further configured to verify the authenticity of further sets of instructions received by the transceiver according to any embodiment of the fifth part of aspect 249SE.

According to some embodiments of the sixth part of aspect 249SE, the computing unit is configured to confirm the connection by: receiving a measured parameter of the patient, the parameter measured by a sensor connected to the implant, receiving a measured parameter of the patient from the external device, comparing the parameter measured by the implant to the parameter measured by the external device, and performing authentication of the connection based on the comparison.

In a seventh part of aspect 249SE, an implant comprising a transceiver configured to establish a connection with an external device when the implant is implanted in a patient is provided. The implant further comprising a computing unit configured to verify the authenticity of instructions received at the transceiver by: receiving, via an electrical connection using conductive communication from the external device, a set of instructions from the external device, storing the set of instructions in the implant to be used for verifying authenticity of a subsequently received set of instructions, wherein the computing unit is configured to verify the authenticity of further sets of instructions received by the transceiver according to any embodiment of the fifth part of aspect 249SE.

In an eight part of aspect 249SE, an implant comprising a transceiver configured to establish a connection with an external device, and a connection with a second external device, when the implant is implanted in a patient is provided. The implant further comprising a computing unit configured to verify the authenticity of instructions received at the transceiver from the external device by: receiving, at the implant a set of instructions from the second external device, storing the set of instructions in the implant to be used for verifying authenticity of a subsequently received set of instructions from the external device, wherein the computing unit is configured to verify the authenticity of further sets of instructions received by the transceiver according to any embodiment of the fifth part of aspect 249SE.

According to some embodiments of the eight part of aspect 249SE, the transceiver is configured to receive the set of instructions from the second external device using a proprietary network protocol.

According to some embodiments of the eight part of aspect 249SE, the set of instructions received by the implant from the second external device is encrypted, wherein the computing unit is configured to decrypt the set of instructions and store the decrypted set of instructions in the implant to be used for verifying authenticity of a subsequently received set of instructions from the external device.

According to some embodiments of any one of the fifth to eight part of aspect 249SE, the implant further comprising a reset switch, wherein the reset switch is configured to delete previously received instructions stored in the implant when being activated.

According to some embodiments of any one of the fifth to eight part of aspect 249SE, the reset switch is further configured to extract factory settings stored in the implant when being activated, wherein the factory settings comprises data to be used for verifying authenticity of a subsequently received set of instructions from the external device, wherein said activation of the reset switch causes said data to be stored in the implant as a set of instructions to be used for verifying authenticity of a subsequently received set of instructions from the external device.

In a ninth part of aspect 249SE, there is provided a system comprising an implant according to embodiments of any one of the fifth part to the eight part of aspect 249SE and an external device. The external device comprises a computing unit configured for: combining a first set of instructions with a previously transmitted set of instructions, forming a combined set of instructions, and transmitting the combined set of instructions to the implant.

In a tenth part of aspect 249SE, there is provided a system comprising an implant according to embodiments of the eight part of aspect 249SE, an external device and a second external device. The external device is configured to receive a set of instructions from the second external device, store said set of instructions, wherein the external device comprises a computing unit configured to combining a first set of instructions with a said stored set of instructions, forming a combined set of instructions, transmitting the combined set of instructions to the implant.

In an eleventh part of aspect 249SE, there is provided a computer program product comprising a computer-readable storage medium with instructions adapted to carry out at least parts of embodiments of any one of the first to third part of aspect 249SE when executed by a device having processing capability.

In a twelfth part of aspect 249SE, there is provided a computer program product configured to be used by the implant of any of embodiment of the first to fourth parts of aspect 249SE, when executed by the implant or external device having processing capability.

In a thirteenth part of aspect 249SE, there is provided a computer program product comprising a computer-readable storage medium with instructions adapted to carry out at least parts of any of embodiments of the fifth to eighth parts of aspect 249SE when executed by the implant or external device having processing capability According to some embodiments the implant of any one of the fifth to eighth parts of aspect 249SE, and/or with ability to use any of the methods of the first to fourth parts of aspect 249SE, and/or of the system of the ninth or tenth parts of aspect 249SE, and/or able to use a computer program product of the eleventh to thirteenth parts of aspect 249SE, wherein the implant comprises at least one of:

- a pacemaker unit, or an implantable cardioverter defibrillators,
- an external heart compression device,
- an apparatus assisting the pump function of a heart of the patient,
- an operable artificial heart valve,
- an implantable drug delivery device,
- a hydraulic, mechanic, and/or electric constriction implant,
- an operable volume filling device,
- an operable gastric band,
- an operable implant for stretching the stomach wall of the patient,
- an operable cosmetic implant,
- an implant controlling the emptying of a urinary bladder,
- an implant hindering urinary leakage,
- an implant hindering anal incontinence,
- an implant controlling the emptying of fecal matter,
- an implant monitoring an aneurysm,
- an implant lubricating a joint,
- an implant with a reservoir for holding bodily fluids
- an implant storing and/or emptying a bodily reservoir or a surgically created reservoir,
- an implant communicating with a database outside the body,
- an implant able to be programmed from outside the body,
- an implant able to be programmed from outside the body with a wireless signal,
- an implant treating impotence,
- an implant controlling the flow of eggs in the uterine tube,
- an implant controlling the flow of sperms,
- an implant treating osteoarthritis,
- an implant performing a test of parameters inside the body,
- an implant controlling specific treatment parameters from inside the body,
- an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

According to some embodiments the implant of any one of the fifth to eighth parts of aspect 249SE, and/or with ability to use any of the methods of the first to fourth parts of aspect 249SE, and/or of the system of the ninth or tenth parts of aspect 249SE, and/or able to use a computer program product of the eleventh to thirteenth parts of aspect 249SE comprises an internal control unit adapted to be involved in at least a part of the actions performed by the implant in at least a part of any one of the other embodiments of aspect 249SE.

In a fifteenth part of aspect 249SE there is provided a system comprising an implant of the fifth to eighth parts of the sixth aspect, an external device and a second external device, wherein the external device is configured to:

a. receive a set of instructions from the second external device, b. store said set of instructions, wherein the external device comprises a computing unit configured to:

c. combining a first set of instructions with a said stored set of instructions, forming a combined set of instructions, d. transmitting the combined set of instructions to the implant.

Aspect 250SE Dual Protocols—Two Wireless Communication Protocols for Communication—Embodiments of Aspect 250SE of the Disclosure In a first part of aspect 250SE, an external device configured for communication with an implant when implanted in a patient, is provided. The external device is further configured to communication with a second external device. The external device comprising at least one wireless transceiver configured for wireless communication with the second external device and the implant, wherein the wireless transceiver is configured to communicate with the implant using a proprietary network protocol, wherein the at least one wireless transceiver is configured to communicate with the second external device using a standard network protocol.

According to some embodiments of the first part of aspect 250SE, the at least one wireless transceiver comprises a first wireless transceiver configured for communicating with the second external device, and a second wireless transceiver) configured for communicating with the implant.

According to some embodiments of the first part of aspect 250SE, the external device further comprising a computing unit adapted for configuring the at least one wireless transceiver to communicate with the implant using the proprietary network protocol and adapted for configuring the at least one wireless transceiver to communicate with the second external device using the standard network protocol.

According to some embodiments of the first part of aspect 250SE, the standard network protocol is one from the list of:

Radio Frequency type protocol

RFID type protocol

WLAN type protocol

Bluetooth type protocol

BLE type protocol

NFC type protocol

3G/4G/5G type protocol

GSM type protocol.

According to some embodiments of the first part of aspect 250SE, a communication range of the proprietary network protocol is less than a communication range of the standard network protocol.

According to some embodiments of the first part of aspect 250SE, a frequency band of the proprietary network protocol differs from a frequency band of the standard network protocol.

According to some embodiments of the first part of aspect 250SE, the frequency band of the proprietary network protocol is 13.56 MHz, wherein the standard network protocol in one from the list of WLAN type protocol;

Bluetooth type protocol.

BLE type protocol

3G/4G/5G type protocol

GSM type protocol.

According to some embodiments of the first part of aspect 250SE, wherein the external device comprises: a sensor for measuring a parameter of the patient, by the external device, and an external computing unit configured for:

i. receiving a parameter of the patient, from the implant, ii. comparing the parameter measured by the external device to the parameter measured by the implant, and iii. performing authentication of a wireless connection with the implant based on the comparison.

According to some embodiments of the first part of aspect 250SE, the sensor is configured to measure a pulse of the patient.

According to some embodiments of the first part of aspect 250SE, the sensor is configured to measure a respiration rate of the patient.

According to some embodiments of the first part of aspect 250SE, the sensor is configured to measure a temperature of the patient.

According to some embodiments of the first part of aspect 250SE, the sensor is configured to measure at least one sound of the patient.

According to some embodiments of the first part of aspect 250SE, the sensor is configured to measure at least one physical movement of the patient.

According to some embodiments of the first part of aspect 250SE, the measured parameter, by the external device is provided with a timestamp and the measured parameter received from the implant is provided with a timestamp, wherein the comparison of the parameter measured at the implant to the parameter measured by the external device comprises comparing the timestamp of the measured parameter received from the implant to the timestamp of the measured parameter by the external device.

According to some embodiments of the first part of aspect 250SE, the external computing unit is configured to calculate a difference value between the parameter measured by the implant and the parameter measured by the external device, and wherein the external computing unit is further configured to authenticate the wireless connection if the difference value is less than a predetermined threshold difference value, and to not authenticate the wireless connection if the difference value equals or exceeds the predetermined threshold difference value.

According to some embodiments of the first part of aspect 250SE, the external device comprises a clock, configured for synchronization with a clock of the implant.

According to some embodiments of the first part of aspect 250SE, external device comprising an interface for receiving, by the patient, input to the external device, resulting in input authentication data, and a receiver for receiving authentication data from the implant, the authentication data relating to a generated sensation of a sensation generator connected to the implant. The external computing unit is configured for:

i. comparing the authentication data to the input authentication data, and ii. performing authentication of the connection based on the comparison.

According to some embodiments of the first part of aspect 250SE, the external device is one from the list of: a wearable external device, and a handset.

According to some embodiments of the first part of aspect 250SE, the external device is configured to be placed in electrical connection with a conductive member, for conductive communication with the implant.

In a second part of aspect 250SE, a method for communicating with an implant when implanted in a patient, and with a second external device, is provided. The method comprising: establishing wireless communication between at least one wireless transceiver of an external device and a second external device and the implant, wherein the communication between the external device and the implant uses a proprietary network protocol, and wherein the wireless communication between the external device and the second external device uses a standard network protocol.

According to some embodiments of the second part of aspect 250SE, the wireless communication between the external device and the second external device is performed by a first wireless transceiver of the at least one wireless transceiver and, wherein the wireless communication between the external device and the implant is performed by a second wireless transceiver of the at least one wireless transceiver.

According to some embodiments of the second part of aspect 250SE, the method further comprising the step of configuring, by a computing unit of the external device, the at least one wireless transceiver to communicate between the external device and the implant using a proprietary network protocol, and to communicate between the external device and the second external device using a standard network protocol.

According to some embodiments of the second part of aspect 250SE, the standard network protocol is one from the list of:

Radio Frequency type protocol
    RFID type protocol
    WLAN type protocol
    Bluetooth type protocol
    BLE type protocol
    NFC type protocol
    3G/4G/5G type protocol
    GSM type protocol.

According to some embodiments of the second part of aspect 250SE, a communication range of the proprietary network protocol is less than a communication range of the standard network protocol.

According to some embodiments of the second part of aspect 250SE, a frequency band of the proprietary network protocol differs from a frequency band of the standard network protocol.

According to some embodiments of the second part of aspect 250SE, the frequency band of the proprietary network protocol is 13.56 MHz, wherein the standard network protocol in one from the list of WLAN type protocol;
    Bluetooth type protocol
    BLE type protocol
    3G/4G/5G type protocol
    GSM type protocol.

According to some embodiments of the second part of aspect 250SE, the wireless communication between the external device and the implant is authenticated by the steps of:

i. measuring a parameter of the patient, by the external device ii. receiving a parameter of the patient, from the implant, iii. comparing the parameter measured by the external device to the parameter measured by the implant, and iv. performing authentication of a wireless connection based on the comparison.

According to some embodiments of the second part of aspect 250SE, the parameter of the patient is a pulse of the patient.

According to some embodiments of the second part of aspect 250SE, the parameter of the patient is a respiration rate of the patient.

According to some embodiments of the second part of aspect 250SE, the parameter of the patient is a temperature of the patient.

According to some embodiments of the second part of aspect 250SE, the parameter of the patient is at least one sound of the patient.

According to some embodiments of the second part of aspect 250SE, the parameter of the patient is at least one physical movement of the patient.

According to some embodiments of the second part of aspect 250SE, the measured parameter, by the external device is provided with a timestamp and the measured parameter received from the implant is provided with a timestamp, wherein the comparison of the parameter measured at the implant to the parameter measured by the external device comprises comparing the timestamp of the measured parameter received from the implant to the timestamp of the measured parameter by the external device.

According to some embodiments of the second part of aspect 250SE, the step of comparing the parameter measured by the implant to the parameter measured by the external device comprises calculating a difference value between the parameter measured by the implant and the parameter measured by the external device, wherein the step of performing authentication comprises: authenticating the wireless connection if the difference value is less than a predetermined threshold difference value, and not authenticating the wireless connection if the difference value equals or exceeds the predetermined threshold difference value.

According to some embodiments of the second part of aspect 250SE, the method further comprises synchronization of a clock of the external device with a clock of the implant.

According to some embodiments of the second part of aspect 250SE, method comprising placing a conductive member, configured to be in connection with the external device, in electrical connection with a skin of the patient for conductive communication with the implant.

According to some embodiments of the second part of aspect 250SE, the wireless communication between the external device and the implant is authenticated by the steps of:

generating, by a sensation generator, a sensation detectable by a sense of the patient, storing, by the implant, authentication data, related to the generated sensation, providing, by the patient, input to the external device, resulting in input authentication data.

authenticating the wireless communication based on a comparison of the input authentication data and the authentication data.

According to some embodiments of the second part of aspect 250SE, the method comprising the step of communicating data between the implant and the external device using the proprietary network protocol following positive authentication.

According to some embodiments of the second part of aspect 250SE, the method comprising establishing communication between the second externa device and a third external device, wherein the communication between the second externa device and the third external device is authenticated using a verification process at the third external device.

According to some embodiments of the second part of aspect 250SE, the third external device is operated by a caretaker of the patient.

According to some embodiments of the second part of aspect 250SE, the method comprising the step of authenticating the wireless communication between the external device and the second external device using a verification process at the second external device, wherein communication between the external device and the second external device requires the communication to be authenticated.

According to some embodiments of the second part of aspect 250SE, the second external device is operated by a caretaker of the patient.

In a third part of aspect 250SE, a computer-readable storage medium is provided. The computer-readable storage medium comprises instructions adapted to carry out the method of any embodiment of the second part of aspect 250SE when executed by a device having processing capability.

In a fourth part of aspect 250SE, a system comprising an external device according to any embodiment of the first part of aspect 250SE, and an implant implanted in the patient, is provided. The implant comprises a wireless receiver configured for receiving communication using the proprietary network protocol.

According to some embodiments of the fourth part of aspect 250SE, the wireless receiver of the implant is configured for only receiving communication using the proprietary network protocol.

According to some embodiments of the fourth part of aspect 250SE, an antenna of the wireless receiver of the implant is configured to only receive in a first frequency band, wherein the frequency band of the proprietary network protocol is included in the first frequency band.

According to some embodiments of the fourth part of aspect 250SE, the frequency band of the standard network protocol is not included in the first frequency band.

According to some embodiments of the fourth part of aspect 250SE, the implant comprises a computing unit configured to only altering an operation of the implant based on data received using the proprietary network protocol.

According to some embodiments of the fourth part of aspect 250SE, the system further comprising a second external device.

According to some embodiments of the fourth part of aspect 250SE, the second external device comprises an interface for authentication of the communication with external device, wherein communication between the external device and the second external device requires the communication to be authenticated.

According to some embodiments of the fourth part of aspect 250SE, the system further comprising a third external device configured to communicate with the second external device.

According to some embodiments of the fourth part of aspect 250SE, the third external device comprises an interface for authentication of the communication with the second external device, wherein communication between the third external device and the second external device requires the communication to be authenticated.

According to some embodiments of the fourth part of aspect 250SE, the third external device comprises an interface for authentication of the communication with the second external device, wherein communication between the third external device and the second external device requires the communication to be authenticated.

According to some embodiments of the fourth part of aspect 250SE, the third external device is operated by a caretaker of the patient.

According to some embodiments of the first part of aspect 250SE the external device is configured to communicate further data via the conductive communication with the implant.

In a fifth part of aspect 250SE, there is provided a computer program product of, or adapted to run on, an external device configured for communication with an implant when implanted in a patient, and with a second external device, the external device comprising at least one wireless transceiver configured for wireless communication with the second external device and the implant, wherein the computer program product is configured to cause the at least one wireless transceiver to communicate with the implant using a proprietary network protocol, wherein the computer program product is configured to cause the at least one wireless transceiver to communicate with the second external device using a standard network protocol.

According to some embodiments of the fifth part of aspect 250SE the at least one wireless transceiver comprises a first wireless transceiver and a second wireless transceiver, wherein the computer program product is configured to cause the first wireless transceiver to communicate with the second external device, and wherein the computer program product is configured to cause the second wireless transceiver to communicate with the implant.

According to some embodiments of the fifth part of aspect 250SE, The external device comprises a computing unit adapted for configuring the computer program product to cause the at least one wireless transceiver to communicate with the implant using the proprietary network protocol and adapted for configuring the computer program product to cause the at least one wireless transceiver to communicate with the second external device using the standard network protocol.

According to some embodiments of the fifth part of aspect 250SE the standard network protocol is one from the list of:
  Radio Frequency type protocol,
  RFID type protocol,
  WLAN type protocol,
  Bluetooth type protocol,
  BLE type protocol,
  NFC type protocol,
  3G/4G/5G type protocol, and
  GSM type protocol.

According to some embodiments of the fifth part of aspect 250SEa communication range of the proprietary network protocol is less than a communication range of the standard network protocol.

According to some embodiments of the fifth part of aspect 250SEa frequency band of the proprietary network protocol differs from a frequency band of the standard network protocol.

According to some embodiments of the fifth part of aspect 250SE the frequency band of the proprietary network protocol is 13.56 MHz, wherein the standard network protocol in one from the list of:
  WLAN type protocol,
  Bluetooth type protocol,
  BLE type protocol,
  3G/4G/5G type protocol, and
  GSM type protocol.

According to some embodiments of the fifth part of aspect 250SE the external device comprises:
  a sensor for measuring a parameter of the patient, by the external device, and
  an external computing unit, wherein the computer program product is configured to cause the external computing unit to:
  i. receive a parameter of the patient, from the implant,
  ii. compare the parameter measured by the external device to the parameter measured by the implant, and
  iii. perform authentication of a wireless connection with the implant based on the comparison, According to some embodiments of the fifth part of aspect 250SE the computer program product is configured to cause the sensor to measure a pulse of the patient.

According to some embodiments of the fifth part of aspect 250SE the computer program product is configured to cause the sensor to measure a respiration rate of the patient.

According to some embodiments of the fifth part of aspect 250SE the computer program product is configured to cause the sensor to measure a temperature of the patient.

According to some embodiments of the fifth part of aspect 250SE the computer program product is configured to cause the sensor to measure at least one sound of the patient.

According to some embodiments of the fifth part of aspect 250SE the computer program product is configured to cause the sensor to measure at least one physical movement of the patient.

According to some embodiments of the fifth part of aspect 250SE the measured parameter, by the external device is provided with a timestamp and the measured parameter received from the implant is provided with a timestamp, wherein the comparison of the parameter measured at the implant to the parameter measured by the external device comprises comparing the timestamp of the measured parameter received from the implant to the timestamp of the measured parameter by the external device.

According to some embodiments of the fifth part of aspect 250SE the computer program product is configured to cause the external computing unit to calculate a difference value between the parameter measured by the implant and the parameter measured by the external device, and wherein the computer program product is configured to cause the external computing unit to authenticate the wireless connection if the difference value is less than a predetermined threshold difference value, and to not authenticate the wireless connection if the difference value equals or exceeds the predetermined threshold difference value.

According to some embodiments of the fifth part of aspect 250SE the computer program product is configured to cause a clock of the external device, to be synchronized with a clock of the implant.

According to some embodiments of the fifth part of aspect 250SE the external device comprises:
  an interface for receiving, by the patient, input to the external device, resulting in input authentication data,
  a receiver for receiving authentication data from the implant, the authentication data relating to a generated sensation of a sensation generator connected to the implant, and
  an external computing unit, wherein the computer program product is configured to cause the external computing unit to:
  i. compare the authentication data to the input authentication data, and
  ii. perform authentication of the connection based on the comparison.

According to some embodiments of the fifth part of aspect 250SE the external device is configured to be placed in electrical connection with a conductive member, for conductive communication with the implant, and wherein the computer program product is configured to cause the external device to communicate further data via the conductive communication with the implant.

According to some embodiments, the implant of the system of the fourth part of aspect 250SE, and/or with ability to communicate with the external device of the first part of aspect 250SE, and/or with ability to use any of the methods of the second part of aspect 250SE, and/or with ability to use a computer program product of the third or fifth parts of aspect 250SE, wherein the implant comprises at least one of:
  a pacemaker unit, or an implantable cardioverter defibrillators,
  an external heart compression device,
  an apparatus assisting the pump function of a heart of the patient.
  an operable artificial heart valve,
  an implantable drug delivery device,
  a hydraulic, mechanic, and/or electric constriction implant,
  an operable volume filling device,
  an operable gastric band,
  an operable implant for stretching the stomach wall of the patient,
  an operable cosmetic implant,
  an implant controlling the emptying of a urinary bladder,
  an implant hindering urinary leakage,
  an implant hindering anal incontinence,
  an implant controlling the emptying of fecal matter,
  an implant monitoring an aneurysm,
  an implant lubricating a joint,
  an implant with a reservoir for holding bodily fluids
  an implant storing and/or emptying a bodily reservoir or a surgically created reservoir,
  an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

According to some embodiments, the implant of the system of the fourth part of aspect 250SE, and/or with ability to communicate with the external device of the first part of aspect 250SE, and/or with ability to use any of the methods of the second part of aspect 250SE, and/or with ability to use a computer program product of the third or fifth parts of aspect 250SE, comprises an internal control unit adapted to be involved in at least a part of the actions performed by the implant in at least a part of any one of the embodiments of aspect 250SE.

Aspect 251SE 2-Part Key NFC—Two Communication Methods for Sending Encryption Keys—Embodiments of Aspect 251SE of the Disclosure In a first part of aspect 251SE, a method for encrypted communication between an external device and an implant implanted in a patient is provided. The external device is adapted to communicate with the implant using two separate communication methods. A communication range of a first communication method is less than a communication range of a second communication method. The method for encrypted communication comprises sending a first part of a key from the external device to the implant, using the first communication method. The method for encrypted communication comprises sending a second part of the key from the external device to the implant, using the second communication method. The method for encrypted communication comprises sending encrypted data from the external device to the implant using the second communication method. The method for encrypted communication comprises deriving, in the implant a combined key from the first part of the key and second part of the key. The method for encrypted communication comprises decrypting the encrypted data, in the implant, using the combined key.

According to some embodiments of the first part of aspect 251SE the first communication method comprises RFID, Bluetooth, BLE, NFC, NFC-V, Infrared based communication, or Ultrasound based communication.

According to some embodiments of the first part of aspect 251SE the communication range of the first communication method is less than 10 meters.

According to some embodiments of the first part of aspect 251SE the communication range of the first communication method is less than 2 meters.

According to some embodiments of the first part of aspect 251SE a center frequency of a frequency band of the first communication method is 13.56 MHz or 27.12 MHz.

According to some embodiments of the first part of aspect 251SE the implant comprises a passive receiver for receiving the first part of the key.

According to some embodiments of the first part of aspect 251SE the passive receiver of the implant comprises a loop antenna.

According to some embodiments of the first part of aspect 251SE the method comprises limiting the communication range of the first communication method by adjusting the frequency and/or phase of the transmitted information.

According to some embodiments of the first part of aspect 251SE the method further comprises wirelessly receiving, at the implant, a third part of the key from a second external device. The combined key is now derived from the first part of the key, the second part of the key and the third part of the key.

According to some embodiments of the first part of aspect 251SE the external device is adapted to be in electrical connection with the implant, using the body as a conductor. The method may then further comprise confirming the electrical connection between the implant and the external device and, as a result of the confirmation, decrypting the encrypted data in the implant and using the decrypted data for instructing the implant.

According to some embodiments of the first part of aspect 251SE the second communication method comprises WLAN, Bluetooth, BLE, 3G/4G/5G, or GSM.

According to some embodiments of the first part of aspect 251SE the encrypted data comprises instructions for updating a control program running in the implant, wherein the implant comprises a computing unit configured to update a control program running in the implant using the decrypted data.

According to some embodiments of the first part of aspect 251SE the encrypted data comprises instructions for operating the implant, wherein the implant comprises a computing unit configured to operate the implant using the decrypted data.

According to some embodiments of the first part of aspect 251SE the method may further comprise the steps of:

Generating, by a sensation generator, a sensation detectable by a sense of the patient.

Storing, by the implant, authentication data, related to the generated sensation.

Providing, by the patient, input to the external device, resulting in input authentication data.

Authenticating the first or second communication method based on a comparison of the input authentication data and the authentication data.

As a result of positive authentication of the first or second communication method, decrypting the encrypted data in the implant and using the decrypted data for instructing the implant.

According to some embodiments of the first part of aspect 251SE the method may further comprise the step of transmitting the input authentication data from the external device to the implant, wherein the comparison is performed by the implant.

According to some embodiments of the first part of aspect 251SE the method may further comprise the steps of:

Measuring a parameter of the patient, by the implant.

Measuring the parameter of the patient, by the external device.

Comparing the parameter measured by the implant to the parameter measured by the external device.

Authenticating the first or second communication method based on the comparison.

As a result of positive authentication of the first or second communication method, decrypting the encrypted data in the implant and using the decrypted data for instructing the implant.

According to some embodiments of the first part of aspect 251SE the method may further comprise the step of transmitting the parameter measured by the external device from the external device to the implant, wherein the comparison is performed by the implant.

According to some embodiments of the first part of aspect 251SE the method further comprises placing a conductive member, configured to be in connection with the external device, in electrical connection with a skin of the patient for conductive communication with the implant.

According to some embodiments of the first part of aspect 251SE the communication is cancelled or amplified for at least one point by destructive or constructive interference respectively.

According to some embodiments of the first part of aspect 251SE the communication has a wavelength, $\lambda$ and the method comprises transmitting the communication from a first point located at a distance, D, away from the at least one point. The communication may be cancelled for the at least one point by transmitting the communication from a second point located at a distance $D \pm \frac{1}{2} z \lambda$ from the at least one point, wherein $z$ is any integer, or alternatively, the communication may be amplified for the at least one point by transmitting the communication from a second point located at a distance $D \pm z \lambda$ from the at least one point.

According to some embodiments of the first part of aspect 251SE the method further comprises transmitting the communication from a first point with a phase, P. The communication may be cancelled for the at least one point by transmitting the communication from a second point with a phase $P \pm z \pi$, wherein $z$ is any integer, or alternatively, the communication may be amplified for the at least one point by transmitting the communication from the second point with a phase $P \pm 2 z \pi$. For this, a distance between the first point and the at least one point equals the distance between the second point and the at least one point plus or minus any integer times a wavelength, $\lambda$, of the communication.

According to some embodiments of the first part of aspect 251SE the first point is a first transmitter and the second point is a second transmitter.

According to some embodiments of the first part of aspect 251SE the first point and the second point may be moved with respect to each other such that the at least one point is spatially shifted.

According to some embodiments of the first part of aspect 251SE the first point is associated with the implant and the second point is associated with the external device.

According to some embodiments of the first part of aspect 251SE the first point is a first slit and the second point is a second slit. The first and second slits may be adapted to receive the same communication from a single transmitter.

According to some embodiments of the first part of aspect 251SE a phase, P. of the communication is alternated as to spatially shift the at least one point.

According to some embodiments of the first part of aspect 251SE the method further comprises the steps of:

Transmitting the communication by the external device via the first and second points.

Measuring by the implant the interference for at least two points.

Comparing the measured interference with reference data pertaining to an authorized external device.

Authenticating the communication based on the results from comparing the measured interference with the reference data.

In a second part of aspect 251SE, there is provided an external device configured for encrypted communication with an implant implanted in a patient. The external device comprises a first and a second wireless transceiver for communication with the implant using two separate communication methods. A communication range of a first communication method is less than a communication range of the second communication method. The first wireless transceiver is configured to send a first part of a key to the implant, using the first communication method. The second wireless transceiver is configured to send a second part of a key to the implant, using the second communication method. The second wireless transceiver is further configured to send encrypted data the implant using the second communication method. The encrypted data is configured to be decrypted by a combined key derived from the first part of the key and second part of the key.

According to some embodiments of the second part of aspect 251SE the first communication method implemented by the first wireless transceiver comprises RFID, Bluetooth, BLE, NFC, NFC-V, Infrared based communication, or Ultrasound based communication.

According to some embodiments of the second part of aspect 251SE the communication range of the first communication method is less than 10 meters.

According to some embodiments of the second part of aspect 251SE the communication range of the first communication method is less than 2 meters.

According to some embodiments of the second part of aspect 251SE a center frequency of a frequency band of the first communication method is 13.56 MHz or 27.12 MHz.

According to some embodiments of the second part of aspect 251SE the first wireless transceiver comprises a loop antenna for transmission of data using the first communication method.

According to some embodiments of the second part of aspect 251SE the first wireless transceiver is configured to limit the communication range of the first communication method by adjusting a frequency and/or a phase of the communication.

According to some embodiments of the second part of aspect 251SE the second communication method implemented by the second wireless transceiver comprises WLAN, Bluetooth, BLE, 3G/4G/5G, or GSM.

According to some embodiments of the second part of aspect 251SE the encrypted data comprises instructions for updating a control program running in the implant.

According to some embodiments of the second part of aspect 251SE the encrypted data comprises instructions for operating the implant.

According to some embodiments of the second part of aspect 251SE the communication has a wavelength, $\lambda$. The external device transmits the communication from a first point located at a distance, D, away from at least one point. The communication may be cancelled for the at least one point by transmitting the communication from a second point located at a distance D±½ $\chi$λ from the at least one point, wherein $\chi$ is any integer, or alternatively, the communication may be amplified for the at least one point by transmitting the communication from a second point located at a distance D±22 from the at least one point.

According to some embodiments of the second part of aspect 251SE the communication has a phase, P. and wherein the external device transmits the communication from a first point. The communication may be cancelled for at least one point by transmitting the communication from a second point with a phase P± $\chi$π, wherein $\chi$ is any integer, or alternatively, the communication may be amplified for the at least one point by transmitting the communication from a second point with a phase P±2 $\chi$π. For this, a distance between the first point and the at least one point may equal the distance between the second point and the at least one point plus or minus any integer times a wavelength, λ, of the communication.

According to some embodiments of the second part of aspect 251SE the first point is a first transmitter and the second point is a second transmitter.

According to some embodiments of the second part of aspect 251SE the first point and the second point may be moved with respect to each other such that the at least one point is spatially shifted.

According to some embodiments of the second part of aspect 251SE the first point is associated with the implant and the second point is associated with the external device.

According to some embodiments of the second part of aspect 251SE the first point is a first slit and the second point is a second slit. The first and second slits are adapted to receive the same communication from a single transmitter.

According to some embodiments of the second part of aspect 251SE a phase, P. of the communication is alternated as to spatially shift the at least one point.

In a third part of aspect 251SE, there is provided an implant configured for encrypted communication with an external device, when implanted in a patient. The implant comprises a first and a second wireless receiver for communication with the external device using two separate communication methods. A communication range of a first communication method is less than a communication range of the second communication method. The first wireless receiver is configured to receive a first part of a key from the external device, using the first communication method. The second wireless receiver is configured to receive a second part of a key from the external device, using the second communication method. The second wireless receiver is further configured to receive encrypted data from the external device using the second communication method. The implant further comprises a computing unit configured to derive a combined key from the first part of the key and the second part of the key, and decrypt the encrypted data using the combined key.

According to some embodiments of the third part of aspect 251SE the first communication method implemented by the first wireless receiver comprises RFID, Bluetooth, BLE, NFC, NFC-V, Infrared based communication, or Ultrasound based communication.

According to some embodiments of the third part of aspect 251SE the communication range of the first communication method is less than 10 meters.

According to some embodiments of the third part of aspect 251SE the communication range of the first communication method is less than 2 meters.

According to some embodiments of the third part of aspect 251SE a center frequency of a frequency band of the first communication method is 13.56 MHz or 27.12 MHz.

According to some embodiments of the third part of aspect 251SE the first wireless receiver is a passive receiver for receiving the first part of the key.

According to some embodiments of the third part of aspect 251SE the passive receiver comprises a loop antenna.

According to some embodiments of the third part of aspect 251SE the implant is configured to wirelessly receive a third part of the key from a second external device. The computing unit may be configured to derive the combined key from the first part of the key, the second part of the key and the third part of the key.

According to some embodiments of the third part of aspect 251SE the implant is in electrical connection with the external device, using the body as a conductor. The implant further comprises an authentication unit configured to confirm the electrical connection between the implant and the external device. The computing unit is configured for, as a result of the confirmation, decrypting the encrypted data and using the decrypted data for instructing the implant.

According to some embodiments of the third part of aspect 251SE the second communication method implemented by the second wireless receiver comprises WLAN, Bluetooth, BLE, 3G/4G/5G, or GSM.

According to some embodiments of the third part of aspect 251SE the encrypted data comprises instructions for updating a control program running in the implant, wherein the computing unit is configured to update a control program running in the implant using the decrypted data.

According to some embodiments of the third part of aspect 251SE the encrypted data comprises instructions for operating the implant, wherein the computing unit is configured to operate the implant using the decrypted data.

According to some embodiments of the third part of aspect 251SE the implant further comprises a first sensor for measuring a parameter of the patient. The computing unit may be further configured for:

Receiving a parameter of the patient, from the external device.

Comparing the parameter measured by the implant to the parameter measured by the external device.

Authenticating the first or second communication method based on the comparison.

As a result of positive authentication of the first or second communication method, decrypting the encrypted data in the implant and using the decrypted data for instructing the implant.

According to some embodiments of the third part of aspect 251SE the implant may be connected to a sensation generator. The implant may be configured for storing authentication data, related to a sensation generated by the sensation generator, and receiving input authentication data from the external device. The implant may further comprise an internal computing unit configured for:

Authenticating the first or second communication method based on the comparison.

As a result of positive authentication of the first or second communication method, decrypting the encrypted data in the implant and using the decrypted data for instructing the implant.

According to some embodiments of the third part of aspect 251SE the implant may be further configured for:

Receiving the communication from a first and a second point of the external device.

Measuring the interference for at least two points.

Comparing the measured interference with reference data pertaining to an authorized external device.

Authenticating the communication based on the results from comparing the measured interference with the reference data.

In a fourth part of aspect 251SE, there is provided a system comprising an external device of the second part of aspect 251SE in communication with an implant of the third part of aspect 251SE.

According to some embodiments of the fourth part of aspect 251SE the system further comprises a conductive member configured to be in electrical connection with the external device. The conductive member may be configured to be placed in electrical connection with a skin of the patient for conductive communication with the implant.

According to some embodiments of the fourth part of aspect 251SE the system further comprises a second external device. The second external device may be configured for communication with the external device. The external device may be configured for receiving the encrypted data from the second external device and relaying the encrypted data to the implant using the second communication method.

According to some embodiments of the fourth part of aspect 251SE second external device comprises an interface for authentication of the communication with the external device. Communication between the external device and the second external device may require the communication to be authenticated.

According to some embodiments of the fourth part of aspect 251SE the second external device is operated by a healthcare provider of the patient.

According to some embodiments of the first part of aspect 251SE the method further comprises confirming, by the patient, the communication between the external device and the implant.

According to some embodiments of the first part of aspect 251SE the method further comprises sending a third part of the key from the external device to the implant, using a conductive communication method, wherein the combined key is derived from the first part of the key, the second part of the key and the third part of the key.

In a fifth part of aspect 251SE, there is provided a system comprising an external device according to the second part of aspect 251SE, further comprising a conductive member configured to be placed in electrical connection with a skin of a patient for conductive communication with an implant implanted in the patient.

According to some embodiments of the fifth part of aspect 251SE the conductive member is integrally connected to the external device.

According to some embodiments of the fifth part of aspect 251SE the conductive member comprises a wireless communication interface and is communicatively connected to the external device.

According to some embodiments of the third part of aspect 251SE the implant comprises at least one of:

a pacemaker unit, or an implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

In a sixth part of aspect 251SE, there is provided a computer program product of, or arranged to run on, an external device configured for encrypted communication with an implant implanted in a patient, the external device comprising a first and a second wireless transceiver for communication with the implant using two separate communication methods, wherein a communication range of a first communication method is less than a communication range of the second communication method, wherein the computer program product is configured to cause the first wireless transceiver to send a first part of a key to the implant, using the first communication method, wherein the computer program product is configured to cause the second wireless transceiver to send a second part of a key to the implant, using the second communication method, wherein the computer program product is configured to cause the second wireless transceiver to send encrypted data the implant using the second communication method, wherein the encrypted data is configured to be decrypted by a combined key derived from the first part of the key and the second part of the key.

According to some embodiments of the sixth part of aspect 251SE the first communication method implemented by the first wireless transceiver comprises one from a list of:

RFID,

Bluetooth,

BLE,

NFC,

NFC-V,

Infrared based communication, and

Ultrasound based communication.

According to some embodiments of the sixth part of aspect 251SE the communication range of the first communication method is less than 10 meters.

According to some embodiments of the sixth part of aspect 251SE the communication range of the first communication method is less than 2 meters.

According to some embodiments of the sixth part of aspect 251SE a frequency of a frequency band of the first communication method is 13.56 MHz or 27.12 MHz.

According to some embodiments of the sixth part of aspect 251SE the computer program product is configured to cause the first wireless transceiver to limit the communication range of the first communication method by adjusting the frequency and/or phase of the transmitted information.

According to some embodiments of the sixth part of aspect 251SE the second communication method implemented by the second wireless transceiver comprises one from a list of:

WLAN,

Bluetooth,

BLE,

3G/4G/5G, and

GSM.

According to some embodiments of the sixth part of aspect 251SE the encrypted data comprises instructions for updating a control program running in the implant.

According to some embodiments of the sixth part of aspect 251SE the encrypted data comprises instructions for operating the implant.

According to some embodiments of the sixth part of aspect 251SE the communication has a wavelength, $\lambda$, and wherein the computer program product is configured to cause the external device to transmit the communication from a first point located at a distance, D, away from at least one point, wherein the communication is cancelled for the at least one point by having the computer program product being configured to cause the external device to:

transmit the communication from a second point located at a distance $D\pm\frac{1}{2}\,\mathbb{Z}\lambda$ from the at least one point, wherein $\mathbb{Z}$ is any integer;

or alternatively, wherein the communication is amplified for the at least one point by having the computer program product being configured to cause the external device to:

transmit the communication from a second point located at a distance $D\pm\mathbb{Z}\lambda$ from the at least one point.

According to some embodiments of the sixth part of aspect 251SE the communication has a phase, P, and wherein the computer program product is configured to cause the external device to transmit the communication from a first point, wherein the communication is cancelled for at least one point by having the computer program product being configured to cause the external device to:

transmit the communication from a second point with a phase $P\pm\mathbb{Z}\pi$, wherein $\mathbb{Z}$ is any integer;

or alternatively, wherein the communication is amplified for the at least one point by having the computer program product being configured to cause the external device to:

transmit the communication from the second point with a phase $P\pm2\,\mathbb{Z}\pi$, wherein a distance between the first point and the at least one point equals the distance between the second point and the at least one point plus or minus any integer times a wavelength, $\lambda$, of the communication.

According to some embodiments of the sixth part of aspect 251SE the first point is a first transmitter and the second point is a second transmitter.

According to some embodiments of the sixth part of aspect 251SE the computer program product is configured to cause the first point and the second point to be moved with respect to each other such that the at least one point is spatially shifted.

According to some embodiments of the sixth part of aspect 251SE the first point is associated with the implant and wherein the second point is associated with the external device.

According to some embodiments of the sixth part of aspect 251SE the first point is a first slit and the second point is a second slit, the first and second slits being adapted to receive the same communication from a single transmitter.

According to some embodiments of the sixth part of aspect 251SE the computer program product is configured to cause a phase, P, of the communication to be alternated as to spatially shift the at least one point.

According to some embodiments the implant according to at least a part of any one of embodiments of the first, fifth, or sixth parts of aspect 251SE, comprises at least one of:

a pacemaker unit, or an implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof.

a vascular treatment device, and an implant adapted to move fluid inside the body of the patient.

According to some embodiments the implant according to, or presented in, any one of the embodiments of aspect 251SE, comprises an internal control unit adapted to be involved in at least a part of the actions performed by the implant in at least a part of any one of the embodiments of aspect 251SE.

Aspect 252SE Dual Systems—Two Communication Systems for Communication Between Implant and External Device—Embodiments of Aspect 252SE of the Disclosure In a first part of aspect 252SE, there is provided a method for communication between an external device and an implant when implanted in a patient, the method comprising:

using a first communication system for sending data from the external device to the implant, and using a second, different, communication system for receiving, at the external device, data from the implant.

According to embodiments of the first part of aspect 252SE, the implant comprises a computing unit configured for: receiving, at the implant, a first key from an external device, deriving a combined key using the first key and a second key held by the implant, decrypting the data using the combined key, and using the decrypted data for instructing the implant.

According to embodiments of the first part of aspect 252SE, the method further comprises:

receiving, at the implant a third key being generated by a second external device, separate from the external device or by another external device being a generator of the second key on behalf of the second external device, the third key being received at the implant from anyone of, the external device, the second external device, and the generator of the second key, and deriving the combined key using the first and third keys and the second key held by the implant.

According to embodiments of the first part of aspect 252SE, the method further comprises: confirming the connection via the first communication system between the implant and the external device, and as a result of the confirmation, instructing the implant based on data sent from the external device.

According to embodiments of the first part of aspect 252SE, the method further comprises: confirming the connection, via the first communication system, between the implant and the external device, and as a result of the confirmation, instructing the implant based on the decrypted data.

According to embodiments of the first part of aspect 252SE, the method further comprises: altering, by the computing unit, the operation of the implant based on the data decrypted in the implant.

According to embodiments of the first part of aspect 252SE, the first communication system is configured for wireless communication using a first network protocol, wherein the second communication system is configured for wireless communication using a second network protocol.

According to embodiments of the first part of aspect 252SE, the first or second network protocol is a proprietary network protocol, wherein the other network protocol is a standard network protocol.

According to embodiments of the first part of aspect 252SE, the method further comprises: using a third communication system, the third communication system being different than the first and second communication system, for sending data from a second external device, separate from the external device, to the implant.

According to embodiments of the first part of aspect 252SE, the data received at the external device from the implant comprises feedback signals from the implant including one or more from the list of: physiological or physical sensor parameters related to the status of the body of the patient, and physical or functional parameters related to status of the implant.

In a second part of aspect 252SE, there is provided an external device configured for communication with an implant when implanted in a patient, the external device comprising a first communication system for sending data to the implant, and a second, different, communication system for receiving data from the implant.

According to embodiments of the second part of aspect 252SE, the external device is configured for sending a first key to the implant using the first communication system, the first key being needed for decrypting the data.

According to embodiments of the second part of aspect 252SE, the external device is configured for sending a third key to the implant using the first communication system, the third key being generated by a second external device, separate from the external device or by another external device being a generator of the second key on behalf of the second external device, the third key being received at the external device and sent to the implant using the first communication system.

According to embodiments of the second part of aspect 252SE, the external device is further configured to: confirming the connection, via the first communication system, between the implant and the external device, wherein the external device is configured to communicate further data to the implant following positive confirmation.

According to embodiments of the second part of aspect 252SE, the further data comprises at least one of:

data for updating a control program running in the implant, and operation instructions for operating the implant.

According to embodiments of the second part of aspect 252SE, the first communication system is configured for wireless communication using a first network protocol, wherein the second communication system is configured for wireless communication using a second network protocol.

According to embodiments of the second part of aspect 252SE, the first or second network protocol is a proprietary network protocol, wherein the other network protocol is a standard network protocol.

According to embodiments of the second part of aspect 252SE, the data received at the external device is encrypted.

According to embodiments of the second part of aspect 252SE, the second communication system is configured to receive a first key from the implant, wherein the external device comprises a computing unit configured for: deriving a combined key using the first key with a second key held by the external device, and decrypting the encrypted data received from the implant using the combined key.

According to embodiments of the second part of aspect 252SE, the data received from the implant via the second communication system comprises feedback signals from the implant including one or more from the list of: physiological or physical sensor parameters related to the status of the body of the patient, and physical or functional parameters related to status of the implant.

In a third part of aspect 252SE, there is provided an implant configured for communication with an external device, when the implant is implanted in a patient, the implant comprising:

a first communication system for receiving data from the external device, a second, different, communication system for: sending data to the external device.

According to embodiments of the third part of aspect 252SE, the first communication system is further configured for receiving, by the first communication system, a first key from the implant, wherein the implant further comprises a computing unit configured to:

deriving a combined key using the first key with a second key held by the implant, decrypting the data using the combined key, using the decrypted data for instructing the implant.

According to embodiments of the third part of aspect 252SE, the implant is configured for receiving, from the external device or a second external device separate from the external device, a third key wherein the computing unit is configured to deriving the combined key using the first, second and third keys, and decrypting the data, in the implant, using the combined key.

According to embodiments of the third part of aspect 252SE, the implant further comprising a computing unit configured for:

confirming the connection via the first communication system between the implant and the external device, and as a result of the confirmation, instructing the implant based on the data sent from the external device.

According to embodiments of the third part of aspect 252SE, the computing unit is configured for altering the operation of the implant based on the data decrypted in the implant.

According to embodiments of the third part of aspect 252SE, the first communication system is configured for wireless communication using a first network protocol, wherein the second communication system is configured for wireless communication using a second network protocol.

According to embodiments of the third part of aspect 252SE, wherein the first or second network protocol is a proprietary network protocol, wherein the other network protocol is a standard network protocol.

According to embodiments of the third part of aspect 252SE, the data transmitted to the external device is encrypted, wherein the implant is further configured to transmit a first part of a key to the external device, the first part of the key being a part of a combined key to be used for decrypting the transmitted encrypted data.

According to embodiments of the third part of aspect 252SE, the data transmitted to the external device comprises feedback signals from the implant including one or more from the list of: physiological or physical sensor parameters related to the status of the body of the patient, and physical or functional parameters related to status of the implant.

According to embodiments of the first part of aspect 252SE, the data sent from the external device to the implant is encrypted data.

According to embodiments of the first part of aspect 252SE, the first communication system is a conductive communication system.

According to embodiments of the second part of aspect 252SE, the data sent to the implant is encrypted data.

According to embodiments of the second part of aspect 252SE, the first communication system is a conductive communication system.

According to embodiments of the third part of aspect 252SE, the data received from the external device is encrypted data.

According to embodiments of the third part of aspect 252SE, the first communication system is a conductive communication system.

According to embodiments the implant according to at least a part of; any one of method embodiments of the first part of aspect 252SE, and/or any of the implant embodiments of the third part of aspect 252SE, and/or any one of the computer product embodiments of the fourth part of aspect 252SE, wherein the implant comprises at least one of:

a pacemaker unit, or an implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

In a fourth part of aspect 252SE, there is provided a computer program product of, or arranged to run on, an external device configured for communication with an implant when implanted in a patient, the external device comprising a. a first communication system, wherein the computer program product is configured to cause the first communication system to be used for sending data to the implant, b. a second, different, communication system wherein the computer program product is configured to cause the second communication system to be used for receiving data from the implant.

According to embodiments of the fourth part of aspect 252SE the computer program product is configured to cause the external device to send a first key to the implant using the first communication system, the first key being needed for decrypting the data.

According to embodiments of the fourth part of aspect 252SE the computer program product is configured to cause the external device to send a third key to the implant using the first communication system, the third key being generated by a second external device, separate from the external device or by another external device being a generator of the second key on behalf of the second external device, the third key being received at the external device and sent to the implant using the first communication system.

According to embodiments of the fourth part of aspect 252SE the computer program product is configured to confirm the connection, via the first communication system, between the implant and the external device, wherein the computer program product is further configured to cause the external device to communicate further data to the implant following positive confirmation.

According to embodiments of the fourth part of aspect 252SE the further data comprises at least one of:

a. data for updating a control program running in the implant, and a. operation instructions for operating the implant.

According to embodiments of the fourth part of aspect 252SE the first communication system is configured for wireless communication using a first network protocol, wherein the second communication system is configured for wireless communication using a second network protocol.

According to embodiments of the fourth part of aspect 252SE the first or second network protocol is a proprietary network protocol, wherein the other network protocol is a standard network protocol.

According to embodiments of the fourth part of aspect 252SE the data received at the external device is encrypted.

According to embodiments of the fourth part of aspect 252SE the second communication system is configured to receive a first key from the implant, wherein the external device comprises a computing unit wherein the computer program product is configured to cause the computing unit to:

derive a combined key using the first key and a second key held by the external device, and decrypt the encrypted data received from the implant using the combined key.

According to embodiments of the fourth part of aspect 252SE the data received from the implant via the second communication system comprises feedback signals from the implant including one or more from the list of: physiological or physical sensor parameters related to the status of the body of the patient, and physical or functional parameters related to status of the implant.

According to embodiments of the fourth part of aspect 252SE the data sent to the implant is encrypted data.

According to embodiments of the fourth part of aspect 252SE the first communication system is a conductive communication system.

According to embodiments the implant according to at least a part of; any one of method embodiments of the first part of aspect 252SE, and/or any of the implant embodiments of the third part of aspect 252SE, and/or any one of the computer product embodiments of the fourth part of aspect 252SE comprising an internal control unit adapted to be involved in at least a part of the actions performed by the implant in at least a part of any one of the other embodiments of aspect 252SE.

Aspect 253SE Passive Proxy—Passive Proxy—Embodiments of Aspect 253SE of the Disclosure In a first part of tenth aspect, there is provided an external device for relaying communication between a second external device and an implant implanted in a patient. The external device comprises a wireless transceiver configured for wireless communication with the second external device and the implant. The wireless transceiver is configured to receive an instruction from the second external device. The wireless transceiver is configured to transmit the instruction to the implant. The external device further comprises a verification unit. The verification unit is configured to:

upon authentication of the relaying functionality of the external device, cause the wireless transceiver to transmit the instruction to the implant; and upon non-authentication or failed authentication of the relaying functionality of the external device, cause the external device to hold the instructions.

According to some embodiments of the first part of aspect 253SE the user is the patient in which the implant is implanted.

According to some embodiments of the first part of aspect 253SE the authentication input is a parameter of the patient.

According to some embodiments of the first part of aspect 253SE the user is a caregiver.

According to some embodiments of the first part of aspect 253SE the authentication input is a parameter of the caregiver.

According to some embodiments of the first part of aspect 253SE the authentication input is a code.

According to some embodiments of the first part of aspect 253SE the wireless transceiver is configured to receive the instruction from the second external device communicated using a first network protocol.

According to some embodiments of the first part of aspect 253SE the wireless transceiver is configured to transmit the instruction to the implant communicated using a second network protocol.

According to some embodiments of the first part of aspect 253SE the first network protocol is a standard network protocol from the list of:

Radio-frequency type protocol

Radio-frequency identification (RFID) type protocol

Wireless local-area network (WLAN)

Bluetooth

Bluetooth low energy (BLE)

Near-field communication (NFC)

3G/4G/5G

GSM

According to some embodiments of the first part of aspect 253SE the second network protocol is a proprietary network protocol.

According to some embodiments of the first part of aspect 253SE the instruction received at the external device is encrypted. The external device may be configured to transmit the instruction to the implant without decrypting the instruction According to some embodiments of the first part of aspect 253SE the second external device comprises an instruction provider adapted to receive instructions from a caregiver generating at least one component of the instruction.

According to some embodiments of the first part of aspect 253SE the external device is further adapted to receive authentication input from the caregiver, comprising at least one of a code and a parameter of the caregiver.

According to some embodiments of the first part of aspect 253SE a code is generated by the instruction provider.

According to some embodiments of the first part of aspect 253SE the authentication input comprises a single use code.

According to some embodiments of the first part of aspect 253SE the external device is configured to be placed in electrical connection with a conductive member, for conductive communication with the implant.

In a second part of tenth aspect, there is provided a method for relaying communication between a second external device and an implant implanted in a patient via a wireless transceiver of an external device.

The method comprises the steps of:

Receiving, by the wireless transceiver, an instruction from the second external device communicated using a first network protocol.

Receiving, by a verification unit, authentication input from a user.

Authenticating a relaying functionality of the external device based on the authentication input.

Upon authentication of the relaying functionality of the external device, transmitting, by the wireless transceiver, the instruction to the implant using a second network protocol, Upon non-authentication or failed authentication of the relaying functionality of the external device, holding the instructions at the external device. According to some embodiments of the second part of aspect 253SE the user is the patient in which the implant is implanted and wherein the implant is using a second network protocol to transmit that the relaying functionality of the external device is authenticated.

According to some embodiments of the second part of aspect 253SE the authentication input is a parameter of the patient.

According to some embodiments of the second part of aspect 253SE the user is a caregiver.

According to some embodiments of the second part of aspect 253SE the authentication input is a parameter of the caregiver.

According to some embodiments of the second part of aspect 253SE the authentication input is a code.

According to some embodiments of the second part of aspect 253SE the first network protocol is a standard network protocol from the list of:

Radio-frequency type protocol

RFID type protocol

WLAN

Bluetooth

BLE

NFC

3G/4G/5G

GSM

According to some embodiments of the second part of aspect 253SE the second network protocol is a proprietary network protocol.

According to some embodiments of the second part of aspect 253SE the instruction received at the external device is encrypted. The step of transmitting the instruction to the implant may then be performed without decrypting the instruction at the external device.

According to some embodiments of the second part of aspect 253SE the method further comprises the steps of:

Receiving, by an instruction provider of the second external device, instructions from a caregiver.

Generating at least one component of the instruction.

According to some embodiments of the second part of aspect 253SE the method further comprises providing, by the caregiver, authentication input comprising at least one of a code and a parameter of the caregiver.

According to some embodiments of the second part of aspect 253SE the method further comprises generation of a code by the instruction provider.

According to some embodiments of the second part of aspect 253SE the authentication input comprises a single use code.

According to some embodiments of the second part of aspect 253SE the method further comprises placing a conductive member, configured to be in connection with the external device, in electrical connection with a skin of the patient for conductive communication with the implant.

In a third part of tenth aspect, there is provided a system comprising an external device according to the first part of aspect 253SE and an implant implanted in a patient. The system further comprises a conductive member configured to be in electrical connection with the external device. The conductive member is configured to be placed in electrical connection with a skin of the patient for conductive communication with the implant.

According to some embodiments of the first part of aspect 253SE the external device is configured to decrypt the communication from the second external device at the external device and wherein the external device is further configured to transmit the decrypted communication to the implant via a short range communication method.

In a fourth part of aspect 253SE, there is provided a computer program product of, or arranged to run on, an external device for relaying communication between a second external device and an implant implanted in a patient, the external device comprising:

a wireless transceiver configured for wireless communication with the second external device and the implant, wherein the computer program product is configured to cause the wireless transceiver to receive an instruction from the second external device, wherein the computer program product is configured to cause the wireless transceiver to transmit the instruction to the implant, and a verification unit configured to receive authentication input from a user, for authenticating a relaying functionality of the external device, wherein the computer program product is configured to:

upon authentication of the relaying functionality of the external device, cause the wireless transceiver to transmit the instruction to the implant; and upon non-authentication or failed authentication of the relaying functionality of the external device, cause the external device to hold the instructions.

According to some embodiments of the fourth part of aspect 253SE the user is the patient in which the implant is implanted.

According to some embodiments of the fourth part of aspect 253SE the authentication input is a parameter of the patient.

According to some embodiments of the fourth part of aspect 253SE the authentication input is a code.

According to some embodiments of the fourth part of aspect 253SE the user is a caregiver.

According to some embodiments of the fourth part of aspect 253SE the authentication input is a parameter of the caregiver.

According to some embodiments of the fourth part of aspect 253SE the authentication input is a code.

According to some embodiments of the fourth part of aspect 253SE the wireless transceiver is configured to receive the instruction from the second external device communicated using a first network protocol.

According to some embodiments of the fourth part of aspect 253SE the wireless transceiver is configured to transmit the instruction to the implant communicated using a second network protocol.

According to some embodiments of the fourth part of aspect 253SE the first network protocol is a standard network protocol from the list of:

Radio-frequency type protocol,
RFID type protocol,
WLAN,
Bluetooth,
BLE,
NFC,
3G/4G/5G, and
GSM.

According to some embodiments of the fourth part of aspect 253SE the second network protocol is a proprietary network protocol.

According to some embodiments of the fourth part of aspect 253SE the instruction received at the external device is encrypted, and wherein the computer program product is configured to cause the external device to transmit the instruction to the implant without decrypting the instruction.

According to some embodiments of the fourth part of aspect 253SE the second external device comprises an instruction provider wherein the computer program product is configured to cause the instruction provider to receive instructions from a caregiver generating at least one component of the instruction.

According to some embodiments of the fourth part of aspect 253SE the computer program product is further configured to cause the external device to receive authentication input from the caregiver, comprising at least one of a code and a parameter of the caregiver.

According to some embodiments of the fourth part of aspect 253SE the computer program product is configured to cause a code to be generated by the instruction provider.

According to some embodiments of the fourth part of aspect 253SE the authentication input comprises a single use code.

According to some embodiments of the fourth part of aspect 253SE the computer program product is configured to cause the external device to decrypt the communication from the second external device at the external device and wherein the computer program product is further configured to cause the external device to transmit the decrypted communication to the implant via a short range communication method.

According to some embodiments the implant according to at least a part of any one of embodiments of aspect 253SE, comprises at least one of:

a pacemaker unit, or an implantable cardioverter defibrillators,
an external heart compression device,
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient,
an operable cosmetic implant,
an implant controlling the emptying of a urinary bladder,
an implant hindering urinary leakage,
an implant hindering anal incontinence,
an implant controlling the emptying of fecal matter,
an implant monitoring an aneurysm,
an implant lubricating a joint,
an implant with a reservoir for holding bodily fluids
an implant storing and/or emptying a bodily reservoir or a surgically created reservoir,
an implant communicating with a database outside the body,
an implant able to be programmed from outside the body,
an implant able to be programmed from outside the body with a wireless signal,
an implant treating impotence,
an implant controlling the flow of eggs in the uterine tube,
an implant controlling the flow of sperms,
an implant treating osteoarthritis,
an implant performing a test of parameters inside the body,
an implant controlling specific treatment parameters from inside the body,
an implant controlling bodily parameters from inside the body,
an implant controlling the blood pressure,
an implant controlling a drug treatment parameter,
an implant controlling a parameter in the blood,
an implant for adjusting or replacing any bone part of a body of the patient,
an implant replacing an organ of the patient or part of an organ of the patient or the function thereof,
a vascular treatment device, and
an implant adapted to move fluid inside the body of the patient.

According to some embodiments the implant according to, or presented in, any one of the embodiments of aspect 253SE, comprises an internal control unit adapted to be involved in at least a part of the actions performed by the implant in at least a part of any one of the embodiments of aspect 251SE.

Aspect 254SE Automatic Update—Automatic
Update of Control Program of
Implant—Embodiments of Aspect 254SE of the
Disclosure In a first part of aspect 254SE, there is provided a method for updating a control program adapted to run in a computing unit of an implant when implanted in a patient, the method comprising: receiving data by the computing unit, and updating, by the computing unit, the control program on the basis of the received data.

According to embodiments of the first part of aspect 254SE, the method further comprises: transmitting data from the implant to an external device, updating the control program, at the external device, on the basis of the received data, wherein the data received by the computing unit comprises the updated control program.

According to embodiments of the first part of aspect 254SE, the data transmitted from the implant comprises at least one physiological parameter of the patient.

According to embodiments of the first part of aspect 254SE, the data transmitted from the implant comprises at least one functional parameter of the implant.

According to embodiments of the first part of aspect 254SE, the method further comprises: sensing at least one parameter using an implantable sensor, wherein the received data by the computing unit comprises said at least one sensed parameter, and updating, by the computing unit, the control program on the basis of the at least one sensed parameter.

According to embodiments of the first part of aspect 254SE, the at least one parameter comprises at least one physiological parameter of the patient.

According to embodiments of the first part of aspect 254SE, the at least one parameter comprises at least one functional parameter of the implant.

According to embodiments of the first part of aspect 254SE, the method further comprises: the patient or a caregiver of the patient controlling the computing unit using at least one of an implantable manual receiver, an implantable switch and a remote control, the patient or caregiver providing feedback related to the operation of the implant, wherein the data received by the computing unit comprises said feedback, and the computing unit updating the control program on the basis of the patient feedback.

According to embodiments of the first part of aspect 254SE, the method further comprises: receiving feedback from at least one of, the patient in whom the implant is implanted and at least one sensor, in response to the control program controlling the implant, and updating, by the computing unit, the control program on the basis of the received feedback.

According to embodiments of the first part of aspect 254SE, the data received by the computing unit comprises said feedback.

According to embodiments of the first part of aspect 254SE, the method further comprises the steps of: —updating the control program, at an external device, on the basis of the said feedback, wherein the data received by the computing unit comprises the updated control program.

According to embodiments of the first part of aspect 254SE, the step of updating the control program comprises adjusting at least one parameter of the implant.

According to embodiments of the first part of aspect 254SE, the method further comprises the steps of: transmitting the received feedback to an external device, and wherein the received data by the computing unit comprises calibration parameters transmitted from the external device, said calibration parameters based on the feedback provided to the external device.

According to embodiments of the first part of aspect 254SE, the method further comprises the steps of: —receiving authentication input from a user for authenticating the updating of the control program, as a result of the authentication input, updating the control program by the computing unit.

According to embodiments of the first part of aspect 254SE, the implant is wirelessly connected to an external device, the external device configured to relay communication between a second external device and an implant, the method comprising the steps of: receiving, by a wireless transceiver in the external device, an instruction from the second external device communicated using a first network protocol, receiving, by a verification unit of the external device, authentication input from a user, authenticating the relay functionality of the external device based on the authentication input, and transmitting, by the wireless transceiver, the instruction to the implant, only if the relaying functionality of the external device is authenticated, using a second network protocol, wherein the data received by the computing unit comprises the instructions.

According to embodiments of the first part of aspect 254SE, the instructions comprises one of the updated control program, and calibration parameters of the implant.

According to embodiments of the first part of aspect 254SE, the authentication input is a parameter of the patient.

According to embodiments of the first part of aspect 254SE, the authentication input is a code.

According to embodiments of the first part of aspect 254SE, the first network protocol is a standard network protocol from the list of: a Radio Frequency type protocol, a RFID type protocol, a WLAN type protocol, a Bluetooth type protocol, a BLE type protocol, a NFC type protocol, a 3G/4G/5G type protocol, a GSM type protocol.

According to embodiments of the first part of aspect 254SE, the second network protocol is a proprietary network protocol.

According to embodiments of the first part of aspect 254SE, the data received by the computing unit is encrypted, the method further comprising the steps of: receiving, by the computing unit, at least one key, and decrypting the encrypted data using the at least one key.

In a second part of aspect 254SE, there is provided an implant, configured to update a control program adapted to run in a computing unit of the implant when implanted in a patient, the computing unit being configured for: receiving data, and updating the control program on basis of the received data.

According to embodiments of the second part of aspect 254SE, the implant is further configured for: transmitting data, using a transceiver, from the implant to an external device, as a response to the transmitted data, receiving, by the transceiver, an updated control program from the external device.

According to embodiments of the second part of aspect 254SE, the implant further comprises a sensor for sensing at least one physiological parameter of the patient, wherein the data transmitted from the implant comprises at least one physiological parameter of the implant.

According to embodiments of the second part of aspect 254SE, the data transmitted from the implant comprises at least one functional parameter of the implant.

According to embodiments of the second part of aspect 254SE, the implant is further in communication with an implantable sensor adapted to sense at least one parameter, wherein the received data by the computing unit comprises said at least one sensed parameter, wherein the computing unit is configured for updating, the control program on the basis of the at least one sensed parameter.

According to embodiments of the second part of aspect 254SE, the at least one parameter comprises at least one physiological parameter of the implant.

According to embodiments of the second part of aspect 254SE, the at least one parameter comprises at least one functional parameter of the implant.

According to embodiments of the second part of aspect 254SE, the computing unit is configured to be controlled by at least one of an implantable manual receiver, an implantable switch or a remote control to received feedback from the patient, wherein the computing unit is configured to update the control program on the basis of the patient feedback.

According to embodiments of the second part of aspect 254SE, the implant is configured to receive feedback from at least one of, the patient in whom the implant is implanted and at least one sensor, in response to the control program controlling the implant, wherein the computing unit is configured to update the control program on the basis of the received feedback.

According to embodiments of the second part of aspect 254SE, the implant is configured to transmit the received feedback to an external device, and as a response there to, receiving data by the computing unit comprising calibration parameters transmitted from the external device, said calibration parameters based on the feedback provided to the external device.

According to embodiments of the second part of aspect 254SE, the computing unit is configured to update the control program by adjusting at least one parameter of the implant.

According to embodiments of the second part of aspect 254SE, the computing unit is configured to receive authentication input from a user for authenticating the updating of the control program, and as a result of the authentication input, update the control program by the computing unit.

According to embodiments of the second part of aspect 254SE, wherein the data received by the computing unit is encrypted, wherein the computing unit is further configured for: receiving at least one key, decrypting the encrypted data using the at least one key.

In a third part of aspect 254SE, there is provided a system comprising an implant according to the second part of aspect 254SE, wirelessly connected to an external device, the external device configured to relay communication between a second external device and an implant, the external device comprising:

a wireless transceiver configured for wireless communication with the second external device and the implant, the wireless transceiver configured to receive an instruction from the second external device communicated using a first network protocol, wherein the wireless transceiver is configured to transmit the instruction to the implant using a second network protocol, and a verification unit configured to receive authentication input from a user, for authenticating the relaying functionality of the external device, wherein the wireless transceiver is configured to transmit the instruction to the implant only if the relaying functionality of the external device is authenticated, wherein the data received by the computing unit of the implant comprises the instructions.

According to embodiments of the third part of aspect 254SE, the instructions comprises one of the updated control program, and calibration parameters of the implant.

According to embodiments of the third part of aspect 254SE, the authentication input is a parameter of the patient.

According to embodiments of the third part of aspect 254SE, the authentication input is a code.

According to embodiments of the third part of aspect 254SE, the first network protocol is a standard network protocol from the list of: a Radio Frequency type protocol, a RFID type protocol, a WLAN type protocol, a Bluetooth type protocol, a BLE type protocol, a NFC type protocol, a 3G/4G/5G type protocol, a GSM type protocol.

According to embodiments of the third part of aspect 254SE, the second network protocol is a proprietary network protocol.

According to embodiments of the first part of aspect 254SE a first communication system is used for receiving data by the computing unit of the implant, and wherein a second communication system is used for transmitting data from the implant to the external device.

According to embodiments of the first part of aspect 254SE the method further comprises relaying data to the second external device and receiving the updated control program at the second external device.

According to embodiments of the first part of aspect 254SE a caregiver transmits data to the implant from a second external device directly or via the external device.

According to embodiments of the first part of aspect 254SE a connection between the implant and the external device is authenticated by a conductive communication or connection between the implant and the external device.

According to embodiments of the second part of aspect 254SE the implant comprises at least one of:

According to some embodiments the implant according to at least a part of any one of embodiments of aspect 254SE, such as the second part of aspect 254SE, comprises at least one of:

a pacemaker unit, or an implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

According to some embodiments the implant according to, or presented in, any one of the embodiments of aspect 254SE, e.g. the second part of aspect 254SE, comprises an internal control unit adapted to be involved in at least a part of the actions performed by the implant in at least a part of any one of the embodiments of aspect 254SE.

Aspect 255SE Information from Implant—Information from Implant—Embodiments of Aspect 255SE of the Disclosure In a first part of aspect 255SE there is provided an implant. The implant comprises at least one sensor for sensing at least one physiological parameter of the patient and a communication unit configured to transmit the sensed parameter from the body of the patient to an external device. The implant comprises at least one vascular portion configured to be placed in proximity to a blood vessel of the patient, and the vascular portion comprises the sensor. The sensor is a sensor configured to sense at least one parameter related to the blood of the patient.

According to some embodiments of the first part of aspect 255SE the vascular portion comprises at least one needle for extracting blood from the blood vessel for transport to the at least one sensor.

According to some embodiments of the first part of aspect 255SE the vascular portion further comprises a needle operating device configured to displace the needle such that the needle can change from extracting blood at a first site to extracting blood at a second site.

According to some embodiments of the first part of aspect 255SE the sensor is an optical sensor configured to optically sense at least one parameter of the blood of the patient.

According to some embodiments of the first part of aspect 255SE the sensor is configured for spectrophotometry.

According to some embodiments of the first part of aspect 255SE the optical sensor is configured to sense visible light.

According to some embodiments of the first part of aspect 255SE the optical sensor is configured to sense UV light.

According to some embodiments of the first part of aspect 255SE the optical sensor is configured to sense IR radiation.

According to some embodiments of the first part of aspect 255SE the at least one sensor is configured to sense at least one of: oxygen saturation, blood pressure, a parameter related to the function of the liver, a parameter related to the existence of cancer, a parameter related to the bile function, glucose, lactate, pyruvate, prostate-specific antigen, cholesterol level, potassium, sodium, cortisol, adrenalin, ethanol, parameters relating to blood composition, platelets, white blood cells, red blood cells, viscosity, a parameter relating to flux, a parameter relating to the direction of flow, a parameter relating to flow velocity, blood plasma concentration, a parameter relating to hormones, a parameter relating to enzyme activity, calcium, iron, iron-binding capacity, transferrin, ferritin, ammonia, copper, ceruloplasmin, phosphate, zinc, magnesium, pH, oxygen partial pressure, carbon dioxide, bicarbonate, protein(s), a parameter relating to blood lipids, tumor markers, vitamins, toxins, antibodies, and electrolytes, a drug level, the level of a drug transposed into different a substance, a treatment marker level, an antigen level, an antibody level, an immunoglobin level.

According to some embodiments of the first part of aspect 255SE the at least one sensor is configured to sense at least one of: a parameter related to the effect of a therapeutic treatment and the presence of a pharmaceutical or a substance caused by the pharmaceutical.

According to some embodiments of the first part of aspect 255SE the at least one sensor is configured to sense the presence of at least one of: an antibiotic pharmaceutical, a chemotherapy pharmaceutical and insulin or a substance caused by anyone of the preceding.

According to some embodiments of the first part of aspect 255SE the at least one sensor is configured to sense a parameter related the effect of at least one of: a cancer treatment and an antibiotic treatment.

In a second part of aspect 255SE there is provided an implant, wherein the implant comprises at least one sensor for sensing at least one physiological parameter of the patient and a communication unit configured to transmit the sensed parameter from the body of the patient to an external device. The implant comprises at least one food passageway portion configured to be placed in proximity to the food passageway of the patient, and wherein the food passageway portion comprises the sensor, and wherein the sensor is a sensor configured to sense at least one parameter related to the food passageway of the patient.

According to some embodiments of the second part of aspect 255SE the sensor is a sensor configured to sense at least one of intestinal activity, activity of the stomach and activity of the esophagus.

According to some embodiments of the second part of aspect 255SE the sensor is at least one of an accelerometer, a motility sensor, and a strain sensor.

According to some embodiments of the second part of aspect 255SE the sensor is a sensor configured to sense an electrical parameter.

According to some embodiments of the second part of aspect 255SE the sensor is a sensor configured to sense any parameter relating to the contents of at least one of: an intestine, the stomach, and the esophagus.

According to some embodiments of the second part of aspect 255SE the food passageway portion comprises at least one needle for extracting contents from the food passageway for transport to the at least one sensor.

According to some embodiments of the second part of aspect 255SE the food passageway portion further comprises a needle operating device configured to displace the needle such that the needle can change from extracting contents from the food passageway at a first site to extracting contents of the food passageway at a second site.

According to some embodiments of the second part of aspect 255SE the sensor is an optical sensor configured to optically sense at least one parameter of the food passageway of the patient.

According to some embodiments of the second part of aspect 255SE the optical sensor is configured for spectrophotometry.

According to some embodiments of the second part of aspect 255SE the optical sensor is configured to sense visible light.

According to some embodiments of the second part of aspect 255SE the optical sensor is configured to sense UV light.

According to some embodiments of the second part of aspect 255SE the optical sensor is configured to sense IR radiation.

According to some embodiments of the second part of aspect 255SE the sensor is a sensor configured to directly or indirectly and precisely or approximately sense the passage of food down the food passageway, including at least one of solid food passing down the food passageway, liquid passing down the food passageway, and the number of swallowing of contents passing down the food passageway of at least one of: an intestine, the stomach and the esophagus.

According to some embodiments of the second part of aspect 255SE the sensor is an audio sensor configured to sense a sound parameter of the food passageway of the patient.

According to some embodiments of the second part of aspect 255SE the sensor is an audio sensor configured to sense a sound parameter of the intestine of the patient.

In a third part of aspect 255SE there is provided an implant, wherein the implant comprises at least one sensor for sensing at least one physiological parameter of the patient and a communication unit configured to transmit the sensed parameter from the body of the patient to an external device. The at least one sensor is an ultrasound sensor configured to sense the at least one parameter of the patient using ultrasound.

According to some embodiments of the third part of aspect 255SE the implant comprises a cardiac portion, and the cardiac portion comprises the ultrasound sensor, and the ultrasound sensor is configured to sense at least one parameter related to the heart of the patient.

According to some embodiments of the third part of aspect 255SE the ultrasound sensor is configured to sense the blood flow in the heart.

According to some embodiments of the third part of aspect 255SE the ultrasound sensor is configured to sense the presence of fluid in the pericardial cavity.

According to some embodiments of the third part of aspect 255SE the ultrasound sensor is configured to sense the presence of an assembly of fluid in the body of the patient.

According to some embodiments of the third part of aspect 255SE the ultrasound sensor is configured to sense the level of urine in the urinary bladder.

In a fourth part of aspect 255SE there is provided an implant, wherein the implant comprises at least one sensor for sensing at least one physiological parameter of the patient and a communication unit configured to transmit the sensed parameter from the body of the patient to an external device, wherein the implant comprises a cardiac portion. The cardiac portion comprises the sensor. The sensor is configured to sense at least one parameter related to the heart of the patient.

According to some embodiments of the fourth part of aspect 255SE the sensor is configured to sense at least one parameter related to the electrical activity of the heart.

According to some embodiments of the fourth part of aspect 255SE the sensor is configured to sense at least one sound parameter related to the heart.

In a fifth part of aspect 255SE there is provided an implant, wherein the implant comprises at least one sensor for sensing at least one physiological parameter of the patient and a communication unit configured to transmit the sensed parameter from the body of the patient to an external device, wherein the implant comprises a pulmonary portion. The pulmonary portion comprises the sensor, and the sensor is configured to sense at least one parameter related to the lungs of the patient.

According to some embodiments of the fifth part of aspect 255SE the sensor is a sensor configured to sense respiratory activity.

According to some embodiments of the fifth part of aspect 255SE the sensor is at least one of an accelerometer, a motility sensor, and a strain sensor.

According to some embodiments of the fifth part of aspect 255SE the sensor is an optical sensor configured to optically sense at least one parameter of the lungs of the patient.

According to some embodiments of the fifth part of aspect 255SE the sensor is an audio sensor configured to sense a sound parameter of the lungs of the patient.

In a sixth part of aspect 255SE there is provided an implant, wherein the implant comprises at least one sensor for sensing at least one physiological parameter of the patient and a communication unit configured to transmit the sensed parameter from the body of the patient to an external device, wherein the implant comprises a urinary portion. The urinary portion comprises the sensor, and the sensor is configured to sense at least one parameter related to the urine bladder of the patient.

According to some embodiments of the sixth part of aspect 255SE the sensor is an optical sensor configured to optically sense at least one parameter of the urine bladder of the patient.

According to some embodiments of the sixth part of aspect 255SE the sensor is a sensor configured to sense activity of the urinary bladder.

According to some embodiments of the sixth part of aspect 255SE the sensor is at least one of an accelerometer, a motility sensor, and a strain sensor.

In a seventh part of aspect 255SE there is provided an implant, wherein the implant comprises at least one sensor for sensing at least one physiological parameter of the patient and a communication unit configured to transmit the sensed parameter from the body of the patient to an external device, wherein the at least one sensor is an audio sensor configured to sense the at least one audio parameter of the patient.

According to some embodiments of the seventh part of aspect 255SE the sensor is a sensor configured to sense an audio parameter related to an activity of the gastrointestinal system.

According to some embodiments of the seventh part of aspect 255SE the sensor is a sensor configured to sense an audio parameter related to an activity of the lungs of the patient.

According to some embodiments of the seventh part of aspect 255SE the sensor is a sensor configured to sense an audio parameter related to an activity of the heart of the patient.

According to some embodiments of the seventh part of aspect 255SE the sensor is a sensor configured to sense an audio parameter related to the voice of the patient.

In an eighth part of aspect 255SE there is provided an implant, wherein the implant comprises at least one sensor for sensing at least one physiological parameter of the patient and a communication unit configured to transmit the sensed parameter from the body of the patient to an external device, wherein the at least one sensor is an audio sensor configured to sense the at least one audio parameter of the patient.

According to some embodiments of the eighth part of aspect 255SE the sensor is a sensor configured to sense an audio parameter related to an activity of the gastrointestinal system.

According to some embodiments of the eighth part of aspect 255SE the sensor is a sensor configured to sense an audio parameter related to an activity of the lungs of the patient.

According to some embodiments of the eighth part of aspect 255SE the sensor is a sensor configured to sense an audio parameter related to an activity of the heart of the patient.

According to some embodiments of the eighth part of aspect 255SE the sensor is a sensor configured to sense an audio parameter related to the voice of the patient.

In a ninth part of aspect 255SE there is provided a system comprising an implant, implanted in a patient, an external device, and a second external device. The external device is configured to transmit data pertaining to the sensed parameter to the second external device. The external device is configured to add information to the data pertaining to the sensed parameter before transmitting to the second external device.

According to some embodiments of the ninth part of aspect 255SE the external device comprises a sensor for recording the information to be added to the data pertaining to the sensed parameter.

According to some embodiments of the ninth part of aspect 255SE the sensor comprises a thermometer or a geographical positioning sensor such as a global navigation satellite system, GNSS, receiver.

According to some embodiments of the ninth part of aspect 255SE the external device is configured to automatically add the information to the data pertaining to the sensed parameter.

According to some embodiments of the ninth part of aspect 255SE the external device is configured to, upon a manual input from a user, add the information to the data pertaining to the sensed parameter.

According to some embodiments of the ninth part of aspect 255SE the information added comprises at least one of:

a weight of the patient,
a height of the patient,
a body temperature of the patient,
eating habits of the patient,
physical exercise habits of the patient,
toilet habits of the patient,
an outside or external temperature of the patient, and
geographic position data of the patient.

According to some embodiments of the first through eighth parts of aspect 255SE the implant comprises at least one of:

a pacemaker unit, or an implantable cardioverter defibrillators,
an external heart compression device,
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient, an operable cosmetic implant,
an implant controlling the emptying of a urinary bladder,
an implant hindering urinary leakage,
an implant hindering anal incontinence,
an implant controlling the emptying of fecal matter,
an implant monitoring an aneurysm,
an implant lubricating a joint,
an implant with a reservoir for holding bodily fluids
an implant storing and/or emptying a bodily reservoir or a surgically created reservoir,
an implant communicating with a database outside the body,
an implant able to be programmed from outside the body,
an implant able to be programmed from outside the body with a wireless signal,
an implant treating impotence,
an implant controlling the flow of eggs in the uterine tube,
an implant controlling the flow of sperms,
an implant treating osteoarthritis,
an implant performing a test of parameters inside the body,
an implant controlling specific treatment parameters from inside the body,
an implant controlling bodily parameters from inside the body,
an implant controlling the blood pressure,
an implant controlling a drug treatment parameter,
an implant controlling a parameter in the blood,
an implant for adjusting or replacing any bone part of a body of the patient,
an implant replacing an organ of the patient or part of an organ of the patient or the function thereof,
a vascular treatment device, and
an implant adapted to move fluid inside the body of the patient.
an implant for adjusting or replacing any bone part of a body of the patient,
an implant replacing an organ of the patient or part of an organ of the patient or the function thereof,
a vascular treatment device, and
an implant adapted to move fluid inside the body of the patient.

According to some embodiments of the first through eighth parts of aspect 255SE the implant comprises an internal control unit adapted to be involved in at least a part of the actions performed by the implant in at least a part of any one of the embodiments of aspect 255SE.

Aspect 256SE Device Synchronization Patient Parameter—Authenticating a Connection Between an Implant and the External Device Using a Patient Parameter—Embodiments of Aspect 256SE of the Disclosure In a first part of aspect 256SE, there is provided a method of authenticating a connection between an implant implanted in a patient, and an external device. The method comprises establishing a connection between the external device and the implant, measuring a parameter of the patient, by the implant, measuring the parameter of the patient, by the external device, comparing the parameter measured by the implant to the parameter measured by the external device, and performing authentication of the connection based on the comparison.

According to some embodiments of the first part of aspect 256SE the method further comprises the step of transmitting the parameter measured by the external device from the external device to the implant, wherein the comparison is performed by the implant.

According to some embodiments of the first part of aspect 256SE the method further comprises the step of transmitting the parameter measured by the implant from the implant to the external device, wherein the comparison is performed by the external device.

According to some embodiments of the first part of aspect 256SE the parameter of the patient is related to a pulse of the patient.

According to some embodiments of the first part of aspect 256SE the parameter of the patient is related to a blood oxygen saturation of a patient.

According to some embodiments of the first part of aspect 256SE the parameter of the patient is related to a respiration rate of the patient.

According to some embodiments of the first part of aspect 256SE the parameter of the patient is related to a temperature of the patient.

According to some embodiments of the first part of aspect 256SE the parameter of the patient is related to at least one sound of the patient.

According to some embodiments of the first part of aspect 256SE the parameter of the patient is related to at least one physical movement of the patient.

According to some embodiments of the first part of aspect 256SE the measured parameter at the implant is provided with a timestamp and the measured parameter at the external device is provided with a timestamp. The step of comparing the parameter measured at the implant to the parameter measured by the external device comprises comparing the timestamp provided by the implant to the timestamp provided by the external device.

According to some embodiments of the first part of aspect 256SE the method further comprises the step of synchronizing a clock of the implant with a clock of the external device.

According to some embodiments of the first part of aspect 256SE the step of comparing the parameter measured by the implant to the parameter measured by the external device comprises calculating a difference value between the parameter measured by the implant and the parameter measured by the external device. The step of performing authentication comprises authenticating the connection if the difference value is less than a predetermined threshold difference value, and not authenticating the connection if the difference value equals or exceeds the predetermined threshold difference value.

According to some embodiments of the first part of aspect 256SE the method further comprises placing a conductive member, configured to be in connection with the external device, in electrical connection with a skin of the patient for conductive communication with the implant.

According to some embodiments of the first part of aspect 256SE the communication between the implant and the external device is a wireless communication.

According to some embodiments of the first part of aspect 256SE the communication between the implant and the external device is a conductive communication.

According to some embodiments of the first part of aspect 256SE further comprising the step of communicating further data between the implant and the external device following positive authentication.

According to some embodiments of the first part of aspect 256SE the method further comprising determining a cryptographic hash based on the parameter as measured by at least one of the external device and the implant, wherein the further data comprises the cryptographic hash.

According to some embodiments of the first part of aspect 256SE the further data is communicated from the external device to the implant, wherein the further data comprises at least one of: data for updating a control program running in the implant, and operation instructions for operating the implant.

According to some embodiments of the first part of aspect 256SE wherein the further data is communicated from the implant to the external device, wherein the further data comprises data sensed by a sensor connected to the implant.

According to some embodiments of the first part of aspect 256SE wherein the comparison is performed by the implant. The method further comprises the step of continuously requesting by the external device, or receiving at the external device, information of an authentication status of the connection between the implant and the external device, and upon determining, at the external device, that the connection is authenticated, transmitting further data from the external device to the implant.

According to some embodiments of the first part of aspect 256SE the comparison is performed by the external device. The method further comprises the step of continuously requesting by the implant, or receiving at the implant, information of an authentication status of the connection between the implant and the external device, and upon determining, at the implant, that the connection is authenticated, transmitting further data from the implant to the external device.

In a second part of aspect 256SE, there is provided an implant, implanted in a patient, adapted for connection with an external device. The implant comprises a first sensor for measuring a parameter of the patient. The implant further comprises an internal computing unit. The internal computing unit is configured for receiving a parameter of the patient, from the external device. The internal computing unit is further configured for comparing the parameter measured by the implant to the parameter measured by the external device. The internal computing unit is further configured for performing authentication of the connection based on the comparison.

According to some embodiments of the second part of aspect 256SE the first sensor is configured to measure a pulse of the patient.

According to some embodiments of the second part of aspect 256SE the first sensor is configured to measure a respiration rate of the patient.

According to some embodiments of the second part of aspect 256SE the first sensor is configured to measure a temperature of the patient.

According to some embodiments of the second part of aspect 256SE the first sensor is configured to measure at least one sound of the patient.

According to some embodiments of the second part of aspect 256SE the first sensor is configured to measure at least one physical movement of the patient.

According to some embodiments of the second part of aspect 256SE the measured parameter, by the implant is provided with a timestamp. The measured parameter received from the external device is provided with a timestamp. The comparison of the parameter measured at the implant to the parameter measured by the external device comprises comparing the timestamp of the measured parameter by the implant to the timestamp of the measured parameter received from the external device.

According to some embodiments of the second part of aspect 256SE the implant comprises a clock, configured for synchronization with a clock of the external device.

According to some embodiments of the second part of aspect 256SE the internal computing unit is configured to calculate a difference value between the parameter measured by the implant and the parameter measured by the external device. The internal computing unit is further configured to authenticate the connection if the difference value is less than a predetermined threshold difference value, and to not authenticate the connection if the difference value equals or exceeds the predetermined threshold difference value According to some embodiments of the second part of aspect 256SE the communication between the implant and the external device is a wireless communication.

According to some embodiments of the second part of aspect 256SE the communication between the implant and the external device is a conductive communication.

According to some embodiments of the second part of aspect 256SE the implant is configured to communicate further data to the external device following positive authentication.

According to some embodiments of the second part of aspect 256SE the implant is further configured to determine a cryptographic hash based on the parameter as measured by at least one of the external device and the implant, wherein the further data comprises the cryptographic hash.

According to some embodiments of the second part of aspect 256SE the further data comprises data sensed by the sensor or another sensor connected to the implant.

In a third part of aspect 256SE, there is provided an external device, adapted for connection with an implant, implanted in a patient. The external device comprises a second sensor for measuring a parameter of the patient, by the external device. The external device further comprises an external computing unit. The external computing unit is configured for receiving a parameter of the patient, from the implant. The external computing unit is further configured for comparing the parameter measured by the external device to the parameter measured by the implant. The external computing unit is further configured for performing authentication of the connection based on the comparison.

According to some embodiments of the third part of aspect 256SE the second sensor is configured to measure a pulse of the patient.

According to some embodiments of the third part of aspect 256SE the second sensor is configured to measure a respiration rate of the patient.

According to some embodiments of the third part of aspect 256SE the second sensor is configured to measure a temperature of the patient.

According to some embodiments of the third part of aspect 256SE the second sensor is configured to measure at least one sound of the patient.

According to some embodiments of the third part of aspect 256SE the second sensor is configured to measure at least one physical movement by the patient.

According to some embodiments of the third part of aspect 256SE the measured parameter, by the external device is provided with a timestamp. The measured parameter received from the implant is provided with a timestamp. The comparison of the parameter measured at the implant to the parameter measured by the external device comprises comparing the timestamp of the measured parameter received from the implant to the timestamp of the measured parameter by the external device.

According to some embodiments of the third part of aspect 256SE the external device comprises a clock, configured for synchronization with a clock of the implant.

According to some embodiments of the third part of aspect 256SE the external computing unit is configured to calculate a difference value between the parameter measured by the implant and the parameter measured by the external device. The external computing unit is further configured to authenticate the connection if the difference value is less than a predetermined threshold difference value, and to not authenticate the connection if the difference value equals or exceeds the predetermined threshold difference value.

According to some embodiments of the third part of aspect 256SE the external device is configured to communicate further data to the implant following positive authentication.

According to some embodiments of the third part of aspect 256SE the implant is further configured to determine a cryptographic hash based on the parameter as measured by at least one of the external device and the implant, wherein the further data comprises the cryptographic hash.

According to some embodiments of the third part of aspect 256SE the further data comprises at least one of: data for updating a control program running in the implant, and operation instructions for operating the implant.

According to some embodiments of the third part of aspect 256SE the external device further comprises a conductive member configured to be in electrical connection with the external device. The conductive member is configured to be placed in electrical connection with a skin of the patient for conductive communication with the implant.

In a fourth part of aspect 256SE, there is provided a computer program product comprising a computer-readable storage medium with instructions adapted to carry out at least parts of the method of the first part of aspect 256SE, when executed by a device having processing capability.

According to embodiments of the second part of aspect 256SE the implant comprises at least one of:

a pacemaker unit, or an implantable cardioverter defibrillators, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal,

US 12,598,458 B2

93 an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

According to embodiments of the second part of aspect 256SE the implant comprises an internal control unit adapted to be involved in at least a part of the actions performed by the implant in at least a part of any one of the embodiments of aspect 256SE.

In a fifth part of aspect 256SE, there is provided a computer program product of, or adapted to run on, an external device, adapted for connection with an implant, implanted in a patient, the external device comprising:

c. a second sensor wherein the computer program product is configured to cause the second sensor to measure a parameter of the patient by the external device, and d. an external computing unit, wherein the computer program product is configured to cause the external computing unit to:

i. receive a parameter of the patient, from the implant, ii. compare the parameter measured by the external device to the parameter measured by the implant, and iii. perform authentication of the connection based on the comparison.

According to embodiments of the fifth part of aspect 256SE the parameter of the patient comprises a pulse of the patient.

According to embodiments of the fifth part of aspect 256SE the parameter of the patient comprises a respiration rate of the patient.

According to embodiments of the fifth part of aspect 256SE the parameter of the patient comprises a temperature of the patient.

According to embodiments of the fifth part of aspect 256SE the parameter of the patient comprises at least one sound of the patient.

According to embodiments of the fifth part of aspect 256SE the parameter of the patient comprises at least one physical movement by the patient.

According to embodiments of the fifth part of aspect 256SE the measured parameter, by the external device is provided with a timestamp and the measured parameter received from the implant is provided with a timestamp, wherein the comparison of the parameter measured at the implant to the parameter measured by the external device comprises comparing the timestamp of the measured parameter received from the implant to the timestamp of the measured parameter by the external device.

According to embodiments of the fifth part of aspect 256SE the computer program product is configured to cause a clock of the external device, to be synchronized with a clock of the implant.

According to embodiments of the fifth part of aspect 256SE the computer program product is configured to cause the external computing unit to calculate a difference value between the parameter measured by the implant and the parameter measured by the external device, and wherein the computer program product is further configured to cause the external computing unit to authenticate the connection if the difference value is less than a predetermined threshold difference value, and to not authenticate the connection if the difference value equals or exceeds the predetermined threshold difference value.

According to embodiments of the fifth part of aspect 256SE the computer program product is configured to cause the external device to communicate further data to the implant following positive authentication.

According to embodiments of the fifth part of aspect 256SE the computer program product is further configured to determine a cryptographic hash based on the parameter as measured by at least one of the external device and the implant, wherein the further data comprises the cryptographic hash.

According to embodiments of the fifth part of aspect 256SE the further data comprises at least one of:

a. data for updating a control program running in the implant, and b. operation instructions for operating the implant.

In a sixth part of aspect 256SE, there is provided an implant for authenticating a connection between an implant implanted in a patient, and an external device, the implant comprising:

a. a sensor adapted to detect a sensation related to the body, as authentication data b. a storing unit adapted to store the authentication data related to the sensation, c. a receiver adapted to receive input from the external device related to the sensation, resulting in input authentication data, and d. authenticating the connection based on an analysis of the input authentication data and the authentication data.

According to embodiments of the sixth part of aspect 256SE the authentication data and/or input authentication data is configured to pertain to a pulse of the patient.

According to embodiments of the sixth part of aspect 256SE the authentication data and/or input authentication data is configured to pertain to a respiration rate of the patient.

According to embodiments of the sixth part of aspect 256SE the authentication data and/or input authentication data is configured to pertain to a temperature of the patient.

According to embodiments of the sixth part of aspect 256SE the authentication data is configured to pertain to at least one sound of the patient.

According to embodiments of the sixth part of aspect 256SE the authentication data and/or input authentication data is configured to pertain to at least one physical movement of the patient.

According to embodiments of the sixth part of aspect 256SE the authentication data and/or input authentication data are provided with a timestamp, wherein the comparison of the authentication data measured at the implant to the input authentication data measured by the external device comprises comparing the timestamp of the measured parameter by the implant to the timestamp of the measured parameter received from the external device.

According to embodiments of the sixth part of aspect 256SE the implant comprises a clock, configured for synchronization with a clock of the external device.

According to embodiments of the sixth part of aspect 256SE the implant comprises an internal computing unit configured to calculate a difference value between the authentication data measured by the implant and the input authentication data measured by the external device, and wherein the internal computing unit is further configured to authenticate the connection if the difference value is less than a predetermined threshold difference value, and to not authenticate the connection if the difference value equals or exceeds the predetermined threshold difference value.

According to embodiments of the sixth part of aspect 256SE the communication between the implant and the external device is a wireless communication.

According to embodiments of the sixth part of aspect 256SE the communication between the implant and the external device is a conductive communication.

According to embodiments of the sixth part of aspect 256SE the communication between the implant and the external device is a conductive communication adapted to transport the input authentication data to the implant.

According to embodiments of the sixth part of aspect 256SE the communication between the implant and the external device is a conductive communication adapted to transport the authentication data to the external device.

In a seventh part of aspect 256SE there is provided a method of authenticating a connection between an implant implanted in a patient, and an external device, the method comprising:

a. using a sensation generated by the body and detectable by the implant and the external device, b. storing, by the implant, authentication data, related to the sensation, c. providing to the implant input from the external device about the sensation, resulting in input authentication data, and d. authenticating the connection based on an analysis of the input authentication data and the authentication data.

Aspect 257SE Device Synchronization Sensation Unit—Sensation Unit for Authenticating a Connection Between an Implant and the External Device—Embodiments of Aspect 257SE of the Disclosure In a first part of aspect 257SE, a method of authenticating a connection between an implant, implanted in a patient, and an external device is provided. The method comprises generating, by a sensation generator of the implant, a sensation detectable by a sense of the patient. The method further comprises storing, by the implant, authentication data, related to the generated sensation. The method further comprises providing, by the patient, input to the external device, resulting in input authentication data. The method further comprises authenticating the connection based on a comparison of the input authentication data and the authentication data.

Similarly, to the first part of aspect 248SE, a main advantage of this way of authenticating a connection is that only the patient may be able to experience the sensation.

Thus, only the patient may be able to authenticate the connection by providing authentication input corresponding to the sensation generation.

According to some embodiments of the first part of aspect 257SE the method further comprises the step of communicating the authentication data from the sensation generator to the implant using a wireless communication.

According to some embodiments of the first part of aspect 257SE the method further comprises the step of communicating the authentication data from the sensation generator to the implant using a wired communication.

According to some embodiments of the first part of aspect 257SE the method further comprises the step of communicating further data between the implant and the external device following positive authentication.

According to some embodiments of the first part of aspect 257SE the authentication data comprises a timestamp of the sensation and wherein the input authentication data comprises a timestamp of the input from the patient According to some embodiments of the first part of aspect 257SE the step of authenticating the connection comprises calculating a time difference between the timestamp of the sensation and the timestamp of the input from the patient, and upon determining that the time difference is less than a threshold, authenticating the connection.

According to some embodiments of the first part of aspect 257SE the authentication data comprises a number of times that the sensation is generated by the sensation generator, and wherein the input authentication data comprises an input from the patient relating to a number of times the patient detected the sensation. Authenticating the connection may then comprise upon determining that the number of times of the authentication data and the input authentication data are equal, authenticating the connection.

According to some embodiments of the first part of aspect 257SE the sensation may comprise a plurality of sensation components.

According to some embodiments of the first part of aspect 257SE the sensation or sensation components may comprise a vibration.

According to some embodiments of the first part of aspect 257SE the sensation or sensation components may comprise a sound.

According to some embodiments of the first part of aspect 257SE the sensation or sensation components may comprise a photonic signal.

According to some embodiments of the first part of aspect 257SE the sensation or sensation components may comprise a light signal.

According to some embodiments of the first part of aspect 257SE the sensation or sensation components may comprise an electric signal.

According to some embodiments of the first part of aspect 257SE the sensation or sensation components may comprise a heat signal.

According to some embodiments of the first part of aspect 257SE the communication between the implant and the external device may be a wireless communication.

According to some embodiments of the first part of aspect 257SE the communication between the implant and the external device may be a conductive communication.

According to some embodiments of the first part of aspect 257SE the method further comprises the step of transmitting the input authentication data from the external device to the implant, wherein the comparison is performed by the implant.

According to some embodiments of the first part of aspect 257SE the method further comprises the step of transmitting the authentication data from the implant to the external device, wherein the comparison is performed by the external device.

According to some embodiments of the first part of aspect 257SE the comparison is performed by the implant and the method further comprises the step of continuously requesting by the external device, or receiving at the external device, information of an authentication status of the connection between the implant and the external device. The method may further comprise upon determining, at the external device, that the connection is authenticated, transmitting further data from the external device to the implant.

According to some embodiments of the first part of aspect 257SE the further data comprises at least data for updating a control program running in the implant, or operation instructions for operating the implant.

According to some embodiments of the first part of aspect 257SE the comparison is performed by the external device and the method further comprises the step of continuously requesting by the implant, or receiving at the implant, information of an authentication status of the connection between the implant and the external device. The method may further comprise upon determining, at the implant, that the connection is authenticated, transmitting further data from the implant to the external device.

According to some embodiments of the first part of aspect 257SE the further data comprises data sensed by a sensor connected to the implant.

According to some embodiments of the first part of aspect 257SE the sensation generator is adapted to be implanted in the patient.

According to some embodiments of the first part of aspect 257SE the sensation generator is configured to be worn in contact with the skin of the patient.

According to some embodiments of the first part of aspect 257SE the sensation generator is configured generate the sensation without being in physical contact with the patient.

In a second part of aspect 257SE, an implant, implanted in a patient and adapted for connection with an external device is provided. The implant may comprise a sensation generator. The implant may be configured for receiving authentication data related to a sensation generated by the sensation generator from the sensation generator. The implant may be further configured for storing the authentication data. The implant may be further configured for receiving input authentication data from the external device. The implant may comprise an internal communication unit. The internal communication unit may be configured for comparing the authentication data to the input authentication data. The internal communication unit may be further configured for performing authentication of the connection based on the comparison.

According to some embodiments of the second part of aspect 257SE the implant may further comprise a wireless communication system configured for receiving the authentication data from the sensation generator.

According to some embodiments of the second part of aspect 257SE the implant may further comprise a wired transceiver configured for receiving the authentication data from the sensation generator.

According to some embodiments of the second part of aspect 257SE the implant may further comprise a wired transceiver configured for receiving the authentication data from the sensation generator.

According to some embodiments of the second part of aspect 257SE the implant may further be configured for communicating further data to the external device following positive authentication.

According to some embodiments of the second part of aspect 257SE the authentication data comprises a timestamp of the sensation and wherein the input authentication data comprises a timestamp of the input from the patient.

According to some embodiments of the second part of aspect 257SE authenticating the connection comprises calculating a time difference between the timestamp of the sensation and the timestamp of the input from the patient, and upon determining that the time difference is less than a threshold, authenticating the connection.

According to some embodiments of the second part of aspect 257SE the authentication data may comprise a number of times that the sensation is generated by the sensation generator. The input authentication data may comprise an input from the patient relating to a number of times the patient detected the sensation. Authenticating the connection may comprise upon determining that the number of times of the authentication data and the input authentication data are equal, authenticating the connection.

According to some embodiments of the second part of aspect 257SE the communication between the implant and the external device is a wireless communication.

According to some embodiments of the second part of aspect 257SE the communication between the implant and the external device is a conductive communication.

In a third part of aspect 257SE, a sensation generator, adapted to generate a sensation detectable by a sense of the patient, is provided. The sensation generator being configured to, upon request, generate the sensation and transmit authentication data, related to the generated sensation, to an implant, when implanted in a patient.

According to some embodiments of the third part of aspect 257SE the sensation generator may further be configured to transmit the authentication data to the implant using wireless communication.

According to some embodiments of the third part of aspect 257SE the sensation generator may further be configured to transmit the authentication data to the implant using wired communication.

According to some embodiments of the third part of aspect 257SE the sensation generator is further configured to receive the request from the implant.

According to some embodiments of the third part of aspect 257SE the sensation generator is further configured to receive the request from an external device.

According to some embodiments of the third part of aspect 257SE the sensation generator is further configured to create the sensation comprising a plurality of sensation components.

According to some embodiments of the third part of aspect 257SE the sensation generator is further configured to create the sensation or sensation components by vibration of the sensation generator.

According to some embodiments of the third part of aspect 257SE the sensation generator is further configured to create the sensation or sensation components by producing a sound.

According to some embodiments of the third part of aspect 257SE the sensation generator is further configured to create the sensation or sensation components by providing a photonic signal.

According to some embodiments of the third part of aspect 257SE the sensation generator is further configured to create the sensation or sensation components by providing a light signal.

According to some embodiments of the third part of aspect 257SE the sensation generator is further configured to create the sensation or sensation components by providing an electric signal.

According to some embodiments of the third part of aspect 257SE the sensation generator is further configured to create the sensation or sensation components by providing a heat signal.

According to some embodiments of the third part of aspect 257SE the sensation generator is adapted to be implanted in the patient.

According to some embodiments of the third part of aspect 257SE the sensation generator is further configured to be worn in contact with the skin of the patient.

According to some embodiments of the third part of aspect 257SE the sensation generator is further configured to generate the sensation without being in physical contact with the patient.

In a fourth part of aspect 257SE, there is provided a system comprising a sensation generator according to the third part of aspect 257SE, an implant according to the second part of aspect 257SE and an external device. The system may be configured for performing methods according to the first part of aspect 257SE.

According to embodiments of the second part of, or other parts of, aspect 257SE the implant comprises at least one of:
a pacemaker unit, or an implantable cardioverter defibril-
    lators,
an external heart compression device,
an apparatus assisting the pump function of a heart of the
    patient,
an operable artificial heart valve,
an implantable drug delivery device,
a hydraulic, mechanic, and/or electric constriction
    implant,
an operable volume filling device,
an operable gastric band,
an operable implant for stretching the stomach wall of the
    patient,
an operable cosmetic implant,
an implant controlling the emptying of a urinary bladder,
an implant hindering urinary leakage,
an implant hindering anal incontinence,
an implant controlling the emptying of fecal matter,
an implant monitoring an aneurysm,
an implant lubricating a joint,
an implant with a reservoir for holding bodily fluids
an implant storing and/or emptying a bodily reservoir or
    a surgically created reservoir,
an implant communicating with a database outside the
    body,
an implant able to be programmed from outside the body,
an implant able to be programmed from outside the body
    with a wireless signal,
an implant treating impotence,
an implant controlling the flow of eggs in the uterine tube,
an implant controlling the flow of sperms,
an implant treating osteoarthritis,
an implant performing a test of parameters inside the
    body,
an implant controlling specific treatment parameters from
    inside the body,
an implant controlling bodily parameters from inside the
    body,
an implant controlling the blood pressure,
an implant controlling a drug treatment parameter,
an implant controlling a parameter in the blood,
an implant for adjusting or replacing any bone part of a
    body of the patient,
an implant replacing an organ of the patient or part of an
    organ of the patient or the function thereof,
a vascular treatment device, and
an implant adapted to move fluid inside the body of the
    patient.

In a fifth part of aspect 257SE there is provided a computer program product comprising a computer-readable storage medium with instructions adapted to carry out at least parts of any one of the embodiments of aspect 257SE, when executed by a the implant or external device having processing capability.

According to embodiments of the second part of, or other parts of, aspect 257SE the implant comprises an internal control unit adapted to be involved in at least a part of the actions performed by the implant in at least a part of any one of the embodiments of aspect 257SE.

According to embodiments of the second part of, or other parts of, aspect 257SE the implant comprises an internal computing unit adapted to be involved in at least a part of the actions performed by the implant in at least a part of any one of the other embodiments of aspect 257SE, or
wherein the internal computing unit is adapted to be
    involved in at least a part of the actions performed by
    the implant in at least a part of any one of the other
    embodiments of aspect 257SE.

Aspect 258SE Device Synchronization
Sensation—Authenticating a Connection Between
an Implant and the External Device by Using
Sensations—Embodiments of Aspect 258SE of the
Disclosure In a first part of aspect 258SE, there is provided a method of authenticating a connection between an implant implanted in a patient, and an external device. The method comprising:
a. using a sensation generated by a body of the patient or
    a sensation generator, the sensation being detectable by
    the implant and the external device,
b. storing, by the implant and by the external device
    authentication data, related to the sensation,
c. providing at least one of; input from the external device
    to the implant and input from the implant to the external
    about the sensation, resulting in input authentication
    data, and
d. authenticating the connection based on an analysis of
    the input authentication data and the authentication
    data.

According to some embodiments of the first part of aspect 258SE the method further comprises the step of communicating further data between the implant and the external device following positive authentication.

According to some embodiments of the first part of aspect 258SE the authentication data comprises a characteristic of the sensation, wherein the input authentication data comprises a second characteristic of the sensation, and wherein authenticating the connection comprises: comparing the characteristic of the sensation with the second characteristic of the sensation.

According to some embodiments of the first part of aspect 258SE the authentication data comprises a timestamp of the sensation, wherein the input authentication data comprises a second timestamp of the sensation, and wherein authenticating the connection comprises: comparing the time stamp of the sensation with the second timestamp of the sensation.

According to some embodiments of the first part of aspect 258SE the authentication data comprises a number of times that the sensation is generated by the sensation generator, and wherein the input authentication data comprises an input from the patient relating to a number of times the patient detected the sensation to be stored in the external device, wherein authenticating the connection comprises: upon determining that the number of times of the authentication data and the input authentication data are equal, authenticating the connection.

According to some embodiments of the first part of aspect 258SE the sensation comprises a plurality of sensation components.

According to some embodiments of the first part of aspect 258SE the sensation or sensation components comprise a vibration.

According to some embodiments of the first part of aspect 258SE the sensation or sensation components comprise a sound.

According to some embodiments of the first part of aspect 258SE the sensation or sensation components comprise a photonic signal.

According to some embodiments of the first part of aspect 258SE the sensation or sensation components comprise a light signal.

According to some embodiments of the first part of aspect 258SE the sensation or sensation components comprise an electric signal.

According to some embodiments of the first part of aspect 258SE the sensation or sensation components comprise a heat signal.

According to some embodiments of the first part of aspect 258SE the sensation generator is contained within the implant.

According to some embodiments of the first part of aspect 258SE the communication between the implant and the external device is a wireless communication or a conductive communication.

According to some embodiments of the first part of aspect 258SE the communication between the implant and the external device is both a wireless communication and a conductive communication.

According to some embodiments of the first part of aspect 258SE the method further comprises the step of:
  transmitting the input authentication data from the external device to the implant,
  wherein the analysis is performed by the implant.

According to some embodiments of the first part of aspect 258SE the method further comprises the step of:
  transmitting the authentication data from the implant to the external device,
  wherein the analysis is performed by the external device.

According to some embodiments of the first part of aspect 258SE the implant comprises a motor for controlling a physical function in the body of the patient, wherein the motor being the sensation generator.

According to some embodiments of the first part of aspect 258SE the sensation is a vibration created by running the motor.

According to some embodiments of the first part of aspect 258SE the sensation is a sound created by running the motor.

According to some embodiments of the first part of aspect 258SE the analysis is performed by the implant, the method further comprising the step of:
  continuously requesting by the external device, or receiving at the external device, information of an authentication status of the connection between the implant and the external device, and upon determining, at the external device, that the connection is authenticated, transmitting further data from the external device to the implant.

According to some embodiments of the first part of aspect 258SE the further data comprises at least one of:
  a. data for updating a control program running in the implant, and
  b. operation instructions for operating the implant.

According to some embodiments of the first part of aspect 258SE the analysis is performed by the external device, the method further comprising the step of:
  continuously requesting by the implant, or receiving at the implant, information of an authentication status of the connection between the implant and the external device, and upon determining, at the implant, that the connection is authenticated, transmitting further data from the implant to the external device.

According to some embodiments of the first part of aspect 258SE the further data comprises data sensed by a sensor connected to the implant.

In a second part of aspect 258SE, there is provided an implant, implanted in a patient, adapted for connection with an external device, the implant connected to a sensation generator or a sensor for recording a sensation generated by the body of a the patient, the implant being configured for:
  a. storing authentication data, related to a sensation generated by the sensation generator or by the body of the patient,
  b. receiving input authentication data from the external device, and wherein the implant comprises an internal computing unit configured for:
    i. analyzing the authentication data and the input authentication data, and
    ii. performing authentication of the connection based on the analysis.

According to some embodiments of the second part of aspect 258SE the implant is further configured for communicating further data to the external device following positive authentication.

According to some embodiments of the second part of aspect 258SE the authentication data comprises a characteristic of the sensation, wherein the input authentication data comprises a second characteristic of the sensation, and wherein authenticating the connection comprises: comparing the characteristic of the sensation with the second characteristic of the sensation.

According to some embodiments of the second part of aspect 258SE authentication data comprises a timestamp of the sensation, wherein the input authentication data comprises a second timestamp of the sensation, and wherein authenticating the connection comprises: comparing the time stamp of the sensation with the second timestamp of the sensation.

According to some embodiments of the second part of aspect 258SE the authentication data comprises a number of times that the sensation is generated by the sensation generator, and wherein the input authentication data comprises an input from the patient relating to a number of times the patient detected the sensation to be stored in the external device, wherein authenticating the connection comprises:

upon determining that the number of times of the authentication data and the input authentication data are equal, authenticating the connection.

According to some embodiments of the second part of aspect 258SE the sensation generator is contained within the implant.

According to some embodiments of the second part of aspect 258SE the sensation generator is configured to create the sensation comprising a plurality of sensation components.

According to some embodiments of the second part of aspect 258SE the sensation generator is configured to create the sensation or sensation components by vibration of the sensation generator.

According to some embodiments of the second part of aspect 258SE the sensation generator is configured to create the sensation or sensation components by playing a sound.

According to some embodiments of the second part of aspect 258SE the sensation generator is configured to create the sensation or sensation components by providing a photonic signal.

According to some embodiments of the second part of aspect 258SE the sensation generator is configured to create the sensation or sensation components by providing a light signal.

According to some embodiments of the second part of aspect 258SE the sensation generator is configured to create the sensation or sensation components by providing an electric signal.

According to some embodiments of the second part of aspect 258SE the sensation generator is configured to create the sensation or sensation components by providing a heat signal.

According to some embodiments of the second part of aspect 258SE the communication between the implant and the external device is both a wireless communication and a conductive communication.

According to some embodiments of the second part of aspect 258SE the implant comprises a motor for controlling a physical function in the body of the patient, wherein the motor being the sensation generator.

According to some embodiments of the second part of aspect 258SE the implant comprises a motor for controlling a physical function in the body of the patient, wherein the motor being the sensation generator.

According to some embodiments of the second part of aspect 258SE the sensation is a vibration created by running the motor.

According to some embodiments of the second part of aspect 258SE the sensation is a sound created by running the motor.

In a third part of aspect 258SE, there is provided an external device, adapted for connection with an implant, implanted in a patient, the external device comprising:
   a. an interface for receiving, by the patient, input to the external device, resulting in input authentication data,
   b. a receiver for receiving authentication data from the implant, the authentication data relating to a generated sensation of a sensation generator connected to the implant or to a measured sensation generated by a body of the patient;
   c. an external computing unit configured for:
     i. analyzing the authentication data and the input authentication data, and
     ii. performing authentication of the connection based on the analysis.

According to some embodiments of the third part of aspect 258SE the external device is further configured for communicating further data to the implant following positive authentication.

According to some embodiments of the third part of aspect 258SE the authentication data comprises a characteristic of the sensation, wherein the input authentication data comprises a second characteristic of the sensation, and wherein authenticating the connection comprises: comparing the characteristic of the sensation with the second characteristic of the sensation.

According to some embodiments of the third part of aspect 258SE authentication data comprises a timestamp of the sensation, wherein the input authentication data comprises a second timestamp of the sensation, and wherein authenticating the connection comprises: comparing the time stamp of the sensation with the second timestamp of the sensation.

According to some embodiments of the third part of aspect 258SE the authentication data comprises a number of times that the sensation is generated by the sensation generator, and wherein the input authentication data comprises an input from the patient relating to a number of times the patient detected the sensation to be stored in the external device, wherein authenticating the connection comprises: upon determining that the number of times of the authentication data and the input authentication data are equal, authenticating the connection.

According to some embodiments of the third part of aspect 258SE the communication between the implant and the external device is a wireless communication or a conductive communication.

According to some embodiments of the third part of aspect 258SE the communication between the implant and the external device is both a wireless communication and a conductive communication.

According to some embodiments of the third part of aspect 258SE the external device further comprises a conductive member configured to be in electrical connection with the external device, wherein the conductive member is configured to be placed in electrical connection with a skin of the patient for conductive communication with the implant.

According to some embodiments of the first part of aspect 258SE the method further comprises transmitting further data between the implant and the external device, wherein the further data is used or acted upon, only after authentication of the connection is performed.

According to some embodiments of the second part of aspect 258SE the implant comprises at least one of:
   a pacemaker unit or implantable cardioverter defibrillators,
   an external heart compression device,
   an apparatus assisting the pump function of a heart of the patient,
   an operable artificial heart valve,
   an implantable drug delivery device,
   a hydraulic, mechanic, and/or electric constriction implant,
   an operable volume filling device,
   an operable gastric band,
   an operable implant for stretching the stomach wall of the patient,
   an operable cosmetic implant,
   an implant controlling the emptying of a urinary bladder,
   an implant hindering urinary leakage,
   an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, and an implant adapted to move fluid inside the body of the patient.

In a fourth part of aspect 258SE there is provided a computer program product of, or adapted to be run on, an external device, adapted for connection with an implant, implanted in a patient, the external device comprising:

a. an interface for receiving, by the patient, input to the external device, resulting in input authentication data, b. a receiver for receiving authentication data from the implant, the authentication data relating to a generated sensation of a sensation generator or to a measured sensation generated by a body of the patient, the receiver being part of the implant or external device, c. an external computing unit, wherein the computer program product is configured to cause the external computing unit to:

i. analyze the authentication data and the input authentication data, and ii. perform authentication of the connection based on the analysis.

According to some embodiments of the fourth part of aspect 258SE the computer program product is configured to cause the external device to communicate further data to the implant following positive authentication.

According to some embodiments of the fourth part of aspect 258SE the authentication data comprises a characteristic of the sensation, wherein the input authentication data comprises a second characteristic of the sensation, and wherein authenticating the connection comprises: comparing the characteristic of the sensation with the second characteristic of the sensation.

According to some embodiments of the fourth part of aspect 258SE authentication data comprises a timestamp of the sensation, wherein the input authentication data comprises a second timestamp of the sensation, and wherein authenticating the connection comprises: comparing the time stamp of the sensation with the second timestamp of the sensation.

According to some embodiments of the fourth part of aspect 258SE the authentication data comprises a number of times that the sensation is generated by the sensation generator, and wherein the input authentication data comprises an input from the patient relating to a number of times the patient detected the sensation to be stored in the external device, wherein authenticating the connection comprises: upon determining that the number of times of the authentication data and the input authentication data are equal, authenticating the connection.

According to some embodiments of the fourth part of aspect 258SE the communication between the implant and the external device is a wireless communication or a conductive communication.

According to some embodiments of the fourth part of aspect 258SE the communication between the implant and the external device is both a wireless communication and a conductive communication.

In a fifth part of aspect 258SE there is provided a computer program product adapted to be run on, an implant, implanted in a patient, adapted for connection with an external device, the implant comprising:

a. an interface for receiving, by the patient, input to the implant, resulting in input authentication data, b. a receiver for receiving authentication data from the external device, the authentication data relating to a generated of a sensation generator of the implant or the external device or to a measured sensation generated by a body of the patient, c. a computing unit, wherein the computer program product is configured to cause the computing unit to:

i. analyze the authentication data and the input authentication data, and ii. perform authentication of the connection based on the analysis.

According to some embodiments of the fifth part of aspect 258SE the computer program product is configured to cause the implant to accept further communication with further data received by the implant following positive authentication.

According to some embodiments of the fifth part of aspect 258SE the authentication data comprises a characteristic of the sensation, wherein the input authentication data comprises a second characteristic of the sensation, and wherein authenticating the connection comprises: comparing the characteristic of the sensation with the second characteristic of the sensation.

According to some embodiments of the fifth part of aspect 258SE authentication data comprises a timestamp of the sensation, wherein the input authentication data comprises a second timestamp of the sensation, and wherein authenticating the connection comprises: comparing the time stamp of the sensation with the second timestamp of the sensation.

According to some embodiments of the fifth part of aspect 258SE the authentication data comprises a number of times that the sensation is generated by the sensation generator, and wherein the input authentication data comprises an input from the patient relating to a number of times the patient detected the sensation to be stored in the external device, wherein authenticating the connection comprises: upon determining that the number.

According to some embodiments of the fifth part of aspect 258SE the further communication between the implant and the external device is a wireless communication.

According to some embodiments of the fifth part of aspect 258SE the communication between the implant and the external device is a wireless communication.

According to some embodiments of the fifth part of aspect 258SE the communication between the implant and the external device is a wireless communication or a conductive communication.

According to some embodiments of the fifth part of aspect 258SE the communication between the implant and the external device is both a wireless communication and a conductive communication.

The implant according to the second part of aspect 258SE and/or with ability to use any of the methods of the first part of aspect 258SE, and/or with ability to perform the authentication process in any of third part of aspect 258SE and/or with ability to use any of the computer program products of the fourth part of aspect 258SE, may comprise an internal control unit adapted to be involved in at least a part of the actions performed by the implant in at least a part of any one of the embodiments of the above.

The embodiments of aspect 258SE may have close similarities with the embodiments of aspect 248SE. When referring to one or the other within this document, it should be understood that both may be considered for reference.

Aspect 307SE Communication Remote Control—Remote Wake Signal—Embodiments of Aspect 307SE of the Disclosure According to a first part of aspect 307SE, a system for controlling a medical implant implanted in a patient is provided. The system comprises an internal control unit adapted to be arranged within the patient's body and communicatively coupled to the medical implant. The internal control unit may comprise a processing unit having a sleep mode and an active mode, and a sensor configured to detect a wake signal. The system further comprises an external control unit adapted to be arranged outside of the patient's body, the external control unit comprises a signal provider configured to provide the wake signal, wherein the internal control unit is further configured to set the processing unit to the active mode in response to the sensor detecting the wake signal.

According to some embodiments of the first part of aspect 307SE, the signal provider is an acoustic source configured to provide an acoustic signal as the wake signal.

According to some embodiments of the first part of aspect 307SE, the signal provider is a magnetic source configured to provide a magnetic signal as the wake signal.

According to some embodiments of the first part of aspect 307SE, the sensor is configured to detect the received signal strength of a signal, and the internal control unit is further configured to set the processing unit to the active mode in response to the sensor detecting a signal exceeding a threshold signal strength.

According to some embodiments of the first part of aspect 307SE, the sensor is configured to provide a control signal indicative of a wake signal, the internal control unit is configured to set the processing unit to the active mode in response to the control signal, and the internal control unit is configured to control a supply of energy to the processing unit in response to the control signal.

According to some embodiments of the first part of aspect 307SE, the wake signal comprises a predetermined signal pattern, and the internal control unit is further configured to set the processing unit to the active mode in response to the sensor detecting the predetermined signal pattern.

According to some embodiments of the first part of aspect 307SE, the magnetic source comprises a first coil.

According to some embodiments of the first part of aspect 307SE, the magnetic source further comprises a second coil arranged perpendicular to the first coil, whereby to collectively provide a substantially even magnetic field.

According to some embodiments of the first part of aspect 307SE, the first coil and/or the second coil is configured to provide a signal as a magnetic field with a frequency of 9 to 315 kilohertz, kHz. The frequency may be less than or equal to 125 kHz, preferably less than 58 kHz. In some examples, the frequency is less than 50 kHz, preferably less than 20 kHz, more preferably less than 10 KHz.

According to some embodiments of the first part of aspect 307SE, the magnetic source comprises a magnet. The magnet may, in some examples, be a permanent magnet.

According to some embodiments of the first part of aspect 307SE, the magnetic source has an off state in which the magnetic source does provides a magnetic field and an on state in which the magnetic source provides a magnetic field. The magnetic source may, in some examples, further comprises a shielding means for preventing, when the magnetic source is in the off state, the magnetic source from providing a magnetic field.

According to some embodiments of the first part of aspect 307SE, the sensor comprises a hall effect sensor, a fluxgate sensor, an ultra-sensitive magnetic field sensor or a magneto-resistive sensor. In some examples, the sensor may comprise a third coil having an iron core.

According to some embodiments of the first part of aspect 307SE, the internal control unit comprises a first communication unit for receiving and/or transmitting data from and/or to the external control unit, and the external control unit comprises a second communication unit for transmitting and/or receiving data to and/or from the internal control unit.

According to some embodiments of the first part of aspect 307SE, the sensor may be comprised in the first communication unit.

According to some embodiments of the first part of aspect 307SE, the system further comprises a frequency detector, communicatively coupled to the internal control unit and configured to detect a frequency for data communication between the first communication unit and the second communication unit. The frequency detector may comprise an antenna.

According to some embodiments of the first part of aspect 307SE, when the system comprises a first communication unit and a second communication unit, the first communication unit and the second communication unit may be configured for data communication using magnetic induction via the first coil.

According to some embodiments of the first part of aspect 307SE, the first communication unit comprises a high-sensitivity magnetic field detector.

According to some embodiments of the first part of aspect 307SE, the first communication unit comprises a fourth coil for communicating with the second communication unit via the first coil.

According to some embodiments of the first part of aspect 307SE, the system further comprises an implantable energy source electrically connected to the first communication unit, wherein the implantable energy source is adapted to be charged by the external control unit via the first communication unit.

According to some embodiments of the first part of aspect 307SE, the implantable energy source is configured to be charged via magnetic induction between the first coil and the fourth coil.

According to some embodiments of the first part of aspect 307SE, the internal control unit is configured to control the charging of the implantable energy source by controlling a receipt of electrical power from the external control unit at the first communication unit.

According to some embodiments of the first part of aspect 307SE, the internal control unit is further configured to control the charging of the implantable energy source by controlling a transmission of electrical power from the external control unit to the first communication unit.

According to some embodiments of the first part of aspect 307SE, the system further comprises a sensation generator configured to generate a sensation detectable by a sense of the patient, the sensation generator being communicatively coupled to the internal control unit or the external control unit and being configured to, upon request, generate the sensation when the medical implant is implanted in the patient. In some examples, the sensation generator is configured to receive the request from the internal control unit of the medical implant. The sensation generator may be configured to receive the request from an external device. In some embodiments, the generated sensation may comprise a plurality of sensation components. The sensation generator may be configured to create the sensation or sensation components by at least one of a vibration of the sensation generator; producing a sound; providing a photonic signal; providing a light signal; providing an electric signal; and a heat signal. The sensation generator may be configured to be implanted in the patient, and/or be configured to be worn in contact with the skin of the patient. In some examples, the sensation generator is configured generate the sensation without being in physical contact with the patient.

According to some embodiments of the first part of aspect 307SE, the external control unit comprises a wireless remote control.

According to some embodiments of the first part of aspect 307SE, the wireless remote control comprises an external signal transmitter, and the internal control unit is further configured to receive one or more control signals transmitted by the external signal transmitter and to control an operation of the medical implant based at least in part on said signal, when the processing unit is in the active state.

According to some embodiments of the first part of aspect 307SE, the one or more control signals is selected from the group consisting of:
   a sound signal;
   an ultrasound signal;
   an electromagnetic signal;
   an infrared signal;
   a visible light signal;
   an ultraviolet light signal;
   a laser signal;
   a microwave signal;
   a radio wave signal;
   an X-ray radiation signal; and
   a gamma radiation signal.

According to a second part of aspect 307SE, a method for controlling an implant implanted in a patient is provided. The method comprises:
   monitoring for signals by a sensor comprised in an internal control unit communicatively coupled to the medical implant;
   providing, from a signal provider comprised in an external control unit, a wake signal, the external control unit being adapted to be arranged outside of the patient's body;
   setting, by the internal control unit and in response to a detected wake signal, a mode of a processing unit comprised in the internal control unit from a sleep mode to an active mode.

According to some embodiments of the second part of aspect 307SE, the method further comprises:
   detecting, using a frequency detector, a frequency for data communication between a first communication unit and a second communication unit, the first communication unit being associated with the internal control unit and the second communication unit being associated with the external control unit,
   wherein the frequency detector is communicatively coupled to the internal control unit.

According to some embodiments of the second part of aspect 307SE, the method further comprises:
   determining, using the frequency detector, the frequency for data communication; and
   initiating data communication between the first communication unit and the second communication unit.

According to some embodiments of the second part of aspect 307SE, the data communication comprises one or more control instructions for controlling the medical implant.

According to some embodiments of the second part of aspect 307SE, the method further comprises generating, using a sensation generator communicatively coupled to the internal control unit, a sensation detectable by a sense of the patient.

According to some embodiments of the second part of aspect 307SE, the data communications further comprise a request to generate the sensation.

According to some embodiments of the second part of aspect 307SE, the sensation is generated in response to a sensor measurement from the implant.

According to a third part of aspect 307SE, an implant is provided. The implant comprises a control unit, and the control unit comprises a processing unit having a sleep mode and an active mode; and a sensor configured to detect a wake signal. The control unit is configured to set the processing unit to the active mode in response to the sensor detecting the wake signal.

According to some embodiments of the third part of aspect 307SE, the sensor is a piezoelectric sensor for detecting acoustic signals.

According to some embodiments of the second part of aspect 307SE, the sensor is a magnetic sensor for detecting magnetic signals.

According to some embodiments of the second part of aspect 307SE, the sensor is configured to detect the received signal strength of a signal.

According to some embodiments of the second part of aspect 307SE, the control unit is further configured to set the processing unit to the active mode in response to the sensor detecting a signal exceeding a threshold signal strength.

According to some embodiments of the second part of aspect 307SE, the wake signal comprises a predetermined signal pattern, and the control unit is further configured to set the processing unit to the active mode in response to the sensor detecting the predetermined signal pattern.

According to some embodiments of the second part of aspect 307SE, the sensor is a hall effect sensor, a fluxgate sensor, an ultra-sensitive magnetic field sensor or a magneto-resistive sensor.

According to some embodiments of the second part of aspect 307SE, the sensor comprises a first coil.

According to some embodiments of the second part of aspect 307SE, the implant further comprises a communication unit for data communication.

According to some embodiments of the second part of aspect 307SE, the sensor is comprised in the first communication unit.

According to some embodiments of the second part of aspect 307SE, the implant further comprises a frequency detector, communicatively coupled to the control unit and configured to detect a frequency for the data communication. The frequency detector may comprise an antenna.

According to some embodiments of the second part of aspect 307SE, the communication unit comprises a high-sensitivity magnetic field detector.

According to some embodiments of the second part of aspect 307SE, the communication unit comprises a fourth coil for communicating with an external communication unit.

According to some embodiments of the second part of aspect 307SE, the implant further comprises an implantable energy source electrically connected to the communication unit, wherein the implantable energy source is adapted to be wirelessly charged by an external charging unit.

According to some embodiments of the second part of aspect 307SE, the implantable energy source is configured to be charged via magnetic induction of the first coil.

According to some embodiments of the second part of aspect 307SE, the implantable energy source is configured to be charged via piezoelectric operation of the piezoelectric sensor.

According to some embodiments of the second part of aspect 307SE, the internal control unit is configured to control the charging of the implantable energy source by controlling a receipt of electrical power at the communication unit.

According to some embodiments of the second part of aspect 307SE, the implant further comprises a sensation generator configured to generate a sensation detectable by a sense of the patient, the sensation generator being communicatively coupled to the control unit and being configured to, upon request, generate the sensation when the medical implant is implanted in the patient.

According to some embodiments of the second part of aspect 307SE, the sensation generator is configured to receive the request from the control unit of the medical implant.

According to some embodiments of the second part of aspect 307SE, the sensation generator is configured to receive the request via the communication unit.

According to some embodiments of the second part of aspect 307SE, the generated sensation comprises a plurality of sensation components.

According to some embodiments of the second part of aspect 307SE, the sensation generator may be configured to create the sensation or sensation components by at least one of:

a vibration of the sensation generator;

producing a sound;

providing a photonic signal;

providing a light signal;

providing an electric signal; and a heat signal.

According to some embodiments of the second part of aspect 307SE, the piezoelectric sensor is the sensation generator or is comprised in the sensation generator, and the sensation or a sensation component comprises a vibration of the sensation generator or producing a sound, and the vibration of the sensation generator or the production of the sound is generated by electric stimulation of the piezoelectric sensor.

The implant according to the third part of aspect 307SE or the system according to the first part of aspect 307SE, and/or with ability to use any of the methods of the second part of aspect 307SE, and/or with ability to perform the authentication process in any of third part of aspect 258SE, may comprise an internal control unit adapted to be involved in at least a part of the actions performed by the implant in at least a part of any one of the embodiments of the above.

The embodiments of aspect 307SE may have close similarities with the embodiments of aspect 315SE. When referring to one or the other within this document, it should be understood that both may be considered for reference.

Aspect 308SE Energy Power-Supply
Capacitor—Energy Burst Provider—Embodiments
of Aspect 308SE of the Disclosure According to a first part of aspect 308SE, an apparatus for powering an implant for a human patient is provided. The apparatus comprises an implantable energy source for providing energy to the implant, an energy provider connected to the implantable energy source and connected to an energy consuming part of the implant, the energy provider being configured to store energy to provide a burst of energy to the energy consuming part, wherein the energy provider is configured to be charged by the implantable energy source and to provide the energy consuming part with electrical power during startup of the energy consuming part.

According to some embodiments, the discharging from the implantable energy source of the energy consuming part is slower than the energy needed for the energy consuming part.

According to some embodiments, the discharging from the implantable energy source during startup of the energy consuming part is slower than the energy needed for startup of the energy consuming part.

According to some embodiments, a maximum energy consumption of the energy consuming part is higher than the maximum energy capable of being delivered by the implantable energy source without causing damage to the implantable energy source, and wherein the energy provider is adapted to deliver energy to the energy consuming part the energy consuming part.

According to some embodiments, a maximum energy consumption of the energy consuming part is higher than the maximum energy capable of being delivered by the implantable energy source without causing damage to the implantable energy source, and wherein the energy provider is adapted to deliver an energy burst corresponding to difference between the required energy consumption and the maximum energy capable of being delivered by the implantable energy source.

According to some embodiments, the implantable energy source is a re-chargeable battery.

According to some embodiments, the implantable energy source is a solid-state battery.

According to some embodiments, the battery is a trionychoid battery.

According to some embodiments, the implantable energy source is connected to the energy consuming part and configured to power the energy consuming part after it has been started using the energy provider.

According to some embodiments, the energy provider is a capacitor.

According to some embodiments, the energy provider is a start capacitor.

According to some embodiments, the energy provider is a run capacitor.

According to some embodiments, the energy provider is a dual run capacitor.

According to some embodiments, the apparatus further comprises a second energy provider configured to be charged by the implantable energy source and to provide the energy consuming part with electrical power.

According to some embodiments, the energy provider is a supercapacitor.

According to some embodiments, the energy consuming part is a motor for operating a device or function of the implant.

According to some embodiments, the energy consuming part is at least one of:

a device for providing electrical stimulation to a tissue portion of the body of the patient, a CPU for encrypting information a transmitting and/or receiving unit for communication with an external unit a measurement unit or a sensor a data collection unit a solenoid a piezo-electrical element a memory metal unit.

According to some embodiments, the energy consuming part is motor for powering a hydraulic pump.

According to some embodiments, the energy consuming part is a feedback unit.

According to some embodiments, the feedback unit is a vibrator.

According to some embodiments, the energy consuming part is configured to operate a valve comprised in the implant.

According to some embodiments, the energy consuming part is a control unit for controlling at least a part of the implant.

According to some embodiments, the control unit has a sleep mode and an operational mode, wherein the apparatus at least is configured to provide the control unit with electrical power for transitioning from the sleep mode to the operational mode.

According to some embodiments, the apparatus is further comprising:

an external energy source configured be arranged outside of the patient's body and configured to provide energy to the implantable energy source, an implantable charger configured to be electrically connected to the implantable energy source and enable charging of the implantable energy source by the external energy source.

According to some embodiments, the charger is configured to control the charging of the implantable energy source by controlling a receipt of electrical power from the external energy source at the implantable charger.

According to some embodiments, the internal charger is configured to control the charging of the implantable energy source by controlling a transmission of electrical power from the external energy source to the implantable charger.

According to some embodiments, the apparatus is further comprising an energy source indicator, wherein the energy source indicator is further configured to indicate a functional status of the implantable energy source.

According to some embodiments, the functional status indicates at least one of charge level and temperature of the implantable energy source.

According to some embodiments, the controller is further configured to include the functional status in a signal transmitted to the outside of the body.

According to some embodiments, the charger comprises an electromagnetic coil configured to receive electrical power wirelessly from the external energy source.

According to some embodiments, the implantable charger or the external energy source is configured to receive the functional status from the energy source indicator and control the charging of the implantable energy source based on the functional status.

According to a part of aspect 308SE, an apparatus for powering an implant for a human patient is provided. The apparatus comprises a first implantable energy source for providing energy to an energy consuming part of the implant, a second implantable energy source connected to the implantable energy source and connected to the energy consuming part, wherein the second implantable energy source is configured to be charged by the implantable energy source and to provide the energy consuming part with electrical power during startup of the energy consuming part, wherein the second implantable energy source has a higher energy density than the first implantable energy source.

According to some embodiments, the second implantable energy source has a higher maximum energy output per time unit.

According to some embodiments, the first implantable energy source is a non-chargeable battery, and wherein the second implantable energy source is a chargeable energy storage.

According to a third part of aspect 308SE, a method for powering an implant for a human patient is provided. The method comprising the steps of:

initiating an energy consuming part of the implant, the energy consuming part being connected to an implantable energy source;

providing an initial burst of energy to the energy consuming part using an energy provider connected to the implantable energy source and to the energy consuming part, the energy provider being adapted to provide a burst of energy to the energy consuming part; and subsequently powering the energy consuming part using the implantable energy source.

According to some embodiments, a maximum energy consumption of the energy consuming part is higher than the maximum energy capable of being delivered by the implantable energy source without causing damage to the implantable energy source, and wherein the energy provider is adapted to deliver an energy burst corresponding to difference between the required energy consumption and the maximum energy capable of being delivered by the implantable energy source.

According to some embodiments, the method further comprises the step of:

charging the energy provider using the implantable energy source.

According to some embodiments, the initiating an energy consuming part comprises transitioning a control unit of the implant from a sleep mode to an operational or active mode.

According to some embodiments, the method further comprises wirelessly charging the implantable energy source, the implantable energy source being connected to an internal charger, by controlling a receipt of electrical power from an external energy source at the implantable charger.

According to some embodiments, the method further comprises wirelessly charging the implantable energy source, the implantable energy source being connected to an internal charger, by transmission of electrical power from an external energy source by the implantable charger.

Aspect 309SE eHealth Broadcasting Data—Broadcasting Sensor Data from Implant—Embodiments of Aspect 309SE of the Disclosure According to a first part of aspect 309SE an implant for transmitting sensor data is provided. The implant comprises:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period.

a predetermined event, or a use of the implant.

According to some embodiments, the communication unit is configured to broadcast the information using a short to mid-range transmitting protocol.

According to some embodiments, the information is broadcasted using at least one of: Radio Frequency type protocol, RFID type protocol, WLAN type protocol, Bluetooth type protocol, BLE type protocol, NFC type protocol, 3G/4G/5G type protocol. GSM type protocol, or Bluetooth 5.

According to some embodiments, the implant further comprises a control unit connected to the sensor and to the communication unit, wherein the control unit is configured to anonymize the information.

According to some embodiments, the implant further comprises a control unit connected to the sensor and to the communication unit, wherein the control unit is configured to encrypt the information.

According to some embodiments, the communication unit further is configured to broadcast the information periodically.

According to some embodiments, the implant further comprises a control unit configured to cause the communication unit to broadcast the information in response to a second parameter being above a predetermined threshold.

According to some embodiments, the sensed parameter is a pressure (such as a pressure at a sphincter or an organ of a patient, or a pressure at a hydraulic reservoir of the implant), a predetermined temperature interval or threshold (such as a temperature of the patient, or a temperature of a processing unit, a control unit, a power supply, or another part of the implant).

According to some embodiments, the implant further comprises an implantable energy source and an energy source indicator, wherein the energy source indicator is configured to indicate a functional status of the implantable energy source.

According to some embodiments, the functional status indicates at least one of charge level and temperature of the implantable energy source.

According to some embodiments, the functional parameter is a parameter relating to the internal control unit.

According to some embodiments, a system comprising the implant according to any preceding embodiment, and an external device comprising a receiver for receiving data from the implant and a transmitter for transmitting data is provided. The external device is configured to receive the broadcasted information, encrypt the received information using a key and transmit the encrypted received information.

According to some embodiments, the internal device is configured to transmit the data using the body of the patient as a conductor, and the external device is configured to receive the data via the body.

According to some embodiments, the communication unit of the implant is configured to transmit the data wirelessly to the external device.

According to a second part of aspect 309SE, a method for transmitting data from an implant comprising a processor and a communication unit is provided. The method comprising:

obtaining sensor measurement data via a sensor connected to or comprised in the implant, the sensor measurement relating to at least one physiological parameter of the patient or a functional parameter of the implant, and transmitting, by a communication unit, the sensor measurement data in response to the sensor measurement being above a predetermined threshold, wherein the sensor is configured to periodically sense the parameter.

According to some embodiments, the transmitting comprises broadcasting the sensor measurement data to an external device.

According to some embodiments, the broadcasting is performed using a short to mid-range transmitting protocol.

According to some embodiments, the transmitting comprises using at least one of a:

Radio Frequency type protocol

RFID type protocol

WLAN type protocol

Bluetooth type protocol

BLE type protocol

NFC type protocol

3G/4G/5G type protocol

GSM type protocol.

According to some embodiments, the method further comprises anonymizing, by the processor, the sensor measurement data before it is transmitted.

According to some embodiments, the method further comprises encrypting the sensor measurement data, using an encryptor comprised in the processing unit, before it is transmitted.

According to some embodiments, the obtaining and the transmitting is performed periodically.

According to some embodiments, the sensor measurement data is transmitted in response to a second parameter being above a predetermined threshold.

According to some embodiments, the parameter is a pressure, such as a pressure at a sphincter or an organ of a patient or a pressure at a hydraulic reservoir of the implant, a predetermined temperature interval or threshold, such as a temperature of the patient, or a temperature of a processing unit, a control unit, a power supply, or another part of the implant.

According to some embodiments, the implant comprises an implantable energy source and an energy source indicator, and wherein the energy source indicator is configured to indicate a functional status of the implantable energy source, and wherein the sensor measurement comprises data related to the energy source indicator.

According to some embodiments, the functional parameter is a parameter relating to the internal control unit, such as, for example, a free memory or free storage, available processing power, a temperature, or a battery indicator.

According to some embodiments, the method further comprises receiving the sensor measurement data at an external device, and at the external device, encrypting the sensor measurement data using a key to obtain encrypted data, and transmitting the encrypted data.

According to some embodiments, the transmitting is performed wirelessly.

According to some embodiments, the internal communication unit comprises a conductive member, and the transmitting comprises transmitting, via the conductive member, the sensor measurement data using the body as a conductor.

According to some embodiments, the transmitting comprises transmitting the sensor measurement to an internal processor configured to cause a sensation generator to cause a sensation detectable by the patient in which the implant is implanted.

According to a third part, a computer program product comprising a computer-readable storage medium with instructions adapted to carry out the method of any one of the second part of aspect 309SE and/or with instructions adapted to carry out an action in any of the implant embodiments of the first part of aspect 309SE, when executed by a computing unit in an external device having processing capability is provided.

Aspect 310SE eHealth Double Encryption—Double Encryption—Embodiments of Aspect 310SE of the Disclosure According to a first part of aspect 310SE, a system for transmitting data between an implant and an external device is provided. The system comprises:

an implant comprising:

a communication unit configured to transmit data from the body of the patient to an external device, and an encryption unit for encrypting the data to be transmitted, and an external device configured to receive the data transmitted by the communication unit, encrypt the received data using a first key and transmit the encrypted received data to a third device.

According to some embodiments, the encryption unit is configured to encrypt the data to be transmitted using a second key.

According to some embodiments, the first key or the second key is implant specific information, a secret key associated with the external device, an identifier of the implant or an identifier of the communication unit.

According to some embodiments, the second key is a key transmitted by the external device to the internal device.

According to some embodiments, the second key is a combined key comprising a third key received by the implant form the external device.

According to some embodiments, the first key is a combined key comprising a fourth key, wherein the fourth key is received by the external device from a verification unit connected to or comprised in the external device.

According to some embodiments, the verification unit is configured to receive authentication input from a user, for authenticating the communication between the implant and the external device.

According to some embodiments, the authentication input is a code.

According to some embodiments, the authentication input is based on a biometric technique selected from the list of a fingerprint, a palm vein structure, image recognition, face recognition, iris recognition, a retinal scan, a hand geometry, and genome comparison.

According to some embodiments, the verification unit is configured to receive a fingerprint from a fingerprint reader.

According to some embodiments, the information is broadcasted using a short to mid-range transmitting protocol.

According to some embodiments, the information is transmitted using at least one of:

Radio Frequency type protocol

RFID type protocol

WLAN type protocol

Bluetooth type protocol

BLE type protocol

NFC type protocol

3G/4G/5G type protocol

GSM type protocol.

Bluetooth 5

According to some embodiments, the internal device comprises a first conductive member and the external device comprises a second conductive member, wherein the first and the second conductive members are configured to transmit the data using the body as a conductor.

According to some embodiments, the communication unit is configured to encrypt the data before transmitting the data.

According to some embodiments, the external device is configured to decrypt the received data and encrypt it before transmitting the data to the third device.

According to some embodiments, the external device is configured to transmit a request for data to the communication unit, and the communication unit is configured to in response to a request for data transmit the data to the external device.

According to some embodiments, the communication unit further is configured to broadcast the information periodically.

According to some embodiments, the system is further comprising an internal control unit configured to cause the communication unit to broadcast the information in response to a second parameter being above a predetermined threshold.

According to a second part of aspect 310SE, a method for encrypted communication between an implant, when implanted in a patient's body, and an external device is provided. The method comprising:

encrypting, by the implant, data relating to the implant or the operation thereof;

transmitting, by a first communication unit comprised in the implant, the data;

receiving, by a second communication unit comprised the external device, the data;

encrypting, by the external device, the data using an encryption key to obtain encrypted data; and transmitting the encrypted data to a third external device.

According to some embodiments, the encrypting, by the implant, comprises encrypting the data using a second key.

According to some embodiments, the first or the second key is implant specific information, a secret key associated with the external device, an identifier of the implant or an identifier of the communication unit.

According to some embodiments, the second key is a key transmitted by the external device to the internal device.

According to some embodiments, the second key is a combined key comprising a third key; and the method further comprises:

receiving, at the implant via a conductive member or wirelessly, the third key from the external device.

According to some embodiments, the method is further comprising:

receiving, at the external device, a fourth key from a verification unit connected to or comprised in the external device, wherein the verification unit is configured to receive authentication input from a user, for authenticating the communication between the implant and the external device, and wherein the first key is a combined key comprising a fourth key.

According to some embodiments, the authentication input is a code.

According to some embodiments, the authentication input is based on a biometric technique selected from the list of a fingerprint, a palm vein structure, image recognition, face recognition, iris recognition, a retinal scan, a hand geometry, and genome comparison.

According to some embodiments, the verification unit is configured to receive a fingerprint from a fingerprint reader.

According to a third part of aspect 310SE, a computer program product is provided. The computer program product comprising a computer-readable storage medium with instructions adapted to carry out the method of any one of embodiments of the second part of aspect 310SE and/or with instructions adapted to carry out an action in any of the embodiments of the first part of aspect 310SE, when executed by a computing unit in an external device having processing capability.

Aspect 311SE eHealth Data Integrity—Verifying Data Integrity from/to Implant and from/to External Device—Embodiments of Aspect 311SE of the Disclosure According to a first part of aspect 311SE, a method for evaluating a functional parameter of an implant implanted in a patient, the implant comprising a processor, a sensor for measuring the functional parameter, and an internal communication unit, is provided. The method comprising:

measuring, using the sensor, the functional parameter to obtain measurement data, establishing a connection between the internal communication unit and an external device configured to receive data from the implant, determining, by the processor, a cryptographic hash or a metadata relating to the measurement data and adapted to be used by the external device to verify the integrity of the received data, and transmitting the cryptographic hash or metadata, and transmitting, from the communication unit, the measurement data.

According to some embodiments, the method is further comprising, at the external device, receiving the transmitted cryptographic hash or metadata, receiving the measurement data, and verifying the integrity of the measurement data with the cryptographic hash, metadata or information relating to the functional parameter.

According to some embodiments, the cryptographic hash or metadata comprises a cryptographic hash, and wherein the verifying the integrity of the measurement data comprises:

calculating a second cryptographic hash for the received measurement data using a same cryptographic hash algorithm as the processor, and determining that the measurement data has been correctly received based on that the cryptographic hash and the second cryptographic hash are equal.

According to some embodiments, the cryptographic hash algorithm comprises one of: MD5, SHA1, or SHA 256.

According to some embodiments, the cryptographic hash is a signature obtained by using a private key of the implant, and wherein the verifying, by the external device, comprises verifying the signature using a public key corresponding to the private key.

According to some embodiments, the cryptographic hash or metadata comprises a metadata, and wherein the verifying the integrity of the data comprises:

obtaining a second metadata for the received measurement data relating to the functional parameter, and determining that the data has been correctly received based on that metadata and the second metadata are equal.

According to some embodiments, the metadata comprises: a length of the data, a timestamp, or a sensor measurement.

According to some embodiments, the method is further comprising, at the external device, evaluating the measurement data relating to the functional parameter.

According to some embodiments, the sensor is a pressure sensor, an electrical sensor, a clock, a temperature sensor, a motion sensor, an optical sensor, a sonic sensor, an ultrasonic sensor.

According to some embodiments, the functional parameter is at least one of a temperature, a pressure, a battery status indicator, a time period length, or a pressure at a sphincter.

According to some embodiments, the method is further comprising, at the external device, to determining, based on the evaluating, that the implant is functioning correctly.

According to some embodiments, the method is further comprising, at the external device, determining based on the evaluating that the implant is not functioning correctly.

According to some embodiments, the method is further comprising sending, from the external device, a corrective command to the implant, receiving the corrective command at the implant, and correcting the functioning of the implant according to the corrective command.

According to some embodiments, the transmitting of the measurement data is transmitted in a plurality of data packets, wherein the cryptographic mash or metadata comprises a plurality of cryptographic hashes or metadata each corresponding to a respective data packet, and wherein the transmitting of each the cryptographic hashes or metadata is performed for each of the corresponding data packets.

According to some embodiments, the method is for evaluating a pressure at a sphincter of the patient.

According to a second part of aspect 311SE, a method of communicating instructions from an external device to an implant implanted in a patient is provided. The method comprising:

establishing a first connection between the external device and the implant, establishing a second connection between a second external device and the implant, transmitting, from the external device, a first set of instructions to the implant over the first connection, transmitting, from the second external device, a first cryptographic hash or metadata corresponding to the first set of instructions to the implant, at the implant, verifying the integrity of the first set of instructions and the first cryptographic hash, based on the first cryptographic hash.

According to some embodiments, the verifying of the integrity of the first set of instructions comprises a cyclic redundancy check.

According to some embodiments, the cryptographic hash or metadata comprises a cryptographic hash, and wherein the verifying the integrity of the first set of instructions comprises:

calculating a second cryptographic hash for the received first set of instructions using a same cryptographic hash algorithm as the processor, and determining that the first set of instructions has been correctly received based on that the cryptographic hash and the second cryptographic hash are equal.

According to some embodiments, the cryptographic hash algorithm comprises one of: MD5, SHA1, or SHA 256.

According to some embodiments, the cryptographic hash is a signature obtained by using a private key of the implant, and wherein the verifying comprises verifying the signature using a public key corresponding to the private key.

According to some embodiments, the cryptographic hash or metadata comprises a metadata, and wherein the verifying the integrity of the data comprises:

obtaining a second metadata for the received first set of instructions, and determining that the first set of instructions has been correctly received based on that metadata and the second metadata are equal.

According to some embodiments, the metadata comprises at least one of a length of the data, or a timestamp.

According to some embodiments, the external device is separate from the second external device.

According to some embodiments, communication using the second connection is performed using a different protocol than a protocol used for communication using the first communication channel.

According to some embodiments, the first connection is a wireless connection and the second connection is an electrical connection.

According to some embodiments, the second connection is an electrical connection using the patient's body as a conductor.

According to some embodiments, the method is further comprising:

transmitting, by the implant, information relating to the received first set of instructions, receiving, by the external device, the information, and verifying, by the external device, that the information corresponds to the first set of instructions sent by the external device.

According to some embodiments, the information comprises a length of the first set of instructions.

According to some embodiments, the method is further comprising:

at the implant, verifying the authenticity of the first set of instructions by i. calculating a second cryptographic hash for the first set of instructions, ii. comparing the second cryptographic hash with the first cryptographic hash, iii. determining that the first set of instructions are authentic based on that the second cryptographic hash is equal to the first cryptographic hash upon verification of the authenticity of the first set of instructions, storing them at the implant.

According to some embodiments, the first set of instructions comprises a cryptographic hash corresponding to a previous set of instructions.

According to some embodiments, the method is further comprising:

measuring, by the implant using a first sensor, a parameter relating to the body of the patient to obtain a first measurement, measuring, by the external device using a second sensor, the parameter relating to the body of the patient to obtain a second measurement, wherein the first set of instructions comprises the second measurement relating to the body of the patient, and wherein the verification of the authenticity of the first set of instructions comprises comparing the first and the second measurements.

According to some embodiments, the first and second parameters relate to a pulse of the patient, a respiration rate of the patient, a temperature of the patient, a sound of the patient, or a physical movement of the patient.

According to some embodiments, the measured parameter by the external device is provided with a timestamp, and the measured parameter measured by the implant is provided with a timestamp, wherein the comparison of the parameter measured at the implant to the parameter measured by the external device comprises comparing the timestamp of the measured parameter received from the implant to the timestamp of the measured parameter by the external device.

According a second part of aspect 311SE, a system for communication instructions is provided, the system comprising:

an implant adapted to be implanted in a patient, the implant comprising an active unit, an internal communication unit and an internal controller, an external device comprising an external communication unit configured to transmit a first set of instructions to the internal communication unit over a first communications connection, a second external device comprising a third communication unit configured to transmit a first cryptographic hash to the internal communication unit, wherein the internal controller is configured to receive, via the internal communication unit, the first set of instructions and the first cryptographic hash and verify the integrity of the first set of instructions based on the first cryptographic hash.

According to some embodiments, the internal controller is configured to verify the integrity of the first set of instructions using a cyclic redundancy check.

According to some embodiments, the cryptographic hash or metadata comprises a cryptographic hash, and wherein the internal controller is configured to verifying the integrity of the first set of instructions by:

calculating a second cryptographic hash for the received first set of instructions using a same cryptographic hash algorithm as the processor, and determining that the first set of instructions has been correctly received based on that the cryptographic hash and the second cryptographic hash are equal.

According to some embodiments, the cryptographic hash algorithm comprises at least one of MD5, SHA1 or SHA256.

According to some embodiments, the cryptographic hash is a signature obtained by using a private key of the implant, and wherein the internal controller is configured to verifying the first set of instructions by the signature using a public key corresponding to the private key.

According to some embodiments, the cryptographic hash or metadata comprises a metadata, and wherein the internal controller is configured to verifying the integrity of the data by:

obtaining a second metadata for the received first set of instructions, and determining that the first set of instructions has been correctly received based on that metadata and the second metadata are equal.

According to some embodiments, the metadata comprises at least one of: a length of the data, and/or a timestamp.

According to some embodiments, the external device is separate from the second external device.

According to some embodiments, the internal controller is configured to communicate with the second external device using a different protocol than a protocol used for communication with the external device.

According to some embodiments, the internal communication unit comprises a wireless transceiver for communication with the external device, and a conductive member for communicating with the second external device, wherein the second external device comprises a second conductive member.

According to some embodiments, the communication between the internal communication unit and the second external device is performed using the patient's body as a conductor.

According to some embodiments, the internal controller is configured to transmit information relating to the received first set of instructions to the external device, and the external device is configured to confirm that the information relates to the first set of instructions transmitted by the external device.

According to some embodiments, the internal controller is configured to:

calculating a second cryptographic hash for the first set of instructions, comparing the second cryptographic hash with the first cryptographic hash, determining that the first set of instructions are authentic based on that the second cryptographic hash is equal to the first cryptographic hash, and upon verification of the authenticity of the first set of instructions, storing them at the implant.

According to some embodiments, the external device is configured to transmit the first set of instructions, and wherein the first set of instructions comprises a cryptographic hash corresponding to a previous set of instructions.

According to some embodiments, the internal controller is connected to or comprising a first sensor adapted to obtain a measurement of a parameter relating to the body of the patient, the external device is connected to or comprising a second sensor adapted to obtain a measurement of the parameter relating to the body of the patient, wherein the first set of instructions comprises the second measurement, and wherein the internal controller is configured to verify the authenticity of the first set of instructions at least based on a comparison of the first and second measurements.

According to some embodiments, the first and second parameters relate to a pulse of the patient, a respiration rate of the patient, a temperature of the patient, a sound of the patient, or a physical movement of the patient.

According to some embodiments, the measured parameter by the external device is provided with a timestamp, and the measured parameter measured by the implant is provided with a timestamp, wherein the comparison of the parameter measured at the implant to the parameter measured by the external device comprises comparing the timestamp of the measured parameter received from the implant to the timestamp of the measured parameter by the external device.

According to a third part of aspect 311SE, a computer program product is provided. The computer program product comprises a computer-readable storage medium with instructions adapted to carry out the method of any one of the embodiments of the first part of aspect 307SE and/or with instructions adapted to carry out an action in any of the system embodiments of the second part of aspect 311SE, when executed by a computing unit in an external device having processing capability.

Aspect 312SE eHealth Programming Predefined Steps—Programming Via Predefined Steps—Embodiments of Aspect 312SE of the Disclosure According to a first part of aspect 312SE, a programmable or updatable implant is provided. The implant comprises:

an internal computing unit configured to control a function of said implant, said internal computing unit comprises an internal memory configured to store:

i. a first control program for controlling the internal computing unit, and ii. a second, configurable or updatable, with predefined program steps, control program for controlling said function of said implant.

iii. a set of predefined program steps for updating the second control program.

an internal communication unit connected to said internal computing unit and configured to communicate with an external device, wherein said internal computing unit is configured to receive an update to the second control program via said internal communication unit, and a verification function of, connected to, or transmitted to said internal computing unit, said verification function being configured to verify that the received update to the second control program comprises program steps comprised in the set of predefined program steps.

According to some embodiments, the predefined program steps comprise setting a variable related to a pressure, a time, a minimum or maximum temperature, a current, a voltage, an intensity, a frequency, an amplitude of electrical stimulation, a feedback mode (such as sensoric or other), a post-operative mode or a normal mode, a catheter mode, a fibrotic tissue mode (for example, semi-open), an time open after urination, a time open after urination before bed-time.

According to some embodiments, the verification function is configured to reject the update in response to the update comprising program steps not comprised in the set of predefined program steps.

According to some embodiments, the verification function is configured to allow the update in response to the update only comprising program steps comprised in the set of predefined program steps.

According to some embodiments, the internal communication unit is configured to communicate with the external device via a first wireless connection for receiving the update to the second control program, and a second connection for performing an authentication of the communication with the external device.

According to some embodiments, the second connection is a wireless short-range connection.

According to some embodiments, the authentication second connection is an electrical connection using the patient's body as a conductor.

According to some embodiments, the internal computing unit is further configured to, upon verification, installing the update.

According to some embodiments, the internal computing unit has a sleep mode and an active mode, and the implant further comprises a sensor configured to detect a wake signal, and wherein the implant is configured to in response to a detected wake signal set the internal computing unit to the active mode.

According to some embodiments, the sensor is configured to detect an acoustic signal as wake signal or wherein the sensor is configured to detect a magnetic signal as the wake signal.

According to some embodiments, the sensor is configured to detect the received signal strength of a signal, and the implant is further configured to set the internal computing unit to the active mode in response to the sensor detecting a signal exceeding a threshold signal strength.

According to some embodiments, the implant is further comprising a second internal computing unit, and wherein the implant is configured to set the internal computing unit to the active mode via the second internal computing unit.

According to some embodiments, the internal computing unit in the sleep mode is substantially without power, and wherein setting the internal computing unit in the active mode comprises providing the internal computing unit with power.

According to some embodiments, the implant comprises an energy controller for controlling the power supplied to the internal computing unit.

According to some embodiments, the sensor is configured to provide the energy controller with a second wake signal in response to detecting the wake signal, and wherein the energy controller is configured to set the computing unit in the active mode in response to the second wake signal.

According to some embodiments, the sensor is configured to detect the received signal strength of a signal, and the internal control unit is further configured to set the internal computing unit to the active mode in response to the sensor detecting a signal exceeding a threshold signal strength.

According to some embodiments, the wake signal comprises a predetermined signal pattern, and the implant is further configured to set the processing unit to the active mode in response to the sensor detecting the predetermined signal pattern.

According to some embodiments, the sensor is a hall effect sensor, a fluxgate sensor, an ultra-sensitive magnetic field sensor or a magneto-resistive sensor.

According to some embodiments, the sensor comprises a third coil having an iron core.

According to some embodiments, the sensor is comprised in the internal communication unit.

According to some embodiments, the implant is further comprising a frequency detector, communicatively coupled to the internal computing unit, and configured to detect a frequency for data communication between the internal communication unit and an external device configured to transmit a frequency indicator signal.

According to some embodiments, the frequency detector comprises an antenna.

According to some embodiments, the internal communication unit comprises a coil or a high-sensitivity magnetic field detector for communicating with the external device.

According to some embodiments, the implant is further comprising a sensation generator configured to generate a sensation detectable by a sense of the patient, the sensation generator being communicatively coupled to the internal control unit and being configured to, upon request, generate the sensation when the implant is implanted in the patient.

According to some embodiments, the sensation generator is configured to receive the request from the internal control unit of the implant.

According to some embodiments, the sensation generator is configured to create the sensation or sensation components by at least one of:

a vibration of the sensation generator;

producing a sound;

providing a photonic signal;

providing a light signal;

providing an electric signal; and a heat signal.

According to some embodiments, the sensation generator is configured to be implanted in the patient.

According to some embodiments, the sensation generator is configured to be worn in contact with the skin of the patient.

According to some embodiments, the sensation generator is configured generate the sensation without being in physical contact with the patient.

According to a second part of aspect 312SE, a method for programming an implant by an external device is provided. The implant comprising an internal computing unit configured to control a function of said implant and an internal memory configured to store: a first control program for controlling the internal computing unit, a second, updatable or configurable, control program for controlling said function of said implant, and a set of predefined program steps for updating the second control program, the external device being configured to communicate with the implant via a first connection. The method comprising:

providing, at the internal computing unit, a set of predefined program steps for updating the second control program;

transmitting, by the external device, an update comprising a subset of the predefined program steps over the first connection;

receiving, at the internal computing unit, the update, verifying, by the internal computing unit, that the update comprises a subset of the predefined program steps, and upon verification of the instructions, running the update at the implant.

According to some embodiments, the predefined program steps comprise setting a variable related to a pressure, a time, a minimum or maximum temperature, a current, a voltage, an intensity, a frequency, an amplitude of electrical stimulation, a feedback, a post-operative mode or a normal mode, a catheter mode, a fibrotic tissue mode, an time open after urination, a time open after urination before bed-time.

According to some embodiments, the verifying comprises rejecting the update in response to the update comprising program steps not comprised in the set of predefined program steps.

According to some embodiments, the verifying comprises allowing the update in response to the update only comprising program steps comprised in the set of predefined program steps.

According to some embodiments, the method is further comprising:

authenticating the communication between the implant and the external device over a second connection.

According to some embodiments, the second connection is a wireless short-range connection.

According to some embodiments, the second connection is an electrical connection using the patient's body as a conductor.

According to some embodiments, the method is further comprising, upon verification, installing the update.

According to some embodiments, the method is further comprising:

monitoring for signals by a sensor connected to the internal computing unit;

providing, from a signal provider comprised in the external control unit, a wake signal;

setting, by the internal computing unit and in response to a detected wake signal, a mode of a portion of the internal control unit from a sleep mode to an active mode.

According to some embodiments, the portion of the internal computing unit is the first control program or the second control program.

According to some embodiments, the method is further comprising detecting, using a frequency detector, a frequency for the first communication channel between a first communication unit and a second communication unit, the first communication unit being associated with the internal control unit and the second communication unit being associated with the external device, wherein the frequency detector is communicatively coupled to the internal computing unit.

According to some embodiments, the method is further comprising:

determining, using the frequency detector, the frequency for the first communication channel.

According to some embodiments, the method is further comprising:

generating, using a sensation generator communicatively coupled to the internal control unit, a sensation detectable by a sense of the patient in response to verifying the update, in response to running the update or in response to the update being installed at the implant.

According to some embodiments, the generating comprises at least one of:

providing a vibration of the sensation generator;

producing a sound;

providing a photonic signal;

providing a light signal;

providing an electric signal; and providing a heat signal.

According to a third part of aspect 312SE, a computer program product is provided. The computer program product comprises a computer-readable storage medium with instructions adapted to carry out the method of any one of the embodiments of the second part of aspect 312SE and/or with instructions adapted to carry out an action in any of the implant embodiments of the first part of aspect 312SE, when executed by a computing unit in an external device having processing capability.

Aspect 313SE eHealth Watchdog—Safety Reset
Function—Embodiments of Aspect 313SE of the
Disclosure According to a first part of aspect 313SE, a programmable or updatable implant is provided. The implant comprises:

an internal processor comprising:

a first control program for controlling a function of the implant, and a first reset function, said first reset function being configured to restart or reset said first control program in response to:

a timer of the first reset function has not been reset, or a malfunction in the first control program.

According to some embodiments, the first control program comprises a second reset function for resetting the timer of the first reset function.

According to some embodiments, the first reset function comprises a timer and the second reset function is configured to reset the timer.

According to some embodiments, the reset function comprises a first reset function and a second reset function, wherein the first reset function is configured to trigger a corrective function for correcting the first control program, and wherein the second reset function is configured to restart the first control program after the corrective function has been triggered.

According to some embodiments, the first or second reset function is configured to invoke a hardware reset by activating an internal or external pulse generator which is configured to create a reset pulse for the internal computing unit or the first control program.

According to some embodiments, the internal computing unit is configured to have an active mode and a sleep mode, and wherein the first reset function is configured to have an active mode and a sleep mode corresponding to the active mode and the sleep mode of the internal computing unit.

According to some embodiments, the implant is further comprising a sensor for measuring a physiological parameter of the patient or a parameter of the implant, and wherein the sensor is configured to invoke the reset function in response to the parameter being above or below a predetermined value.

According to some embodiments, the sensor is a pressure sensor adapted to measure a pressure in a part of the implant.

According to some embodiments, the pressure sensor is configured to measure a pressure in a reservoir or a restriction device of the implant.

According to some embodiments, the sensor is a pressure sensor adapted to measure a pressure in an organ of the patient's body.

According to some embodiments, the reset function is configured to be invoked by an electrical reset pulse, and wherein the sensor is adapted to invoke the reset function by activating an internal or external pulse generator which is configured to create a reset pulse for the reset function.

According to some embodiments, the physiological parameter of the patient or a parameter of the implant is a temperature.

According to some embodiments, the reset function comprises invoking a second control program comprising a safety measure.

According to some embodiments, the safety measure comprises controlling a function of the implant.

According to some embodiments, the internal computing unit is configured to invoke the reset function periodically.

According to some embodiments, periodically comprises every 24 hours.

According to some embodiments, the internal computing unit further comprises a monitoring function for monitoring a function of the implant or the first control program, and wherein the reset function is configured to in response to an incorrect or absent response for the monitoring program, reset or restart the first control program.

According to some embodiments, the internal computing unit has an active mode and a sleep mode, the sleep mode having a lower energy consumption than the active mode, and wherein the implant further comprises an internal control unit connected to the internal computing unit and adapted to control the mode of the internal computing unit.

According to some embodiments, the implant further comprises a second sensor for measuring a physiological parameter of the patient or a parameter of the implant, the second sensor being connected to the internal control unit, and, in response to a sensor measurement differing from, exceeding or being less than a predetermined value, setting the internal computing unit in the active mode.

According to some embodiments, the sensor is configured to measure the physical parameter periodically.

According to some embodiments, the sensor and the second sensor is the same sensor.

According to some embodiments, the sensor is a pressure sensor.

According to some embodiments, the sensor is adapted to measure a pressure in one or more of: an organ of a patient; a reservoir; and a restriction device.

According to some embodiments, the implant further comprises a third sensor for detecting a wake signal from an external device, the second sensor being connected to the internal control unit, and, in response to a measurement differing from, exceeding or being less than a predetermined value, setting the internal computing unit in the active mode.

According to some embodiments, the signal is a magnetic signal or an acoustic signal.

According to some embodiments, the sensor is configured to detect the received signal strength of a signal; and the internal control unit is further configured to set the processing unit to the active mode in response to the sensor detecting a signal exceeding a threshold signal strength.

According to some embodiments, the wake signal comprises a predetermined signal pattern; and the internal control unit is further configured to set the processing unit to the active mode in response to the sensor detecting the predetermined signal pattern.

According to some embodiments, the sensor comprises a hall effect sensor, a fluxgate sensor, an ultra-sensitive magnetic field sensor, a magneto-resistive sensor, a coil, or a coil having an iron core.

According to some embodiments, the internal control unit comprises a first communication unit for receiving and/or transmitting data from and/or to the external control unit; and the external control unit comprises a second communication unit for transmitting and/or receiving data to and/or from the internal control unit.

According to some embodiments, the implant is further comprising a frequency detector, communicatively coupled to the internal control unit, and configured to detect a frequency for data communication between the first communication unit and the second communication unit.

According to some embodiments, the frequency detector comprises an antenna.

According to a second part of the twenty-eighth aspect, a method for controlling a control program of an implant, when implanted in a patient, is provided. The implant comprising a processor for running the first control program, and the method comprising: executing the first control program at the internal computing unit; executing a first reset function; resetting or restarting the first control program by the first reset function in response a detection of a malfunction in the first control program.

According to some embodiments, the resetting or restarting of the first control program comprises triggering a corrective function for correcting the first control program.

According to some embodiments, the method is further comprising:
  periodically resetting, by the first control program, the first reset function,
  wherein the detecting of a malfunction comprises determining that the first reset function has not been reset for a predetermined period of time.

According to some embodiments, the detecting of a malfunction comprises detecting that a sensor measurement relating to a physiological parameter of the patient or a parameter of the implant being less than, exceeding or differing from a predetermined value.

According to some embodiments, the sensor measurement relates to a pressure in a part of the implant.

According to some embodiments, the sensor measurement is related to a pressure in a reservoir or a restriction device of the implant.

According to some embodiments, the sensor measurement is related to a pressure in an organ of the patient's body.

According to some embodiments, the physiological parameter of the patient or a parameter of the implant is a temperature.

According to some embodiments, the reset function comprises invoking a second control program comprising a safety measure.

According to some embodiments, the safety measure comprises controlling a function of the implant.

According to some embodiments, periodically comprises every 24 hours.

According to some embodiments, the method is further comprising:

monitoring a function of the implant or the first control program, and wherein the reset function is configured to in response to an incorrect or absent response for the monitoring program, reset or restart the first control program.

According to a third part of the twenty-eighth aspect, a computer program product comprising a computer-readable storage medium with instructions adapted to carry out the method of any one of embodiments of the second part of the twenty-eighth aspect, and/or with instructions adapted to carry out an action in any of the implant embodiments of the first part of the twenty-eighth aspect, when executed by a computing unit in an external device having processing capability, is provided.

Aspect 314SE eHealth Logging—Update Confirmation—Embodiments of Aspect 314SE of the Disclosure According to a first part of aspect 314SE, a method for updating a control program of an internal computing unit comprised in an implant is provided. The implant is adapted for communication with a first external device and a second external device, and the method comprises:

receiving, by the internal computing unit, an update or configuration to the control program from the first external device, wherein the update is received using a first communication channel;

installing, by the internal computing unit, the update; and transmitting, by the internal computing unit, logging data relating to the receipt of the update or configuration and/or logging data relating to an installation of the update to the second external device using the second communication channel;

wherein the first and the second communication channels are different communication channels.

According to some embodiments, the update or configuration comprises a set of instructions for the control program.

According to some embodiments, the steps comprises a subset of a set of predefined steps.

According to some embodiments, the method is further comprising confirming, by a user or by an external control unit, that the update or configuration is correct based on the received logging data.

According to some embodiments, the logging data is related to the receipt of the update or configuration, and the internal computing unit is configured to install the update or configuration in response to receipt of a confirmation that the logging data relates to a correct set of instructions.

According to some embodiments, the method is further comprising:

installing, in response to the confirmation that the update or configuration is correct, the update or configuration.

According to some embodiments, the logging data is related to the installation of the update or configuration.

According to some embodiments, the method is further comprising:

activating the installation in response to the confirmation that the update or configuration is correct.

According to some embodiments, the update or configuration comprises a plurality of steps, and the receiving of the update or configuration further comprises receiving the plurality of steps in two or more subsets.

According to some embodiments, the method is further comprising confirming, by a user or by an external device, that each of the subsets are correct.

According to some embodiments, the method is further comprising confirming that the installation is complete by producing a sound or a vibration detectable by the user.

According to some embodiments, the configuration or update comprises a value for a predetermined parameter.

According to some embodiments, the method is further comprising receiving, by the first external device, an update or a configuration to the control program by a user.

According to some embodiments, the method is further comprising:

selecting, by a user of the first external device, a step from a set of predetermined steps, to be comprised in the update or configuration, and/or setting, by a user of the first external device, a value for a parameter to be comprised in the update or configuration.

According to some embodiments, the communication over the first communication channel is performed using a first network protocol, and communication over the second communication channel is performed using a second network protocol, the first and second protocols being different.

According to some embodiments, the network protocol is at least one from the list of:

Radio Frequency type protocol

RFID type protocol

WLAN type protocol

Bluetooth type protocol

BLE type protocol

NFC type protocol

3G/4G/5G type protocol

GSM type protocol.

According to some embodiments, the second network protocol is at least one from the list of:

Radio Frequency type protocol

RFID type protocol

WLAN type protocol

Bluetooth type protocol

BLE type protocol

NFC type protocol

3G/4G/5G type protocol

GSM type protocol.

According to some embodiments, the method is, after transmitting the logging data to the second external device, further comprising the step of:

verifying the update via a confirmation from the second external device via the second communication channel.

According to a second part of aspect 314SE, an implant adapted for communication with a first external device and a second external device, when the implant is adapted to be implanted in a patient, is provided. The implant comprising:

a communication unit comprising a wireless receiver configured to receive data from the first external device, and a transmitter configured to transmit data to the second external device, an internal computing unit comprising an updatable control program for controlling a function of said implant, the internal computing unit being connected to the communication unit, and being configured to receive an update or a configuration to the updatable control program from the first external via the communication unit, and the internal computing unit being configured to, when updating the control program, transmit logging data relating to the update to the second external device, and wherein the communication unit is configured to receive data from the first external device via a first communication channel and transmit data to the second external device via a second communication channel, the first and second communication channels being different communication channels.

According to some embodiments, the update or configuration comprises a set of instructions for the control program.

According to some embodiments, the steps comprises a subset of a set of predefined steps.

According to some embodiments, the second external device is configured to confirm that the update or configuration is correct based on the received logging data.

According to some embodiments, the logging data is related to the receipt of the update or configuration, and the internal computing unit is configured to install the update or configuration in response to receipt of a confirmation that the logging data relates to a correct set of instructions.

According to some embodiments, the logging data is related to the installation of the update or configuration, and wherein the internal computing unit is configured to activate the installation in response to a confirmation that the update or configuration is correct.

According to some embodiments, the update or configuration comprises a plurality of steps, and the update or configuration is received by the internal computing unit in two or more sub steps.

According to some embodiments, the method is further comprising a sensation generator adapted to create a sensation detectable by the user.

According to some embodiments, the internal computing unit is configured to cause the sensation generator to create a sensation detectable by the user in response to the update or configuration being received, in response to the update or configuration being installer or in response to the update or configuration being confirmed.

According to some embodiments, the sensation generator is a vibrator or a speaker.

According to some embodiments, the configuration or update comprises a value for a predetermined parameter.

According to some embodiments, the configuration or update comprises a step from a set of predetermined steps.

According to some embodiments, the communication over the first communication channel is performed using a first network protocol, and communication over the second communication channel is performed using a second network protocol, the first and second protocols being different.

According to some embodiments, the network protocol is at least one from the list of:

Radio Frequency type protocol
RFID type protocol
WLAN type protocol
Bluetooth type protocol
BLE type protocol
NFC type protocol
3G/4G/5G type protocol
GSM type protocol.

According to some embodiments, the second network protocol is at least one from the list of:

Radio Frequency type protocol
RFID type protocol
WLAN type protocol

Bluetooth type protocol
BLE type protocol
NFC type protocol
3G/4G/5G type protocol
GSM type protocol.

According to some embodiments, the second communication channel is an electrical connection.

According to a third part of aspect 314SE, a computer program product comprising a computer-readable storage medium with instructions adapted to carry out the method of any one of embodiments of the first part of aspect 314SE and/or with instructions adapted to carry out an action in any of the implant embodiments of the second part of aspect 314SE, when executed by a computing unit in an external device having processing capability, is provided.

Aspect 315SE eHealth Sleeping Internal Control Unit—Sleep Mode for Internal Controller—Embodiments of Aspect 315SE of the Disclosure According to first part of aspect 315SE, an implant having a controller with a sleep mode is provided. The implant comprises:

a controller connected to or comprised in the implant, the controller comprising:

a sensor, the sensor being a passive sensor; and a processor having a sleep mode and an active mode;

wherein:

the sensor is configured to measure a physiological parameter of the patient or a parameter of the implant, and the controller is further configured to, in response to a sensor measurement having a value outside of a predetermined interval, set the processor in the active mode.

According to some embodiments, the sensor is configured to measure periodically.

According to some embodiments, the sensor is a mechanical sensor.

According to some embodiments, the sensor comprises a pressure sensor, a piezoelectric sensor, or a bimetal.

According to some embodiments, the sensor is configured to measure a physiological parameter of the patient; and the sensor is a pressure sensor.

According to some embodiments, the pressure sensor is adapted to measure a pressure in one or more of: an organ of a patient; a reservoir; and a restriction device.

According to some embodiments, the sensor is configured to measure a parameter of the implant; and the sensor is adapted to measure one or more of: a battery status of a battery of the implant and a temperature of the implant.

According to some embodiments, the sensor is an analog sensor or a digital sensor.

According to some embodiments, the implant is further comprising a sensation generator configured to, upon request, generate a sensation detectable by a sense of the patient.

According to some embodiments, the sensation generator is configured to receive the request from the controller of the implant.

According to some embodiments, the request is generated by the controller in response to the sensor measurement having a value outside of the predetermined interval.

According to some embodiments, the sensation generator is configured to receive the request from an external controller.

According to some embodiments, the generated sensation comprises a plurality of sensation components.

According to some embodiments, the sensation generator is configured to create the sensation or sensation components by at least one of: a vibration of the sensation generator; producing a sound; providing a photonic signal; providing a light signal; providing an electric signal; and providing a heat signal.

According to some embodiments, the implant is further comprising an active unit, communicatively coupled to the processor, for performing controlling or monitoring a bodily function in the patient.

According to some embodiments, the sensor is configured to measure a physiological parameter of the patient; and the active unit is configured to perform the controlling or monitoring in response to a sensor measurement having a value outside of the predetermined interval, after the processor has been set in the active state. By "a value outside of a predetermined interval" it may be meant that the value is outside of an interval determined by a control unit, that the value is less than (or less than or equal) to a predetermined threshold, and/or that the value is exceeding (or exceeding or equal to) a predetermined threshold.

According to some embodiments, the controller further comprises a communication unit communicatively coupled to the processor, and the processor is configured to transmit data relating to the measurement via the communication unit.

According to some embodiments, the implant is further comprising a frequency detector, communicatively coupled to the controller and configured to detect a frequency for data communication to or from the communication unit.

According to some embodiments, the frequency detector comprises an antenna.

According to a second part of aspect 315SE, a system is provided. The system comprising:

the implant according to any of the embodiments of the first part of aspect 315SE; and an external controller, adapted to be arranged outside of the patient's body, configured to communicate with the communication unit.

According to some embodiments, the external controller is a wireless remote control.

According to some embodiments, the communication unit is further configured to:

receive one or more control signals from the external controller, and control an operation of the implant based on the one or more control signals, when the processor is in the active state.

According to some embodiments, the one or more control signals is selected from the group consisting of:

a sound signal;
an ultrasound signal;
an electromagnetic signal;
an infrared signal;
a visible light signal;
an ultraviolet light signal;
a laser signal;
a microwave signal;
a radio wave signal;
an X-ray radiation signal; and
a gamma radiation signal.

According to some embodiments, the system is further comprising a frequency detector, communicatively coupled to the external controller, and configured to detect a frequency for data communication between the communication unit and the external controller.

According to some embodiments, the frequency detector comprises an antenna.

According to some embodiments, the system is further comprising an external sensation generator adapted to be arranged outside of the patient's body and to, upon request, generate a sensation detectable by a sense of the patient.

According to some embodiments, the external controller is configured to generate the request.

According to some embodiments, the external sensation generator is configured to be worn in contact with the skin of the patient.

According to some embodiments, the external sensation generator is configured to generate the sensation without being in physical contact with the patient.

According to a third part of aspect 315SE, a method for controlling an implant implanted in a patient is provided. The method comprising:

measuring, with a passive sensor of a controller connected to or comprised in the implant, a physiological parameter of the patient or a parameter of the implant; and in response to a sensor measurement having an value outside of a predetermined interval, setting, by the controller, a processor of the controller from a sleep mode to an active mode. By "a value outside of a predetermined interval" it may be meant that the value is outside of a interval, that the value is less than (or less than or equal) to a predetermined threshold, and/or that the value is exceeding (or exceeding or equal to) a predetermined threshold.

According to some embodiments, the measuring is carried out periodically.

According to some embodiments, the method is further comprising generating, with a sensation generator comprised in or connected to the implant, a sensation detectable by a sense of the patient.

According to some embodiments, the method is further comprising generating, by the controller, a request to generate a sensation with the sensation generator in response to the sensor measurement having a value outside of a predetermined interval.

According to some embodiments, the method is further comprising:

performing, with an active unit comprised in or connected to the implant, a medical intervention in the patient.

According to some embodiments, the method is further comprising:

performing the medical intervention in response to a sensor measurement having a value outside of a predetermined interval, after setting the processor in the active state.

According to some embodiments, the method is further comprising:

detecting, using a frequency detector, a frequency for data communication to or from a communication unit, the frequency detector being communicatively coupled to the controller.

According to some embodiments, the detecting is initiated in response to setting the processor in the active state.

According to some embodiments, the method is further comprising:

exchanging data communications between the communication unit and an external controller, adapted to be arranged outside of the patient's body, wherein the data communications comprise at least one of:

data relating to the measurement, and one or more control signals transmitted by the external controller.

According to some embodiments, the method is further comprising:

controlling an operation of the implant based on the one or more control signals, when the processor is in the active state.

According to some embodiments, the method is further comprising:

detecting, using an external frequency detector, a frequency for data communication between the communication unit and the external controller, the external frequency detector being communicatively coupled to the external controller.

According to a fourth part of aspect 315SE, a computer program product comprising a computer-readable storage medium with instructions adapted to carry out the method of any one of embodiments of the third part of aspect 315SE, and/or with instructions adapted to carry out an action in any of the implant embodiments of the first part or any of the system embodiments of the second part, when executed by a computing unit in an external device having processing capability, is provided.

Aspect 316SE eHealth Relay
Instructions—Relaying of
Instructions—Embodiments of Aspect 316SE According to a first part of aspect 316SE, a method for transmitting an instruction from a first external device to an implant is provided. The method comprising:

transmitting an instruction for the implant from the first external device to a second external device, the instruction relating to a function of the implant, encrypting, at the second external device and using a first encryption key, the instruction into an encrypted instruction, and transmitting the encrypted instruction from the second external device to the implant, decrypting, at the implant, the instructions using a second encryption key corresponding to the first encryption key.

According to some embodiments, the transmitting of the encrypted instruction from the second external device to the implant comprises:

transmitting the encrypted instruction from the second external device to the first external device, and transmitting the encrypted instruction from the first external device to the implant.

According to some embodiments, the transmitting of the encrypted instruction from the second external device to the implant comprises:

transmitting the encrypted instruction from the second external device to a third external device, and transmitting the encrypted instruction from the third external device to the implant.

According to some embodiments, the second external device is an encryption device communicatively coupled to the first external device, and wherein the communication of the instruction between the second external device and the implant is relayed through the first external device.

According to some embodiments, the method is further comprising, at the implant, running the instruction.

According to some embodiments, the method is further comprising receiving, at the first external device, the instruction.

According to some embodiments, the method is further comprising displaying, at the external device, a user interface for receiving the instruction.

According to some embodiments, the implant comprises a set of a predefined program steps, and wherein the method further comprises verifying, by the implant, that the received instruction is comprised in the predefined program steps.

According to some embodiments, the verifying comprises rejecting the instruction in response to the instruction not being comprised in the set of predefined program steps.

According to some embodiments, the verifying comprises allowing the instruction in response to the instruction being comprised in the set of predefined program steps.

According to some embodiments, the first external device and the implant are configured to communicate over a wireless connection.

According to some embodiments, the wireless connection comprises using at least one of the following protocols:

Radio Frequency type protocol

RFID type protocol

WLAN type protocol

Bluetooth type protocol

BLE type protocol

NFC type protocol

3G/4G/5G type protocol

GSM type protocol

Bluetooth 5.

According to some embodiments, the transmitting of data between the first external device and the second external device is performed a wireless connection.

According to some embodiments, the method is further comprising authenticating the connection between the first external device and the implant over which the encrypted instruction is to be transmitted.

According to some embodiments, the implant comprises an internal control unit for controlling a function of the implant, and wherein the internal control unit is configured to run the instruction.

According to a second part of aspect 316SE, A system for transmitting an instruction from a first external device to an implant is provided. The system comprising:

an implant implanted in a human patient, the implant comprising an internal control unit configured to control a function of the implant and configured to receive an instruction from an external device;

a first external device configured to receive or determine an instruction to be transmitted to the implant, and to transmit the instruction to a second external device; and a second external device configured to receive the instruction transmitted from the first external device, encrypt the instruction, and transmit the encrypted instruction to the implant, wherein the implant is configured to received and decrypt the instruction.

According to some embodiments, the second external device is configured to transmit the encrypted instruction by transmitting the encrypted instruction to the first external device, and wherein the first external device is configured to transmit the encrypted instruction to the implant.

According to some embodiments, the second external device is configured to transmit the encrypted instruction by transmitting the encrypted instruction to a third external device, and wherein the third external device is configured to transmit the encrypted instruction to the implant According to some embodiments, the second external device is an encryption device communicatively coupled to the first external device, and wherein any communication between the implant and the second external device is relayed through the first external device.

According to some embodiments, the internal control unit is configured to run the decrypted instruction for controlling a function of the implant.

According to some embodiments, the first external device is configured to display a user interface for receiving the instruction.

According to some embodiments, the implant comprises a set of a predefined program steps, and wherein the implant is configured to verify that the received instruction is comprised in the predefined program steps.

According to some embodiments, the implant is configured to reject the instruction in response to the instruction not being comprised in the set of predefined program steps.

According to some embodiments, the implant is configured to allow the instruction in response to the instruction being comprised in the set of predefined program steps.

According to some embodiments, the first external device and the implant are configured to communicate over a wireless connection.

According to a third part of aspect 316SE, a computer program product comprising a computer-readable storage medium with instructions adapted to carry out the method of any one of embodiments of the first part and/or with instructions adapted to carry out an action in any of the system embodiments of the second part, when executed by a computing unit in an external device having processing capability, is provided.

Aspect 317SE Energy General
Microphone—Microphone Sensor—Embodiments
of Aspect 317SE of the Disclosure According to a first part of aspect 317SE, a controller for controlling an energized implant is provided. According to a first part of this aspect there is provided an implantable controller for controlling an energized implant, when implanted in a patient, the controller comprises a computing unit and at least one microphone, wherein the at least one microphone is configured to register a sound related to at least one of: a bodily function, and a function of the implant.

According to some embodiments of the first part of aspect 317SE, the implantable controller further comprises at least one implantable housing for sealing against fluid, and wherein the computing unit and the microphone are placed inside of the housing.

According to some embodiments of the first part of aspect 317SE, wherein the computing unit is configured to derive a pulse of the patient from the registered sound related to a bodily function.

According to some embodiments of the first part of aspect 317SE, the computing unit is configured to derive information related to the patient urinating from the registered sound related to a bodily function.

According to some embodiments of the first part of aspect 317SE, the computing unit is configured to derive information related to a bowel activity of the patient from the registered sound related to a bodily function.

According to some embodiments of the first part of aspect 317SE, the computing unit is configured to derive information related to a functional status of the implant from the registered sound related to a function of the implant.

According to some embodiments of the first part of aspect 317SE, the computing unit is configured to derive information related to the functional status of an operation device of the implant, from the registered sound related to a function of the implant.

According to some embodiments of the first part of aspect 317SE, the computing unit is configured to derive information related to the functional status of at least one of: a motor, a pump and a transmission of the operation device of the implant from, the registered sound related to a function of the implant.

According to some embodiments of the first part of aspect 317SE, the implantable controller further comprises a transceiver, and wherein the controller is configured to transmit a parameter derived from the sound registered by the at least one microphone using the transceiver.

According to a second part of aspect 317SE there is provided a method of authenticating an energized implant implanted in a patent, performed in a system comprising the energized implant and an external device, the energized implant comprising at least one microphone, and a transmitter, and the external device comprising a receiver and a computing unit. The method comprises: registering a sound related to at least one of: a bodily function and a function of the implant, using the at least one microphone, transmitting a signal derived from the registered sound, using the transmitter, receiving, in the external device, the signal derived from the registered sound, using the receiver, and comparing, in the external device, a parameter derived from the received signal with a reference parameter, using the computing unit.

According to some embodiments of the second part of aspect 317SE, the method further comprises the step of authenticating the energized implant on the basis of the comparison.

According to some embodiments of the second part of aspect 317SE, the method further comprises receiving, at the receiver of the external device, a parameter to be used as reference parameter.

According to some embodiments of the second part of aspect 317SE the step of receiving a parameter to be used as reference parameter comprises receiving the parameter from a sensor external to the patient.

According to some embodiments of the second part of aspect 317SE the registered sound is related to a pulse of the patient, and wherein the reference parameter is related to the pulse of the patient.

According to a third part of aspect 317SE there is provided a method of authenticating an energized implant implanted in a patent, performed in a system comprising the energized implant and an external device, the energized implant comprising at least one microphone, a receiver, and a computing unit, and the external device comprising a transmitter. The method comprising the steps of registering a sound related to at least one of: a bodily function and a function of the implant, using the at least one microphone, deriving a parameter from the sound using the computing unit, receiving, in the energized implant, a reference parameter, from the external device, using the receiver, and comparing, in the energized implant, the parameter derived from the sound with the received reference parameter, using the computing unit.

According to some embodiments of the third part of aspect 317SE, the method further comprises the step of authenticating the energized implant on the basis of the comparison.

According to some embodiments of the third part of aspect 317SE, the method further comprises receiving, at a receiver of the external device, a parameter to be used as reference parameter.

According to some embodiments of the third part of aspect 317SE, the step of receiving a parameter to be used as reference parameter comprises receiving the parameter from a sensor external to the patient.

According to some embodiments of the third part of aspect 317SE, the registered sound is related to a pulse of the patient, and wherein the reference parameter is related to the pulse of the patient.

Aspect 318SE Energy Appetite Control Microphone—Microphone Sensor for Appetite Control—Embodiments of Aspect 318SE of the Disclosure According to a first part of aspect 318SE there is provided an implantable controller for controlling an energized implant for stretching the stomach wall of a patient to thereby create satiety, when implanted in a patient. The controller comprises at least one microphone configured to register a sound related to the patient swallowing, and a computing unit configured to derive a parameter related to the patient swallowing from the sound.

According to some embodiments of the first part of aspect 318SE, the computing unit is configured to derive a parameter related to the size and/or shape and/or viscosity of a swallowed contents.

According to some embodiments of the first part of aspect 318SE, the computing unit is configured to determine if a swallowed content is a liquid or a solid.

According to some embodiments of the first part of aspect 318SE, the computing unit is configured to determine an accumulated amount of swallowed content over a time period.

According to some embodiments of the first part of aspect 318SE, the implantable controller further comprises a transmitter, and wherein the controller is configured to transmit the parameter derived from the sound registered by the at least one microphone using the transmitter.

According to some embodiments of the first part of aspect 318SE, the implantable controller further comprises a receiver wherein the controller is configured to receive a signal from an external device.

According to some embodiments of the first part of aspect 318SE, the computing unit is further configured to generate a control signal for controlling the energized implant for stretching the stomach wall of a patient on the basis of the derived parameter related to the patient swallowing, or the signal received from the external device, or a combination of the derived parameter related to the patient swallowing and the signal received from the external device.

According to a second part of aspect 318SE there is provided a system for controlling an energized implant for stretching the stomach wall of a patient to thereby create satiety, the system comprising an implantable controller for controlling the energized implant and an external device. The implantable controller comprising at least one microphone configured to register a sound related to the patient swallowing, a computing unit configured to derive a parameter related to the patient swallowing from the registered sound, a transmitter configured to transmit the derived parameter, and a receiver configured to receive control signals from the external device. Wherein the external device comprises a receiver configured to receive a parameter derived from a sound related to the patient swallowing, a computing unit configured to generate a control signal on the basis of the received parameter, and a transmitter configured to transmit the control signal to the implantable controller for controlling the energized implant for stretching the stomach wall of a patient to thereby create satiety.

According to some embodiments of the second part of aspect 318SE, the computing unit of the external device is configured to derive a parameter related to the size and/or shape and/or viscosity of a swallowed contents on the basis of the received parameter derived from the sound related to the patient swallowing.

According to some embodiments of the second part of aspect 318SE, wherein the computing unit of the external device is configured to determine if a swallowed content is a liquid or a solid on the basis of the received parameter derived from the sound related to the patient swallowing.

According to some embodiments of the second part of aspect 318SE, the computing unit of the external device is configured to determine an accumulated amount of swallowed content over a time period.

According to some embodiments of the second part of aspect 318SE, the computing unit of the external device is configured to generate the control signal on the basis of the accumulated amount of swallowed content over a time period.

According to a third part of aspect 318SE there is provided a method in an implantable controller for controlling an energized implant for stretching the stomach wall of a patient to thereby create satiety, when implanted in a patient, the implantable controller comprises at least one microphone and a computing unit. The method comprises the steps of registering a sound related to the patient swallowing, using the at least one microphone, and deriving a parameter related to the patient swallowing from the sound, using the computing unit.

According to some embodiments of the third part of aspect 318SE, the method further comprises deriving a parameter related to the size and/or shape and/or viscosity of a swallowed contents, using the computing unit.

According to some embodiments of the third part of aspect 318SE, the method comprises determining if a swallowed content is a liquid or a solid, using the computing unit.

According to some embodiments of the third part of aspect 318SE, the method further comprises determining an accumulated amount of swallowed content over a time period, using the computing unit.

According to some embodiments of the third part of aspect 318SE, wherein the implantable controller further comprises a transmitter, and wherein the method further comprises transmitting a parameter derived from the sound registered by the at least one microphone, to an external device, using the transmitter.

According to some embodiments of the third part of aspect 318SE, the implantable controller further comprises a receiver, and wherein the method further comprises receiving a signal from an external device.

According to some embodiments of the third part of aspect 318SE, the method further comprises generating a control signal for controlling the energized implant for stretching the stomach wall of a patient, using the computing unit, on the basis of: the derived parameter related to the patient swallowing, or the signal received from the external device, or a combination of the derived parameter related to the patient swallowing and the signal received from the external device.

According to a fourth part of aspect 318SE there is provided a method of authenticating an implantable controller for controlling an energized implant for stretching the stomach wall of a patient to thereby create satiety, performed in a system comprising the energized implant and an external device, the energized implant comprising at least one microphone, and a transmitter, and the external device comprising a receiver and a computing unit. The method comprising the steps of registering a sound related to the patient swallowing, using the at least one microphone, and transmitting a signal derived from the registered sound, using the transmitter, receiving, in the external device, the signal derived from the registered sound, using the receiver, and comparing, in the external device, a parameter derived from the received signal with a reference parameter, using the computing unit.

According to some embodiments of the fourth part of aspect 318SE, the method further comprises the step of authenticating the energized implant on the basis of the comparison.

According to some embodiments of the fourth part of aspect 318SE, the method further comprises receiving, at the receiver of the external device, a parameter to be used as reference parameter.

According to some embodiments of the fourth part of aspect 318SE, the step of receiving a parameter to be used as reference parameter comprises receiving the parameter from a sensor external to the patient.

According to some embodiments of the fourth part of aspect 318SE, the step of receiving the parameter from a sensor external to the patient comprises receiving the parameter from a sensor configured to sense the patient swallowing.

According to some embodiments of the fourth part of aspect 318SE, the step of receiving a parameter to be used as reference parameter comprises receiving input from the patient.

An external device configured for communication with an implantable medical device, when implanted in a patient, is provided. The external device comprises at least one first wireless transceiver configured for communication with the implantable medical device using a first network protocol, for determining a distance between the external device and the implantable medical device, and at least one second wireless transceiver configured for communication with the implantable medical device using a second network protocol, for transferring data between the external device and the implantable medical device.

According to one embodiment, the first wireless transceiver comprises an UWB transceiver.

According to one embodiment, the first wireless transceiver is configured for transcutaneous energy transfer for at least one of powering an energy consuming component of the implantable medical device and charging an implantable energy storage unit.

According to one embodiment, the second network protocol is a standard network protocol. The standard network protocol may be one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the second wireless transceiver comprises a Bluetooth transceiver.

According to one embodiment, the external device is further configured to communicate with a second external device using said at least one wireless transceiver.

According to one embodiment, the external device is configured for determining a distance between the external device and the implantable medical device by determining the RSSI.

According to one embodiment, a communication range of the first network protocol is less than a communication range of the second network protocol.

According to one embodiment, a frequency band of the first network protocol differs from a frequency band of the second network protocol.

According to one embodiment, the external device is configured to authenticate the implantable medical device if the determined distance between the external device and the implantable medical device is less than a predetermined threshold value.

According to one embodiment, the external device is configured to allow the transfer of data between the external device and the implantable medical device after the implantable medical device has been authenticated.

According to one embodiment, the external device is one from the list of: a wearable external device, and a handset.

An implantable medical device configured for communication with an external device is provided. The implantable medical device comprises at least one first wireless transceiver configured for communication with the external device using a first network protocol, for determining a distance between the external device and the implantable medical device, and at least one second wireless transceiver configured for communication with the external device using a second network protocol, for transferring data between the external device and the implantable medical device.

According to one embodiment, the first wireless transceiver comprises an UWB transceiver.

According to one embodiment, the first wireless transceiver is configured for transcutaneous energy transfer for at least one of: powering an energy consuming component of the implantable medical device, and charging an implantable energy storage unit.

According to one embodiment, the second network protocol is a standard network protocol, such as selected from the list of Radio Frequency type protocol, RFID type protocol, WLAN type protocol, Bluetooth type protocol, BLE type protocol, NFC type protocol, 3G/4G/5G type protocol, and GSM type protocol.

According to one embodiment, the second wireless transceiver comprises a Bluetooth transceiver.

According to one embodiment, the implantable medical device is further configured to communicate with a second external device using said at least one wireless transceiver.

According to one embodiment, the implantable medical device is configured for determining a distance between the external device and the implantable medical device by determining the RSSI.

According to one embodiment, a communication range of the first network protocol is less than a communication range of the second network protocol.

According to one embodiment, a frequency band of the first network protocol differs from a frequency band of the second network protocol.

According to one embodiment, the implantable medical device is configured to authenticate the external device if the determined distance between the external device and the implantable medical device is less than a predetermined threshold value.

According to one embodiment, the implantable medical device is configured to allow the transfer of data between the implantable medical device and the external device after the external device has been authenticated.

According to one embodiment, the implantable medical device comprises at least one of:

an external heart compression device.

an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries, an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device.

an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A patient external device configured for communication with an implantable medical device, when implanted in a patient, is provided. The patient external device comprises a wireless communication unit configured for wireless transmission of control commands to the implantable medical device and configured for wireless communication with a patient display device, and a computing unit configured for running a control software for creating the control commands for the operation of the implantable medical device. The computing unit is configured to transmit a control interface as a remote display portal to a patient display device configured to display the control interface to a user, receive user input from the patient display device, and transform the user input into the control commands for wireless transmission to the implantable medical device.

According to one embodiment, the wireless communication unit comprises a wireless transceiver for wireless transmission of control commands to the implantable medical device, and wireless transmission of the control interface as the remote display portal to the patient display device.

According to one embodiment, the wireless communication unit comprises a first wireless transceiver for wireless transmission of control commands to the implantable medical device, and a second wireless transceiver for wireless transmission of the control interface to the patient display device.

According to one embodiment, the wireless communication unit is configured for wireless communication with the patient display device using a standard network protocol.

According to one embodiment, the wireless communication unit is configured for wireless communication with the implantable medical device using a proprietary network protocol.

According to one embodiment, the wireless communication unit comprises a Bluetooth transceiver.

According to one embodiment, at least one of the first and second wireless transceiver comprises a Bluetooth transceiver.

According to one embodiment, the wireless communication unit comprises a UWB transceiver.

According to one embodiment, at least one of the first and second wireless transceiver comprises a UWB transceiver.

According to one embodiment, the wireless communication unit comprises at least one first wireless transceiver configured for communication with the implantable medical device using a first network protocol, for determining a distance between the patient external device and the implantable medical device, and at least one second wireless transceiver configured for communication with the implantable medical device using a second network protocol, for transferring data between the patient external device and the implantable medical device.

According to one embodiment, the first wireless transceiver is configured for transcutaneous energy transfer for at least one of: powering an energy consuming component of the implantable medical device and charging an implantable energy storage unit.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, a communication range of the first wireless transceiver is less than a communication range of the second wireless transceiver.

According to one embodiment, at least one of:
the patient external device is configured to authenticate the implantable medical device if a distance between the patient external device and the implantable medical device is less than a predetermined threshold value,
the patient external device is configured to be authenticated by the implantable medical device if a distance between the patient external device and the implantable medical device is less than a predetermined threshold value,
the patient external device is configured to authenticate the patient display device if a distance between the patient external device and the patient display device is less than a predetermined threshold value, and
the patient external device is configured to be authenticated by the implantable medical device if a distance between the patient external device and the patient display device is less than a predetermined threshold value.

According to one embodiment, the patient external device is configured to allow the transfer of data between at least one of: the patient external device and the implantable medical device, and the patient external device and the patient display device, on the basis of the authentication.

According to one embodiment, the computing unit is configured to encrypt at least one of the control interface and the control commands.

According to one embodiment, the implantable medical device comprises at least one of:
an external heart compression device,
an apparatus assisting the pump function of a heart of the patient,
an apparatus assisting the pump function comprising a turbine bump placed within a patient's blood vessel for assisting the pump function of the heart,
an operable artificial heart valve,
an operable artificial heart valve for increasing the blood flow to the coronary arteries.
an implantable drug delivery device,
an implantable drug delivery device for injecting directly into a blood vessel and change the position of the injection site, all from within the patient's body,
an implantable drug delivery device for injecting potency enhancing drugs into an erectile tissue of the patient,
a hydraulic, mechanic, and/or electric constriction implant,
an operable volume filling device,
an operable gastric band,
an operable implant for stretching the stomach wall of the patient for creating satiety,
an implant configured to sense the frequency of the patient ingesting food,
an operable cosmetic implant,
an operable cosmetic implant for adjust the shape and/or size in the breast region of a patient,
an implant controlling medical device for the emptying of a urinary bladder,
an implant hindering urinary leakage,
an implant hindering anal incontinence,
an implant controlling the emptying of fecal matter,
an implant monitoring an aneurysm,
an implant for hindering the expansion of an aneurysm,
an implant lubricating a joint,
an implant for affecting the blood flow to an erectile tissue of the patient,
an implant for simulating the engorgement of an erectile tissue,
an implant with a reservoir for holding bodily fluids,
an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A patient display device for communication with a patient remote external device for communication with an implantable medical device is provided. The patient display device comprises a wireless communication unit configured for wirelessly receiving an implant control interface as a remote display portal from the patient remote external device and configured for wirelessly transmitting implant control user input to the patient remote external device, a display for displaying the received implant control interface, and an input device for receiving implant control input from the user.

According to one embodiment, the patient display device further comprises an auxiliary wireless communication unit. The auxiliary wireless communication unit is configured to be disabled to enable at least one of: wirelessly receiving the implant control interface as the remote display portal from the patient remote external device, and wirelessly transmitting implant control user input to the patient remote external device.

According to one embodiment, the wireless communication unit is configured for wireless communication with the patient remote external device using a standard network protocol. The standard network protocol may be one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the wireless communication unit is configured for wireless communication with the patient remote external device using a proprietary network protocol.

According to one embodiment, the wireless communication unit comprises a Bluetooth transceiver.

According to one embodiment, the wireless communication unit comprises a UWB transceiver.

According to one embodiment, a communication range of the wireless communication unit is less than a communication range of the auxiliary wireless communication unit.

According to one embodiment, the patient display device is configured to authenticate the patient remote external device if a distance between the patient display device and the patient remote external device is less than a predetermined threshold value, or to be authenticated by the patient remote external device if a distance between the patient display device and the patient remote external device is less than a predetermined threshold value.

According to one embodiment, the patient display device is configured to allow the transfer of data between the patient display device and the patient remote external device on the basis of the authentication.

According to one embodiment, the patient display device is a wearable external device or a handset.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A communication system for enabling communication between a patient display device and an implantable medical device, when implanted, is provided. The communication system comprises: a patient display device.

a server, and a patient remote external device. The patient display device comprises a wireless communication unit configured for wirelessly receiving an implant control interface as a remote display portal being provided by the patient remote external device. The wireless communication unit is further configured for wirelessly transmitting implant control user input to the server, destined for the patient remote external device. The system further comprises a display for displaying the received remote display portal, and an input device for receiving implant control input from the user, wherein the patient remote external device comprises a wireless communication unit configured for wireless transmission of control commands to the implantable medical device, and a computing unit. The computing unit is configured for running a control software for creating the control commands for the operation of the implantable medical device, transmitting a control interface to the patient display device, receiving implant control user input generated at the patient display device, from the server, and transforming the user input into the control commands for wireless transmission to the implantable medical device.

According to one embodiment, the computing unit is configured to encrypt at least one of the control interface and the control commands.

According to one embodiment, the patient display device is configured to encrypt the user input.

According to one embodiment, the server is configured to encrypt at least one of the user input received from the patient display device and the control interface received from the patient remote external device.

According to one embodiment, the computing unit is configured to encrypt the control interface and the patient display device is configured to decrypt the encrypted control interface.

According to one embodiment, the server is configured to act as a router, transferring the encrypted control interface from the patient remote external device to the patient display device without decryption.

According to one embodiment of the communication system or patient display device the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body.

an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach.

an implant configured for adjusting the position of a female's urinary tract or bladder neck, an implant configured for stimulating the ampulla vas deference and creating temporary constriction.

According to one embodiment, the communication system further comprises a server. The server may comprise a wireless communication unit configured for wirelessly receiving an implant control interface received from the patient remote external device and wirelessly transmitting the implant control interface as a remote display portal to the patient display device. The wireless communication unit is further configured for wirelessly receiving implant control user input from a patient EID external device and wirelessly transmitting the implant control user input to the patient display device.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A patient display device for communication with a patient external device for communication with an implantable medical device, when implanted, is provided. The patient display device comprises a wireless communication unit, a display, and an input device for receiving implant control input from the user. The patient display device is configured to run a first application for wireless communication with a server and/or DDI, and run a second application for wireless communication with the patient external device for transmission of the implant control input to a remote display portal of the patient external device for the communication with the implantable medical device, wherein the second application is configured to be accessed through the first application. The patient display device comprises a first log-in function and a second log-in function, wherein the first log-in function gives the user access to the first application and wherein the first and second log-in function in combination gives the user access to the second application. The first log-in function may be configured to use at least one of a password, pin code, fingerprint, voice and face recognition. A second log-in function within the first application may be configured to use a private key from the user to authenticate, for a defined time period, a second hardware key of the patient external device.

According to one embodiment, the first log-in is a PIN-based log-in.

According to one embodiment, at least one of the first and second log-in is a log-in based on a biometric input or a hardware key.

According to one embodiment, the patient display device further comprises an auxiliary wireless communication unit, and wherein the auxiliary wireless communication unit is configured to be disabled to enable wireless communication with the patient external device.

According to one embodiment, the patient display device is configured to wirelessly receive an implant control interface as a remote display portal from the patient external device to be displayed on the display.

According to one embodiment, the wireless communication unit is configured for wireless communication with the patient external device using a standard network protocol.

According to one embodiment, the wireless communication unit is configured for wireless communication with the patient external device using a proprietary network protocol.

According to one embodiment, the wireless communication unit is configured for wireless communication with the patient external device using a first network protocol and with the server using a second network protocol.

According to one embodiment, the wireless communication unit is configured for wireless communication with the patient external device using a first frequency band and with the server using a second frequency band.

According to one embodiment, the wireless communication unit comprises a Bluetooth transceiver.

According to one embodiment, the wireless communication unit comprises a UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, a communication range of the wireless communication unit is less than a communication range of the auxiliary wireless communication unit.

According to one embodiment, the wireless communication unit comprises a first wireless transceiver for communication with the patient external device and a second wireless transceiver for communication with the server.

According to one embodiment, the second wireless transceiver is configured to be disabled to enable wireless communication using the first wireless transceiver.

According to one embodiment, the patient display device is configured to authenticate the patient external device if a distance between the patient display device and the patient external device is less than a predetermined threshold value, or to be authenticated by the patient external device if a distance between the patient display device and the patient external device is less than a predetermined threshold value.

According to one embodiment, the patient display device is configured to allow the transfer of data between the patient display device and the patient external device on the basis of the authentication.

According to one embodiment, the patient display device is a wearable external device or a handset.

According to one embodiment, the second application is configured to receive data related to a parameter of the implanted medical device.

According to one embodiment, the second application is configured to receive data related to a sensor value received from the implanted medical device.

According to one embodiment, the second application is configured to receive data related to a parameter related to at least one of: a battery status, a temperature, a time, and an error.

According to one embodiment, the patient display device is configured to encrypt the user input.

According to one embodiment, the display is configured to encrypt the user input for decryption by the implantable medical device.

According to one embodiment, the patient display device is configured to decrypt the control interface received from the patient external device, for displaying the control interface on the display.

According to one embodiment, at least one of the first and second application is configured to receive data from an auxiliary external device and present the received data to the user.

According to one embodiment, at least one of the first and second application is configured to receive data from an auxiliary external device comprising a scale for determining the weight of the user.

According to one embodiment, at least one of the first and second application is configured to receive data related to the weight of the user from an auxiliary external device comprising a scale.

According to one embodiment, the patient display device is configured to: wirelessly transmit the data related to the weight of the user to the patient external device, or wirelessly transmit an instruction derived from the data related to the weight of the user, or wirelessly transmit an instruction derived from a combination of the data related to the weight of the user and the implant control input received from the user.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A communication system for enabling communication between a patient display device and an implantable medical device, when implanted, is provided. The communication system comprises a patient display device, a server or DDI, and a patient remote external device. The patient display device comprises a wireless communication unit configured for wirelessly receiving an implant control interface as a remote display portal from the patient remote external device, the wireless communication unit further being configured for wirelessly transmitting implant control user input to the patient remote external device, a display for displaying the received implant control interface as a remote display portal, and an input device for receiving implant control input from the user. The patient display device is configured to run a first application for wireless communication with the server, and to run a second application for wireless communication with the patient remote external device for transmission of the implant control input to the remote display portal of the patient remote external device for the communication with the implantable medical device. The patient remote external device comprises a wireless communication unit configured for wireless transmission of control commands based on the implant control input to the implantable medical device and configured for wireless communication with the patient display device.

According to one embodiment, the patient display device comprises a first log-in function and a second log-in function, and wherein the first log-in function gives the user access to the first application and wherein the first and second log-in function in combination gives the user access to the second application.

According to one embodiment, the second application is configured to receive data related to a parameter of the implanted medical device.

According to one embodiment, the second application is configured to receive data related to a sensor value received from the implanted medical device.

According to one embodiment, the second application is configured to receive data related to a parameter related to at least one of: a battery status, a temperature, a time, or an error.

According to one embodiment, the patient display device is configured to encrypt the user input.

According to one embodiment, the display is configured to encrypt the user input for decryption by the implantable medical device.

According to one embodiment, the patient remote external device is configured to act as a router, transferring the encrypted user input from the patient display device to the implantable medical device without decryption.

According to one embodiment, the patient remote external device is configured to encrypt at least one of the control interface and the control commands.

According to one embodiment, the patient remote external device is configured to encrypt the control interface and wherein the patient display device is configured to decrypt the encrypted control interface.

A computer program product is provided, configured to run in a patient display device comprising a wireless communication unit, a display for displaying the received implant control interface as a remote display portal, and an input device for receiving implant control input from a user. The computer program product comprises:

a first application for communication with a server or DDI,
   a second application for communication with an patient remote external device for transmission of the implant control input via the remote display portal of the patient remote external device for the communication with an implantable medical device, wherein the second application is configured to be accessed through the first application,
   a first log-in function using at least one of a password, pincode, fingerprint, or face recognition, and
   a second log-in function within the first application, using a private key from the user to authenticate for a defined time period a second hardware key of the patient remote external device. The first log-in function gives the user access to the first application and the first and second log-in function in combination gives the user access to the second application.

According to one embodiment, the second application is configured to receive data related to a parameter of the implanted medical device.

According to one embodiment, the second application is configured to receive data related to a sensor value received from the implanted medical device.

According to one embodiment, the second application is configured to receive data related to a parameter related to at least one of: a battery status, a temperature, a time, or an error.

According to one embodiment of the communication system, patient display device or computer program product, the implantable medical device comprises at least one of:

an external heart compression device,
   an apparatus assisting the pump function of a heart of the patient,
   an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A communication system for enabling communication between a patient display device, a patient external device, a server and an implantable medical device, is provided. The communication system comprises a server.

a patient display device, a patient external device, and an implantable medical device. The patient display device comprises a wireless communication unit for wirelessly communicating with at least one of the patient external device and the server, a display, and an input device for receiving input from the user. The patient external device comprises a wireless communication unit configured for wireless transmission of control commands to the implantable medical device and configured for wireless communication with at least one of the patient display device and the server. Further, the server comprises a wireless communication unit configured for wireless communication with at least one of the patient display device and the patient external device, wherein the implantable medical device comprises a wireless communication unit configured for wireless communication with the patient external device. The implantable medical device further comprises an encryption unit and is configured to: encrypt data destined for the server, transmit the data to the server via the patient external device, wherein the patient external device acts as a router transferring the data without full decryption. In an example, the implantable medical device comprises an encryption unit and is configured to: encrypt data destined for the patient display device, transmit the data to the patient display device via the patient external device, wherein the patient external device acts as a router transferring the data without full decryption. In an example, the server comprises an encryption unit and is configured to: encrypt data destined for the implantable medical device, transmit the data to the implantable medical device via the patient external device, wherein the patient external device acts as a router transferring the data without full decryption. In an example, the server comprises an encryption unit and is configured to: encrypt data destined for the implantable medical device, transmit the data to the implantable medical device via the patient display device and the patient external device, wherein the patient display device and the patient external device acts as a router transferring the data without full decryption. In an example, the patient display device comprises an encryption unit and is configured to: encrypt data destined for the implantable medical device, transmit the data to the implantable medical device via the patient external device, wherein the patient external device acts as a router transferring the data without full decryption. In an example, the patient display device comprises an encryption unit and is configured to: encrypt data destined for the implantable medical device, transmit the data to the implantable medical device via the server and the patient external device, wherein the server and the patient external device acts as a router transferring the data without full decryption.

According to one embodiment, the patient display device is configured to wirelessly receive an implant control interface from the patient external device to be displayed on the display.

According to one embodiment, at least two of: the wireless communication unit of the server, the wireless communication unit of the patient display device, the wireless communication unit of the patient external device, and the wireless communication unit of the implantable medical device, are configured for wireless communication using a standard network protocol.

According to one embodiment, wherein at least two of: the wireless communication unit of the server, the wireless communication unit of the patient display device, the wireless communication unit of the patient external device, and the wireless communication unit of the implantable medical device, are configured for wireless communication using a proprietary network protocol.

According to one embodiment, the wireless communication unit of the patient external device is configured to use a first network protocol for communication with the implantable medical device and use a second network protocol for communication with the server, or use a first network protocol for communication with the implantable medical device and use a second network protocol for communication with the patient display device.

According to one embodiment, the wireless communication unit of the patient external device is configured to use a first frequency band for communication with the implantable medical device and use a second frequency band for communication with the server, or use a first frequency band for communication with the implantable medical device and use a second frequency band for communication with the patient display device.

According to one embodiment, the wireless communication unit of the patient display device is configured to use a first network protocol for communication with the patient external device and use a second network protocol for communication with the server.

According to one embodiment, the wireless communication unit of the patient display device is configured to use a first frequency band for communication with the patient external device and use a second frequency band for communication with the server.

According to one embodiment, the wireless communication unit of the server is configured to use a first network protocol for communication with the patient external device and use a second network protocol for communication with the patient display device.

According to one embodiment, the wireless communication unit of the server is configured to use a first frequency band for communication with the patient external device and use a second frequency band for communication with the patient display device.

According to one embodiment, the wireless communication unit of at least one of the server, the patient display device, the patient external device, and the implantable medical device comprises a Bluetooth transceiver.

According to one embodiment, the wireless communication unit of at least one of the server, the patient display device, the patient external device, and the implantable medical device comprises a UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the wireless communication unit of the patient external device comprises a first wireless transceiver for wireless communication with the implantable medical device, and a second wireless transceiver for wireless communication with the server, and wherein the second wireless transceiver has a longer effective range than the first wireless transceiver.

According to one embodiment, the wireless communication unit of the patient external device comprises a first wireless transceiver for wireless communication with the implantable medical device, and a second wireless transceiver for wireless communication with the patient display device, and wherein the second wireless transceiver has a longer effective range than the first wireless transceiver.

According to one embodiment, the wireless communication unit of the patient display device comprises a first wireless transceiver for wireless communication with the patient external device, and a second wireless transceiver for wireless communication with the server, and wherein the second wireless transceiver has a longer effective range than the first wireless transceiver.

According to one embodiment, the second wireless transceiver has an effective range being one of: 2 times, 4 times, 8 times 20 times, 50 times or 100 times longer than the first wireless transceiver.

According to one embodiment, the second wireless transceiver is configured to be disabled to enable wireless communication using the first wireless transceiver.

According to one embodiment, at least one of:

the patient display device is configured to authenticate the patient external device if a distance between the patient display device and the patient external device is less than a predetermined threshold value, the patient display device is configured to be authenticated by the patient external device if a distance between the patient display device and the patient external device is less than a predetermined threshold value, the patient display device is configured to authenticate the implantable medical device if a distance between the patient display device and the implantable medical device is less than a predetermined threshold value, the patient display device is configured to be authenticated by the implantable medical device if a distance between the patient display device and the implantable medical device is less than a predetermined threshold value, the patient external device is configured to authenticate the patient display device if a distance between the patient external device and the patient display device is less than a predetermined threshold value, the patient external device is configured to be authenticated by the patient display device if a distance between the patient external device and the patient display device is less than a predetermined threshold value, the patient external device is configured to authenticate the implantable medical device if a distance between the patient external device and the implantable medical device is less than a predetermined threshold value, and the patient external device is configured to be authenticated by the implantable medical device if a distance between the patient external device and the implantable medical device is less than a predetermined threshold value.

According to one embodiment, the patient display device is configured to allow the transfer of data between the patient display device and the patient external device on the basis of the authentication.

According to one embodiment, the patient external device is configured to allow the transfer of data between the patient display device and the patient external device on the basis of the authentication.

According to one embodiment, the patient external device is configured to allow the transfer of data between the patient external device and the implantable medical device on the basis of the authentication.

According to one embodiment, the patient display device is a wearable patient external device or a handset.

According to one embodiment, the data encrypted by the implantable medical device is related to at least one of: a battery status, a temperature, a time, or an error.

A server for use in the communication system according to any one of the above embodiments is provided.

A patient display device for use in the communication system according to any one of the above embodiments is provided.

A patient external device for use in the communication system according to any one of the above embodiments is provided.

An implantable medical device for use in the communication system according to any one of the above embodiments is provided.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A system configured for changing pre-programmed treatment settings of an implantable medical device, when implanted in a patient, from a distant remote location in relation to the patient, is provided. The system comprises at least one health care provider, HCP, EID external device, and a HCP private key device. HCP EID external device is adapted to receive a command from the HCP to change said pre-programmed treatment settings of an implanted medical device, and further adapted to be activated and authenticated and allowed to perform said command by the HCP providing the HCP private key device, wherein the HCP private key device is adapted to be provided to the HCP EID external device via at least one of: a reading slot or comparable for the HCP private key device, and a RFID communication or other close distance wireless activation communication. The HCP EID external device comprises at least one of: a reading slot or comparable for the HCP private key device, a RFID communication, and other close distance wireless activation communication or electrical direct contact. The HCP EID external device further comprises at least one wireless transceiver configured for communication with a data infrastructure server, DDI, through a first network protocol. Further, the system comprises a data infrastructure server, DDI, adapted to receive command from said HCP EID external device and to relay the received command without modifying said command to a patient EID external device, wherein the DDI comprises one wireless transceiver configured for communication with said patient external device, and a patient EID external device adapted to receive the command relayed by the DDI, further adapted to send this command to the implanted medical device, further adapted to receive a command from the HCP EID external device via the DDI to change said pre-programmed treatment settings of the implanted medical device, and further adapted to be activated and authenticated and allowed to perform said command by the patient providing a patient private key device adapted to be provided to the patient EID external device by the patient via at least one of: a reading slot or comparable for the patient private key device, a RFID communication or other close distance wireless activation communication or electrical direct contact. The patient EID external device comprises at least one of a reading slot or comparable for the HCP private key device, a RFID communication, and other close distance wireless activation communication or electrical direct contact. The patient EID external device further comprises at least one wireless transceiver configured for communication with the implanted medical device through a second network protocol. Further, the implanted medical device is configured to treat the patient or perform a bodily function.

According to one embodiment, at least one of the patient private key device or HCP private key device comprises a hardware key.

According to one embodiment, the private key device is at least one of, a smartcard, a key-ring device, a watch an arm or wrist band a neckless or any shaped device.

According to one embodiment of the system, at least two of: the HCP EID external device, the patient EID external device, the HCP private key device, the patient private key device, and the DDI are configured for wireless communication using a standard network protocol.

According to one embodiment, at least two of: the HCP EID external device, the patient EID external device, the HCP private key device, the patient private key device, and the DDI are configured for wireless communication using a proprietary network protocol.

According to one embodiment, the patient EID external device is configured to use a first network protocol for communication with the implantable medical device and use a second network protocol for communication with the DDI.

According to one embodiment, the patient EID external device is configured to use a first frequency band for communication with the implantable medical device and use a second frequency band for communication with the DDI.

According to one embodiment, the DDI is configured to use a first frequency band for communication with the patient EID external device and a second frequency band for communication with the patient private key device.

According to one embodiment, at least one of the HCP EID external device, the patient EID external device, the HCP private key device, the patient private key device and the DDI comprises a Bluetooth transceiver.

According to one embodiment, at least one of the HCP EID external device, the patient EID external device, the HCP private key device, the patient private key device and the DDI comprises a UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the patient EID external device comprises a first wireless transceiver for wireless communication with the implantable medical device, and a second wireless transceiver for wireless communication with the DDI, and wherein the second wireless transceiver has longer effective range than the first wireless transceiver.

According to one embodiment, the patient private key device comprises a first wireless transceiver for wireless communication with the HCP EID external device, and a second wireless transceiver for wireless communication with the DDI, and wherein the second wireless transceiver has longer effective range than the first wireless transceiver.

According to one embodiment, the second wireless transceiver has an effective range being one of: 2 times, 4 times, 8 time, 20 times, 50 times or 100 times longer than the effective range of the first wireless transceiver.

According to one embodiment, the second wireless transceiver is configured to be disabled to enable wireless communication using the first wireless transceiver.

According to one embodiment, the patient EID external device is configured to allow transfer of data between the EID external device and the implantable medical device on the basis of an authentication of the patient EID external device.

According to one embodiment, the patient EID external device is a wearable patient external device or a handset.

According to one embodiment, the data encrypted by the implantable medical device is related to at least one of: a battery status, a temperature, a time, or an error.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A system is provided, configured for changing pre-programmed treatment settings of an implantable medical device, when implanted in a patient, by a health care provider, HCP, in the physical presence of the patient. The system comprises at least one HCP EID external device adapted to receive a command from the HCP, directly or indirectly, to change said pre-programmed treatment settings in steps of an implantable medical device, when implanted, wherein the HCP EID external device is further adapted to be activated, authenticated, and allowed to perform said command by the HCP providing an HCP private key device comprising a HCP private key. The HCP private key device comprises at least one of: a smart card, a keyring device, a watch, a arm or wrist band, a necklace, and any shaped device. The HCP EID external device is adapted to be involved in at least one of: receiving information from the implant, receiving information from a patient remote external device, actuating the implanted medical device, changing pre-programmed settings, and updating software of the implantable medical device, when implanted. The HCP EID external device is further adapted to be activated, authenticated, and allowed to perform said command also by the patient. The system further comprises a patient private key device comprising a patient private key, wherein the patient private key device comprising at least one of: a smart card, a keyring device, a watch, a arm or wrist band, a necklace, and any shaped device. The HCP private key and the patient private key are required for performing said actions by the HCP EID external device to at least one of: receive information from the implant, to receive information from a patient remote external device, to actuate the implanted medical device, to change pre-programmed settings, and to update software of the implantable medical device, when the implantable medical device is implanted.

According to one embodiment, the HCP EID external device further comprises a wireless transceiver configured for communication with the implanted medical device through a second network protocol.

According to one embodiment, the HCP private key device is adapted to be provided to the at least one HCP external device via at least one of: a reading slot or comparable for the HCP private key device, a RFID communication, and a close distance wireless activation communication unit, or electrical direct contact.

According to one embodiment, the HCP EID external device comprises at least one of reading slot or comparable for the HCP private key device, a RFID communication and a close distance wireless activation communication unit, or electrical direct contact.

According to one embodiment, the HCP EID external device is adapted to receive a command from a HCP dedicated device to change said pre-programmed treatment steps of the implantable medical device, when implanted, wherein the HCP dedicated device is further adapted to be activated, authenticated, and allowed to perform said command by the HCP providing their private key.

According to one embodiment, at least two of: the HCP EID external device, the patient EID external device, the HCP private key device, and the patient private key device, are configured for wireless communication using a standard network protocol.

According to one embodiment, at least two of: the HCP EID external device, the patient EID external device, the HCP private key device, and the patient private key device, are configured for wireless communication using a proprietary network protocol.

According to one embodiment, the patient EID external device is configured to use a first network protocol for communication with the implantable medical device and use a second network protocol for communication with the patient private key device.

According to one embodiment, the patient EID external device is configured to use a first frequency band for communication with the implantable medical device and use a second frequency band for communication with the patient private key device.

According to one embodiment, at least one of the HCP EID external device, the patient EID external device, the HCP private key device, and the patient private key device comprises a Bluetooth transceiver.

According to one embodiment, at least one of the HCP EID external device, the patient EID external device, the HCP private key device, and the patient private key device comprises a UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the patient EID external device comprises a first wireless transceiver for wireless communication with the implantable medical device, and a second wireless transceiver for wireless communication with the patient private key device, and wherein the second wireless transceiver has longer effective range than the first wireless transceiver.

According to one embodiment, the second wireless transceiver has an effective range being one of: 2 times, 4 times, 8 time, 20 times, 50 times or 100 times longer than the effective range of the first wireless transceiver.

According to one embodiment, the second wireless transceiver is configured to be disabled to enable wireless communication using the first wireless transceiver.

According to one embodiment, the patient EID external device is configured to allow transfer of data between the EID external device and the implantable medical device on the basis of an authentication of the patient EID external device.

According to one embodiment, the patient EID external device is a wearable patient external device or a handset.

According to one embodiment, the data encrypted by the implantable medical device is related to at least one of: a battery status, a temperature, a time, or an error.

A system is provided, configured to change pre-programmed and pre-selected treatment actions of an implantable medical device, when implanted in a patient, by command from the patient. The system comprises an implantable medical device, a patient remote external device, a wireless transceiver configured for communication with the implantable medical device, when the medical device is implanted, through a second network protocol, and a remote display portal. The remote display portal is configured to receive content delivered from the patient remote external device to expose buttons to express the will to actuate the functions of the implanted medical device by the patient through the patient remote external device, and further configured to present the display portal remotely on a patient display device allowing the patient to actuate the functions of the implanted medical device through the display portal of the patient remote external device visualised on the patient display device.

According to one embodiment, the wireless transceiver, the remote display portal, and the remote display portal are comprised in the patient remote external device.

According to one embodiment, the system further comprises the patient display device, which may comprise a supporting application, a display which hosts the Remote Display Portal, and a patient display device private key.

According to one embodiment, the remote display portal is capable of generating a command to be signed by the patient display device private key.

According to one embodiment, the patient remote external device is adapted to accept input from the patient via said patient display device through its remote display portal.

According to one embodiment, the patient remote external device comprises a graphical user interface arranged on a touch-responsive display exposing buttons to express actuation functions of the implanted medical device.

According to one embodiment, the system is configured to allow the patient to actuate the implant at home through the patient remote external device by means of an authorization granted by a patient private key.

According to one embodiment, the patient private key comprises at least one of: a smart card, a keyring device, a watch, a arm or wrist band, a necklace, and any shaped device.

According to one embodiment, the system is configured to allow the patient to actuate the implantable medical device, when implanted, at home through the patient remote external device, using an authorization granted by the patient private key.

According to one embodiment, system further comprises a patient EID external device comprising at least one of: a reading slot or comparable for the patient private key device, a RFID communication, and a close distance wireless activation communication, or electrical direct contact.

According to one embodiment, the patient EID external device is adapted to be synchronised with the patient remote external device.

According to one embodiment, the patient EID external device further comprises at least one of: a wireless transceiver configured for communication with the patient, a remote external device, and a wired connector for communication with the patient remote external device.

According to one embodiment, the patient EID external device is adapted to generate an authorization to be signed by the patient private key to be installed into at least one of: the patient remote external device through the patient EID external device, and the implantable medical device.

According to one embodiment, the system comprises a patient display device comprising a supporting application capable of displaying the remote display portal with content delivered from the patient remote external device.

According to one embodiment, the remote display portal and patient remote external device are adapted to expose buttons to express the will to actuate the functions of the implanted medical device by the patient through the patient remote external device.

According to one embodiment, the patient display device comprises at least one of: a display which hosts the remote display portal, and a patient display device private key.

According to one embodiment, the remote display portal is capable of generating a command to be signed by the patient private key.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A system is provided, configured for providing information from an implantable medical device, when implanted in a patient, from a distant remote location in relation to the patient. The system comprises at least one patient EID external device adapted to receive information from the implant, adapted to send such information further on to a server or dedicated data infrastructure, DDI, further adapted to be activated and authenticated and allowed to receive said information by the implanted medical device by the patient providing a private key. Further, the system comprises a patient private key device comprising the private key adapted to be provided to the patient EID external device via at least one of: a reading slot or comparable for the patient private key device, a RFID communication or other close distance wireless activation communication or direct electrical connection. The patient EID external device comprises at least one of: a reading slot or comparable for the patient private key device, an RFID communication, and other close distance wireless activation communication or direct electrical contact. Further, the patient EID external device comprises at least one wireless transceiver configured for communication with the DDI, through a first network protocol.

According to one embodiment, the at least one patient EID external device is adapted to receive information from the implant, through a second network protocol.

According to one embodiment, the system comprises the DDI, wherein the DDI is adapted to receive information from said patient EID external device, and wherein the DDI comprises a wireless transceiver configured for communication with said patient EID external device.

According to one embodiment, the patient EID external device is adapted to receive a command relayed by the DDI, to further send the command to the implanted medical device to change said pre-programmed treatment settings of the implanted medical device, and further adapted to be activated and authenticated and allowed to perform said command by the patient providing the patient private key.

According to one embodiment, the patient private key device is adapted to provide the patient private key to the patient EID external device by the patient via at least one of: a reading slot or comparable for the patient private key device, an RFID communication or other close distance wireless activation communication, or electrical direct contact.

According to one embodiment, the patient EID external device comprises at least one of: a reading slot or comparable for the HCP private key device, a RFID communication, and other close distance wireless activation communication, or direct electrical contact.

According to one embodiment, the patient EID external device further comprising at least one wireless transceiver configured for communication with the implanted medical device through a second network protocol.

According to one embodiment, the system comprises the implantable medical device, which may be adapted to, when implanted, treat the patient or perform a bodily function.

According to one embodiment, the patient private key comprises at least one of: a smart card, a keyring device, a watch, an arm band or wrist band, a necklace, and any shaped device.

According to one embodiment, at least two of: the patient EID external device, the IDD, and the patient private key device, are configured for wireless communication using a standard network protocol.

According to one embodiment, at least two of: the patient EID external device, the IDD, and the patient private key device, are configured for wireless communication using a proprietary network protocol.

According to one embodiment, the patient EID external device is configured to use a first network protocol for communication with the implantable medical device and use a second network protocol for communication with the patient private key device.

According to one embodiment, the patient EID external device is configured to use a first frequency band for communication with the implantable medical device and use a second frequency band for communication with the patient private key device.

According to one embodiment, at least one of the patient EID external device, the patient private key device and the IDD comprises a Bluetooth transceiver.

According to one embodiment, at least one of the patient EID external device, the patient private key device and the IDD comprises a UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the patient EID external device comprises a first wireless transceiver for wireless communication with the implantable medical device, and a second wireless transceiver for wireless communication with the patient private key device, and wherein the second wireless transceiver has longer effective range than the first wireless transceiver.

According to one embodiment, the second wireless transceiver has an effective range being one of: 2 times, 4 times, 8 time, 20 times, 50 times or 100 times longer than the effective range of the first wireless transceiver.

According to one embodiment, the second wireless transceiver is configured to be disabled to enable wireless communication using the first wireless transceiver.

According to one embodiment, the patient EID external device is a wearable patient external device or a handset.

According to one embodiment, the data encrypted by the implantable medical device is related to at least one of: a battery status, a temperature, a time, or an error.

According to one embodiment, the system comprises a master private key device configured to allow issuance of a new private key device, wherein the HCP or HCP admin have such master private key device adapted to able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A system is provided, comprising, an implantable medical device adapted to, when implanted in a patient, to communicate with an external device, the external device comprising at least one of a patient remote external device or a patient EID external device. The system further comprises the patient EID external device adapted to communicate with and send commands to the implantable medical device when implanted, to change pre-programmed settings, and a patient private key device comprising a patient private key, adapted to activate and authenticate and allow to perform said command by the patient EID external device, wherein said private key is adapted to be provided to the external device via at least one of: a reading slot or comparable for the HCP private key device, an RFID communication or other close distance wireless activation communication, or direct electrical contact. Further the system comprises a data infrastructure server, DDI, adapted to send commands to the patient EID external device for further transport to the implanted medical device, to inactivate the authority and authenticating function of the patient private key.

According to one embodiment, the at least one patient remote external device comprises a patient remote external device private key, wherein the DDI via the patient EID external device is able to inactivate the authority and authenticating function of the patient remote external device, thereby inactivating the patient remote external device.

According to one embodiment, the patient EID external device comprises at least one wireless transceiver configured for communication with the DDI via a first network protocol.

According to one embodiment, the system comprises the DDI, wherein the DDI is adapted to receive command from a HCP EID external device, and to send the received command to the patient EID external device, wherein the DDI comprises a wireless transceiver configured for communication with said patient external device.

According to one embodiment, the patient EID external device is adapted to receive the command from the DDI, wherein the command originates from a health care provider, HCP, and wherein the patient EID is adapted to inactivate the patient private key and to send the command to the implanted medical device.

According to one embodiment, the patient EID external device is adapted to receive the command from the DDI, wherein the command originates from a health care provider, HCP, wherein the patient EID external device is adapted to receive the command from the HCP via the DDI to inactivate the patient remote external device comprising a patient remote external device private key, and wherein the patient EID external device is further adapted to send this command to the implanted medical device.

According to one embodiment, the patient EID external device further comprises at least one wireless transceiver configured for communication with the implanted medical device through a second network protocol.

According to one embodiment, at least one of the patient private key and a patient remote external device private key comprises a hardware key.

According to one embodiment, the private key device is at least one of, a smartcard, a key-ring device, a watch an arm or wrist band a neckless or any shaped device.

According to one embodiment, at least two of: the patient remote external device, the patient EID external device, the patient private key device, and the DDI, are configured for wireless communication using a standard network protocol.

According to one embodiment, wherein at least two of: the patient remote external device, the patient EID external device, the patient private key device, and the DDI, are configured for wireless communication using a proprietary network protocol.

According to one embodiment, the patient EID external device is configured to use a first network protocol for communication with the implantable medical device and use a second network protocol for communication with the patient private key device.

According to one embodiment, the patient EID external device is configured to use a first frequency band for communication with the implantable medical device and use a second frequency band for communication with the patient private key device.

According to one embodiment, at least one of the patient remote external device, the patient EID external device, the patient private key device, and the DDI, comprise a Bluetooth transceiver.

According to one embodiment, at least one of the patient remote external device, the patient EID external device, the patient private key device, and the DDI, comprise an UWB transceiver.

According to one embodiment, the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to one embodiment, the patient EID external device comprises a first wireless transceiver for wireless communication with the implantable medical device, and a second wireless transceiver for wireless communication with the patient private key device, and wherein the second wireless transceiver has longer effective range than the first wireless transceiver.

According to one embodiment, the second wireless transceiver has an effective range being one of: 2 times, 4 times, 8 time, 20 times, 50 times or 100 times longer than the effective range of the first wireless transceiver.

According to one embodiment, the second wireless transceiver is configured to be disabled to enable wireless communication using the first wireless transceiver.

According to one embodiment, the patient EID external device is a wearable patient external device or a handset.

According to one embodiment, the data encrypted by the implantable medical device is related to at least one of: a battery status, a temperature, a time, or an error.

According to one embodiment, the system comprises a master private key device configured to allow issuance of new private key device, wherein the HCP or HCP admin have such master private key device adapted to be able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallows solid food or is drinking fluid, wherein said food sensor is connected to the control unit of a medical device to cause an action to stretch the stomach after a determined amount of food intake.

A system is provided, configured for changing pre-programmed treatment settings in steps of an implantable medical device, when implanted in a patient, by a health care provider, HCP, either in the physical presence of the patient or remotely with the patient on distance. The system comprises at least one HCP EID external device adapted to receive a command directly or indirectly from the HCP to change said pre-programmed treatment settings in steps of the implantable medical device, when implanted. The HCP EID external device is further adapted to be activated, authenticated, and allowed to perform said command by the HCP providing a HCP private key device comprising a HCP private key. The HCP private key comprises at least one of: a smart card, a keyring device, a watch, an arm or wrist band, a necklace, and any shaped device. The system further comprises a patient private key device comprising a patient private key, comprising at least one of: a smart card, a keyring device, a watch, an arm or wrist band, a necklace, and any shaped device. Both the HCP and patient private key is required for performing said action by the HCP EID external device to change the pre-programmed settings in the implant and to update software of the implantable medical device, when the implantable medical device is implanted. The patient private key is adapted to activate, be authenticated, and allowed to perform said command provided by the HCP, either via the HCP EID external device or when the action is performed remotely via a patient EID external device.

According to one embodiment, the system comprises a master private key device that allow issuance of new private key device wherein the HCP or HCP admin have such master private key device adapted to be able to replace and pair a new patient private key device or HCP private key device into the system, through the HCP EID external device.

According to one embodiment, the patient remote external device and the patient EID external device are an integrated unit.

According to one embodiment, the HCP dedicated device and the HCP EID external device are an integrated unit.

According to one embodiment, the system further comprises a measurement device or sensor adapted to deliver a measurement to at least one of the DDI, patent EID external device and a patient display device.

According to one embodiment, the system further comprises a food sensor adapted to measure at least if the patient swallows solid food or is drinking fluid, wherein said food sensor is configured to be connected to the control unit of a medical device to cause an action to stretch the stomach after a determined amount of food intake.

According to one embodiment, the HCP EID external device further comprises a wireless transceiver configured for communication with the implanted medical device through a second network protocol.

According to one embodiment, the HCP private key device is adapted to be provided to the at least one HCP external device via at least one of: a reading slot or comparable for the HCP private key device, a RFID communication, and a close distance wireless activation communication unit, or electrical direct contact.

According to one embodiment, the HCP EID external device comprises at least one of: reading slot or comparable for the HCP private key device, a RFID communication, and a close distance wireless activation communication unit, or electrical direct contact.

According to one embodiment, the HCP EID external device is adapted to receive a command from an HCP dedicated device to change said pre-programmed treatment steps of the implantable medical device, when implanted, wherein the HCP dedicated device is further adapted to be activated, authenticated, and allowed to perform said command by the HCP providing their private key.

According to one embodiment, the HCP EID external device and the HCP private key device are configured for wireless communication using a standard network protocol.

According to one embodiment, the HCP EID external device and the HCP private key device are configured for wireless communication using a proprietary network protocol.

According to one embodiment, the HCP EID external device is configured to use a first network protocol for communication with the implantable medical device and use a second network protocol for communication with the HCP private key device.

According to one embodiment, the HPC EID external device is configured to use a first frequency band for communication with the implantable medical device and use a second frequency band for communication with the HCP private key device.

According to one embodiment, at least one of the HCP EID external device and the HCP private key device comprises a Bluetooth transceiver.

According to one embodiment, at least one of the HCP EID external device and the HCP private key device comprises a UWB transceiver.

A system is provided, configured for changing pre-programmed treatment settings in steps of an implantable medical device, when implanted in a patient, by a health care provider, HCP, with the patient on remote on distance. The system comprises at least one HCP EID external device adapted to receive a command from the HCP direct or indirect, to change said pre-programmed treatment settings in steps of an implantable medical device, when implanted, wherein the HCP EID external device is further adapted to be activated, authenticated, and allowed to perform said command by the HCP. The action by the HCP EID external device to change pre-programmed settings in the implant and to update software of the implantable medical device, when the implantable medical device is implanted, is adapted to be authenticated by a HCP private key device and a patient private key device.

According to one embodiment, the HCP private key device comprising a HCP private key, comprising at least one of: a smart card, a keyring device, a watch, an arm or wrist band, a necklace, and any shaped device.

According to one embodiment, the patient private key device comprises a patient private key, comprising at least one of: a smart card, a keyring device, a watch, an arm or wrist band, a necklace, and any shaped device.

According to one embodiment, the patient private key is adapted to activate, be authenticated, and allowed to perform said command provided by the HCP, either via the HCP EID external device or when the action is performed remotely via a patient EID external device.

According to one embodiment, the system further comprises a dedicated data infrastructure, DDI, the patient EID external device, and the HCP EID external device, wherein the communication between the patient EID external device and the HCP EID external device is performed via the DDI.

According to one embodiment, the system comprises a master private key device that allows issuance of new private key device wherein the HCP or HCP admin have such master private key device adapted to be able to replace and pair a new patient private key device or HCP private key device into the system.

According to one embodiment, the patient remote external device and the patient EID external device are an integrated unit.

According to one embodiment, the HCP dedicated device and the HCP EID external device are an integrated unit.

According to one embodiment, the system further comprises a measurement device or sensor adapted to deliver a measurement to at least one of the DDI, patent EID external device and patient display device.

According to one embodiment, the system comprises a food sensor, adapted to measure at least if the patient swallow solid food or is drinking fluid, wherein said food sensor is connected to the control unit of a medical device to cause an action to stretch the stomach after a determined amount of food intake.

According to one embodiment, the HCP EID external device further comprises a wireless transceiver configured for communication with the implanted medical device through a second network protocol.

According to one embodiment, the HCP private key device is adapted to be provided to the at least one HCP external device via at least one of: a reading slot or comparable for the HCP private key device, a RFID communication, and a close distance wireless activation communication unit, or electrical direct contact.

According to one embodiment, the HCP EID external device comprises at least one of: reading slot or comparable for the HCP private key device, a RFID communication, and a close distance wireless activation communication unit, or electrical direct contact.

According to one embodiment, the HCP EID external device is adapted to receive a command from an HCP dedicated device to change said pre-programmed treatment steps of the implantable medical device, when implanted, wherein the HCP dedicated device is further adapted to be activated, authenticated, and allowed to perform said command by the HCP providing their private key.

According to one embodiment, the HCP EID external device and the HCP private key device are configured for wireless communication using a standard network protocol.

According to one embodiment, the HCP EID external device and the HCP private key device are configured for wireless communication using a proprietary network protocol.

According to one embodiment, the HCP EID external device is configured to use a first network protocol for communication with the implantable medical device and use a second network protocol for communication with the HCP private key device.

According to one embodiment, the HPC EID external device is configured to use a first frequency band for communication with the implantable medical device and use a second frequency band for communication with the HCP private key device.

According to one embodiment, at least one of the HCP EID external device and the HCP private key device comprises a Bluetooth transceiver.

According to one embodiment, at least one of the HCP EID external device and the HCP private key device comprises a UWB transceiver.

A system is provided, which is configured for changing pre-programmed treatment settings of an implantable medical device, when implanted in a patient, from a distant remote location in relation to the patient. The system comprises at least one health care provider. HCP, external device adapted to receive a command from the HCP to change said pre-programmed treatment settings of an implanted medical device. The HCP external device is further adapted to be activated and authenticated and allowed to perform said command by the HCP providing a HCP private key device adapted to be provided to an HCP EID external device via at least one of; a reading slot or comparable for the HCP private key device, a RFID communication or other close distance wireless activation communication. The HCP EID external device comprises at least one of: a reading slot or comparable for the HCP private key device, a RFID communication, and other close distance wireless activation communication or electrical direct contact. The HCP EID external device further comprises at least one wireless transceiver configured for communication with a patient EID external device, through a first network protocol. The system comprises the patient EID external device, the patient EID external device being adapted to receive command from said HCP external device, and to relay the received command without modifying said command to the implanted medical device. The patient EID external device comprises one wireless transceiver configured for communication with said patient external device, wherein the patient EID is adapted to send the command to the implanted medical device, to receive a command from the HCP to change said pre-programmed treatment settings of the implanted medical device, and further to be activated and authenticated and allowed to perform said command by the patient providing a patient private key device comprising a patient private key.

According to one embodiment, at least one of the patient private key device or HCP private key device comprises a hardware key.

According to one embodiment, the private key device is at least one of, a smartcard, a key-ring device, a watch an arm or wrist band a neckless or any shaped device.

According to one embodiment, the system comprises a master private key device that allow issuance of new private key device wherein the HCP or HCP admin have such master private key device adapted to be able to replace and pair a new patient private key device or HCP private key device into the system, through the HCP EID external device.

According to one embodiment, the patient remote external device and the patient EID external device is an integrated unit.

According to one embodiment, the HCP dedicated device and the HCP EID external device are an integrated unit.

According to one embodiment, the system comprises a measurement device or sensor adapted to deliver a measurement to at least one of the DDI, patent EID external device and a patient display device.

According to one embodiment, the system comprises a food sensor, adapted to measure at least if the patient swallow solid food or is drinking fluid, wherein said food sensor is connected to the control unit of a medical device to cause an action to stretch the stomach after a determined amount of food intake.

According to one embodiment, the HCP EID external device further comprises a wireless transceiver configured for communication with the implanted medical device through a second network protocol.

According to one embodiment, the HCP private key device is adapted to be provided to the at least one HCP external device via at least one of; a reading slot or comparable for the HCP private key device, a RFID communication, and a close distance wireless activation communication unit, or electrical direct contact.

According to one embodiment, the HCP EID external device comprises at least one of: reading slot or comparable for the HCP private key device, a RFID communication, and a close distance wireless activation communication unit, or electrical direct contact.

According to one embodiment, the HCP EID external device is adapted to receive a command from an HCP dedicated device to change said pre-programmed treatment steps of the implantable medical device, when implanted, wherein the HCP dedicated device is further adapted to be activated, authenticated, and allowed to perform said command by the HCP providing their private key.

According to one embodiment, the HCP EID external device and the HCP private key device are configured for wireless communication using a standard network protocol.

According to one embodiment, the HCP EID external device and the HCP private key device are configured for wireless communication using a proprietary network protocol.

According to one embodiment, the HCP EID external device is configured to use a first network protocol for communication with the implantable medical device and use a second network protocol for communication with the HCP private key device.

According to one embodiment, the HPC EID external device is configured to use a first frequency band for communication with the implantable medical device and use a second frequency band for communication with the HCP private key device.

According to one embodiment, at least one of the HCP EID external device and the HCP private key device comprises a Bluetooth transceiver.

According to one embodiment, at least one of the HCP EID external device and the HCP private key device comprises a UWB transceiver.

Aspect 330SE eHealth General Communication Housing

An external device configured for communication with an implantable medical device when implanted in a patient is further provided. The external device comprising, a display device, a housing unit configured to mechanically, disconnectably connect to the display device, the housing comprises a first communication unit for receiving communication from the display device, and a second communication unit for wirelessly transmitting communication to the implantable medical device.

According to one embodiment, the external device comprises a handheld electronic device.

According to one embodiment, the external device is configured for communicating with the implantable medical device for changing the operational state of an implantable medical device. The advantage of the embodiment is that the operational state of the implantable medical device can be changed remotely.

According to one embodiment, the first communication unit is a wireless communication unit for wireless communication with the display device. The advantage of the embodiment is that the display device can be communicated with, without having to have electric wires.

According to one embodiment, the first communication unit is configured to communicate wirelessly with the display device using a first communication frequency, the second communication unit is configured to communicate wirelessly with the implantable medical device using a second communication frequency, and the first and second communication frequencies are different. The advantage of the embodiment is that the likelihood of interferences is reduced.

According to one embodiment, the second communication unit is configured to communicate wirelessly with the implantable medical device using electromagnetic waves at a frequency below 100 KHz.

According to one embodiment, the second communication unit is configured to communicate wirelessly with the implantable medical device using electromagnetic waves at a frequency below 40 kHz. The advantage of the embodiment is that titanium which is commonly used for medical devices is transparent for electromagnetic waves below 40 KHz.

According to one embodiment, the first communication unit is configured to communicate wirelessly with the display device using electromagnetic waves at a frequency above 100 kHz. The advantage of the embodiment is that the frequency spectrum below 100 kHz remains noise free for the communication with the medical implantable device.

According to one embodiment, the first communication unit is configured to communicate wirelessly with the display device using a first communication protocol, the second communication unit is configured to communicate wirelessly with the implantable medical device using a second communication protocol, and the first and second communication protocols are different. The advantage of the embodiment is that the protocol can be independently chosen for the communication of the first and second communication unit, depending on which protocol better suits the needs of the communication units.

According to one embodiment, the housing unit comprises, a first antenna configured for wireless communication with the display device, and a second antenna configured for wireless communication with the implantable medical device. The advantage of the embodiment is that the antenna can be independently chosen for the communication of the first and second communication unit, depending on which antenna better suits the needs of the communication units.

According to one embodiment, the first communication unit is a wire-based communication unit for wire-based communication with the display device. The advantage of the embodiment is that the communication of the first communication unit is reliable and secure.

According to one embodiment, the display device comprises, a first communication unit for communication with the housing unit, and a second communication unit for wireless communication with a second external device. The advantage of the embodiment is that an additional external device can be communicated with, thereby introducing redundancy and reliability.

According to one embodiment, the second communication unit of the display device is configured for communicating with the second external device over the Internet. The advantage of the embodiment is that the display device can communicate with devices far away.

According to one embodiment, the first communication unit of the display device is a wireless communication unit for wireless communication with the housing unit. The advantage of the embodiment is that the communication unit can be connected to the housing unit without the use of wires.

According to one embodiment, the first communication unit of the display device is configured to communicate wirelessly with the housing unit using a first communication frequency, the second communication unit of the display device is configured to communicate wirelessly with the second external device using a second communication frequency, and the first and second communication frequencies are different. The advantage of the embodiment is that the likelihood of interferences is reduced and the signal to interference and noise ratio is increased.

According to one embodiment, the first communication unit of the display device is configured to communicate wirelessly with the housing unit using a first communication protocol, the second communication unit of the display device is configured to communicate wirelessly with the second external device using a second communication protocol, and the first and second communication protocols are different. The advantage of the embodiment is that the protocol can be independently chosen for the communication of the first and second communication unit, depending on which protocol better suits the needs of the communication units.

According to one embodiment, the display device comprises, a first antenna configured for wireless communication with the housing, and a second antenna configured for wireless communication with the second external device. The advantage of the embodiment is that the antenna can be independently chosen for the communication of the first and second communication unit, depending on which antenna better suits the needs of the communication units.

According to one embodiment, the first communication unit is a wire-based communication unit for wire-based communication with the housing unit. The advantage of the embodiment is that the communication of the first communication unit is reliable and secure.

According to one embodiment, the display device is configured to display a user interface to the patient. The advantage of the embodiment is that the patient can use his familiar display device to communicate with the housing unit.

According to one embodiment, the housing unit is configured to transmit information pertaining to the display of the user interface to the display device. The advantage of the embodiment is that the patient can receive information using his familiar display device.

According to one embodiment, the display device is configured to, receive input pertaining to communication to or from the implantable medical device from the patient, and transmit signals based on the received input to the housing unit. The advantage of the embodiment is that the patient can use his familiar display device to communicate with the housing unit.

According to one embodiment, the display device comprises a touch screen configured to display the user interface and receive the input from the patient. The advantage of the embodiment is that the patient can use a familiar way of interacting with the information.

According to one embodiment, the housing unit is configured to display a user interface to the patient. The advantage of the embodiment is that the housing unit can receive user input.

According to one embodiment, the first communication unit of the housing unit is configured to receive communication from the implantable medical device pertaining to input from the patient, and wirelessly transmit signals based on the received input to the implantable medical device, using the second communication unit. The advantage of the embodiment is that the housing unit acts as an extra node in the communication between the display device and the medical implantable device, allowing it to monitor the communication.

According to one embodiment, the second communication unit of the housing unit is configured for wireless communication with the implantable medical device using a standard network protocol. The advantage of the embodiment is that the implementation of the communication units is cheap and the protocols reliable.

According to one embodiment, the standard network protocol is one from the list of, Radio Frequency type protocol, RFID type protocol, WLAN type protocol, Bluetooth type protocol, BLE type protocol, NFC type protocol, 3G/4G/5G type protocol, and GSM type protocol.

According to one embodiment, the second communication unit of the housing unit comprises a Bluetooth transceiver.

According to one embodiment, the second communication unit of the housing unit is configured for wireless communication with the implantable medical device using a proprietary network protocol. The advantage of the embodiment is that the housing unit is compatible with implantable medical devices that use proprietary network protocols.

According to one embodiment, the second communication unit of the housing unit comprises a UWB transceiver. The advantage is that high data rates can be communicated via the second communication unit.

According to one embodiment, the first communication unit of the housing unit is configured for wireless communication with the display device using a standard network protocol. The advantage of the embodiment is that the implementation of the communication units is cheap and the protocols reliable.

According to one embodiment, the standard network protocol is an NFC type protocol. The advantage of the embodiment is that the distance between the communicating devices is limited, protecting against eavesdropping attacks.

According to one embodiment, the first communication unit of the housing unit is configured for wireless communication with the display device using a proprietary network protocol. The advantage of the embodiment is that the housing unit is compatible with implantable medical devices that use proprietary network protocols.

According to one embodiment, the communication range of the first communication unit of the housing unit is less than a communication range of the second communication unit of the housing unit. The advantage of the embodiment is that energy is saved by selecting the first communication unit when its range suffices.

According to one embodiment, a communication range of the first communication unit of the display device is less than a communication range of the second communication unit of the display device. The advantage of the embodiment is that energy is saved by selecting the first communication unit when it's range suffices.

According to one embodiment, at least one of the housing unit and the display device is configured to allow communication between the housing unit and the display device on the basis of a distance between the housing unit and the display device. The advantage of the embodiment is that the distance is used as a safety and authorization factor.

According to one embodiment, at least one of the housing unit and the display device is configured to allow communication between the housing unit and the display device on the basis of the housing unit being mechanically connected to the display device. The advantage of the embodiment is that the safety against a man in the middle attacks is increased.

According to one embodiment, the housing unit is configured to allow communication between the housing unit and the implantable medical device on the basis of a distance between the housing unit and the implantable medical device. The advantage of the embodiment is that the distance is used as a safety and authorization factor.

According to one embodiment, the housing unit further comprises an encryption unit configured to encrypt communication received from the display device. The advantage of the embodiment is that the encrypted communication is protected against unwanted third-party access.

According to one embodiment, the housing unit is further adapted to transmit the encrypted communication, using the second communication unit, to the implantable medical device. The advantage of the embodiment is that the encrypted communication is protected against unwanted third-party access.

According to one embodiment, the second communication unit of the display device is configured to be disabled to enable at least one of, communication between the display device and the housing unit, and communication between the housing unit and the implantable medical device.

The display device in any of the embodiment herein could be a wearable device or a handset. The advantage of the embodiment is that the device is mobile and can be used where needed.

According to one embodiment, the housing unit comprises a case for the wearable device or handset. The advantage of the embodiment is that the wearable device or handset can be protected from mechanical trauma.

According to one embodiment, the implantable medical device is an implantable medical device configured to exert a force on a body portion of the patient and the implantable medical device may comprise an electrical motor and a controller for controlling the electrical motor. The advantage of the embodiment is that the motor and the motor controller enables manipulation of the patient's body in a controlled fashion.

The implantable medical device may comprise at least one of, an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries, an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

A housing unit configured for communication with an implantable medical device when implanted in a patient is further provided. The housing unit being configured to mechanically connect to a display device and comprising, a first communication unit for communication with the display device, a second communication unit for wireless communication with the implantable medical device.

According to one embodiment, the display device is a wearable device or a handset and the housing unit comprises a case for the wearable device or handset.

According to one embodiment, the first communication unit is a wireless communication unit for wireless communication with the display device.

According to one embodiment, the first communication unit is configured to communicate wirelessly with the display device using a first communication frequency, the second communication unit is configured to communicate wirelessly with the implantable medical device using a second communication frequency, and the first and second communication frequencies are different.

According to one embodiment, the housing unit is configured to transmit information pertaining to the display of a user interface to the display device.

According to one embodiment, the housing unit is configured to receive patient input from the display device.

According to one embodiment, the housing unit is configured to display a user interface to the patient.

According to one embodiment, the housing unit is configured allow communication between the housing unit and the display device on the basis of a distance between the housing unit and the display device.

According to one embodiment, the housing unit is configured allow communication between the housing unit and the display device on the basis of the housing unit being mechanically connected to the display device.

According to one embodiment, the housing unit is configured allow communication between the housing unit and the implantable medical device on the basis of a distance between the housing unit and the implantable medical device.

According to one embodiment, the housing unit further comprises an encryption unit configured to encrypt communication received from the display device.

According to one embodiment, the housing unit is further adapted to transmit the encrypted communication, using the second communication unit, to the implantable medical device.

According to one embodiment, the minimum bounding box of the housing unit and the display device when mechanically connected, is no more than, 10% wider, 10% longer or 100% higher, than the minimum bounding box of the display device.

According to one embodiment, the housing unit comprises one or more switches configured to, when the housing is not mechanically connected to the display device, be used by the patient.

According to one embodiment, the switches are at least partly covered by the display device, when the display device is mechanically connected to the housing unit.

According to one embodiment, at least a part of the housing bends to mechanically connect to the display device.

According to one embodiment, at least a part of the housing is configured to clasp the display device.

According to one embodiment, the housing is configured to cover at least one side of the display device, when mechanically connected to the display device.

According to one embodiment, the housing is configured to be mechanically connected to the display device by a device mechanically connected to the housing and the display device.

Aspect 331SE eHealth General Security Module

An implantable controller for an implantable medical device is further provided. The implantable controller comprises a wireless transceiver for communicating wirelessly with an external device, a security module, and a central unit configured to be in communication with the wireless transceiver, the security module and the implantable medical device. The wireless transceiver is configured to receive communication from the external device including at least one instruction to the implantable medical device and transmit the received communication to the central unit. The central unit is configured to send secure communication to the security module, derived from the received communication from the external device, and the security module is configured to decrypt at least a portion of the secure communication and/or verify the authenticity of the secure communication. The security module is configured to transmit a response communication to the central unit, and the central unit is configured to communicate the at least one instruction to the implantable medical device, the at least one instruction being based on the response communication, or a combination of the response communication and the received communication from the external device.

According to one embodiment, the security module comprises a set of rules for accepting communication from the central unit.

According to one embodiment, the wireless transceiver is configured to be placed in an off-mode, in which no wireless communication can be transmitted or received by the wireless transceiver, and wherein the set of rules comprises a rule stipulating that communication from the central unit is only accepted when the wireless transceiver is placed in the off-mode.

According to one embodiment, the set of rules comprises a rule stipulating that communication from the central unit is only accepted when the wireless transceiver has been placed in the off-mode for a specific time period.

According to one embodiment, the central unit is configured to verify a digital signature of the received communication from the external device.

According to one embodiment, the set of rules comprises a rule stipulating that communication from the central unit is only accepted when the digital signature of the received communication has been verified by the central unit.

According to one embodiment, the central unit is configured to verify the size of the received communication from the external device.

According to one embodiment, the set of rules comprises a rule stipulating that communication from the central unit is only accepted when the size of the received communication has been verified by the central unit.

The wireless transceiver of any of the preceding embodiments may be configured to receive a message from the external device being encrypted with at least a first and second layer of encryption and the central unit may be configured to decrypt a first layer of decryption and transmit at least a portion of the message comprising the second layer of encryption to the security model. The security module may be configured to decrypt the second layer of encryption and transmit a response communication to the central unit based on the portion of the message decrypted by the security module.

According to one embodiment, the central unit may be configured to decrypt a portion of the message comprising a digital signature, such that the digital signature can be verified by the central unit.

According to one embodiment, the central unit is configured to decrypt a portion of the message comprising message size information, such that the message size can be verified by the central unit.

According to one embodiment, the central unit is configured to decrypt a first and second portion of the message, and the first portion comprises a checksum for verifying the authenticity of the second portion.

According to one embodiment, the response communication transmitted from the security module comprises a checksum, and the central unit may be configured to verify the authenticity of at least a portion of the message decrypted by the central unit using the received checksum.

According to one embodiment, the set of rules comprises a rule related to the rate of data transfer between the central unit and the security module.

The security module in any of the embodiments herein may be configured to decrypt a portion of the message comprising a digital signature, encrypted with the second layer of encryption, such that the digital signature can be verified by the security module.

The central unit could be configured such that it is only capable of decrypting a portion of the receive communication from the external device when the wireless transceiver is placed in the off-mode.

According to one embodiment, the central unit is only capable of communicating the at least one instruction to the implantable medical device when the wireless transceiver is placed in the off-mode.

According to one embodiment, the implantable controller is configured to receive, using the wireless transceiver, a message from the external device comprising a first un-encrypted portion and a second encrypted portion, decrypt the encrypted portion, and use the decrypted portion to verify the authenticity of the un-encrypted portion.

According to one embodiment, the central unit is configured to transmit the encrypted portion to the security module, receive a response communication from the security module, based on information contained in the encrypted portion being decrypted by the security module, and use the response communication to verify the authenticity of the un-encrypted portion.

According to one embodiment, the un-encrypted portion comprises at least a portion of the at least one instruction to the implantable medical device.

The implantable controller may be configured to receive, using the wireless transceiver, a message from the external device comprising information related to at least one of: a physiological parameter of the patient and a physical parameter of the implanted medical device, and use the received information to verify the authenticity of the message.

The physiological parameter of the patient may comprise at least one of: a temperature, a heart rate and a saturation value.

The physical or functional parameter of the implanted medical device may comprise at least one of: a current setting or value of the implanted medical device, a prior instruction sent to the implanted medical device or an ID of the implanted medical device.

According to one embodiment, the portion of the message comprising the information is encrypted, and the central unit is configured to transmit the encrypted portion to the security module and receive a response communication from the security module, based on the information having been decrypted by the security module.

According to one embodiment, the security module comprises a hardware security module comprising at least one hardware-based key. The hardware-based key may correspond to a hardware-based key in the external device, which may be a hardware-based key on a key-card connectable to the external device.

According to one embodiment, the security module comprises a software security module comprising at least one software-based key. The software-based key may correspond to a software-based key in the external device. The software-based key could correspond to a software-based key on a key-card connectable to the external device. The security module may in any of the embodiments comprise a combination of a software-based key and a hardware-based key.

The implantable controller may in any of the preceding embodiments comprise at least one cryptoprocessor.

The wireless transceiver may in any of the embodiments be configured to receive communication from a handheld external device.

According to one embodiment, the at least one instruction to the implantable medical device may comprise an instruction for changing an operational state of the implantable medical device.

The wireless transceiver may be configured to communicate wirelessly with the external device using electromagnetic waves at a frequency below 100 kHz or at a frequency below 40 KHz.

According to one embodiment, the wireless transceiver is configured to communicate wirelessly with the external device using a first communication protocol, and the central unit is configured to communicate with the security module using a second different communication protocol.

The wireless transceiver may in any of the embodiments herein be configured to communicate wirelessly with the external device using a standard network protocol. The standard network protocol may be selected from a list comprising RFID type protocols, WLAN type protocols, Bluetooth type protocols, BLE type protocols, NFC type protocols, 3G/4G/5G type protocols, and GSM type protocols.

The wireless transceiver may in some embodiments be configured to communicate wirelessly with the external device using a proprietary network protocol.

According to one embodiment, the wireless transceiver comprises a UWB transceiver.

According to one embodiment, the security module and/ or the central unit and/or the wireless transceiver are comprised in the controller.

The external unit in any of the embodiments herein could be a wearable device or a handset. The advantage of the embodiment is that the device is mobile and can be used where needed.

According to one embodiment, the implantable medical device is an implantable medical device configured to exert a force on a body portion of the patient and the implantable medical device may comprise an electrical motor and a controller for controlling the electrical motor. The advantage of the embodiment is that the motor and the motor controller enables manipulation of the patient's body in a controlled fashion.

The implantable medical device may comprise at least one of, an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries, an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

An implantable medical device comprising a receiving unit is further provided. The implantable medical device comprises at least one coil configured for receiving transcutaneously transferred energy, a measurement unit configured to measure a parameter related to the energy received by the coil, a variable impedance electrically connected to the coil, a switch placed between the variable impedance and the coil for switching off the electrical connection between the variable impedance and the coil. The implantable medical device further comprises a controller configured to control at least one of the variable impedance for varying the impedance and thereby tune the coil based on the measured parameter, and the switch for switching off the electrical connection between the variable impedance and the coil in response to the measured parameter exceeding a threshold value.

According to one embodiment, the controller is configured to vary the variable impedance in response to the measured parameter exceeding a threshold value.

According to one embodiment, the measurement unit is configured to measure a parameter related to the energy received by the coil over a time period.

According to one embodiment, the measurement unit is configured to measure a parameter related to a change in energy received by the coil.

According to one embodiment, the first switch is placed at a first end portion of the coil, and the implantable medical device further comprises a second switch placed at a second end portion of the coil, such that the coil can be completely disconnected from other portions of the implantable medical device.

According to one embodiment, the receiving unit is configured to receive transcutaneously transferred energy in pulses according to a pulse pattern, and the measurement unit is configured to measure a parameter related to the pulse pattern.

According to one embodiment, the controller is configured to control the variable impedance in response to the pulse pattern deviating from a predefined pulse pattern.

According to one embodiment, the controller is configured to control the switch for switching off the electrical connection between the variable impedance and the coil in response to the pulse pattern deviating from a predefined pulse pattern.

According to one embodiment, the measurement unit is configured to measure a temperature in the implantable medical device or in the body of the patient, and the controller is configured to control the first and second switch in response to the measured temperature.

According to one embodiment, the variable impedance comprises a resistor and a capacitor, a resistor and an inductor and/or an inductor and a capacitor.

The variable impedance may comprise a digitally tuned capacitor. The variable impedance may comprise a digital potentiometer. The variable impedance may comprise a variable inductor.

According to one embodiment, the variation of the impedance is configured to lower the active power that is received by the receiving unit.

According to one embodiment, the variable impedance is placed in series with the coil.

According to one embodiment, the variable impedance is placed parallel to the coil.

According to one embodiment, the implantable medical device further comprises an energy storage unit connected to the receiving unit. The energy storage unit is configured for storing energy received by the receiving unit.

An external system for providing remote instructions to an implantable medical device is further provided. The external system being configured to provide instructions to be transmitted to the implantable medical device, derive a checksum from the instructions, electronically sign the instructions and the checksum. The external system is further configured to form a data packet from the instructions, the electronic signature and the checksum. The implantable medical device further comprises a wireless transmitter configured to wirelessly send the data packet to the implantable medical device. The external system may further be configured to encrypt the data packet at the external system. The checksum is configured to verify that no changes have been made to the bit stream forming the instructions.

According to one embodiment, the wireless transmitter is part of a wireless transceiver comprised in the external system.

According to one embodiment, the external system comprises a first external device and a second external device, and the first external device is configured to transmit the data packet to the second external device, and the second external device is configured to transmit the data packet wirelessly to the implantable medical device without changing the data packet and/or without full decryption of the data packet.

The external system may be configured to transmit at least one instruction for altering the control program of the implantable medical device, to the implantable medical device, which may include altering at least one parameter for affecting the control of the implantable medical device, which may include updating at least one parameter of the control program to a parameter value comprised in a set of parameter values stored in the implantable medical device.

According to one embodiment, the first external device is configured to send the data packet from the first external device to the second external device using a first network protocol and send the data packet from the second external device to the implantable medical device using a second network protocol.

According to one embodiment, the first external device is configured to send the data packet from the first external device to the second external device using wired communication and send the data packet from the second external device to the implantable medical device using wireless communication.

According to one embodiment, the first external device is configured to wirelessly send the data packet from the first external device to the second external device using a first network protocol, and wirelessly send the data packet from the second external device to the implantable medical device using a second network protocol.

According to one embodiment, the first external device is configured to wirelessly send the data packet from the first external device to the second external device using a first frequency band, and wirelessly send the data packet from the second external device to the implantable medical device using a second frequency band.

According to one embodiment, the first external device is configured to wirelessly send the data packet from the first external device to the second external device using a first wireless technology, and wirelessly send the data packet from the second external device to the implantable medical device using a second wireless technology.

According to one embodiment, the external system is configured to electronically sign the instructions at the external system using a key of the external system. The key may be a non-extractable key.

According to one embodiment, the second external device is configured to perform a proof of possession operation comprising the steps of transmitting, form the first external device to the second external device, a query based on a public key associated with the private of the external system, receiving, at the second external device, a response based on the possession of the private key in the first external device, and verifying that the response based on the possession of the private key matches the query based on a public key.

According to one embodiment, the first external device is configured to form the data packet and electronically sign the instruction using a first private key, and the second external device is configured to: receive the data packet from the first external device, verify that the first external device is a trusted transmitter, in response to the verification, electronically sign the data packet using a second private key, and transmit the data packet from the second external device to the medical implant.

According to one embodiment, the first external device is configured to electronically sign the instructions and encrypt the data packet using a key placed on a key device external to the first external device. The external system may comprise a key device configured to hold at least one private key which is part of a public-private key pair used for asymmetric encryption.

According to one embodiment, the key device comprises a wireless transmitter for wirelessly transmitting the at least one private key or a signal based on the private key, to the first external device. The second external device may be configured to at least one of: electronically sign the instructions and encrypt the data packet using a key placed on a key device external to the second external device.

According to one embodiment, the external system further comprises a second key device configured to hold at least one second private key and the second key device may comprise a wireless transmitter for wirelessly transmitting the at least one private key or a signal based on the private key to the second external device.

According to one embodiment, 5, the external system further comprises a second key device comprising a wireless transmitter for wirelessly transmitting at least one second private key or a signal based on the second private key to the first external device.

According to one embodiment, at least one of the key device and the second key device comprises at least one of: a key card, a wearable device and a handset.

The first and/or second external device may be configured to be unlocked by user credentials provided to the first external device. The user credentials may comprise a username and a password and/or a PIN-code.

According to one embodiment, the first external device is configured to verify the user credentials by comparing the user credentials with user credentials stored in the first external device. The user credentials may be stored in the first external device by the manufacturer of the first external device. The user credentials may be stored as hardware or software in the first external device.

According to one embodiment, the first external device is configured to verify the user credentials by communicating with a remote server.

The external system may in any of the embodiments herein be configured to function without connection to the Internet and may be configured to communicate with the implantable medical device independently of time.

The first and second private keys may be different in any of the embodiments. However, the first and second private keys may comprise at least one common element. At least one first and second external devices are configured to be unlocked by at least one of the first and second private key.

According to one embodiment, the external system comprises a central server, and the central server is configured to form a data packet from the instructions, the electronic signature and the checksum and further configured to provide the formed data packet to the first external device.

The central server may be accessed by at least one healthcare professional, such that the healthcare professional can provide input to the central server for forming the instructions to be sent to the implantable medical device.

The central server may be accessed by at least one patient, such that the patient can provide input to the central server for verifying at least one of: the authenticity of the healthcare professional and the correctness of the instructions. The healthcare provider and/or the patient can electronically sign the instructions at the central server.

According to one embodiment, the central server is configured to verify the authenticity of the first and second key and electronically sign the instructions using the first and second key. The second key may be a user key, and wherein the external system may be configured to use the second key for at least one of approving that communication is transmitted to the implantable medical device, and approving that a healthcare provider prepares an instruction to the implantable medical device.

According to one embodiment, the approval step can be performed by first or second external device.

According to one embodiment, the first key is required to create an instruction to the implantable medical device and the second key is required to transmit the created instruction to the implantable medical device.

According to one embodiment, at least one of the first and second external device comprises an input button configured to be used for verifying user presence.

According to one embodiment, the input button con be configured to replace at least one of: input of at least one key to at least one of the first and second external device, and input of credentials into at least one of the first and second external device. The input button may be configured to replace the second key.

According to one embodiment, the external system is configured to transmit the data packet to the implantable medical device, and the data packet comprises at least one instruction signed by a first key and a public key including information about which root have created the public key.

According to one embodiment, at least one of the first and second external device may be configured to enable communication with the implantable medical device based on at least one password being provided to at least one of the first and second external device.

According to one embodiment, at least one of the first and second external device is configured to enable communication with the implantable medical device based on two passwords being provided to at least one of the first and second external device.

According to one embodiment, at least one of the first and second external device is configured to enable communication with the implantable medical device based on one patient password and one healthcare provider password being provided to at least one of the first and second external device.

According to one embodiment, at least one of the first and second external devices are configured to perform a verification query operation with at least one of the first and second key device, the verification query operation comprising: transmitting, from the first or second external devices, a query comprising a computational challenge to at least one of the first and second key device, receiving, at the first or second external devices, a response based on the transmitted computational challenge, and verifying, at the first or second external devices, the received response. The verification query operation may be in the form of a proof of possession operation comprising: receiving a public key of at least one of the first and second key devices, the public key being associated with a private key of the first or second key device, transmitting, from at least one of the first and second external devices, a computational challenge to the first or second key device, based on the public key received from the first or second key device, receiving a response from the first or second key device based on the possession of the private key in the first or second key device, and verifying that the response based on the possession of the private key matches the query based on a public key.

An implantable medical device configured to receive remote instructions from an external system is further provided. The implantable medical device comprises a wireless receiver configured to receive wirelessly transmitted data packets from the external system, a computing unit configured to: verify the electronic signature, and use a checksum provided in the data packet to verify the integrity of the instructions. The computing unit may further be configured to decrypt the data packet. The computing unit may be configured to use the checksum to verify that the bit stream making up the instructions is unchanged.

The wireless receiver may be part of a wireless transceiver.

According to one embodiment, the computing unit comprises a memory unit configured to store electronic signatures, and the computing unit may be configured to verify the electronic signature by comparing the electronic signature with the electronic signatures stored in the memory unit.

According to one embodiment, the implantable medical device comprises a control program configured to control at least one function of the implantable medical device, and the computing unit may be configured to alter the control program on the basis of the received instructions.

According to one embodiment, the implantable medical device comprises an internal computing unit configured to run a control program for controlling a function of the implantable medical device. The control program may comprise at least one adjustable parameter affecting the control of the implantable medical device, and the method of providing remote instructions may comprise providing instructions for altering the at least one parameter for affecting the control of the implantable medical device.

According to one embodiment, the implantable medical device comprises a central unit, comprising at least one of a wireless receiver and a wireless transceiver, and a security module connected to the central unit. The implantable medical device may be configured to transfer the data packet from the central unit to the security module, and the security module may be configured to perform at least a portion of at least one of the decryption and the signature verification.

The security module may comprise a set of rules for accepting communication from the central unit, and the security module may be configured to verify compliance with the set of rules.

According to one embodiment, the wireless receiver or wireless transceiver may be configured to be placed in an off-mode, in which no wireless communication can be received by the wireless transceiver, and the set of rules may comprise a rule stipulating that communication from the central unit is only accepted at the security module when the wireless transceiver is placed in the off-mode.

According to one embodiment, the implantable medical device may be configured to decrypt the data packet and/or verify the electronic signature using a private key of the implantable medical device. The private key may be a non-extractable key. The private key may be provided in the implantable medical device by the manufacturer of the implantable medical device and may be stored as hardware or software in the implantable medical device.

According to one embodiment, the implantable medical device is configured to perform a proof of possession operation comprising: transmitting, from the implantable medical device to the external system, a query based on a public key associated with the private key of the external system, receiving, at the implantable medical device, a response based on the possession of the private key in the external system, and verifying that the response based on the possession of the private key matches the query based on a public key.

The implantable medical device may be configured to communicate with the external system independently of time.

According to one embodiment, the implantable medical device is configured to: verify a first electronic signature made using at least one of a first key and a second key, and verifying a second electronic signature made using at least one of a first key and a second key. At least one of the first and second keys may be a private key, and the first and second keys may be different, and the first and second keys may comprise at least one common element.

According to one embodiment, the implantable medical device is configured to verify a first electronic signature to allow communication from the external system to the implantable medical device, and verify a second electronic signature to allow an instruction received in the communication to alter the control program running on the implantable medical device.

According to one embodiment, the first electronic signature is an electronic signature linked to the user of the implantable medical device and the second electronic signature is an electronic signature linked to a healthcare provider.

According to one embodiment, only a portion of the private key is needed to at least one of: decrypt the data packet and verify the electronic signature.

The implantable medical device trusts any external device holding the private key.

According to one embodiment, the implantable medical device is configured to receive the data packet comprising: at least one instruction signed by a private key of the external system, and a public key including information about which root have created the public key.

According to one embodiment, the implantable medical device is configured to accept communication from an external system based on at least one password being provided to the implantable medical device. According to one embodiment, the implantable medical device is configured to accept communication from an external system based on two passwords being provided to the implantable medical device.

According to one embodiment, the implantable medical device is configured to accept communication from an external system based on one patient password and one healthcare provider passwords being provided to the implantable medical device.

A method of providing remote instructions from an external system to an implantable medical device is further provided. The method comprises deriving a checksum, at the external system, from the instructions to be sent to the implantable medical device, electronically signing the instructions and the checksum, at the external system, wherein: the instructions, the checksum and the electronic signature form a data packet, wirelessly sending the data packet to the implantable medical device, verifying the electronic signature, and using the checksum to verify the integrity of the instructions.

According to one embodiment, the method further comprises the steps of encrypting the data packet at the external system using a private key of the external system, and decrypting, at the implantable medical device, the data packet using a private key of the implantable medical device.

According to one embodiment, the step of verifying the electronic signature comprises comparing the electronic signature with electronic signatures stored in the implantable medical device.

According to one embodiment, the step of wirelessly sending the data packet to the implantable medical device comprises sending the data packet from a first external device to a second external device using wired communication and wirelessly sending the data packet from the second external device to the implantable medical device.

According to one embodiment, the step of wirelessly sending the data packet to the implantable medical device comprises sending the data packet from a first external device to a second external device and further wirelessly sending the data packet from the second external device to the implantable medical device. The second external device transmits the data packet without changing the data packet and/or without full decryption.

According to one embodiment, the step of wirelessly sending the data packet to the implantable medical device comprises: wirelessly sending the data packet from a first external device to a second external device using a first network protocol, and wirelessly sending the data packet from the second external device to the implantable medical device using a second network protocol.

According to one embodiment, the step of wirelessly sending the data packet to the implantable medical device comprises: wirelessly sending the data packet from a first external device to a second external device using a first frequency band, and wirelessly sending the data packet from the second external device to the implantable medical device using a second frequency band.

According to one embodiment, the step of wirelessly sending the data packet to the implantable medical device comprises: wirelessly sending the data packet from a first external device to a second external device using a first wireless technology, and wirelessly sending the data packet from the second external device to the implantable medical device using a second wireless technology, wherein the first wireless technology has an effective range being one of: 2 times, 4 times, 8 times 20 times, 50 times or 100 times longer than the first wireless technology.

According to one embodiment, the implantable medical device comprises a central unit, comprising a wireless transceiver, and a security module connected to the central unit. The step of decrypting, at the implantable medical device, the data packet, comprises transferring the data packet from the central unit to the security module, and performing at least a portion of the decryption in the security module.

According to one embodiment, the security module comprises a set of rules for accepting communication from the central unit, and the step of transferring the data packet from the receiving unit of the implant to the security module comprises verifying compliance with the set of rules.

According to one embodiment, the wireless transceiver is configured to be placed in an off-mode, in which no wireless communication can be received by the wireless transceiver, and the set of rules comprises a rule stipulating that communication from the central unit is only accepted at the security module when the wireless transceiver is placed in the off-mode.

According to one embodiment, the step of electronically signing the instructions at the external system comprises electronically signing the instructions at the external system using a private key of the external system.

According to one embodiment, the step of verifying the electronic signature comprises performing a proof of possession operation comprising the steps of: transmitting, form the medical device to the external system, a query based on a public key associated with the private of the external system, receiving, at the medical device, a response based on the possession of the private key in the external system, and verifying that the response based on the possession of the private key matches the query based on a public key.

According to one embodiment, the step of forming the data packet is performed at a first external device, and the step of electronically signing the instructions comprises electronically signing the instruction using a first private key, and wherein the method further comprises: transmitting the data packet from the first external device to a second external device, verifying, at the second external device, that the transmitter is a trusted transmitter, in response to the verification, electronically signing the data packet using a second private key, and transmitting the data packet from the second external device to the medical implant, and verifying, at the medical implant, the electronic signatures generated using the first and second private keys. The method may further comprise using the checksum to verify the integrity of the instructions.

According to one embodiment, the method according to any one of the preceding embodiments is performed without connection to the Internet and/or independently of time.

According to one embodiment, the method further comprises the central server being accessed by at least one healthcare professional, and the healthcare professional providing input to the central server for forming the instructions to be sent to the implantable medical device.

According to one embodiment, the central server is accessed by at least one patient, such that the patient can provide input to the central server for verifying at least one of: the authenticity of the healthcare professional and the correctness of the instructions.

According to one embodiment, the healthcare provider may electronically sign the instructions at the central server and/or the patient may electronically sign the instructions at the central server.

According to one embodiment, the method further comprising the steps of: verifying the authenticity of the first and second key at the central server, and electronically signing the instructions using the first and second key.

According to one embodiment, the second key is a user key, and the method may comprise the steps of using the second key for at least one of: approving that communication is transmitted to the implantable medical device, and approving that a healthcare provider prepares an instruction to the implantable medical device.

According to one embodiment, the approval step can be performed by first or second external device.

According to one embodiment, the first key is required to create an instruction to the implantable medical device and the second key is required to transmit the created instruction to the implantable medical device.

At least one of the first and second external device may comprise an input button, and the method may further comprise the step of pressing the button for verifying user presence. The input button may be placed on the second external device.

According to one embodiment, the method further comprises a verification query operation between at least one of the first and second external devices and at least one of the first and second key devices, the verification query operation comprising: transmitting, from the first or second external devices, a query comprising a computational challenge to at least one of the first and second key device, receiving, at the first or second external devices, a response based on the transmitted computational challenge, and verifying, at the first or second external devices, the received response. The verification query operation may be in the form of a proof of possession operation comprising: receiving a public key of at least one of the first and second key devices, the public key being associated with a private key of the first or second key device, transmitting, from at least one of the first and second external devices, a computational challenge to the first or second key device, based on the public key received from the first or second key device, receiving a response from the first or second key device based on the possession of the private key in the first or second key device, and verifying that the response based on the possession of the private key matches the query based on a public key.

A method of providing remote instructions from an external system to an implantable medical device is further provided. The implantable medical device comprises a list of codes and the external system comprises a list of codes. The method comprising encrypting the instructions at the external system using a code from a position on the list of codes, wirelessly sending the encrypted instructions to the implantable medical device, and decrypting, at the implantable medical device, the instructions using a code from a position on the list of codes.

According to one embodiment, the method further comprises the steps of: wirelessly sending position information from the external device to the implantable medical device, and using the information at the implantable medical device for selecting the code from the list of codes.

According to one embodiment, the step of encrypting, at the external system, the instructions using a code from a position on the list of codes comprises selecting the code on a current position on the list of codes, wherein the method further comprises the step of updating the current position to a new current position after using the code.

According to one embodiment, the step of decrypting, at the implantable medical device, the instructions using a code from a position on the list of codes comprises selecting the code on a current position on the list of codes, wherein the method further comprises the step of updating the current position to a new current position after using the code.

According to one embodiment, the current position comprises a number and wherein the step of updating the current position comprises updating the number to a sequential number.

According to one embodiment, the step of wirelessly sending the encrypted instructions to the implantable medical device comprises sending the encrypted instructions from a first external device to a second external device and further wirelessly sending the encrypted instructions from the second external device to the implantable medical device, and wherein the second external device transmits the encrypted instructions without changing the encrypted instructions and/or without full decryption of the instructions.

The implantable medical device according to any one of the preceding embodiments may further comprise an energy consuming part. The energy consuming part of the implantable medical device may be configured to exert a force on a body portion of the patient. According to one embodiment, the energy consuming part of the implantable medical device comprises an electrical motor, and the controller is configured for controlling the electrical motor.

According to one embodiment, the energy consuming part comprises at least one of: an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries, an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 447A, B, C
Data_Packet_Encryption-Implant, External, Method

According to an aspect, an implantable medical device configured to receive remote instructions from an external system is provided. The implantable medical device comprises a wireless receiver configured to receive wirelessly transmitted data packets from the external system, and a computing unit configured to verify the electronic signature, and use a checksum provided in the data packet to verify the integrity of the instructions.

According to an embodiment, the computing unit is configured to decrypt the data packet.

According to an embodiment, the computing unit is configured to use the checksum to verify that the bit stream making up the instructions is unchanged.

According to an embodiment, the wireless receiver is part of a wireless transceiver.

According to an embodiment, the computing unit comprises a memory unit configured to store electronic signatures, and wherein the computing unit is configured to verify the electronic signature my comparing the electronic signature with the electronic signatures stored in the memory unit.

According to an embodiment, the implantable medical device comprises a control program configured to control at least one function of the implantable medical device, and wherein computing unit is configured to alter the control program on the basis of the received instructions.

According to an embodiment, the implantable medical device comprises an internal computing unit configured to run a control program for controlling a function of the implantable medical device, wherein the control program comprises at least one adjustable parameter affecting the control of the implantable medical device, and wherein the method of providing remote instructions comprises providing instructions for altering the at least one parameter for affecting the control of the implantable medical device.

According to an embodiment, the computing unit comprises a memory unit configured to store parameter values, and wherein the method further comprises the step of verifying that the instructions for altering the at least one parameter will result in the at least one parameter being updated to a parameter value comprised in the set of stored parameter values.

According to an embodiment, the implantable medical device comprises a central unit, comprising at least one of a wireless receiver and a wireless transceiver, and a security module connected to the central unit, wherein the implantable medical device is configured to transfer the data packet from the central unit to the security module and wherein the security module is configured to performing at least a portion of at least one of the decryption and the signature verification.

According to an embodiment, the security module comprises a set of rules for accepting communication from the central unit, and wherein the security module is configured to verify compliance with the set of rules.

According to an embodiment, wireless receiver or wireless transceiver is configured to be placed in an off-mode, in which no wireless communication can be received by the wireless transceiver, and wherein the set of rules comprises a rule stipulating that communication from the central unit is only accepted at the security module when the wireless transceiver is placed in the off-mode.

According to an embodiment, wherein the implantable medical device is configured to at least one of decrypting the data packet and verifying the electronic signature using a private key of the implantable medical device.

According to an embodiment, the private key is a non-extractable key.

According to an embodiment, the implantable medical device is configured to perform a proof of possession operation comprising transmitting, from the implantable medical device to the external system, a query based on a public key associated with the private key of the external system, receiving, at the implantable medical device, a response based on the possession of the private key in the external system, and verifying that the response based on the possession of the private key matches the query based on a public key.

According to an embodiment, the implantable medical device is configured to communicate with the external system independently of time.

According to an embodiment, the private key is provided in the implantable medical device by the manufacturer of the implantable medical device.

According to an embodiment, the private key is stored as hardware or software in the implantable medical device.

According to an embodiment, the implantable medical device is configured to verify a first electronic signature made using at least one of a first key and a second key, and verifying a second electronic signature made using at least one of a first key and a second key.

According to an embodiment, at least one of the first and second keys is a private key.

According to an embodiment, the first and second keys are different.

According to an embodiment, the first and second keys comprises at least one common element.

According to an embodiment, the implantable medical device is configured to verify a first electronic signature to allow communication from the external system to the implantable medical device, and verify a second electronic signature to allow an instruction received in the communication to alter the control program running on the implantable medical device.

According to an embodiment, the first electronic signature is an electronic signature linked to the user of the implantable medical device and the second electronic signature is an electronic signature linked to a healthcare provider.

According to an embodiment, only a portion of the private key is needed to at least one of: decrypt the data packet and verify the electronic signature.

According to an embodiment, the implantable medical device trusts any external device holding the private key.

According to an embodiment, the implantable medical device is configured to receive the data packet comprising at least one instruction signed by a private key of the external system, and a public key including information about which root have created the public key.

According to an embodiment, the implantable medical device is configured to accept communication from an external system based on at least one password being provided to the implantable medical device.

According to an embodiment, the implantable medical device is configured to accept communication from an external system based on two passwords being provided to the implantable medical device.

According to an embodiment, the implantable medical device is configured to accept communication from an external system based on one patient password and one healthcare provider passwords being provided to the implantable medical device.

According to an aspect, an external system for providing remote instructions to an implantable medical device is provided. The external system is configured to provide instructions to be transmitted to the implantable medical device, derive a checksum from the instructions, electronically sign the instructions and the checksum, form a data packet from the instructions, the electronic signature and the checksum, wherein the external system comprises a wireless transmitter configured to wirelessly send the data packet to the implantable medical device.

According to an embodiment, the external system is further configured to encrypt the data packet at the external system.

According to an embodiment, the wireless transmitter is part of a wireless transceiver comprised in the external system.

According to an embodiment, the external system comprises a first external device and a second external device, and wherein the first external device is configured to transmit the data packet to the second external device, and wherein the second external device is configured to transmit the data packet wirelessly to the implantable medical device without changing the data packet.

According to an embodiment, the external system comprises a first external device and a second external device, and wherein the first external device is configured to transmit the data packet to the second external device, and wherein the second external device is configured to transmit the data packet wirelessly to the implantable medical device without full decryption of the data packet.

According to an embodiment, the external system is configured to transmit at least one instruction for altering the control program of the implantable medical device, to the implantable medical device.

According to an embodiment, the external system is configured to provide at least one instruction to the implantable medical device for altering at least one parameter for affecting the control of the implantable medical device.

According to an embodiment, the external system is configured to provide at least one instruction for updating at least one parameter of the control program to a parameter value comprised in a set of parameter values stored in the implantable medical device.

According to an embodiment, the first external device is configured to send the data packet from the first external device to the second external device using a first network protocol and send the data packet from the second external device to the implantable medical device using a second network protocol.

According to an embodiment, the first external device is configured to send the data packet from the first external device to the second external device using wired communication and send the data packet from the second external device to the implantable medical device using wireless communication.

According to an embodiment, the first external device is configured to wirelessly send the data packet from the first external device to the second external device using a first network protocol, and wirelessly send the data packet from the second external device to the implantable medical device using a second network protocol.

According to an embodiment, the first external device is configured to wirelessly send the data packet from the first external device to the second external device using a first frequency band, and wirelessly send the data packet from the second external device to the implantable medical device using a second frequency band.

According to an embodiment, the first external device is configured to wirelessly send the data packet from the first external device to the second external device using a first wireless technology, and wirelessly send the data packet from the second external device to the implantable medical device using a second wireless technology.

According to an embodiment, the external system is configured to electronically sign the instructions at the external system using a key of the external system.

According to an embodiment, the key is a non-extractable key.

According to an embodiment, the second external device is configured to perform a proof of possession operation comprising the steps of transmitting, form the first external device to the second external device, a query based on a public key associated with the private of the external system, receiving, at the second external device, a response based on the possession of the private key in the first external device, and verifying that the response based on the possession of the private key matches the query based on a public key.

According to an embodiment, the first external device is configured to form the data packet and electronically sign the instruction using a first private key, and the second external device is configured to: receive the data packet from the first external device, verify that the first external device is a trusted transmitter, in response to the verification, electronically sign the data packet using a second private key, and transmit the data packet from the second external device to the medical implant.

According to an embodiment, the checksum is configured to verify that no changes have been made to the bit stream forming the instructions.

According to an embodiment, the first external device is configured to at least one of: electronically sign the instructions and encrypt the data packet using a key placed on a key device external to the first external device.

According to an embodiment, the external system further comprises a key device configured to hold at least one private key.

According to an embodiment, the key device comprises a wireless transmitter for wirelessly transmitting the at least one private key or a signal based on the private key, to the first external device.

According to an embodiment, the second external device is configured to at least one of: electronically sign the instructions and encrypt the data packet using a key placed on a key device external to the second external device.

According to an embodiment, the external system further comprises a second key device configured to hold at least one second private key.

According to an embodiment, the second key device comprises a wireless transmitter for wirelessly transmitting the at least one private key or a signal based on the private key to the second external device.

According to an embodiment, the external system further comprises a second key device comprising a wireless transmitter for wirelessly transmitting at least one second private key or a signal based on the second private key to the first external device.

According to an embodiment, at least one of the key device and the second key device comprises at least one of: a key card, a wearable device and a handset.

According to an embodiment, the first external device is configured to be unlocked by user credentials provided to the first external device.

According to an embodiment, the first external device is configured to be unlocked by user credentials comprising a username and a password.

According to an embodiment, the first external device is configured to be unlocked by user credentials comprising a PIN-code.

According to an embodiment, the first external device is configured to verify the user credentials by comparing the user credentials with user credentials stored in the first external device.

According to an embodiment, the first external device is configured to verify the user credentials by comparing the user credentials with user credentials stored in the first external device by the manufacturer of the first external device.

According to an embodiment, the first external device is configured verify the user credentials by comparing the user credentials with user credentials stored as hardware or software in the first external device.

According to an embodiment, the first external device is configured verify the user credentials by communicating with a remote server.

According to an embodiment, the second external device is configured to be unlocked by user credentials provided to the second external device.

According to an embodiment, the first external device is configured to be unlocked by user credentials comprising a username and a password.

According to an embodiment, the first external device is configured to be unlocked by user credentials comprising a PIN-code.

According to an embodiment, the second external device is configured to verify the user credentials by comparing the user credentials with user credentials stored in the second external device.

According to an embodiment, the second external device is configured to verify the user credentials by comparing the user credentials with user credentials stored in the second external device by the manufacturer of the second external device.

According to an embodiment, the second external device is configured verify the user credentials by comparing the user credentials with user credentials stored as hardware or software in the second external device.

According to an embodiment, the second external device is configured verify the user credentials by communicating with a remote server.

According to an embodiment, the external system is configured to function without connection to the Internet.

According to an embodiment, the external system is configured to communicate with the implantable medical device independently of time.

According to an embodiment, the first and second private keys are different.

According to an embodiment, the first and second private keys comprises at least one common element.

According to an embodiment, at least one first and second external device are configured to be unlocked by at least one of the first and second private key.

According to an embodiment, the external system comprises a central server, and wherein the central server is configured to form a data packet from the instructions, the electronic signature and the checksum and further configured to provide the formed data packet to the first external device.

According to an embodiment, the central server can be accessed by at least one healthcare professional, such that the healthcare professional can provide input to the central server for forming the instructions to be sent to the implantable medical device.

According to an embodiment, the central server can be accessed by at least one patient, such that the patient can provide input to the central server for verifying at least one of: the authenticity of the healthcare professional and the correctness of the instructions.

According to an embodiment, the healthcare provider can electronically sign the instructions at the central server.

According to an embodiment, the patient can electronically sign the instructions at the central server.

According to an embodiment, the central server is configured to verify the authenticity of the first and second key and electronically sign the instructions using the first and second key.

According to an embodiment, the second key is a user key, and wherein the external system is configured to use the second key for at least one of approving that communication is transmitted to the implantable medical device, and approving that a healthcare provider prepares an instruction to the implantable medical device.

According to an embodiment, the approval step can be performed by first or second external device.

According to an embodiment, the first key is required to create an instruction to the implantable medical device and the second key is required to transmit the created instruction to the implantable medical device.

According to an embodiment, at least one of the first and second external device comprises an input button configured to be used for verifying user presence.

According to an embodiment, the input button con be configured to replace at least one of: input of at least one key to at least one of the first and second external device, and input of credentials into at least one of the first and second external device.

According to an embodiment, the input button is configured to replace the second key.

According to an embodiment, the external system is configured to transmit the data packet to the implantable medical device, and wherein the data packet comprises at least one instruction signed by a first key and a public key including information about which root have created the public key.

According to an embodiment, at least one of the first and second external device is configured to enable communication with the implantable medical device based on at least one password being provided to at least one of the first and second external device.

According to an embodiment, at least one of the first and second external device is configured to enable communication with the implantable medical device based on two passwords being provided to at least one of the first and second external device.

According to an embodiment, at least one of the first and second external device is configured to enable communication with the implantable medical device based on one patient password and one healthcare provider passwords being provided to at least one of the first and second external device.

According to an embodiment, at least one of the first and second external devices are configured to perform a verification query operation with at least one of the first and second key device, the verification query operation comprising transmitting, from the first or second external devices, a query comprising a computational challenge to at least one of the first and second key device, receiving, at the first or second external devices, a response based on the transmitted computational challenge, and verifying, at the first or second external devices, the received response.

According to an embodiment, at least one of the first and second external devices are configured to perform a verification query operation in the form of a proof of possession operation comprising receiving a public key of at least one of the first and second key devices, the public key being associated with a private key of the first or second key device, transmitting, from at least one of the first and second external devices, a computational challenge to the first or second key device, based on the public key received from the first or second key device, receiving a response from the first or second key device based on the possession of the private key in the first or second key device, and verifying that the response based on the possession of the private key matches the query based on a public key.

A medical system comprising the external system according to any one of the preceding embodiments and an implantable medical device is also provided.

A method corresponding to any one of the embodiments of aspects 447A and/or 447B is provided.

Aspect 447D Single-Use_Codes_Encryption

A method of providing remote instructions from an external system to an implantable medical device, wherein the implantable medical device comprises a list of codes and the external system comprises a list of codes, is provided. The method comprises encrypting the instructions at the external system using a code from a position on the list of codes, wirelessly sending the encrypted instructions to the implantable medical device, and decrypting, at the implantable medical device, the instructions using a code from a position on the list of codes.

According to an embodiment, the method further comprises the steps of wirelessly sending position information from the external device to the implantable medical device, and using the information at the implantable medical device for selecting the code from the list of codes.

According to an embodiment, the step of encrypting, at the external system, the instructions using a code from a position on the list of codes comprises selecting the code on a current position on the list of codes, wherein the method further comprises the step of updating the current position to a new current position after using the code.

According to an embodiment, the step of decrypting, at the implantable medical device, the instructions using a code from a position on the list of codes comprises selecting the code on a current position on the list of codes, wherein the method further comprises the step of updating the current position to a new current position after using the code.

According to an embodiment, the current position comprises a number and wherein the step of updating the current position comprises updating the number to a sequential number.

According to an embodiment, the step of wirelessly sending the encrypted instructions to the implantable medical device comprises sending the encrypted instructions from a first external device to a second external device and further wirelessly sending the encrypted instructions from the second external device to the implantable medical device, and wherein the second external device transmits the encrypted instructions without changing the encrypted instructions.

According to an embodiment, the step of wirelessly sending the encrypted instructions to the implantable medical device comprises sending the encrypted instructions from a first external device to a second external device and further wirelessly sending the encrypted instructions from the second external device to the implantable medical device, and wherein the second external device transmits the encrypted instructions without full decryption.

According to an embodiment, the implantable medical device comprises a control program configured to control at least one function of the implantable medical device, and wherein the method further comprises altering the control program on the basis of the received instructions.

According to an embodiment, the implantable medical device comprises an internal computing unit configured to run a control program for controlling a function of the implantable medical device, wherein the control program comprises at least one adjustable parameter affecting the control of the implantable medical device, and wherein the method of providing remote instructions comprises providing instructions for altering the at least one parameter for affecting the control of the implantable medical device.

According to an embodiment, the implantable medical device comprises a set of stored parameter values, and wherein the method further comprises the step of verifying that the instructions for altering the at least one parameter will result in the at least one parameter being updated to a parameter value comprised in the set of stored parameter values.

According to an embodiment, the step of wirelessly sending the encrypted instructions to the implantable medical device comprises wirelessly sending the encrypted instructions from a first external device to a second external device using a first network protocol, and wirelessly sending the encrypted instructions from the second external device to the implantable medical device using a second network protocol.

According to an embodiment, the step of wirelessly sending the encrypted instructions to the implantable medical device comprises wirelessly sending the encrypted instructions from a first external device to a second external device using a first frequency band, and wirelessly sending the encrypted instructions from the second external device to the implantable medical device using a second frequency band.

According to an embodiment, the step of wirelessly sending the encrypted instructions to the implantable medical device comprises wirelessly sending the encrypted instructions from a first external device to a second external device using a first wireless technology, and wirelessly sending the encrypted instructions from the second external device to the implantable medical device using a second wireless technology, wherein the first wireless technology has an effective range being one of: 2 times, 4 times, 8 times 20 times, 50 times or 100 times longer than the first wireless technology.

According to an embodiment, the implantable medical device comprises a central unit, comprising a wireless transceiver, and a security module connected to the central unit, wherein the step of decrypting, at the implantable medical device, the encrypted instructions, comprises transferring the encrypted instructions from the central unit to the security module, and performing at least a portion of the decryption in the security module.

According to an embodiment, the security module comprises a set of rules for accepting communication from the central unit, and wherein the step of transferring the encrypted instructions from the receiving unit of the implant to the security module comprises verifying compliance with the set of rules.

According to an embodiment, the wireless transceiver is configured to be placed in an off-mode, in which no wireless communication can be received by the wireless transceiver, and wherein the set of rules comprises a rule stipulating that communication from the central unit is only accepted at the security module when the wireless transceiver is placed in the off-mode.

According to an embodiment, the step of electronically signing the instructions at the external system comprises electronically signing the instructions at the external system using a private key of the external system.

According to an embodiment, the private key is a non-extractable key.

According to an embodiment, the step of wirelessly sending the encrypted instructions to the implantable medical device comprises wirelessly sending the encrypted instructions from a first external device to a second external device using a first wireless technology, and wirelessly sending the encrypted instructions from the second external device to the implantable medical device using a second wireless technology, wherein the first wireless technology has an effective range being one of: 2 times, 4 times, 8 times 20 times, 50 times or 100 times longer than the first wireless technology.

Aspect 454: Dual Remote Controls

A communication system for transmission of data to or from an implantable medical device is provided. The communication system comprises an implantable medical implant, a first remote control comprising a first wireless communication unit configured for wireless transmission of data to or from the implantable medical device, the first remote control being operable by a user, and a second remote control comprising a second wireless communication unit configured for wireless transmission of control commands or data to or from the implantable medical device, and a third communication unit for communicating with a patient display device, the second remote control being inoperable by a user.

According to an embodiment, the first remote control comprises an input device for receiving a first user input, and wherein the first remote control is configured to transmit the first user input to the implantable medical device.

According to an embodiment, the second remote control is configured to receive second user input from the patient display device and to transmit the second user input to the implantable medical implant.

According to an embodiment, the data comprises a control command for the medical implant.

According to an embodiment, at least one of the first wireless communication unit and the second wireless communication unit is configured to send or receive data using near-field magnetic induction.

According to an embodiment, at least one of the first wireless communication unit and the second wireless communication unit comprises a transmitter coil for modulating a magnetic field for transmitting the data, and wherein the implantable medical implant comprises a receiving coil and an NFMI receiver connected to the receiving coil to receive the data.

According to an embodiment, the transmitter coil is configured to modulate a magnetic field, and the NFMI receiver is adapted to measure the magnetic field in the receiving coil.

According to an embodiment, at least one of the first wireless communication unit and the second wireless communication unit is configured to wirelessly charge the medical implant using near-field magnetic induction.

According to an embodiment, the medical implant comprises a coil for receiving wireless energy for charging the implant via near-field magnetic induction.

According to an embodiment, the second and third communication units are configured to transmit and/or receive data using different network protocols.

According to an embodiment, wherein the second and third communication units are configured to transmit and/or receive data using different frequency bands.

According to an embodiment, at least one of the first remote control, the second remote control and the implantable medical device comprises a Bluetooth transceiver.

According to an embodiment, at least one of first remote control, the second remote control and the implantable medical device comprises a UWB transceiver.

According to an embodiment, the network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

According to an embodiment, the second communication unit has a longer effective range than the third communication unit.

According to an embodiment, the second remote control is configured to communicate with a consumer electronics device.

According to an embodiment, the patient display device comprises the consumer electronics device.

According to an embodiment, the first remote control is configured to control functions of the implantable medical device based on user input to the first remote control.

According to an embodiment, a method corresponding to the communication system according to the previous aspect is provided.

Aspect 457: Controlling Energy Transfer

According to an aspect, a method for wireless energy transfer from an external energy source located outside the patient to an internal energy receiver located inside the patient, the internal energy receiver being connected to an implantable medical device for supplying received energy thereto, is provided. The method comprises determining an accumulated amount of received energy over a time period, determining a current change in the received energy, determining a control signal reflecting the accumulated received energy and the change in the received energy, and controlling the energy transfer based on the control signal.

According to an embodiment, determining an accumulated amount of received energy is determined by the internal energy receiver.

According to an embodiment, determining a current change is performed by the internal energy receiver.

According to an embodiment, the internal energy receiver comprises a PID regulator for controlling the energy transfer.

According to an embodiment, the PID regulator is implemented in a microcontroller.

According to an embodiment, determining a control signal is performed by the internal energy receiver.

According to an embodiment, the control signal is transmitted to the external energy source, and wherein the external energy source is configured to adjust the transmitted energy base on the control signal.

According to an embodiment, controlling the energy transfer is controlled by the internal energy receiver.

According to an embodiment, controlling the energy transfer is performed by the external energy source.

According to an embodiment, controlling the energy transfer comprises adjusting the energy transfer efficiency.

According to an embodiment, the external device comprises a transmitter coil for modulating a magnetic field for transmitting data or transmitting energy, and wherein the implantable medical implant comprises a receiving coil and an NFMI receiver connected to the receiving coil to receive the data or the energy.

According to an embodiment, at least one of the first wireless communication unit and the second wireless communication unit is configured to wirelessly charge the medical implant using near-field magnetic induction.

According to an embodiment, the medical implant comprises a coil for receiving wireless energy for charging the implant via near-field magnetic induction.

According to an embodiment, the method further comprises receiving energy in pulses according to a pulse pattern, and measuring the received pulse pattern.

According to an embodiment, the method further comprises determining that the pulse pattern deviates from a predefined pulse pattern, and controlling the energy transfer based on the determination.

According to an embodiment, the method further comprises measuring a temperature in the implantable medical device or in the body of the patient, and controlling the energy transfer in response to the measured temperature.

According to an embodiment, the implantable medical device comprises at least one coil connected to a variable impedance, the method further comprising controlling the energy transfer by controlling the variable impedance.

According to an embodiment, the implantable medical device comprises at least one coil having a plurality of windings, wherein the plurality of windings each are connected to a respective variable impedance, the method further comprising controlling the energy transfer by controlling the respective variable impedance individually.

According to an aspect, an implantable medical device, a first remote control and/or a second remote control configured to perform the method according to the previous aspect are provided. A corresponding method is also provided.

Aspect 453: Voice Control 2

A method of teaching a voice-controlled medical implant to recognize a voice command is provided. The method comprises inputting a first audio training phrase to the medical implant, when the medical implant is implanted in the body of the patient and creating a transfer function, the transfer function being based on the first audio training phrase, wherein the transfer function is configured to adjust the amplitude of at least one frequency of audio received at the medical device for enhancing audio received at the medical implant to facilitate detection of voice commands. The method further comprises inputting a second audio training phrase to the medical implant, the second audio training phrase comprising the voice command. The voice command comprises an instruction for the control of the medical implant. The method further comprises using the transfer function for generating an enhanced second audio training phrase in the medical implant, and associating the enhanced second audio training phrase with the instruction for the control of the medical implant.

In an embodiment, adjusting the amplitude comprises at least one of: filtering, cancelling and amplifying the at least one frequency.

In an embodiment, at least one of the first and second audio training phrase is a spoken audio training phrase.

In an embodiment, the spoken audio training phrase is spoken by the patient the implant is implanted in.

In an embodiment, the first audio training phrase comprises the voice command.

In an embodiment, the first and second audio training phrases is the same voice command.

In an embodiment, the first and second audio training phrases are different.

In an embodiment, creating the transfer function comprises amplifying frequencies muffled by the location of the medical implant in the body of the patient.

In an embodiment, creating the transfer function comprises filtering or cancelling noise generated by the body.

In an embodiment, the medical implant is configured to receive voice commands related to an instruction for control of the medical implant.

In an embodiment, the voice command relates to at least one of: performing a function of the medical device; using a sensor to measure a parameter relating to a condition of the patient or a condition of the medial implant; and sending or receiving data from the medical implant.

A system corresponding to the preceding aspect is also provided.

Aspect Large Coil

According to an aspect, a system for wirelessly charging an implantable medical implant, when implanted in a body of a patient, is provided. The system comprises an internal energy receiver comprising a secondary coil, the internal energy receiver being connected to the implantable medical implant and an external energy transmitter comprising a primary coil for wirelessly transmitting energy to the internal energy receiver via the secondary coil, wherein a diameter of the primary coil is larger than a diameter of the secondary coil.

According to an embodiment, the system further comprises an internal controller connected to the internal energy receiver, for controlling the amount of energy received by the internal energy receiver.

According to an embodiment, the internal energy receiver further comprises a measurement unit for measuring a parameter related to the implantable medical implant or the body of the patient.

According to an embodiment, the controller is configured to measure the accumulated energy received by the internal energy receiver over a period of time and to measure a current change in energy received, and to control the energy received based on the accumulated energy and the current change.

According to an embodiment, the controlled comprises a Proportional-Integral-Derivative, PID, regulator for controlling the received energy.

According to an embodiment, the internal energy received comprises a variable impedance.

According to an embodiment, the internal energy receiver is configured to control the resonant frequency by controlling the variable impedance.

According to an embodiment, the controller is configured to vary the variable impedance in response to a measured parameter deviating from a predetermined interval or exceeding a threshold value.

According to an embodiment, the parameter relates to the energy received by the coil over a time period.

According to an embodiment, the measurement unit is configured to measure a parameter related to a change in energy received by the coil.

According to an embodiment, the receiving unit is configured to receive transcutaneously transferred energy in pulses according to a pulse pattern, and wherein the measurement unit is configured to measure a parameter related to the pulse pattern.

According to an embodiment, the receiving unit is configured to receive transcutaneously transferred energy in pulses according to a pulse pattern, and wherein the measurement unit is configured to measure a parameter related to the pulse pattern.

According to an embodiment, the controller is configured to control the variable impedance in response to the pulse pattern deviating from a predefined pulse pattern.

According to an embodiment, the variable impedance comprises a resistor and a capacitor, the variable impedance comprises a resistor and an inductor, the variable impedance comprises an inductor and a capacitor, the variable impedance comprises a digitally tuned capacitor, the variable impedance comprises a digital potentiometer, or the variable impedance comprises a variable inductor.

According to an embodiment, the diameter of the primary coil is at least one of more than 0.5 cm, more than 10 cm, more than 15 cm, more than 20 cm, coil is more than 30 cm, or is more than 50 cm.

According to an embodiment, the area of the primary coil is more than 0.5 cm2, more than 2 cm2, more than 10 cm2, more than 100 cm2, more than 300 cm2, more than 500 cm2, or more than 800 cm2.

According to an embodiment, a method corresponding to the system for wirelessly charging an implant according to the previous aspect is provided.

Aspect 456: NFMI

According to an aspect, a system for communication with an implantable medical device, when implanted in a body of a patient, is provided. The system comprises an internal communications unit, connected to or comprised in the implantable medical device, and an external communications unit, wherein the internal communications unit and the external communications unit are configured to communicate using near field magnetic induction, NFMI.

According to an embodiment, the internal communication unit comprises an internal NFMI receiver and an internal coil connected to the internal NFMI receiver, the internal NFMI receiver being configured to measure an induced voltage in the internal coil. The external communications unit comprises an external NFMI transmitter and an external coil connected to the external NFMI transmitter, and the external coil and the external NFMI transmitter are configured to modulate a magnetic field for sending data to the implantable medical device via the internal coil.

According to an embodiment, the external NFMI transmitter further comprises a capacitor for tuning.

According to an embodiment, the internal NFMI receiver comprises a tunable resistor and capacitor tank.

According to an embodiment, the internal communication unit comprises an internal NFMI transmitter and an internal coil connected to the internal NFMI transmitter. The external communications unit comprises an external NFMI receiver and an external coil connected to the external NFMI receiver, the external NFMI receiver being configured to measure an induced voltage in the external coil, and the internal coil and the internal NFMI transmitter are configured to modulate a magnetic field for sending data to the external communications unit via the external coil.

According to an embodiment, the internal NFMI transmitter further comprises a capacitor for tuning the internal coil and the internal NFMI transmitter.

According to an embodiment, the external NFMI receiver comprises a tunable resistor and capacitor tank for tuning the external coil and the external NFMI receiver.

According to an embodiment, the implantable medical device comprises an active portion configured to monitor, treat or perform a function of a body of a patient.

According to an embodiment, the active portion is not a pacemaker, a hearing aid or a neurostimulation implant.

According to an embodiment, the internal communications unit is adapted to be implanted at a tissue depth of at least 8 cm or at least 15 cm.

According to an embodiment, the internal communications unit is adapted to be implanted in an abdomen of a patient.

According to an embodiment, the external communications unit is configured to communicate with another external device.

According to an embodiment, the internal communications unit is configured to encrypt data before transmitting it to the external communications unit.

According to an embodiment, the external communications unit is configured to relay the encrypted data to the another external device without decrypting it.

Aspect 459: Resonant Circuits

According to an aspect, an implantable medical device adapted to receive wirelessly transmitted energy is provided, the implantable medical device comprises an energy consuming part, and a first energy receiving unit, the first energy receiving unit comprising a first coil configured for receiving wirelessly transferred energy, and a first impedance unit electrically connected to the first coil, the receiving unit being configured to transfer the received energy to the energy consuming part. The implantable medical device further comprises a second energy receiving unit, the second energy receiving unit comprising a second coil configured for receiving wirelessly transferred energy and a second impedance unit electrically connected to the second coil, the receiving unit being configured to transfer the received energy to the energy consuming part. The implantable medical device further comprises a measurement unit configured to measure a parameter related to energy transfer, and a controller configured to control the subcutaneously received energy based on the parameter by controlling the first or the second impedance unit.

According to an embodiment, the first energy receiving unit has a first resonant frequency based on the inductance of the first coil and the impedance of the first impedance unit, and the second energy receiving unit has a second resonant frequency based on the inductance of the second coil and the impedance of second impedance unit.

According to an embodiment, the first receiving unit has a resonant frequency different from the resonant frequency of the second receiving unit.

According to an embodiment, the first and second impedance units are connected in parallel to the respective coil.

According to an aspect, an implantable medical device adapted to receive wirelessly transmitted energy, the implantable medical device comprises an energy consuming part, and a receiving unit configured for receiving wirelessly transferred energy and transferring the received energy to the energy consuming part, the receiving unit comprising a first coil portion and a second coil portion, and a first impedance unit and a second impedance unit, wherein the first impedance unit is connected to the first coil portion and the second impedance unit is connected to the second coil portion. The implantable medical device further comprises a measurement unit configured to measure a parameter related to energy transfer, and a controller configured to control the subcutaneously received energy based on the parameter by controlling the first or the second impedance unit.

According to an embodiment, the first coil portion and the second coil portion are at least one of: portions of the same coil, or portions or different coils connected in series.

According to an embodiment, the first coil portion and the second coil portion have the same inductance, or the first coil portion has a different inductance than the second coil portion.

According to an embodiment, the first impedance is connected in parallel to the first coil portion and the second impedance is connected in parallel to the second coil portion.

According to an embodiment, one of the first coil portion and the second coil portion are overlapping the other of the first coil portion and the second coil portion, or the first coil portion and the second coil portion are not overlapping with the other of the first coil portion and the second coil portion.

According to an embodiment, the first coil portion and the first impedance unit has a first resonance frequency, and the second coil portion and the second impedance unit has a second resonance frequency.

According to an embodiment, the first resonance frequency is different from the second resonance frequency.

According to an embodiment, the first or second impedance unit is a capacitor.

According to an embodiment, the first impedance unit and the second impedance unit have different impedances.

According to an aspect, an implantable medical device adapted to receive wirelessly transmitted energy, the implantable medical device comprises an energy consuming part, and a first receiving unit comprising a first coil configured for receiving wirelessly transferred energy and transferring the received energy to the energy consuming part, and a first impedance electrically connected to the coil. The implantable medical device further comprises a second receiving unit comprising a second coil portion and a third coil portion configured for receiving wirelessly transferred energy and transferring the received energy to the energy consuming part, and a second impedance unit and a third impedance unit, wherein the second impedance unit is connected to the second coil portion and the third impedance unit is connected to the third coil portion. The implantable medical device further comprises a measurement unit configured to measure a parameter related to energy transfer, and a controller configured to control the subcutaneously received energy based on the parameter by controlling the first, the second or the third impedance unit.

BRIEF DESCRIPTION OF THE DRAWINGS

Figures are to be considered schematic rather than photorealistic illustrations. Intermittent or dashed borders for flowchart borders may indicate optional steps.

FIGS. 12-17 illustrate flowcharts of methods according to embodiments of the first part of aspect 245SE.

FIGS. 22-29 illustrate flowcharts of methods according to embodiments of the first part of aspect 246SE.

FIGS. 32-35 illustrate flowcharts of methods according to embodiments of the second part of aspect 247SE.

FIGS. 40-48 illustrate flowcharts of methods according to embodiments of the first part of aspect 249SE.

FIGS. 53-55 illustrate flowcharts of methods according to embodiments of the second part of aspect 250SE.

FIGS. 56-60 illustrate flowcharts of methods according to embodiments of the first part of aspect 251SE.

FIG. 65-67 illustrate flowcharts of methods according to embodiments of the first part of aspect 252SE.

FIGS. 74-82 illustrate flowcharts of methods according to embodiments of the first part of aspect 254SE.

FIGS. 88-89 illustrate flowcharts of methods according to embodiments of the first part of aspect 256SE.

FIG. 93 illustrates a flowchart of methods according to embodiments of the first part of aspect 257SE.

FIG. 120 shows an elevated perspective view from the left of a housing unit.

FIG. 121 shows a plain view from the left of a housing unit.

FIG. 122 shows an elevated perspective view from the left of a housing unit.

FIG. 123 shows a plain view from the left of a housing unit.

FIG. 126A schematically shows a medical implant configured to recognize a voice command when implanted in a patient.

FIG. 126B shows a flow chart for a method for training a medical implant to recognize a voice command, according to some embodiments;

FIG. 126C shows a flow chart for a method for using voice commands to control a medical implant, according to some embodiments.

DETAILED DESCRIPTION OF EMBODIMENTS

Figures 1A, 1B, 1C:
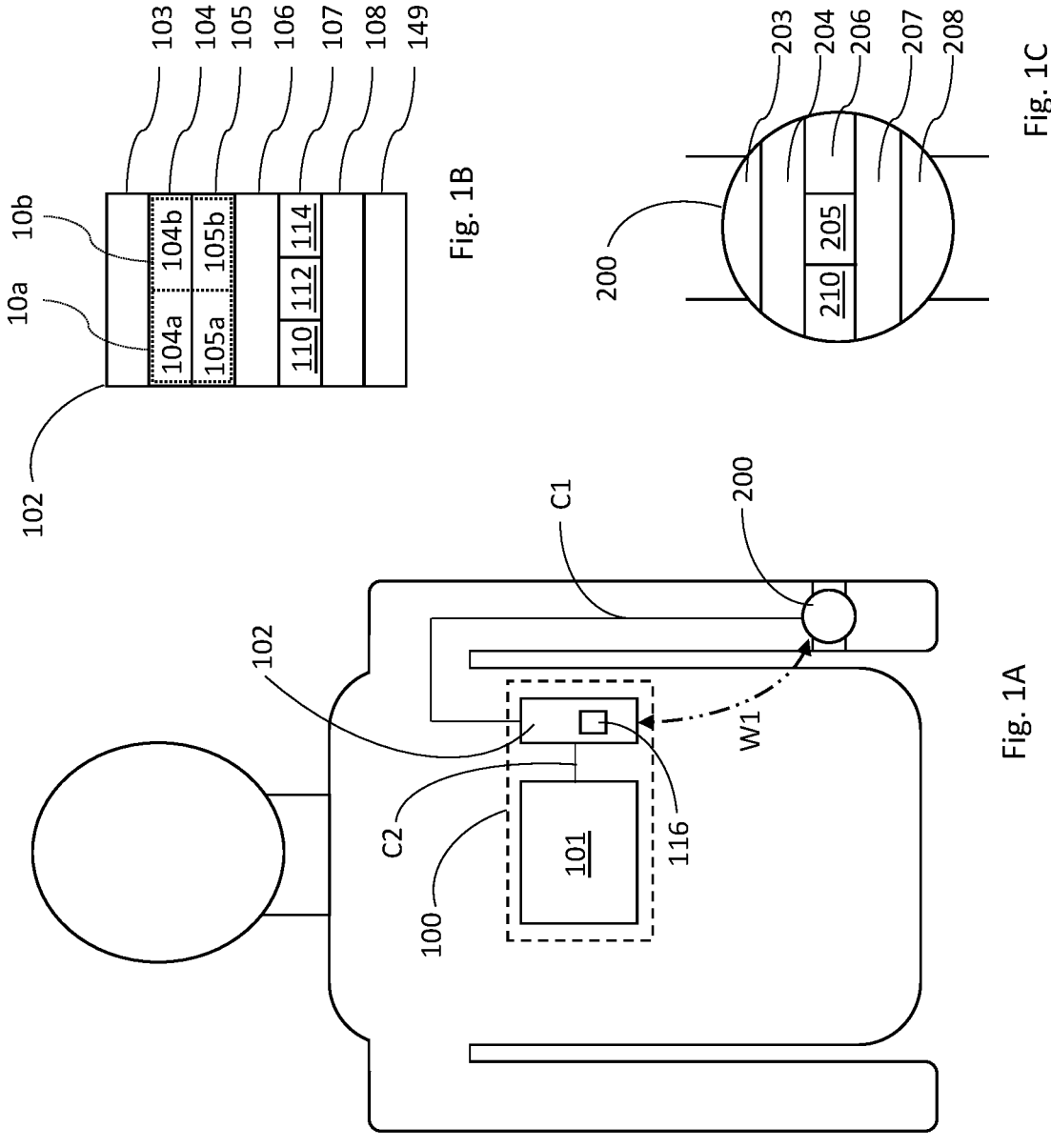
FIG. 1A illustrates a system comprising an implant, further illustrated in FIG. 1B, and an external device, further illustrated in FIG. 1C, all according to the aspect 244SE.

In the following, embodiments will be described in conjunction with a plurality of drawings. To simplify for the reader, here follows a general description of features used when exemplifying the different embodiments. It should be noted however, that the invention is defined by the independent claims. It should be noted that in the drawings, the same reference number is used throughout the drawings for defining the same feature. Consequently, if a reference number in a particular drawing is not explained or defined in the description relating to that particular drawing, any other part of the text which define that particular reference number may be used for explaining the feature in the context of the particular drawing. It should also be noted that all features in the drawings which are not described in conjunction with a particular drawing should be considered optional unless stated otherwise.

General Definition of Features Used in this Disclosure

An implant, or operable implant, is to be understood as any implant that could be operated for performing a function in relation to the body of the patient when implanted in the patient. A medical device adapted for implantation in a body is also to be understood as an implant. The patient may also be called user, person, or be referred to as a "body" or mammal.

In the drawings, the implant is generally illustrated as being placed in the abdominal area of the patient. It could, however, equally be placed in other parts of the patient's body.

To be operated includes the altering of the size and/or shape of a portion of the implant, delivering an active or inactive substance to the body of the patient, electrically stimulating a portion of the body of the patient, sensing a physical or functional parameter of the operable implant and/or a physiological or physical parameter of the patient, communicating with an external unit on the outside of the skin of the patient and receiving or transmitting energy at the operable implant, from an external unit. An operable implant could for example be a pacemaker unit, an implantable cardioverter defibrillator, an external heart compression device, an apparatus assisting the pump function of the heart, such as an LVAD device, an operable artificial heart valve, an implantable drug delivery device, such as an implantable device for delivering insulin or chemotherapeutic agents, a hydraulic, mechanic and/or electric constriction implant for constricting for example: an intestine for treating anal incontinence, an intestine for handling a stoma, the urethra for treating urinary incontinence, the bile duct for treating gall bladder malfunction, an oviduct for purpose of fertility control, the vas deference for the purpose of potency control, a blood vessel for purpose of increasing the blood volume in an erectile tissue, or for the purpose of constricting or restraining an aneurysm. An operable implant may further be an operable implant for treating obesity, such as an operable volume filling device for reducing the volume of the stomach, an operable gastric band for limiting the food passageway, or an operable implant for stretching the stomach wall for creating a feeling of satiety. The operable implant may be an operable device for treating GERD an operable cosmetic implant, such as an operable breast augmentation implant, or an implant for adjusting or replacing any bone part of the body. Furthermore, the implant could be replacing an organ or part of an organ, or the function thereof could be adjusted or replaced. Other examples of implants are implants treating impotence by implanted drug delivery, implants affecting blood flow, vascular treatment devices which may include blood clot removal, implants affecting fertility and/or infertility, or implants adapted to move fluid inside the body. The above listed examples of an operable implant are to be seen as examples not in any way limiting the possible application areas of the operable implant.

Body engaging portion (alternatively called an active portion) is to be understood as any part or portion of the operable implant that is directly or indirectly connected to the body of the patient for performing a function in relation to the body of the patient. The function could for example be pressing and/or pulling against a portion of the body of the patient, delivering a substance to the body of the patient, collecting a sample from the body of the patient, electrically stimulating a portion of the body of the patient and/or filling or emptying an implantable volume filling device with a hydraulic fluid. The body engaging portion may alternatively be referred to as the active unit or the active device of the implant.

A physical or functional parameter of the operable implant could for example be an electrical parameter, such as voltage, current or impedance, a parameter related to a fluid, such as pressure, flow rate, temperature, volume, weight, or viscosity. The parameter could be related to energy received at the operable implant, energy delivered to the body of the patient, fluid received at the operable implant, fluid delivered to the body of the patient, force exerted on the body of the patient or time elapsed since an action was performed in relation to the body of the patient. These physical or functional parameters can be measured or sensed by means of sensor(s), further described herein with reference to aspect 255SE. In such cases, the implant comprises the necessary sensor(s) needed to perform such sensing/measurement(s).

A physiological or physical parameter of the patient could for example be the blood pressure of the patient, a blood flow, a parameter related to blood saturation, a parameter related to an ischemia marker, a temperature of the body of the patient, a parameter related to muscle activity or a parameter related to the activity of the gastro-intestinal system. These physiological or physical parameters can be measured or sensed by means of sensor(s), further described herein with reference to aspect 255SE. In such cases, the implant comprises the necessary sensor(s) needed to perform such sensing/measurement(s).

The operation device in the operable implant may comprise an electrical motor for transforming electrical energy into mechanical work. The electrical motor could for example be an alternating current (AC) electrical motor, such as a three-phase electrical motor (which may be controlled using variable-frequency drive), a direct current (DC) electrical motor, a linear electrical motor, an AC or DC axial electrical motor, a piezo-electric motor, a bimetal motor, or a memory metal motor.

Alternatively, other types of motors may be used such as a hydraulic motor, a pneumatic motor, or a thermodynamic motor such as a Stirling engine.

As an alternative to a motor, an actuator may perform the required mechanical work within in the operable implant. Compared to a motor, an actuator generally only provides work between end points within a limited rotational range and does generally not provide full rotations to a drive shaft like a motor. The actuator may be electrically powered and controlled in same or similar ways as the electrical motor described in the above. An actuator may also be hydraulic, pneumatic, or thermodynamically based.

Generally, a medical system including an operable implant comprising an implantable body engaging portion and an implantable operation device, and components thereof, is described herein. The implantable operation device could be adapted to electrically, mechanically or hydraulically operate the body engaging portion and could be powered by means of wireless energy transfer from the outside of the body of the patient, or by means of an implantable battery adapted to store electrical energy in the body of the patient. The operation device may comprise an electrical motor for transferring electrical energy to mechanical work (force*distance) and the electrical motor may be connected to one or more gear systems for altering the velocity and/or force/torque and/or direction of the supplied force. The operable implant may additionally comprise a communications unit for communicating with portions of the operable implant, other operable implants and/or external units. The communication with the external unit could comprise control signals from the external unit for controlling the operable implant or could comprise feedback signals from the operable implant, which for example could be sensor parameters such as physiological or physical sensor parameters related to the status of the body of the patient, or physical or functional parameters related to status of the operable implant.

The implant may comprise a communication unit. The unit may alternatively be called the internal communication unit or the communication unit of the implant. Alternatively, the communication unit may be called a controller. The communication unit may comprise a collection of communication related sub-units such as a wired transceiver, a wireless transceiver, energy storage, an energy receiver, a computing unit, a memory, or a feedback unit. The sub-units of the communication unit may cooperate with each other or operate independently with different purposes. The sub-units of the internal communication unit may inherit the prefix "internal". This is to distinguish these sub-units from the sub-units of the external communication unit as similar sub-units may be present for both communication units. The sub-units of the external communication unit may similarly inherit the prefix "external".

A wireless transceiver may comprise both a wireless transmitter and a wireless receiver. The wireless transceiver may also comprise a first wireless transceiver and a second wireless transceiver. In this case, the wireless transceiver may be part of a first communication system (using the first wireless transceiver) and a second communication system (using the second wireless transceiver).

In some embodiments, two communication systems may be implemented using a single wireless transceiver in e.g. the implant and a single wireless transceiver in e.g. an external device (i.e. one antenna at the implant and one antenna at the external device), but where for example the network protocol used for data transmission from the external device to the implant is different from the network protocol used for data transmission from the implant to the external device, thus achieving two separate communication systems.

Alternatively, the wireless transceiver may be referred to as either a wireless transmitter or a wireless receiver as not all embodiments of secure wireless communication discussed herein require two-way communication capability of the wireless transceiver. The wireless transceiver may transmit or receive wireless communication via wireless connections. The wireless transceiver may connect to both the implant and to external devices. i.e. devices not implanted in the patient.

The wireless connections may be based on radio frequency identification (RFID), near field charge (NFC), Bluetooth, Bluetooth low energy (BLE), or wireless local area network (WLAN), or near-filed magnetic induction (NFMI). The wireless connections may further be based on mobile telecommunication regimes such as 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

A wired transceiver may comprise both a wired transmitter and a wired receiver. The wording wired transceiver aims to distinguish between it and the wireless transceiver. It may generally be considered a conductive transceiver. The wired transceiver may transmit or receive conductive communi-cation via conductive connections. Conductive connections may alternatively be referred to as electrical connections or as wired connections. The wording wired however, does not imply there needs to be a physical wire for conducting the communication. The body tissue of the patient may be considered as the wire. Conductive connection may use the body of the patient as a conductor. Conductive connections may still use ohmic conductors such as metals to at least some extent, and more specifically at the interface between the wired transceiver and the chosen conductor.

Communication, conductive or wireless may be understood as digital or analogue. In analogue communication, the message signal is in analogue form i.e., a continuous time signal. In digital communication, usually digital data i.e., discrete time signals containing information is transmitted.

Energy storage may refer to an apparatus or means for electrochemical storage of energy such as batteries. The energy storage may comprise primary batteries or secondary. i.e. rechargeable, batteries. Some types of rechargeable batteries that may be used include lithium-ion (Li-ion) batteries, nickel cadmium (Ni—Cd) batteries, or Ni-metal hydride (Ni-MH) batteries. A single battery cell may be used. Alternatively, several battery cells may be coupled in parallel or series to form the energy storage. Energy storage may have a voltage in the range from 0.5V to 12V and feature an energy storage capacity in the range of 10 to 5000 mAh.

An energy receiver may refer to an apparatus or means for receiving energy at the implant from external devices or transmitters of energy. The receiver may be adapted to receiver energy conductively, via an electric conductor, in which case the energy being transmitted and received may be in an electrical form, e.g. a current or a voltage. The receiver may be adapted to receive energy wirelessly, in which case the energy may be in an electromagnetic wave form, e.g. a radio wave or a light pulse. The energy receiver may be adapted to directly operate a function of the implant or replenish an energy level of the energy storage.

A sensation generator is a device or unit that generates a sensation. The sensation generated may be configured to be experienceable by the patient such that the patient may take actions to authenticate a device, connection, or communication. The sensation generator may be configured to generate a single sensation or a plurality of sensation components. The sensation or sensation components may comprise a vibration (e.g. a fixed frequency mechanical vibration), a sound (e.g. a superposition of fixed frequency mechanical vibrations), a photonic signal (e.g. a non-visible light pulse such as an infra-red pulse), a light signal (e.g. a visual light pulse), an electric signal (e.g. an electrical current pulse) or a heat signal (e.g. a thermal pulse). The sensations generated by the sensation generator may be configured to be experienceable by a sensory function or a sense of the patient from the list of tactile, pressure, pain, heat, cold, taste, smell, sight, and hearing. Sensations may be generated of varying power or force as to adapt to sensory variations in the patient. Power or force may be increased gradually until the patient is able to experience the sensation. Variations in power or force may be controlled via feedback. Sensation strength or force may be configured to stay within safety margins. The sensation generator may be connected to the implant. The sensation generator may be comprised within the implant or be a separate unit.

A motor, e.g. of the active device or unit of the implant, for controlling a physical function in the body of the patient may provide a secondary function as a sensation generator, generating a vibration or sound. Generation of vibrations or sounds of the motor may be achieved by operating the motor at specific frequencies. When functioning as to generate a sensation the motor may operate outside of its normal ranges for frequency controlling a physical function in the body. The power or force of the motor when operating to generate a sensation may also vary from its normal ranges for controlling a physical function in the body.

An external device is a device which is external to the patient in which the implant is implanted in. The external device may be also be enumerated (first, second, third, patient, health care provider, etc.) to separate different external devices from each other. Two or more external devices may be connected by means of a wired or wireless communication as described above, for example through IP (internet protocol), or a local area network (LAN). The wired or wireless communication may take place using a standard network protocol such as any suitable IP protocol (IPv4. IPv6) or Wireless Local Area Network (IEEE 802.11), Bluetooth, NFC. RFID, NFMI, etc. The wired or wireless communication may take place using a proprietary network protocol. Any external device may also be in communication with the implant using wired or wireless communication according to the above. Communication with implanted devices may be thus accomplished with a wired connection or with wireless radiofrequency (RF) telemetry. Other methods of wireless communication may be used to communicate with implants, including optical and ultrasound. Alternatively, the concept of intrabody communication may be used for wireless communication, which uses the conductive properties of the body to transmit signals. i.e. conductive (capacitive or galvanic) communication with the implant. Means for conductive communication between an external device and an implant may also be called "electrical connection" between an external device and an implant. The conductive communication may be achieved by placing a conductive member of the external device in contact with the skin of the patient. By doing this, the external device and/or the implant may assure that it is in direct electrical connection with the other device. The concept relies on using the inherent conductive or electrical properties of a human body. Signals may preferably be configured to affect the body or body functions minimally. For conductive communication this may mean using low currents. A current may flow from an external device to an implant or vice versa. Also, for conductive communication, each device may have a transceiver portion for transmitting or receiving the current. These may comprise amplifiers for amplifying at least the received current. The current may contain or carry a signal which may carry e.g. an authentication input, implant operation instructions, or information pertaining to the operation of the implant.

Alternatively, conductive communication may be referred to as electrical or ohmic or resistive communication.

The conductive member may be an integrated part of the external device (e.g. in the surface of a smartwatch that is intended to be in contact with the wrist of the person wearing it), or it may be a separate device which can be connected to the external device using a conductive interrace such as the charging port or the headphone port of a smartphone.

A conductive member may be considered any device or structure set up for data communication with the implant via electric conductive body tissue. The data communication to the implant may be achieved by e.g. current pulses transmitted from the conductive member through the body of the patient to be received by a receiver at the implant. Any suitable coding scheme known in the art may be employed.

The conductive member may comprise an energy source such as a battery or receive energy from e.g. a connected external device.

The term conductive interface is representing any suitable interface configured for data exchange between the conductive member and the external device. The conductive member may in an alternative configuration receive and transmit data to the external device through a radio interface, NFC, and the like.

An external device may act as a relay for communication between an implant and a remote device, such as e.g. second, third, or other external devices. Generally, the methods of relaying communication via an external device may be preferable for a large number of reasons. The transmission capabilities of the implant may be reduced, reducing its technical complexity, physical dimensions, and medical effects on the patient in which the implant is implanted. Communication may also be more efficient as direct communication, i.e. without a relaying device, with an implant from a remote device may require higher energy transmissions to account for different mediums and different rates of attenuation for different communication means. Remote communication with lower transmission energy may also increase the security of the communication as the spatial area or volume where the communication may be at all noticeable may be made smaller. Utilizing such a relay system further enables the use of different communication means for communication with the implant and communication with remote devices that are more optimized for their respective mediums.

An external device may be any device having processing power to perform the methods and functions needed to provide safe operation of the implant and provide the patient or other stakeholders (caregiver, spouse, employer etc.) with information and feedback from the implant. The external device may for example be a handset such as a smartphone, smartwatch, tablet etc. handled by the patient or other stakeholders. The external device may be a server or personal computer handled by the patient or other stakeholders. The external device may be cloud based or a virtual machine. In the drawings, the external device handled by the patient is often shown as a smart watch, or a device adapted to be worn by the patient at the wrist of the patient. This is merely by way of example and any other type of external device, depending on the context, is equally applicable.

Several external devices may exist such as a second external device, a third external device, or another external device. The above listed external devices may e.g. be available to and controllable by a patient, in which an implant is implanted, a caregiver of the patient, a healthcare professional of the patient, a trusted relative of the patient, an employer or professional superior of the patient, a supplier or producer of the implant or its related features. By controlling the external devices may provide options for e.g. controlling or safeguarding a function of the implant, monitoring the function of the implant, monitoring parameters of the patient, updating or amending software of the implant etc.

An external device under control by a supplier or producer of the implant may be connected to a database comprising data pertaining to control program updates and/ or instructions. Such database may be regularly updated to provide new or improved functionality of the implant, or to mitigate for previously undetected flaws of the implant. When an update of a control program of an implant is scheduled, the updated control program may be transmitted from the database in a push mode and optionally routed via one or more further external devices before received by the implant. In another embodiment, the update is received from the database by request from e.g. an external device under control by the patient having the implant implanted in his/her body, a pull mode.

The external device may require authentication to be operated in communication with other external devices or the implant. Passwords, multi-factor authentication, biometric identification (fingerprint, iris scanner, facial recognition, etc.) or any other way of authentication may be employed.

The external device may have a user interface (UI) for receiving input and displaying information/feedback from/to a user. The UI may be a graphical UI (GUI), a voice command interface, speaker, vibrators, lamps, etc.

The communication between external devices, or between an external device and the implant may be encrypted. Any suitable type of encryption may be employed such as symmetric or asymmetric encryption. The encryption may be a single key encryption or a multi-key encryption. In multi-key encryption, several keys are required to decrypt encrypted data. The several keys may be called first key, second key, third key, etc. or first part of a key, second part of the key, third part of the key, etc. The several keys are then combined in any suitable way (depending on the encryption method and use case) to derive a combined key which may be used for decryption. In some cases, deriving a combined key is intended to mean that each key is used one by one to decrypt data, and that the decrypted data is achieved when using the final key.

In other cases, the combination of the several key result in one "master key" which will decrypt the data. In other words, it is a form of secret sharing, where a secret is divided into parts, giving each participant (external device(s), internal device) its own unique part. To reconstruct the original message (decrypt), a minimum number of parts (keys) is required. In a threshold scheme this number is less than the total number of parts (e.g. the key at the implant and the key from one of the two external device are needed to decrypt the data). In other embodiments, all keys are needed to reconstruct the original secret, to achieve the combined key which may decrypt the data.

In should be noted that it is not necessary that the generator of a key for decryption is the unit that in the end sends the key to another unit to be used at that unit. In some cases, the generator of a key is merely a facilitator of encryption/decryption, and the working in behalf of another device/user.

A verification unit may comprise any suitable means for verifying or authenticating the use (i.e. user authentication) of a unit comprising or connected to the verification unit, e.g. the external device. For example, a verification unit may comprise or be connected to an interface (UI, GUI) for receiving authentication input from a user. The verification unit may comprise a communication interface for receiving authentication data from a device (separate from the external device) connected to the device comprising the verification unit. Authentication input/data may comprise a code, a key, biometric data based on any suitable techniques such as fingerprint, a palm vein structure, image recognition, face recognition, iris recognition, a retinal scan, a hand geometry, and genome comparison, etc. The verification/authentication may be provided using third party applications, installed at or in connection with the verification unit.

The verification unit may be used as one part of a two-part authentication procedure. The other part may e.g. comprise conductive communication authentication, sensation authentication, or parameter authentication.

The verification unit may comprise a card reader for reading a smart card. A smart card is a secure microcontroller that is typically used for generating, storing, and operating on cryptographic keys. Smart card authentication provides users with smart card devices for the purpose of authentication. Users connect their smart card to the verification unit. Software on the verification unit interacts with the keys material and other secrets stored on the smart card to authenticate the user. In order for the smart card to operate, a user may need to unlock it with a user-PIN. Smart cards are considered a very strong form of authentication because cryptographic keys and other secrets stored on the card are very well protected both physically and logically, and are therefore hard to steal.

The verification unit may comprise a personal e-ID that is comparable to, for example, passport and driving license. The e-ID system comprises is a security software installed at the verification unit, and a e-ID which is downloaded from a web site of a trusted provided or provided via a smart card from the trusted provider.

The verification unit may comprise software for SMS-based two-factor authentication. Any other two-factor authentication systems may be used. Two-factor authentication requires two things to get authorized: something you know (your password, code, etc.) and something you have (an additional security code from your mobile device (e.g. a SMS, or a e-ID) or a physical token such as a smart card).

Other types of verification/user authentication may be employed. For example, a verification unit which communicate with an external device using visible light instead of wired communication or wireless communication using radio. A light source of the verification unit may transmit (e.g. by flashing in different patterns) secret keys or similar to the external device which uses the received data to verify the user, decrypt data or by any other means perform authentication. Light is easier to block and hide from an eavesdropping adversary than radio waves, which thus provides an advantage in this context. In similar embodiments, electromagnetic radiation is used instead of visible light for transmitting verification data to the external device.

In some embodiments, the data transmitted between the implant and an external device may be encrypted and/or decrypted with public and/or private keys. In some examples, the communication unit or the implant may comprise a private key and a corresponding public key, and the external device may comprise a private and a corresponding public key. The communication unit and the external device may exchange public keys and the communication may thus be performed using public key encryption. The person skilled in the art may utilize any known method for exchanging the keys. The communication unit may encrypt data to be sent to the external device using a public key corresponding to the external device. The encrypted data may be transmitted over a wired, wireless, or electrical/conductive communication channel to the external device. The external device may receive the encrypted data and decode it using the private key comprised in the external device, the private key corresponding to the public key with which the data has been encrypted. The external device may transmit encrypted data to the communication unit of the implant. The external device may encrypt the data to be sent using a public key corresponding to the private key of the implant. The external device may transmit the encrypted data over a wired, wireless, or electrical/conductive connection directly or indirectly, to the communication unit of the implant. The communication unit may receive the data and decode it using the private key comprised in the implant or in the communication unit.

In an alternative to the public key encryption, the data to be sent between an implant and an external device or between an external device and the implant may be signed. Data transmitted from the transmitting one of the implant and the external device may be signed using the private key of transmitting one. The receiving one of external device or the implant may receive the message and verify the authenticity of the data using the public key corresponding to the private key used for the signing. In this way, the receiving one of external device or the implant may determine that the sender of the data was correct and not from another device or source.

Parameters relating to functionality of the implant may comprise for example a status indicator of the implant such as battery level, version of control program, properties of the implant, status of a motor of the implant, etc.

Data comprising operating instructions sent to the implant may comprise a new or updated control program, parameters relating to specific configurations of the implant, etc. Such data may for example comprise instructions how to operate the body engaging unit (active unit etc.) of the implant, switch body engaging unit in a multi functionality implant, instructions to collect patient data at the implant, instructions to transmit feedback from the implant to the external device, etc.

The expressions "confirming the electrical connection between an implant and an external device" or "authenticating a connection between an implant and an external device", or similar expressions, are intended to encompass methods and processes for ensuring or be reasonably sure that the connection has not been compromised. Due to weaknesses in the wireless communication protocols, it is a simple task for a device to 'listen' to the data and grab sensitive information, e.g. personal data regarding the patient sent from the implant, or even to try to compromise (hack) the implant by sending malicious commands or data to the implant. Encryption may not always be enough as a security measure (encryption schemes may be predictable), and other means of confirming or authenticating the external device being connected to the implant may be needed.

The expression "network protocol" is intended to encompass communication protocols used in computer networks, a communication protocol is a system of rules that allow two or more entities of a communications system to transmit information via any kind of variation of a physical quantity. The protocol defines the rules, syntax, semantics and synchronization of communication and possible error recovery methods. Protocols may be implemented by hardware, software, or a combination of both. Communication protocols have to be agreed upon by the parties involved. In this field, the term "standard" and "proprietary" is well defined. A communication protocol may be developed into a protocol standard by getting the approval of a standards organization. To get the approval the paper draft needs to enter and successfully complete the standardization process. When this is done, the network protocol can be referred to a "standard network protocol" or a "standard communication protocol". Standard protocols are agreed and accepted by whole industry. Standard protocols are not vendor specific. Standard protocols are often, as mentioned above, developed by collaborative effort of experts from different organizations.

Proprietary network protocols, on the other hand, are usually developed by a single company for the devices (or Operating System) which they manufacture. A proprietary network protocol is a communications protocol owned by a single organization or individual. Specifications for proprietary protocols may or may not be published, and implementations are not freely distributed. Consequently, any device may not communicate with another device using a proprietary network protocol, without having the license to use the proprietary network protocol, and knowledge of the specifications for proprietary protocol. Ownership by a single organization thus gives the owner the ability to place restrictions on the use of the protocol and to change the protocol unilaterally.

A control program is intended to define any software used for controlling the implant. Such software may comprise an operating system of the implant, of parts of an operating system or an application running on the implant such as software controlling a specific functionality of the implant (e.g. the active unit of the implant, feedback functionality of the implant, a transceiver of the implant, encoding/decoding functionality of the implant, etc.). The control program may thus control the medical function of the implant, for example how much insulin the implant should deliver, etc. Alternatively, or additionally, the control program may control internal hardware functionality of the implant such as energy usage, transceiver functionality, etc.

The systems and methods disclosed hereinabove may be implemented as software, firmware, hardware, or a combination thereof. In a hardware implementation, the division of tasks between functional units referred to in the above description does not necessarily correspond to the division into physical units; to the contrary, one physical component may have multiple functionalities, and one task may be carried out by several physical components in cooperation. Certain components or all components may be implemented as software executed by a digital signal processor or microprocessor or be implemented as hardware or as an application-specific integrated circuit. Such software may be distributed on computer readable media, which may comprise computer storage media (or non-transitory media) and communication media (or transitory media). As is well known to a person skilled in the art, the term computer storage media includes both volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information, and which can be accessed by a computer. Further, it is well known to the skilled person that communication media typically embodies computer readable instructions, data structures, program modules or other data in a modulated data signal such as a carrier wave or other transport mechanism and includes any information delivery media.

The system and methods disclosed herein will now be generally exemplified using patients with different implants as use cases. This is just by way of example to aid the understanding of the disclosure to the reader and should not be seen as limiting the scope of the disclosure in any way.

In the first use case, the system and methods are exemplified using patients with implanted insulin pumps. An implanted insulin pump is a pump device designed to be implanted in the body and deliver insulin, preferably into the peritoneal cavity, of patients suffering from diabetes. The peritoneal cavity holds a vast amount of blood vessels that are routed straight to the liver, which makes injection here a fast and effective way of delivering insulin. The insulin comprised in the pump is delivered through a catheter, and a medical professional will have to refill the pump through a refill port when the insulin has run out. The implanted insulin pump usually comes with a handheld controller that can be controlled by the patient or doctor and communicates wirelessly with the pump. With the controller, the patient can set basal patterns or deliver boluses. Some pumps are fully automated and delivers the right amount of insulin based on measured sugar levels, thus requiring little controller input from the user. Some pumps can comprise sensors that measure physiological parameters, such as temperature, pulse, glucose levels etc., The measured data can then be securely communicated, as described herein with reference to aspects 1-14, from the insulin pump to the patient or physician (healthcare provider) in order to adjust the delivery settings of the pump. The delivery setting can then be securely communicated from an external device to the insulin pump, as described herein with reference to aspects 1-14. The patient could for example provide authentication by speaking such that the implanted pump, provided with necessary means for sensing audio, registers the voice and thereby provides the measured data as for example numeral values displayed on the controller. By demanding such authorization, it is ensured that no unauthorized persons gain access to the patient's medical status or that the adjustment of the delivery settings is done by an unauthorized device.

Should the patient visit a hospital to get his/her pump refilled, a similar authorization process would take place between the implant and the doctor. The manufacturer of the pump can provide updates to the software in the pump in order to optimize its performance. Such updates must also be approved and authorized by the doctor and/or patient. This kind of authorization chain ensures that no unauthorized persons, such as passer-by's or unauthorized personnel at a hospital, can gain access to the patient's medical data or alter the settings on the device.

In the second use case, the system and methods are exemplified using patients with implanted devices for treating obesity. The purpose of most implanted device for treating obesity is to control the patient's appetite. The implant, such as the one described in WO2009/096859 (the content of which is hereby incorporated by reference), can comprise a stretching device which is inserted in the stomach such that it is surrounded by a portion of the stomach wall. When enlarging the device, its circumference is increased, thereby stretching the surrounding stomach wall. Therefore, by expanding and/or constricting the stretching device, the receptors in the stomach can be manipulated to indicate the feeling of a full and/or empty stomach. This creates or impacts the feeling of satiety to the patient. The expansion and contraction of the stretching device is controlled by a control unit which can be controlled either automatically or directly by the patient. The patient could for example have a switch placed subcutaneously, which he or she can control from the outside of his or her body by applying pressure. When eating, the patient can press the switch, thereby controlling the size of the stretching device, and indirectly the feeling of satiety. The constriction and/or expansion of the stretching device can be performed by for example hydraulic, mechanical, or electrical means. Some implants for affecting the feeling of satiety can have stretching device that comprise multiple parts, mechanical or hydraulic. The different parts engage and stretch different parts of the stomach wall. In these implants, the different parts are adapted to be stretched independently from each other with regards to the force used for stretching the wall, as well as the time period during which the stretching occurs and the time at which the stretching occurs. The patient, or caregiver, could also wirelessly control the stretching of the device from outside the body by utilizing a wireless remote control, such as a mobile smart phone, that communicates with the implant. In some cases, the implant also comprises a sensor which senses physical parameters related to the patient, such as body temperature, blood pressure or blood flow. It is especially useful to measure parameters relating to the patient's food intake. The sensor could for example be adapted to sense an esophagus movement, muscle activity or stomach pressure. The control device, in communication with the sensor, can then control the stretching of the device based on the sensed parameters. In cases where the sensor is placed in the esophagus, parameters relating to for example the movement, bending, motility, stretching or pressure of the esophagus can be sensed. Placing a sensor in or in relation to the esophagus is especially advantageous since the movement pattern of the esophagus directly relates to the patient's food intake. Such sensor placed in the esophagus could for example be a strain gauge or any other sensor adapted to sense mechanical strain. When a patient having an implant as described above, or in WO2009/096859, wants to eat, he or she can activate the implant either by pressing the switch or, wirelessly through a mobile phone with an app connected to the implant. Depending on the size of the meal, number of calories, feeling of hunger or other parameter relating to the food intake, the patient can adapt the stretching by using different settings on the switch or app. The wireless communication between the implant and the app can be securely executed according to the aspects 1-14 described herein. The communication between the implant and the app does not always have to be encrypted, and technologies such as NFC can be utilized for less sensitive data. The patient could for example, prior to eating, provide information in the app that will control the stretching of the implant. Such information could for example be feeling of hunger, time since last meal or parameters relating to the food, such as estimated number of calories or food weight. The patient could also take a picture of the food, which the app can analyze. By analyzing the photo, the app can estimate parameters such as calories and then adjust the implant properly. In order to provide the optimal obesity treatment, the control of the implant. i.e. the app in this case, must be calibrated. This calibration could for example entail a text message being sent to the patient post eating, in which the patient is asked to rate his feeling of satiety. This text message could come automatically after each meal to continuously calibrate the implant. If the patient's answer does not correspond to the level of stretching of the implant, the stretching must be adjusted accordingly. Should the patient for example not experience a feeling of satiety after eating a big meal, the app must send instructions to the implant to increase the stretching. In the cases where multiple different stretching parts are utilized, the adjusting can sometimes be done by altering which part(s) is being used. This could be done completely automatically without requiring any input from the user. It is important not only to protect the data being sent between the app and implant, but also to ensure that the information from the app is communicated to the right implant. Otherwise, someone could accidentally send instructions to another patient's implant, thereby inadvertently controlling their device. The calibration of the implant would not work either if the app accidently receives information from the wrong implant. To ensure that this does not happen, the app and implant can be synced. This synchronization could for example involve a sensor in the esophagus which measures the esophagus movement patterns. The app and implant are synched only if the measured movement pattern of the esophagus corresponds to the entered food data in the app. Another way to synchronize the implant with the app is to incorporate a gyroscope in the implant. The implant's gyroscope can then be controlled against the gyroscope in the patient's mobile phone. This of course requires that the patient has the mobile phone on him. Both of these synchronization methods ensure that no passer-by with an implant, accidentally or intentionally receives or sends instructions or information to another person's implant. The app on the phone could also have security measures in order to ensure that only authorized users control the app and implant. This authorization can be performed by for example voice or face recognition, allowing only the right user to enter data in the app. In cases where the implant comprises means for detecting sound, voice recognition could also be utilized for synchronizing the mobile phone with the implant.

After the synchronization, and after the information from the implant sensor (i.e. the esophagus movement pattern, abdominal movement or any other sensed physical parameter) has been communicated to the app, this information can be sent to a doctor and/or manufacturer for evaluation. This information is encrypted and communicated securely as described herein in aspects 1-14. This information can comprise not only the sensed implant parameters, but also added app information input by the patient. Such information could be anything from pictures of food he has eaten, weight or satiety status. All information can be utilized by the doctor and/or manufacturer to improve and calibrate the implant's behavior. Should the doctor or manufacturer want to update the settings or software of the implant, this is communicated securely, by means of aspects 1-14 as described herein, back to the app on the patient's mobile phone. Should the patient for example experience a sense of satiety despite having a low food intake, he or she enters this in the app and/or responds to the text message. This information is then communicated wirelessly to the doctor or medical professional, who in turn can evaluate this information and decide whether or not the implant must be adjusted. It is also possible to have a feature in the app in which a picture informs the user how much he or she should eat to feel satiety. The picture could instruct the user by showing which volume, weight and/or calorie amount the food should have in order to be adequate. How much food, measured in calories or volume, a patient should intake can be decided by the doctor, who then sends settings and/or instructions securely to the patient's app and/or device. The doctor and/or manufacturer could update the software on the app and send these updates directly to the app without requiring any action from the patient. The patient can be informed of the update by an email, text message, app notification or any other notification method. Anytime a doctor or employee at the manufacturing company wants to update or alter the settings of the implant he or she must be verified. This could for example be done by requiring electronic identification. To further ensure that the information being sent between the implant, the app, and the doctor and/or manufacturer's database is protected, blockchains can be utilized as defined below. It is also possible to allow another person, such as a family member, friend, or physician, to gain access to implant information or adjust the settings of the implant through the app on their mobile phone. This could for example be convenient if the patient himself is ill or in any other acute situations where the patient is not suited to manage the app himself. The authentication could then entail a verification code provided by the patient's app which the other user is required to enter on his app.

In the third use case, the system and methods are exemplified using patients with implanted devices for urinary control. Involuntary urinary retention is a condition in which the patient cannot empty the bladder completely. Besides the possibility of the condition being very painful if acute, it is also, among other, associated with urinary infections and renal damages. Patients suffering from this condition can benefit from an implant, such as the one described in WO2009048373, the content of which is hereby incorporated by reference. Such implant has a powered member which exerts a force on the urinary bladder which aids in the discharge of urine. The powered member can be controlled by a control device, such as a switch implanted subcutaneously at a, for the patient, convenient and easy to access location. When engaging the switch, a force is applied to the powered member which acts as a bladder press and presses against the outside of the urinary bladder and thereby releases urine. The implant can also comprise an artificial urinary sphincter, which acts as a urine stopper and is also controlled by the control device. When the control device activates the urine stopper, the artificial sphincter retracts which stops urine from exiting the urine bladder and entering the urethra. If the control device is a wireless device, such as a mobile phone, the implant. i.e. the bladder press and urine stopper, communicates securely and wirelessly with the mobile phone according to the aspects 1-14 described herein. The implant could also comprise sensors for sensing different physical parameters such as, pressure. This is especially essential since many patients with urinary dysfunctions cannot feel when the bladder needs to be emptied. The pressure sensor(s) can then indicate that the bladder is full to the control device. The patient could for example receive a text message or a notification in an app connected to the implant telling him that the bladder is full. The patient can then control the bladder pressure via his app at a convenient time as a regular toilet visit. It is also possible that the patient has an ultrasound sensor implanted for measuring the level of urine in the bladder. If the sensor indicates that there is little to no urine in the bladder, it can communicate this to the patient via the app, thereby letting him or her know that no toilet visit is necessary. The ultrasound sensor could also measure other features, such as the quality of the content in the bladder. Should the ultrasound sensor for example sense blood in the bladder, the patient can get notified, as this can be a sign of infection or kidney disease. Since the bladder pressure is attached to a support structure in the body, such as the pelvic bone, for exerting the force of the bladder pressure against the structure, the implant could also comprise sensors for sensing the mechanical strain. Should the patient experience that the bladder isn't fully emptied despite activation via the app, he or she can indicate this in the app which communicates this and adjusts the strain by tightening the attachment to the support structure. It is also possible that the sensors, without input from the patient, senses that the bladder is full (i.e. is expanded thereby influencing the strain) and alerts the patient that he or she needs to empty the bladder. The urine stopper. i.e. the artificial urinary sphincter, can be controlled in a similar manner. If the sensor(s) connected to the urine stopper senses that the patient is lying down (gyroscope sensor) it can release the pressure exerted on the urethra. The patient can indicate in the app that he or she is ready to sleep, thereby release the pressure over night. In the morning, he or she can increase the pressure again by informing the app that they intend to get up and start the day. After the patient has emptied his or her bladder, the pressure sensed by the sphincter's sensors will automatically go down. Should the patient however engage in physical activities, he or she can actively increase the pressure of the stopper by using the settings in the app. The patient can calibrate the implants by giving feedback in the app. If a certain bladder pressure setting does not fully empty the bladder, the strain in the attachment portion might have to be adjusted. Or if the patient indicates on a rating scale that he will engage in very heavy physical activity, and the urine stopper doesn't retract enough to keep the urine from leaking into the urethra, the patient can indicate this in the app. This will require the stopper to exert more force next time the patient engages in an equally rated activity. The muscles of the urinary bladder can be stimulated to contract the bladder and thereby prevent unwanted leakage. If the implant is further equipped with a stimulating device for electrically stimulating the muscles, the patient can indicate that he wishes to stimulate the muscles occasionally.

In the fourth use case, the system and methods are exemplified using patients with implanted devices for intestinal disorders. In a similar manner as the bladder presser, patients suffering from intestinal disorders can benefit from an implant that can empty a reservoir on demand. Patients suffering from intestinal disorders can have trouble to control the flow of intestinal contents, and especially to control when feces are exiting the patient's body. An implant as described in WO2011128124, the content of which is hereby incorporated by reference, is suitable for treating such patients. The implant acts on a reservoir formed from surgically modified intestine and comprises an implantable artificial flow control device. The flow control device can be a pump which reduces the reservoir's volume, thereby emptying it. Patient's with this type of implant can control the pump through an app on their mobile phone. Such wireless communication between the pump and app is securely performed by means of aspects 1-14 as described herein. The implant can further comprise sensors that can indicate parameters such as reservoir volume or pressure. When the sensors indicate that the reservoir is full, the implant communicates this to the patient's mobile phone via some sort of notification. The patient can then activate the pump as soon as convenient.

In the fifth use case, the system and methods are exemplified using patients with implanted devices for treating aneurysms. An aneurysm is a localized blood-filled dilation of a blood vessel. They most commonly occur in the arteries at the base of the brain, called Circle of Willis, and in the aorta. Aneurysms grow larger with time, therefore they exercise a great threat if left untreated. An implant for treating aneurysms is described in WO2008000574 and WO2009048378, the content of which is hereby incorporated by reference. These implants provide a member placed around the vessel on which a force can be applied. The implants can communicate wirelessly with an external unit, such as a mobile phone. Sensors can be present in the implant for sensing parameters relating to pressure, blood flow, and strain, among other things. Should the sensors detect an increase in pressure, if the aneurysm is about to burst, or if the patient is exercising, it notifies the mobile phone and thereby the patient. The patient could also prior to engaging in physical activities, actively increase the pressure the implant exerts on the vessel to prevent it from bursting. Should the sensors notice a too quick expansion, which might indicate an acute burst, the implant could directly alert a doctor or medical emergency team. It could also trigger an alarm in the patient's mobile phone to alert the patient. It is possible to continuously measure parameters such as blood pressure, and send this information to an app on the patient's mobile phone. In this way, the patient can get continuous information on his or her aneurysm status.

In the sixth use case, the system and methods are exemplified using patients with implanted devices for treating heart arrhythmia. Heart arrhythmia are conditions relating to the electrical conduction system of the heart. In a healthy heart, the sinoatrial node located in the right atrium wall spontaneously sends electrical impulses causing the heart to contract regularly. In patient's suffering from arrhythmia however, a damaged sinoatrial node, or a blockage in the electrical pathways of the heart, causes too fast, too slow, or irregular heart contractions. An artificial pacemaker is an implantable medical device designed to monitor the heart and alleviate such conditions. The pacemaker is implanted just below the collarbone and provides electrical impulses to the heart through electrodes inserted through a large vein leading directly to the heart. Depending on the patient's specific condition, the artificial pacemaker may have electrodes placed in both the ventricle and atrium walls. The pacemaker continuously monitors the heart, and in many cases, it is programmed to only electrically stimulate the heart when the natural heart rate falls below a set lower limit. Since modern pacemakers are able to communicate wirelessly, remote physician follow-ups and remote continuous monitoring of the patient's heart is enabled, resulting in less travels back and forth to the hospital. If the physician recognizes that the pacemaker is malfunctioning somehow, the software can be remotely updated or altered. This does however make the pacemakers vulnerable to unauthorized people also gaining access to its data and/or altering its settings such as reducing battery life or increasing impulse activity. Therefore, it is important that the monitored data from the pacemaker is securely communicated as described herein with reference to aspects 1-14 to the physician. The data could for example be transferred to a secure server to which a physician can only gain access by identifying himself via an electronic identification card. Should he then want to alter the settings of the pacemaker, an update is sent back to the implant, likewise securely communicated as described herein with reference to aspects 1-14.

If a patient with an implanted pacemaker experiences any abnormal behavior related to the heart, such as chest pain, sudden drop/increase of heart rate or rapid or irregular pulse, he could authenticate himself to the pacemaker by any means describe herein with reference to aspects 1-14. An example of this could be utilizing face recognition on a smart phone. The physician in charge could then be contacted and gain access to the pacemakers monitored activity by for example authenticating himself using electronic identification as described above. Should the settings on the pacemaker need to be altered or the software updated, the physician can communicate this update and the authentication process might have to be repeated at both the physician's and patient's end. Some less sensitive data, such as reading the battery status of the implant, does not always have to be encrypted, and could be done by the patient at home by using methods such as NFC.

Of course, the reasoning above equally applies for patients with implantable cardio-defibrillators.

More summarily, the implant may e.g. comprise, be, or act as at least one of:

a pacemaker unit or implantable cardioverter defibrillators.

an external heart compression device.

an apparatus assisting the pump function of a heart of the patient.

an operable artificial heart valve.

an implantable drug delivery device.

a hydraulic, mechanic, and/or electric constriction implant.

an operable volume filling device.

an operable gastric band, an operable implant for stretching the stomach wall of the patient, an operable cosmetic implant, an implant for adjusting or replacing any bone part of a body of the patient, an implant controlling the emptying of a urinary bladder, an implant hindering urinary leakage, an implant hindering anal incontinence, an implant controlling the emptying of fecal matter, an implant monitoring an aneurysm, an implant lubricating a joint, an implant with a reservoir for holding bodily fluids an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms, an implant treating osteoarthritis, an implant performing a test of parameters inside the body, an implant controlling specific treatment parameters from inside the body, an implant controlling bodily parameters from inside the body, an implant controlling the blood pressure, an implant controlling a drug treatment parameter, an implant controlling a parameter in the blood, an active electrically controlled implant devoid of an electrical heart stimulation system, an active electrically controlled non-heart stimulation implant, an implant adapted for electrical stimulation of muscles, a non-nerve stimulation system, an active non-stimulation implant, an implant for high current electrical stimulation defined as current above 1 mA or current above 5 mA, 10 mA, or 20 mA, an implant replacing an organ of the patient or part of an organ of the patient or the function thereof, a vascular treatment device, and an implant adapted to move fluid inside the body of the patient.

The implant may comprise an internal control unit adapted to be involved in at least a part of the actions performed by the implant.

All aspects or part of aspects in the different aspects herein could be combined with any and/or all other aspects or parts thereof in any order, thus comprising; aspects or parts thereof in the same aspect in any order or combined with any and/or all aspects or parts thereof in any different aspect in any order. The connection herein between the aspects and any of its aspects or parts thereof are just examples and they are intended to be combined with each other in any combination or order. The aspects or parts thereof may therefore be connected to each other in any order of connection between the aspects or parts thereof.

Thus, all the different aspects or parts thereof could be combined with each other in any combination. Any and/or all aspects or parts thereof in one aspect could be combined with any and/or all aspects or parts thereof in any and/or all other aspects, aspect(s) or parts thereof, described elsewhere in any order or combination.

Aspect 244SE Implantable Reset Switch—Implant Comprising a Reset Function—Embodiments of the Aspect 244SE of the Disclosure In aspect 244SE, an implantable reset function and methods for controlling such implantable reset functions are provided. FIGS. 1-7 show embodiments of this aspect. Generally, the embodiments of the aspect 244SE provide a secure way of controlling the implant, updating the control program of the implant, and managing the control program of the implant.

A first embodiment of the aspect 244SE will now be described with reference to FIGS. 1a-c. FIG. 1a shows a patient with an implant 100. The implant 100 is in FIG. 1 placed in the abdominal area of the patient but could equally be placed in other parts of the body. The implant 100 comprises an active unit (further described in other sections of the description) 101 which is directly or indirectly connected to the body of the patient for performing a function in relation to the body of the patient. This function could for example be expanding and/or retracting a blood vessel, contracting muscles such as the heart, or in any other way perform a physical influence on the body. The active unit is connected to a communication unit 102 via an electrical connection C2. The communication unit 102 (further described with reference to FIG. 1B) is configured to communicate with an external device 200 (further described with reference to FIG. 1c). The communication unit 102 can communicate wirelessly with the external device 200 through a wireless connection W1, and/or through an electrical connection C1.

Referring now to FIG. 1B, the communication unit 102 will be describe in more detail. The communication unit 102 comprises an internal computing unit 106 configured to control the function performed by the implant 100. The computing unit 106 comprises an internal memory 107 configured to store programs thereon. The internal memory 107 comprises a first control program 110 which can control the function of the implant. The first control program may be seen as a program with minimum functionality to be run at the implant only during updating of the second control program. When the implant is running with the first control program, the implant may be seen as running in safe mode, with reduced functionality. For example, the first control program may result in that no sensor data is stored in the implant while being run, or that no feedback is transmitted from the implant while the first control program is running. By having a low complexity first control program, memory at the implant is saved, and the risk of failure of the implant during updating of the second control program is reduced.

The second control program is the program controlling the implant in normal circumstances, providing the implant with full functionality and features.

The memory 107 can further comprise a second, updatable, control program 112. The term updatable is to be interpreted as the program being configured to receive incremental or iterative updates to its code or be replaced by a new version of the code. Updates may provide new and/or improved functionality to the implant as well as fixing previous deficiencies in the code. The computing unit 106 can receive updates to the second control program 112 via the communication unit 102. The updates can be received wirelessly W1 or via the electrical connection C1. As shown in FIG. 1B, the internal memory 107 of the implant 100 can possibly store a third program 114. The third program 114 can control the function of the implant 100 and the computing unit 106 updates the second program 112 to the third program 114. The third program 114 can be utilized when rebooting an original state of the second program 112. The third program 114 may thus be seen as providing a factory reset of the implant 100, e.g. restore it back to factory settings. The third program 114 may thus be included in the implant 100 in a secure part of the memory 107 to be used for resetting the software (second control program 112) found in the implant 100 to original manufacturer settings.

A reset function 116 is connected to or part of the internal computing unit 106 or transmitted to said internal computing unit. The reset function is configured to make the internal computing unit 106 switch from running the second control program 112 to the first control program 110. The reset function 116 could be configured to make the internal computing unit 106 delete the second control program 112 from the memory 107. The reset function 116 can be operated by palpating or pushing/put pressure on the skin of the patient. This could be performed by having a button on the implant. Temperature sensors and/or pressure sensors can be utilized for sensing the palpating. The reset function 116 could also be operated by penetrating the skin of the patient. It is further plausible that the reset function 116 can be operated by magnetic means. This could be performed by utilizing a magnetic sensor and applying a magnetic force from outside the body. The reset function 116 could be configured such that it only responds to magnetic forces applied for a duration of time exceeding a limit, such as 2 seconds. The time limit could equally plausible be 5 or 10 seconds, or longer. In these cases, the implant could comprise a timer. The reset function 116 may thus include or be connected to a sensor for sensing such magnetic force.

The communication unit 102 can further comprise an internal wireless transceiver 108. The transceiver 108 communicates wirelessly with the external device 200 through the wireless connection W1. The communication unit 102 can further be electrically connected C1 to the external device 200 and communicate by using the patient's body as a conductor.

The confirmation/authentication of the electrical connection can be performed as described herein under the fifth, thirteenth or fifteenth aspect. In these cases, the implant and/or external device(s) comprises the necessary features and functionality (described in the respective sections of this document) for performing such confirmation/authentication. By authenticating according to these aspects, security of the authentication may be increased as it may require a malicious third party to know or gain access to either the transient physiological parameter of the patient or detect randomized sensations generated at or within the patient.

In FIGS. 1a-c the patient is a human, but other mammals are equally plausible. It is also plausible that the communication is performed by inductive means. It is also plausible that the communication is direct.

The communication unit 102 of the implant 100 according to FIG. 1B further comprises a feedback unit 149. The feedback unit 149 provides feedback related to the switching from the second control program 112 to the first control program 110. The feedback could for example represent the information on when the update of the software. i.e. the second control program 112, has started, and when the update has finished. This feedback can be visually communicated to the patient, via for example a display on the external device 200. This display could be located on a watch, or a phone, or any other external device 200 coupled to the communication unit 102. Preferably, the feedback unit 149 provides this feedback signal wirelessly W1 to the external device 200. Potentially, the words "Update started", or "Update finished", could be displayed to the patient, or similar terms with the same meaning. Another option could be to display different colors, where green for example could mean that the update has finished, and red or yellow that the update is ongoing. Obviously, any color is equally plausible, and the user could choose these depending on personal preference. Another possibility would be to flash a light on the external device 200. In this case the external device 200 comprises the light emitting device(s) needed. Such light could for example be a LED. Different colors could, again, represent the status of the program update. One way of representing that the update is ongoing and not yet finished could be to flash the light. i.e. turning the light on and off. Once the light stops flashing, the patient would be aware of that the update is finished. The feedback could also be audible, and provided by the implant 100 directly, or by the external device 200. In such cases, the implant 100 and external device 200 comprises means for providing audio. The feedback could also be tactile. In such case, either the implant 100 or external device comprises means for providing a tactile sensation, such as a vibration.

As seen in FIG. 1B, the communication unit 102 can further comprise a first power supply 10*a*. The first power supply 10*a* runs the first control program 110. The communication unit 102 further comprises a second power supply 10*b* which runs the second control program 112. This may further increase security during update, since the first control program has its own separate energy supply. The first power supply 10*a* can comprise a first energy storage 104*a* and/or a first energy receiver 105*a*. The second power supply 10*b* can comprise a second energy storage 104*b* and/or a second energy receiver 105*b*. The energy can be received wirelessly by inductive or conductive means. An external energy source can for example transfer an amount of wireless energy to the energy receiver 105*a*. 105*b* inside the patient's body by utilizing an external coil which induces a voltage in an internal coil (not shown in figures). It is plausible that the first energy receiver 105*a* receives energy via a RFID pulse. The feedback unit 149 can the provide feedback pertaining to the amount of energy received via the RFID pulse. The amount of RFID pulse energy that is being received can be adjusted based on the feedback, such that the pulse frequency is successively raised until a satisfying level is reached.

The external device is represented in FIG. 1c. In the first embodiment, the external device 200 is placed around the patient's arm. It is equally plausible that the external device is placed anywhere on the patient's body, preferably on a convenient and comfortable place. The external device 200 could be a wristband, and/or have the shape of a watch. It is also plausible that the external device is a mobile phone or other device not attached directly to the patient. The external device as shown in FIG. 1c comprises a wired transceiver 203, and an energy storage 204. It also comprises a wireless transceiver 208 and an energy transmitter 205. It further comprises a computing unit 206 and a memory 207. The feedback unit 210 in the external device 200 is configured to provide feedback related to the computing unit 206. The feedback provided by the feedback unit 210 could be visual. The external device 200 could have a display showing such visual feedback to the patient. It is equally plausible that the feedback is audible, and that the external device 200 comprises means for providing audio. The feedback given by the feedback unit 210 could also be tactile, such as vibrating. The feedback could also be provided in the form of a wireless signal W1.

Figures 2A, 2B:
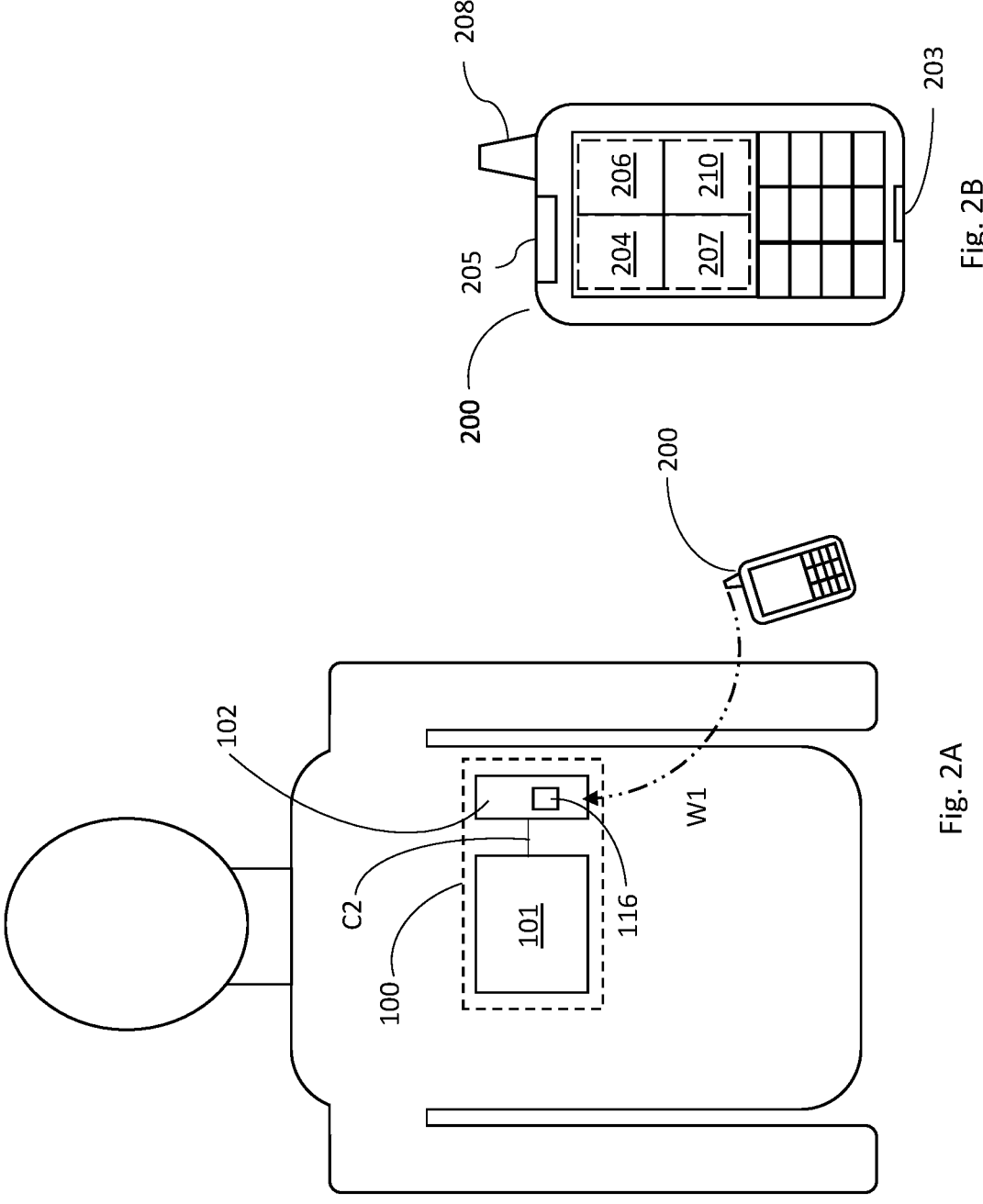
FIG. 2A illustrates a system according to the aspect 244SE, comprising an implant and an external device, further illustrated in 2B.

FIG. 2A shows another embodiment of the aspect 244SE in which a patient has an implant 100 and an external device 200 in the form of a mobile phone. The external device 200 communicates wirelessly W1 with the internal communication unit 102. The external device 200 is shown in FIG. 2B. In FIG. 2A, the external device 200 is displayed as a mobile phone, however, it is equally plausible that the external device 200 is a watch, necklace, or any other wearable unit. Preferably, the external device 200 is at least one of small, portable, easy to access, inconspicuous and/or easy to disguise as part of a patient's daily look.

FIG. 2B shows the external device 200 in the form of a mobile phone. The external device 200 comprises all of the features as described earlier with reference to FIG. 1c.

Such an implant 100 as described in this aspect 244SE, with, or alternatively in electrical or wireless connection with, the reset function 116 further increases the security of the communication with and the operation of the implant 100 as the reset function 116 may be under the direct control of the patient in which the implant is implanted. In a case where the reset function is implanted or comprised within an implanted implant 100, extra security is granted as an effect of the reset function location being non-obvious to a malicious third party aiming to access or affect the implant 100.

A method for controlling an implantable reset function according to the aspect 244SE will now be described with reference to FIGS. 3-7. It is to be understood that the implant referred to in FIGS. 3-7 may comprise all required features described earlier with reference to FIGS. 1-2.

Figure 3:
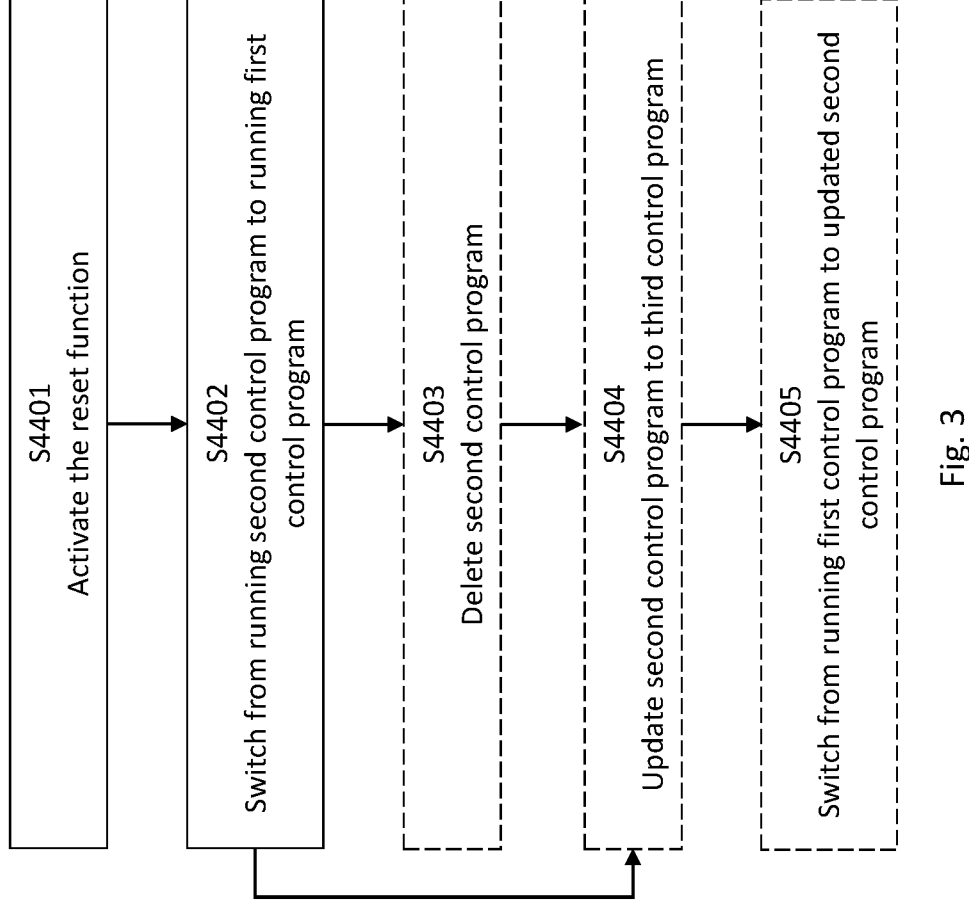
FIGS. 3-7 illustrate flowcharts of methods according to embodiments of the second part of the aspect 244SE.
Figure 4:
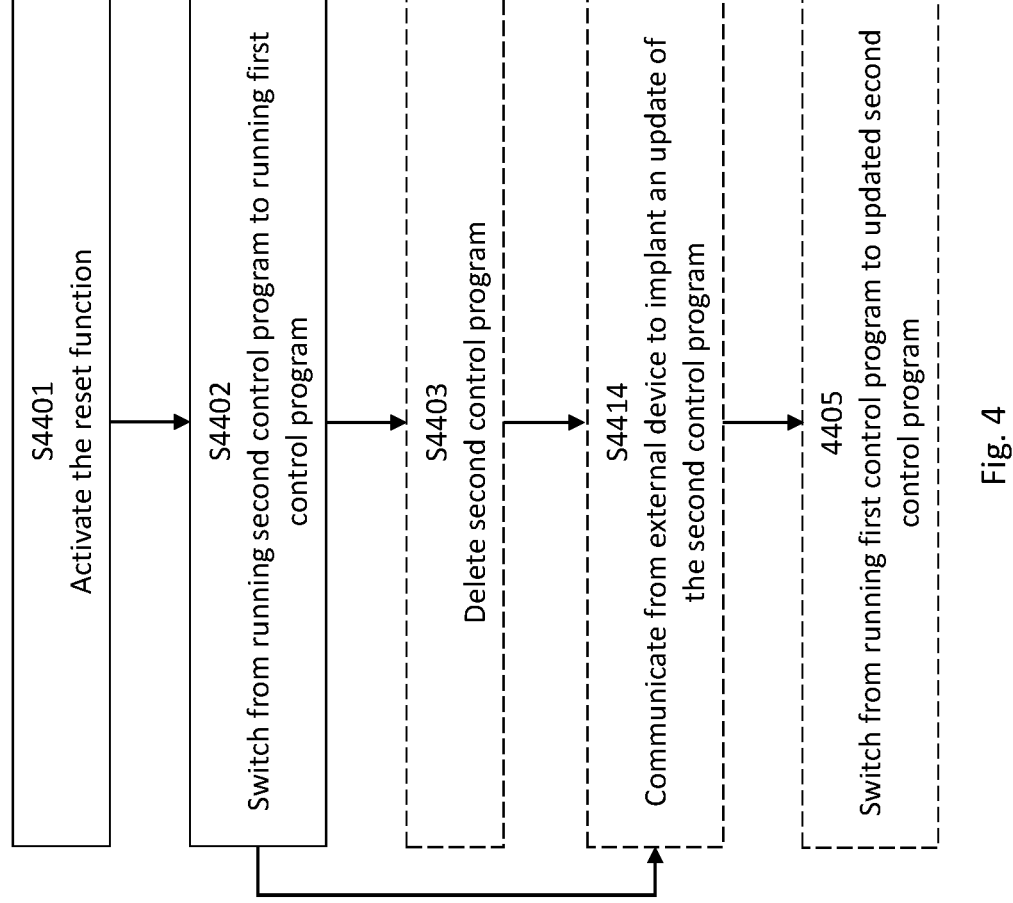
Figure 5:
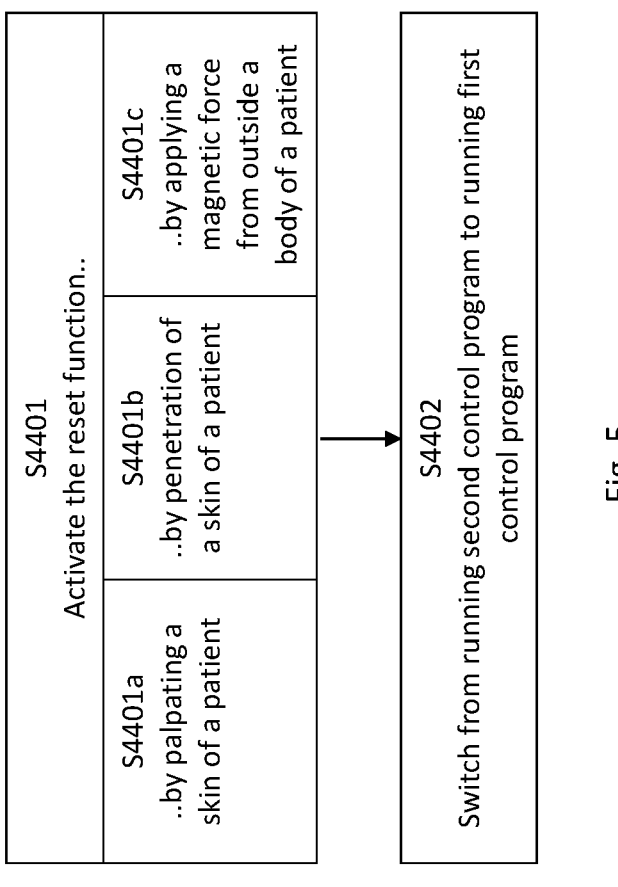
Figures 6, 7:
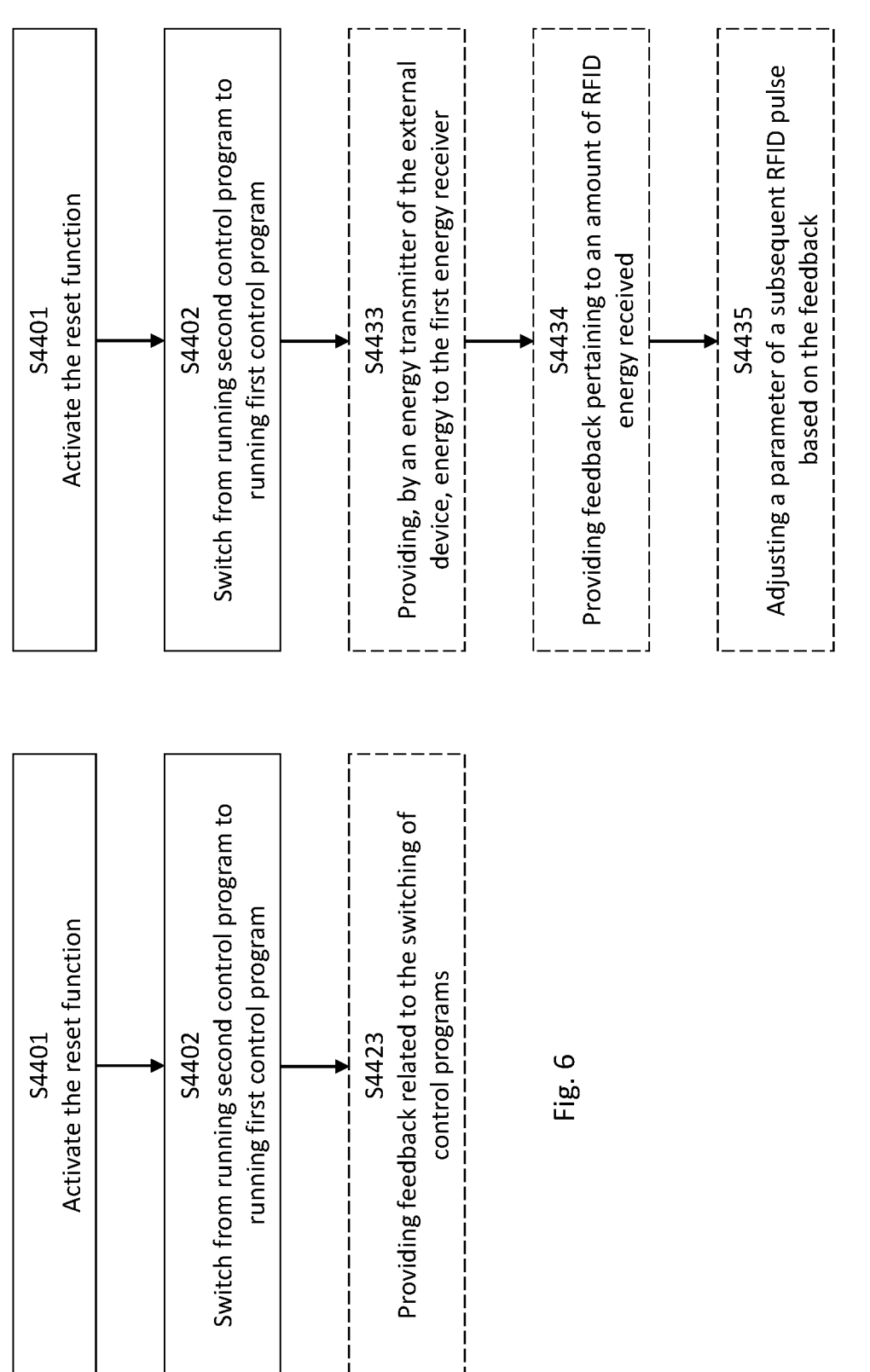
Figures 8A, 8B, 8C:
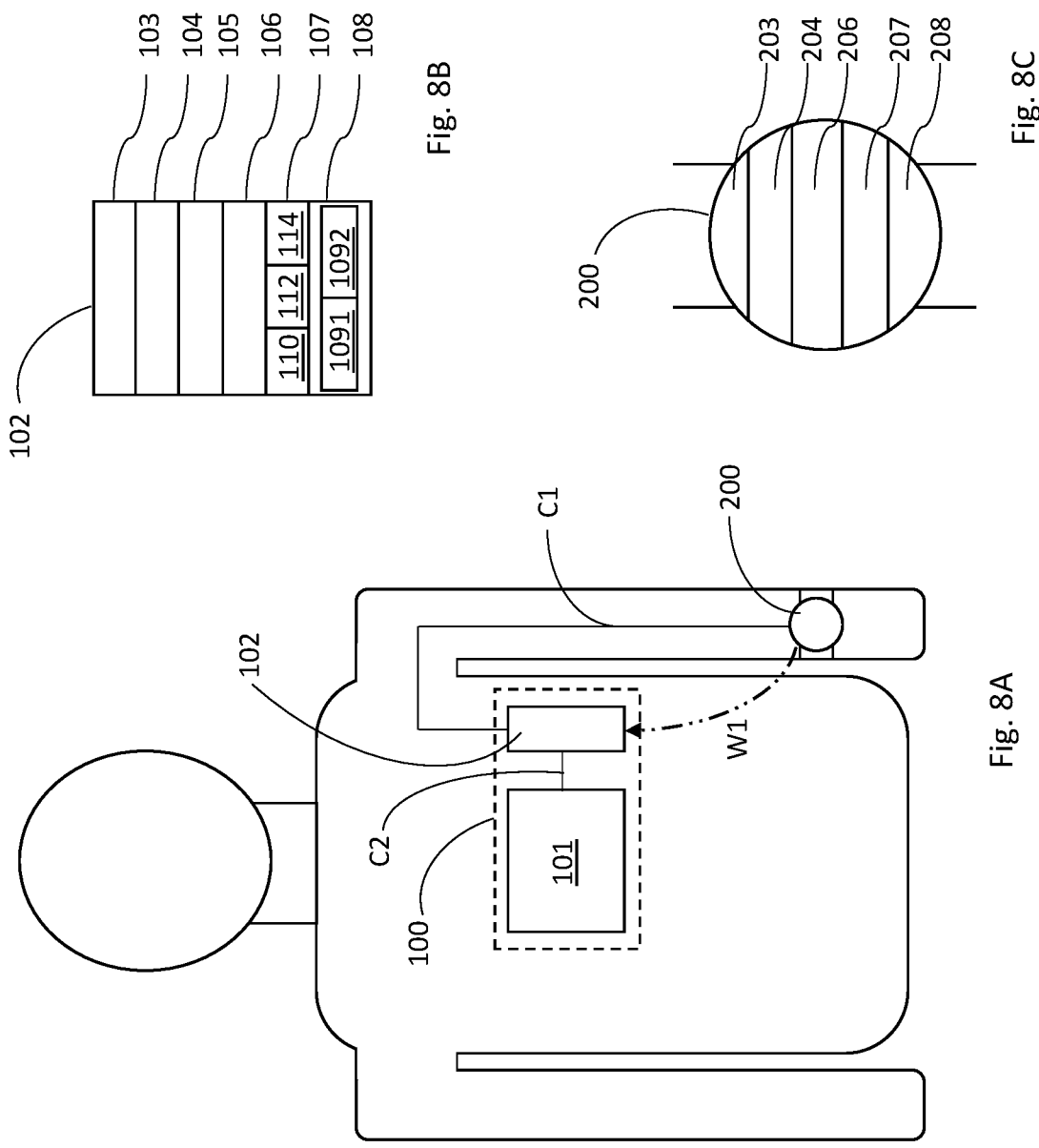
FIG. 8A illustrates a system comprising an implant, further illustrated in FIG. 8B, and an external device, further illustrated in FIG. 8C, all according to aspect 245SE.
Figure 9:
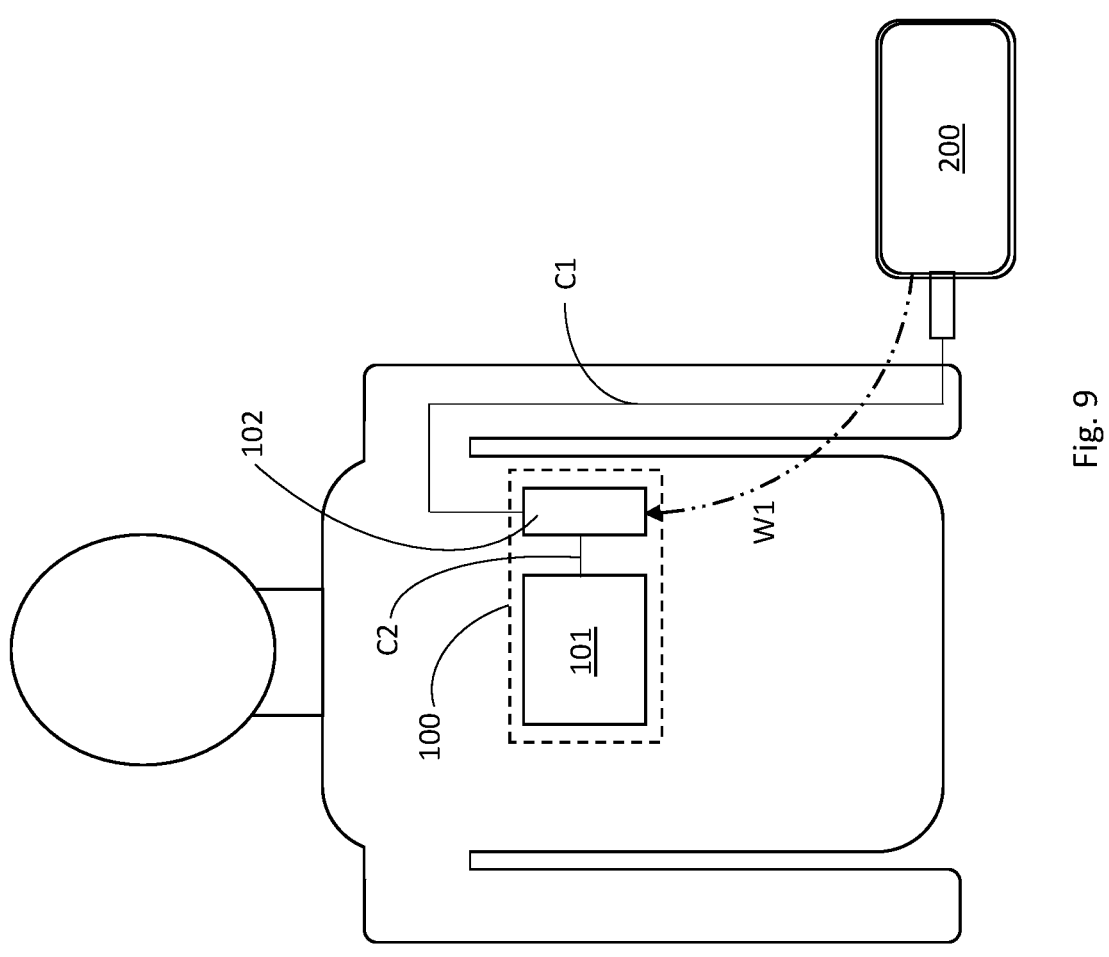
FIG. 9 illustrates a system according to aspect 245SE comprising an implant in connection with an external device.

FIG. 3 shows a method for controlling the function of an implant 100. The reset function 116 is activated S4401, and then the internal computing unit 106 is instructed S4402 by the reset function 116 to switch from running the second control program 112 to running the first control program 110. Optionally, the internal computing unit 106 deletes S4403 the second control program 112 from the internal memory 107. For some embodiments, the memory 107 is configured to store a third control program 114. The method then includes updating S4404 the second program 112 to the third program 114. The third program 114 can for example be utilized when rebooting to an original state of the second program 112. As can be seen in FIG. 3, the internal computing unit 106 can then switch S4405 from running the first program 110 to running the updated second program 112. FIG. 4 shows a method for controlling an implant 100 in which after the activation S4401 of the reset function 116, and after switching S4402 from running the second program 112 to the first program 110, an update of the second program 112 is communicated S4414 from the external device 200 to the internal communication unit 102. This is followed by switching S4405 from running the first program 110 to running the update second program 112. FIG. 5 shows various ways of activating S4401 the reset function 116. The function 116 can for example be activated by palpating S4401a the skin of the patient. Palpating is to be understood as applying pressure to the skin, by means of for example the patient's or a doctor's hand(s). The activation S4401 could also be performed by penetrating S4401b the skin of the patient. This could for example entail penetrating S4401b the skin of the patient using a needle or other suitable medical equipment. The reset function 116 may thus comprise a push button or similar with a suitable form/function to be activated by the penetration S4401b of the skin using the applicable equipment. It is equally plausible that the activation S4401 is performed by applying a magnetic force S4401c from outside the body of the patient. In such case, the implant 100 and/or external device 200 comprises means for applying and/or sensing such magnetic force. After the activation S4401 is done, the computing unit 106 switches S4402 from running the second program 112 to running the first program 110. FIG. 6 shows a method for controlling the implant 100 by activating S4401 the reset function 116, switching S4402 from running the second program 112 to running the first program 110, and then providing S4423 feedback related to the switching of programs. This feedback is performed by means of a feedback unit 149 as described in detail with reference to FIGS. 1a-c. FIG. 7 shows a method for controlling an implant 100 in which after the switching S4402 is performed, energy is provided S4433 to the first energy receiver 105a by an energy transmitter 205 of the external device 200. The energy could for example be provided using RFID pulses. In the method of FIG. 7, the feedback unit 149 provides feedback to the energy transmitter 205 pertaining to the amount of RFID energy received. A parameter such as the frequency and/or amplitude of a subsequent RFID pulse can then be adjusted S4435 based on the feedback. It is further possible to have a computer program product with a computer-readable storage medium with instructions, that can carry out the methods as described herein with reference to FIGS. 3-7 when executed by a device with processing capability (not shown). The communication referred to with respect to the embodiment of the aspect 244SE and the accompanying FIGS. 1-7 can be securely performed as described herein under the second, third, sixth, seventh and tenth aspects. In these cases, the implant and/or external device(s) comprises the necessary features and functionality (described in the respective sections of this document) for performing such secure communication. For example, the data communicated from the external device 200 to the implant 100 comprising an update of the second control program may advantageously be encrypted, for example as described herein under the second or third aspect.

The reset function 116 may be a reset switch. Such a reset switch 116 may be in the form of an electrical switch. The reset switch 116 may alternatively be in the form of a magnetic switch. The reset switch 116 may be based on application of mechanical pressure. The reset switch 116 may be spring loaded to automatically flip back once pressure is no longer applied.

The internal computing unit 106 may be configured for receiving, from said external device 200, an update of the second control program 112.

updating the second control program 112,
switching, by the internal computing unit 106, from running said first control program 110 to running said second program 112 after updating the second control program 112.

The reset functionality of the implant 100, as discussed in the above, may be utilized in the case that the main control program, e.g. the second control program 112, malfunctions.

An example of a malfunction could be if the active control program fails to control mechanical actuators or an active device 101 of the implant 100. The failing mechanical actuator could for example fail in performing its objective of opening and closing a noose around a urinary tract of a patient.

In such cases, the reset functionality may be utilized to reset and/or amend the control program with the aim of resolving the issues by fixing the control program or at least restoring it to a more stable or uncorrupted version.

The functionality may further be utilized as the control program is regularly updated, without any underlying malfunction forcing swift action to be taken.

The reset function 116 may be triggered by an update of the first or second control program 110, 112.

The reset function 116 may be triggered by a malfunction of the first or second control program 110, 112.

The reset function 116 may be triggered by a malfunction of an active device 101 of the implant 100.

The reset function 116 may be configured to be operated by Near Field Communication (NFC).

The reset function 116 may be configured to trigger implant diagnostics to be transmitted from the implant 100 to the external device 200. The implant diagnostics may comprise information or data pertaining to an error mode, an error code, or other diagnostics of the implant 100.

The reset function 116 may be configured to be operated by said magnetic force being applied at least two times. A reset may be triggered after e.g. two magnetic forces applications have been detected within a set time interval. The implant 100 may comprise at least one Hall element for detecting externally applied magnetic forces.

The first energy receiver 105a may be configured to receive energy conductively or inductively. As such, the need for an emergency battery may be negated.

The reset function 116 may be configured to be triggered if the first energy receiver 105a is receiving energy.

The first control program 110 may be configured to be running, powered by conductively or inductively received energy. This may be advantageous for emergency powering.

Said amount of energy received via the RFID pulse may be encoded in a variable pulse feedback signal provided by the feedback unit 149. The amount of energy received may be encoded in a frequency, an amplitude, an offset, a duty cycle, or a waveform of the variable pulse feedback signal.

The implant may comprise at least one of:
a pacemaker unit or implantable cardioverter defibrillators,
an external heart compression device,
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient,
an operable cosmetic implant,
an implant for adjusting or replacing any bone part of a body of the patient,
an implant controlling the emptying of a urinary bladder,
an implant hindering urinary leakage,
an implant hindering anal incontinence,
an implant controlling the emptying of fecal matter,
an implant monitoring an aneurysm,
an implant lubricating a joint,
an implant with a reservoir for holding bodily fluids
an implant storing and/or emptying a bodily reservoir or a surgically created reservoir,
an implant communicating with a database outside the body,
an implant able to be programmed from outside the body,
an implant able to be programmed from outside the body with a wireless signal,
an implant treating impotence,
an implant controlling the flow of eggs in the uterine tube,
an implant controlling the flow of sperms,
an implant treating osteoarthritis,
an implant performing a test of parameters inside the body,
an implant controlling specific treatment parameters from inside the body,
an implant controlling bodily parameters from inside the body,
an implant controlling the blood pressure,
an implant controlling a drug treatment parameter,
an implant controlling a parameter in the blood,
an active electrically controlled implant devoid of an electrical heart stimulation system,
an active electrically controlled non-heart stimulation implant,
an implant adapted for electrical stimulation of muscles, a non-nerve stimulation system,
an active non-stimulation implant,
an implant for high current electrical stimulation defined as current above 1 mA or current above 5 mA, 10 mA, or 20 mA,
an implant replacing an organ of the patient or part of an organ of the patient or the function thereof,
a vascular treatment device, and
an implant adapted to move fluid inside the body of the patient.

The implant may comprise an internal control unit adapted to be involved in at least a part of the actions performed by the implant.

Aspect 245SE 2-Part Key—Encrypted Communication Between Implant and External Device—Embodiments of Aspect 245SE of the Disclosure In aspect 245SE, increased security for communication between an external device(s) and an implant is provided. FIGS. 8-17 shows embodiments of this aspect.

A first embodiment of aspect 245SE will now be described in conjunction with FIGS. 8A-C and 12. In this embodiment, a method of communication between an external device 200 and an implant 100 is provided, when the implant 100 is implanted in a patient and the external device 200 is positioned external to the body of the patient. The external device 200 is adapted to be in electrical connection C1 with the implant 100, using the body as a conductor. The electrical connection C1 is used for conductive communication between the external device 200 and the implant 100. The implant 100 comprises a communication unit 102. Both the implant 100 and the external device 200 comprises a wireless transceiver 108, 208 for wireless communication C1 between the implant 100 and the external device 200. The wireless transceiver 108 (included in the communication unit 102) may in some embodiments comprise sub-transceivers 1091, 1092 for receiving data from the external device 200 and other external devices, e.g. using different frequency bands, modulation schemes etc.

In a first step of the method of FIG. 12, the electrical connection C1 between the implant 100 and the external device 200 is confirmed S4501 and thus authenticated. The confirmation and authentication of the electrical connection may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

The implant may comprise a first transceiver 103 configured to be in electrical connection C1 with the external device, using the body as a conductor. The external device may comprise a first external transmitter 203 configured to be in electrical connection C1 with the implant, using the body as a conductor, and the wireless transmitter 208 configured to transmit wireless communication W1 to the implant 100. The first transmitter 203 of the external device may be wired or wireless. The first transmitter 203 and the wireless transmitter 208 may be the same or separate transmitters. The first transceiver 103 of the implant 100 may be wired or wireless. The first transceiver 103 and the wireless transceiver 102 may be the same or separate transceivers. The implant 100 may comprise a computing unit 106 configured to confirm the electrical connection between the external device 200 and the internal transceiver 103 and accept wireless communication W1 (of the data) from the external device 200 on the basis of the confirmation.

Data is transmitted S4502 from the external device 200 to the implant 100 wirelessly, e.g. using the respective wireless transceiver 108, 208 of the implant and the external device. Data may alternatively be transmitted through the electrical connection. As a result of the confirmation, the received data is used S4503 for instructing the implant. For example, as shown in FIG. 17, a control program 110 running in the implant 100 may be updated S4541, the implant 100 may be operated S4542 using operation instructions in the received data. This may be handled by the computing unit 106.

The embodiment of FIG. 12 may be extended to further increase security. This will be described below. The step S4502 of transmitting data from the external device 200 to the implant 100 wirelessly comprises transmitting S4512 encrypted data wirelessly. To decrypt the encrypted data (for example using the computing unit 106), several methods may be used.

In one embodiment, shown in FIG. 13, a key is transmitted using the confirmed conductive communication channel C1 (i.e. the electrical connection) from the external device 200 to the implant 100. The key is received S4505 at the implant (by the first internal transceiver 103). The key is then used for decrypting S4508 the encrypted data.

In some embodiments the key is enough to decrypt S4508 the encrypted data. In other embodiments, further keys are necessary to decrypt the data. In FIG. 14, one such embodiment is shown. In this embodiment, a key is transmitted using the confirmed conductive communication channel C1 (i.e. the electrical connection) from the external device 200 to the implant 100. The key is received S4505 at the implant (by the first internal transceiver 103). A second key is transmitted S4504 (by the wireless transceiver 208) from the external device 200 using the wireless communication W1 and received S4515 at the implant 100 by the wireless transceiver 108. The computing unit 106 is then deriving S4516 a combined key from the key and second key and uses this for decrypting S4518 the encrypted data.

Figure 10:
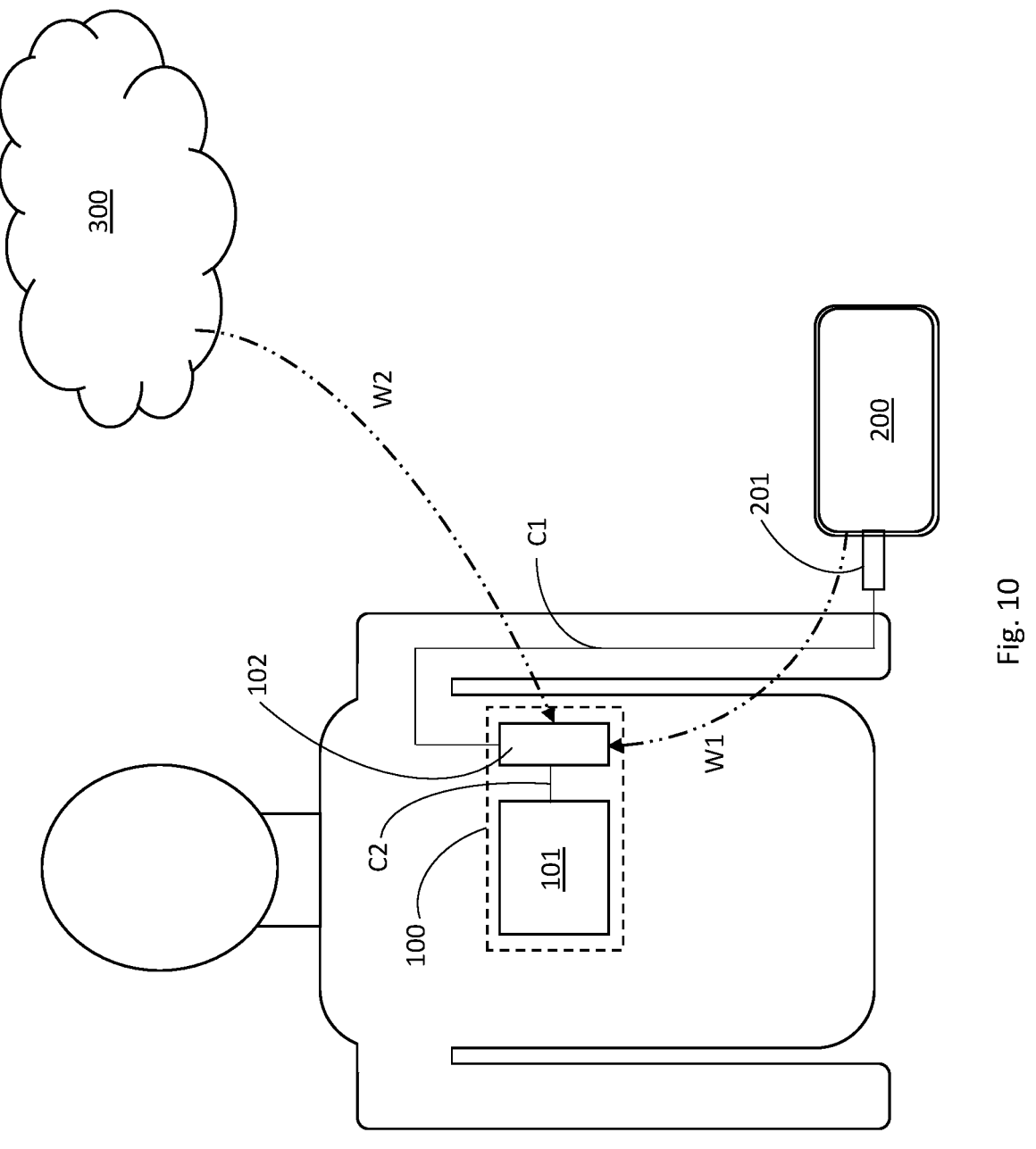
FIG. 10 illustrates a system according to aspect 245SE comprising an implant in connection with an external device and a second external device.

In yet other embodiments, shown in FIG. 15 in conjunction with FIG. 10, a key is transmitted using the confirmed conductive communication channel C1 (i.e. the electrical connection) from the external device 200 to the implant 100. The key is received S4505 at the implant (by the first internal transceiver 103). A third key is transmitted S4524 from a second external device 300, separate from the external device 200, to the implant wirelessly W2. The third key may be received S4525 by a second wireless receiver 1092 (part of the wireless transceiver 108) of the implant 100 configured for receiving wireless communication W2 from second external device 300.

The first and third key may be used to derive S4526 a combined key by the computing unit 106, which then decrypts S4512 the encrypted data. The decrypted data is then used for instructing S4503 the implant 100 as described above.

The second external device 300 may be controlled by for example a caregiver, to further increase security and validity of data sent and decrypted by the implant 100.

Figure 11:
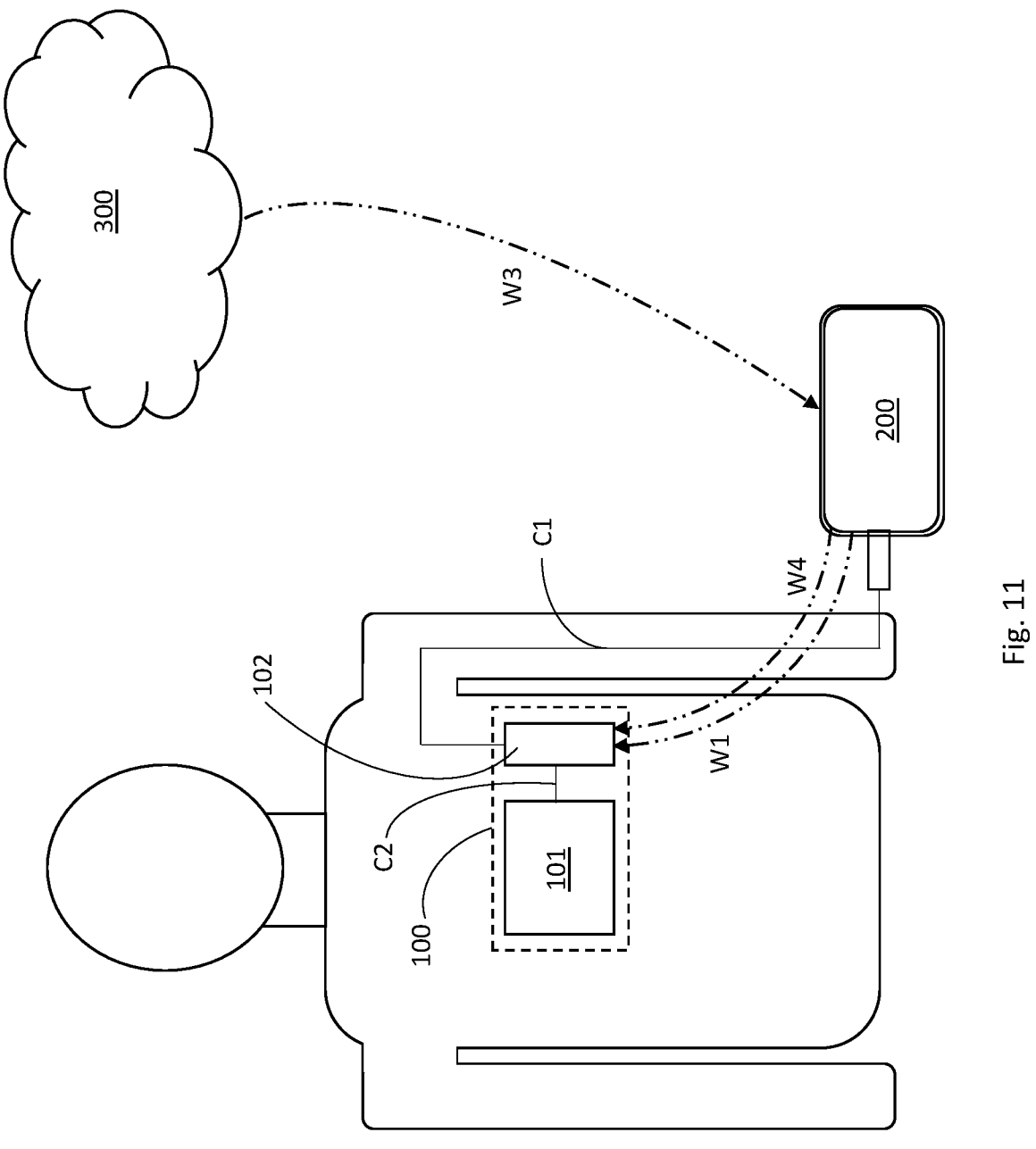
FIG. 11 illustrates a system according to aspect 245SE comprising an implant in connection with an external device wherein the external device is in connection with a second external device.

It should be noted that in some embodiments shown in FIG. 11, the external device is further configured to receive W3 secondary wireless communication from the second external device 300, and transmit data received from the secondary wireless communication W3 to the implant. This routing of data may be achieved using the wireless transceivers 108, 208 (i.e. the wireless connection W1, or by using a further wireless connection W4 between the implant 100 and the external device 200. The routing may be performed as described herein under aspect 253SE. In these cases, the implant and/or external device(s) comprises the necessary features and functionality (described in the respective sections of this document) for performing such routing. Consequently, in some embodiments, the third key is generated by the second external device 300 and transmitted W3 to the external device 200 which routes the third key to the implant 100 to be used for decryption of the encrypted data. In other words, the step of transmitting a third key from a second external device, separate from the external device, to the implant wirelessly, comprises routing the third key through the external device. Using the external device 200 as a relay, with or without verification from the patient, may provide an extra layer of security as the external device 200 may not need to store or otherwise handle decrypted information. As such, the external device 200 may be lost without losing decrypted information.

In yet other embodiments, shown in FIG. 16 in conjunction with FIG. 10, a key is transmitted using the confirmed conductive communication channel C1 (i.e. the electrical connection) from the external device 200 to the implant 100. The key is received S4505 at the implant (by the first internal transceiver 103). A second key is transmitted S4514 from the external device 200 to the implant 100 wirelessly W1, received S4515 at the at the implant. A third key is transmitted S4524 from the second external device (300), separate from the external device, to the implant 100 wirelessly W2, received S4525 at the implant. Encrypted data transmitted S4512 from the external device 200 to the implant 100 is then decrypted S4538 using a derived S4526 combined key from the key, the second key and the third key.

wherein the external device is a wearable external device.

The external device 200 may be a handset.

The second external device 300 may be a handset.

The second external device 300 may be a server.

The second external device 300 may be cloud based.

In some embodiments, shown in FIG. 10, the electrical connection C1 between the external device 200 and the implant 100 is achieved by placing a conductive member 201, configured to be in connection with the external device 200, in electrical connection with a skin of the patient for conductive communication C1 with the implant. This feature may be achieved as described herein under aspect 247SE. In these cases, the implant and/or external device(s) comprises the necessary features and functionality (described in the respective sections of this document) for performing such conductive communication. The communication may thus be provided with an extra layer of security in addition to the encryption by being electrically confined to the conducting path e.g. external device 200, conductive member 201, conductive connection C1, implant 100, meaning the communication will be excessively difficult to be intercepted by a third party not in physical contact with, or at least proximal to, the patient.

The keys described in this section may in some embodiments be generated based on data sensed by sensors described herein under the twelfth or thirteenth aspect, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys. A computer program product of, or adapted to be run on, an external device is also provided, which comprises a computer-readable storage medium with instructions adapted to make the external device perform the actions as described above.

Aspect 246SE 3-Part Key—Multi-Party Encrypted Communication Between Implant and External Device—Embodiments of Aspect 246SE of the Disclosure In aspect 246SE, increased security for communication between an external device(s) and an implant is provided. FIGS. 18-29 shows embodiments of this aspect.

First embodiments of aspect 246SE will now be described in conjunction with FIGS. 19-21 and 22. In these embodiments, a method for communication between an external device 200 and an implant 100 is provided. The implant 100 is implanted in a patient and the external device 200 is positioned external to the body of the patient. The implant and the external device each comprise a wireless transceiver 108, 208 for wireless communication W1 between the implant 100 and the external device 200. The wireless transceiver 108 (included in a communication unit 102 of the implant) may in some embodiments comprise sub-transceivers for receiving data from the external device 200 and other external devices 300, 400, 500, e.g. using different frequency bands, modulation schemes etc.

A first step of the method of FIG. 22 comprises receiving S4601, at the implant, by a wireless transmission W1 or otherwise, a first key from an external device 300. The method further comprises receiving S4602, at the implant, by a wireless transmission W1. W2. W3, a second key. The second key may be generated by a second external device, separate from the external device or by another external device 500 being a generator of the second key on behalf of the second external device 300. The second key may be received at the implant from anyone of, the external device

200, the second external device 300, and the generator 500 of the second key. The second external device may be controlled by a caretaker, or any other stakeholder. Said another external device 500 may be controlled by a manufacturer of the implant, or medical staff, caretaker, etc.

In case the implant is receiving the second key from the external device 200, this means that the second key is routed through the external device from the second external device 300 or from the another external device 500 (generator). The routing may be performed as described herein under aspect 253SE. In these cases, the implant and/or external device(s) comprises the necessary features and functionality (described in the respective sections of this document) for performing such routing. Using the external device 200 as a relay, with or without verification from the patient, may provide an extra layer of security as the external device 200 may not need to store or otherwise handle decrypted information. As such, the external device 200 may be lost without losing decrypted information.

The implant comprises a computing unit 106 configured for deriving S4604$a$ a combined key by combining the first key and the second key with a third key held by the implant 100, for example in memory 107 of the implant. The combined key may be used for decrypting S4606, by the computing unit 106, encrypted data transmitted S4605 by a wireless transmission W1 from the external device 200 to the implant 100. Optionally, the decrypted data may be used for altering S4608, by the computing unit 106 an operation of the implant. The altering an operation of the implant may comprise controlling or switching an active unit 101 of the implant. In some embodiments, as described in FIG. 26, the method further comprises at least one of the steps S4640 of, based on the decrypted data, updating a control program running in the implant, and operating the implant 100 using operation instructions in the decrypted data.

In some embodiments, further keys are necessary to derive a combined key for decrypting the encrypted data received at the implant 100. Such embodiments are described in FIG. 23. In these embodiments, the first and second key are received S4601. S4062 as described in conjunction with FIG. 22. Further, the method comprises receiving S4603, at the implant, a fourth key from a third external device 400, the third external device being separate from the external device, deriving S4604$b$ a combined key by combining the first, second and fourth key with the third key held by the implant 100, and decrypting S4606 the encrypted data, in the implant 100, using the combined key. Optionally, the decrypted data may be used for altering S4608, by the computing unit 106, an operation of the implant as described above. In some embodiments, the fourth key is routed through the external device from the third external device. The routing may be performed as described herein under aspect 253SE. In these cases, the implant and/or external device(s) comprises the necessary features and functionality (described in the respective sections of this document) for performing such routing.

In some embodiments, further security measures are needed before using the decrypted data for altering S4608, by the computing unit 106, an operation of the implant. For example, an electrical connection C1 between the implant and the external device, using the body as a conductor, may be used for further verification of validity of the decrypted data. Such embodiments are described in e.g. FIGS. 18-19 and FIG. 24. The electrical connection C1 may be achieved by placing a conductive member 201, configured to be in connection with the external device, in electrical connection with a skin of the patient for conductive communication C1 with the implant. This feature may be achieved as described herein under aspect 247SE. In these cases, the implant and/or external device(s) comprises the necessary features and functionality (described in the respective sections of this document) for performing such conductive communication. The communication may thus be provided with an extra layer of security in addition to the encryption by being electrically confined to the conducting path e.g. external device 200, conductive member 201, conductive connection C1, implant 100, meaning the communication will be excessively difficult to be intercepted by a third party not in physical contact with, or at least proximal to, the patient.

Accordingly, in some embodiments, the method comprising confirming S4607 the electrical connection between the implant and the external device, and as a result of the confirmation, altering S4608 an operation of the implant based on the decrypted data. The confirmation and authentication of the electrical connection may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

Figure 25:
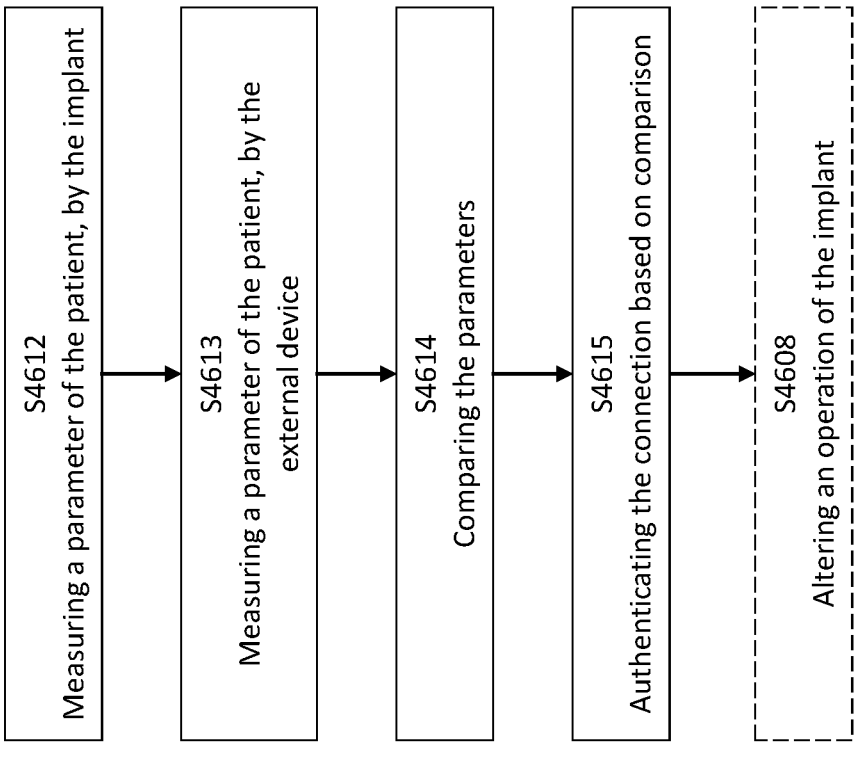
Figure 29:
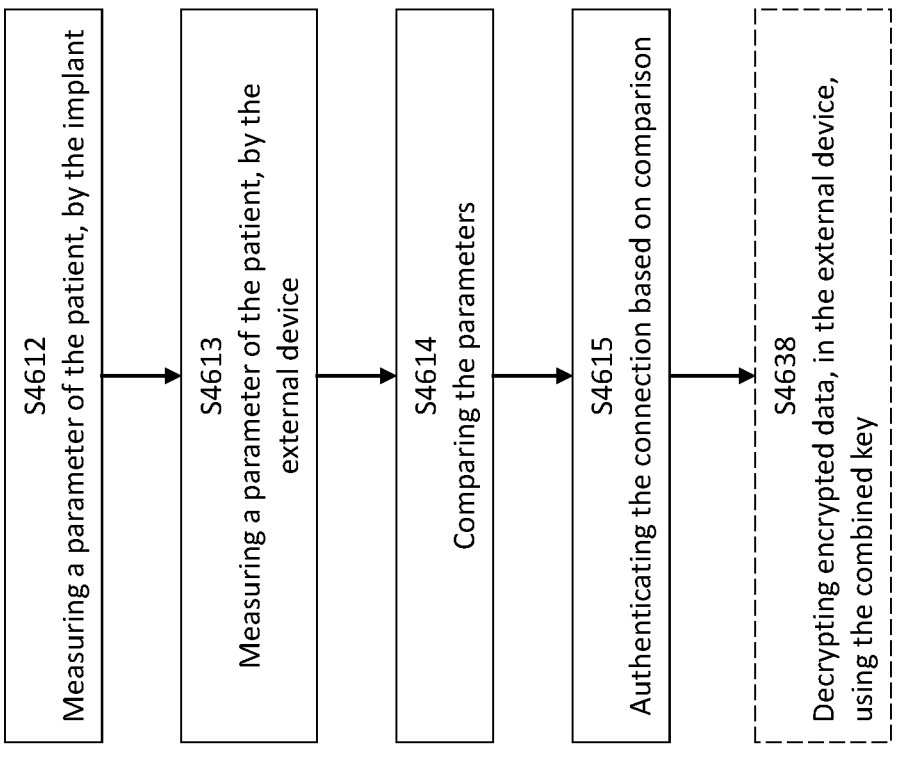

Some of these embodiments will now be described for convenience of the reader in conjunction with FIG. 25. In these embodiments, the confirmation S4607 of the electrical connection comprises: measuring S4612 a parameter of the patient, by the implant, measuring S4613 the parameter of the patient, by the external device, comparing S4614 the parameter measured by the implant to the parameter measured by the external device, and authenticating S4615 the connection based on the comparison. As mentioned above, as a result of the confirmation, an operation of the implant may be altered S4608 based on the decrypted data.

It should be noted that the above concepts of aspect 246SE may be used also for reducing the risk that data transmitted from the implant ends up in the wrong hands. Such embodiments are described in FIGS. 27-28. In the embodiments described in FIG. 27, methods for encrypted communication between an external device 200 and an implant 100 are provided. These methods comprise:

receiving S4621, at the external device 100 by a wireless receiver 208, a first key, the first key being generated by a second external device 300, separate from the external device 200 or by another external device 500 being a generator of the second key on behalf of the second external device 200, the first key being received from anyone of the second external device 200 and the generator 500 of the second key, receiving S4622, at the external device 200 by the wireless receiver 208, a second key from the implant 100, deriving S4624a a combined key, by a computing unit 206 of the external device 200, by combining the first key and the second key with a third key held by the external device 200 (e.g. in memory 207), transmitting S4625 encrypted data from the implant to the external device and receiving the encrypted data at the external device by the wireless receiver 208, and decrypting S4626, by the computing unit 206, the encrypted data, in the external device 200, using the combined key.

As described above, further keys may be necessary to decrypt the data. Consequently, as described in FIG. 28, the wireless transceiver 208 is configured for:

receiving S4603 a fourth key from a third external device 400, wherein the computing unit 206 is configured for:

deriving S4604b a combined key by combining the first, second and fourth key with the third key held by the external device, and decrypting the encrypted data using the combined key.

In some embodiments, the communication between the implant 100 and the external device 200 needs to be confirmed (authenticated) before decrypting the data. The confirmation of the communication may be implemented similar to what is described above, and consequently also as described herein under the fifth, thirteenth and fifteenth aspect. In these cases, the implant and/or external device(s) comprises the necessary features and functionality (described in the respective sections of this document) for performing such authentication.

These embodiments further increase the security in the communication. These embodiments are exemplified in FIG. 29 where the computing unit 206 is configured to confirm the communication between the implant and the external device, wherein the confirmation comprises:

measuring a parameter of the patient, by the external device, receiving a measured parameter of the patient, from the implant, comparing the parameter measured by the implant to the parameter measured by the external device, performing confirmation of the connection based on the comparison, and as a result of the confirmation, decrypting the encrypted data, in the external device, using the combined key.

The external device 200 may be a wearable external device.

The external device 200 may be a handset.

The second/third external device 300 may be is a handset.

The second/third external device 300 may be a server.

The second/third external device 300 may be cloud based.

One or more of the first, second and third key may comprise a biometric key.

The keys described in this section may in some embodiments be generated based on data sensed by sensors described herein under the twelfth or thirteenth aspect, e.g. using the sensed data as seed for the generated keys. A seed is an initial value that is fed into a pseudo random number generator to start the process of random number generation. The seed may thus be made hard to predict without access or knowledge of the physiological parameters of the patient which it is based on, providing an extra level of security to the generated keys.

The first key may be received at the implant 100 from the external device 200, by a wireless transmission.

The first key may be transmitted by the external device 200.

The encrypted data may be received from the external device 200 or the second external device 300 or another external device via the internet.

The third external device 300 may be a server comprising a database, the database comprising data pertaining to control program updates and/or instructions. The server may be a device with computing capacity.

The database may communicate with a caregiver and/or the implant 100.

The database may communicate with a caregiver and/or the implant 100 via the external device 200.

The implant 100 may comprises at least one of:

a pacemaker unit.

an external heart compression device.

an apparatus assisting the pump function of a heart of the patient, an operable artificial heart valve, an implantable drug delivery device.

a hydraulic, mechanic, and/or electric constriction implant, an operable volume filling device.

an operable gastric band.

an operable implant for stretching the stomach wall of the patient, an operable cosmetic implant, an implant for adjusting or replacing any bone part of a body of the patient, an implant replacing an organ of the patient or part of an organ of the patient or the function thereof, a vascular treatment device, and an implant adapted to move fluid inside the body of the patient.

A computer program product of, or adapted to be run on, an external device is also provided, which comprises a computer-readable storage medium with instructions adapted to make the external device perform the actions as described above.

Aspect 247SE Electrical Connection—Conductive Member in Electrical Connection with the External Device—Embodiments of Aspect 247SE of the Disclosure In aspect 245SE, increased security for communication between an external device(s) and an implant is provided. FIGS. 30-35 shows embodiments of this aspect.

Figures 30A, 30B, 30C:
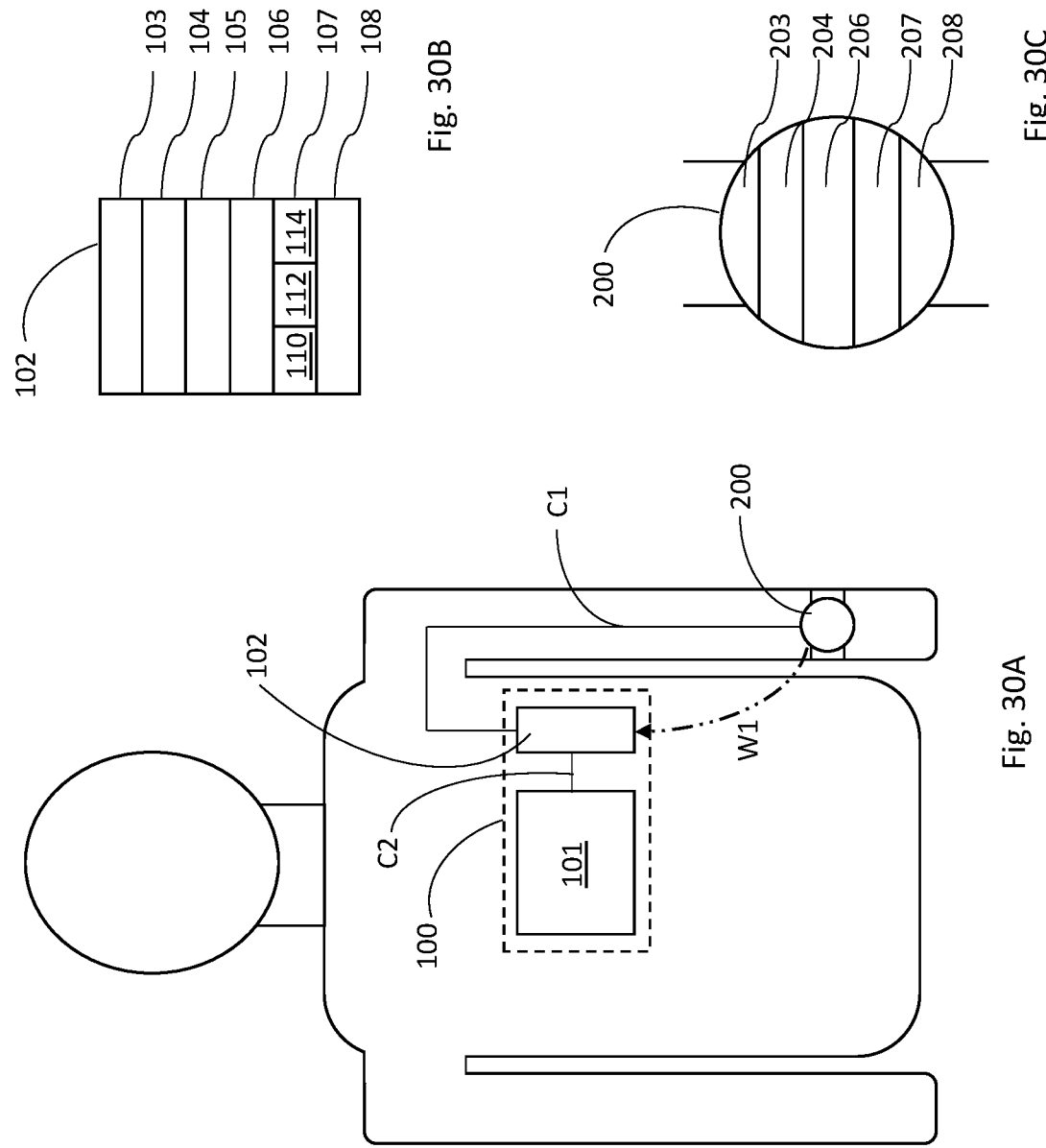
FIG. 30A illustrates a system comprising an implant, further illustrated in FIG. 30B, and an external device, further illustrated in FIG. 30C, all according to aspect 247SE.
Figure 31:
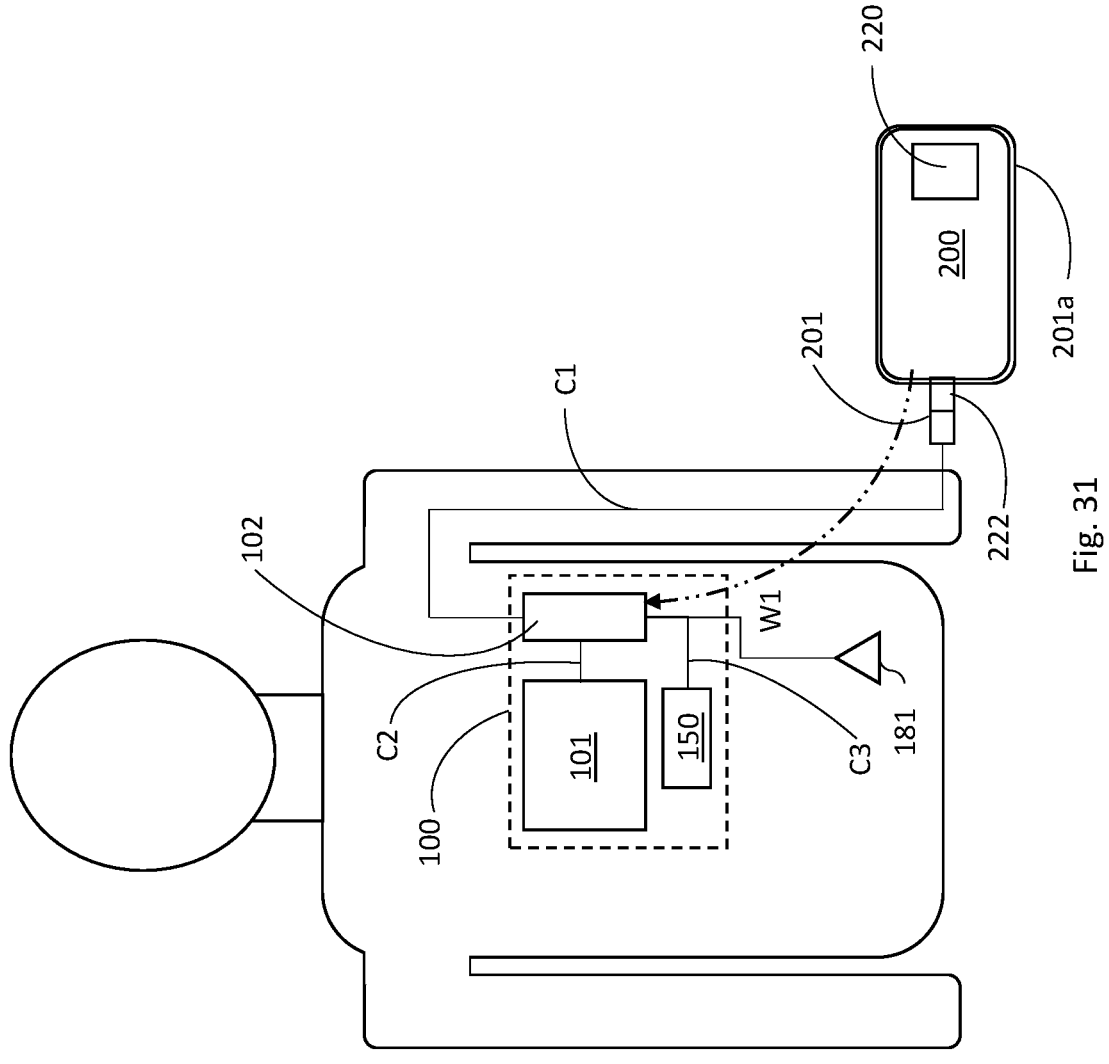
FIG. 31 illustrates a system according to aspect 247SE comprising an implant in connection with an external device.

FIGS. 30-31 shows a system for communication between an external device 200 and an implant 100 implanted in a patient. The system comprises a conductive member 201 configured to be in connection (electrical/conductive or wireless or otherwise) with the external device, the conductive member 201 being configured to be placed in electrical connection with a skin of the patient for conductive communication C1 with the implant 100. By using a conductive member 201 as defined herein, an increased security for communication between the external device and the implant may be achieved. For example, when a sensitive update of a control program of the implant 100 is to be made, or if sensitive data regarding physical parameters of the patient is to be sent to the externa device 200 (or otherwise), the conductive member 201 may ensure that the patient is aware of such communication and actively participate in validating that the communication may take place. The conductive member may, by being placed in connection with the skin of the patient, open the conductive communication channel C1 between the external device and the implant to be used for data transmission.

Electrical or conductive communication, such as this or as described under the other aspects, may be very hard to detect remotely, or at least relatively so, in relation to wireless communications such as radio transmissions. Direct electrical communication may further safeguard the connection between the implant and the external device from electromagnetic jamming i.e. high-power transmissions other a broad range of radio frequencies aimed at drowning other communications within the frequency range. Electrical or conductive communication will be excessively difficult to be intercepted by a third party not in physical contact with, or at least proximal to, the patient, providing an extra level of security to the communication.

In some embodiments, the conductive member comprises a conductive interface for connecting the conductive member to the external device.

The conductive interface may be any suitable hardware interface, such as a charging port of the external device, a headphone port, a USB port, a serial port, an ethernet port, a DVI port, printer port etc. By using a hardware port for connection, the security aspect is further facilitated since it may be ensured that both the external device and the conductive member are present near the patient and connected using a wired interface.

In other embodiments, the conductive member is wirelessly connected to the external device using a wireless communication channel (Radio), such as WLAN, Wi-Fi, cellular network, Bluetooth, NFC, RFID etc.

In some embodiments, the conductive member 201 is a device which is plugged into the external device 200, and easily visible and identifiable for simplified usage by the patient. In other embodiments, the conductive member 201 is to a higher degree integrated with the external device 200, for example in the form of a case 201a of the external device 200, the case 201a comprising a capacitive area configured to be in electrical connection with a skin of the patient. In FIG. 31, the case 201a is exemplified as a mobile phone case (smartphone case) for a mobile phone, but the case may in other embodiments be a case for a personal computer, or a body worn camera or any other suitable type of external device as described herein. The case may for example be connected to the phone using a wire from the case and connected to the headphone port or charging port of the mobile phone.

The conductive communication C1 may be used both for communication between the implant 100 and the external device 200 in any or both directions. Consequently, according to some embodiments, the external device 200 is configured to transmit a conductive communication (conductive data) to the implant 100 via the conductive member 201.

According to some embodiments, the implant 100 is configured to transmit a conductive communication to the external device 200. The content of the conductive communication is exemplified in FIG. 32. These embodiments start by placing S4701 the conductive member 201, configured to be in connection with the external device, in electrical connection with a skin of the patient for conductive communication C1 with the implant. The conductive communication between the external device 200 and the implant 100 may follow an electrically/conductively confined path comprising e.g. the external device 200, conductive member 201, conductive connection C1, implant 100.

For the embodiments when the external device 200 transmits data to the implant, the communication may comprise transmitting S4704a a conductive communication to the implant 100 by the external device 200.

The transmitted data may comprise instructions for operating the implant. Consequently, some embodiments comprise operating S4730 the implant 100 using operation instructions, by an internal computing unit 106 of the implant 100, wherein the conductive communication C1 comprises instructions for operating the implant. The operation instruction may for example involve adjusting or setting up (e.g. properties or functionality of) an active unit 101 of the implant.

The transmitted data may comprise instructions for updating a control program 110 stored in memory 107 of the implant 100. Consequently, some embodiments comprise updating S4740 the control program 110 running in the implant, by the internal computing unit 106 of the implant, wherein the conductive communication comprises instructions for updating the control program.

For the embodiments when the implant 100 transmits data to the external device 200, the communication may comprise transmitting S4704*b* conductive communication C1 to the external device 200 by the implant 100. The conductive communication may comprise feedback parameters (battery status, properties, version number etc.) relating to functionality of the implant. In other embodiments, the conductive communication C1 comprises data pertaining to least one physiological parameter of the patient, such as blood pressure etc. The physiological parameter(s) may be stored in memory 107 of the implant 100 or sensed in prior (in real time or with delay) to transmitting S4704*b* the conductive communication C1. Consequently, in some embodiments, the implant comprises a sensor 150 for sensing S4750 at least one physiological parameter of the patient, wherein the conductive communication comprises said at least one physiological parameter of the patient.

To further increase security of the communication between the implant 100 and the external device 200, different types of authentication, verification and/or encryption may be employed. In some embodiments, as described in FIG. 33 in conjunction with FIG. 31, the external device 200 comprises a verification unit 220. The verification unit may be any type of unit suitable for verification of a user. i.e. configured to receive authentication input from a user, for authenticating the conductive communication between the implant and the external device. In some embodiments, the verification unit and the external device comprises means for collecting authentication input from the user (which may or may not be the patient). Such means may comprise a fingerprint reader, a retina scanner, a camera, a GUI for inputting a code, a microphone, device configured to draw blood, etc. The authentication input may thus comprise a code or any be based on a biometric technique selected from the list of: a fingerprint, a palm vein structure, image recognition, face recognition, iris recognition, a retinal scan, a hand geometry, and genome comparison. The means for collecting the authentication input may alternatively be part of the conductive member which comprise any of the above examples of functionality, such as a fingerprint reader 222 or other type of biometric reader 222.

Figures 32, 33:
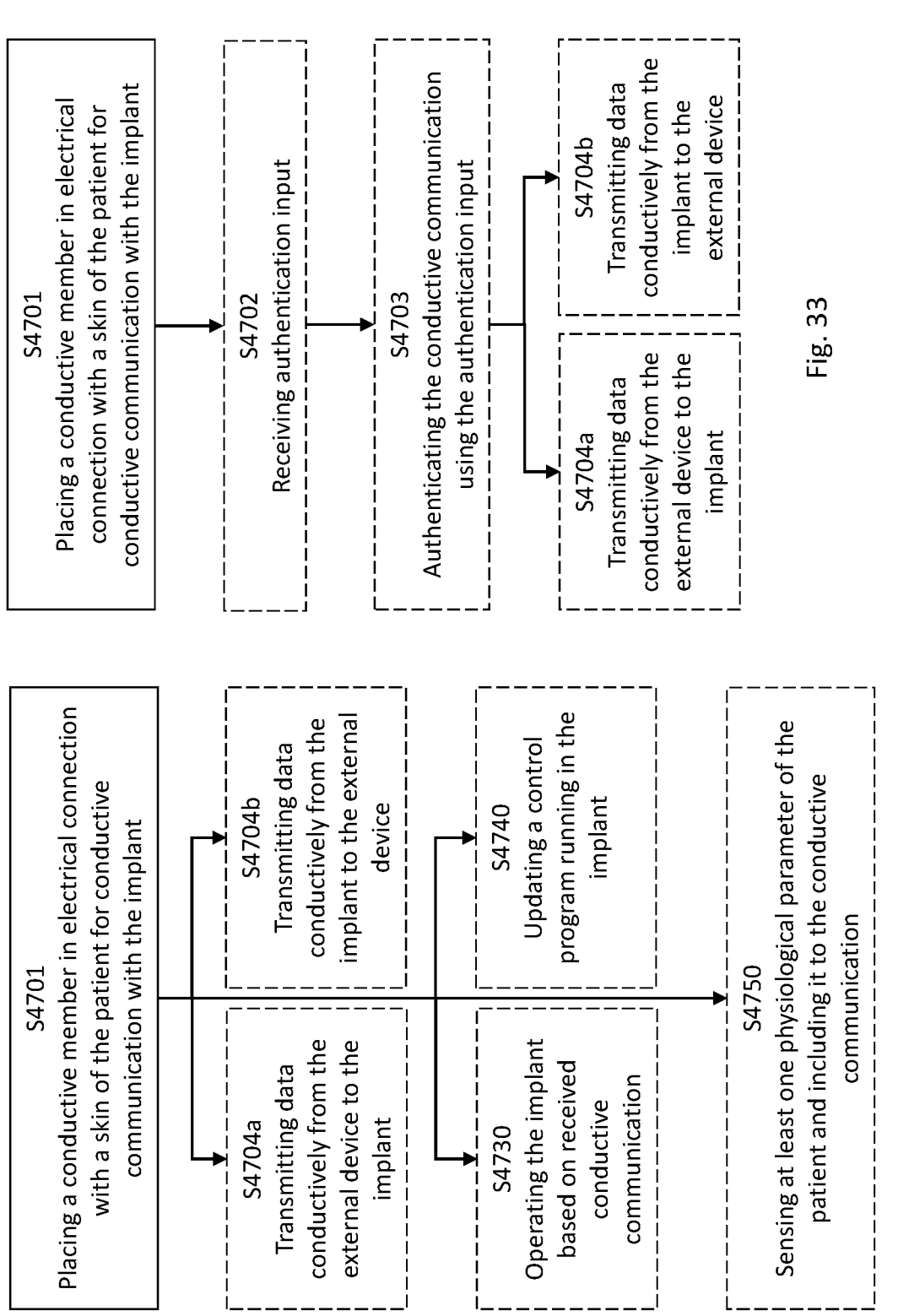

In some embodiment, as exemplified in FIG. 33, the security may thus be increased by receiving S4702 an authentication input from a user by a verification unit 220 of the external device, and authenticating S4703 the conductive communication between the implant and the external device using the authentication input. Upon a positive authentication S4703, the conductive communication channel C1 may be employed for comprising transmitting a S4704*a* conductive communication to the implant 100 by external device 200 and/or transmitting S4704*b* a conductive communication to the external device 200 by the implant 100. In other embodiments, a positive authentication is needed prior to operating S4730 the implant based on received conductive communication, and/or updating S4740 a control program running in the implant as described above.

Other ways of performing authentication of the conductive communication are equally possible. For example, as exemplified in FIG. 34, secure communication may be achieved by the implant comprising: a sensor 150 (e.g.

connected through a wire C3, or wirelessly connected, to the implant) for measuring S4712 a parameter of the patient, by the implant, and an internal computing unit 106 configured for:

i. receiving S4713 a parameter of the patient, from the external device 200 (via conductive communication C1 or via a wireless communication W1), ii. comparing S4714 the parameter measured by the implant 100 to the parameter measured by the external device, and iii. performing S4715 authentication of the conductive communication based on the comparison.

In other embodiments, the implant 100 being connected to a sensation generator 181 (included in the implant or separate from the implant), the implant being configured for: storing authentication data (in memory 107), related to a sensation generated by the sensation generator, receiving input authentication data from the external device 200. The implant 100 comprises an internal computing unit 106 configured for:

i. comparing the authentication data to the input authentication data, and ii. performing authentication of the conductive communication based on the comparison.

Upon a positive authentication, the conductive communication channel C1 may be employed for comprising transmitting a S4704*a* conductive communication to the implant 100 by external device 200 and/or transmitting S4704*b* a conductive communication to the external device 200 by the implant 100. In other embodiments, a positive authentication is needed prior to operating S4730 the implant based on received conductive communication, and/or updating S4740 a control program running in the implant as described above.

The confirmation and authentication of the conductive communication (electrical connection) may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication and communication may be increased as it may require a malicious third party to know or gain access to either the transient physiological parameter of the patient or detect randomized sensations generated at or within the patient in addition to accessing the implant via a conductive path.

In other embodiments, the conductive communication comprises a key or a part of the key to be used for decrypting encrypted data received by the external device or the implant. Such embodiment is exemplified in FIG. 35. This embodiment starts by placing S4701 the conductive member 201, configured to be in connection with the external device, in electrical connection with a skin of the patient for conductive communication C1 with the implant. The external device is configured to transmit S4722 a first part of the key to the implant 100 using the conductive communication C1, and to wirelessly W1 transmit a second part of the key to the implant 100, wherein the implant 100 (e.g. the computing unit 106) is adapted to decrypt S4725 the encrypted data, using a combined S4724 key derived from the received first and second parts of the key. Wireless communication may be achieved by wireless transceivers 108, 208 of the implant 100 and the external device 200. Further examples and details of how to perform encryption of data transmitted between the implant 100 and the external device 200 can be found as described herein under the second, third or sixth aspect. In these cases, the implant and/or external device(s) comprises the necessary features and functionality (described in the respective sections of this document) for performing such encryption/decryption.

The conductive member may be arranged as an arm or wrist band being integrally formed with, or connected to, the external device. The arm or wrist band may be configured to be worn, around an arm or wrist, of the patient in which the implant is implanted.

The conductive member may be configured to be in conductive or electrical connection with the external device.

The conductive member may be configured to be in wireless connection with the external device.

The conductive member may be configured to be a screen of the external device, the screen being configured to receive data using electric charge.

The conductive member may comprise the verification unit.

The external device may comprise the verification unit.

The establishment of conductive communication may be configured to authenticate or partially authenticate the conductive communication between the implant and the external device.

The external device may be a smartwatch. The smartwatch may be configured to be worn, around an arm or wrist, of the patient in which the implant is implanted. The smartwatch may additionally function as a mobile computing and communication device or a device for displaying the time, i.e. a clock.

The implant may comprise at least one of:
a pacemaker unit,
an external heart compression device,
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient,
an operable cosmetic implant,
an implant for adjusting or replacing any bone part of a body of the patient,
an implant replacing an organ of the patient or part of an organ of the patient or the function thereof,
a vascular treatment device, and
an implant adapted to move fluid inside the body of the patient.

A computer program product of, or adapted to be run on, an external device is also provided, which comprises a computer-readable storage medium with instructions adapted to make the external device perform the actions as described above.

Figures 36A, 36B, 36C:
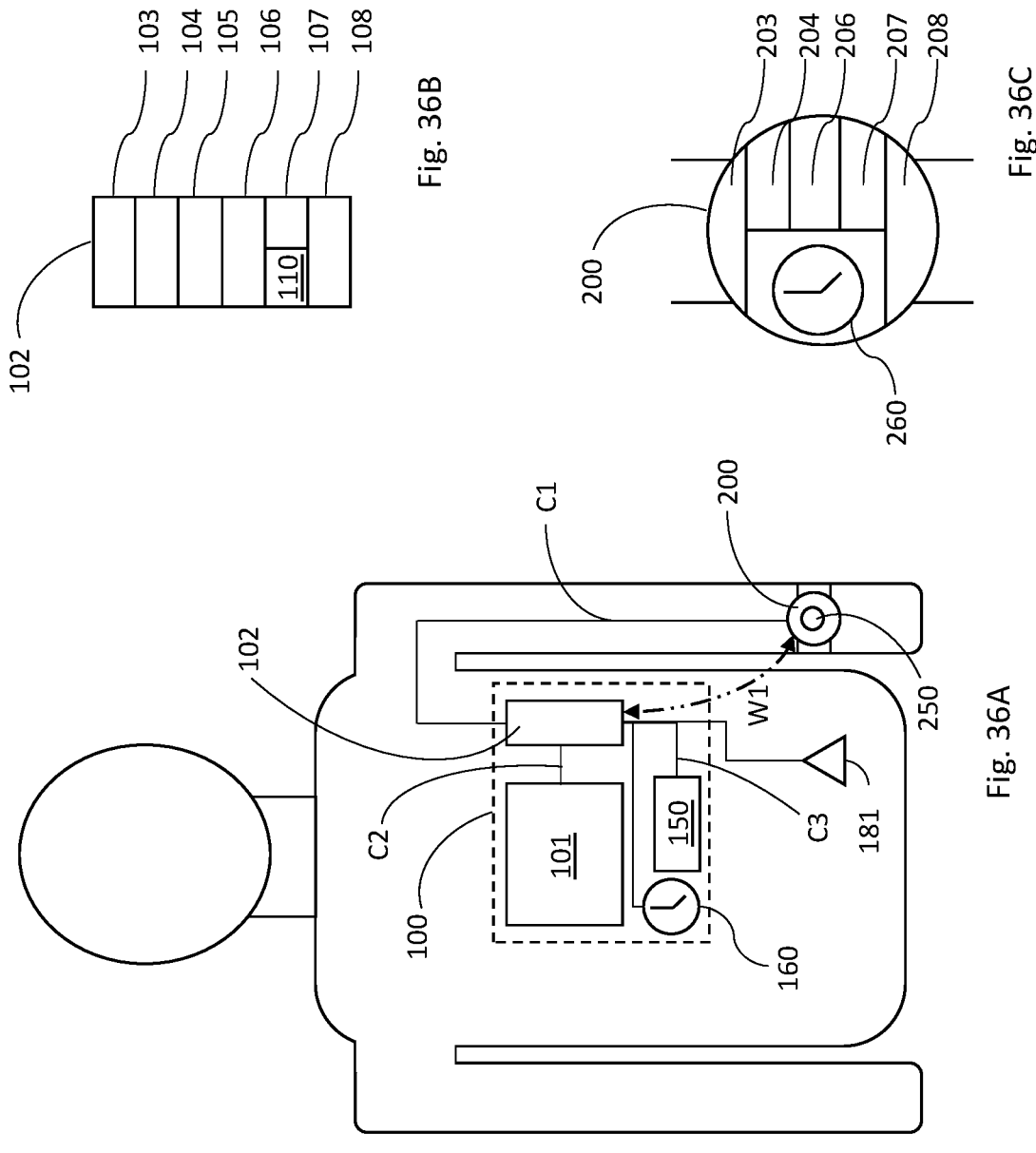
FIG. 36A illustrates a system comprising an implant, further illustrated in FIG. 36B, and an external device, further illustrated in FIG. 36C, all according to aspect 248SE.
Figure 37:
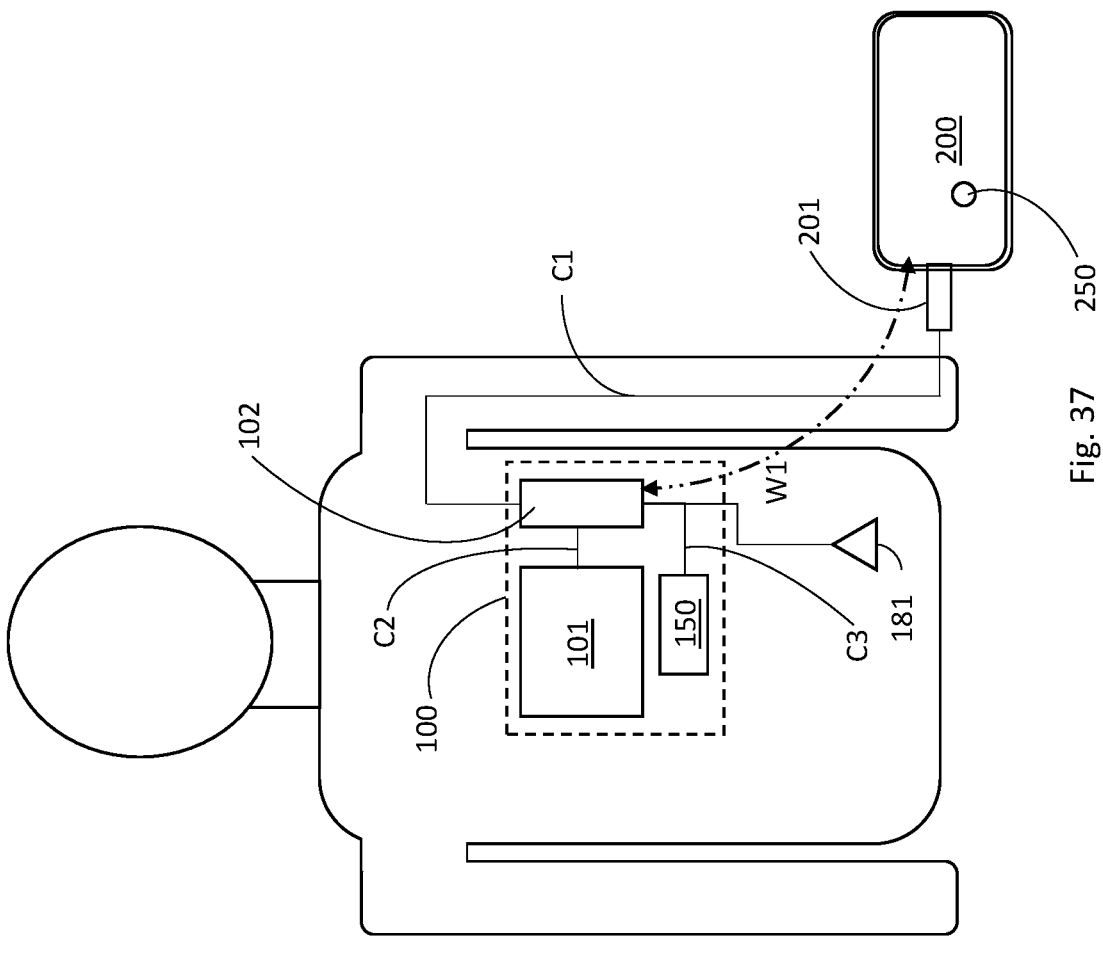
FIGS. 37-38 illustrate systems according to aspect 248SE comprising an implant in connection with an external device.
Figure 38:
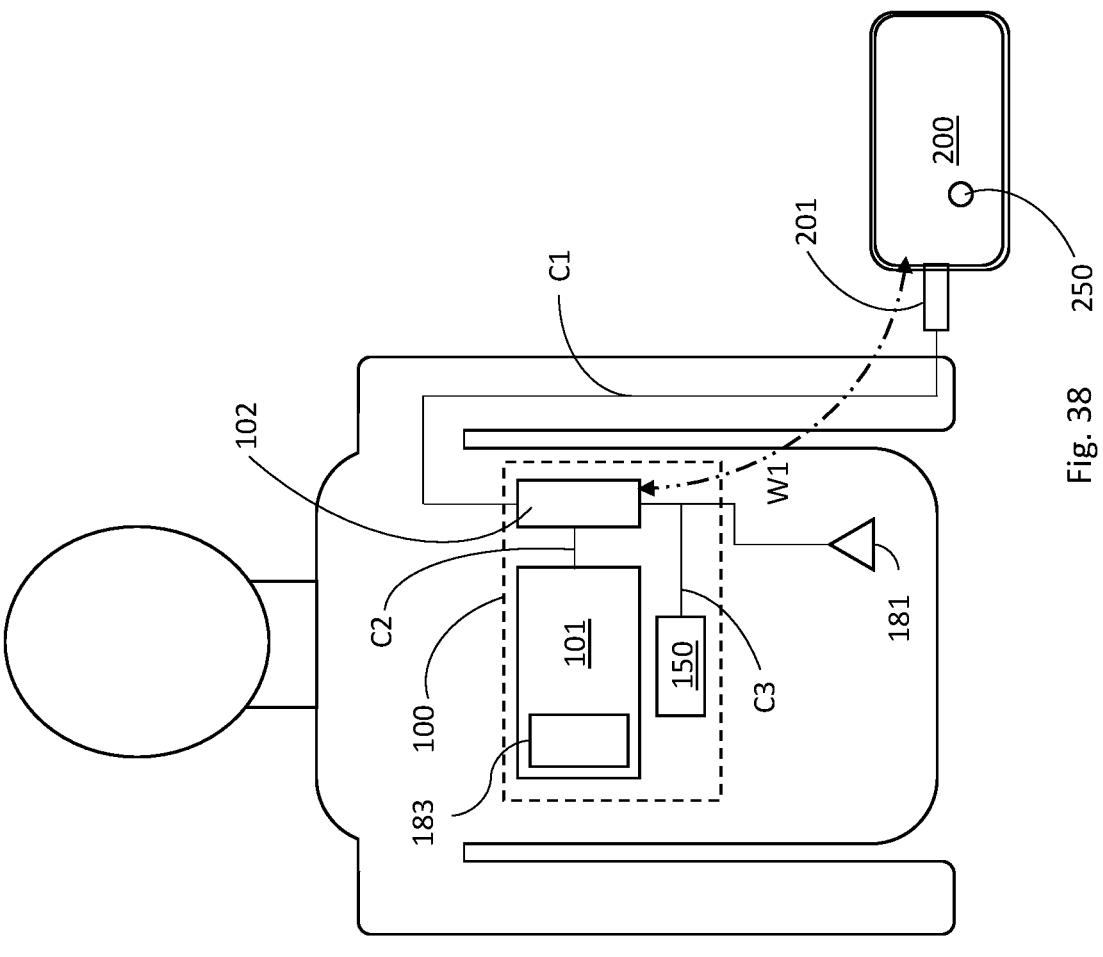

Aspect 248SE Device Synchronization
Sensation—Authenticating a Connection Between
an Implant and the External Device Using
Sensations—Embodiments of Aspect 248SE of the
Disclosure FIGS. 36, 37, and 38 show an implant 100 implanted in a patient and an external device 200. The figures further show the implant 100 being connected to a sensation generator 181.

The sensation generator 181 may be configured to generate a sensation. The sensation generator 181 may be contained within the implant 100 or be a separate unit. The sensation generator 181 may be implanted. The sensation generator 181 may also be located so that it is not implanted as such but still is in connection with a patient so that only the patient may experience sensations generated. The implant 100 is configured for storing authentication data, related to the sensation generated by the sensation generator 181.

The implant 100 is further configured for receiving input authentication data from the external device 200. Authentication data related to the sensation generated may by stored by a memory 107 of the implant 100. The authentication data may include information about the generated sensation such that it may be analyzed, e.g. compared, to input authentication data to authenticate the connection, communication, or device. Input authentication data relates to information generated by a patient input to the external device 200. The input authentication data may be the actual patient input or an encoded version of the patient input, encoded by the external device 200. Authentication data and input authentication data may comprise a number of sensations or sensation components.

The authentication data may comprise a timestamp. The input authentication data may comprise a timestamp of the input from the patient. The timestamps may be a time of the event such as the generation of a sensation by the sensation generator 181 or the creation of input authentication data by the patient. The timestamps may be encoded. The timestamps may feature arbitrary time units, i.e. not the actual time. Timestamps may be provided by an internal clock 160 of the implant 100 and an external clock 260 of the external device. The clocks 160, 260 may be synchronized with each other. The clocks 160, 260 may be synchronized by using a conductive connection C1 or a wireless connection W1 for communicating synchronization data from the external device 200, and its respective clock 260, to the implant 100, and its respective clock 160, and vice versa. Synchronization of the clocks 160, 260 may be performed continuously and may not be reliant on secure communication.

Authentication of the connection may comprise calculating a time difference between the timestamp of the sensation and the timestamp of the input from the patient, and upon determining that the time difference is less than a threshold, authenticating the connection. An example of a threshold may be 1 s. The analysis may also comprise a low threshold as to filter away input from the patient that is faster than normal human response times. The low threshold may e.g. be 50 ms.

Authentication data may comprise a number of times that the sensation is generated by the sensation generator, and wherein the input authentication data comprises an input from the patient relating to a number of times the patient detected the sensation. Authenticating the connection may then comprise: upon determining that the number of times that the authentication data and the input authentication data are equal, authenticating the connection.

FIG. 36 shows the implant 100 comprising a communication unit 102 which in turn may comprise an internal computing unit 106 and the memory 107. The internal computing unit 106 may be configured for analyzing the authentication data and the input authentication data and performing authentication of the connection based on the analysis. The internal computing unit 106 may form integrally a part of the communication unit 120, as shown, or be a separate unit of the implant 100.

The external device 200, adapted for connection with the implant, may comprise an interface for an input from the patient resulting in input authentication data. This interface may e.g. comprise an electrical switch, a biometric input sensor or a digital interface running on the external device 200 to name just a few examples. A biometric sensor may provide an extra level of authentication as the identity of the patient may be verified by providing input authentication. A digital interface may also provide an extra level of authentication by requiring for example input of a pass code known by the patient. An example of the biometric input sensor would be a fingerprint reader.

The external device 200 may further comprise a receiver for receiving the authentication data from the implant, the authentication data relating to a generated sensation of the sensation generator 181 connected to the implant 100. The receiver may be a transceiver 208 of the external device 200 or a separate unit. The external device 200 may further comprise an external computing unit 206. The external computing unit 206 may be configured for analyzing the authentication data to the input authentication data and performing authentication of the connection based on the analysis.

FIG. 36 further shows the implant 100 being in wireless W1 or conductive C1 communication with the external device 200. The connections may be used for communicating further data from the implant 100 to the external device 200 following positive authentication and vice versa. Further data may be communicated between the implant 100 and the external device 200 following positive authentication.

FIG. 38 shows the implant 100 comprising a motor 183. The motor may be adapted for controlling a physical function in the body of the patient. The motor 183 may be related to the active device 101 of the implant 100. The motor may further function as the sensation generator 181. The motor 183 may be used to generate the sensation. The motor 183 may specifically be adapted to generate a vibration or a sound by running or operating the motor 183. FIG. 38 further shows the implant 100 comprising a sensor 150, connected to the implant. The sensor 150 may be comprised within the implant 100 or be a separate unit.

The conductive connection or communication C1 discussed herein may be routed between the external device 200 and the implant 100 via a conductive member 201. Features of such communication are a subject of aspect 247SE. The communication may thus be provided with an extra layer of security by being electrically confined to the conducting path e.g. external device 200, conductive member 201, conductive connection C1, implant 100, meaning the communication will be excessively difficult to be intercepted by a third party not in physical contact with, or at least proximal to, the patient. Using the conductive connection C1 for communication input authentication data and authentication data related to.

Figure 39:
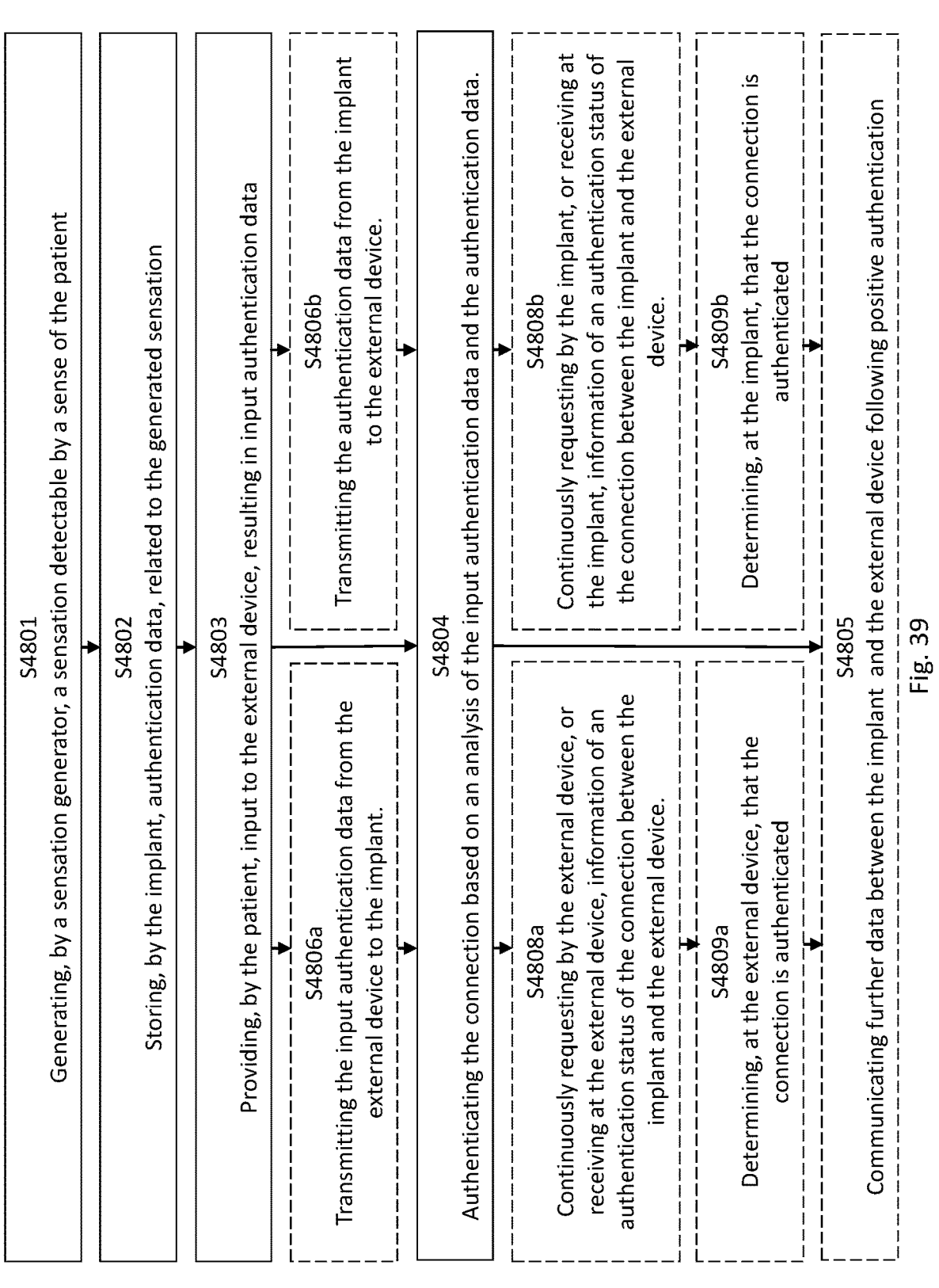
FIG. 39 illustrates a flowchart of methods according to embodiments of the first part of aspect 248SE.

FIG. 39 shows a schematic flow chart of the steps for the method of authenticating the connection between an implant 100 implanted in a patient, and an external device 200 according to the first part of aspect 248SE. The method includes the following steps.

Generating S4801, by a sensation generator 181, a sensation detectable by a sense of the patient. The sensation may comprise a plurality of sensation components. The sensation or sensation components may comprise a vibration, a sound, a photonic signal, a light signal, an electric signal, or a heat signal.

A vibration may comprise a single or sequence of vibrations of at least one frequency. A sound may be an audible sound with a frequency in the range 20-20000 Hz. A sound may comprise a plurality or a sequence of fixed frequency vibrations. Such a signal may be audible to an ear of the patient. Vibrations and sounds may also be configured to be registered by tactile, pressure, and pain receptors of the patient.

A photonic signal may be any electromagnetic wave-based signal such as a radio wave signal or an infrared light signal within the infrared wavelength range 700-1 mm. A light signal may comprise a signal based on visible light pulses in the wavelength range from 380-750 nm. A light signal is more preferably in the red sub-range of visible light i.e. >600 nm. Light signals may be visible to an eye of the patient. In general, longer wavelength photonic and light signals may be preferable for longer tissue penetration depths. An infrared signal may be configured to be visible by an infrared sensor or camera external to the body of the patient.

An electric signal may comprise a faint electric pulse configured to be felt by the patient. The power of the electric signal may be configured with feedback to increase until the signal is felt by the patient. Such a signal may be configured to be felt by pain receptors of the patient. A heat signal may comprise a thermodynamic signal with higher and lower temperature pulses. Such a signal may be configured to be felt by thermal receptors or pain receptors of the patient. A heat signal may be created by a thermal element.

Sensations may be configured to be consistently felt by a sense of the patient while not risking harm to or affecting internal biological processes of the patient.

The sensation generator 181, may be contained within the implant 100 or be a separate entity connected to the implant 100. The sensation may be generated by a motor 183 of the implant 100 for controlling a physical function in the body of the patient, wherein the motor being the sensation generator 181. The sensation may be a vibration, or a sound created by running the motor 183. The sensation generator 181 may be located close to a skin of the patient and thus also the sensory receptors of the skin. Thereby the strength of some signal types may be reduced.

Storing S4802, by the implant 100, authentication data, related to the generated sensation.

Providing S4803, by the patient input to the external device, resulting in input authentication data. Providing the input may e.g. comprise an engaging an electrical switch, using a biometric input sensor or entry into digital interface running on the external device 200 to name just a few examples.

Transmitting S4806a the input authentication data from the external device to the implant 100. If step S4806a was performed, the analysis may be performed by the implant 100.

Transmitting S4806b the authentication data from the implant 100 to the external device 200. If step S4806b was performed, the analysis may be performed by the external device 200. The wireless connection W1 or the conductive connection C1 may be used to transmit the authentication data or the input authentication data of steps S4806a and S4806b.

Authenticating S4804 the connection based on an analysis of the input authentication data and the authentication data e.g. by comparing a number of sensations generated and experienced or comparing timestamps of the authentication data and the input authentication data. If step S4806a was performed, the analysis may be performed by the implant 100.

Communicating S4805 further data between the implant and the external device following positive authentication.

The wireless connection W1 or the conductive connection C1 may be used to communicate the further data. The further data may comprise data for updating a control program 110 running in the implant 100, or operation instructions for operating the implant 100. The further data may also comprise data sensed by a sensor 150 connected to the implant 100.

If the analysis was performed by the implant 100, the external device 200 may continuously request or receive S4808*a*, information of an authentication status of the connection between the implant 100 and the external device 200, and upon determining S4809*a*, at the external device 200, that the connection is authenticated, transmitting S4805 further data from the external device 200 to the implant 100.

If the analysis was performed by the external device 200, the implant 100 may continuously request or receive S4808*b*, information of an authentication status of the connection between the implant 100 and the external device 200, and upon determining S4809*b*, at the implant 100, that the connection is authenticated, transmitting S4805 further data from the implant 100 to the external device 200.

A main advantage of authenticating a connection according to this fifth aspect is that only the patient may be able to experience the sensation. Thus, only the patient may be able to authenticate the connection by providing authentication input corresponding to the sensation generation.

The sensation generator 181, sensation, sensation components, authentication data, input authentication data, and further data may be further described herein under aspect 257SE. In these cases, the implant and/or external device(s) comprises the necessary features and functionality (described in the respective sections of this document). Further information and definitions can be found in this document in conjunction with the other aspects.

The method may further comprise transmitting further data between the implant and the external device, wherein the further data is used or acted upon, only after authentication of the connection is performed.

The analysis or step of analyzing may be understood as a comparison or a step of comparing.

The implant may comprise at least one of:
a pacemaker unit,
an external heart compression device,
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient,
an operable cosmetic implant,
an implant for adjusting or replacing any bone part of a body of the patient,
an implant replacing an organ of the patient or part of an organ of the patient or the function thereof,
a vascular treatment device, and
an implant adapted to move fluid inside the body of the patient.

A computer program product of, or adapted to be run on, an external device is also provided, which comprises a computer-readable storage medium with instructions adapted to make the external device perform the actions as described above.

Figures 49A, 49B, 49C:
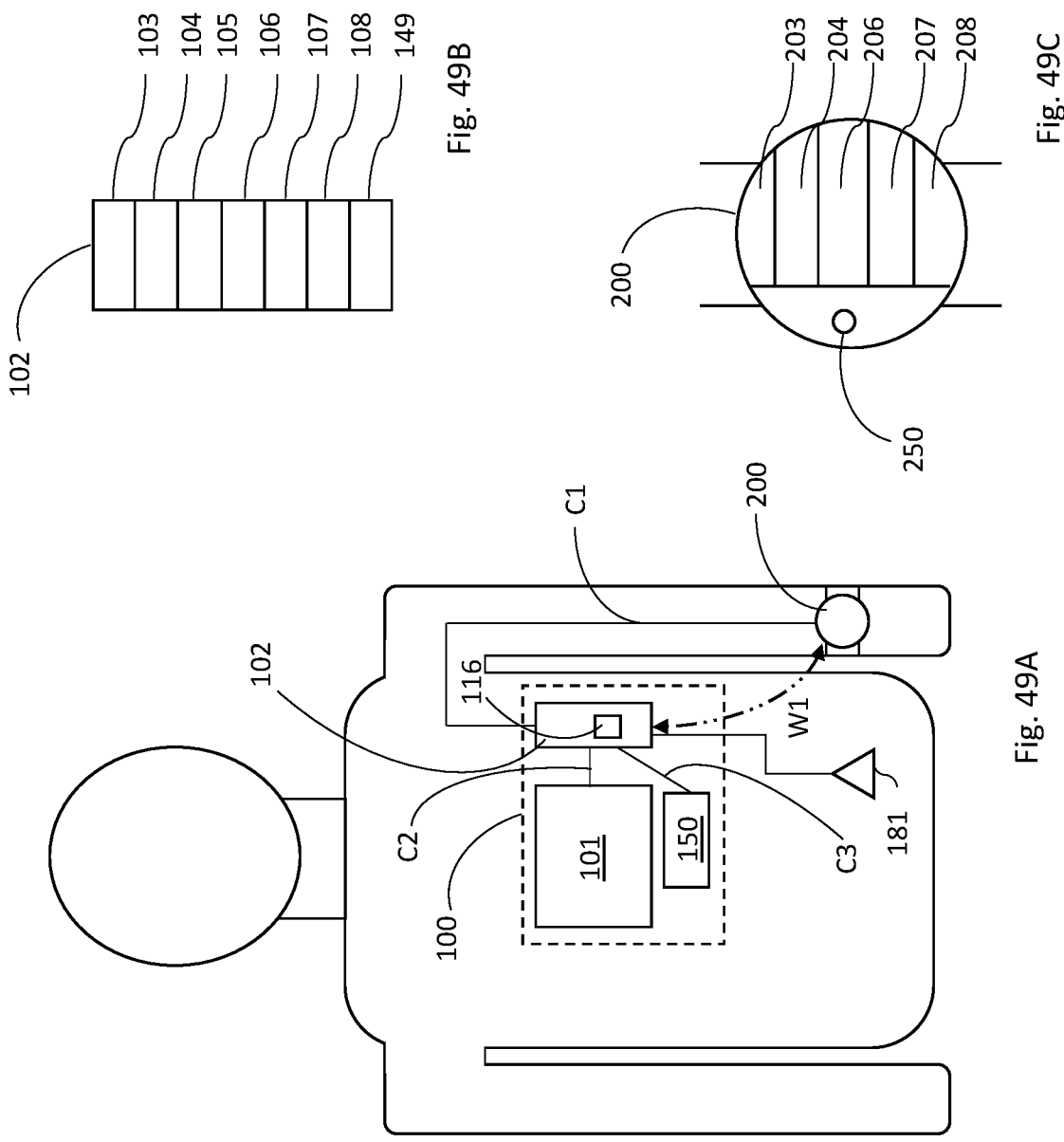
FIG. 49A illustrates a system comprising an implant, further illustrated in FIG. 49B, and an external device, further illustrated in FIG. 49C, all according to aspect 249SE.
Figure 50:
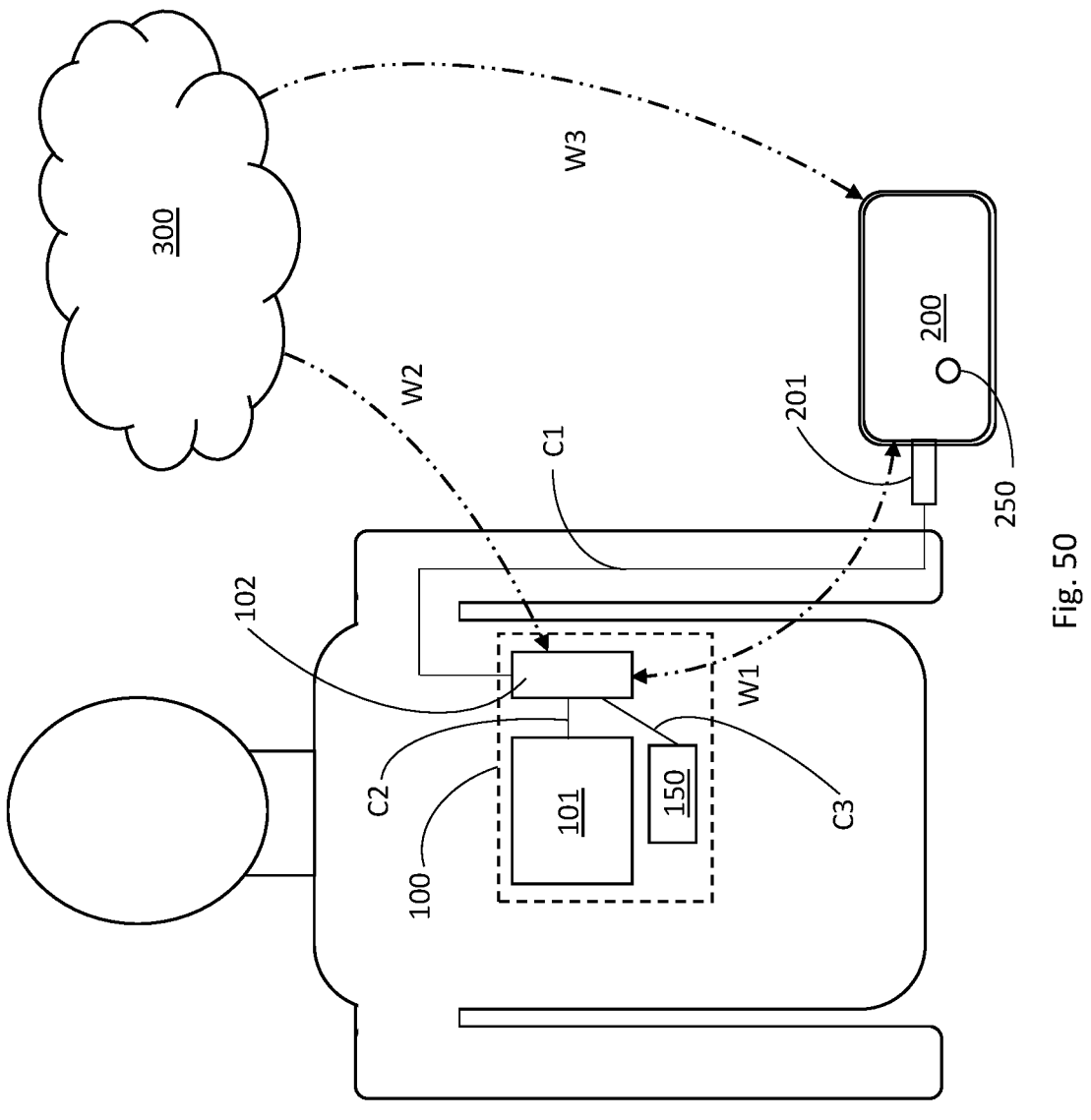
FIG. 50 illustrates a system according to aspect 249SE comprising an implant, an external device, and a second external device, all connected with each other.

Aspect 249SE Prior Verified Communication—Verifying Authenticity of Instructions Sent from the External Device to the Implant—Embodiments of Aspect 249SE of the Disclosure In aspect 249SE, increased security for communication between an external device(s) and an implant is provided. FIGS. 40-50 shows embodiments of this aspect. FIG. 49A-C shows embodiments of an implant 100, a communication unit 102 and an external device 200 which may form a system.

The implant 100 comprises a transceiver 108, 103 configured to establish a connection with an external device 200. i.e. with a corresponding transceiver 208, 203. The connection may be an electrical connection C1 using the transceivers 103, 203, or a wireless connection W1 using the transceivers 108, 208. The implant further comprising a computing unit 106 configured to verify the authenticity of instructions received at the transceiver 108, 103 from the external device 200. In this aspect, the concept of using previously transmitted instructions for verifying a currently transmitted instructions are employed. Consequently, the transmitting node (in this case the external device) need to be aware of previously instructions transmitted to the implant, which reduces the risk of a malicious device instructing the implant without having the authority to do so.

FIG. 40 shows one embodiment of verifying the authenticity of instructions received at the implant, the embodiment relating to communicating instructions from an external device 200 to an implant 100 implanted in a patient, using an established S4910 connection between the external device 200 and the implant 100. The connection may be a conductive communication link, or a wireless communication link.

In this embodiment, the computing unit 106 is configured to verify the authenticity of instructions received at the transceiver 108, 103 by extracting a previously transmitted set of instructions from a first combined set of instructions received by the transceiver. The external device 200 may thus comprise an external device comprising a computing unit 206 configured for: combining a first set of instructions with a previously transmitted set of instructions, forming a combined set of instructions, and transmitting the combined set of instructions to the implant. The previously transmitted set of instructions, or a representation thereof, may be stored in memory 207 of the external device 200.

The combined set of instructions may have a data format which facilitates such extraction, for example including metadata identifying data relating to the previously transmitted set of instructions in the combined set of instructions. In some embodiments, the combined set of instructions comprises the first set of instructions and a cryptographic hash of the previously transmitted set of instructions. Consequently, the method comprises combining S4920, at the external device, a first set of instructions with a previously transmitted set of instructions, forming a first combined set of instructions. A cryptographic hash function is a special class of hash function that has certain properties which make it suitable for use in cryptography. It is a mathematical algorithm that maps data of arbitrary size to a bit string of a fixed size (a hash) and is designed to be a one-way function, that is, a function which is infeasible to invert. Examples include MD 5, SHA 1. SHA 256, etc. Increased security is thus achieved.

The first combined set of instructions is then transmitted S4930 to the implant 100, where it is received by e.g. the transceiver 103, 108. The first combined set of instructions may be transmitted to the implant using a proprietary network protocol. The first combined set of instructions may be transmitted to the implant using a standard network protocol. More embodiments describing network protocols may be implemented as described herein under aspect 250SE. In these cases, the implant and/or external device(s) comprises the necessary features and functionality (described in the respective sections of this document) for performing transmission of data. By using different communication protocols, at the external device 200, for communication to the implant 100 and a second external device 300, as described in aspect 250SE, an extra layer of security is added as the communication between implant and the external device may be made less directly accessible to remote third parties.

At the implant 100, the computing unit verifies S4930 the authenticity of the received first combined set of instructions, by: extracting S4941 the previously transmitted set of instructions from the first combined set of instructions, and comparing S4942*a* the extracted previously transmitted set of instructions with previously received instructions stored in the implant.

Upon determining that the extracted previously transmitted set of instructions equals the previously received instructions stored in the implant, the authenticity of the received first combined set of instructions may be determined as valid, and consequently, the first set of instructions may be safely run S4943*a* at the implant, and the first combined set of instructions may be stored in memory 107 of the implant, to be used for verifying a subsequent received set of instructions.

In some embodiments, upon determining by the internal computing unit 106 that the extracted previously transmitted set of instructions differs from the previously received instructions stored in the implant, feedback related to an unauthorized attempt to instruct the implant may be provided S4943*b*. For example, the transceiver 108, 103 may send out a distress signal to e.g. the external device 200 or to any other connected devices. The implant 100 may otherwise inform the patient that something is wrong by e.g. vibration or audio. The implant 100 may be run in safe mode, using a preconfigured control program which is stored in memory 107 and specifically set up for these situations, e.g. by requiring specific encoding to instruct the implant, or only allow a predetermined device (e.g. provided by the manufacturer) to instruct the implant 100. In some embodiments, when receiving such feedback at the external device 200, the external device 200 retransmits S4930 the first combined set of instructions again, since the unauthorized attempt may in reality be an error in transmission (where bits of the combined set of instructions are lost in transmission), and where the attempt to instruct the implant is indeed authorized.

The step of comparing S4942 the extracted previously transmitted set of instructions with previously received instructions stored in the implant may be done in different ways. For example, as shown in FIG. 41 the step of comparing S4942 the extracted previously transmitted set of instructions with previously received instructions stored in the implant comprises calculating S4942*a* a difference between the extracted previously transmitted set of instructions with previously received instructions stored in the implant, and comparing S4942*b* the difference with a threshold value, wherein the extracted previously transmitted set of instructions is determined to equal the previously received instructions stored in the implant in the case of the difference value not exceeding the threshold value. This embodiment may be used when received instructions is stored in clear text, or a representation thereof, in the implant, and where the combined set of instructions, transmitted S4930 from the external device also includes such a representation of the previously transmitted instructions. This embodiment may be robust against error in transmission where bits of information are lost or otherwise scrambled.

In other embodiments, shown in FIG. 42, the combined set of instructions comprises the first set of instructions and a cryptographic hash of the previously transmitted set of instructions, wherein the method further comprises, at the implant, calculating S4944*a* a cryptographic hash of the previously received instructions stored in the implant and comparing S4944*b* the calculated cryptographic hash to the cryptographic hash included in the first combined set of instructions. This embodiment provides increased security since the cryptographic hash is difficult to decode or forge.

Figure 43:
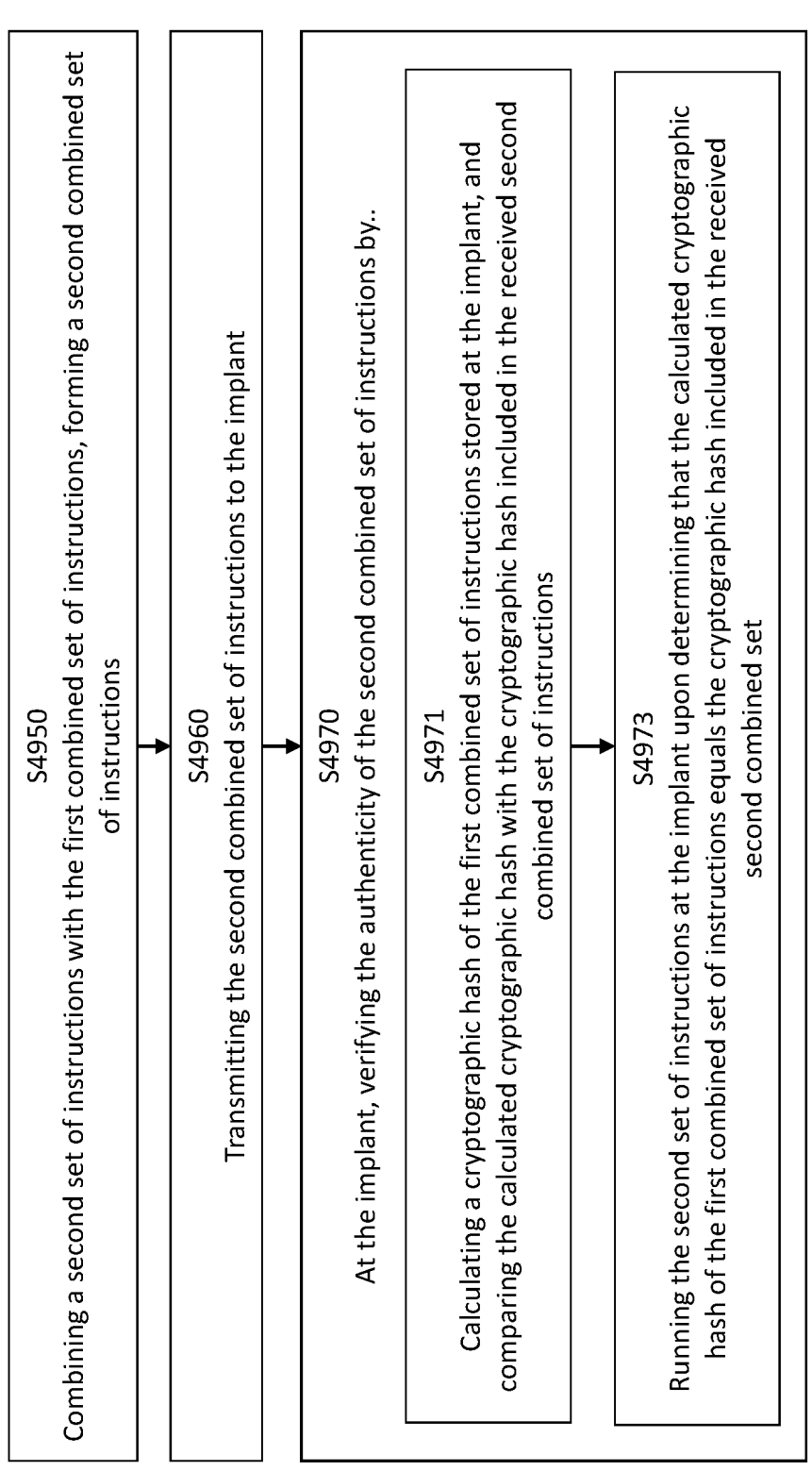

As shown in FIG. 43, the above way of verifying the authenticity of received instructions at the implant may be iteratively employed for further sets if instructions. These embodiments comprise combining S4950, at the external device 200, a second set of instructions with the first combined set of instructions, forming a second combined set of instructions, wherein the second combined set of instructions comprises a cryptographic hash of the first combined set of instructions. The second combined set of instructions is transmitted S4960 to the implant 100. At the implant, the authenticity of the second combined set of instructions may be verified S4970 by: calculating S4971 a cryptographic hash of the first combined set of instructions stored in the implant, and comparing the calculated cryptographic hash with the cryptographic hash included in the received second combined set of instructions, and upon determining that the calculated cryptographic hash of the first combined set of instructions equals the cryptographic hash included in the received second combined set, running S4973 the second set of instructions at the implant and storing the second combined set of instruction in the implant, to be used for verifying a subsequent received set of instructions. Since the first combined set of instructions stored at the implant comprises the hash of the data of the received previous sets of instructions (above called the previously received instructions stored in the implant, which herein refers to the genesis block, or the originally received first set of instructions at the implant), the security of the authenticity of the received set of instructions may be further increased for each received set of instructions.

To further increase security, the transmission of a first set of instructions, to be stored at the implant 100 for verifying subsequent sets of combined instructions, where each set of received combined instructions will comprise data which in some form will represent, or be based on the first set of instruction, may be performed according to the following examples.

Figure 44:
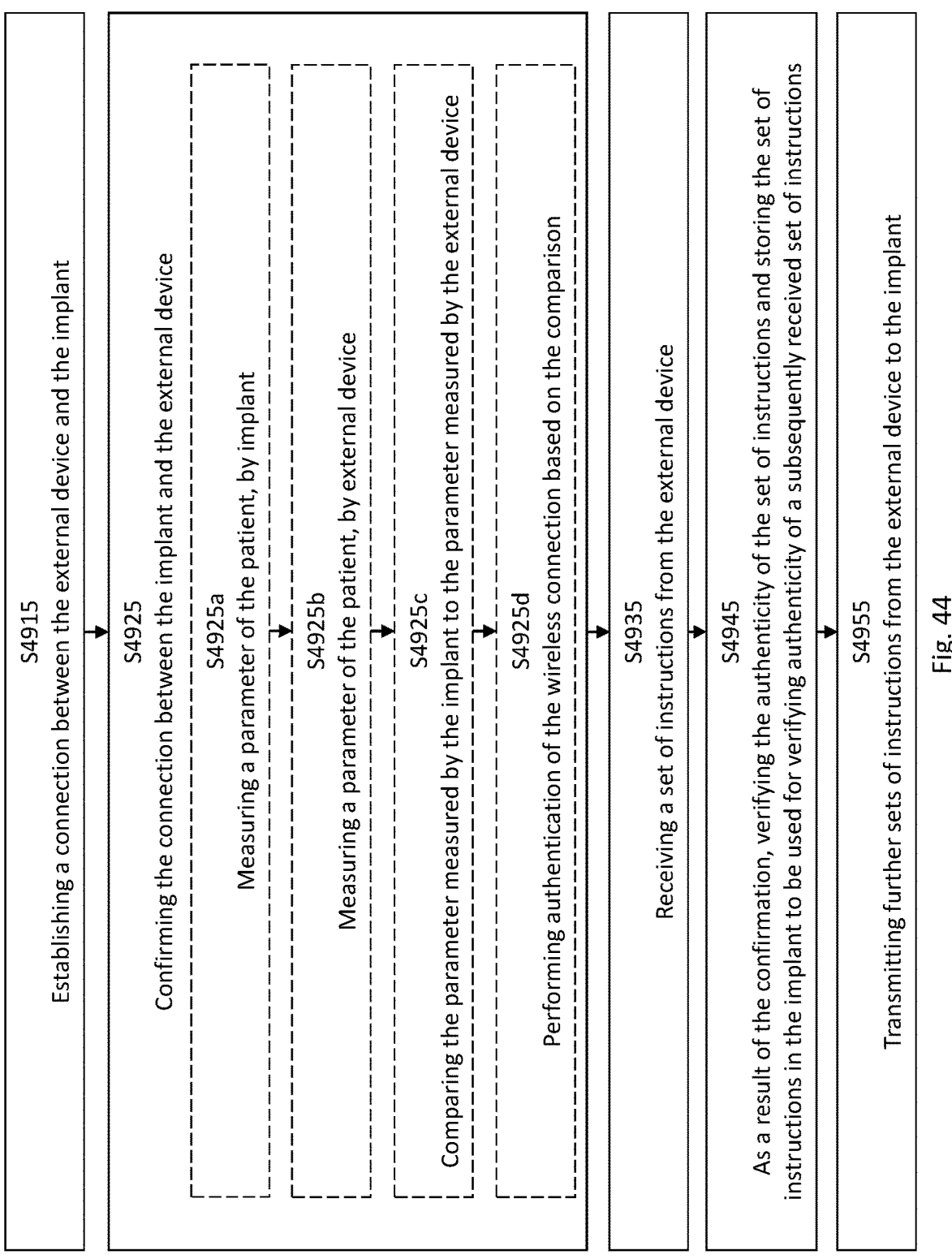

In some embodiments, shown in FIG. 44, method of communicating instructions from the external device 200 to the implant 100 implanted in a patient is disclosed, comprising the steps of: establishing S4915 a connection between the external device and the implant, confirming S4925 the connection between the implant and the external device, receiving S4935 a set of instructions from the external device, as a result of the confirmation, verifying S4945 the authenticity of the set of instructions and storing the set of instructions in the implant to be used for verifying authenticity of a subsequently received set of instructions.

The set of instructions may subsequently be included according to the above in a received combined set of instructions, and the set of instructions stored in the implant may be used to verify the authenticity of the combined set of instructions according to the above.

The step of confirming S4925 the connection between the implant and the external device may include: measuring S4925a a parameter of the patient, by implant, measuring S4925b a parameter of the patient, by external device, comparing S4925c the parameter measured by the implant to the parameter measured by the external device, and performing S4925d authentication of the connection based on the comparison. This is shown in FIG. 44.

Figure 45:
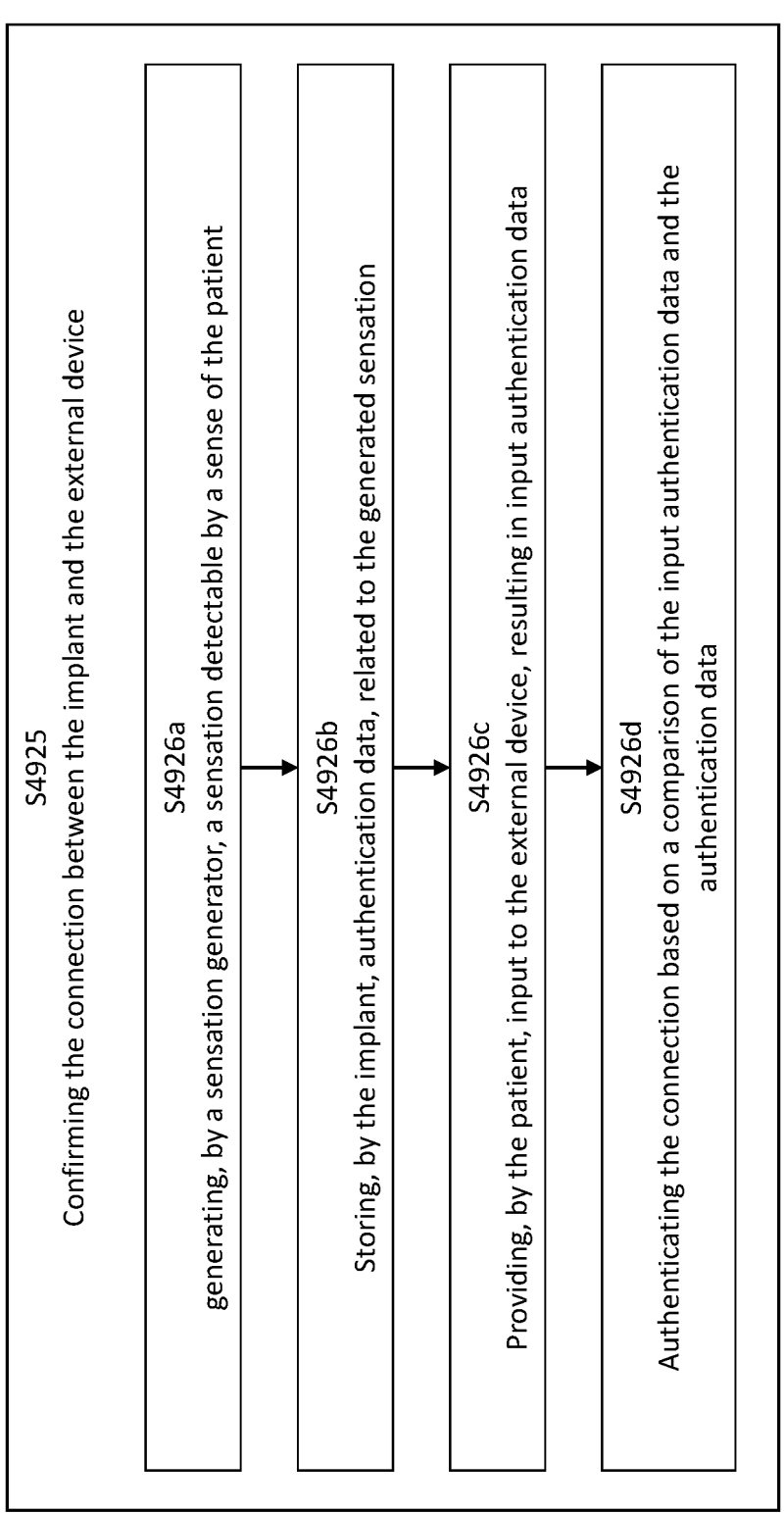

The step of confirming S4925 the connection between the implant and the external device may include: generating S4926a, by a sensation generator, a sensation detectable by a sense of the patient, storing S4926b, by the implant, authentication data, related to the generated sensation, providing S4926c, by the patient, input to the external device, resulting in input authentication data, authenticating S4926d the connection based on a comparison of the input authentication data and the authentication data. This is shown in FIG. 45.

The confirmation and authentication of the connection may be performed as described herein under the fifth, thirteenth and fifteenth aspect. In these cases, the implant and/or external device(s) comprises the necessary features and functionality (described in the respective sections of this document) for performing such authentication. By authenticating according to these aspects, security of the authentication may be increased as it may require a malicious third party to know or gain access to either the transient physiological parameter of the patient or detect randomized sensations generated at or within the patient.

In other embodiments, other ways of increasing the security of the genesis block, i.e. the transmission of a first set of instructions, to be stored at the implant 100 for verifying subsequent sets of combined instructions, may be employed. For example, as shown in FIG. 46, by placing S4951 a conductive member 201 (see FIG. 50), configured to be in connection with the external device 200, in electrical connection C1 with a skin of the patient for conductive communication with the implant, transmitting S4952, via the electrical connection using conductive communication, a set of instructions from the external device, receiving S4953, at the implant the set of instructions from the external device, storing S4954 the set of instructions in the implant to be used for verifying authenticity of a subsequently received set of instructions. Consequently, it may be ensured that the genesis block is transmitted from a device under control of the patient in which the implant is implanted. Optionally, prior to transmitting, via the electrical connection using conductive communication, a set of instructions from the external device, authentication input may be received S4956 from a user by a verification unit 220 of the external device, and the conductive communication between the implant and the external device may be authenticated S4957 using the authentication input. As a result of the authentication, i.e. if the verification is correct/valid (correct code, valid finger print, etc.), the set of instructions may be transmitted S4952, via the electrical connection C1 using conductive communication, from the external device 200 to the implant 100.

Further information and details around the conductive member and other involved devices and processes for achieving a conductive communication may be performed as described herein under aspect 247SE. In these cases, the implant and/or external device(s) comprises the necessary features and functionality (described in the respective sections of this document) for performing such a conductive communication.

In other embodiments, other ways of increasing security for an authorized transmission of the genesis block may be employed. For example, as shown in FIG. 47, a set of instructions may be received S4963, using a wireless transmission W2, at the implant 100 from a second external device 300, which set of instructions may be stored S4954 in the implant to be used for verifying authenticity of a subsequently received set of instructions from the external device 100. The second external device 300 may be a device with higher trust, such as for example a device under control of the hospital, care taker, manufacturer etc. The second external device 300 may transmit the set of instructions using a proprietary network protocol to further increase security (e.g. as described herein under aspect 250SE). This may improve security of authentication by adding another layer in the communication.

In this embodiment, the external device is configured to receive W3 a set of instructions (e.g. the genesis block) from the second external device 300, store said set of instructions, wherein the external device comprises a computing unit 206 configured to combining a first set of instructions with a said stored set of instructions, thus forming a combined set of instructions, transmitting the combined set of instructions to the implant.

Optionally, the set of instructions received by the implant 100 from the second external device 200 is encrypted, wherein the method further comprising decrypting S4966 the set of instructions and storing S4954 the decrypted set of instructions in the implant to be used for verifying authenticity of a subsequently received set of instructions from the external device.

According to some embodiments, as shown in FIG. 48, a reset function or switch 116 (shown in FIG. 49A) at the implant may be employed to delete S4982 any previously received instructions stored in the implant 100, by being activated S4981. Further information and details around the reset function or switch 116 and other involved devices and processes for handling such reset function or switch 116 may be performed as described herein under the aspect 244SE. In these cases, the implant and/or external device(s) comprises the necessary features and functionality (described in the respective sections of this document) for performing such a resetting of the implant 100. Such a scheme for resetting or deleting instructions from the implant may increase the security of the implant by requiring a physical reset action to be performed. As such, remote resetting, with malicious intent, may be prevented.

Any of the above embodiments for transmitting a "new" genesis block to the implant 100 may subsequently be employed.

The implant may comprise at least one of:
a pacemaker unit.
an external heart compression device.
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient.

an operable cosmetic implant, an implant for adjusting or replacing any bone part of a body of the patient.

an implant replacing an organ of the patient or part of an organ of the patient or the function thereof, a vascular treatment device, and an implant adapted to move fluid inside the body of the patient.

Further information and definitions of features, functionality of this aspect can be found in this document in conjunction with the other aspects.

Aspect 250SE Dual Protocols—Two Wireless Communication Protocols for Communication—Embodiments of Aspect 250SE of the Disclosure In aspect 250SE, methods and devices and systems for communication between external device(s) and an implant are provided. FIGS. 51-55 show embodiments of this aspect. Generally, the use of standard network protocols for communication between the external devices, and a proprietary network protocol for communication between an external device and the implant provides an increased security for communication in such a system. When limiting communication with the implant to the use of a proprietary network protocol, the risk of a malicious device instructing the implant without having the authority to do so is reduced.

Figures 51A, 51B, 51C:
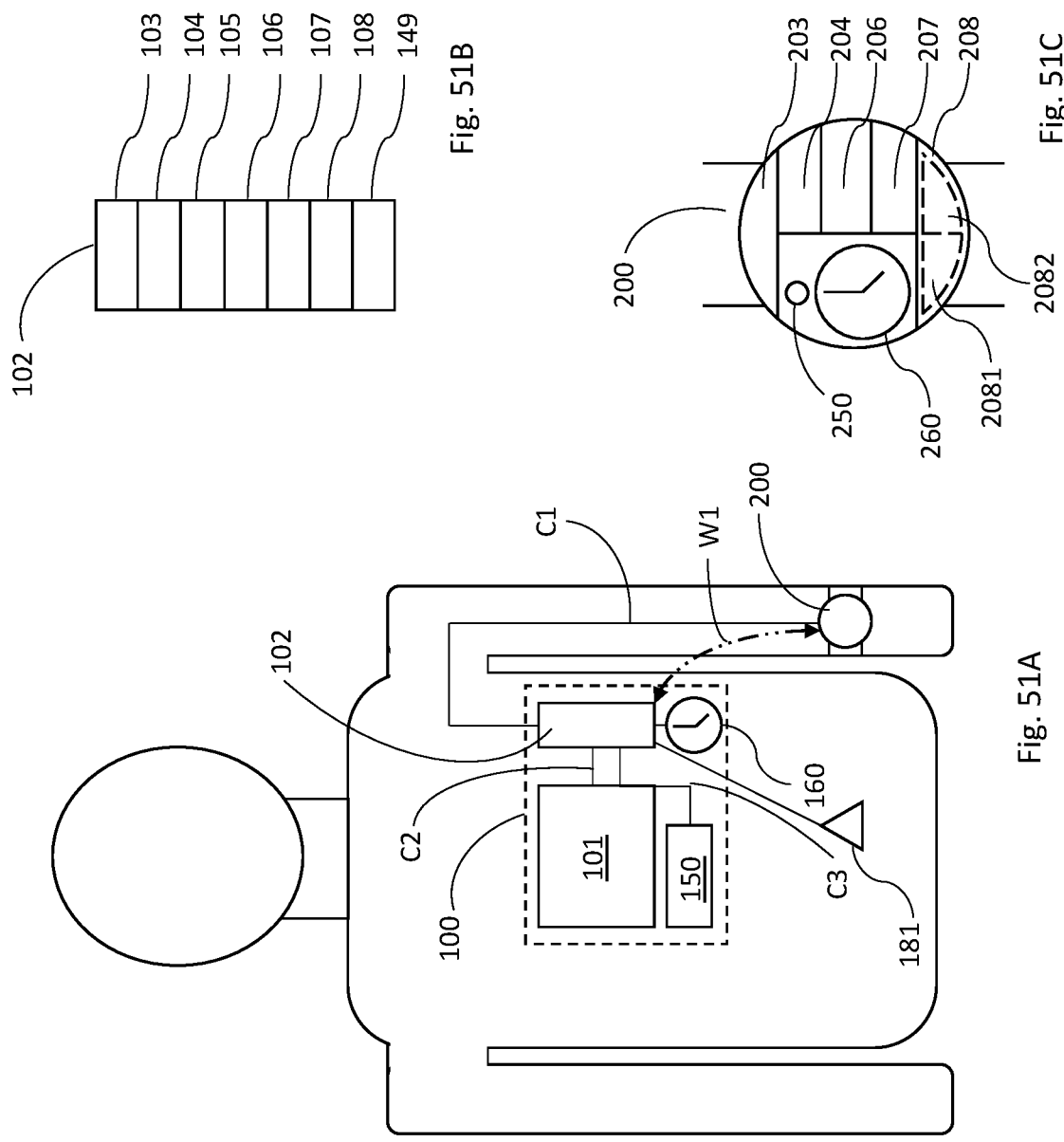
FIG. 51A illustrates a system comprising an implant, further illustrated in FIG. 51B, and an external device, further illustrated in FIG. 51C, all according to aspect 250SE.
Figure 52:
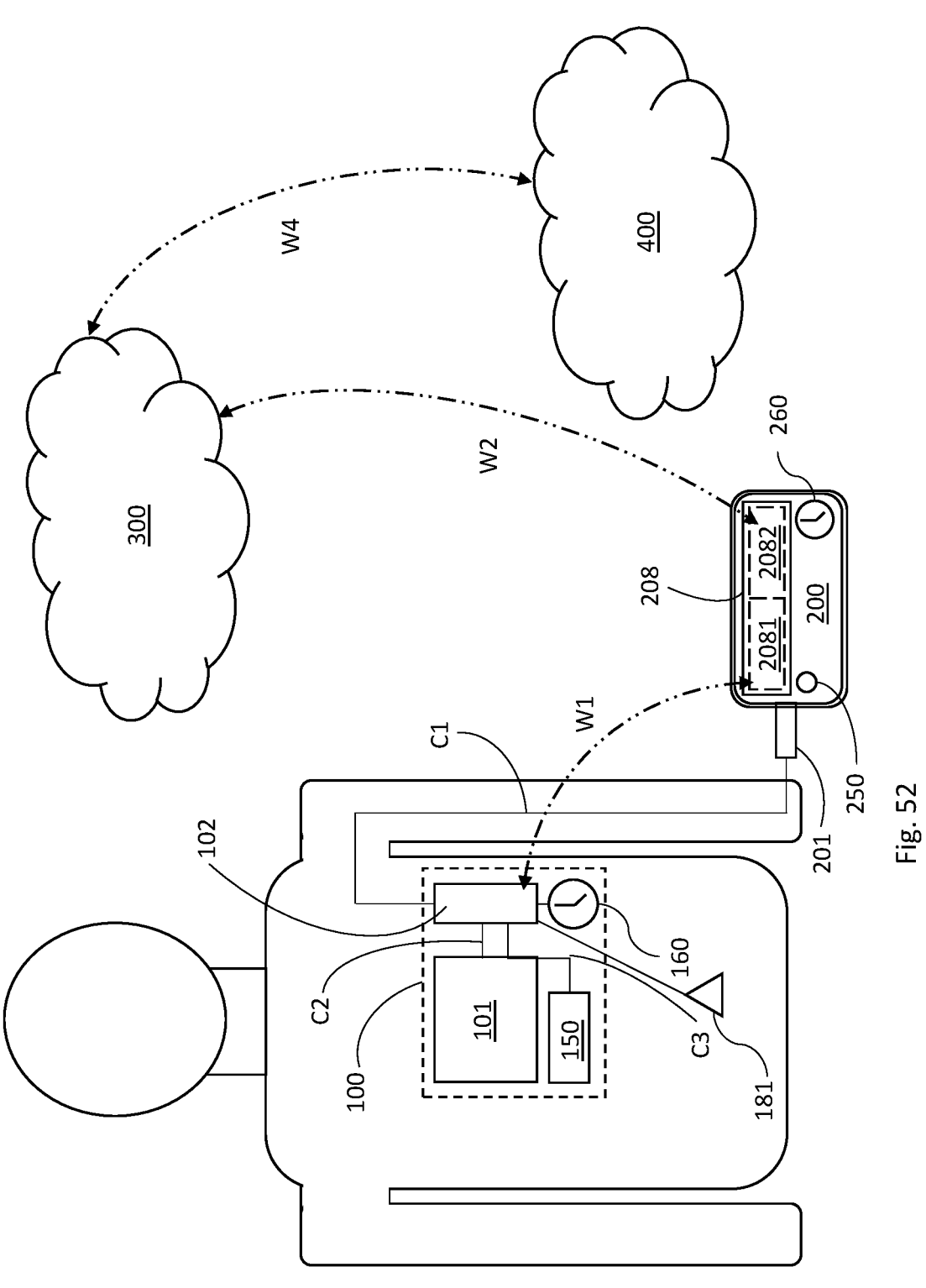
FIG. 52 illustrates a system according to aspect 250SE comprising an implant in connection with an external device wherein the external device is in connection with a second external device wherein the second is in connection with a third external device.

FIG. 51A-C shows example embodiments of an implant 100, a communication unit 102 of an implant 100 and an external device 200 configured to communicate with the implant. FIG. 52 shows embodiments of an implant 100, external devices 200, 300, 400 which may form a system.

As shown in FIGS. 51C and 52, the external device 200 comprises at least one wireless transceiver 208 configured for wireless communication W1. W2 with the second external device 300 and the implant 100, wherein the wireless transceiver 208 is configured to communicate W1 with the implant 100 using a proprietary network protocol. As shown in FIG. 53, the communication from the external device 200 may comprise establishing S5001 wireless communication W1. W2 between at least one wireless transceiver 208 of an external device 200 and a second external device 300 and the implant 100, wherein the communication W1 between the external device 200 and the implant 100 uses S5002 a proprietary network protocol, and wherein the wireless communication W2 between the external device 200 and the second external device uses S5003 a standard network protocol.

The implant 100 comprises a wireless receiver configured for receiving W1 communication using the proprietary network protocol. The wireless receiver of the implant 100 may be configured for only receiving communication using the proprietary network protocol, for example by having an antenna of the wireless receiver of the implant 100 configured to only receive in a first frequency band, wherein frequency band of the proprietary network protocol is included in the first frequency band. In other embodiments, a computing unit 106 of the implant may be configured to discard any communication received by the implant 100 which is not in the proprietary network protocol. In yet other embodiments, the computing unit 106 of the implant 100 may be configured to operate the implant 100 or otherwise instruct the implant 100 (or an active unit 101 thereof) only using instructions received in the proprietary network protocol. In other words, the computing unit 106 may be configured to only altering an operation of the implant 100 based on data received using the proprietary network protocol.

The frequency band of the standard network protocol may in some embodiments not be included in the first frequency band of the proprietary network protocol.

The communication between the implant 100 and the external device 200 may be further authenticated, to further increase security of communication. Such embodiments are described in FIGS. 54-55. The wireless communication between the external device 200 and the implant may be authenticated S5004. In these embodiments, following positive authentication, data between the implant and the external device (in any direction) using the proprietary network protocol may be communicated W1.

In the embodiment of FIG. 54, the authentication S5004 comprises measuring S5005 a parameter of the patient, by the external device, receiving S5006 a parameter of the patient, from the implant, comparing S5007 the parameter measured by the external device to the parameter measured by the implant, and performing S5008 authentication of a wireless connection based on the comparison. The external device may comprise sensor 250 for measuring S5005 a parameter of the patient, an external computing unit 206 configured for: receiving S5006 a parameter of the patient, from the implant, comparing S5007 the parameter measured by the external device to the parameter measured by the implant, and performing S5008 authentication of a wireless connection with the implant based on the comparison. The implant comprises an internal sensor 150 for measuring the parameter of the patient. The sensors 150, 250 may be configured to measure a pulse of the patient. The sensors 150, 250 may be configured to measure a respiration rate of the patient. The sensors 150, 250 may be configured to measure a temperature of the patient. The sensors 150, 250 may be configured to measure at least one sound of the patient. The sensors 150, 250 may be configured to measure at least one physical movement of the patient. The measured parameter, by the external device 200 may be provided with a timestamp and the measured parameter received from the implant 100 may be provided with a timestamp, wherein the comparison S5007 of the parameter measured at the implant 100 to the parameter measured by the external device 200 may comprise comparing the timestamp of the measured parameter received from the implant 100 to the timestamp of the measured parameter by the external device 200. For this reason, the external device may comprise a clock 260, configured for synchronization with a clock 160 of the implant. For example, in case the timestamps differ more than a threshold period, the wireless communication W1 is not authenticated S5008. In some embodiments, step of comparing S5007 the parameter measured by the implant 100 to the parameter measured by the external device 200 comprises calculating a difference value between the parameter measured by the implant 100 and the parameter measured by the external device 200, wherein the step of performing authentication comprises: authenticating S5008 the wireless connection W1 if the difference value is less than a predetermined threshold difference value, and not authenticating S5008 the wireless connection W1 if the difference value equals or exceeds the predetermined threshold difference value. In other embodiments, the authentication is performed by the implant 100. Further information, details and embodiments of the confirmation/authentication of the communication W1 described in FIG. 54 may be found herein under aspect 256SE. In these cases, the implant and/or external device(s) comprises the necessary features and functionality (described in the respective sections of this document) for performing such authentication.

Figure 55:
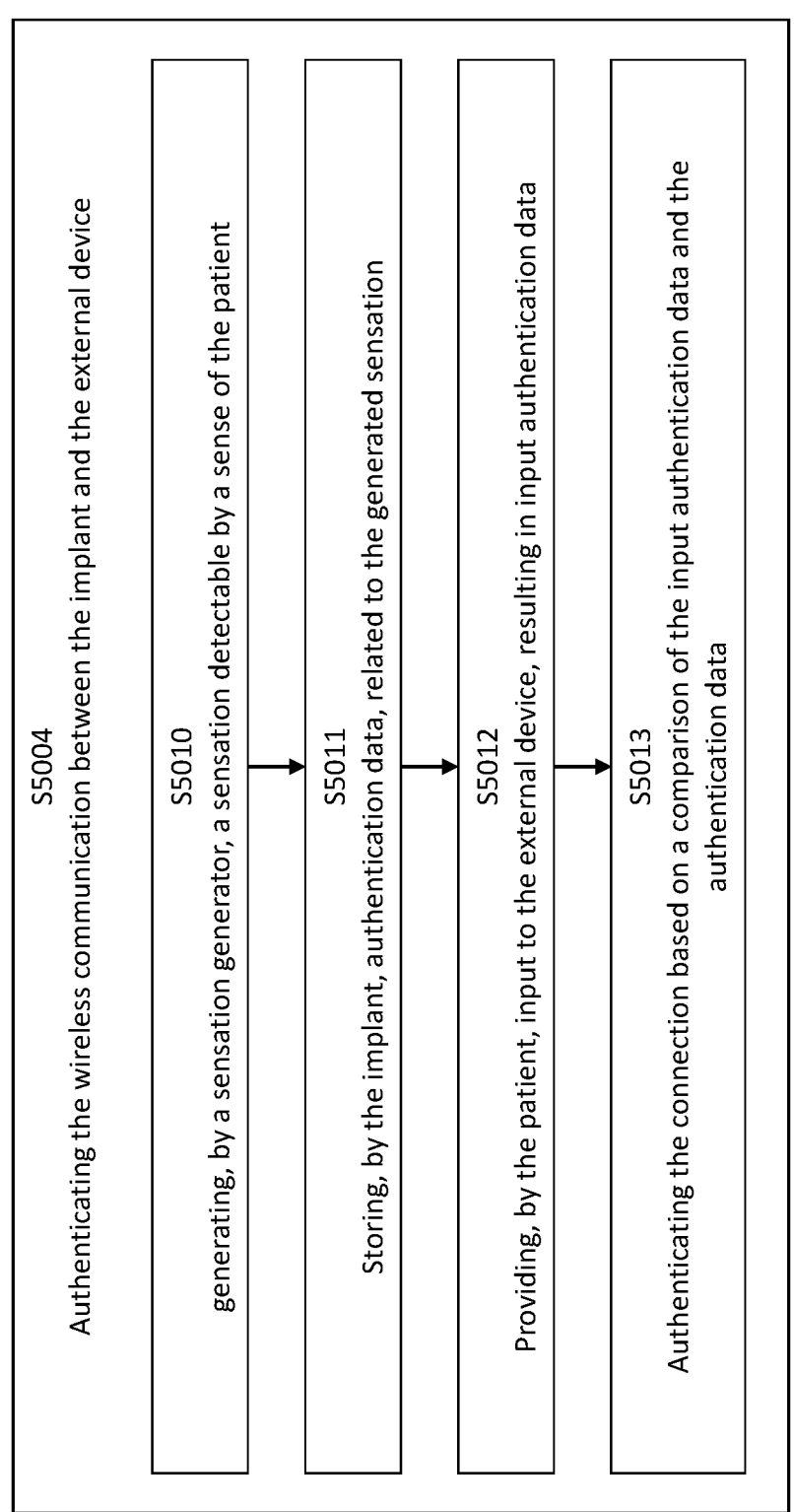

In the embodiment of FIG. 55, the authentication S5004 comprises generating S510, by a sensation generator 181 of the implant 100, a sensation detectable by a sense of the patient, storing S5011, by the implant (in memory 107), authentication data, related to the generated sensation, providing S5012, by the patient, input to the external device 200, resulting in input authentication data, and authenticating S5013 the wireless communication W1 based on a comparison of the input authentication data and the authentication data. The authentication S5013 may be performed by either the external device 200 or the implant 100. Further information, details and embodiments of the confirmation/ authentication of the communication W1 described in FIG. 55 may be found herein under the fifth and fifteenth aspects. In these cases, the implant and/or external device(s) comprises the necessary features and functionality (described in the respective sections of this document) for performing such authentication.

In some embodiments, the external device is configured to be placed in electrical connection C1 with a conductive member 201, for conductive communication with the implant. In some embodiments, such conductive communication path C1 needs to be established before the computing unit 106 of the implant alters an operation of the implant based on data received using the proprietary network protocol. In other embodiments, such conductive communication path C1 needs to be established before the wireless receiver of the implant will received wireless communication W1 from the implant. Further information, details and embodiments of conductive communication between the implant 100 and the external device 200 using a conductive member 201 connected to the external device may be found herein under aspect 247SE. In these cases, the implant and/or external device(s) comprises the necessary features and functionality (described in the respective sections of this document) for performing such authentication.

It should also be noted that the wireless communication W1 between the external device 200 and the implant may be encrypted, for example as described herein under the second and third aspects. In these cases, the implant and/or external device(s) comprises the necessary features and functionality (described in the respective sections of this document) for performing such authentication. Consequently, even if the encrypted communication is intercepted by a third party, that third part may need to acquire ciphers or keys to decrypt the communication and access the information. This adds extra security to the communication.

Returning now to FIGS. 1-2. Further, the at least one wireless transceiver 208 is configured to communicate W2 with the second external device 300 using a standard network protocol. The external device 200 may in some embodiments be a wearable external device (such as a smart watch as in FIG. 51A. C) or a handset (such as a smart phone as in FIG. 52).

The second external device 300 may be a physical device or cloud based and may in some embodiments be operated by a caretaker of the patient, such as medical staff.

The system may in some embodiments further comprise a third external device 400, which may communicate with the second external device 300, for example using a wireless communication W4, or a wired communication. The third external device may be operated by a caretaker of the patient.

The at least one wireless transceiver 208 may comprise a first wireless transceiver 2081 configured for communicating W2 with the second external device 300, and a second wireless transceiver 2082 configured for communicating W1 with the implant 100. The external device 200 may in other embodiments comprise a computing unit 206 adapted for configuring the at least one wireless transceiver 208 to communicate W1 with the implant using the proprietary network protocol and adapted for configuring the at least one wireless transceiver 208 to communicate W2 with the second external device using the standard network protocol.

Any suitable standard protocol may be used for communication between the external device 200 and the second external device 300. Consequently, the second external device may be any device (from any manufacturer) adapted to communicate using the standard protocol. Flexibility of the system is thus improved. The standard network protocol may be one from the list of: a Radio Frequency type protocol, a RFID type protocol, a WLAN type protocol, a Bluetooth type protocol, a BLE type protocol, a NFC type protocol, a 3G/4G/5G type protocol, and a GSM type protocol.

The communication range of the proprietary network protocol may be less than a communication range of the standard network protocol. For example, the communication range may be less than 1 meter, or less than 0.5 meters. Embodiments for achieving such short-range communication is described herein under aspect 251SE. In these cases, the implant and/or external device(s) comprises the necessary features and functionality (described in the respective sections of this document) for performing such authentication. Consequently, security is further improved since the external device 200 may need to be closely positioned to the implant 100 (i.e. under control of the patient in which the implant 100 is implanted) to be able to communicate with the implant. In one embodiment, the frequency band of the proprietary network protocol is 13.56 MHZ, which is the available unlicensed radio frequency ISM band for NFC/ RFID type protocols. In this case, the standard network protocol may be one from the list of WLAN type protocol;
Bluetooth type protocol
BLE type protocol
3G/4G/5G type protocol
GSM type protocol.

Advantageously, the antenna of the wireless receiver 108 of the implant 100 may be configured to only receive in this (13.56 MHZ) frequency band.

In some embodiments, the wireless communication W2 between the second external device 300 and the external device 200 requires authentication to be conducted. In other words, the communication W2 between the external device 200 and the second external device 300 requires the communication to be authenticated, wherein a verification process at the second external device 300 may be used for this. Example of such verification includes authentication input at the second external device 300 being a code. In other embodiments, the authentication input at the second external device 300 is based on a biometric technique selected from the list of: a fingerprint, a palm vein structure, image recognition, face recognition, iris recognition, a retinal scan, a hand geometry, and genome comparison. Consequently, the second external device 300 may comprise an interface for authentication of the communication W2 with external device 200.

As shown in FIG. 2, the system may comprise a third external device 400, and communication W4 between the second externa device 300 and a third external device 400 may be established. The communication between the second externa device 300 and the third external device may be authenticated using a verification process at the third external device 400. Example of such verification includes authentication input at the third external device 400 being a code. In other embodiments, the authentication input at the third external device 400 is based on a biometric technique selected from the list of: a fingerprint, a palm vein structure, image recognition, face recognition, iris recognition, a retinal scan, a hand geometry, and genome comparison. Consequently, the third external device 400 may comprise an interface for authentication of the communication W4 with second external device 300.

Further information and definitions of features, functionality of this aspect can be found in this document in conjunction with the other aspect.

The external device may be configured to communicate further data via the conductive communication with the implant.

A computer program product of, or adapted to be run on, an external device is also provided, which comprises a computer-readable storage medium with instructions adapted to make the external device perform the actions as described above.

Aspect 251SE 2-Part Key NFC—Two Communication Methods for Sending Encryption Keys—Embodiments of Aspect 251SE of the Disclosure In an eight aspect, increased security for communication between an external device(s) and an implant is provided. FIGS. 56-64 shows embodiments of this aspect.

FIG. 56 shows a flow chart for methods of encrypted communication between an external device 200 and an implant 100 implanted in a patient. The external device 200 may be adapted to communicate with the implant 100 using two separate communication methods. A communication range of a first communication method W1 may be less than a communication range of a second communication method W2.

The method may comprise the steps of:

Sending S5101 a first part of a key from the external device 200 to the implant 100, using the first communication method W1.

Sending S5102 a second part of the key from the external device 200 to the implant 100, using the second communication method W2.

Sending S5103 encrypted data from the external device 200 to the implant 100 using the second communication method W2.

Deriving S5104*a*, in the implant a combined key from the first part of the key and the second part of the key.

Decrypting S5105 the encrypted data, in the implant 100, using the combined key.

The external device 200 may be adapted to be in electrical connection C1 with the implant 100 (and vice versa), using the body as a conductor. The method may then further comprise confirming S5107 the electrical connection C1 between the implant 100 and the external device 200 and as a result of the confirmation, decrypting the encrypted data in the implant 100 and using the decrypted data for instructing the implant 100.

The method may also comprise placing a conductive member 201, configured to be in connection with the external device 200, in electrical connection with a skin of the patient for conductive communication with the implant 100. By means of the electrical connection an extra layer of security is added as a potential hacker would have to be in contact with the patient to access or affect the operation of an implant.

Using a plurality of communication methods, as described in this eighth aspect, may increase the security of the authentication and the communication with the implant as more than one channel for communication may need to be hacked or hijacked by an unauthorized entity to gain access to the implant or the communication.

The electrical connection C1 the conductive member 201 and conductive communication may be further described herein under aspect 247SE. In these cases, the implant 100 and/or external device 200 comprise the necessary features and functionality (described in the respective sections of this document).

It should also be noted that any one of the first and second communication methods W1, W2 may be needed to be confirmed in order to decrypt the encrypted data in the implant 100 and using the decrypted data for instructing the implant 100. Examples of such confirmation methods is described herein under the fifth, thirteenth and fifteenth aspect. In these cases, the implant and/or external device(s) comprises the necessary features and functionality (described in the respective sections of this document) for performing such authentication. Such example embodiments are further described below.

FIG. 57 shows the method further comprising the step of wirelessly receiving S5106, at the implant 100, a third part of the key from the second external device 300. In this case, the combined key may be derived S5104*b* from the first part of the key, the second part of the key and the third part of the key.

The first communication method W1 may be a wireless form of communication. The first communication method W1 may preferably be a form of electromagnetic or radio-based communication however, other forms of communication are not excluded. The first communication method W1 may comprise or be related to the items of the following list:

Radio-frequency identification (RFID)

Bluetooth

Bluetooth Low Energy (BLE)

Near Field Communication (NFC)

NFC-V

Infrared (IR) based communication

Ultrasound based communication

RFID communication may enable the use of a passive receiver circuit such as those in a RFID access/key or payment card. IR based communication may comprise fiber optical communication and IR diodes. IR diodes may alternatively be used directly, without a fiber, such as in television remote control devices. Ultrasound based communication may be based on the non-invasive, ultrasound imaging found in use for medical purposes such as monitoring the development of mammal fetuses.

The first communication method W1 may use a specific frequency band. The frequency band of the first communication method W1 may have a center frequency of 13.56 MHz or 27.12 MHz. These bands may be referred to as industrial, scientific, and medical (ISM) radio bands. Other ISM bands not mentioned here may also be utilized for the communication methods W1, W2. A bandwidth of the 13.56 MHz centered band may be 14 kHz and A bandwidth of the 27.12 MHz centered band may be 326 kHz.

The communication range of the first communication method W1 may be less than 10 meters, preferably less than 2 meters, more preferably less than 1 meter and most preferably less than 20 centimeters. The communication range of the first communication method W1 may be limited by adjusting a frequency and/or a phase of the communication. Different frequencies may have different rates of attenuation. By implementing a short communication range of the first communication method, security may be increased since it may be ensured or made probable that the external device is under control of the patient (holding the external device close to the implant)

The communication range of the first communication method W1 should be evaluated by assuming that a patient's body, tissue, and bones present the propagation medium. Such a propagation medium may present different attenuation rates as compared to a free space of an air-filled atmosphere or a vacuum.

By restricting the communication range, it may be established that the external device communicating with the implant is in fact on, or at least proximal to, the patient. This may add extra security to the communication.

The second communication method W2 may be a wireless form of communication. The second communication method W2 may preferably be a form of electromagnetic or radio-based communication. The second communication method W2 may be based on telecommunication methods. The second communication method W2 may comprise or be related to the items of the following list:

Wireless Local Area Network (WLAN)
Bluetooth
BLE
GSM or 2G (2nd generation cellular technology)
3G
4G
5G The second communication method W2 may utilize the ISM bands as mentioned in the above for the first communication method W1.

A communication range of the second communication method W2 may be longer than the communication range of the first communication method W1. The communication range of the second communication method W2 may preferably be longer than 10 meters, more preferably longer than 50 meters, and most preferably longer than 100 meters.

Encrypted data may comprise instructions for updating a control program 110 running in the implant 100. Encrypted data may further comprise instructions for operating the implant 100.

Figure 58:
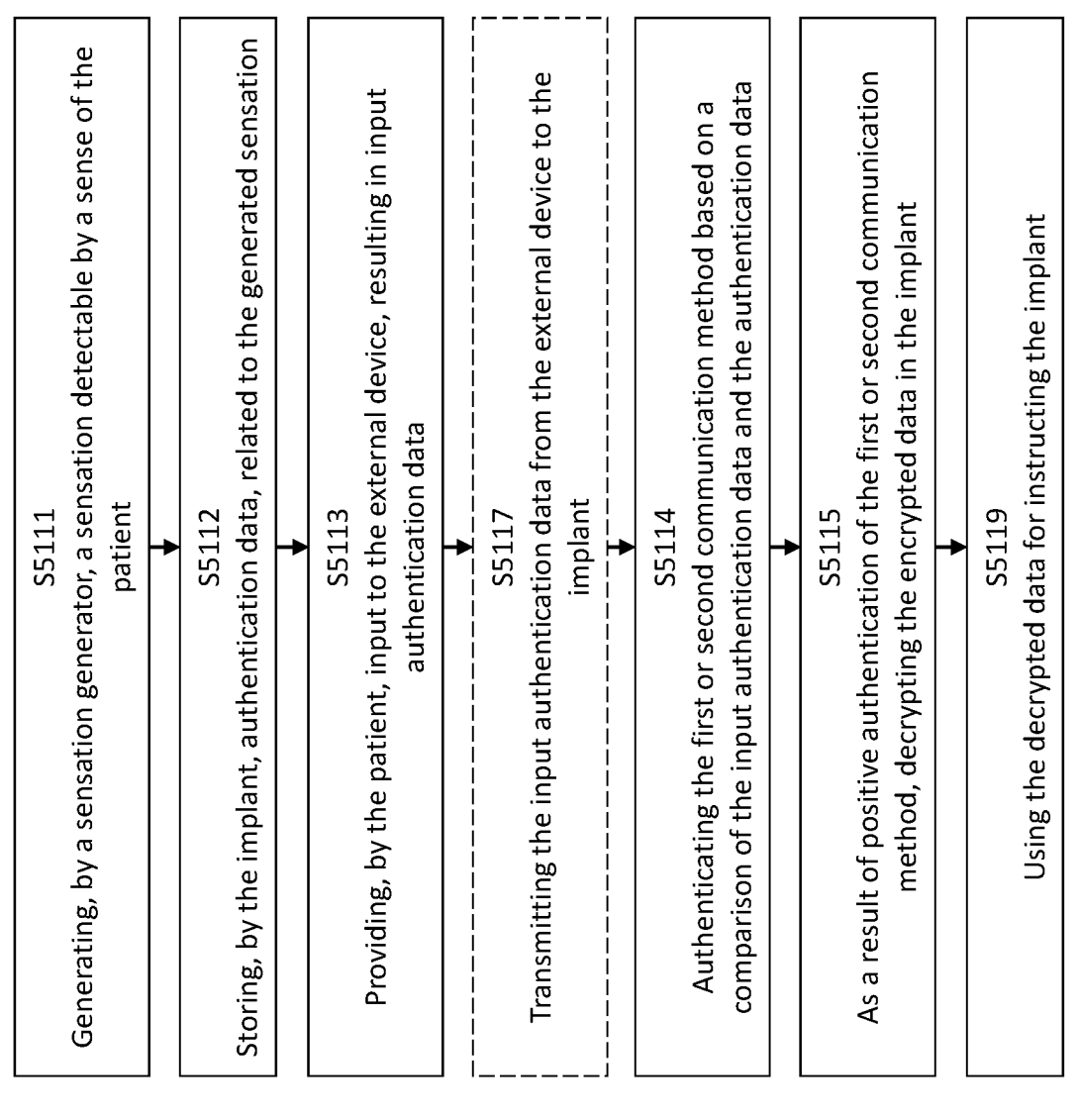

FIG. 58 shows a flow chart of further steps which may be appended to the method for authenticating the communication methods W1, W2 by generating sensations detectable by the patient in which the implant 100 is implanted. For this the method may further comprise:

Generating S5111, by a sensation generator 181, a sensation detectable by a sense of the patient.

Storing S5112, by the implant 100, authentication data, related to the generated sensation.

Providing S5113, by the patient, input to the external device 200, resulting in input authentication data.

Authenticating S5114 the first or second communication W1, W2 method based on a comparison of the input authentication data and the authentication data.

As a result of positive authentication of the first or second communication method W1, W2, decrypting S5115 the encrypted data in the implant 100.

Using S5119 the decrypted data for instructing the implant.

The method may further comprise the step of transmitting S5117 the input authentication data from the external device 200 to the implant 100. In this case the comparison of the input authentication data and the authentication data may be performed by or at the implant 100.

The sensation generator 181, sensation, authentication data, input authentication data, as well as further methods for authentication based on sensations may be further described herein under the fifth and fifteenth aspects. In these cases, the implant 100 and/or external device(s) comprises the necessary features and functionality (described in the respective sections of this document). Using sensations for authenticating the communication or communication method provides an extra level of security as sensations may be adapted to only be sensible by the patient, thus preventing unauthorized access or authentication.

Figure 59:
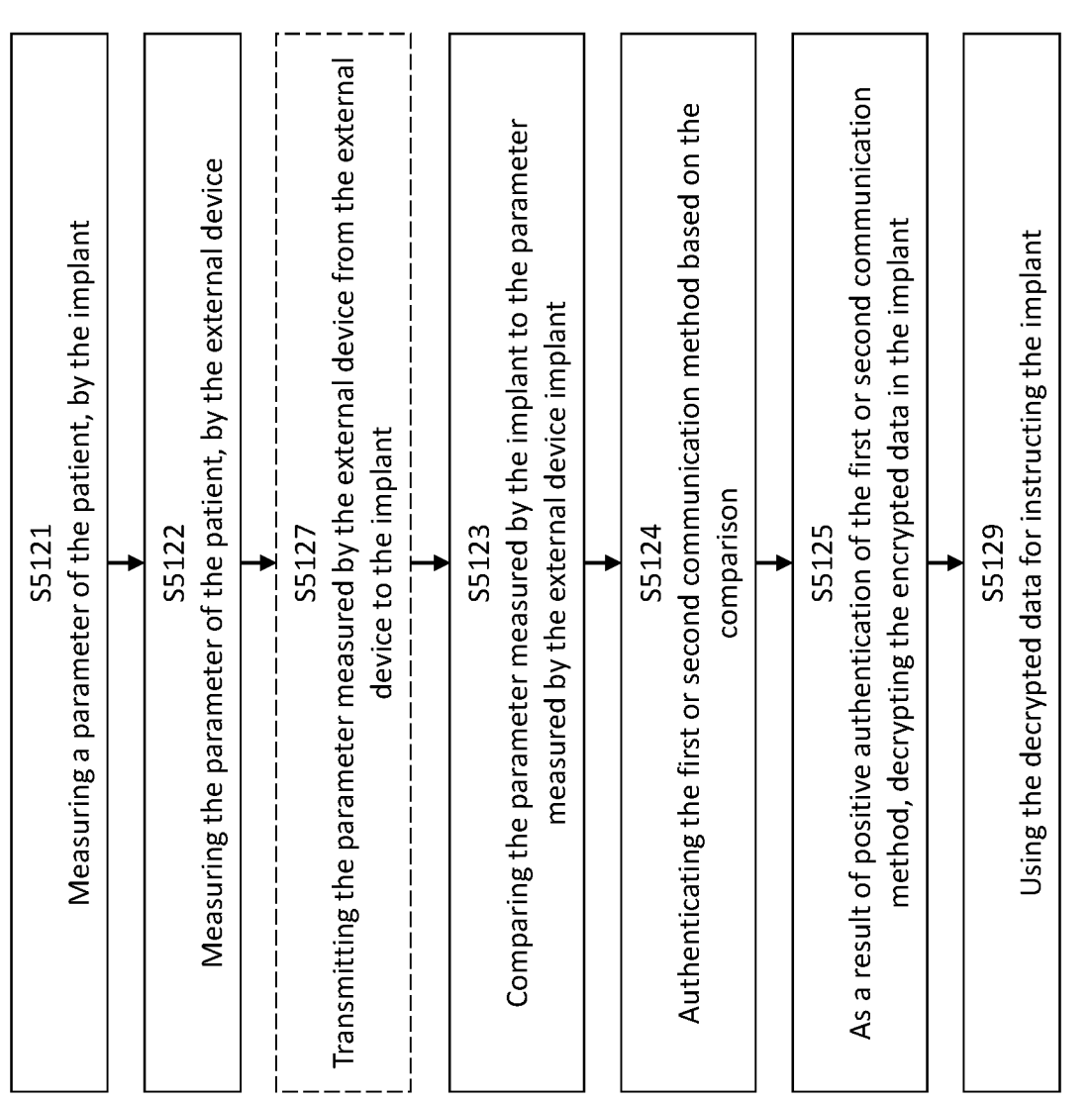
Figures 61A, 61B, 61C:
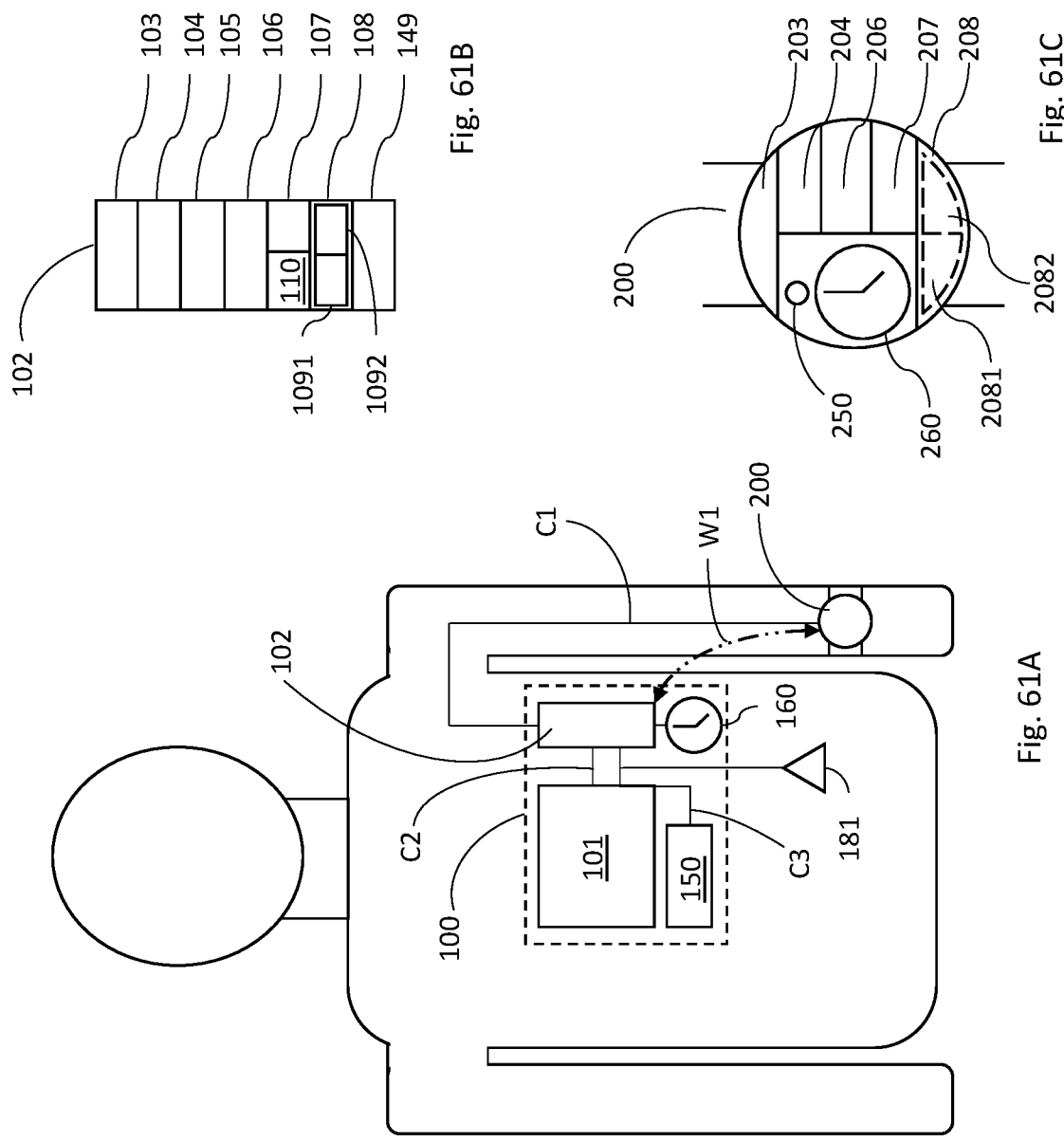
FIG. 61A illustrates a system comprising an implant, further illustrated in FIG. 61B, and an external device, further illustrated in FIG. 61C, all according to aspect 251SE.
Figure 62:
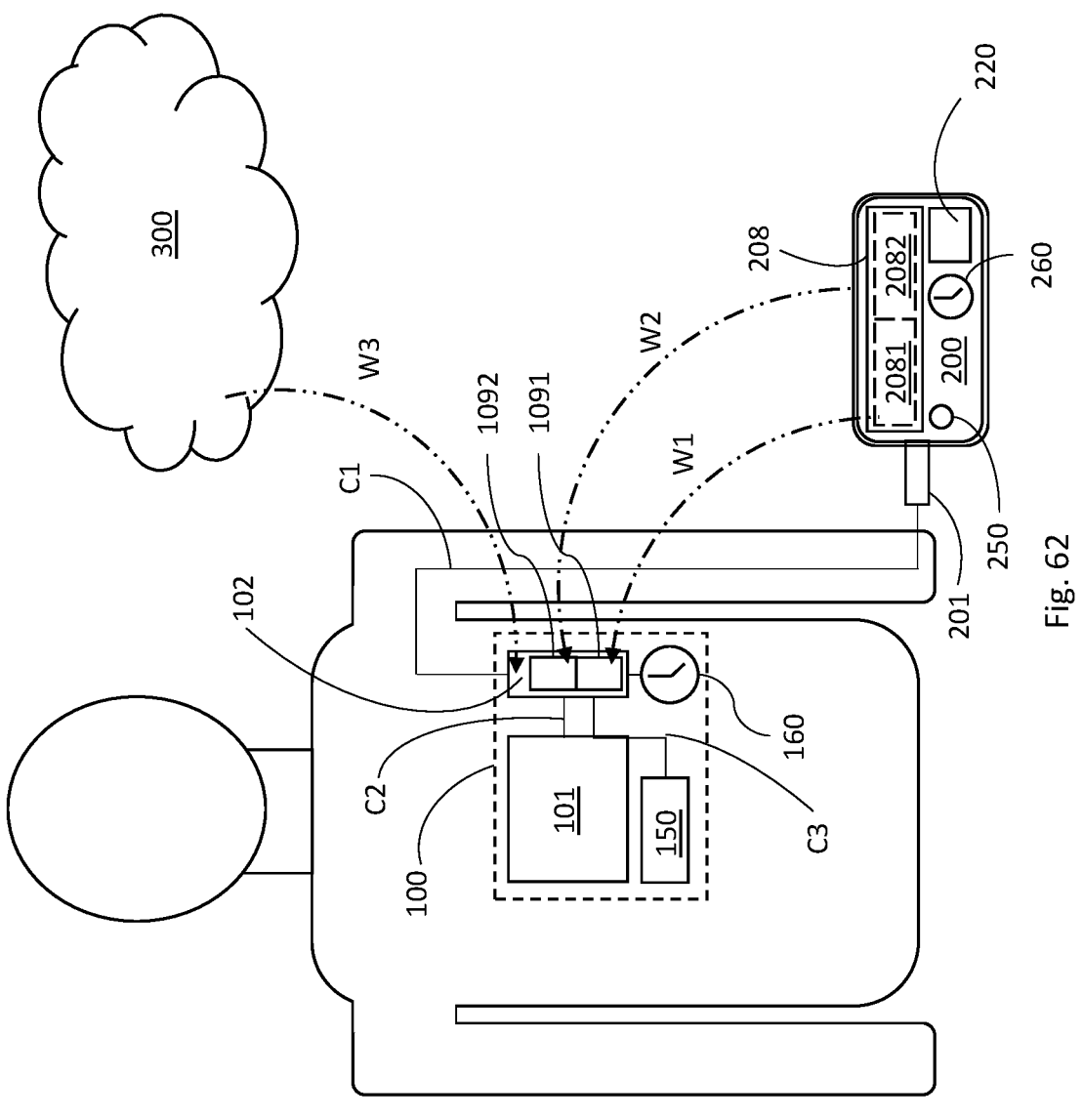
FIG. 62 illustrates a system according to aspect 251SE comprising an implant in connection with an external device and a second external device.

FIG. 59 shows a flow chart of further steps which may be appended to the method for authenticating the communication methods W1. W2 by measuring a parameter of the patient by the implant 100 and the external device 200. For this the method may further comprise:

Measuring S5121 a parameter of the patient, by the implant 100.

Measuring S5122 the parameter of the patient, by the external device 200.

Comparing S5123 the parameter measured by the implant 100 to the parameter measured by the external device 200.

Authenticating S5124 the first or second communication method W1, W2 based on the comparison.

As a result of positive authentication of the first or second communication method W1, W2, decrypting S5125 the encrypted data in the implant 100.

Using S5129 the decrypted data for instructing the implant 100.

The method may further comprise transmitting S5127 the parameter measured by the external device 200 from the external device 200 to the implant 100. In this case, the comparison of the parameter of the patient measured by the external device 200 and the parameter of the patient measured by the implant 100 may be performed by the implant 100. The implant 100 may comprise a first sensor 150 for measuring the parameter of the patient at the implant 100. The external device 200 may comprise an external sensor 250 for measuring the parameter of the patient at the external device 200.

The parameters of the patient, the first and second sensors 150, 250, as well as further methods for authentication based on measuring parameters of the patient may be further described herein under aspect 256SE. In these cases, the implant 100 and/or external device(s) comprises the necessary features and functionality (described in the respective sections of this document). The use of parameters of the patient may provide extra security for the communication or communication method.

Figures 63A, 63B:
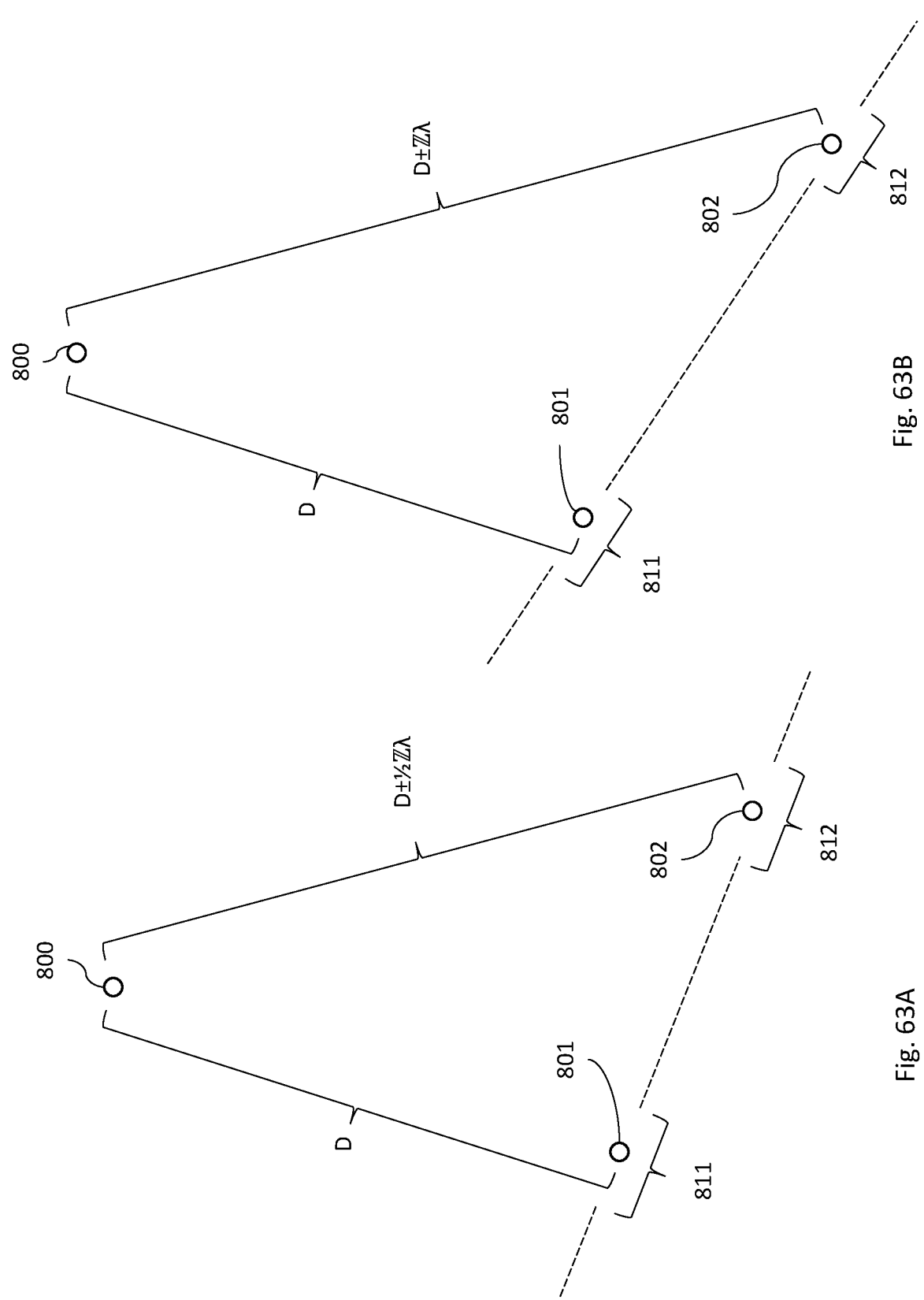
FIG. 63A illustrates a system with the first and the second point transmitting such that destructive interference occurs at the at least one point located at different distances from the first and second points.
FIG. 63B illustrates a system with the first and the second point transmitting such that constructive interference occurs at the at least one point located at different distances from the first and second points.

The communication or communication methods W1, W2 between the implant 100 and the external device 200 may be cancelled or amplified for at least one point 800 by destructive or constructive interference/diffraction. As illustrated by FIGS. 63A-B, this may be achieved by transmitting the communication with a wavelength, $\lambda$, from a first point 801 located a distance, D, away from the at least one point 800, and by also transmitting the communication from a second point 802, located at either a distance $D\pm\frac{1}{2}z\lambda$ or $D\pm z\lambda$ from the at least one point 800. Herein, $z$ may be any integer, e.g. −4, −3, −2, −1, 0, 1, 2, 3, 4 etc. The communication may be cancelled for the at least one point 800 by transmitting from the second point 802, located at a distance $D\pm\frac{1}{2}z\lambda$ from the at least one point 800, as shown in FIG. 63A. The communication may be amplified for the at least on point 800 by transmitting from the second point 802, located at a distance D± ⌀λ from the at least one point 800, as shown in FIG. 63B.

Figure 64:
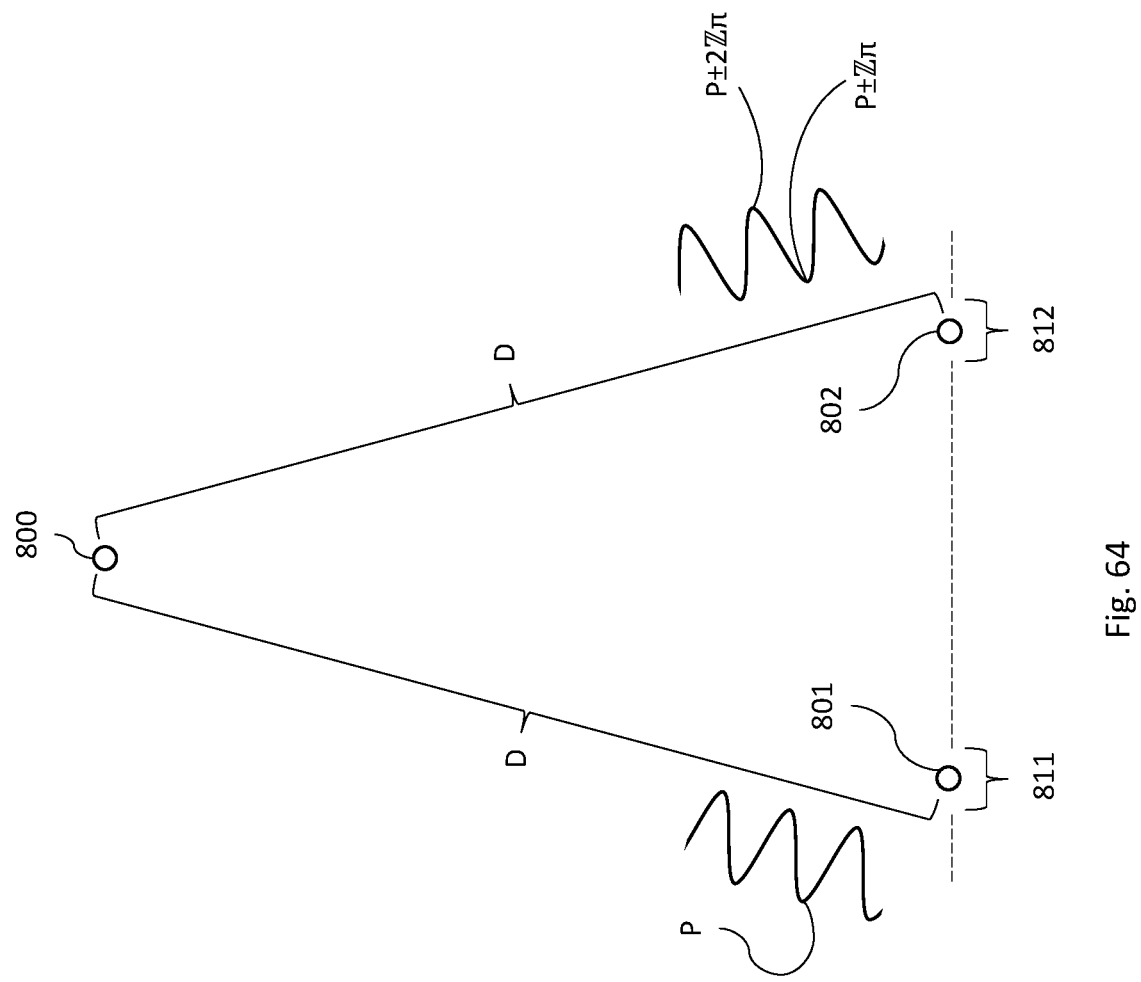
FIG. 64 illustrates a system with the first and the second point being equidistant to the at least one point and how constructive and destructive interference may be achieved by phase shifting the transmission from the second point relative to the transmission from the first point
Figures 68A, 68B, 68C:
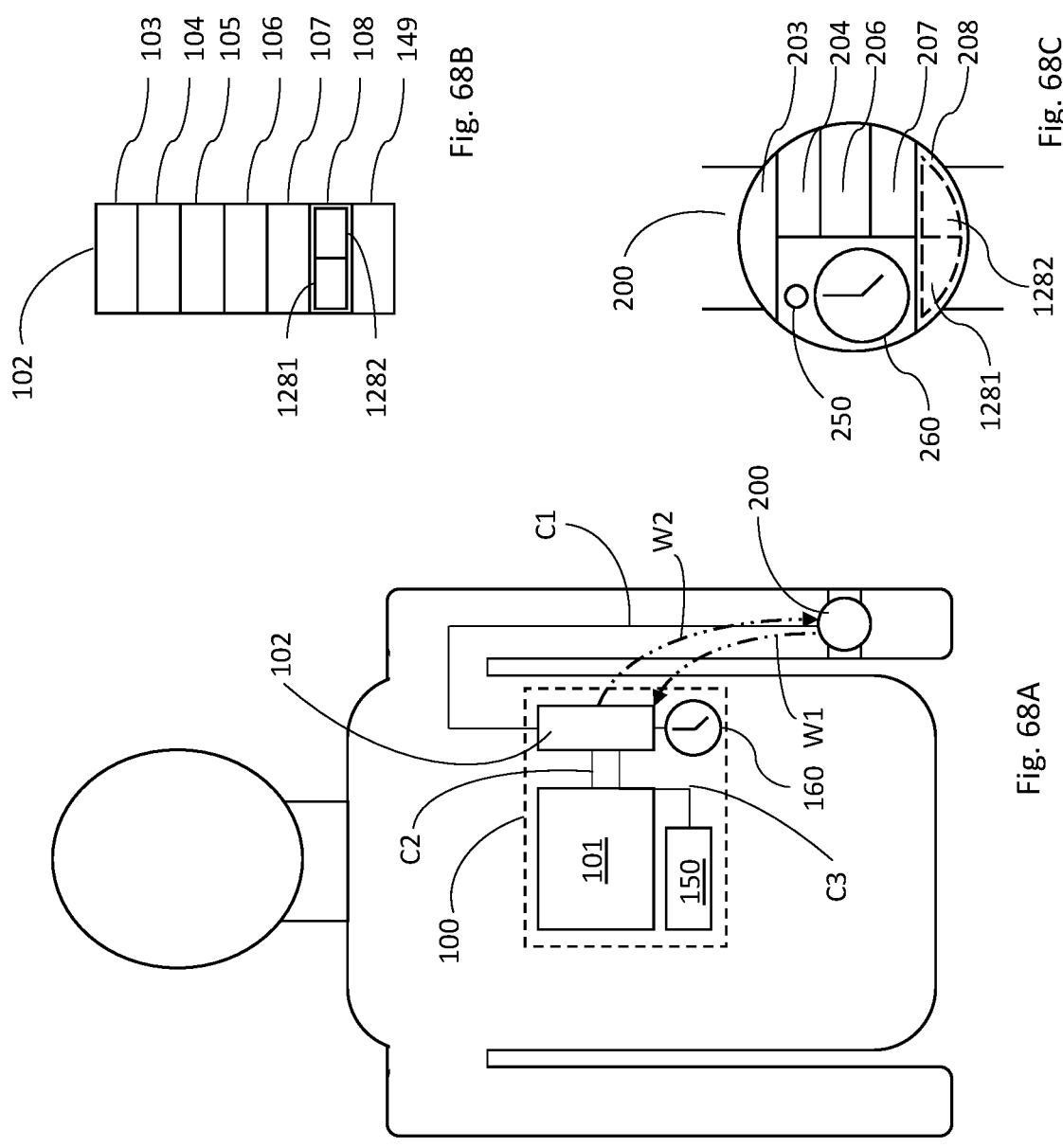
FIG. 68A illustrates a system comprising an implant, further illustrated in FIG. 68B, and an external device, further illustrated in FIG. 68C, all according to aspect 252SE.
Figure 69:
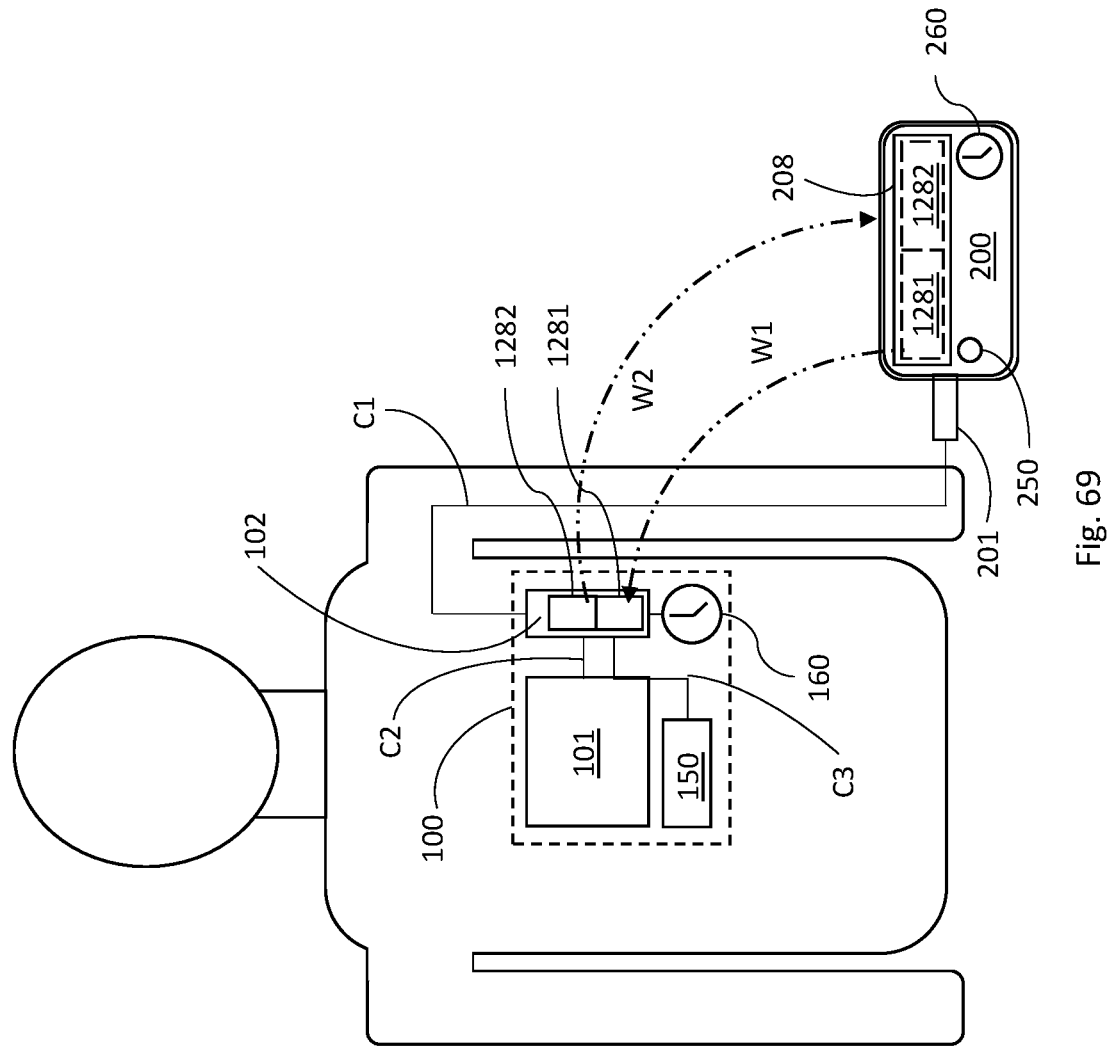
FIG. 69 illustrates a system according to aspect 252SE comprising an implant in connection with an external device.

FIG. 64 illustrates another way for cancelling or amplifying the communication. The communication may in this example be transmitted from a first point 801 with a phase, P. The communication may be cancelled for the at least one point 800 by transmitting the communication from a second point 802 with a phase P± ⌀π. The communication may instead be amplified for the at least one point 800 by transmitting the communication from the second point 802 with a phase P±2 ⌀π. Once more, λ may be any integer, e.g. −4, −3, −2, −1, 0, 1, 2, 3, 4 etc.

A distance between the first point 801 and the at least one point 800 may equal the distance between the second point 802 and the at least one point 800 plus or minus any integer times a wavelength, λ, of the communication.

Alternatively, combinations of using different phases for the communication transmitted from the first and second points 801, 802 and using different distances between the first and second points 801, 802 and the at least one point 800 may be used to cancel or amplify the communication.

The first point 801 may be a first transmitter and the second point 802 may be a second transmitter. The first point 801 and the second 802 point may be moved with respect to each other such that the at least one point 800 is spatially shifted. Preferably, the first point 801 and the second point 802 are associated with the external device 200 and the at least one point 800 is associated with the implant 100.

The at least one point 800 may be one of a plurality of points where the communication is cancelled or amplified. The first point 801 may be associated with the implant 100 and the second point 802 may be associated with the external device 200 (or vice versa). The first point 801 may be a first slit 811 and the second point 802 may be a second slit 812. The first and second slits 811, 812 may be adapted to receive the same communication from a single transmitter. The transmitter may be located equidistant to the first and second slits 811, 812.

A phase, P. of the communication may be alternated as to spatially shift the at least one point. This may be done to provide, a moveable, localized point where even very low amplitude signals may interfere and have a high amplitude such that the communication may be improved. This may aid in calibrating an implant and external device system towards individual and different patient bodies.

FIG. 60 shows a flow chart of a method for authenticating the communication based on patterns of constructive and/or destructive interference. The method may then comprise:

Transmitting S5132 by the external device 200 via the first and second points 801, 802.

Measuring S5132 by the implant 100 the interference for at least two points.

Comparing S5133 the measured interference with reference data pertaining to an authorized external device 200.

Authenticating S5134 the communication based on the results from comparing the measured interference with the reference data.

Such a method may provide increased security by verifying that the external device is at specific positions, or at least specific directions, relative to the implant. This is made possible by comparing expected interference patterns with measurements of signal strength at actual points (first and second) by the implant. A precise distance may also be evaluated based on the interference pattern and thus further narrow the tolerance for the spatial positioning of the external device 200. A plurality of points, larger than two, may be measured and compared against for authenticating the communication. Reference data pertaining to an authorized external device 200 may comprise an interference pattern or data related to interference observed or expected from a trusted or authorized external device 200. The reference data may be calibrated to match a trusted or authorized external device 200.

An interference pattern may be dependent on the following factors:

Type of transmission (i.e. electromagnetic, sound, etc.)
Number of transmitters
Location of transmitters
Directivity of transmitters
Power of transmission
Wavelength of transmission
Phase of transmission
Medium
Reflections FIGS. 61A-C and 62 show an implant 100 and an external device 200 as well as a system comprising both and an optional second external device 300. The implant 100, the external device 200, and the system may be configured for performing the methods and actions discussed herein.

The external device 200 may comprise a wireless transceiver 208. The wireless transceiver 208 may in turn comprise a first wireless transceiver 2081 and a second wireless transceiver 2082. The first wireless transceiver 2081 may be configured for communication with the implant 10 using the first communication method W1. The second wireless transceiver 2082 may be configured for communication with the implant 10 using the second communication method W2.

The first wireless transceiver 2081 may be configured to send a first part of a key to the implant 100, using the first communication method W1. The second wireless transceiver 2082 may be configured to send a second part of a key to the implant 100, using the second communication method W2. The second wireless transceiver 2082 may further be configured to send encrypted data to the implant using the second communication method W2. The first communication method W1 may be used by the first wireless transceiver 2081. The second communication method W2 may be used by the second wireless transceiver 2082.

The first wireless transceiver 2081 may be configured to limit the communication range of the first communication method W1 by adjusting the frequency and/or phase of the transmitted information.

The external device 200 may comprise a loop antenna. The loop antenna may be part of the wireless transceiver 208 or the first or second wireless transceiver 2081, 2082.

The external device 200, or the wireless transceiver 208 may be used to transmit the communication from the first and second points 801, 802. The first point 801 may correspond to the first wireless transceiver 2081 and the second point 802 may correspond to the second wireless transceiver 2082. The at least one point 800 may correspond to a wireless transceiver 108 of the implant 100. By configuring the points and the phases of transmission such that the communication is amplified at the at least on point 800, the communication transmission strength/power at the first and second points 801, 802 may be reduced.

The implant 100 may comprise a wireless receiver. The implant 100 may comprise a first wireless receiver 1091. The implant 100 may comprise a second wireless receiver 1092. The wireless receivers 1091, 1092 may be part of the wireless transceiver 108. The first communication method W1 may be received by the first wireless receiver 1091. The second communication method W2 may be received by the second wireless receiver 1092

The implant 100 may comprise a passive receiver for receiving the first part of the key. The passive receiver of the implant 100 may comprise a loop antenna. The first and second wireless receivers 1091, 1092 may comprise the passive receiver. The passive receiver may be a receiver that does not require a power source but rather uses the energy of the radio waves it receives to power it. Generally, such a passive receiver would need the received communication to be transmitted with higher power or by a transmitter located closer to the receiver. The passive receiver may be adapted to only receive transmitted communication. Such a receiver may conserve energy of the implant as the passive receiver may be powered by the received radio waves.

The implant 100 may comprise a computing unit 106. The computing unit 106 may be configured to update the control program 110 running in the implant 100 using the decrypted data. The computing unit 106 may be configured to operate the implant 100 using the decrypted data. The computing unit 106 may be configured to derive a combined key from the first part of the key and the second part of the key, and decrypt the encrypted data using the combined key.

The computing unit 106 may further be configured for:

Receiving a parameter of the patient, from the external device 200.

Comparing the parameter measured by the implant 100 to the parameter measured by the external device 200.

Authenticating the first or second communication method W1, W2 based on the comparison.

As a result of positive authentication of the first or second communication method W1, W2, decrypting the encrypted data in the implant 100 and using the decrypted data for instructing the implant 100.

The implant 100 may further be configured to wirelessly receive a third part of the key from the second external device 300. The computing unit 106 may then be configured to derive the combined key from the first part of the key, the second part of the key and the third part of the key.

The implant 100 may comprise an authentication unit configured to confirm an electrical connection C1 between the implant 100 and the external device 200. The computing unit 106 may then be configured for, as a result of the confirmation, decrypting the encrypted data and using the decrypted data for instructing the implant.

The implant 100 may be connected to or comprise the sensation generator 181 and be configured for:

Storing authentication data, related to a sensation generated by the sensation generator 181.

Receiving input authentication data from the external device 200.

The internal computing unit 106 may then be configured for:

Authenticating the first or second communication method W1, W2 based on the comparison.

As a result of positive authentication of the first or second communication method W1, W2, decrypting the encrypted data in the implant 100 and using the decrypted data for instructing the implant 100.

Authentication data and measured parameters of the patient may be stored by a memory 107 of the implant 100. The control program 110 may also be stored by the memory 107. The memory 107 may be a digital storage medium, adapted for storing digital information or data.

The implant 100 may be configured for:

Receiving the communication from the first and second points 801, 802 of the external device 200.

Measuring the interference for at least two points.

Comparing the measured interference with reference data pertaining to an authorized external device 200.

Authenticating the communication based on the results from comparing the measured interference with the reference data.

The system comprising the implant 100, external device 200 and the optional second external device 300 may comprise the conductive member 201 configured to be in electrical connection with the external device 200. The conductive member 201 may be configured to be placed in electrical connection with a skin of the patient for conductive communication with the implant 100 using the electrical/conductive connection C1.

The second external device 300 may be configured for communication with the external device 200. The external device 200 may be configured for receiving the encrypted data from the second external device 300 and relaying the encrypted data to the implant 100 using the first and/or the second communication method W1, W2.

The communication between the second external device 300 and the external device 200 may use a third communication method W3. The third communication method W3 may be a wireless communication method as those proposed for the first and second communication methods W1, W2. The third communication method W3 may alternatively be a wired/electrical/conductive communication method.

The second external device 300 may comprise an interface for authentication of the communication with the external device 200. Communication between the external device 200 and the second external device 300 may require the communication to be authenticated. Authentication may be performed by the various methods described herein under this and the other aspects.

The relaying of encrypted data between the second external device 300 and the external device 200 is further described herein under aspect 253SE. In these cases, the implant 100 and/or external device 200 comprise the necessary features and functionality (described in the respective sections of this document). Using the external device 200 as a relay, with or without verification from the patient, may provide an extra layer of security as the external device 200 may not need to store or otherwise handle decrypted information. As such, the external device 200 may be lost without losing decrypted information. The combination using two communication methods with a relaying device may be advantageous as the incoming and outgoing transmissions may interfere less with each other.

The second external device 300 may be operated by a healthcare provider of the patient. A healthcare provider may be a healthcare professional such as a physician or a nurse.

The term communication may in some cases refer to the first communication method at least within this aspect. The term may in some cases refer to the second communication method at least within this aspect. The term may in some cases refer to the third communication method at least within this aspect.

NFC-V may be understood as relating to a longer-range NFC class. The maximum communication range of NFC-V may be understood as being in the range from 1-2 meters.

The method may further comprise confirming, by the patient, the communication between the external device and the implant.

The method may further comprise sending a third part of the key from the external device to the implant, using a conductive communication method, wherein the combined key is derived from the first part of the key, the second part of the key and the third part of the key.

Figure 95:
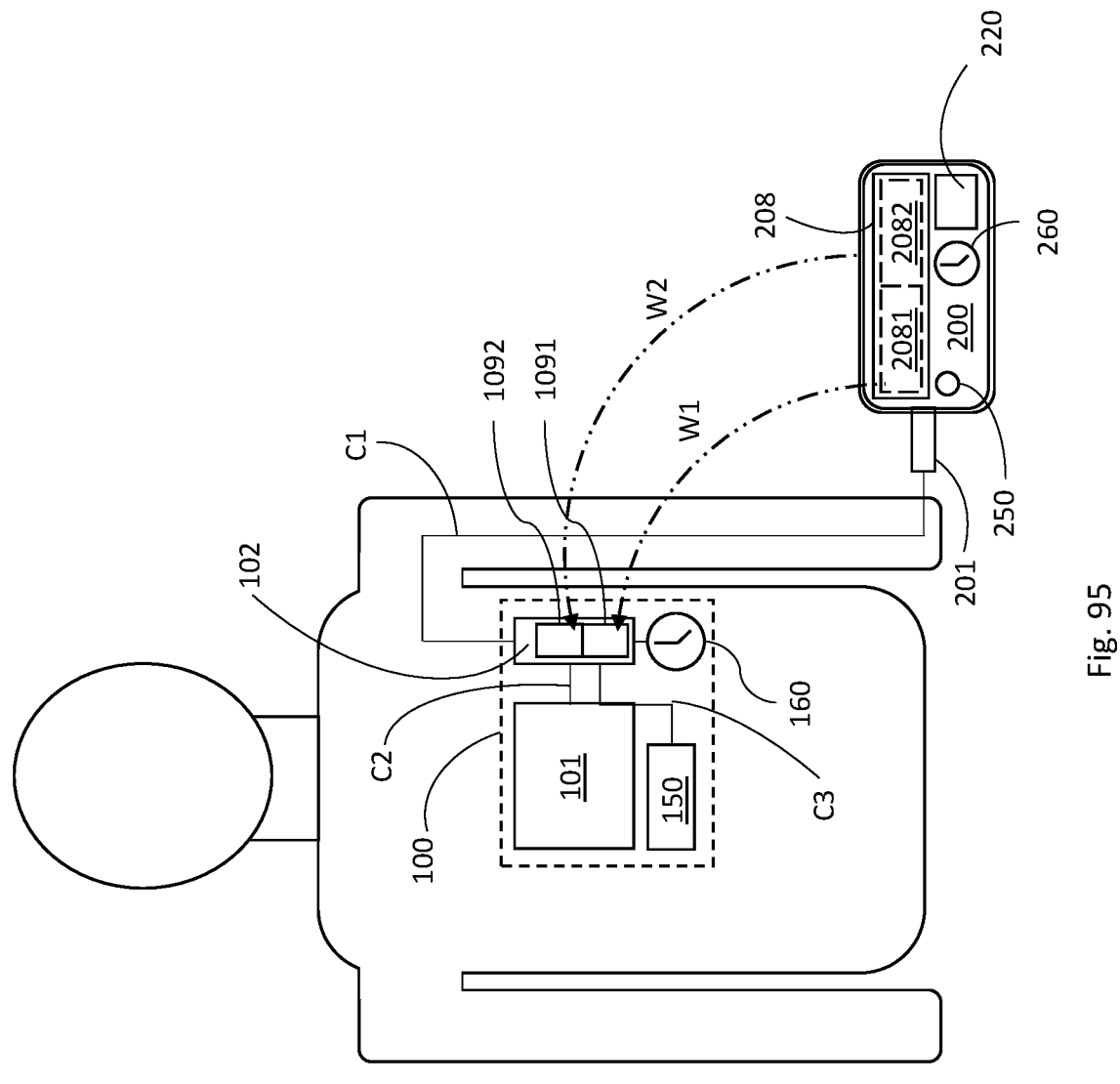
FIG. 95 illustrates a system according to the fifth part of aspect 251SE comprising an external device in connection with an implant.
Figure 96:
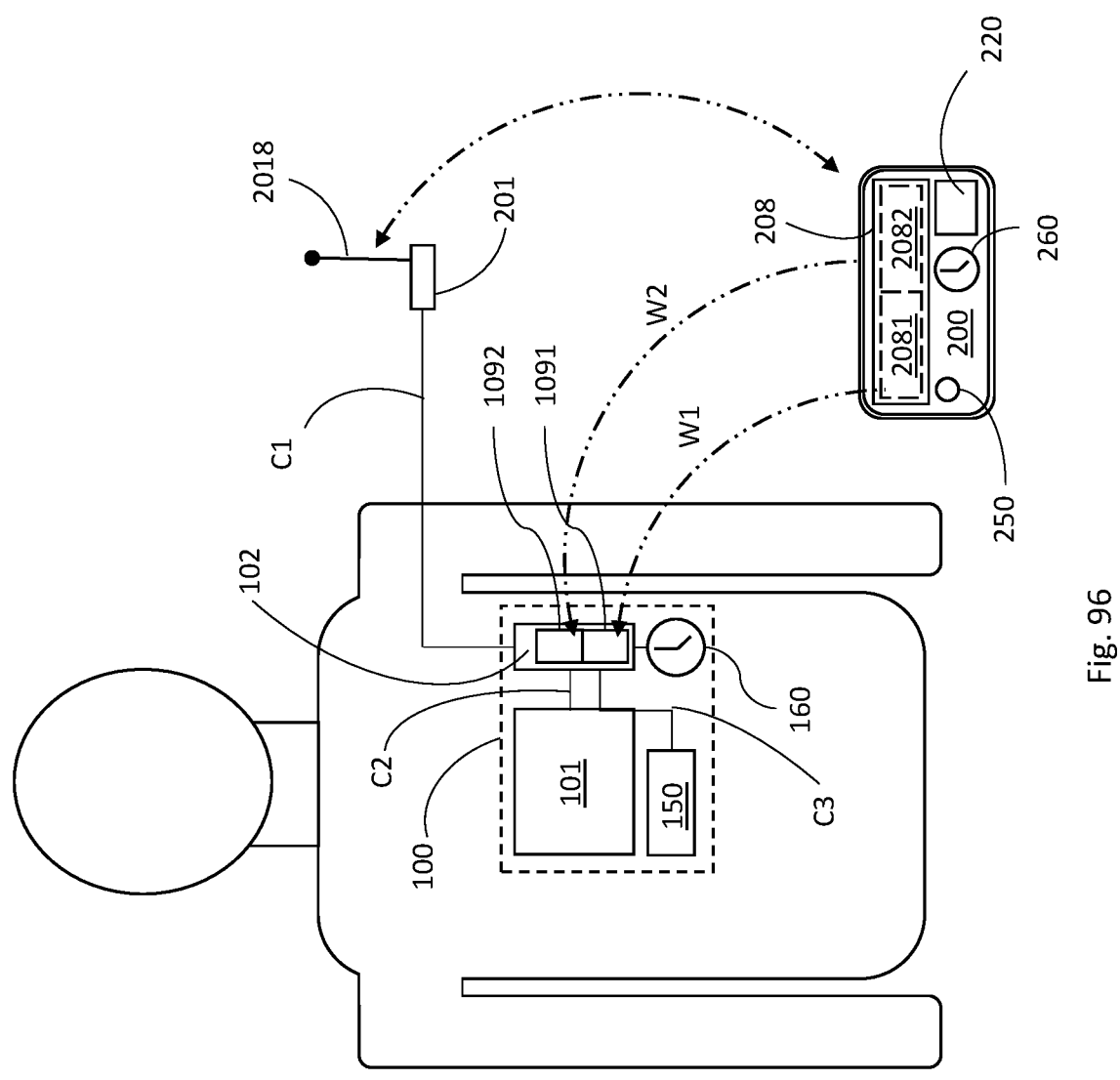
FIG. 96 illustrates a system according to embodiments of the fifth part of aspect 251SE.

A system comprising an external device 200 is shown in FIG. 95 and FIG. 96. The system further comprises a conductive member 201 configured to be placed in electrical connection with a skin of a patient for conductive communication C1 with an implant 100 implanted in the patient. The conductive member 201 may be integrally connected to the external device 200. The conductive member 201 may comprise a wireless communication interface 2018 and is communicatively connected to the external device 200. The wireless communication interface may be at least one antenna element.

The implant may comprise at least one of:
a pacemaker unit,
an external heart compression device.
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient,
an operable cosmetic implant,
an implant for adjusting or replacing any bone part of a body of the patient.
an implant replacing an organ of the patient or part of an organ of the patient or the function thereof,
a vascular treatment device, and
an implant adapted to move fluid inside the body of the patient.

A computer program product of, or adapted to be run on, an external device is also provided, which comprises a computer-readable storage medium with instructions adapted to make the external device perform the actions as described above.

Aspect 252SE Dual Systems—Two Communication Systems for Communication Between Implant and External Device—Embodiments of Aspect 252SE of the Disclosure In aspect 252SE, increased security for communication between external device(s) and an implant is provided. FIGS. 65-70 shows embodiments of this aspect.

FIG. 1 shows a first embodiment of aspect 252SE, which will be described in conjunction with FIGS. 68A-C and 69. In this embodiment, communication between an external device 200 and an implant 100 when implanted in a patient is provided. This is achieved by a first communication system (transmitting wireless communication W1) for sending S5201 data, that may or may not be encrypted, from the external device 200 to the implant 100, and using a second, different, communication system (transmitting wireless communication W2) for receiving S5202, at the external device 200, data from the implant 100. By using different communication systems, a more flexible approach to transmission of data between the implant 100 and the external device 200 is provided. For example, different levels of security for transmissions to and from the implant 100 may be implemented. For example, the implant 100 may be configured to only receive data to be used for instructing the implant 100 from the external device 200. This may be achieved by using a proprietary network protocol for communication using the first communication system. In other embodiments, the communication of data from the implant 100 to the external device 200 is sensitive such that a proprietary network protocol for communication using the second communication system is implemented. Consequently, the first communication system may be configured for wireless communication W1 using a first network protocol, and the second communication system may be configured for wireless communication W2 using a second, different, network protocol. In some embodiments, the first or second network protocol is a proprietary network protocol, wherein the other network protocol is a standard network protocol.

Further details relating to different network protocols is described herein under aspect 250SE. In applicable cases, the implant and/or external device(s) comprises the necessary features and functionality (described in the respective sections of this document) for achieving transmissions with different network protocols.

In other embodiments, different communication ranges of the first and second communication systems are implemented. For example, the communication range of the first communication system may be less than the communication range of the second communication system or vice versa. For example, the communication range of the first or second communication system may be less than 1 meter, or less than 0.5 meters. Embodiments for achieving such short-range communication is described herein under aspect 251SE. In these cases, the implant and/or external device(s) comprises the necessary features and functionality (described in the respective sections of this document) for achieving such short-range communication. In these cases, the two communication systems may correspond to the two communication methods or communication protocols. Having the communications physically separated on different systems further increase security, compared to using the same physical system for all communications, presenting a single point of failure.

Consequently, security is further improved since the external device 200 may need to be closely positioned to the implant 100 (i.e. under control of the patient in which the implant 100 is implanted) to be able to transmit data to the implant 100 or receive data from the implant 100.

The data received S5201 at the implant may be decrypted according to embodiments described in FIGS. 66-67.

In one embodiment, the implant comprises a computing unit 106 configured for receiving S5203, at the implant, a first key from an external device. The key may be received using the first communication system by wireless communication W1. In other embodiments, conductive communication C1 may be used for transmitting the first key. Conductive communication may be achieved by the use of a conductive member 201 configured to be in electrical connection with the external device 200, the conductive member 201 being configured to be placed in electrical connection with a skin of the patient for conductive communication C1 with the implant 100. The feature of conductive communication C1 may be achieved as described herein under aspect 247SE. In these cases, the implant and/or external device(s) comprises the necessary features and functionality (described in the respective sections of this document) for performing such conductive communication. The communication may thus be provided with an extra layer of security in addition to the encryption by being electrically confined to the conducting path e.g. external device 200, conductive member 201, conductive connection C1, implant 100, meaning the communication will be excessively difficult to be intercepted by a third party not in physical contact with, or at least proximal to, the patient.

The computing unit 106 is further configured for deriving S5204 a combined key using the first key and a second key held by the implant (e.g. in memory 107), decrypting S5205 the data using the combined key, and using the decrypted data for instructing S5208 the implant.

In some embodiments, to further increase security, the connection W1 between the implant 100 and the external device 200 (i.e. the first communication system) needs to be authenticated/confirmed before instructing S5207 the implant using the decrypted data. Consequently, in some embodiments, the computing unit 106 is configured for confirming the connection via the first communication system between the implant and the external device. As a result of the confirmation (i.e. upon positive confirmation/authentication) the computing unit may instruct S5208 the implant based on the decrypted data. The decrypted data may comprise at least one of data for updating a control program running in the implant, and operation instructions for operating the implant.

The confirmation and authentication of the wireless communication W1 may be performed as described herein under the fifth, thirteenth and fifteenth aspect. In these cases, the implant and/or external device(s) comprises the necessary features and functionality (described in the respective sections of this document) for performing such authentication. By communication according to these aspects, security of the communication may be increased as it may require a malicious third party to know or gain access to either the transient physiological parameter of the patient or detect randomized sensations generated at or within the patient.

Figure 70:
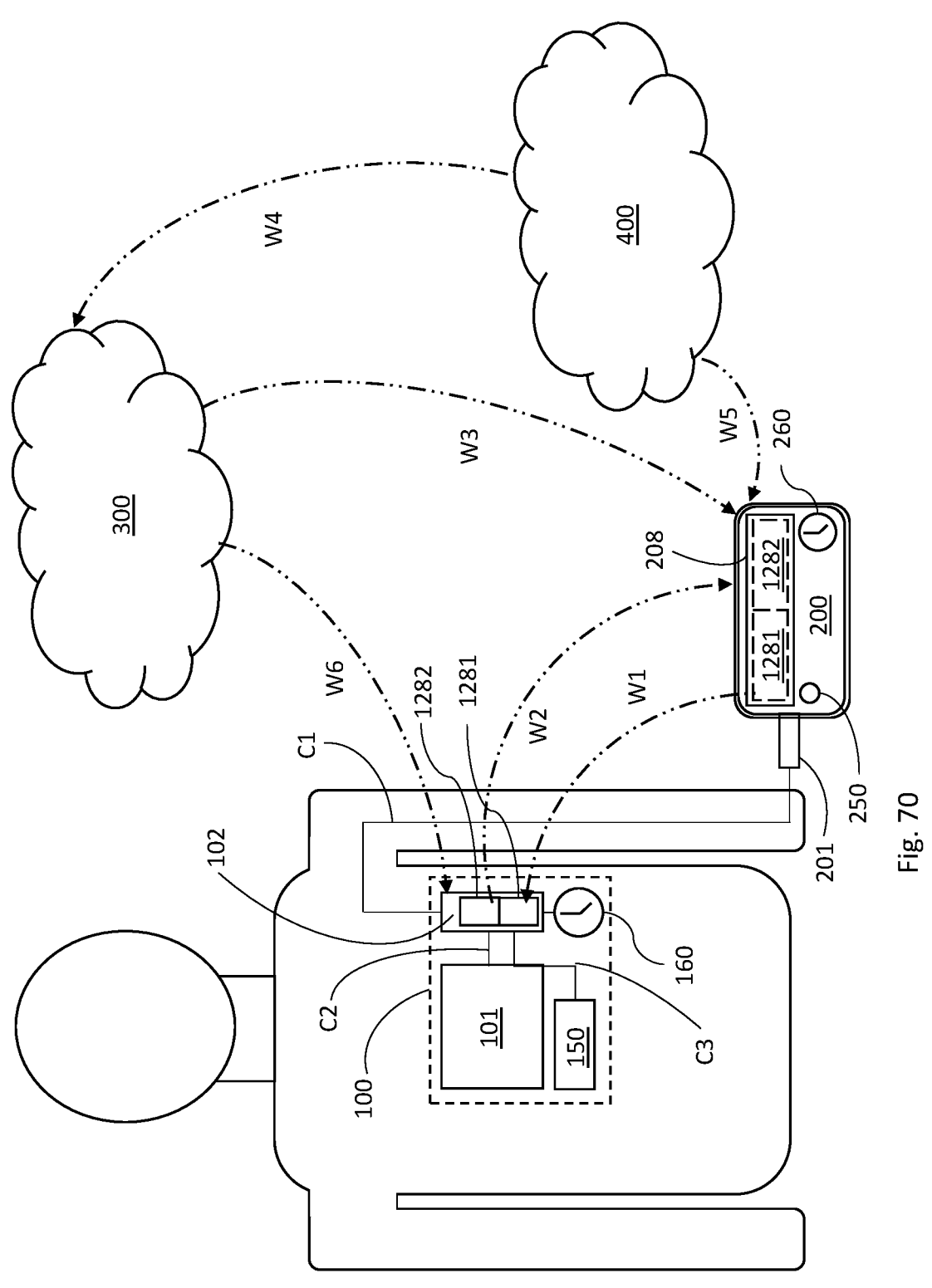
FIG. 70 illustrates a system according to aspect 252SE comprising an implant, an external device, a second external device and a third external device including connections between them.

In other embodiments, the external device 200 is configured to confirm the connection W1, via the first communication system, between the implant and the external device, and the external device 200 is configured to communicate further data to the implant following positive confirmation, which then may be used for instructing S5207 the implant. Such further data may be transmitted using the first communication system and may or may not be encrypted as described herein. The further data may comprise at least one of: data for updating a control program running in the implant, and operation instructions for operating the implant FIG. 67 and FIG. 70 shows other embodiments for increasing security of communication between the implant 100 and the external device 200. In these embodiments, a third key is used for encryption/decryption of the data sent S5201 from the external device 200 to the implant 100. The third key is generated by a second external device 300, separate from the external device or by a another external device 400 being a generator of the second key on behalf of the second external device. The second external device 300 may be under control of a caretaker of the patient, such as medical staff. The another external device 400 may e.g. be a device under control of the IT department of a hospital which is adapted to compute encryption keys on behalf of (upon being instructed by) the second external device.

The third key is received S5209 at the implant from anyone of the external device 200 (e.g. using the wireless communication W2 of the first communication system, or using conductive communication C1), the second external device (using the wireless communication W6), and the generator of the second key (using wireless communication not included in FIG. 70). In some embodiments, there may exist a third communication system (wireless communication W6), the third communication system being different than the first and second communication system, for sending data (e.g. the third key) from the second external device 300, separate from the external device 200, to the implant 100.

In case the external device 200 is transmitting the third key, the external device 200 may receive the third key from the second external device 300 using wireless transmission W3, or wired communication (i.e. ethernet, LAN, not included in the drawings). The external device 200 may receive the third key from another external device 400 using wireless transmission W5, or wired communication (i.e. ethernet, LAN, not included in the drawings). The routing/relaying functionality of the third key at the external device 200 may be performed as described herein under aspect 253SE. In these cases, the implant and/or external device(s) comprises the necessary features and functionality (described in the respective sections of this document) for performing such routing/relaying functionality. Using the external device 200 as a relay, with or without verification from the patient, may provide an extra layer of security as the external device 200 may not need to store or otherwise handle decrypted information. As such, the external device 200 may be lost without losing decrypted information. The combination using two communication systems with a relaying device may be advantageous as the incoming and outgoing transmissions may interfere less with each other.

The second external device 300 may be connected to said another external device 400 and receive data using wireless transmission W4, or wired communication (i.e. ethernet, LAN, not included in the drawings).

When the third key is used, the computing unit 106 may be configured to derive S5204 the combined key using the first and third keys and the second key held by the implant to decrypt the data. The decrypted data may then be used for instructing S5208 the implant. Also, in this embodiment, the computing unit 106 may be configured to first authenticate/confirm S5206 the wireless communication W1 prior to using the decrypted data for instructing the implant 100.

The data received S5202 at the external device from the implant 100 using the second communication system (i.e. wireless communication W2) may comprise feedback signals from the implant including one or more from the list of: physiological or physical sensor parameters related to the status of the body of the patient, and physical or functional parameters related to status of the implant. Further examples on what feedback the implant may transmit (based on functionality the implant) is described herein under aspect 255SE in which cases, the implant and/or external device(s) comprises the necessary features and functionality (described in the respective sections of this document).

The two communication systems may be achieved by one or more wireless transceivers (or separate receiver(s), transmitter(s)) 108 in a communication unit 102 of the implant, which communication unit 102 is connected to an active unit 101 of the implant. The one or more wireless transceivers 108 of the implant 100 are adapted for communication with one or more wireless transceivers 208 (or separate receiver(s), transmitter(s)) of the external device 200. The first communication system is schematically referred to as 1281 in the drawings. The second communication system is schematically referred to as 1282 in the drawings The two communication systems 1281, 1282 may for example be implemented according to the following.

The first communication system 1281 may be implemented using a first wireless receiver at the implant 100, or a first wireless transceiver at the implant 100. The first wireless receiver/transceiver may be configured for receiving data from a first wireless transmitter/transceiver in the external device 200. The second communication system 1282 may be implemented using a first wireless transmitter at the implant 100, or a second wireless transceiver at the implant 100. The first wireless transmitter, or second wireless transceiver may be configured for transmitting data to a first wireless receiver, or a second wireless transceiver in the external device 200. In these embodiments, the first communication system 1281 is implemented using a first antenna of the implant and a first antenna of the external device, and the second communication system 1282 is implemented using a second antenna of the implant and a second antenna of the external device In some embodiments, the first and second communication systems 1281, 1282 may be implemented using a single wireless transceiver in the implant and a single wireless transceiver in the external device (i.e. one antenna at the implant and one antenna at the external device), but where for example the network protocol used for data transmission from the external device 200 to the implant 100 is different from the network protocol used for data transmission from the implant 100 to the external device 200, thus achieving two separate communication systems 1281, 1282.

Further information and definitions of features and functionality of this aspect can be found in this document in conjunction with the other aspects.

The data sent from the external device to the implant may be encrypted data. The data sent to the implant may be encrypted data. The data received from the external device may be encrypted data.

According to embodiments of the third part of aspect 252SE, the first communication system may be a conductive communication system, configured for conductive communication. The feature of conductive communication C1 may be achieved as described herein under aspect 247SE. In these cases, the implant and/or external device(s) comprises the necessary features and functionality (described in the respective sections of this document) for performing such conductive communication.

The implant may comprise at least one of:

a pacemaker unit, an external heart compression device.

an apparatus assisting the pump function of a heart of the patient, an operable artificial heart valve, an implantable drug delivery device.

a hydraulic, mechanic, and/or electric constriction implant, an operable volume filling device, an operable gastric band, an operable implant for stretching the stomach wall of the patient, an operable cosmetic implant, an implant for adjusting or replacing any bone part of a body of the patient, an implant replacing an organ of the patient or part of an organ of the patient or the function thereof, a vascular treatment device, and an implant adapted to move fluid inside the body of the patient.

A computer program product of, or adapted to be run on, an external device is also provided, which comprises a computer-readable storage medium with instructions adapted to make the external device perform the actions as described above.

Figure 71:
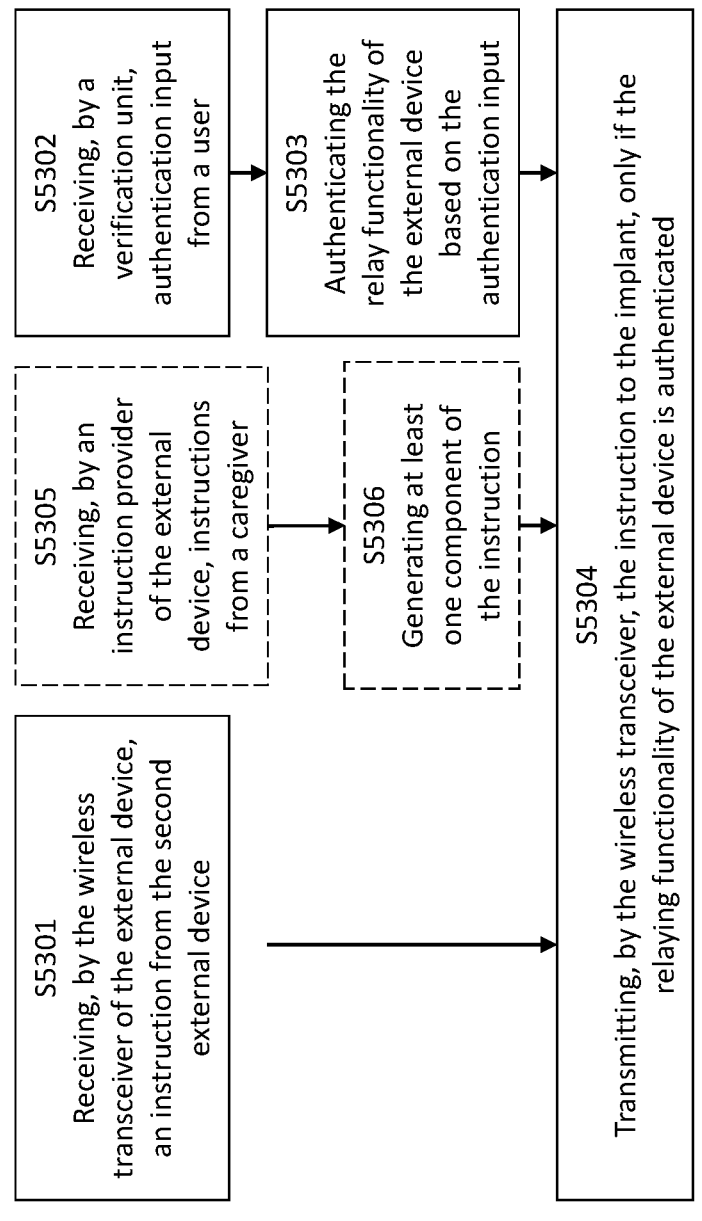
FIG. 71 illustrates a flowchart of methods according to embodiments of the second part of aspect 253SE.
Figures 72A, 72B, 72C:
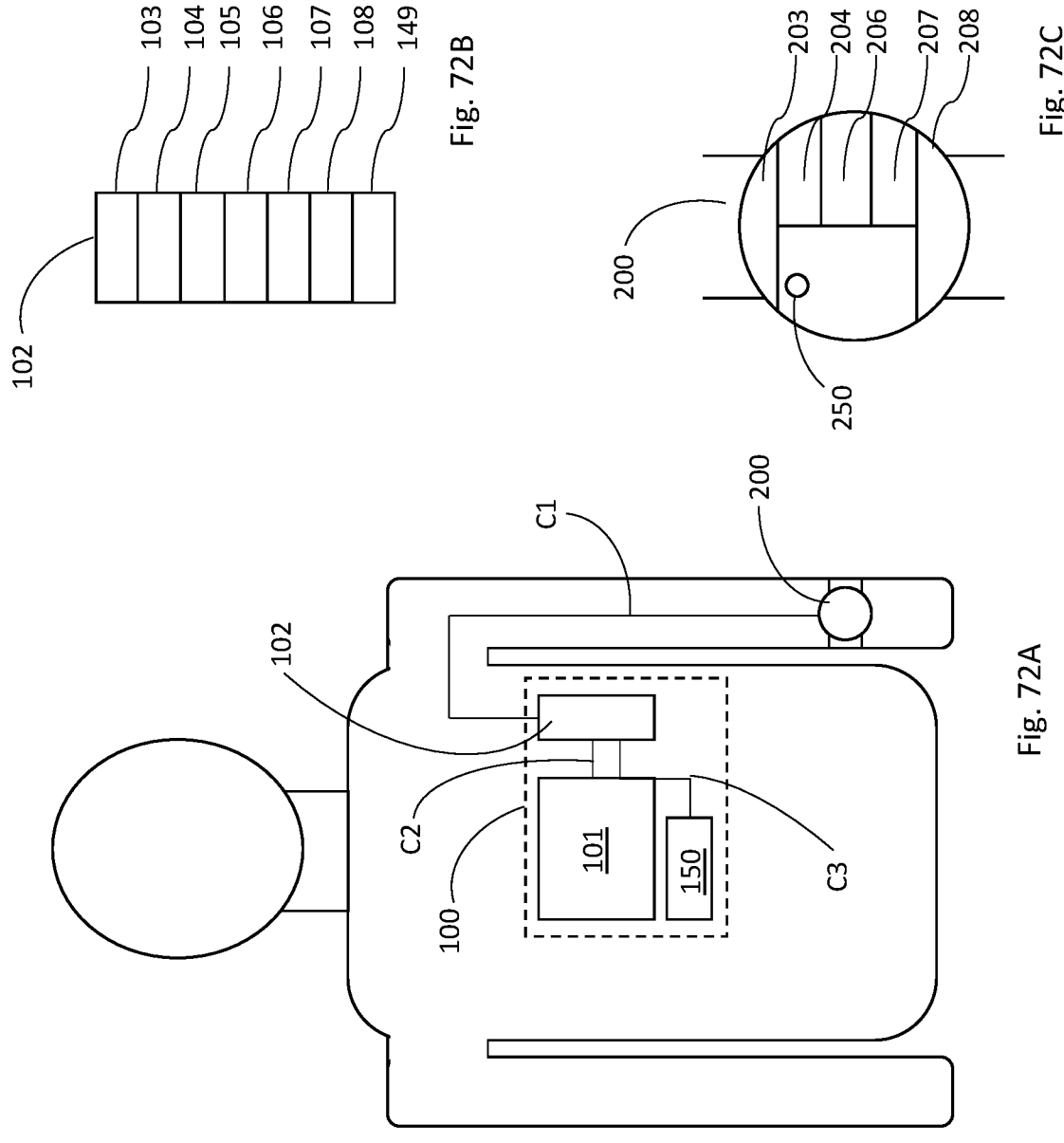
FIG. 72A illustrates a system comprising an implant, further illustrated in FIG. 72B, and an external device, further illustrated in FIG. 72C, all according to aspect 253SE.
Figure 73:
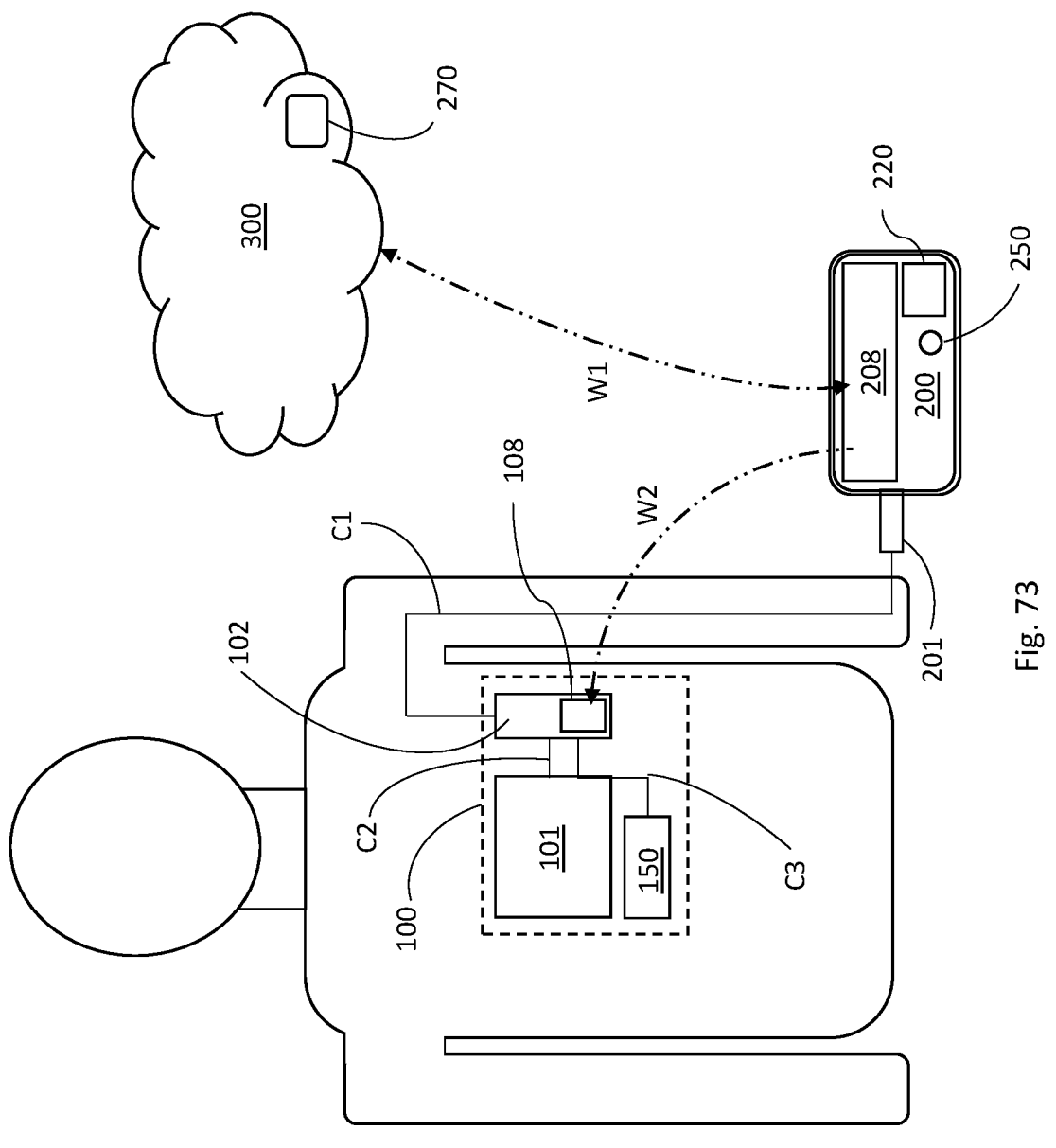
FIG. 73 illustrates a system according to aspect 253SE comprising an implant in connection with an external device wherein the external device is in connection with a second external device.
Figures 83A, 83B, 83C:
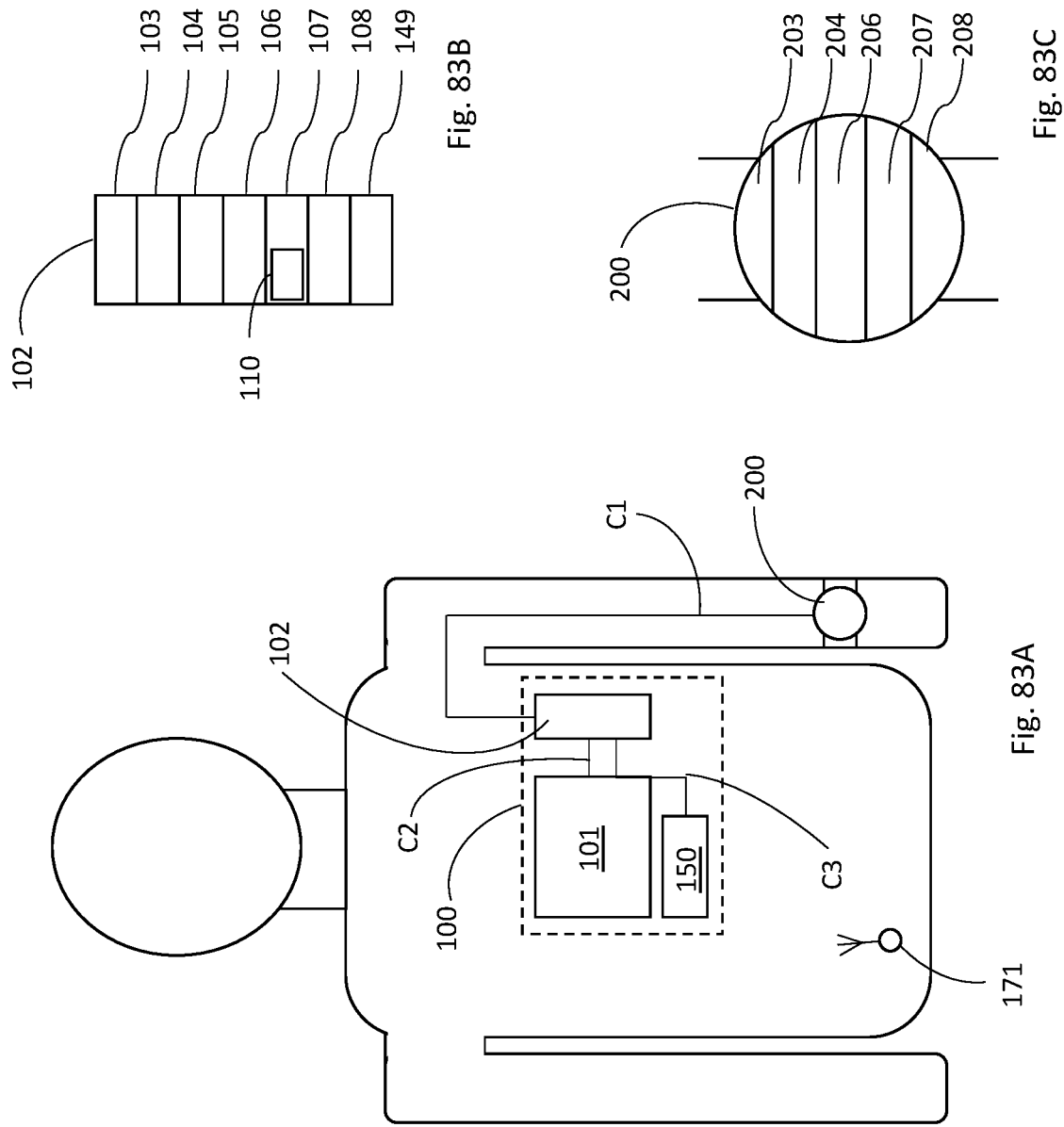
FIG. 83A illustrates a system comprising an implant, further illustrated in FIG. 83B, and an external device, further illustrated in FIG. 83C, all according to aspect 254SE.

Aspect 253SE Passive Proxy—Passive
Proxy—Embodiments of Aspect 253SE of the
Disclosure In aspect 253SE, increased security for communication between external device(s) and an implant is provided. FIGS. 71-73 shows embodiments of this aspect.

FIGS. 72A-C and 73 show a system comprising an external device 200, an implant 100, implanted in a patient, and a second external device 300, other than the external device 200.

The external device 200 may comprise a wireless transceiver 208. The wireless transceiver may be configured for wireless communication with the second external device 300 and the implant 100. The wireless communication may use a wireless connection W1 between the second external device 300 and the external device 200. The wireless communication may use a wireless connection W2 between the external device 200 and the implant 100.

The wireless transceiver 208 may be configured to receive an instruction from the second external device 300. The instruction may or may not be communicated using a first network protocol. The wireless transceiver 208 may further be configured to transmit the instruction to the implant 100. The instruction may or may not be transmitted using a second network protocol.

The wireless transceiver 208 may comprise more than one transceiver. Separate transceivers may be utilized for the first and the second network protocols. The external device 200 may alternatively comprise separate transmitters and receivers rather than having them integrated or comprised in a transceiver.

The first network protocol may be a standard or open network protocol. Types of standard network protocols include:

Radio-frequency type protocol

RFID type protocol

WLAN

Bluetooth

BLE

NFC

3G/4G/5G

GSM

Generally, the first network protocol may be any type of standard wireless communication method such as wireless telecommunication methods or radio communication methods.

The second network protocol may be a proprietary network protocol. The second network protocol may be based on non-public, non-standard, or limited access wireless communication methods with increased security.

Further examples of communication methods and communication protocols that may be utilized for transmitting the instructions, in conjunction with or instead of using, the first and second network protocols as well as the wireless transceiver 208 may be described herein under the eighth and ninth aspects. In these cases, the implant 100 and/or external device 200 comprise the necessary features and functionality (described in the respective sections of this document). The combination using two communication methods or systems with a relaying device may be advantageous as the incoming and outgoing transmissions may interfere less with each other.

Alternatively, to using the wireless connection W2 for transmitting the instructions from the external device 200 to the implant 100, an electrical/conductive connection C1 may be used. For this, the system may further comprise a conductive member 201, configured to be in electrical connection with the external device 200. The conductive member 201 may be configured to be placed, or placed, in electrical connection with a skin of the patient for conductive communication with the implant 100. The external device 200 may be configured to be placed in electrical connection with the conductive member 201, for conductive communication with the implant 100. Conductive communication using the electrical/conductive connection C1 may be used to communicate the instructions between the external device 200 and the implant 100. Conductive communication using the electrical/conductive connection C1 may also be used for authenticating the external device 200 and its authenticity as an authorized relaying device of the instructions from the second external device 300 to the implant 100 via the external device 200.

The electrical/conductive connection C1 the conductive member 201 and conductive communication may be further described herein under aspect 247SE. In these cases, the implant 100 and/or external device 200 comprise the necessary features and functionality (described in the respective sections of this document).

The instruction may comprise instructions for operating the implant 100 or instructions for updating a control program of the implant 100. The instruction received at the external device 200 may be encrypted. The external device 200 may be configured to transmit the instruction to the implant 100 without decrypting the instruction.

The instruction may be provided to the second external device 300 by a trusted source of origin, such as a manufacturer/supplier of the implant 100 or a caregiver of the patient, in which the implant is implanted. The caregiver may be a health care provider of the patient. The caregiver may be a healthcare professional such as a physician or a nurse. The second external device 300 may be controlled, operated or in the possession of the caregiver.

The external device 200 may also comprise a verification unit 220. The verification unit 220 may be configured to receive authentication input form a user for authenticating a relaying functionality of the external device 200. The wireless transceiver 208 may further be configured to:

upon authentication of the relaying functionality of the external device 200, cause the wireless transceiver 208 to transmit the instruction to the implant 100; and upon non-authentication or failed authentication of the relaying functionality of the external device 200, cause the external device 200 to hold the instructions. In this context, to hold means to keeping the instructions in place i.e. not transmitting them to the implant 100.

Such an external device, as described in this tenth aspect, may be made simple with a small footprint and yet enable secure communication as user authentication/verification is required for the external device to relay communication to the implant.

The relaying functionality of the external device 200 refers to its role as a relaying device of the instructions from the second external device 300 to the implant 100 via the external device 200.

The user may be the patient in which the implant 100 is implanted. The user may alternatively be the caregiver.

The authentication input may comprise a parameter of the patient, in which case the authentication input may be provided by the patient. Authentication input may also comprise a parameter of the caregiver, in which case the authentication input may be provided by the caregiver. The authentication input from the user may comprise a code. The code may be provided by either a patient or a caregiver. The authentication input may comprise a single use code.

The external device 200 may comprise an instruction provider 270. Alternatively, the second external device 300 may be considered to be or comprise the instruction provider 270. The instruction provider may be adapted to receive instructions from a caregiver generating at least one component of the instruction. The external device 200 or the instruction provider 270 may be adapted to receive authentication input from the caregiver, comprising at least one of a code and a parameter of the caregiver.

A code may be generated by the instruction provider 270. The code may be generated by the instruction provider 270 as a result of receiving authentication input from the caregiver.

The parameter of the patient may be measured by a sensor 250 of the external device 200. The parameter of the patient measured by the external device 200 may be compared against verified parameter data pertaining to the patient. The parameter of the patient measured by the external device by the external device 200 may also be compared against the same parameter of the patient being measured by a sensor 150 of the implant. The parameter of the patient may be a biometric parameter.

The sensors 150, 250, the parameter of the patient, as well as further methods and devices related to external device 200 authentication based on measuring parameters of the patient may be further described herein under aspect 256SE. In these cases, the implant 100 and/or external device(s) comprises the necessary features and functionality (described in the respective sections of this document). Such authentication may operate automatically, not requiring any actions to be performed by the user or patient while still providing secure authentication.

The parameter of the caregiver may, similarly to the parameter of the patient, be measured by a sensor of a device associated with the caregiver e.g. the second external device 300. The parameter of the caregiver may be compared against verified parameter data pertaining to the caregiver.

FIG. 71 shows a flow chart over methods related to relaying communication between the second external device 300 and the implant 100 implanted in the patient via the wireless transceiver 208 of an external device 200. The method may comprise the steps of:

Receiving S5301, by the wireless transceiver, the instruction from the second external device communicated using the first network protocol.

Receiving S5302, by the verification unit 220, authentication input from the user.

Authenticating S5303 the relaying functionality of the external device based on the authentication input.

Upon authentication of the relaying functionality of the external device, transmitting S5304, by the wireless transceiver, the instruction to the implant, using a second network protocol Upon non-authentication or failed authentication of the relaying functionality of the external device, holding the instructions at the external device The step of transmitting the instruction to the implant 100, when the instruction received at the external device 200 is encrypted, may be performed without decrypting the instruction at the external device 200.

The external device 200 may thus be made less complex and without decryption capability. Since the instruction is encrypted at the external device, the physical loss or theft of such an external device will not come with the loss of potentially sensitive decrypted implant instructions.

The method may further comprise the step of receiving S5305, by the instruction provider 270 of the second external device 300, instructions from the caregiver, and the step of generating S5306 at least one component of the instruction.

The instruction provided by the caregiver may comprise a decision or confirmation to run a functionality or program of the implant. The generated at least one component of the instruction may comprise actual physical actions required by the implant 100 in order to perform the desired functionality or program.

The caregiver, may provide, authentication information input comprising at least one of the code and the parameter of the caregiver. The instruction provider 270 may generate the code.

The wireless transceiver may be configured to receive the instruction from the second external device communicated using a first network protocol.

The wireless transceiver may be configured to transmit the instruction to the implant communicated using a second network protocol.

The external device may be configured to decrypt the communication from the second external device at the external device and wherein the external device may be further configured to transmit the decrypted communication to the implant via a short-range communication method. The short-range communication method may e.g. be an NFC or RFID type method.

A computer program product of, or adapted to be run on, an external device is also provided, which comprises a computer-readable storage medium with instructions adapted to make the external device perform the actions as described above.

Aspect 254SE Automatic Update—Automatic Update of Control Program of Implant—Embodiments of Aspect 254SE of the Disclosure In aspect 254SE, increased security for updating a control program of an implant and associated communications between an external device(s) and the implant is provided. FIGS. 74-84 shows embodiments of this aspect.

Generally, aspect 254SE defines a method, as shown in FIG. 74 in conjunction with FIGS. 83A-C and 84, for updating a control program 110 (e.g. stored in a memory 107) adapted to run in a computing unit 106 of an implant 100 when implanted in a patient. The method comprises receiving S1101 data by the computing unit, and updating S1102 by the computing unit, the control program on the basis of the received data.

The expression "updating" is intended to encompass similar terms such as adjusting, overriding, or calibrating the control program. Any updates or additions (such as installing a new software application) may be done to the control program 110 using this embodiment. A flexible approach is thus achieved, where the control unit 106 uses received S1101 data for updating S1102 the control program of the implant 100. In one embodiment, updating the control program comprises adjusting at least one parameter of the implant.

Figure 84:
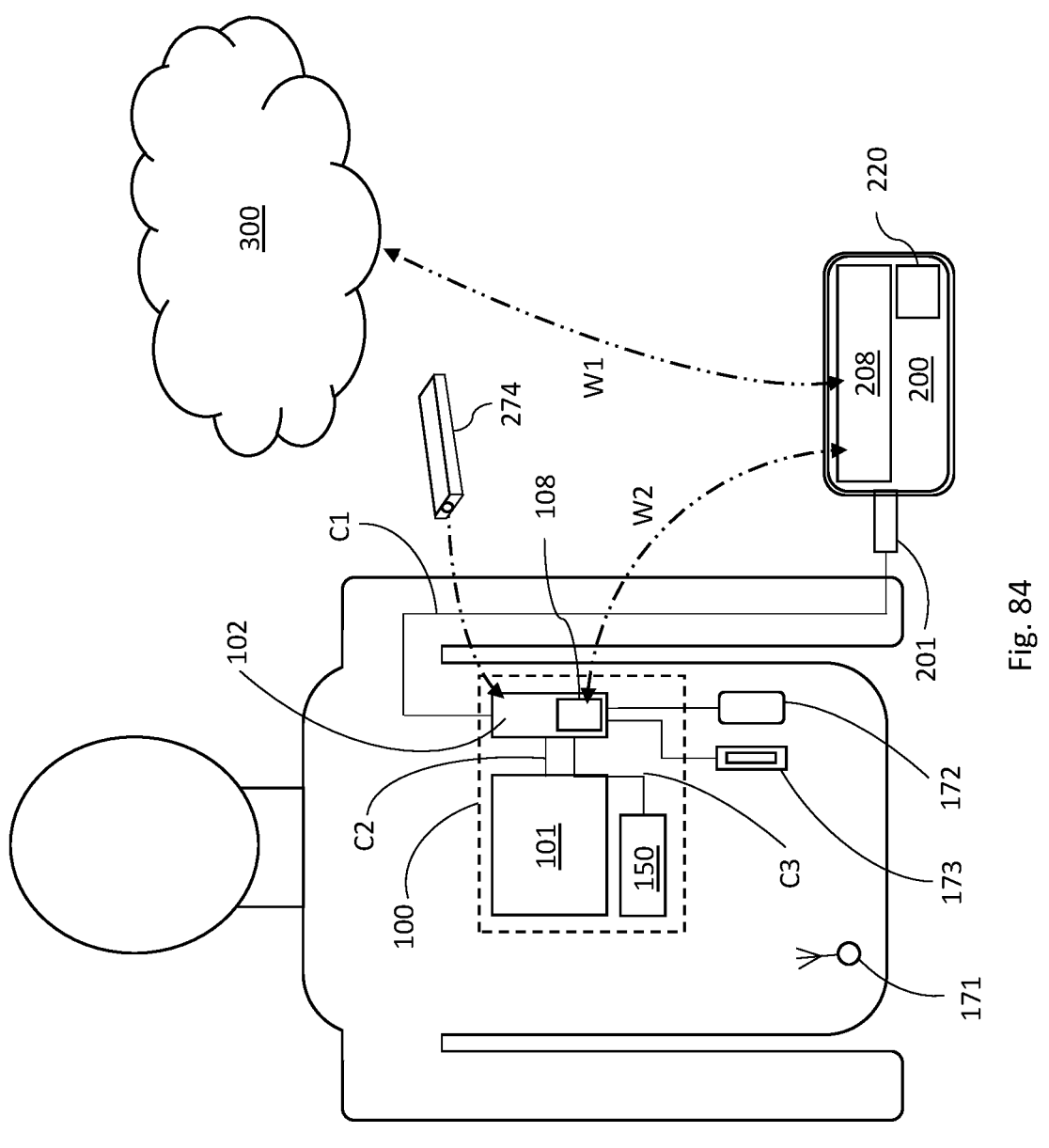
FIG. 84 illustrates a system according to aspect 254SE comprising an implant in connection with an external device wherein the external device is in connection with a second external device.

The method of FIG. 74 may be extended as shown in FIG. 75 in conjunction with FIG. 84. In this embodiment, data is transmitted S1103 from the implant 100 to an external device 200. The data may be wirelessly transmitted W2 using a wireless transceiver 108 or transmitted using conductive communication C1 using a wired transmitter 103.

Conductive communication may be achieved as described herein under aspect 247SE. In these cases, the implant and/or external device(s) comprise the necessary features and functionality (described in the respective sections of this document) for performing such conductive communication. Using a conductive communication for communication relating to updating of the control program 110 may be preferable as it makes it harder for malicious third parties to access the system and implement unauthorized control programs in e.g. implant.

In the external device, the data is received (e.g. using a wireless transceiver 208 or a wired transceiver 203. In this embodiment, the external device has the control program of the implant stored (e.g. in memory 207) and the external device 200 updates S1104 the control program (e.g. using a computing unit 206 of the external device 200) on the basis of the received data. The updated control program is then transmitted to the implant (by wire C1 or wirelessly W2) such that the data received S1101 by the computing unit 106 comprises the updated control program. The updated control program is then installed or similar in the implant. In other words, the computing unit 106 updates S1102 the control program on the basis of the received data.

In some embodiments, the updated control program transmitted to the implant 100 from the external device 200 is encrypted. In this case, the method of updating the control program at the implant 100 further comprises receiving S1105, by the computing unit 106, at least one key, and decrypting S1106 the encrypted data using the at least one key. To further increase security, the received key may be combined with a key stored at the implant 100, where the encrypted data may only be decrypted using the combined key.

Further examples and details of how to perform encryption of data transmitted between the implant 100 and the external device 200 can be found as described herein under the second, third or sixth aspect. In these cases, the implant and/or external device(s) comprises the necessary features and functionality (described in the respective sections of this document) for performing such encryption/decryption. Encryption of the communication in relation to update of the control program provides extra security in the update process as unauthorized update attempts may be disregarded and place the implant in a safe lockdown mode.

The key may be transmitted using conductive communication C1 or wireless communication W1.

Improved security may further be achieved by requiring, at the implant, that the connection used for transmission of the updated control program. i.e. the wireless W1 or wired connection C1 needs to be authenticated before the computing unit 106 updates the control program 110 on basis of the received updated control program from the external device 200. In these embodiments, upon positive authentication of the connection, the computing unit 106 updates the control program 110. If the connection is not authenticated, the computing unit may disregard the received update of the control program 110. The confirmation/authentication of the connection between the implant and the external device can be performed as described herein under the fifth, thirteenth or fifteenth aspect. In these cases, the implant and/or external device(s) comprises the necessary features and functionality (described in the respective sections of this document) for performing such confirmation/authentication.

In some embodiment, the data transmitted S1103 from the implant 100 comprises at least one physiological parameter of the patient (such as blood pressure, pulse, etc.). This embodiment is further described herein under the twelfth or thirteenth aspect. In these cases, the implant and/or external device(s) comprises the necessary features and functionality (described in the respective sections of this document) for sensing the physiological parameter. For example, in case the sensor senses that the values for blood pressure and pulse of the patient adequately match known or expected values, based on patient history or statistics, the control program may be updated S1104. Another example comprises that the sensor senses that the variability of the blood sugar values is to large, where the blood sugar value controls the amount of insulin that is ejected by the implant. In this case, the regulator algorithm used for controlling the insulin ejection of the implant may need to be updated S1104 at the external device to better suit the patient in which the implant is implanted into.

In some embodiments, the data transmitted S1103 from the implant 100 comprises at least one functional parameter (such as status of a battery, version of the control program, error log of the implant etc.) of the implant. In one embodiment, the sensor 150 senses that the power of a battery of the implant 100 is low, whereby the control program is updated at the external device such that some functionality of the implant (e.g. a feedback functionality or other features of the implant) is turned off. When the sensor 150 senses that power has been increased, the control program may be updated such that the previously disabled functionality is enabled again.

In some embodiments, the updating of the control program 110 is performed at the implant without any external involvement. An example of such embodiment is shown in FIG. 76. In this embodiment, the method of updating the control program comprises sensing S1107 at least one parameter using an implantable sensor 150. The sensor 150 may be included in the implant or external to the implant 100 but in connection (by wire or wirelessly) with the implant. The sensed data thus constitute the received S1101 data by the computing unit 106, whereby the computing unit 106 updates S1102 the control program on the basis of the at least one sensed parameter.

For example, the sensor 150 may be for sensing at least one physiological parameter of the patient, wherein the received S1101 data by the computing unit comprises at least one physiological parameter of the of the patient. Examples of physiological parameter of the patient as further described under the twelfth or thirteenth aspect. In these cases, the implant comprises the necessary features and functionality (described in the respective sections of this document) for sensing the physiological parameter. The computing unit may then update the control program on basis of the received at least one senses parameter. For example, in case the sensor senses that senses that the variability of the blood sugar values is to large, where the blood sugar value controls the amount of insulin that is ejected by the implant. In this case, the implant may itself update S1102 the regulator algorithm used for controlling the insulin ejection of the implant may need to be updated to better suit the patient in which the implant is implanted into.

Alternatively, or additionally, the sensor 150 may be for sensing at least one functional parameter of the implant, wherein the received S1101 data by the computing unit comprises at least one functional parameter of the implant. In one embodiment, the sensor 150 senses that the power of a battery of the implant 100 is low, whereby the control program is updated by the computing unit such that some functionality of the implant (e.g. a feedback functionality or other features of the implant) is turned off. When the sensor 150 senses that the power has been increased, the control program may be updated such that the previously disabled functionality is enabled again.

The implant may be in communication with further sensors (external to the implant 100), such as an implantable sensor 171 adapted to sense at least one parameter (functional and/or physiological as described above), wherein the received S1101 data by the computing unit 106 comprises said at least one sensed parameter, wherein the computing unit 106 is configured for updating S1102, the control program on the basis of the at least one sensed parameter.

In some cases, the patient may provide input to the implant to be used for updating the control program. One example of such embodiment is shown in FIG. 77, which comprises the patient, or a caregiver of the patient, controlling S1108 the computing unit 106 using at least one of an implantable manual receiver 172, an implantable switch 173 and a remote control 274, the patient, or caregiver, providing feedback related to the operation of the implant, wherein the data received S1101 by the computing unit comprises said feedback. The computing unit 106 updates S1102 the control program on basis of the patient feedback.

The switch 173 may be a reset function or switch 173. Further information and details around the reset switch 173 and other involved devices and processes for handling such reset switch 173 may be performed as described herein under the aspect 244SE. In these cases, the implant and/or external device(s) comprises the necessary features and functionality (described in the respective sections of this document) for performing such a resetting of the implant 100.

In some embodiments shown in FIG. 79, the method of updating the control program 110 of the implant 100 comprises, receiving S1109 feedback from at least one of, the patient in whom the implant is implanted and at least one sensor 150, 171, in response to the control program controlling the implant, and updating S1102, by the computing unit, the control program on the basis of the received feedback. The updating process may thus be iterative, where an update S1102 result in new data received S1101 by the computing unit 106 as a result of the update (e.g. patient feedback relating to the updated functionality of the implant 100, or sensor data relating to the updated functionality of the implant 100), whereby the control program 110 is again updated S1102.

The iterative update may also involve the external device 200. One example of this embodiment is shown in FIGS. 79-80. For example, the feedback from at least one of, the patient in whom the implant is implanted and at least one sensor 150, 171, in response to the control program controlling the implant may be received directly by the externa device 200 or transmitted from the implant 100 to the external device 200, which updates S1104 the control program on the basis of the said feedback, wherein the data received S1101 by the computing unit comprises the updated control program. In another embodiment, the received S1101 data by the computing unit 106 comprises calibration parameters transmitted from the external device 200, said calibration parameters based on the feedback provided to the external device.

In some embodiments, shown in FIG. 81, authentication input from a user is required to update the control program. In these embodiments, the external device comprises an interface for inputting authentication data, e.g. using a verification unit 220 of the implant. The method of updating the control program 110 of the implant 100 thus may comprise receiving S1111 authentication input from a user for authenticating the updating of the control program, and as a result of the authentication input, updating S1102 the control program by the computing unit. In other words, upon valid authentication, the control program 110 may be updated. The authentication input may comprise a code, a biometric input (fingerprint, iris scanner etc.) or any other suitable means for authentication. In some embodiments, the updated control program, or calibration parameters, etc., may not be transmitted from the external device unless valid authentication is inputted. In other embodiments, the control unit 106 may not update, install, or calibrate the control program 110 in the implant 100 unless a valid authentication is determined. The implant 100 may comprise the data needed for determining if the authentication is valid or not (i.e. the correct code, the approved fingerprints etc.). In other embodiments, the external device 200 may comprise the data needed for determining if the authentication is valid or not (i.e. the correct code, the approved fingerprints etc.).

In some embodiments, a second external device 300 is involved in the updating of the control program. The second external device 300 may be controlled by medical staff, manufacturer of the implant 100 or any other suitable individual or organization for updating the control program 110. In this embodiment, the implant 100 is wirelessly connected to an external device 200, the external device configured to relay communication between a second external device 300 and the implant 100. A system of the implant 100, the external device 200 and the second external device 300 is thus formed. The external device 200 comprising a wireless transceiver 208 configured for wireless communication W1. W2 with the second external device and the implant, the wireless transceiver 208 configured to receive S1112 an instruction (using the wireless communication W1) from the second external device 300 communicated using a first network protocol, wherein the wireless transceiver 208 is configured to transmit (using the wireless communication W2) the instruction to the implant 100 using a second network protocol.

The relaying functionality may in some embodiments need to be authenticated by the user/holder of the external device. In these embodiments, the method for updating the control program 110 comprises receiving S1113, by the verification unit 220 of the external device 200, authentication input (code, parameter of the patient, etc. as described herein) from a user, authenticating S1114 the relay functionality of the external device based on the authentication input. In these embodiments, the wireless transceiver 208 transmits the instruction to the implant, only if the relaying functionality of the external device is authenticated, using a second network protocol, wherein the data received S1101 by the computing unit 108 comprises the instructions. The computing unit 106 may then update S1102 the control program 110 accordingly.

The instructions received S1112 from the second external device may comprise one of the updated control program, and calibration parameters of the implant. In some embodiments, not shown in the figures, feedback and/or sensed parameters are transmitted from the implant/external device to the second external device 300 prior to the wireless transceiver 208 receives S1112 the instruction from the second external device 300. The second external device 300 may thus base the instructions on such received data.

The first network protocol may a standard network protocol from the list of:
a Radio Frequency type protocol
a RFID type protocol
a WLAN type protocol a Bluetooth type protocol
a BLE type protocol
a NFC type protocol
a 3G/4G/5G type protocol
a GSM type protocol
The second network protocol may be a proprietary network protocol.

More embodiments describing network protocols may be implemented as described herein under aspect 250SE. In these cases, the implant and/or external device(s) comprises the necessary features and functionality (described in the respective sections of this document) for performing transmission of data.

The routing may be performed as described herein under aspect 253SE. In these cases, the implant and/or external device(s) comprises the necessary features and functionality (described in the respective sections of this document) for performing such routing.

Further information and definitions of features, functionality of aspect 254SE can be found in this document in conjunction with the other aspects.

A first communication system may be used for receiving data by the computing unit 106 of the implant 100. A second communication system may be used for transmitting data from the implant 100 to the external device 200.

The method may further comprise relaying data to the second external device 300 and receiving the updated control program at the second external device 300.

A caregiver may transmit data to the implant 100 from a second external device 300 directly or via the external device 200.

According to embodiments of the first part of aspect 254SE a connection between the implant 100 and the external device 200 is authenticated by a conductive communication or connection between the implant 100 and the external device 200.

This feature may be achieved as described herein under aspect 247SE. In these cases, the implant and/or external device(s) comprises the necessary features and functionality (described in the respective sections of this document) for performing such conductive communication. The communication may thus be provided with an extra layer of security in addition to the encryption by being electrically confined to the conducting path e.g. external device 200, conductive member 201, conductive connection C1, implant 100, meaning the communication will be excessively difficult to be intercepted by a third party not in physical contact with, or at least proximal to, the patient.

The implant may comprise at least one of:
a pacemaker unit,
an external heart compression device.
an apparatus assisting the pump function of a heart of the patient.
an operable artificial heart valve,
an implantable drug delivery device.
a hydraulic, mechanic, and/or electric constriction implant,
an operable volume filling device,
an operable gastric band,
an operable implant for stretching the stomach wall of the patient.
an operable cosmetic implant,
an implant for adjusting or replacing any bone part of a body of the patient, an implant replacing an organ of the patient or part of an
    organ of the patient or the function thereof, a vascular treatment device, and an implant adapted to move fluid inside the body of the
    patient.

Aspect 255SE Information from Implant—Information from Implant—Embodiments of Aspect 255SE of the Disclosure In aspect 255SE, communication of sensor parameters between an implant and an external device is provided. FIGS. 85A-H show embodiments of this aspect.

FIGS. 85A-H shows an implant 100 implanted in various places of a patient's body. It is to be understood that the implant 100 could be placed anywhere in the patient's body and is not restricted to the placements shown in FIGS. 85A-H.

Figure 85A:
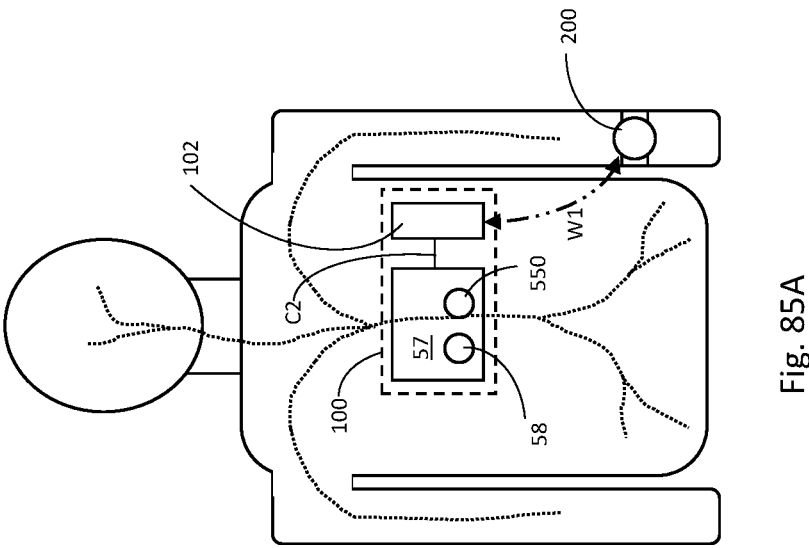
FIG. 85A illustrates an implant according to aspect 255SE being implanted in connection with the vascular system of a patient.

FIG. 85A shows an implant 100 in the abdominal area of a patient's body. The implant 100 comprises a vascular portion 57, adapted to be placed in proximity to a blood vessel. In FIG. 85A the vascular portion 57 is placed in the abdominal area, but it could be placed near any blood vessel in the body, such as for example the aorta, common carotid artery, subclavian artery, common iliac arteries, subclavian vein, inferior vena cava, renal veins, common iliac vein, and pulmonary arteries. The vascular portion 57 further comprises a sensor 550. In FIG. 85A, the implant 100 comprises one sensor 550, it is however plausible to have more sensors. The sensor 550 can sense physiological parameters of the patient, such as for example blood pressure and temperature. The sensor 550 in FIG. 85A is configured to sense at least one parameter related to the blood of the patient. The implant 100 also comprises a communication unit 102. The communication unit 102 may comprise different means for communication, for example a wireless transceiver, and/or a wired transceiver. In the following, wireless communication is used by way of example. The communication unit 102 is connected to the vascular portion 57 by a connection C2 (it should be noted that wired, or wireless connection may be employed between the implant 100 or the communication unit 102 and the sensor 150, further described herein with reference to the other aspects). The communication unit 102 can wirelessly (or by wire) transmit W1 the parameter sensed by the sensor 550 to an external device 200. The external device could be any device external to the body, in some embodiments, handheld and easily accessible. The external device 200 can have a display on which information regarding the sensed parameter can be presented to the patient. This information can be presented in various ways, such as displaying the measured value of the parameter, or displaying a phrase or color code, or any other information that guides the patient on how to proceed. The vascular portion 57 can comprise a needle (not shown), with which blood can be extracted from the blood vessel to the sensor 550. In FIG. 85A, the vascular portion 57 comprises a needle operating device 58. The needle operating device 58 can operate the needle such that it can extract blood at a first site, and then change and extract blood at a second site. One advantage of this is that unnecessary damage due to repeated punctures at the same site of the vessel can be avoided or minimized. It is further possible that the sensor 550 is an optical sensor that could sense optical parameters of the blood. The optical sensor 550 could in such case also be configured for spectrophotometry. The sensor 550 could also further sense visible light. UV light and/or IR radiation. It is further possible that the sensor 550 in FIG. 85A can sense a parameter relating to at least one of the following: oxygen saturation, blood pressure, a function of the liver, the existence of cancer, the bile function, glucose, lactate, pyruvate, prostate-specific antigen, cholesterol level, potassium, sodium, cortisol, adrenalin, ethanol, blood composition, platelets, white blood cells, red blood cells, viscosity, flux, the direction of flow, flow velocity, blood plasma concentration, hormones, enzyme activity, calcium, iron, iron-binding capacity, transferrin, ferritin, ammonia, copper, ceruloplasmin, phosphate, zinc, magnesium, pH, oxygen partial pressure, carbon dioxide, bicarbonate, protein(s), blood lipids, tumor markers, vitamins, toxins, antibodies, electrolytes. The sensor 550 could also sense a parameter related to the effect of a therapeutic treatment, or the presence of a pharmaceutical. If for example the patient has consumed a too high a dose of a medicine (or, equally, too low) the sensor 550 senses this and the communication unit 102 can communicate this to the external device 200. This makes the patient, doctor or any other caretaker aware of the dose issue and enables them to adjust the dose accordingly. The sensor 550 could further sense the presence of at least one of the following: an antibiotic pharmaceutical, a chemotherapy pharmaceutical and insulin. If the implant 100 is utilized by diabetes patients, the sensor 550 senses the insulin levels in the blood and communicates this to the external device 200. In cases where the external device 200 is a watch, smart phone or any other easily accessible device, the patient can immediately, and discretely, get information on how to act. This direct and reliable information ensures that the patient doesn't have to guess or estimate the dose needed, thus avoiding the risks of over or underdosing. The sensor 550 could also be configured to sense a parameter related to cancer treatments and/or antibiotic treatments.

Figure 85B:
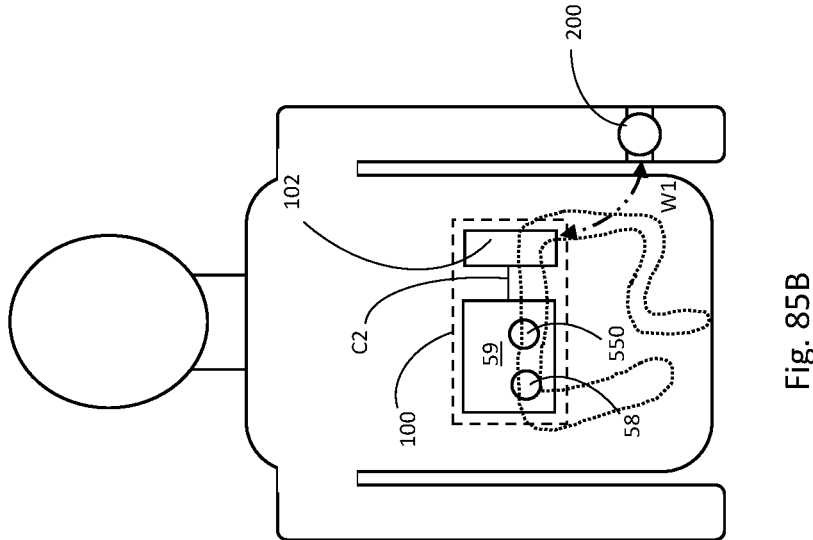
FIG. 85B illustrates an implant according to aspect 255SE being implanted in connection with the intestinal system of a patient.

FIG. 85B shows another embodiment of aspect 255SE. In this embodiment, the implant 100 comprises a food passageway portion 59 which is placed in proximity to the food passageway of a patient. The sensor 550 can sense at least one of intestinal activity, activity of the stomach or activity of the esophagus and can be for example an accelerometer, a motility sensor and/or a strain sensor. It is also plausible that the sensor 550 can sense an electrical parameter. In some cases, the sensor 550 can also sense contents in the esophagus, the stomach or in an intestine. It is possible that the sensor 550 in FIG. 85B comprises a needle, with which contents in the food passageway can be extracted and transported to the sensor 550. In this case, the food passageway portion 59 comprises a needle operating device 58 which can displace the needle such that it can change from extracting contents at a first site of the food passageway to extracting contents at a second site of the food passageway. The sensor 550 could also be an optical sensor and configured to utilize spectrophotometry. The optical sensor 550 can sense visible light. UV light and/or IR radiation. It is also possible that the sensor 550 in FIG. 85B is an audio sensor adapted to sense sound. When the hollow intestines move, they produce sounds that can give information on a patient's condition. The audio sensor 550 could for example be utilized for determining ileus, a condition in which there is a lack of intestinal activity and thus effects the sounds coming from the bowel. In some cases, the bowel sounds are unable to be heard by the patient and/or medical professional trying to listen and considering that acute abdominal diseases is a prominent death cause if left untreated, the audio sensor 550 is a very powerful tool. In these cases, the audio sensor 550 picks up and communicates via the communication unit 102 information to the patient and/or doctor. The food passageway is to be understood as the entire length through which the food passes, notably the moth, the esophagus, the stomach, the intestines, and the rectal region.

Figure 85C:
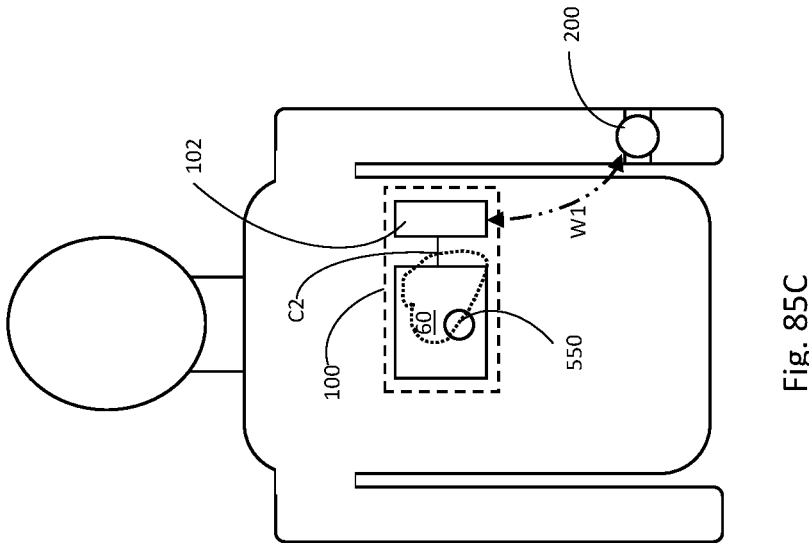
FIG. 85C-D illustrates an implant according to aspect 255SE being implanted in connection with the heart of a patient.

FIG. 85C shows an embodiment in which the implant 100 comprises an ultrasound sensor 550. In FIG. 85C, the ultrasound sensor 550 is placed in a cardiac portion 60 of the implant 100. The cardiac portion 60 is placed near the patient's heart, it is however equally possible that the implant 100 is placed in another part of the patient's body, and that the ultrasound sensor 550 is in proximity to another body part. The ultrasound sensor 550 in FIG. 85C can sense the blood flow in the heart. Should for example the blood flow suddenly decrease, myocardial ischemia occurs, which can lead to a heart attack. Silent myocardial ischemia is a condition in which the patient doesn't experience any noticeable signs or symptoms. Such condition could therefore be avoided by utilizing the sensor 550 of FIG. 85C. The ultrasound sensor 550 could also sense presence of fluid in the body of the patient, for example in the pericardial cavity. It could also sense the level of urine in the urinary bladder, in which case the sensor 550 and implant 100 is placed in proximity to the renal system.

Figure 85D:
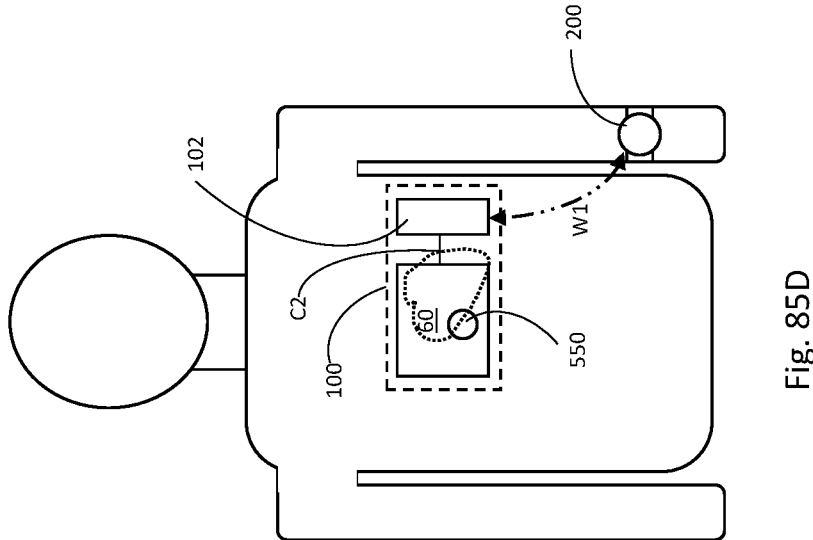

FIG. 85D shows an embodiment of aspect 255SE in which the implant 100 comprises a cardiac portion 60 and has a sensor 550 configured to sense a parameter related to the patient's heart. The sensor 550 could for example sense a parameter related to the electrical activity of the heart. It could also be adapted to sense a sound parameter related to the heart. In these cases, the implant comprises the necessary features and functionality for performing such sensing.

Figure 85E:
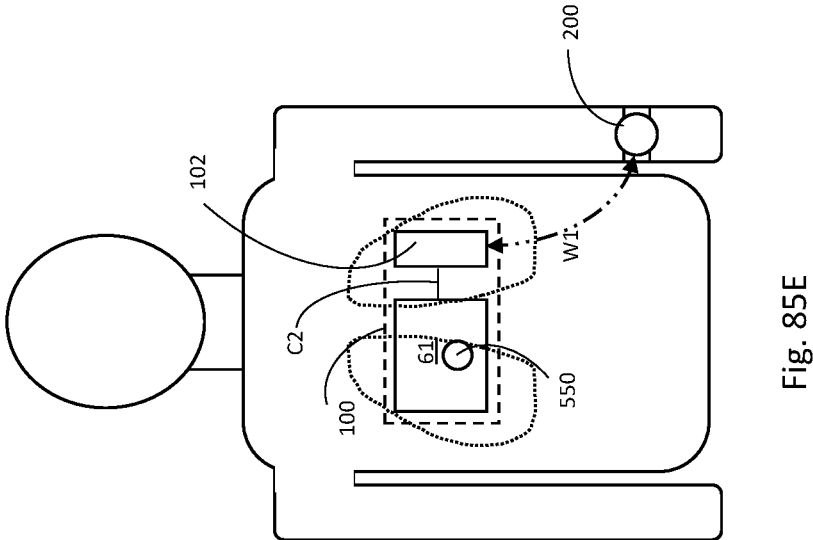
FIG. 85E illustrates an implant according to aspect 255SE being implanted in connection with the pulmonary system of a patient.

FIG. 85E shows an implant 100 with a pulmonary portion 61. The pulmonary portion 61 comprises the sensor 550 and is located in proximity to the patient's lungs. The sensor 550 is adapted to sense parameters relating to the lungs. The sensor 550 could for example sense respiratory activity. In this case, the sensor 550 could be an accelerometer, a motility sensor and/or a strain sensor. It is also possible that the sensor 550 In FIG. 85F is an optical sensor, and/or an audio sensor.

Figure 85F:
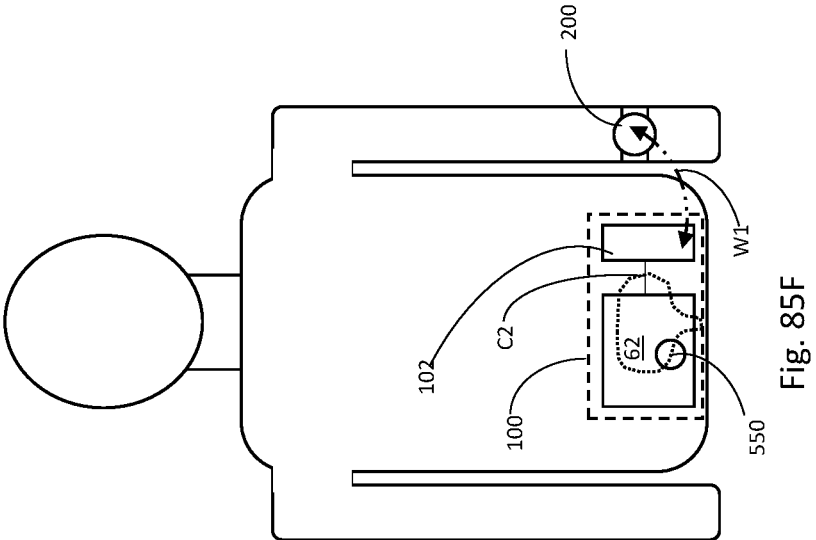
FIG. 85F illustrates an implant according to aspect 255SE being implanted in connection with the urinary system of a patient.

FIG. 85F shows an implant 100 being implanted in proximity to the renal system. The implant 100 comprises a urinary portion 62 and a sensor 550 which senses parameters relating to the urine bladder of the patient. It is possible that the sensor 550 is an optical sensor, and that it senses activity of the urinary bladder. The sensor 550 in FIG. 85F could also be an accelerometer, a motility sensor, and/or a strain sensor.

Figure 85G:
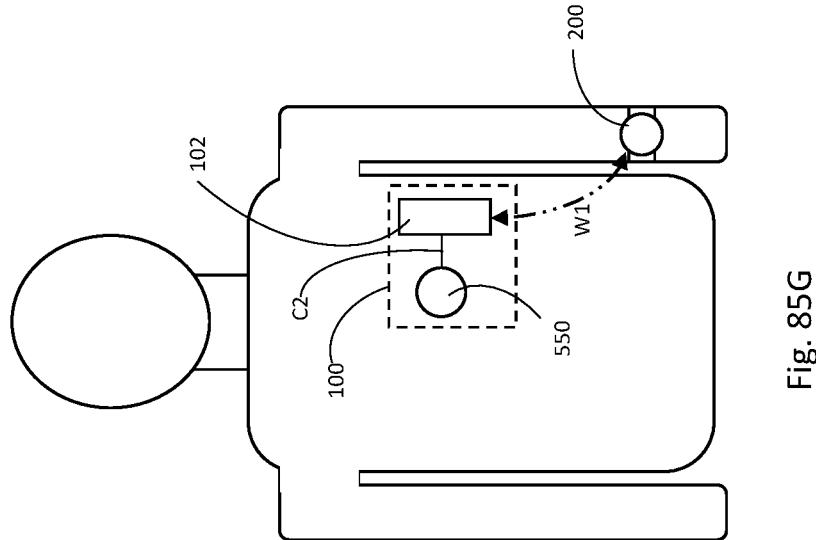
FIG. 85G illustrates an audio implant according to aspect 255SE being implanted in a patient.

FIG. 85G shows an implant 100 placed in the upper abdominal area of a patient. It is to be noted that the implant 100 could equally be placed in other parts of the body. The implant 100 in FIG. 85G has an audio sensor 550 which sense audio parameters of the patient. The audio parameter could pertain to at least one of: the activity of the gastrointestinal system, the activity of the lungs, the activity of the heart, and the patient's voice. One way of utilizing the patient's voice (or any other sound or person's voice) is to compare the received audio in the implant 100 with the received audio in the external device 200. The comparison can then be used to synchronize the implant 100 with external device 200.

Figure 85H:
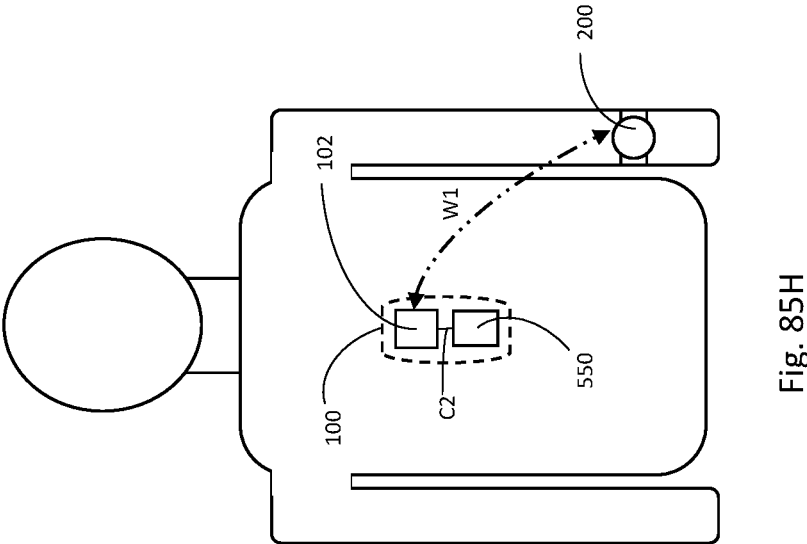
FIG. 85H illustrates an audio implant according to aspect 255SE being ingested by a patient.
Figures 86A, 86B, 86C:
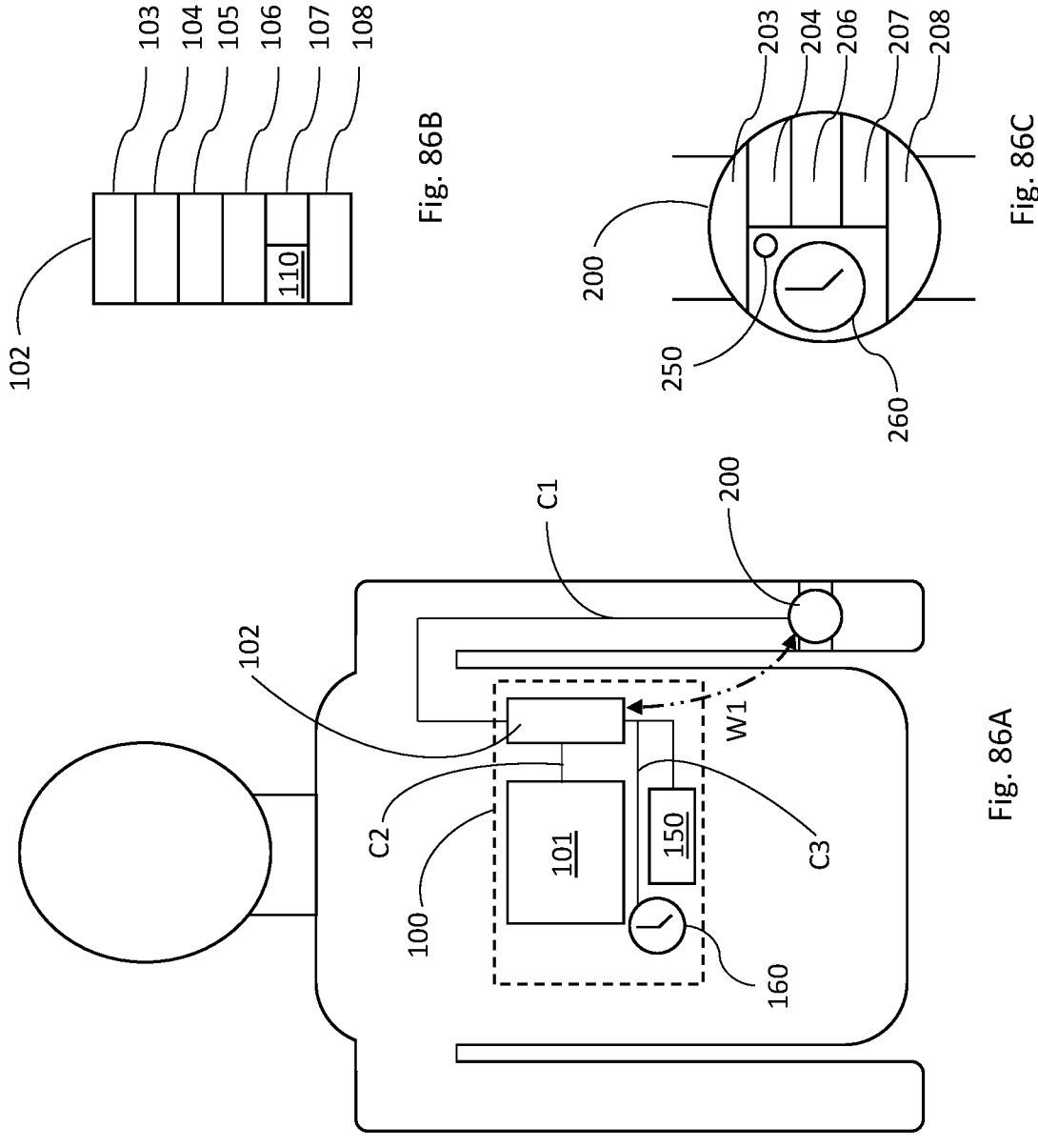
FIG. 86A illustrates a system comprising an implant, further illustrated in FIG. 86B, and an external device, further illustrated in FIG. 86C, all according to aspect 256SE.

FIG. 85H shows an implant 100 ingested by the patient. The ingested implant 100 has an audio sensor 550 which can sense audio parameters. The audio parameter could pertain to at least one of: the activity of the gastrointestinal system, the activity of the lungs, the activity of the heart, and the patient's voice.

It is to be understood, that any and all of the sensor(s) described herein with reference to FIGS. 85A-H are also compatible with, and could be integrated in, the embodiments pertaining to the first, second, third, fourth, fifth, sixth, seventh, eighth, ninth, tenth, eleventh, thirteenth and fifteenth aspects. In these cases, the implant and/or external device(s) comprises the necessary features and functionality (described in the respective sections of this document) for performing such communication. It is also noted that the communication, wireless or electrical, between the sensor(s) described with reference to FIGS. 85A-H and any external device may be performed as described herein under the first, second, third, fourth, fifth, sixth, seventh, eighth, ninth, tenth, eleventh, thirteenth and fifteenth aspects. In these cases, the implant and/or external device(s) comprises the necessary features and functionality (described in the respective sections of this document) for performing such communication. It is to be noted, however, that even though the communication between the communication unit 102 and the external device 200 is wireless by way of example in the FIGS. 85A-H, it is plausible that the communication is electrical or by any other means wired. Further, the communicated and/or encrypted information referred to herein in the second, third, sixth, seventh, ninth, tenth, and thirteenth aspects can pertain to the sensed parameters described with reference to FIGS. 85A-H.

Figure 94:
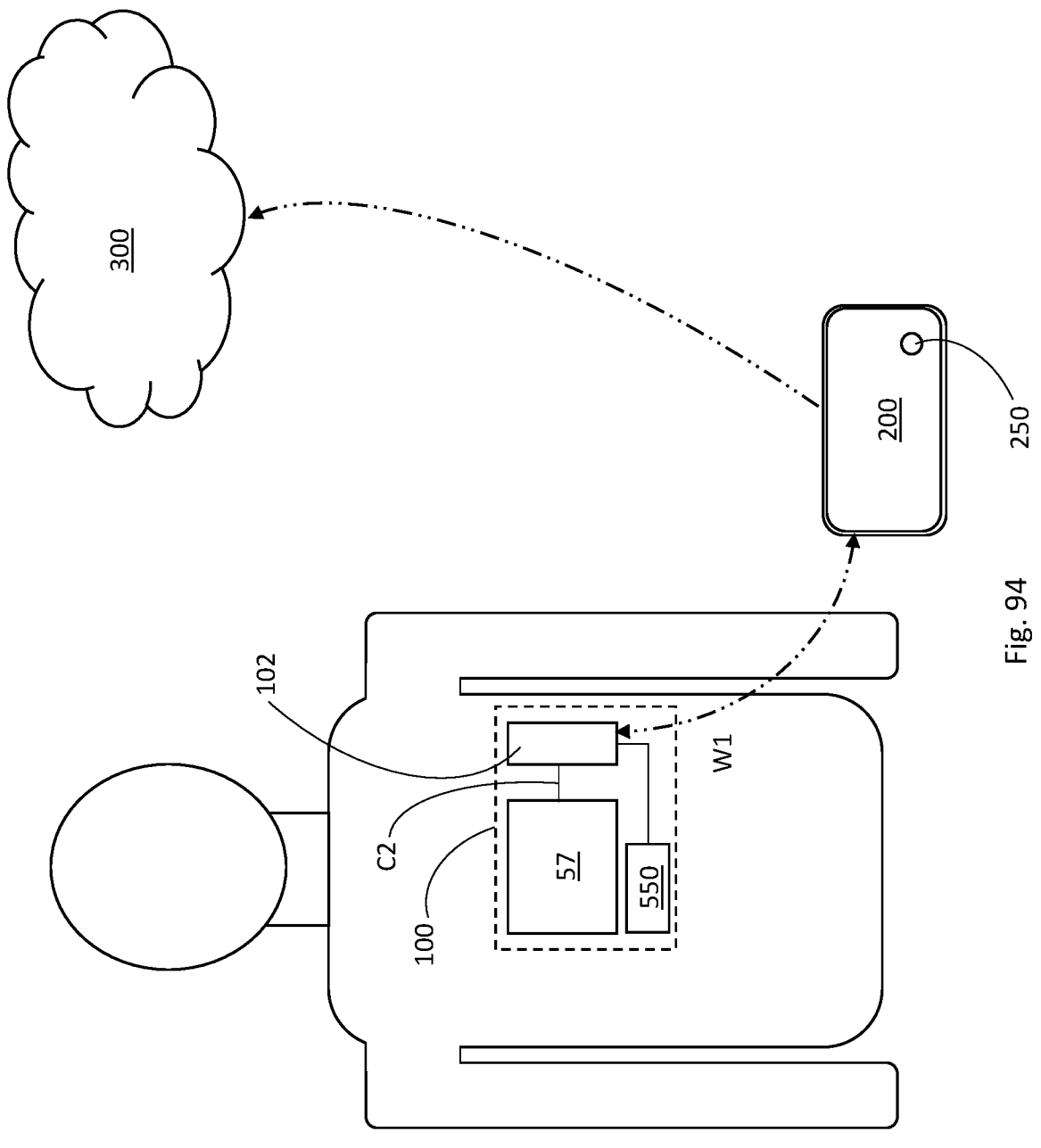
FIG. 94 illustrates a system according to embodiments of the ninth part of aspect 255SE.

FIG. 94 illustrates a system comprising an implant 100, implanted in a patient, an external device 200, and a second external device 300. The external device 200 is configured to transmit data pertaining to the sensed parameter to the second external device 300. The external device 200 is configured to add information to the data pertaining to the sensed parameter before transmitting to the second external device 300.

The information added may comprise at least one of:
a weight of the patient,
a height of the patient,
a body temperature of the patient,
eating habits of the patient.
physical exercise habits of the patient,
toilet habits of the patient,
an outside or external temperature of the patient, and
geographic position data of the patient.

The external device 200 may comprise a sensor 250 for recording the information to be added to the data pertaining to the sensed parameter. The sensor 250 may comprise a thermometer, e.g. for measuring a body temperature of the patient, or a geographical positioning sensor such as a global navigation satellite system, GNSS, receiver, e.g. for recording geographic position data of the patient.

The external device 200 may be configured to automatically add the information to the data pertaining to the sensed parameter. The external device may alternatively or also be configured to add information to the data pertaining to the sensed parameter upon receiving a manual input from a user. Such a manual input may relate to the information added such as e.g. a weight of the patient. Input may be performed by the patient interacting with a user interface of the external device. Such a user interface may comprise a display and/or a keypad. The manual input may comprise authentication or verification of the user to transmit automatically provided data. Authentication may be established by the patient inputting a code or providing a biometric input such as e.g. a fingerprint to a fingerprint reader/sensor of the external device 200.

The second external device 300 may e.g. be a device controlled by a healthcare provider of the patient or a provider/manufacturer of the physical implant.

The implant 100, the external device 200, the second external device 300, and the communication between these may be further described in the other aspects of this document. Authentication and verification may also be further described in the other aspects of this document.

Further information and definitions of the wireless connection W1, the electrical connection C2 and the external device 200 can be found in this document in conjunction with the aspect 244SE and the general definition of features used in this disclosure.

The implant may comprise at least one of:

a pacemaker unit, an external heart compression device, an apparatus assisting the pump function of a heart of the patient, an operable artificial heart valve, an implantable drug delivery device, a hydraulic, mechanic, and/or electric constriction implant, an operable volume filling device, an operable gastric band, an operable implant for stretching the stomach wall of the patient, an operable cosmetic implant.

an implant for adjusting or replacing any bone part of a body of the patient, an implant replacing an organ of the patient or part of an organ of the patient or the function thereof, a vascular treatment device, and an implant adapted to move fluid inside the body of the patient.

Aspect 256SE Device Synchronization Patient Parameter—Authenticating a Connection Between an Implant and the External Device Using a Patient Parameter—Embodiments of Aspect 256SE of the Disclosure In aspect 256SE, increased security for communication between an external device(s) and an implant is provided. FIGS. 86-89 shows embodiments of this aspect.

FIGS. 86A-C and 87 show an implant 100 implanted in a patient and an external device 200.

Figure 87:
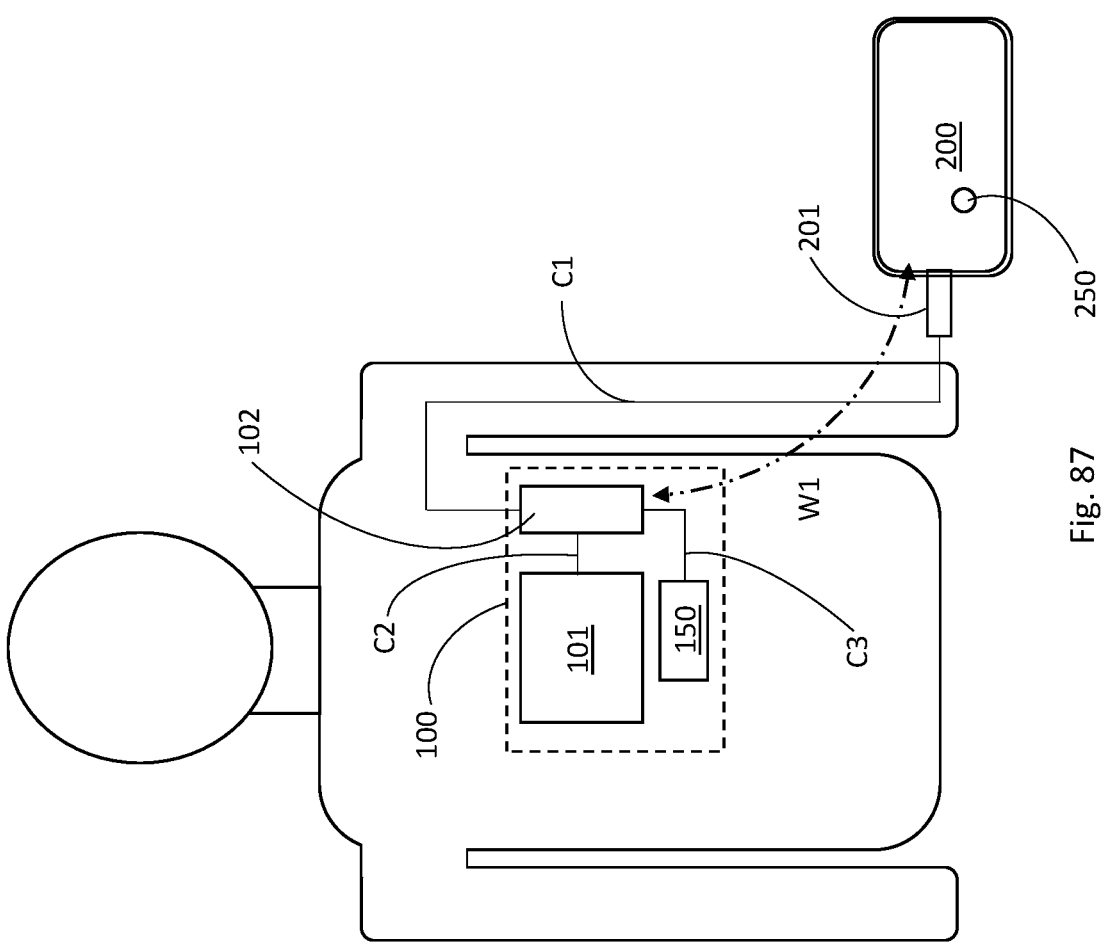
FIG. 87 illustrates a system according to aspect 256SE comprising an implant in connection with an external device.

The implant 100 may comprise a first sensor 150 for measuring a parameter of the patient by the implant 100. The first sensor 150 may be configured to measure a pulse of the patient, a respiration rate of the patient, a temperature of the patient, at least one sound of the patient, or at least one physical movement (e.g. an acceleration of the physical movement) of the patient. The first sensor 150 may comprise a microphone, a thermometer, an accelerometer, a gyroscopic sensor, a pressure sensor, or a flow sensor. The first sensor may be wired or wirelessly connected to the implant. In FIGS. 86-87, a wired (electrical) connection C3 is shown by way of example. Further example of sensors may be found herein under aspect 255SE. As such, the communication may serve a dual purpose of transmitting the information for purposes such as e.g. collection and analysis as well as authentication of the connection.

The external device 200 may comprise a second sensor 250 for measuring a parameter of the patient by the external device 200. The second sensor 250 may be configured to measure a pulse of the patient, a respiration rate of the patient, a temperature of the patient, at least one sound of the patient, or at least one physical movement (e.g. an acceleration of the physical movement) of the patient. The second sensor 250 may comprise a microphone, a thermometer, an accelerometer, a gyroscopic sensor, a pressure sensor, or a flow sensor. The second sensor 250 may be wired or wirelessly connected to the external device 200. The second sensor 250 may be integrally a part of the external device 200 (as is shown in FIGS. 86-87) or a physically separate unit from but connected to the external device 200. An example of a separate second sensor 250 may be a bracelet. Such a bracelet second sensor 250 may be adapted to measure a pulse at a wrist of the patient and communicate data or metrics pertaining to the measurement to the external device 200 conductively by a wire or wirelessly.

The second sensor 250 should correspond to the first sensor 150 in that comparable sensed parameters should be measured by the sensors 150, 250.

The implant 100 may further comprise an internal computing unit 106. The internal computing 106 unit may be configured for receiving a parameter of the patient, from the external device 200. The internal computing unit 106 may be further configured for comparing the parameter measured by the implant 100 to the parameter measured by the external device 200. The internal computing unit 106 may be further configured for performing authentication of the connection based on the comparison.

The external device may further comprise an external computing unit 206. The external computing unit 206 may be configured for receiving a parameter of the patient, from the implant 100. The external computing unit 206 may be further configured for comparing the parameter measured by the external device 200 to the parameter measured by the implant 100. The external computing unit 206 may be further configured for performing authentication of the connection based on the comparison.

FIGS. 88 and 89 show flow charts of methods for authenticating a connection between an implant 100 implanted in a patient, and an external device 200. The method may comprise the step of establishing a connection S5601 between the external device 200 and the implant 100. The method may further comprise the step of measuring a parameter S5602 of the patient, by the implant 100. The method may further comprise the step of measuring the parameter S5603 of the patient, by the external device 200. The method may further comprise the step of comparing the parameter S5604 measured by the implant 100 to the parameter measured by the external device 200. The method may further comprise the step of performing authentication S5605 of the connection based on the comparison.

The method may ensure that authentication may not occur unless parameters of the patient measured by the external device and the implant match. In effect, this may prevent, or at least reduce the risk of, unauthorized connection or communication to and from the implant or the external device. Another advantage of the method is that the authentication may be performed automatically with the external device and the implant communicating with each other without requiring any verification or input authentication from the patient.

The parameter of the patient may be measured by the sensors 150, 250. The measurement may comprise recording a parameter event such as e.g. a movement detected by the sensors 150, 250 being an accelerometer. A strength or power of the parameter measured may need to exceed a set threshold value of the sensors 150, 250 for an event to be recorded. This approach may be considered a digital approach where an event is either recorded or not. As an alternative, data pertaining to the measured parameter may be recorded, e.g. a value for an acceleration of the movement detected by the sensors 150, 250 being an accelerometer as in the previous example. This may be considered a more analogue approach to measuring the parameters.

The sensors 150, 250 may also record the parameter of the patient for a set amount of time resulting in a time sequence of data pertaining to the parameter. The comparison (made by the internal 106 or external 206 computing unit) may comprise a comparison of the time sequences recorded by the external device 200 via the second sensor 250 and the implant 100 via the first sensor 150. Time sequence duration may preferably be in the range 0.01-60 s, more preferably 0.1-30 s, and most preferably 1-10 s.

The parameter of the patient may be related to biological processes that are largely out of the patient's control such as a pulse, a respiration rate, or a temperature. Alternatively, the parameter of the patient may be controllable to the patient and configured to register for specific actions of the patient.

An example of such a controllable action may include shouting, or by other means, producing a loud sound such that both sensors 150, 250, being in relatively close proximity to each other, are able to measure. Another example of an action of the patient may be a jump or a spin such that both sensors 150, 250, located implanted inside and carried externally by the patient, may measure the same physical movement related to the jump or spin.

A relative momentary vertical acceleration exceeding 1 g (i.e. 9.8 ms^-2) in a normal direction of a surface, on which the patient is located, may be measured by an accelerometer in order to register a jump of the patient. Relative in this context means relative or in addition to ever present or inherent accelerations such as a 1 g acceleration due to gravity. The first and second sensor 150, 250 may record substantially the same acceleration. Differences may be dependent on how structurally fixed the accelerometers are. For example, if the external device 200 with the second sensor 250 is located in a pocket of a clothing item of the patient, some extra inertia may be expected. Such differences may be accounted for by calibration of the implant 100 and the external device 200 with their respective sensors 150, 250. Similar actions for calibration may be performed regardless of the types of parameters or sensors used.

A noise level exceeding 70 dB may be measured by a microphone in order to register a sound of the patient. Due to attenuation, a noise level of an external sound may be reduced upon reaching the implant implanted internally in the body of the patient. The reduction may be accounted for by calibration of the implant 100 and the external device 200 with their respective sensors 150, 250.

The pulse, heart rate, or cardiac rate of the patient may refer to a rate or frequency at which a heart cycles through its steps for pumping blood through a cardiovascular system of the patient. The cardiovascular system, vascular system, circulatory system may comprise the heart and blood vessels such as veins and arteries of the patient. The pulse of the patient may be characterized by the frequency of peaks or troughs of a pressure of a blood flow at a specific location in the cardiovascular system. A peak of the blood flow pressure exceeding 90 mmHg may be measured by a pressure sensor in order to register a peak of the pulse of the patient.

The parameter of the patient may also comprise a blood pressure of the patient.

The blood pressure of the patient, comprising a systolic pressure (peak) and a diastolic pressure (trough) may be measured similarly to the pulse and used for authenticating the connection between the implant 100 and the external device 200.

FIG. 89 specifically relates to various ways of performing the step of comparing the parameters S5604. The parameter of the patient measured by the external device 200 may be transmitted to and used for the comparison S5604a at the internal computing unit 106 of the implant 100. The parameter of the patient measured by the external device 200 may alternatively be transmitted to the external computing unit 206 for comparison. The parameter of the patient measured by the implant 100 may be transmitted to and used for the comparison S5604b at the external computing unit 206 of the external device 200. The parameter of the patient measured by the implant 100 may alternatively be transmitted to the internal computing unit 106 for comparison.

The parameters measured by the implant 100 or the external device 200 may be provided with a timestamp. The comparison of the parameter measured at the implant 100 to the parameter measured by the external device 200 may comprise comparing S5604c the corresponding timestamps. The timestamps may comprise a time related to the measurement of the parameter of the patient e.g. a time for initializing the measurement. The timestamp may be encoded at the implant 100 or the external device 200. The timestamp may be communicated between the implant 100 and the external device 200 encoded and be decoded at the receiving end of the two.

The implant 100 may further comprise a clock 160. The external device 200 may comprise a clock 260. The clocks 160, 260 may be configured for synchronization with each other. The methods of authentication may comprise the step of synchronizing the clocks 160, 260. The clocks 160, 260 may be configured to provide the timestamp to the parameters measured by the implant 100 and the external device 200. The clocks 160, 260 may comprise a crystal oscillator.

The comparison may be performed by either the internal computing unit 106 or the external computing unit 206 calculating and comparing S5604d a difference value between the parameters measured by the implant 100 and the parameter measured by the external device 200. The internal computing unit 106 or the external computing unit 206 may be configured to authenticate the connection if the difference value is less than a predetermined threshold value, and not to authenticate the connection if the difference value equals or exceeds the predetermined threshold difference value.

The threshold difference may refer to a threshold for the difference in time between the timestamp of the parameter measured by the implant 100 and timestamp of the parameter measured by the external device 200. The threshold difference value may be a percentage value of how much the parameters or time sequence of the parameters match. The threshold difference value may preferably be in the range 50-100%, more preferably 75-100%, and most preferably 90-100%.

The communication between the implant 100 and the external device 200 may be a wireless communication using a wireless connection W1. The communication between the implant 100 and the external device may be a conductive communication using a conductive connection C1. The implant 100 and the external device 200 may be configured for wireless and conductive communication accordingly.

FIG. 87 shows the external device 200 comprising a conductive member 201 configured to be in electrical connection with the external device 200, wherein the conductive member 201 is configured to be placed in electrical connection with a skin of the patient for conductive communication with the implant 100. The method of authenticating the connection may comprise placing the conductive member 201, configured to be in electrical connection with the external device 200, in electrical connection with a skin of the patient for conductive communication with the implant 100.

Further information and definitions of conductive communication and the conductive member 201 can be found in this document in conjunction with aspect 247SE. In these cases, the implant and/or external device(s) comprises the necessary features and functionality (described in the respective sections of this document) for performing such conductive communication.

The implant 100 and the external device 200 may be configured to communicate further data S5606 between each other following positive authentication. The further data may comprise data sensed by the sensor 150 or another sensor connected to the implant 100. The further data may comprise data for updating a control program 110 running in the implant 100. The further data may comprise operation instructions for operating the implant 100. The further data may be communicated from the implant 100 to the external device 200. The further data may comprise data sensed by the sensor 150 connected to the implant 100. The further data may be encoded as described herein under the second, third and sixth aspect. In these cases, the implant and/or external device(s) comprises the necessary features and functionality (described in the respective sections of this document) for performing such encoding. The implant 100 and/or the external device 200 may be configured to determine a cryptographic hash based on the measured parameter measured by at least one of the implant 100 and/or the external device 200. The cryptographic hash may then be comprised in all future data or at least all future data during a data transfer session. Accordingly, the implant 100 and/or the external device 200 may be configured to verify the further data based on the cryptographic hash.

The cryptographic hash is determined based on the measured parameter and is represented with a sequence of symbols such as a number. For instance, the cryptographic hash is a number indicating the pulse or oxygen saturation of the patient. Each time data is conveyed between the implant and the external device the cryptographic hash is included in the conveyed data and the external and/or the implant can thereby authenticate or verify the data by the presence of the correct cryptographic hash in the data. The cryptographic hash may be included in all data conveyed during a predetermined time interval or for a predetermined number of data transmissions which form the communication session. Upon completion of a communication session the method of aspect 256SE is repeated an a new cryptographic hash may be determined and used during a subsequent communication session.

In some implementations, the measured by the external device 200 or implant 100 is transmitted to the other one of the external device or implant wherein the comparison is performed in the one of the external device and the implant which received the transmitted measurement. The cryptographic hash may be based on the transmitted measured parameter only which is accessible at both of the implant and the external device after transmission of the measured parameter from one to the other. The cryptographic hash is determined only in response to the comparison resulting in an authentication of the connection (e.g. connection if the difference value is less than a predetermined threshold difference value).

The method for authenticating the connection may further comprise, if the comparison is performed by the implant 100, continuously requesting by the external device 200, or receiving at the external device 200, information of an authentication status of the connection between the implant 100 and the external device 200, and upon determining, at the external device 200, that the connection is authenticated, transmitting further data from the external device 200 to the implant 100. In this context, continuously may refer, requesting by or receiving at the external device 200 at fixed intervals of e.g. 5, 10, 60 s. The clocks 160, 260 may be used to keep the timing of the intervals.

Authentication of the connection between the implant 100 and the external device 200 may be performed automatically without input, authentication, or verification from a user or patient. This is because the comparison of parameters measured internally and externally, by the internal and external sensors 150, 250 respectively may be enough to authenticate the connection. This may typically be the case when the parameter of the patient is related to an automatically occurring physiological function of the patient such as e.g. a pulse of the patient. Certain types of authentication may however require actions from the patient, e.g. having the patient perform specific movements.

The method for authenticating the connection may further comprise, if the comparison is performed by the external device 200, continuously requesting by the implant 100, or receiving at the implant 100, information of an authentication status of the connection between the implant 100 and the external device 200, and upon determining, at the implant 100, that the connection is authenticated, transmitting further data from the implant 100 to the external device 200. In this context, continuously may refer, requesting by or receiving at the implant 100 at fixed intervals of e.g. $10s$. The clocks 160, 260 may be used to keep the timing of the intervals.

The implant may comprise at least one of:
a pacemaker unit,
an external heart compression device,
an apparatus assisting the pump function of a heart of the patient,
an operable artificial heart valve,
an implantable drug delivery device,
a hydraulic, mechanic, and/or electric constriction implant,
an operable volume filling device,
an operable gastric band,
an operable implant for stretching the stomach wall of the patient,
an operable cosmetic implant,
an implant for adjusting or replacing any bone part of a body of the patient,
an implant replacing an organ of the patient or part of an organ of the patient or the function thereof,
a vascular treatment device, and
an implant adapted to move fluid inside the body of the patient.

A computer program product of, or adapted to be run on, an external device is also provided, which comprises a computer-readable storage medium with instructions adapted to make the external device perform the actions as described above.

Further information and definitions can be found in this document in conjunction with the other aspects.

Aspect 257SE Device Synchronization Sensation Unit—Sensation Unit for Authenticating a Connection Between an Implant and the External Device—Embodiments of Aspect 257SE of the Disclosure In aspect 257SE, increased security for communication between an external device 200 and an implant 100 is provided. FIGS. 90-93 shows embodiments of this aspect.

Figures 90A, 90B, 90C:
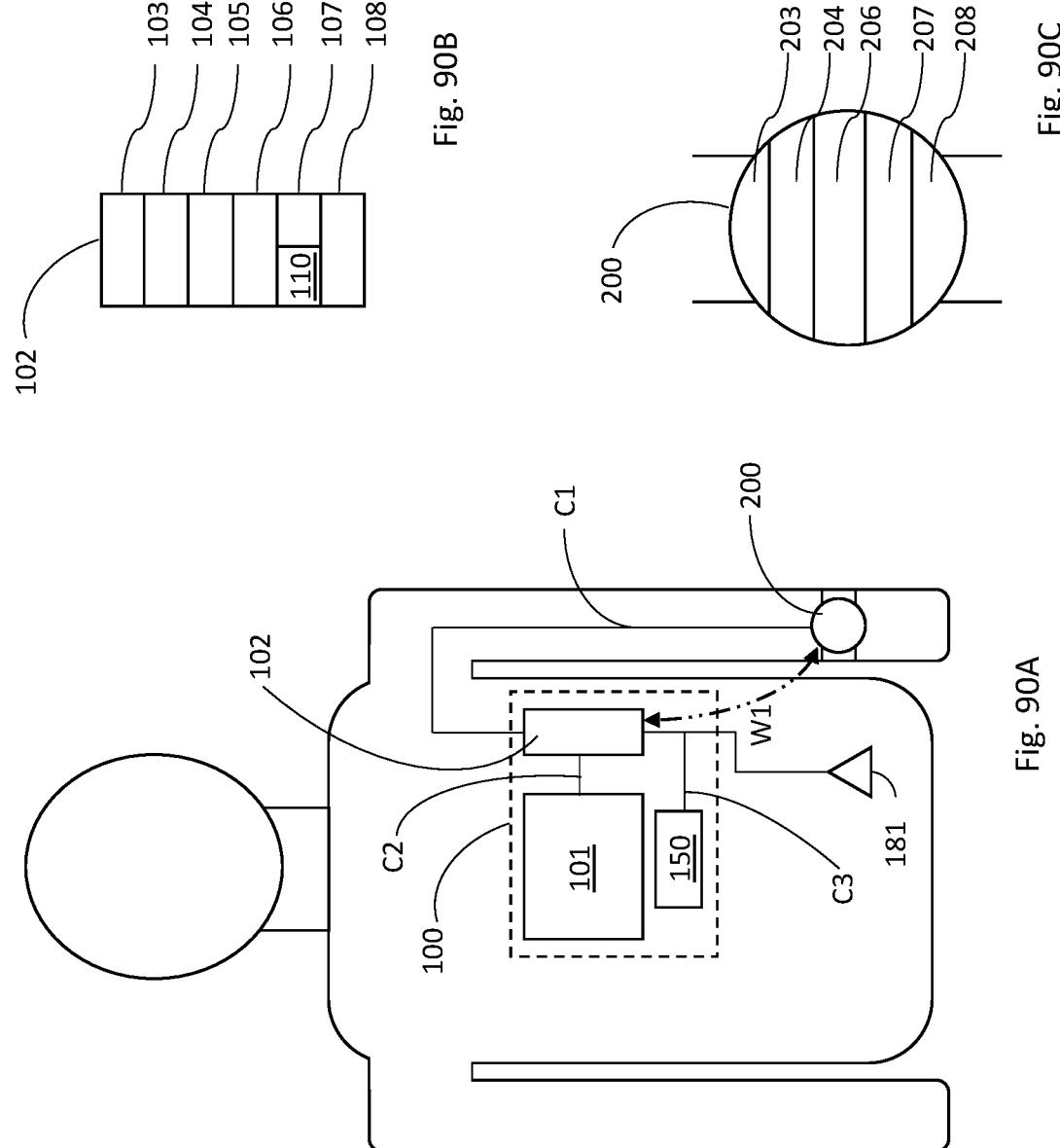
FIG. 90A illustrates a system comprising an implant, further illustrated in FIG. 90B, and an external device, further illustrated in FIG. 90C, all according to aspect 257SE.
Figure 91:
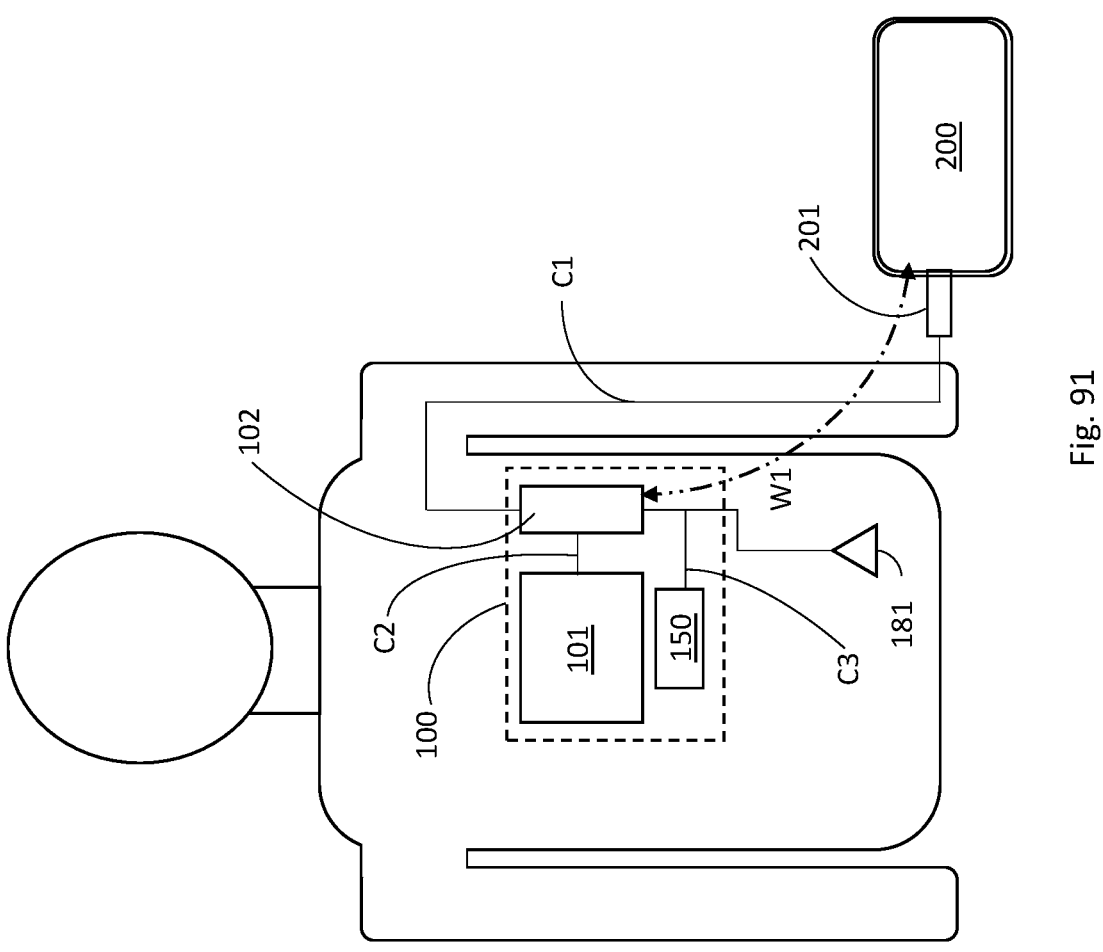
FIG. 91 illustrates a system according to aspect 257SE comprising an implant in connection with an external device and a sensation generator within the body of a patient.

FIGS. 90A-C. 91 and 92 show an implant 100 implanted in a patient and an external device 200. The figures further show a sensation generator 181. The sensation generator 181 may be configured to generate a sensation. The sensation generator 181 may be contained within the implant 100 or be a separate unit. The sensation generator 181 may be implanted. The sensation generator 181 may also be located so that it is not implanted as such but still is in connection with a patient so that only the patient may experience sensations generated.

The implant 100 may be adapted for connection with the external device 200 and connected to a sensation generator 181 external to the implant 100. The implant 100 may be configured for receiving authentication data related to a sensation generated by the sensation generator 181 from the sensation generator 181. The implant 100 may be configured for storing the authentication data. The authentication data may be stored by a memory 107 of a communication unit 102 of the implant 100. The implant 100 may be configured to receive input authentication data from the external device 200. The implant 100 may further comprise an internal computing unit 106. The internal computing unit 106 may be configured for comparing the authentication data to the input authentication data and performing authentication of the connection between the implant 100 and the external device 200 based on the comparison.

The implant 100 may be configured for communicating further data to the external device 200 following positive authentication. The further data may be encoded as described herein under the second, third and sixth aspect. In these cases, the implant 100 and/or external device(s) comprises the necessary features and functionality (described in the respective sections of this document) for performing such encoding.

The sensation generator 181 may be adapted to generate a sensation detectable by a sense of the patient. The sensation generator 181 may be configured to, upon request, generate the sensation and transmit authentication data, related to the generated sensation, to the implant 100, implanted in the patient.

The sensation generator 181 may be configured to transmit the authentication data to the implant 100 using a wireless communication or connection. The implant 100 may for this reason comprise a wireless transceiver 108, configured for receiving the authentication data from the sensation generator 181 The sensation generator 181 may be configured to transmit the authentication data to the implant 100 using a wired or conductive communication or connection. The implant 100 may for this action comprise a wired transceiver 103, configured for receiving the authentication data from the sensation generator 181. The sensation generator 181 may further be configured to receive the request from the implant 100. The sensation generator 181 may be configured to receive the request from the external device 200. The sensation generator 181 may be configured to receive the request from other external devices than the external device 200 such as for example a second external device being controlled by a health care provider of the patient.

Figure 92:
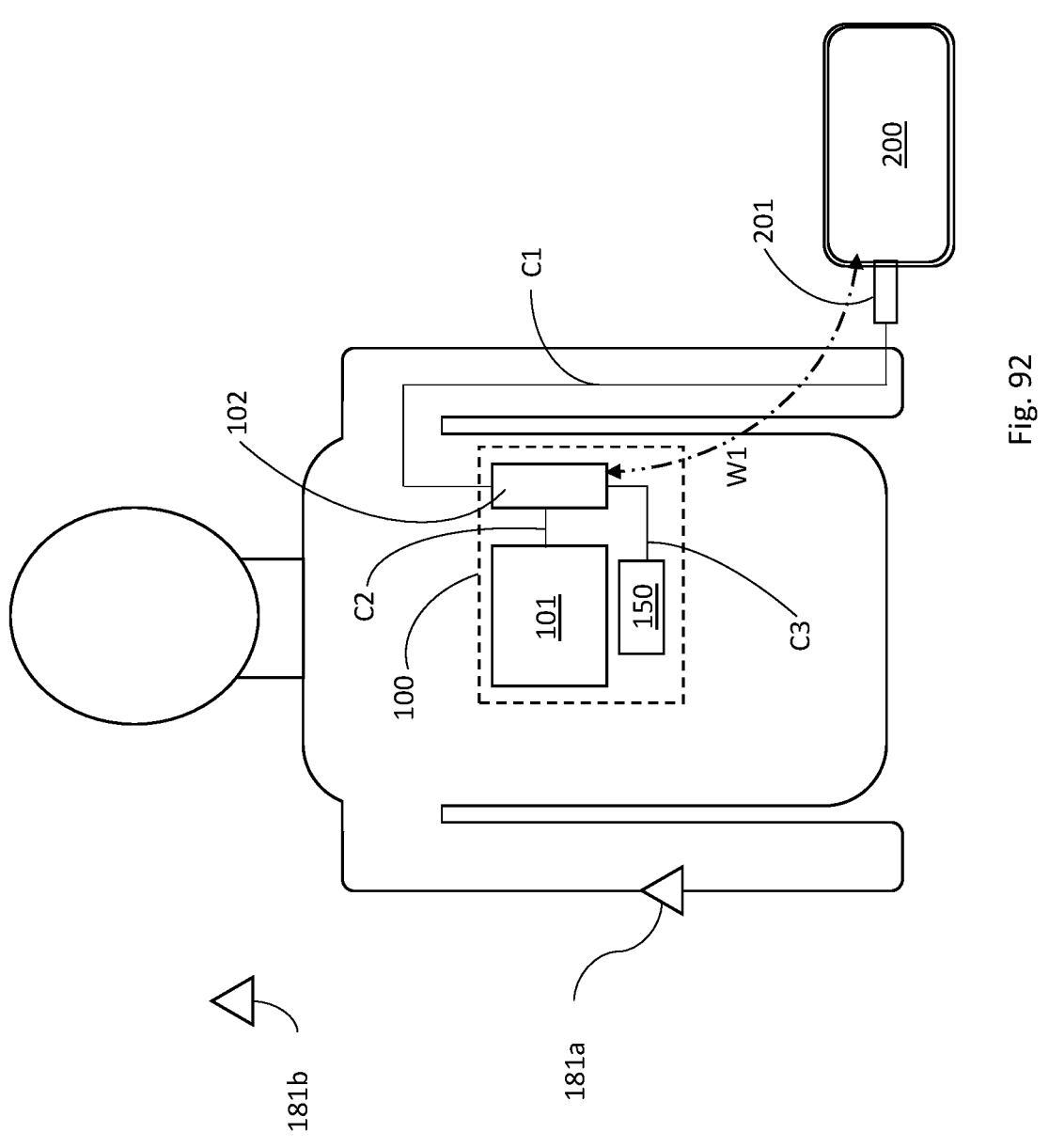
FIG. 92 illustrates a system according to aspect 257SE comprising an implant in connection with an external device and a sensation generator located on or outside of the body of a patient.

The sensation generator 181 may be adapted to be implanted in the patient. FIG. 92 shows a sensation generator 181a being configured to be worn in contact with the skin of the patient. This may e.g. be realized by having the sensation generator 181a being woven into or formed as a part of a clothing item of the patient. The sensation generator 181a may also be part of or worn as a bracelet of the patient or using any other suitable means of attachment.

FIG. 92 also shows a sensation generator 181b being configured to generate the sensation without being in physical contact with the patient. This may e.g. be realized by having a sensation generator 181b, normally only accessible to the patient, generating a visual sensation by a device not being implanted in the patient.

The sensation generator 181 may be configured to create the sensation comprising a plurality of sensation components. The sensation or sensation components may be created by providing a vibration, a sound, a photonic signal, a light signal, an electric signal, or a heat signal.

The sensation generator 181 may comprise a mechanical element for providing the vibration. The sensation generator 181 may comprise a loudspeaker for providing the sound. The sensation generator 181 may comprise a photon source for providing the photonic signal. The sensation generator 181 may comprise a light source for providing the light signal. The sensation generator 181 may comprise a power (current/voltage) source for providing the electric signal. The sensation generator 181 may comprise a thermal element for providing the heat signal. The heat signal may also be referred to as a thermal signal.

The mechanical element may be an electric, pneumatic, hydraulic, or thermodynamic motor or actuator. The loudspeaker may be adapted to provide sound of frequencies in the whole audible range from 20 Hz to 20 KHz. The loudspeaker may more preferably be adapted to provide low frequency sound in the range 20 Hz to 2 kHz.

The photon source and the light source may comprise light-emitting diodes (LEDs). The LEDs may be adapted to emit photons in the visible wavelength range from 380 nm to 750 nm. The LEDs may be adapted to emit photons in the infrared (IR) wavelength range 700 nm to 1 mm, but preferably in the near-infrared (NIR) wavelength range from 750 nm to 1400 nm. Note that visible wavelength range and IR wavelength range may overlap. The heat signal may be provided or generated by a photon source or a light source emitting in the IR wavelength range. The electric signal may be an electric signal in the form of a pulse or pulses.

The location of the sensation generator 181 may be configured to best fit the chosen sensory function of the patient and mitigate adverse physiological side effects as sensation power or strength may not need be as large. E.g. a mechanical sensation generator such as a vibration generator may be positioned with respect to the body of the patient and in particular mechanical sensory systems of the skin of the patient such that sensations i.e. vibrations need not be excessively powerful and cause the patient to feel discomfort, pain or other adverse effects as a result of the vibration. The sensation generator may also, due to this, be more discrete in its operation and with what type of sensation it generates, further increasing the security of the authentication as malicious third parties will find it harder to notice or find out what means of authentication an implant may require. An implanted sensation generator increases its discretion and thus the authentication security with it being effectively hidden within or by the body of the patient. A malicious third party, aiming to harm or gather medical information about the patient in which the implant is implanted by accessing the implant, may therefore need to perform a medical operation on the patient in question just to acquire information about how the implant may be accessed, essentially making the endeavor pointless, in the sense of hacking or accessing the implant remotely.

The sensation generator 181, the implant 100 and the external device 200 may be configured as a system for performing the methods.

FIG. 93 shows a flow chart for methods of authenticating a connection between an implant 100 implanted in a patient and an external device 200. The method may comprise the step of generating S5701, by a sensation generator 181, a sensation detectable by a sense of the patient. The sensation may comprise a plurality of sensation components. The sensation or sensation components may comprise a vibration, a sound, a photonic signal, a light signal, an electric signal, or a heat signal.

The method may further comprise storing S5702, by the implant 100, authentication data, related to the generated sensation.

The method may further comprise providing S5703, by the patient, input to the external device 200, resulting in input authentication data. The method may further comprise authenticating S5704 the connection based on a comparison of the input authentication data and the authentication data. The authentication S5704 may be performed by either the implant 100 or the external device 200 which is further described below.

The authentication data may be communicated from the sensation generator 181 to the implant 100 using a wired communication. The authentication data may be communicated from the sensation generator 181 to the implant 100 using a wireless communication.

The step of authenticating S5704 the connection may comprise calculating a time difference between the timestamp of the sensation and the timestamp of the input from the patient, and upon determining that the time difference is less than a threshold, authenticating the connection.

The authentication data may comprise a timestamp of the sensation. The input authentication data may comprise a timestamp of the input from the patient. Authentication of the connection between the implant 100 and the external device 200 may comprise calculating a time difference between the timestamp of the sensation and the timestamp of the input from the patient, and upon determining that the time difference is less than a threshold, authenticating the connection. For example, if a sensation is generated by the sensation generator 181 with a timestamp referring to a time X and the user provides the input with a timestamp referring to a time Y, the difference between Y and X (Y-X) should be less than the threshold value T for authentication of the connection to occur. An example of a threshold value T may be 1 s. The comparison may also comprise a low threshold as to filter away input from the patient that is faster than normal human response times. The low threshold may e.g. be 50 ms. The patient input should be rejected if it is created before the actual sensation.

Patient inputs may require a waiting period after each input before the next one may be input. Continuous excessive inputs may cause the implant 100 or external device 200 to enter a security/lockdown mode wherein an even more secure form of authentication is required for it to be unlocked. Vital functions of e.g. the implant 100 may still be performed. The threshold, the low threshold, and the waiting period may further improve the security of the authentication.

The authentication data may comprise a number of times that the sensation is generated by the sensation generator 181. The input authentication data may comprise an input from the patient relating to a number of times the patient detected the sensation. Authenticating the connection may in this case comprise: upon determining that the number of times of the authentication data and the input authentication data are equal, authenticating the connection. A process for authentication may comprise the sensation generator 181 producing a sensation or sensation components pertaining to a specific number. This could e.g. mean producing a sensation or sensation components as a sequence of pulses, chronologically spaced such that they are, easily sensed by the patient. For example, the sensation or the sensation components may be generated such that a period of sensation has a duration. The sensation period may be followed by a duration period of no sensation before a next sensation period may commence. The patient may count the number of periods of sensation detected and input this number to authenticate the connection by comparing the number input by the patient to a number of sensation periods generated by the sensation generator 181 and stored by the implant 100 or other devices adapted to receive the data number of periods generated by the sensation generator 181.

The number of periods generated may be a randomly generated number and may preferably be in a range from 1-20. More preferably, the range is 1-10 and most preferably the range is 1-5.

The duration of a sensation period may preferably be in the range from 0-5 s. More preferably, the range is from 0.1-3 s. Most preferably the range is from 0.5-1.5 s. Several sequences of sensation periods may be used to increase the security of the authentication and avoid unauthorized access rewarded to a would-be accessor merely guessing the right number.

These embodiments add extra security to the authentication as a number of sensations generated may not be predicted or otherwise acquired by a malicious third party via means such as, e.g. patient journals. Authentication in these ways may comprise a sequence of several sub-authentications which may be performed for even greater security and a rapidly reduced chance of "lucky guessing" by a malicious third party as the number of sub-authentications increase. Randomized values for sensation duration or the number of sensations generated may further increase security.

As is shown in FIG. 93, the method of authenticating may further and optionally comprise, communicating S5705 further data between the implant 100 and the external device 200 following positive authentication. The communication may use a wireless connection W1 or a wired/conductive connection C1. Further data may be transmitted both ways. i.e. from the implant 100 to the external device 200 and vice versa. Further data may also be communicated between the implant 100 or external device 200 and other external devices. Further data may comprise data sensed by a sensor 150 connected to the implant. The sensor 150 may be further described herein under aspect 256SE. In these cases, the implant 100 and/or external device(s) comprises the necessary features and functionality (described in the respective sections of this document).

Communication between the implant 100 and the external device 200 may be a wireless communication, using a wireless connection W1 or a wired/conductive communication, using a wired/conductive connection C1. Communication may be performed both ways.

Authentication data may be transmitted S5706b from the implant 100 to the external device 200. The step of authenticating S5704 the connection based on a comparison may then be performed by the external device 200. In this case, the implant 100 may continuously request (for example every 10 second, every 20 second, every minute, every two minute, etc.), or receive S5708b, information of an authentication status of the connection between the implant 100 and the external device 200, and upon determining S5709a, at the implant 100, that the connection is authenticated, transmitting S5705 further data from the implant 100 to the external device 200.

Input authentication data may be transmitted S5706*a* from the external device 200 to the implant 100. The step of authenticating S5704 the connection based on a comparison may then be performed by the implant 100. In this case, the external device 200 may continuously request (for example every 10 second, every 20 second, every minute, every two minute, etc.), or receive S5708*a*, information of an authentication status of the connection between the implant 100 and the external device 200, and upon determining S5709*a*, at the external device 200, that the connection is authenticated, transmitting S5705 further data from the external device 200 to the implant 100.

The further data may comprise data for updating a control program 110 running in the implant 100. The control program 110 may be stored by the memory 107. Further data may comprise operation instructions for operating the implant 100.

The sensation generator 181, sensation, sensation components, authentication data, input authentication data, and further data may be further described herein under aspect 248SE. In these cases, the implant 100 and/or external device(s) comprises the necessary features and functionality (described in the respective sections of this document). Providing a specialized sensation generator 181 for the generation of sensations may be advantageous is it may be optimized for the most ideal sensation generation. This may be put in contrast with e.g. an active unit or a motor that provides sensations as an effect of its operation. A specialized sensation generator 181 may also be preferable as the dual use of a motor or active unit may reduce its longevity by the extra stress associated with the dual use. This may be exemplified by a motor using its battery charge quicker when also used for authentication. It may be easier to optimize a sensation generator 181 compared to e.g. a motor or active device which needs to not neglect its main physiological purpose.

The implant may comprise at least one of:

a pacemaker unit, an external heart compression device.

an apparatus assisting the pump function of a heart of the patient, an operable artificial heart valve, an implantable drug delivery device, a hydraulic, mechanic, and/or electric constriction implant, an operable volume filling device.

an operable gastric band, an operable implant for stretching the stomach wall of the patient, an operable cosmetic implant.

an implant for adjusting or replacing any bone part of a body of the patient.

an implant replacing an organ of the patient or part of an organ of the patient or the function thereof, a vascular treatment device, and an implant adapted to move fluid inside the body of the patient.

Aspect 258SE Device Synchronization Sensation—Authenticating a Connection Between an Implant and the External Device by Using Sensations—Embodiments of Aspect 258SE of the Disclosure The detailed description of embodiments for aspect V is hereby incorporated by reference.

The characteristics of the sensation characteristics may refer to different parts of the same signal or two entirely different physical signals. Parts of the same signal may be confined within a set amount of time and/or spaced by another set amount of time from each other. Different physical signals may be understood as one characteristic being a light-based sensation and as another characteristic (e.g. the second) being a sound-based sensation.

Figure 97:
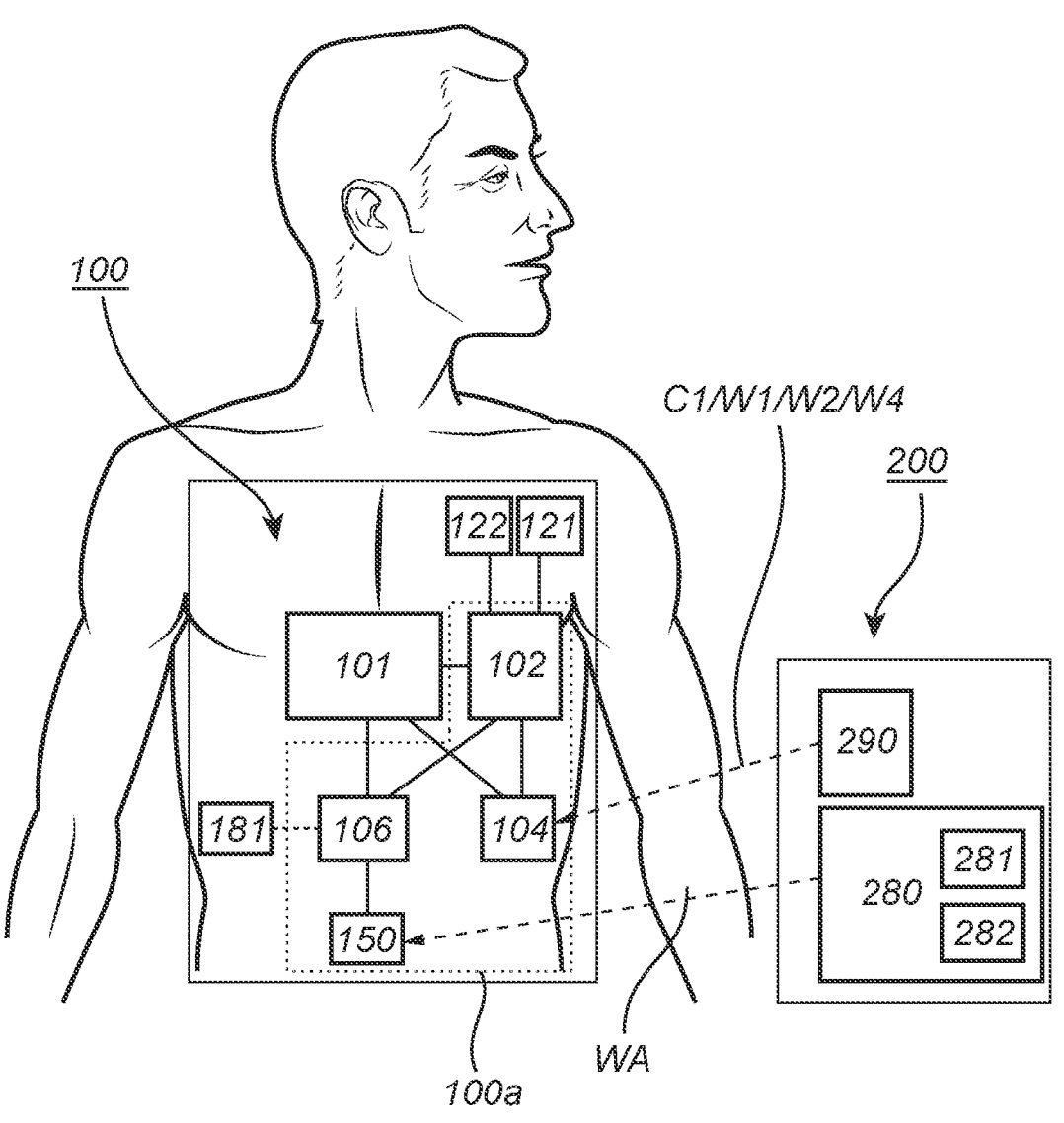
FIG. 97 illustrates a system according to aspect 307SE.
Figure 98:
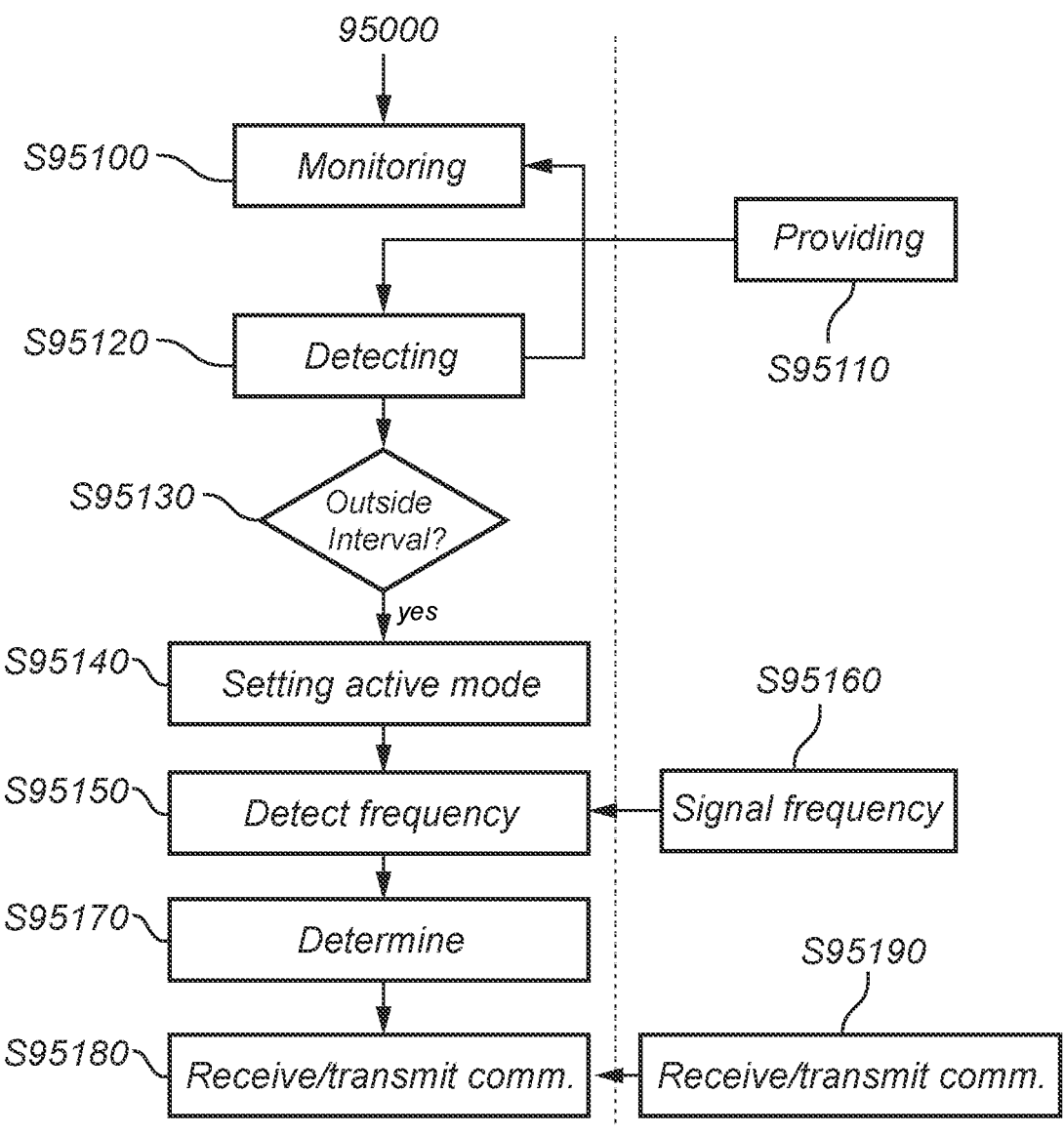
FIG. 98 illustrates a method according to aspect 307SE.

Aspect 307SE Communication Remote Control—Remote Wake Signal—Embodiments of Aspect 307SE of the Disclosure In aspect 307SE, a system and a method for communication between an external device 200 and an implant 100 is provided. FIGS. 97-98 shows embodiments of this aspect.

Generally, aspect 307SE defines a method, as shown in FIG. 98, adapted to run in a processor 106 comprised on an internal control unit 100*a* of an implant 100 when implanted in a patient, as shown in FIG. 97. The implant 100 and the external device 200 may be any of the implants 100 or external devices 200 described with reference to aspects one through twenty-one, further comprising the features described below.

FIG. 94 shows a system comprising an implant 100 and an external control unit 200. The implant comprises an internal control unit 100*a* for controlling a function of the implant. The internal control unit 100*a* comprises a processor 106 having a sleep mode and an active mode. The internal control unit 100*a* comprises a sensor 150 adapted to detect a magnetic field. The external control unit 200 comprises a signal provider 280 adapted to provide a magnetic field detectable by the internal sensor 150. The internal control unit 100*a* is further configured to, in response to a detected magnetic field exceeding a predetermined value, setting the processing unit 106 in an active mode.

By sleeping mode, it may be meant a mode with less battery consumption and/or processing power used in the processing unit 106, and by "active mode" it may be meant that the processing unit 106 is not restricted in its processing.

By an having a processing unit having a sleep mode and an active mode, the battery consumption of the processing unit may be decreased.

By having a sensor 150 adapted to detect an magnetic field and an internal control unit 200 adapted to set the processing unit 106 in the active mode in response to a detected signal, the external device 200 may cause a sleeping internal control unit 100*a* or processor 106 to "wake up". In this way, the processing unit 106 may be set in the active mode when needed for communication with the external control unit 200.

In this example the processor 106 is shown separately from the communication unit 102, but in an alternative the processor may be comprised in the communication unit 102. The implant may comprise an implantable energy source 104, which in this example is shown as separate from the communication unit 102. As shown in FIG. 1, the implantable energy source may alternatively be comprised in the communication unit 102.

The sensor 150 may, for example, be a hall effect sensor, a fluxgate sensor, an ultra-sensitive magnetic field sensor, a magneto-resistive sensor, an AMR or GMR sensor, or the sensor may comprise a third coil having an iron core.

The magnetic field provider 280 comprised in the external control unit 200 may have an off state, wherein it does not provide any magnetic field, and an on state, wherein it provides a magnetic field. For example, the magnetic field provider 280 may comprise a magnet 281, a coil 281, a coil having a core 281, or a permanent magnet 281. In some embodiments, the magnetic field provider 280 may comprise a shielding means for preventing a magnet 281 or permanent magnet 281 from providing a magnetic field in the off state. In order to provide a substantially even magnetic field, the magnetic field provider may comprise a first and a second coil arranged perpendicular to each other.

After the processing unit 106 has been set in an active mode, i.e. when the processing unit 106 has been woken up, the implant may determine a frequency for further communication between the internal communication unit 102 and the external device 200. The implant 100 may thus comprise a frequency detector 121 for detecting a frequency for communication between the first 102 and the second communication units 290. The frequency detector 121 is, for example, an antenna. The external device 200 may comprise a frequency indicator 282, for transmitting a signal indicative of a frequency. The frequency indicator 282, may, for example, be a magnetic field provider capable of transmitting a magnetic field with a specific frequency. In some examples the frequency indicator is comprised in or the same as the magnetic field provider 281. In this way, the frequency signal is detected using means separate from the sensor, and can, for example, be detected using a separate pin or antenna comprised in the internal control unit 100a.

Alternatively, the internal communication unit 102 and the external device 200 may communicate using a predetermined frequency or a frequency detected by means defined by a predetermined method according to a predetermined protocol to be used for the communication between the internal communication unit 102 and the external device 200. The communication may comprise any of the protocols, authentication methods and/or encryption methods of aspects one through twenty-one described herein.

In some embodiments, the sensor 150 may be used for the communication. The communication may in these embodiments be performed with such that a frequency of the magnetic field generated by the coil is 9-315 kHz, or the magnetic field generated by the coil is less than or equal to 125 kHz, preferably less than 58 kHz. The frequency may be less than 50 Hz, preferably less than 20 Hz, more preferably less than 10 Hz, in order to be transmittable through a titan box.

In some embodiments, the internal control unit 100a comprises a receiver unit 122, and the internal control unit and the external control unit are configured to transmit and/or receive data via the receiver unit 122 via magnetic induction. The receiver unit 122 may comprise a high-sensitivity magnetic field detector, or the receiver unit may comprise a fourth coil for receiving the magnetic induction.

The system may implement a method 95000 for controlling a medical implant implanted in a patient as described with reference to FIG. 94. The method 95000 will now be described with reference to FIG. 95. The method 95000 comprises monitoring S95100 for signals by a sensor 150 comprised in an internal control unit 100a communicatively coupled to the active unit 101, providing S85110, from a signal provider 280 comprised in an external device 200, a wake signal, the external device 200 being adapted to be arranged outside of the patient's body, and setting S95120, by the internal control unit 100a and in response to a detected wake signal WS, a mode of a processing unit 106 comprised in the internal control unit from a sleep mode to an active mode.

The method 95000 may also comprise detecting S95120, using a frequency detector 121, a frequency for data communication between a first communication unit 102 and a second communication unit 290, the first communication unit 102 being associated with the internal control unit 100a and the second communication unit 290 being associated with the external device 200, wherein the frequency detector 121 is communicatively coupled to the internal control unit 100a or the external device 200. The detection may be performed using a detection sequence for detecting the frequency. This detection sequence may, for example, be a detection sequence defined in the protocol to be used for communication between the first and the second communication units. Potential protocols that may be used for communication between an internal communication unit 102 and an external device 200 has been described earlier in this description with reference to aspects one through twenty-two. The method 95000 may further comprise determining S95130, that the detected signal is above a predetermined threshold. Thus, the method 95000 may comprise determining S95170, using the frequency detector 121, the frequency for data communication, and initiating S95170. S95190 data communication between the first communication unit 102 and the second communication unit 290. The data communication can, for example, comprise one or more control instructions for controlling the medical implant 100 transmitted from the external device, or, for example, comprise data related to the operation of the medical implant 100 and be transmitted from the internal control unit 102. The second communication unit may comprise the features with figure references 201-270 which may comprise e.g. a wireless transceiver 208 and/or a computing unit 206.

Figure 99:
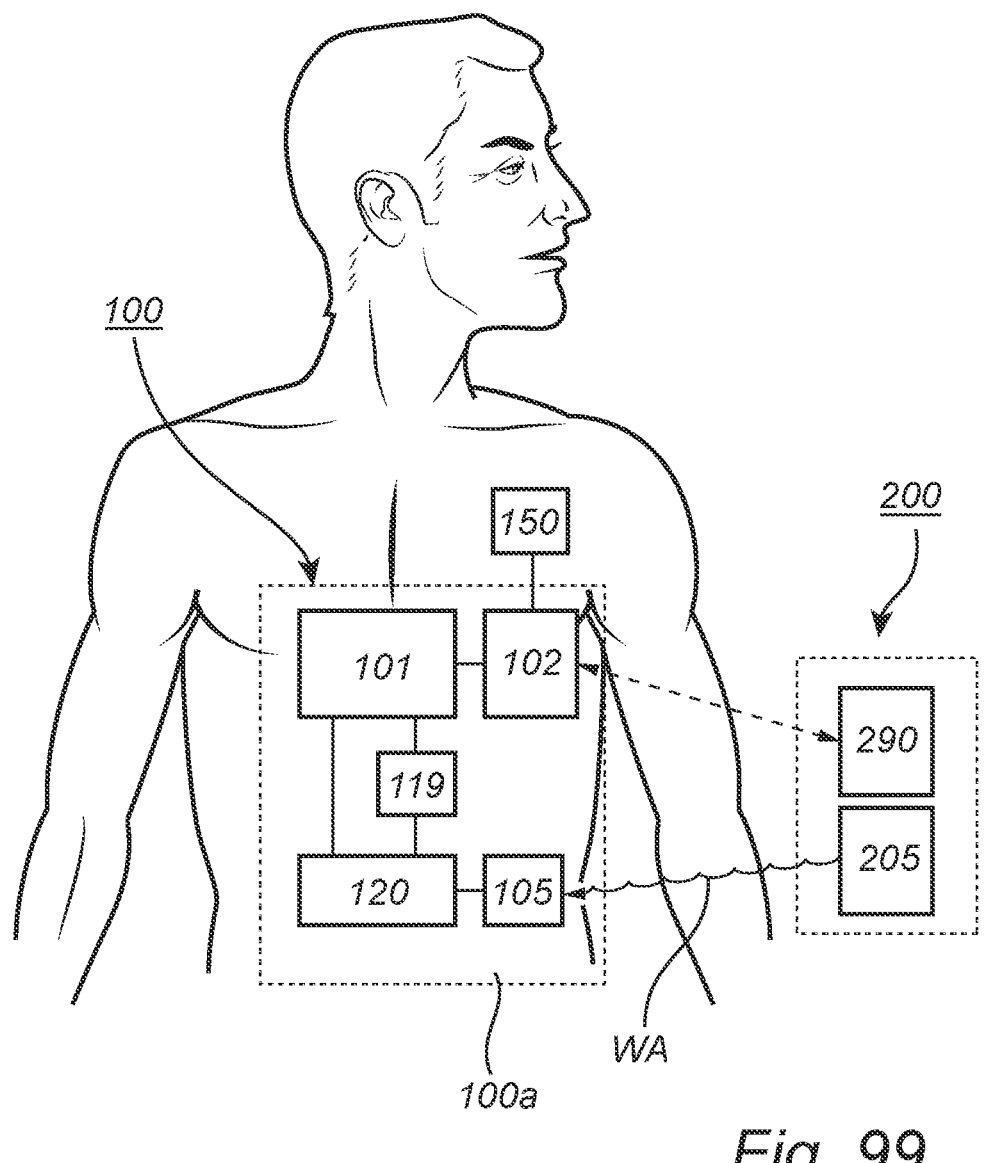
FIG. 99 illustrates a system according to aspect 308SE.
Figure 100:
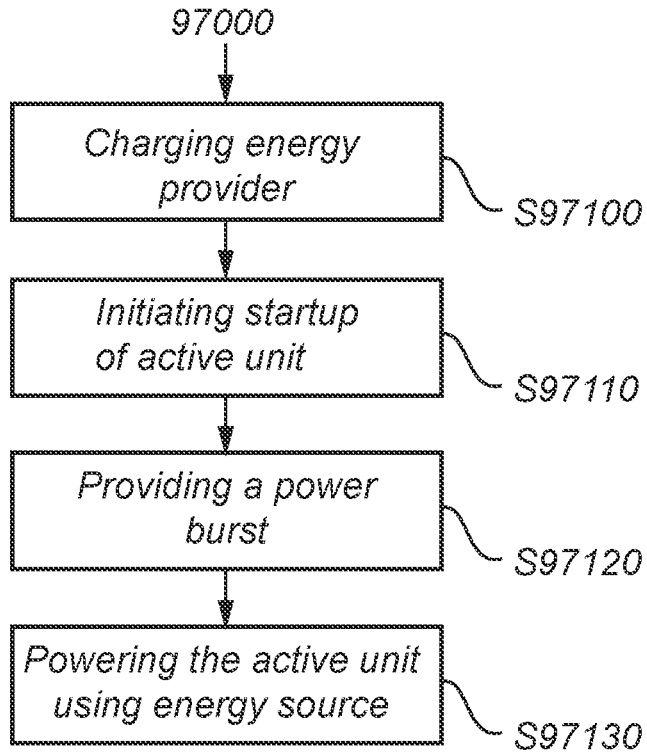
FIG. 100 illustrates a method according to aspect 308SE.

Aspect 308SE Energy Power-Supply
Capacitor—Energy Burst Provider—Embodiments
of Aspect 308SE of the Disclosure In aspect 308SE, an implant, and a method for powering an implant 100 is provided. FIGS. 99-100 shows embodiments of this aspect.

Generally, aspect 308SE defines an implant, as shown in FIG. 99, comprising an implant 100 comprising or be connected to a power supply for powering the implant 100. The implant 100, and the external device(s) 200 may comprise elements described above with reference to aspects one through twenty-two.

The power supply may comprise an implantable energy source 120 for providing energy to the implant 100 and/or the active unit 101, and an energy provider 119 connected to the implantable energy source 120 and connected to an energy consuming part 101 of the medical implant, the energy provider 119 being configured to store energy to provide a burst of energy to the energy consuming part 101, wherein the energy provider 119 is configured to be charged by the implantable energy source 120 and to provide the energy consuming part with electrical power during startup of the energy consuming part 101.

Alternatively, the implant 100 may comprise a first implantable energy source 120 for providing energy to an energy consuming part 101 of the medical implant 100, a second implantable energy source 119 connected to the implantable energy source 120 and connected to the energy consuming part, wherein the second implantable energy source 119 is configured to be charged by the implantable energy source 120 and to provide the energy consuming part 101 with electrical power during startup of the energy consuming part 101, wherein the second implantable energy source 119 has a higher energy density than the first implantable energy source 120. By having a "higher energy density" it may be meant that the second implantable energy source 119 has a higher maximum energy output per time unit than the first implantable energy source 120. The second energy storage 119 may be an energy provider as discussed below.

In this way, an energy consuming part 101 requiring a quick start or an energy consuming part which requires a high level or burst of energy for a start may be provided with sufficient energy. This may be beneficial as instead of having an idle energy consuming part 101 continuously using energy, the energy consuming part 101 may be completely turned off and quickly turned on when needed. Further, this may allow the use of an energy consuming part 101 needing a burst of energy for a startup while having a lower energy consumption when already in use. In this way, a battery or an energy source 120 having a slower discharging (or where a slower discharging is beneficial for the lifetime or health of the battery) may be used for the implant, as the extra energy needed for the startup may be provided by the energy provider.

Further, energy losses may occur in a battery or energy source of an implant if the battery or energy source is discharged too fast. These energy losses may for example be in the form of heat, which may damage the battery or energy source, or the body of the patient. By the implant described in these examples, energy may be provided from the battery or energy source in a way that does not damage the battery or energy source, which may improve the lifetime of the battery or energy source and thereby the lifetime of the medical implant.

The energy consuming part 101 may be any part of an implant requiring energy, such as a motor for operating a device or function of the medical implant, motor for powering a hydraulic pump, a restriction device, a stimulation device, a processing or computing unit, a communication unit, a device for providing electrical stimulation to a tissue portion of the body of the patient, a CPU for encrypting information, a transmitting and/or receiving unit for communication with an external unit (not shown as part of the energy consuming part 101 in the drawings, however, the communication unit 102 may be connected to the energy storage 120 and to the energy provider 119), a measurement unit or a sensor, a data collection unit, a solenoid, a piezo-electrical element, a memory metal unit, a vibrator, a part configured to operate a valve comprised in the medical implant, or a feedback unit.

In some examples, the discharging from the implantable energy source 120 during startup of the energy consuming part 101 is slower than the energy needed for startup of the energy consuming part 101. i.e. the implantable energy source 120 is configured to have a slower discharging than the energy needed for startup of the energy consuming part. That is, there may be a difference between the energy needed by the energy consuming part 101 and the energy the implantable energy source 120 is capable of providing without damaging the implantable energy source 120. In other words, a maximum energy consumption of the energy consuming part 101 may be higher than the maximum energy capable of being delivered by the implantable energy source 120 without causing damage to the implantable energy source, and the energy provider 119 may be adapted to deliver an energy burst corresponding to the difference between the required energy consumption and the maximum energy capable of being delivered by the implantable energy source 120. The implantable energy source 120 may be configured to store a substantially larger amount of energy than the energy burst provider 119 but may in some examples be slower to charge.

The implantable energy source 120 may be any type of energy source suitable for an implant 100, such as a rechargeable battery or a solid-state battery, such as a trionychoid battery. The implantable energy source 120 may be connected to the energy consuming part 101 and configured to power the energy consuming part 101 after it has been started using the energy provider 119.

The energy provider 119 may be any type of part configured to provide a burst of energy for the energy consuming part 101. In some examples, the energy provider 119 is a capacitor, such as a start capacitor, a run capacitor, a dual run capacitor or a supercapacitor. The energy provider 119 may be connected to the implantable energy source 120 and be adapted to be charged using the implantable energy source 120. In some examples, the energy provider 119 may be a second energy provider 119 configured to be charged by the implantable energy source 120 and to provide the energy consuming part 101 with electrical energy.

A corresponding method 97000 for powering a medical implant will not be described with reference to FIG. 100. The method 97000 comprises the steps of initiating S97110 an energy consuming part 101 of the implant, the energy consuming part being connected to an implantable energy source 120, providing S97120 an initial burst of energy to the energy consuming part 101 using an energy provider 119 connected to the implantable energy source 120 and to the energy consuming part 101, the energy provider 119 being adapted to provide a burst of energy to the energy consuming part 101, and subsequently powering S97130 the energy consuming part 101 using the implantable energy source 120.

In some examples, a maximum energy consumption of the energy consuming part 101 is higher than the maximum energy capable of being delivered by the implantable energy source 120 without causing damage to the implantable energy source 120, and the energy provider 119 is adapted to deliver an energy burst corresponding to difference between the required energy consumption and the maximum energy capable of being delivered by the implantable energy source 120.

The method 97000 may further comprise the step of charging the energy provider 19 using the implantable energy source 120.

Initiating S97110 an energy consuming part 101 may comprise transitioning a control unit of the medical implant from a sleep mode to an operational or active mode.

The implantable energy source 120 may be adapted to be wirelessly charged and the implantable energy source may be connected to an internal charger 105 for receiving wireless energy from an external device 200 via an external charger 205, and the method 97000 may comprise wirelessly charging the implantable energy source 120. In some examples the method 97000 comprises controlling a receipt of electrical power from an external energy source at the internal charger 105. The internal energy 120 source may be charged via the receipt of a transmission of electrical power from an external energy source 205 by the internal charger 105.

Aspect 309SE eHealth Broadcasting
Data—Broadcasting Sensor Data from
Implant—Embodiments of Aspect 309SE of the
Disclosure In aspect 309SE, a system and a method for communication between an external device 200 and an implant 100 is provided. FIGS. 101A-C and 102 shows embodiments of this aspect.

Figures 101A, 101B, 101C:
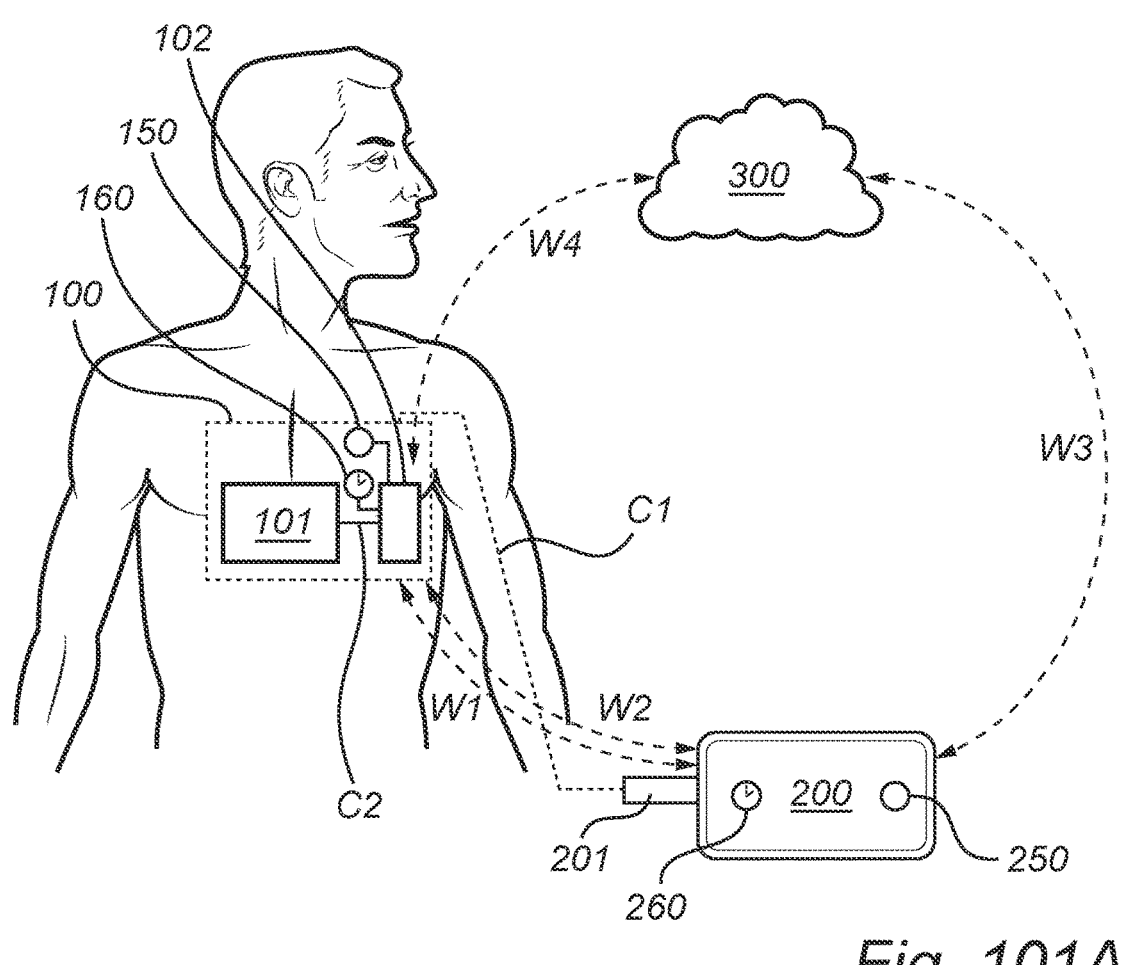
FIGS. 101A, 101B and 101C illustrate a system according to aspect 309SE.
Figure 102:
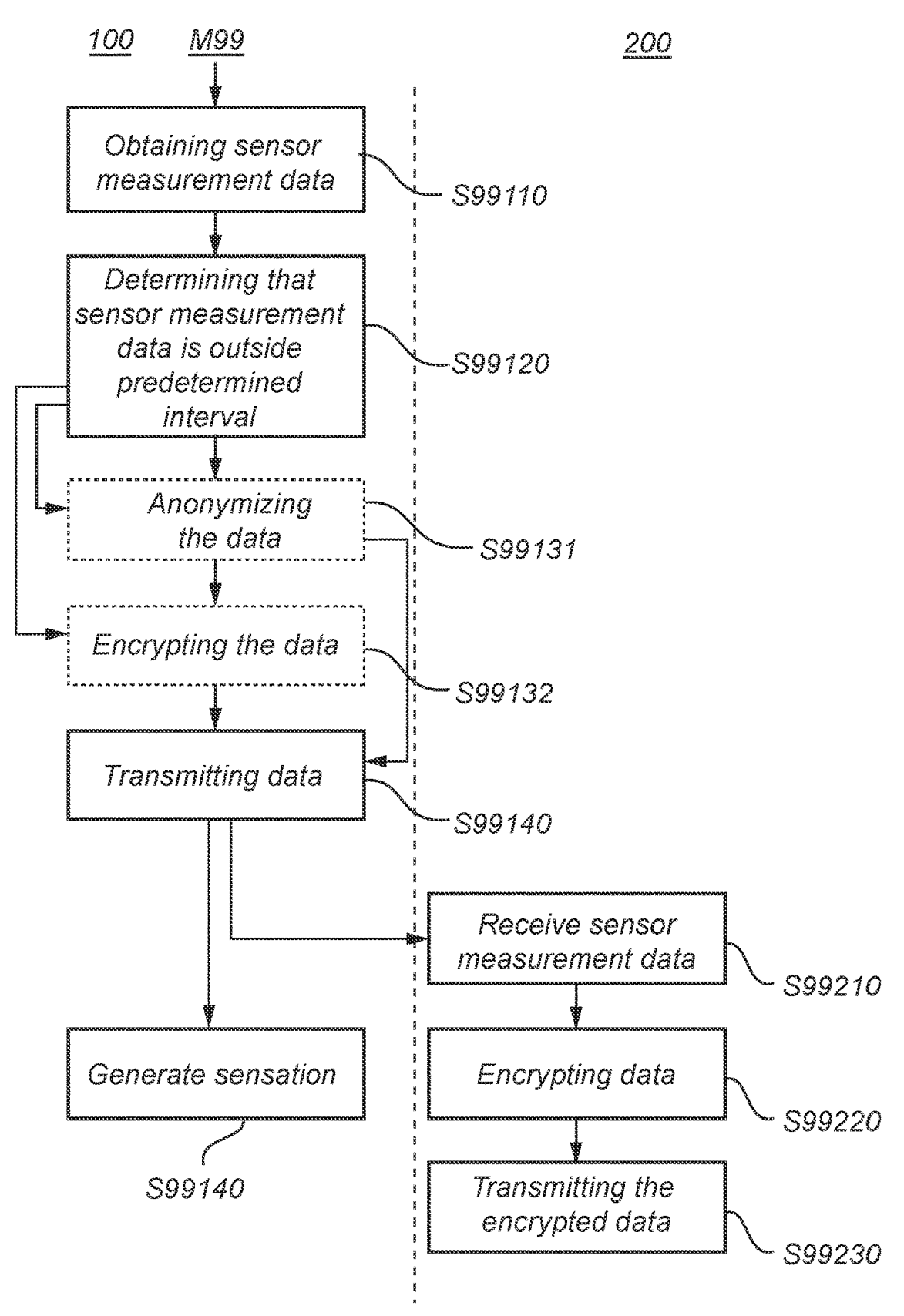
FIG. 102 illustrates a method according to aspect 309SE.

Generally, aspect 309SE defines a system, as shown in FIG. 101A, adapted to run in a processor 106 comprised in an internal control unit 100*a* of an implant 100 when implanted in a patient, as shown in FIG. 101A. The implant 100 and the external device 200 may be any of the implants 100 or external devices 200 described with reference to aspects one through twenty-three, further comprising the features described below.

According to the twenty fourth aspect, the system comprises at least one sensor 150 connected to the implant or comprised in the implant, for sensing at least one physiological parameter of the patient or a functional parameter of the implant. The sensor 150 is configured to periodically sense the parameter and the communication unit 102 is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period.

a predetermined event, or a use of the implant.

By broadcasting or transmitting information relating to the sensed parameter in response to a sensed parameter differing from a predetermined threshold or interval, an external device may detect that the implant is not functioning as expected, malfunctioning or not having the intended effect in the patient, or that a function of the patient's body is not functioning as expected. This malfunction or unexpected effect may be detected by the sensor measurements, and thus be transmitted to the external device. In this way, the implant may automatically, without any request from the external device, transmit data indicative of a malfunction or unexpected event, thus allowing for a safer device.

The transmission of data must however not be related to a malfunction or unexpected event but can be part of the normal workings of the implant. For example, the predetermined threshold or interval may be an expected threshold or interval, such as a pressure at a sphincter of a patient or in an organ of a patient, where the implant may be an artificial sphincter adapted to release as pressure of the sphincter in order to restore the pressure to a level within the predetermined interval. In this way, the external device may receive data indicative of the sensor measurements being outside of a predetermined interval or differing from a predetermined threshold, so that the user can, via the external device, perform any necessary adjustments or actions using the implant. This further allows for a safer implant.

The sensor 150 may, for example, be a pressure sensor, an electrical sensor, a clock, a temperature sensor, a motion sensor, an optical sensor, a sonic sensor, an ultrasonic sensor. The predetermined threshold or interval may depend on the sensor, and can for example be a predetermined interval for a pressure (such as a pressure at a sphincter or an organ of a patient, or a pressure at a hydraulic reservoir of the implant), a predetermined temperature interval or threshold (such as a temperature of the patient, or a temperature of a processing unit, a control unit, a power supply, or another part of the implant).

The internal communication unit 102 may be configured to broadcast or transmit the information using a short- to mid-range transmitting protocol, such as a Radio Frequency type protocol, a RFID type protocol, a WLAN type protocol, a Bluetooth type protocol, a BLE type protocol, a NFC type protocol, a 3G/4G/5G type protocol, or a GSM type protocol.

The control unit 100*a* of the implant may be connected to the sensor 150 and to the communication unit 102, and the control unit 100*a* may be configured to anonymize the information before it is transmitted. The transmission of data may comprise broadcasting of data.

In addition to, or as an alternative to, transmitting the data when the sensed parameter is differing form a predetermined threshold or interval, the communication unit 102 may be configured to broadcast the information periodically. The control unit 100*a* may be configured to cause the communication unit 102 to broadcast the information in response to a second parameter being above a predetermined threshold. The second parameter may, for example, be related to the control unit 100*a* itself, such as a free memory or free storage space parameter, or a battery status parameter. When the implant comprises an implantable energy source and an energy source indicator, the energy source indicator is configured to indicate a functional status of the implantable energy source and the indication may be comprised in the transmitted data. The functional status may indicate at least one of charge level and temperature of the implantable energy source.

In some embodiments the external device 200 is configured to receive the broadcasted information, encrypt the received information using an encryption key and transmit the encrypted received information. In this way, the external device 200 may add an additional layer of encryption or exchange the encryption performed by the internal communication unit. The encryption may be performed using any of the methods or systems described with reference to aspects one through nine.

In an embodiment, the internal communication unit 102 is configured to transmit the data using the body of the patient as a conductor C1, and the external device 200 is configured to receive the data via the body. Alternatively, or in combination, the communication unit of the implant is configured to transmit the data wirelessly to the external device W2.

Further, a method 99000 for transmitting data from an implant comprising a processor 106 and a communication unit 102, will now be described with reference to FIG. 99, comprising: obtaining S99110 sensor measurement data via a sensor 150 connected to or comprised in the implant 100, the sensor measurement relating to at least one physiological parameter of the patient or a functional parameter of the implant 100, and transmitting S99140 by the communication unit 102 the sensor measurement data in response to the sensor measurement differing from a predetermined threshold or being outside of a predetermined interval S99120, wherein the sensor 150 is configured to periodically sense the parameter. The method may further comprise broadcasting S99140 the sensor measurement data, to be received S 99210 by an external device 200. The transmitting or broadcasting may comprise using at least one of a Radio Frequency type protocol, RFID type protocol, WLAN type protocol, Bluetooth type protocol, BLE type protocol, NFC type protocol, 3G/4G/5G type protocol, or a GSM type protocol.

The method 99000 may further comprise, at the processor 106, anonymizing S99131, by the processor, the sensor measurement data before it is transmitted, or encrypting S99132 the sensor measurement data, using an encryptor 182 comprised in the processing unit, before it is transmitted. The encryption may be performed using any step(s) from the method described with reference to aspects one through nine described herein.

The transmitting S99140 of the data may further comprise to encode the data before the transmitting. The type of encoding may be dependent on the communication channel or the protocol used for the transmission.

The transmitting S99140 may be performed periodically, or in response to a signal received by the processor, for example, by an internal part of the implant such as a sensor 150, or by an external device 200.

The parameter may, for example, be at least one of a functional parameter of the implant (such as a battery parameter, a free memory parameter, a temperature, a pressure, an error count, a status of any of the control programs, or any other functional parameter mentioned in this description) or a parameter relating to the patient (such as a temperature, a blood pressure, or any other parameter mentioned in this description). In an example, the implant 100 comprises an implantable energy source 104 and an energy source indicator 104c, and the energy source indicator 104c is configured to indicate a functional status of the implantable energy source 104, and the sensor measurement comprises data related to the energy source indicator.

In one example, the transmitting S99140 comprises transmitting the sensor measurement to an internal processor 106 configured to cause a sensation generator 181 to cause a sensation S99150 detectable by the patient in which the implant 100 is implanted.

The method 99000 may be implemented in a system comprising the implant 100 and an external device 200, and further comprise receiving the sensor measurement data at the external device 200, and, at the external device 200, encrypting the sensor measurement data using a key to obtain encrypted data, and, transmitting the encrypted data. The transmitting may, for example, be performed wirelessly W3 or conductively C1.

Figure 103:
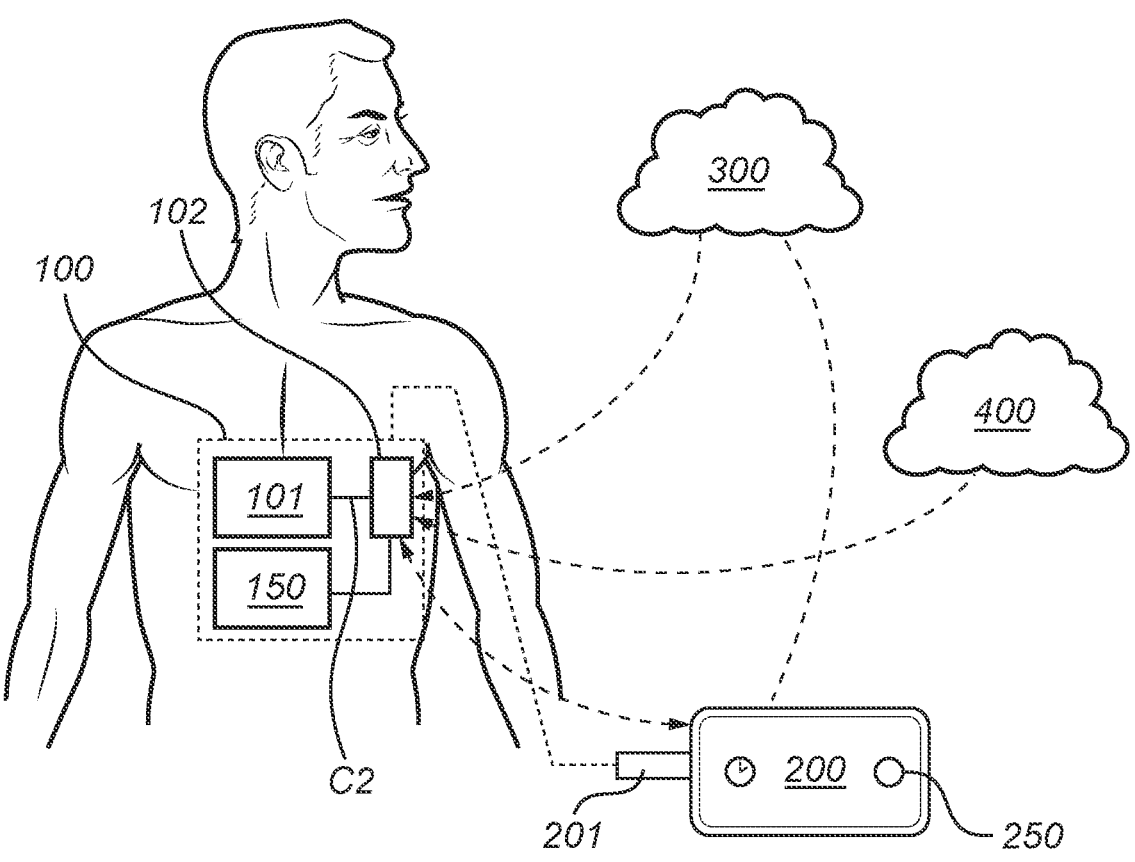
FIG. 103 illustrates a system according to aspect 310SE.
Figure 104:
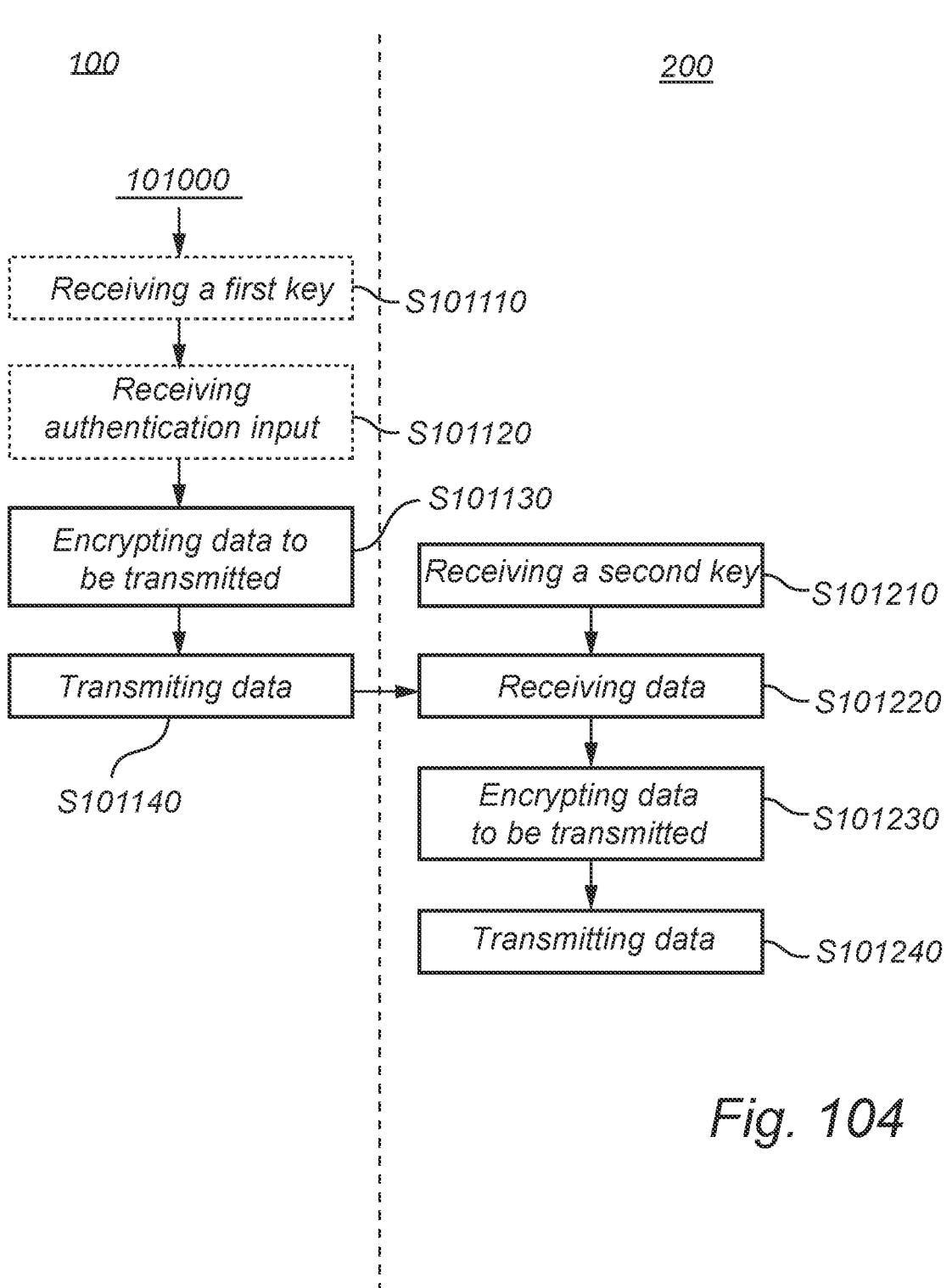
FIG. 104 illustrates a method according to aspect 310SE.

Aspect 310SE eHealth Double Encryption—Double Encryption—Embodiments of Aspect 310SE of the Disclosure In aspect 310SE, a system and a method for communication between an external device 200 and an implant 100 is provided. FIGS. 103-104 shows embodiments of this aspect.

Generally, aspect 310SE defines a method, as shown in FIG. 104, adapted to run in a communication unit 102 comprised in an implant 100 when implanted in a patient, as shown in FIG. 103A. The implant 100 and the external device 200 may be any of the implants 100 or external devices 200 described with reference to aspects one through twenty-four, further comprising the features described below.

According to the system of aspect 310SE, a system is provided. The system comprises an implant 100 having a communication unit 102 configured to transmit data from the body of the patient to an external device 200, and an encryption unit 182 for encrypting the data to be transmitted. The system further comprises an external device 200 configured to receive the data transmitted by the communication unit 102, encrypt the received data using a first key and transmit the encrypted received data to a third external device 300. The encryption can be performed using any of the keys described above or below. In some embodiments, the external device 200 is configured to decrypt the data received from the internal communication unit 102 before encrypting and transmitting the data.

Thus, the implant 100 may transmit data to an external device 200 which may add an additional layer of encryption and transmit the data to a second external device 300. By having the external device add an additional layer of encryption, less computing resources may be needed in the implant, as the implant may transmit unencrypted data or data encrypted using a less secure or less computing resource requiring encryption. In this way, data can still be relatively securely transmitted to a third device. The transmission of data can be performed using any of the method described herein in addition to the method or in the system described below.

In one embodiment, the external device 200 may encrypt and transmit the data received from the internal communication unit 102 without decrypting it first.

In one example, the encryption unit 182 is configured to encrypt the data to be transmitted using a second key. The first key or the second key may, for example, implant specific information, a secret key associated with the external device, an identifier of the implant or an identifier of the communication unit 102. The second key could be a key transmitted by the external device 200 to the internal communication unit 102. In some examples, the second key is a combined key comprising a third key received by the implant from the external device 200.

The first key may be a combined key comprising a fourth key, wherein the fourth key is received by the external device 200 from a fourth device. The fourth device may be a verification unit, either comprised in the external device, or external to the external device and connected to it. The verification unit may have a sensor 250 for verification, such as a fingerprint sensor. More details in regard to this will be described below. Alternatively, the verification unit may be a generator, as described above.

The encryption performed by the internal 100 and/or external device 200 may be performed using any of the methods described with reference to aspect one through nine.

The system may be configured to perform authentication of the connection between the implant and the external device before transmitting of the data. The authentication may be performed using a sensed parameter, as described in aspect five. The implant 100 may in thus embodiment comprise a first sensor 150 for measuring the parameter of the patient at the implant 100. The external device 200 may comprise an external sensor 250 for measuring the parameter of the patient at the external device 200. The system may alternatively be configured to perform any of the authentication methods described in aspects one through four.

Further, a method for improving the security of data transmitted from an implant is provided. The method will now be described with reference to FIG. 104. The method 101000, for encrypted communication between an implant 100, when implanted in a patient's body, and an external device 200, comprises encoding or encrypting S101130, by the implant 100 or a processor 106 comprised in or connected to the implant 100, data relating to the implant 100 or the operation thereof; transmitting S101140, by a first communication unit 102 comprised in the implant 100, the data; receiving S101220, by a second communication unit comprised the external device 200, the data; encrypting S101230, by the external device 200, the data using an encryption key to obtain encrypted data; and transmitting S101340 the encrypted data to a third external device 300.

In this way, the external device 200 may add or exchange the encryption, or add an extra layer of encryption, to the data transmitted by the implant 100. When the implant encodes the data to be transmitted it may be configured to not encrypt the data before transmitting, or only using a light weight encryption, thus not needing as much processing power as if the implant were to fully encrypt the data before the transmission. By having an external device further encrypt the data, an improved security may be achieved while using relatively little processing power at the implant.

The encrypting S101130, by the implant 100, may comprise encrypting the data using a second key. The encryption using the second key may be a more light-weight encryption than the encryption performed by the external device using the second key. i.e. an encryption that does not require as much computing resources as the encryption performed by the external device 200.

The first or the second key may comprise a private key exchanged as described above with reference to encryption and authentication, or the first or the second key may comprise an implant specific information, a secret key associated with the external device, an identifier of the implant 100 or an identifier of the communication unit 102. They may be combined keys as described in this description, and the content of the keys, any combination of keys, and the exchange of a key or keys is described in the encryption and/or authentication of the general definition of features section. Thus, the method may comprise receiving S101110 a first key to be used for the encryption S101130 of the data, and/or receive 101120 authentication input for authenticating the connection with the external device in which the data will be transmitted. The external device may receive S101210 a second key to be used for the encryption S101230 of the data to be transmitted.

Aspect 331SE Security Module

According to one embodiment described with reference to FIG. 113A-113C, the communication unit 102 or internal controller 102 or control unit 102 comprises a wireless transceiver 108 for communicating wirelessly with an external device, a security module 189, and a central unit, also referred to herein as a computing unit 106, which is to be considered as equivalent. The central unit 106 is configured to be in communication with the wireless transceiver 108, the security module 189 and the implantable medical device or active unit 101. The wireless transceiver 108 is configured to receive communication from the external device 200 including at least one instruction to the implantable medical device 100 and transmit the received communication to the central unit or computing unit 106. The central unit or computing unit 106 is configured to send secure communication to the security module 189, derived from the received communication from the external device 200, and the security module 189 is configured to decrypt at least a portion of the secure communication and verify the authenticity of the secure communication. In one embodiment, the security module is further configured to transmit a response communication to the central unit or computing unit 106 and the central unit or computing unit is configured to communicate the at least one instruction to the active unit 101. In another embodiment, the security module is configured to communicate the at least one instruction to the active unit 302 directly. In the embodiment shown in FIG. 113A-113C, the at least one instruction is based on the response communication, or a combination of the response communication and the received communication from the external device 200.

Figures 113A, 113B, 113C:
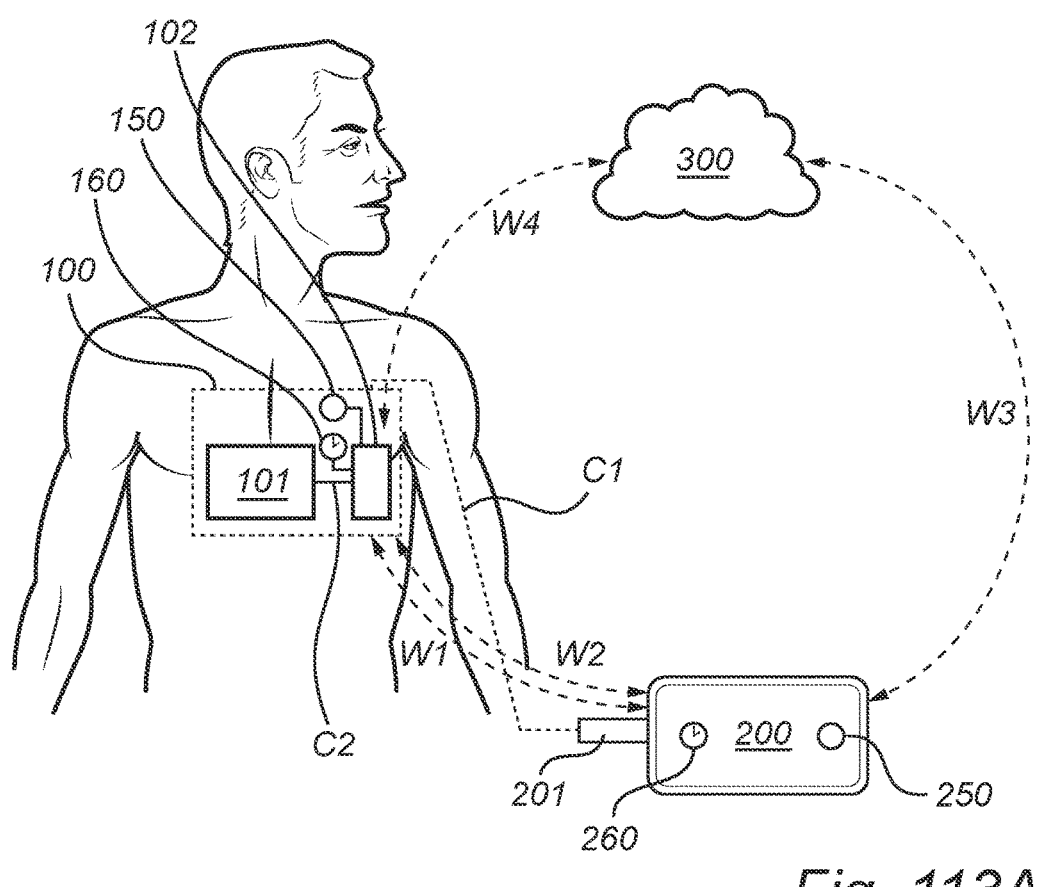
FIGS. 113A, 113B, 113BB and 113C generally illustrates a system for communication with an implanted medical device.

In the embodiment shown in FIG. 113A-113C, the security module 189 comprises a set of rules for accepting communication from the central unit or computing unit 106. In the embodiment shown in FIG. 113A-113C, the wireless transceiver 108 is configured to be able to be placed in an off-mode, in which no wireless communication can be transmitted or received by the wireless transceiver 108. The set of rules comprises a rule stipulating that communication from the central unit or computing unit 106 to the security module 189 or to the active unit 101 is only accepted when the wireless transceiver 108 is placed in the off-mode.

In the embodiment shown in FIG. 113A-113C, the set of rules comprises a rule stipulating that communication from the central unit or computing unit 106 is only accepted when the wireless transceiver 108 has been placed in the off-mode for a specific time period.

In the embodiment shown in FIG. 113A-113C, the central unit or computing unit 106 is configured to verify a digital signature of the received communication from the external device 200. The digital signature could be a hash-based digital signature which could be based on a biometric signature from the patient or a medical professional. The set of rules further comprises a rule stipulating that communication from the central unit 106 is only accepted when the digital signature of the received communication has been verified by the central unit 106. The verification could for example comprise the step of comparing the digital signature or a portion of the digital signature with a previously verified digital signature stored in the central unit 106. The central unit 106 may be configured to verify the size of the received communication from the external device and the set of rules could comprise a rule stipulating that communication from the central unit 106 is only accepted when the size of the received communication has been verified by the central unit 106. The central unit could thus have a rule stipulating that communication above or below a specified size range is to be rejected.

In the embodiment shown in FIG. 113A-113C, the wireless transceiver is configured to receive a message from the external device 200 being encrypted with at least a first and second layer of encryption. The central unit 106 the decrypts the first layer of decryption and transmit at least a portion of the message comprising the second layer of encryption to the security model 189. The security module 189 then decrypts the second layer of encryption and transmits a response communication to the central unit 106 based on the portion of the message decrypted by the security module 189 389 or transmits the decrypted data to the active unit 101.

In the embodiment shown in FIG. 113A-113C, the central unit 106 is configured to decrypt a portion of the message comprising a digital signature, such that the digital signature can be verified by the central unit 106, also the central unit 106 is configured to decrypt a portion of the message comprising message size information, such that the message size can be verified by the central unit 106.

In the embodiment shown in FIG. 113A-113C, the central unit 106 is configured to decrypt a first and second portion of the message, and the first portion comprises a checksum for verifying the authenticity of the second portion.

In the embodiment shown in FIG. 113A-113C, the response communication transmitted from the security module 189 comprises a checksum, and the central unit 106 is configured to verify the authenticity of at least a portion of the message decrypted by the central unit 106 using the received checksum. i.e. by adding portions of the message decrypted by the central unit 106 and comparing the sum to the checksum.

In the embodiment shown in FIG. 113A-113C, the set of rules further comprise a rule related to the rate of data transfer between the central unit 106 and the security module 189. The rule could stipulate that the communication should be rejected or aborted if the rate of data transfer exceeds a set maximum rate of data transfer, which may make it harder for unauthorized persons to inject malicious code or instructions to the medical implant.

In the embodiment shown in FIG. 113A-113C, the security module 189 is configured to decrypt a portion of the message comprising the digital signature being encrypted with the second layer of encryption, such that the digital signature can be verified by the security module 189. The security module 189 then transmits a response communication to the central unit 106 based on the outcome of the verification, which can be used by the central unit 106 for further decryption of the message or for determining if instructions in the message should be communicated to the active unit 101. Alternatively, the security module determines at least one instruction for the active unit 302 based on the message, and transmits the message to the active unit 203 directly.

In the embodiment shown in FIG. 113A-113C, the central unit 106 is only capable of decrypting a portion of the received communication from the external device 200 when the wireless transceiver 108 is placed in the off-mode. In the alternative, or as an additional layer of security, the central unit 106 may be limited such that the central unit 106 is only capable of communicating instructions to the active unit 101 of the implantable medical device 100 when the wireless transceiver 108 is placed in the off-mode. This ensures that no attacks can take place while the central unit 106 is communicating with the active unit 101.

In the embodiment shown in FIG. 113A-113C, the implantable controller 102 is configured to receive, using the wireless transceiver 108, a message from the external device 200 comprising a first un-encrypted portion and a second encrypted portion. The implantable controller 102 (e.g. the central unit 106 or the security module 189) then decrypts the encrypted portion, and uses the decrypted portion to verify the authenticity of the un-encrypted portion. As such, computing power and thereby energy can be saved by not encrypting the entire communication, but rather only the portion required to authenticate the rest of the message (such as a checksum and/or a digital signature)

In the embodiment shown in FIG. 113A-113C, the central unit 106 is configured to transmit an encrypted portion to the security module 189 and receive a response communication from the security module 189 based on information contained in the encrypted portion being decrypted by the security module. The central unit 106 is then configured to use the response communication to verify the authenticity of the un-encrypted portion. The un-encrypted portion could comprise at least a portion of the at least one instruction to the implantable medical device 106. Alternatively, the central unit 306 is configured to transmit an encrypted portion and an unencrypted portion to the security module 389 and the security module 398 decrypts the encrypted portion and, using the decrypted portion, verifies the authenticity of the un-encrypted portion.

In the embodiment shown in FIG. 113A-113C, the implantable controller 102 is configured to receive, using the wireless transceiver 108, a message from the external device 200 comprising information related to at least one of: a physiological parameter of the patient and a physical parameter of the implanted medical device 100, and use the received information to verify the authenticity of the message. The physiological parameter of the patient could be a parameter such as a parameter based on one or more of: a temperature, a heart rate and a saturation value.

The physical parameter of the implanted medical device 100 could comprise at least one of a current setting or value of the implanted medical device 100, a prior instruction sent to the implanted medical device 100 or an ID of the implanted medical device 100.

The portion of the message comprising the information related to the physiological parameter of the patient and/or physical or functional parameter of the implanted medical device 100 could be encrypted, and the central unit 106 may be configured to transmit the encrypted portion to the security module 189 and receive a response communication from the security module 189 based on the information having been decrypted by the security module 189.

In the embodiment shown in FIG. 113A-113C, the security module 189 is a hardware security module comprising at least one hardware-based key. The security module 189 may have features that provide tamper evidence such as visible signs of tampering or logging and alerting. It may also be so that the security module 189 is "tamper resistant", which makes the security module 189 inoperable in the event that tampering is detected. For example, the response to tampering could include deleting keys is tampering is detected. The security module 189 could comprise one or more secure cryptoprocessor chip. The hardware-based key(s) in the security module 189 could have a corresponding hardware-based key placeable in the external device 200. The corresponding external hardware-based key could be placed on a key-card connectable to the external device 200.

In one embodiment, the security module 387 and the central unit 309 are both comprised in a multi-processor, wherein the security module 387 runs on a first processor and the central unit runs on second processor, different from the first.

In alternative embodiments, the security module 189 is a software security module comprising at least one software-based key, or a combination of a hardware and software-based security module and key. The software-based key may correspond to a software-based key in the external device 200. The software-based key may correspond to a software-based key on a key-card connectable to the external device 200.

In the embodiment shown in FIG. 113A-113C, the external device 200 is a handheld external device, however, in alternative embodiments, the external device may be a remote external device or a cloud based external device In the embodiment shown in FIG. 113A-113C, the at least one instruction to the implantable medical device 100 comprises an instruction for changing an operational state of the implantable medical device 100.

In the embodiment shown in FIG. 113A-113C, the wireless transceiver 108 is configured to communicate wirelessly with the external 200 device using electromagnetic waves at a frequency below 100 kHz, or more specifically below 40 kHz. The wireless transceiver 108 is thus configured to communicate with the external device 200 using "Very Low Frequency" communication (VLF). VLF signals have the ability to penetrate a titanium housing of the implantable medical device 100, such that the electronics of the implantable medical device 100 can be completely encapsulated in a titanium housing.

The wireless transceiver 108 is configured to communicate wirelessly with the external device 200 using a first communication protocol and the central unit 106 is configured to communicate with the security module 189 using a second, different, communication protocol. This adds an additional layer of security as security structures could be built into the electronics and/or software in the central unit 106 enabling the transfer from a first to a second communication protocol. The wireless transceiver 108 may be configured to communicate wirelessly with the external device using a standard network protocol, which could be one of an RFID type protocol, a WLAN type protocol, a Bluetooth (BT) type protocol, a BLE type protocol, an NFC type protocol, a 3G/4G/5G type protocol, and a GSM type protocol. In the alternative, or as a combination, the wireless transceiver 108 could be configured to communicate wirelessly with the external device 200 using a proprietary network protocol. The wireless transceiver 108 could comprises a Ultra-Wide Band (UWB) transceiver and the wireless communication between the implantable controller 102 and the external device 200 could thus be based on UWB. The use of UWB technology enables positioning of the remote control 320" which can be used by the implanted medical device 100 as a way to establish that the external device 200 is at a position which the implanted medical device 100 and/or the patient can acknowledge as being correct, e.g. in the direct proximity to the medical device 100 and/or the patient, such as within reach of the patient and/or within 1 or 2 meters of the implanted medical device 100. In the alternative, a combination of UWB and BT could be used, in which case the UWB communication can be used to authenticate the BT communication, as it is easier to transfer large data sets using BT.

Aspect 332SE—Variable Impedance

According to one embodiment described with reference to FIG. 113A-113C, the communication unit 102 or controller of the implantable medical device 100 comprises a receiving unit 105 or energy receiver 105 comprising a coil 192 (specifically shown in FIG. 113BB) configured for receiving transcutaneously transferred energy. The receiving unit further comprises a measurement unit 194 configured to measure a parameter related to the energy received by the coil 192 and a variable impedance 193 electrically connected to the coil 192. The receiving unit 105 further comprises a switch 195a placed between the variable impedance 193 and the coil 192 for switching off the electrical connection between the variable impedance 193 and the coil 192. The communication unit 102 or controller 102 is configured to control the variable impedance 193 for varying the impedance and thereby tune the coil 192 based on the measured parameter. The communication unit 102 or controller 102 is further configured to control the switch 195a for switching off the electrical connection between the variable impedance 193 and the coil 192 in response to the measured parameter exceeding a threshold value. The controller 102 may further be configured to vary the variable impedance in response to the measured parameter exceeding a threshold value. As such, the coil can be tuned or turned off to reduce the amount of received energy if the amount of received energy becomes excessive. The measurement unit 194 is configured to measure a parameter related to the energy received by the coil 192 over a time period and/or measure a parameter related to a change in energy received by the coil 192 by for example measure the derivative of the received energy over time. The variable impedance 193 is in the embodiment shown in FIG. 113BB placed in series with the coil 192. In alternative embodiments it is however conceivable that the variable impedance is placed parallel to the coil 192.

The first switch 195a is placed at a first end portion 192a of the coil 192, and the implantable medical device 100 further comprises a second switch 195b placed at a second end portion of the coil 192, such that the coil 192 can be completely disconnected from other portions of the implantable medical device 100. The receiving unit 105 is configured to receive transcutaneously transferred energy in pulses according to a pulse pattern. The measurement unit 194 is in the embodiment shown in FIG. 113BB configured to measure a parameter related to the pulse pattern. The controller 102 is configured to control the variable impedance in response to the pulse pattern deviating from a predefined pulse pattern. The controller 102 is configured to control the switch 195a for switching off the electrical connection between the variable impedance 193 and the coil 192 in response to the pulse pattern deviating from a predefined pulse pattern. The measurement unit is configured to measure a temperature in the implantable medical device 100 or in the body of the patient, and the controller 102 is configured to control the first and second switch 195a. 195b in response to the measured temperature.

The variable impedance 193 may comprise a resistor and a capacitor and/or a resistor and an inductor and/or an inductor and a capacitor. The variable impedance 193 may comprise a digitally tuned capacitor or a digital potentiometer. The variable impedance 193 may comprise a variable inductor. The first and second switch comprises a semiconductor, such as a MOSFET. The variation of the impedance is configured to lower the active power that is received by the receiving unit. As can be seen in FIG. 113BB, the variable impedance 193, the first and second switch 195a. 195b and the measurement unit 194 are connected to the communication unit/controller 102 and the receiving unit 105 is connected to an energy storage unit 10 such that the energy storage unit 10 can store energy received by the receiving unit 105.

Aspect 311SE eHealth Data Integrity—Verifying Data Integrity from/to Implant and from/to External Device—Embodiments of Aspect 311SE of the Disclosure In aspect 311SE, a system and a method for communication between an external device 200 and an implant 100 is provided. FIGS. 105A-C and 106-107 show embodiments of this aspect.

Figures 105A, 105B, 105C:
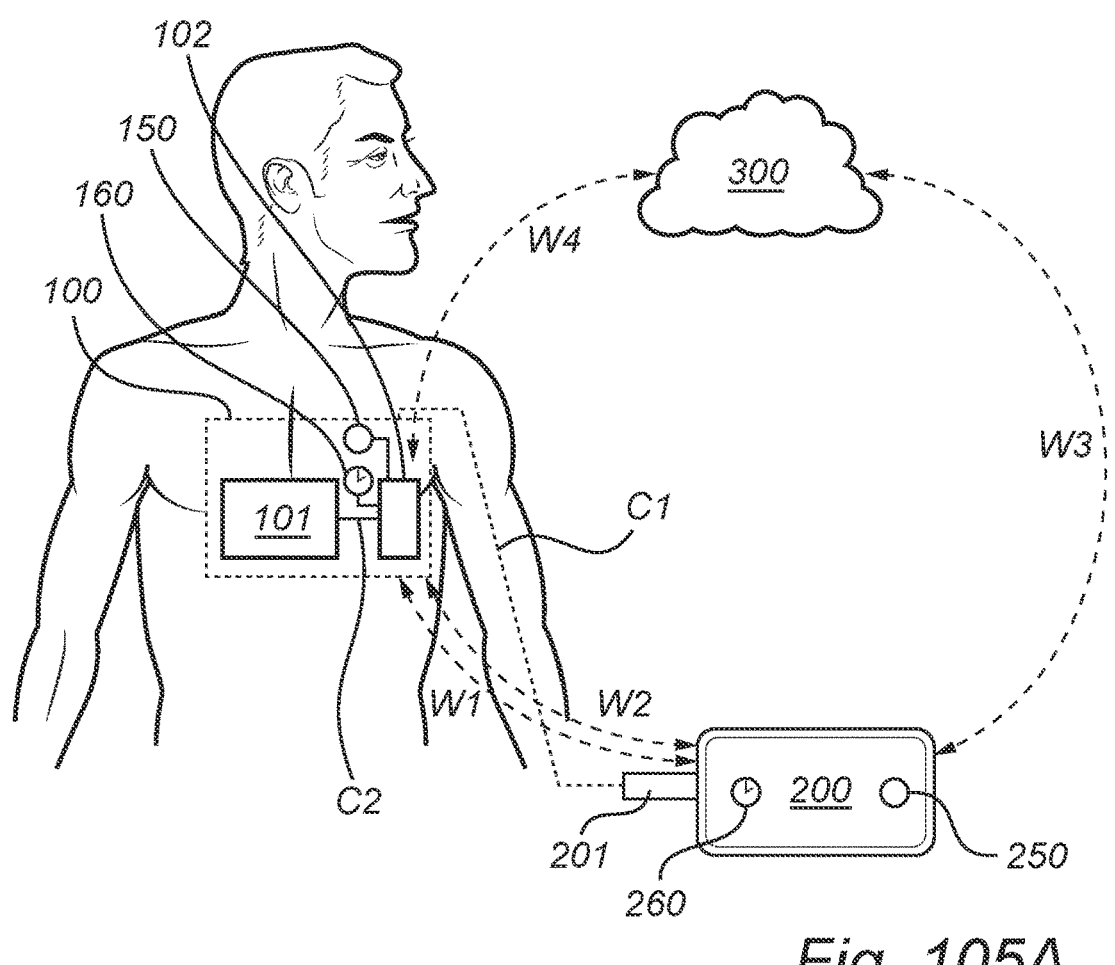
FIGS. 105A, 105B and 105C illustrate a system according to aspect 311SE.
Figure 106:
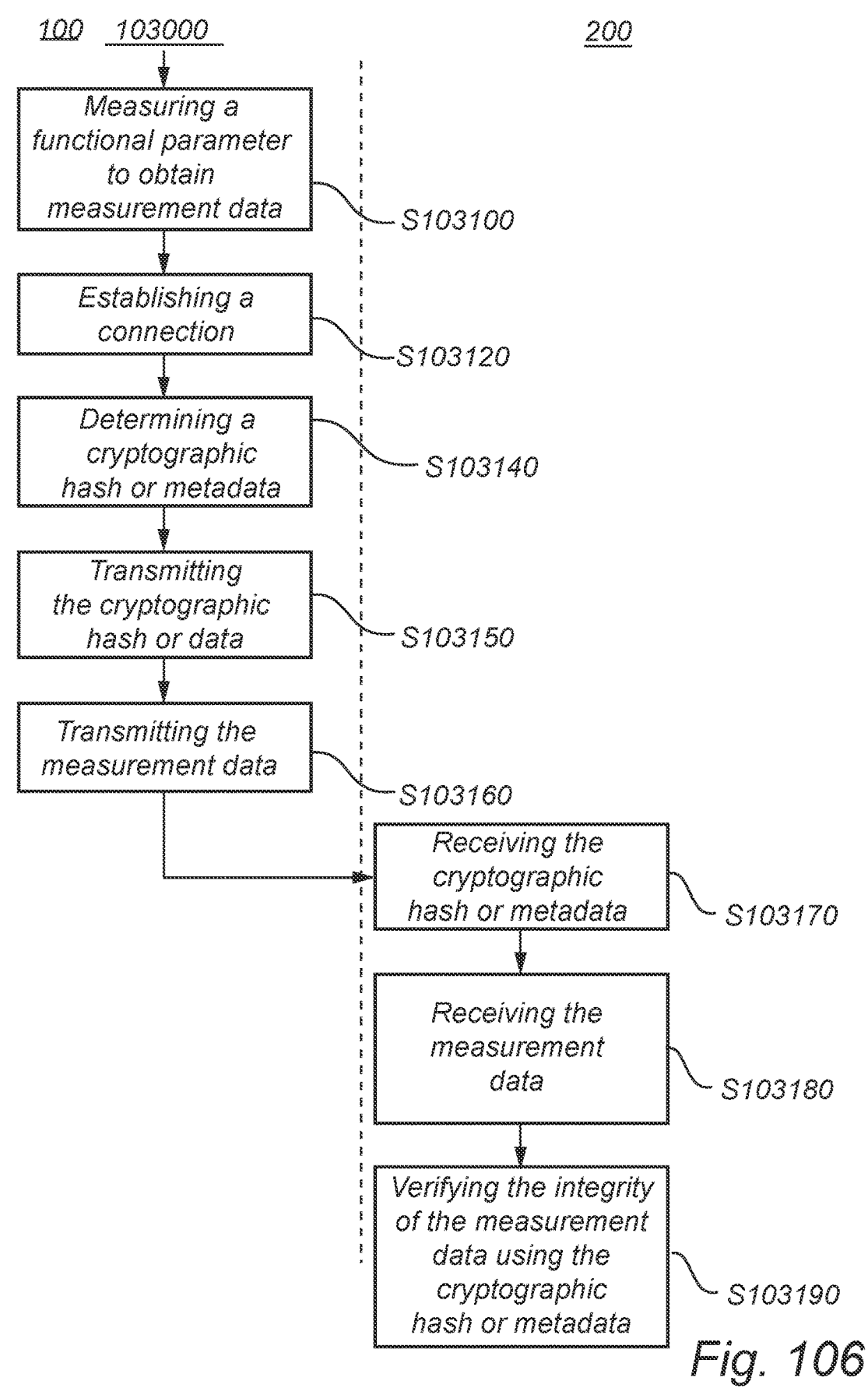
FIG. 106 illustrates a method according to aspect 311SE.
Figure 107:
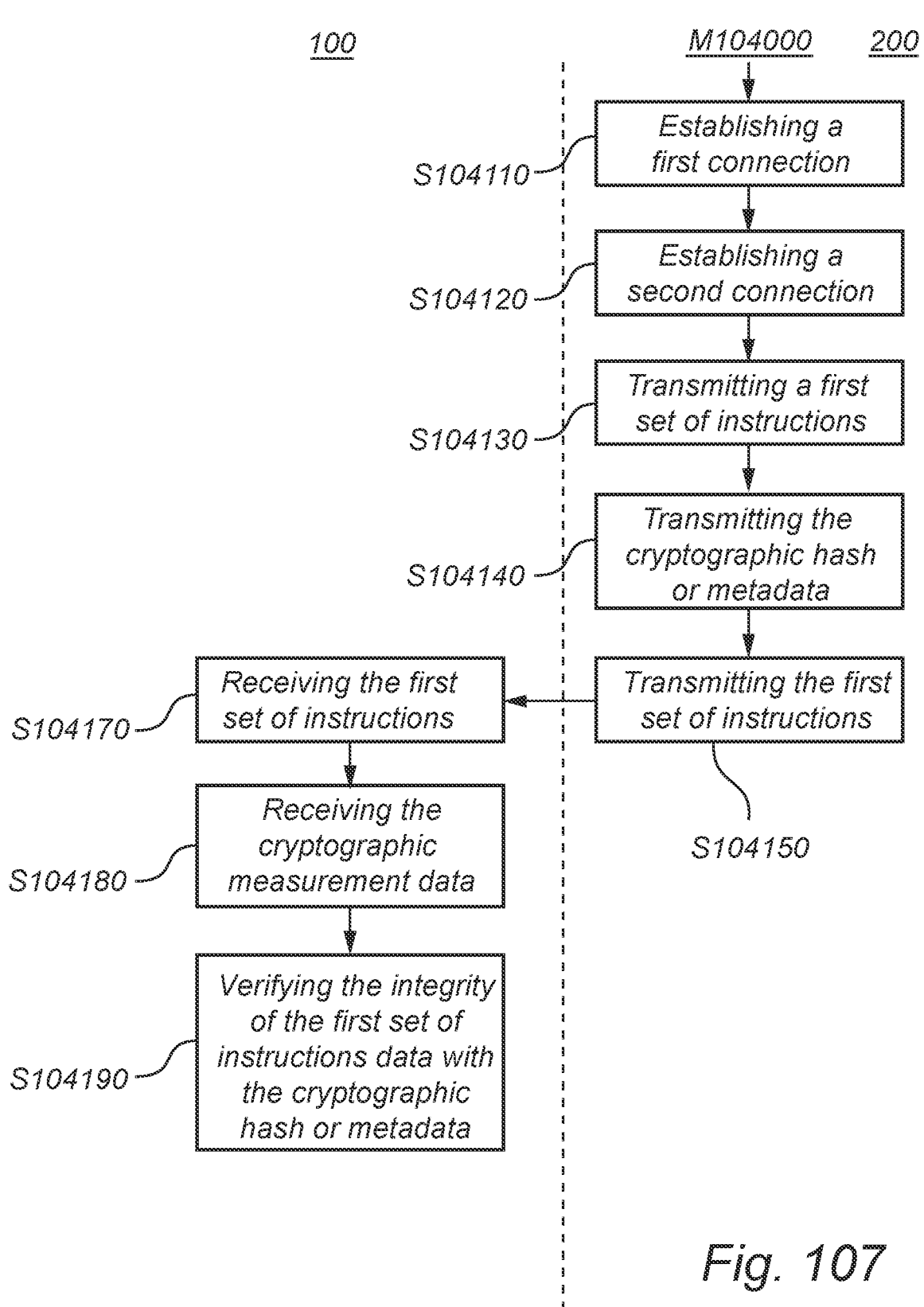
FIG. 107 illustrates a method according to aspect 311SE.

Generally, aspect 311SE defines a method, as shown in FIG. 106, and a method, as shown in FIG. 107, both adapted to run in a communication unit 102 comprised in an implant 100 when implanted in a patient, as shown in FIGS. 105A-C. The implant 100 and the external device 200 may be any of the implants 100 or external devices 200 described with reference to aspects one through twenty-five, further comprising the features described below.

In the examples or embodiments transmitting data from or to the implant 100, the following method may be implanted in order to verify the integrity of the data, described with reference to FIGS. 105A-C. By verifying the integrity of the data, an external device 200 or a processor 106 comprised in the implant may verify that the data has not been corrupted or tampered with during the transmission. In some examples, data integrity for data communicated between an implant 100 and an external device 200 or between an external device 200 and an implant 100 may be performed using a cyclic redundancy check.

Thus, a system for transmitting data related to a parameter of the implant is provided and will not be described with reference to FIGS. 105A-C. The system comprises an implant 100 and an external device 200. The implant 100 comprises a processor 106, a sensor 150 for measuring the parameter, and an internal communication unit 102. The sensor 150 is configured to obtain measurement data related to the parameter, and the communication unit is configured to establish a connection between the internal communication unit 102 and the external device 200, the external device being configured to receive data from the implant. The processor 106 is further configured to determine a cryptographic hash or a metadata relating to the measurement data and adapted to be used by the external device 200 to verify the integrity of the received data. The processor 106 is further configured to transmit the cryptographic hash or metadata and to transmit the measurement data.

The parameter may, for example, be a parameter of the implant, such as a temperature, a pressure, a battery status indicator, a time period length, a pressure at a restriction device, a pressure at a sphincter, or a physiological parameter of the patient, such as a pulse, a blood pressure, or a temperature. In some examples, multiple parameters may be used. The sensor may, for example, be a pressure sensor, an electrical sensor, a clock, a temperature sensor, a motion sensor, an optical sensor, a sonic sensor, an ultrasonic sensor.

The processor 106 or the external device 200 may be further configured to evaluate the measurement data relating to the functional parameter. By evaluating it may be meant to determine if the parameter is exceeding or less than a predetermined value, differing from a predetermined interval, to extract another parameter from the measurement data, compare the another parameter to a predetermined value, or displaying the another parameter to a user. For example, the external device 200 may be configured to determine, based on the evaluating, that the implant 100 is functioning correctly, or determining based on the evaluating that the implant 100 is not functioning correctly.

If it is determined that the implant 100 is not functioning correctly, the external device 200 may be configured to transmit a corrective command to the implant 100. The corrective command may be received at the implant 100, and the implant may run the corrective command correcting the functioning of the implant 100 according to the corrective command. The corrective command or process referred to here could, for example, be the reset function described with reference to the aspect 244SE.

Thus, the external device 200 is configured to receive the transmitted cryptographic hash or metadata, receive the measurement data, and verifying the integrity of the measurement data using the cryptographic hash or metadata. The cryptographic hash algorithm be any type of hash algorithm. i.e. an algorithm comprising a one-way function configured to have an input data of any length as input and produce a fixed-length hash value. For example, the cryptographic hash algorithm may be MD5, SHA1. SHA 256, etc.

In some examples, the cryptographic hash is a signature obtained by using a private key of the implant, and wherein the verifying, by the external device 200, comprises verifying the signature using a public key corresponding to the private key.

When using a cryptographic hash, the external device may calculate a second cryptographic hash for the received measurement data using a same cryptographic hash algorithm as the processor, and determining that the measurement data has been correctly received based on that the cryptographic hash and the second cryptographic hash are equal (i.e. have the same value).

When using a metadata the verifying the integrity of the data may comprise obtaining a second metadata for the received measurement data relating to the functional parameter, and determining that the data has been correctly received based on that metadata and the second metadata are equal. The metadata may, for example, be a length of the data, or a timestamp, or other data for verifying the integrity of the received measurement data.

In some examples the measurement data is transmitted in a plurality of data packets. In those examples, the cryptographic hash or metadata comprises a plurality of cryptographic hashes or metadata each corresponding to a respective data packet, and the transmitting of each the cryptographic hashes or metadata is performed for each of the corresponding data packets.

A corresponding method for evaluating a functional parameter of an implant when implanted in a patient will also be described with reference to FIG. 106. The method 103000 comprises measuring S103100, using the sensor, the functional parameter to obtain measurement data, establishing S103120 a connection between the internal communication unit and an external device configured to receive data from the implant, determining S103140, by the processor, a cryptographic hash or a metadata relating to the measurement data and adapted to be used by the external device to verify the integrity of the received data, and transmitting S103150 the cryptographic hash or metadata, and transmitting S103160, from the communication unit, the measurement data.

The method 103000 may further comprise, at the external device, receiving S103170 the transmitted cryptographic hash or metadata, receiving S103180 the measurement data, and verifying S103190 the integrity of the measurement data with the cryptographic hash, metadata or information relating to the functional parameter. The verification may be performed as described above with reference to FIGS. 105A-C.

When the cryptographic hash or metadata comprises a cryptographic hash, the verifying S103190 the integrity of the measurement data may comprise calculating a second cryptographic hash for the received measurement data using a same cryptographic hash algorithm as the processor, and determining that the measurement data has been correctly received based on that the cryptographic hash and the second cryptographic hash are equal.

The cryptographic hash algorithm may comprise one of: MD5, SHA1, or SHA 256. The person skilled in the art would know several options for exchanging keys for implementing the cryptographic hash algorithms. Further, any exchange of keys described herein, for example with reference to any of aspects 1-10, may be used.

In some examples, the cryptographic hash is a signature obtained by using a private key of the implant, and wherein the verifying, by the external device, comprises verifying the signature using a public key corresponding to the private key.

When the cryptographic hash or metadata comprises a metadata, the verifying the integrity of the data may comprise obtaining a second metadata for the received measurement data relating to the functional parameter, and determining that the data has been correctly received based on that metadata and the second metadata are equal.

The metadata may be any data related to the measurement date, such as for example, a length of the data, a timestamp, or a sensor measurement. The sensor measurement may, for example, be used as described with reference to aspect eight.

The method may further comprise, at the external device, evaluating the measurement data relating to the functional parameter. The evaluating may be performed as described above with reference to FIGS. 105A-C. The method may further comprise, at the external device, determining, based on the evaluating, that the implant is functioning correctly. For example, if the parameter or measurement data is within a predetermined interval or less than or exceeding a predetermined threshold, the external device may determine that the implant is functioning correctly.

Correspondingly, the method may comprise determining that the implant is not functioning correctly of if the parameter or measurement data is not within a predetermined interval or not less than or exceeding a predetermined threshold sending. The method may in those examples further comprise, transmitting, from the external device, a corrective command to the implant, receiving the corrective command at the implant, and correcting the functioning of the implant according to the corrective command. The corrective command may, for example, be a command related to the active unit or a command related to the processor or communications unit. In some examples, the corrective command is a command to restart the processor, reset the processor or invoking a corrective signal for the active unit.

In some examples, the measurement data is transmitted in a plurality of data packets, wherein the cryptographic mash or metadata comprises a plurality of cryptographic hashes or metadata each corresponding to a respective data packet, and wherein the transmitting of each the cryptographic hashes or metadata is performed for each of the corresponding data packets.

In a specific embodiment of the method, the method is for evaluating a pressure at a sphincter of the patient.

A similar method may be utilized for communicating instructions from an external device 200 to an implant 100 implanted in a patient, the method will now be described with reference to FIG. 107. The method 104000 is configured to be performed, for example, in a system as described with reference to FIGS. 105A-C. The method 104000 comprises establishing S104110 a first connection between the external device 200 and the implant 100, establishing S104120 a second connection between a second external device 300 and the implant 100, transmitting S104130, from the external device 200, a first set of instructions to the implant 1200 over the first connection, transmitting S104140, from the second external device 300, a first cryptographic hash or metadata corresponding to the first set of instructions to the implant, and, at the implant 100, verifying S104180 the integrity of the first set of instructions and the first cryptographic hash or metadata, based on the first cryptographic hash or metadata. The external device 200 may be separate from the second external device 300.

The first connection may be established between the internal communication unit 102 and a transceiver of the external communication unit 201, 203. In some examples, the communication using the second connection is performed using a different protocol than a protocol used for communication using the first communication channel. In some examples, the first connection is a wireless connection and the second connection is an electrical connection. The second connection may, for example, be an electrical connection using the patient's body as a conductor. The protocols and ways of communicating may be any communication protocols described in this description with reference to C1, and W1-W8. The establishing of the first and second connections are performed according to the communication protocol used for each of the first and the second connections.

When using a cryptographic hash, the verifying S104180 the integrity of the first set of instructions may comprise calculating a second cryptographic hash for the received first set of instructions using a same cryptographic hash algorithm as the processor 106, and determining that the first set of instructions has been correctly received based on that the cryptographic hash and the second cryptographic hash are equal. The cryptographic hash may, for example, be a signature obtained by using a private key of the implant 100, and wherein the verifying comprises verifying the signature using a public key corresponding to the private key. In some examples, the cryptographic hash is a signature obtained by using a private key of the implant, and wherein the verifying comprises verifying the signature using a public key corresponding to the private key. The private keys and public keys, as well as the exchange or transmittal of keys have been described in this description. Alternatively, other well-known methods can be used for transmitting or exchanging a key or keys between the external device 200 and the implant 100.

When using a metadata, and wherein the verifying S104180 the integrity of the data may comprise obtaining a second metadata for the received first set of instructions, and determining that the first set of instructions has been correctly received based on that metadata and the second metadata are equal. The metadata may, for example, be any type of data relating to the data to be transmitted, in this example the first set of instructions. For example, the metadata may be a length of the data to be transmitted, a timestamp on which the data was transmitted or retrieved or obtained, a size, a number of packets, or a packet identifier.

In some examples, the implant 100 may transmit data to an external device 200 relating to the data information in order to verify that the received data is correct. The method 104000 may thus further comprise, transmitting, by the implant 100, information relating to the received first set of instructions, receiving, by the external device 200, the information, and verifying, by the external device 200, that the information corresponds to the first set of instructions sent by the external device 200. The information may, for example, comprise a length of the first set of instructions.

The method 104000 may further comprise, at the implant 100, verifying the authenticity of the first set of instructions by i, calculating a second cryptographic hash for the first set of instructions, ii, comparing the second cryptographic hash with the first cryptographic hash, iii. determining that the first set of instructions are authentic based on that the second cryptographic hash is equal to the first cryptographic hash, and upon verification of the authenticity of the first set of instructions, storing them at the implant.

In some examples, the first set of instructions comprises a cryptographic hash corresponding to a previous set of instruction, as described in other parts of this description.

In some examples, the first set of instructions may comprise a measurement relating to the patient of the body for authentication, as described in other parts of this description.

Figure 108A:
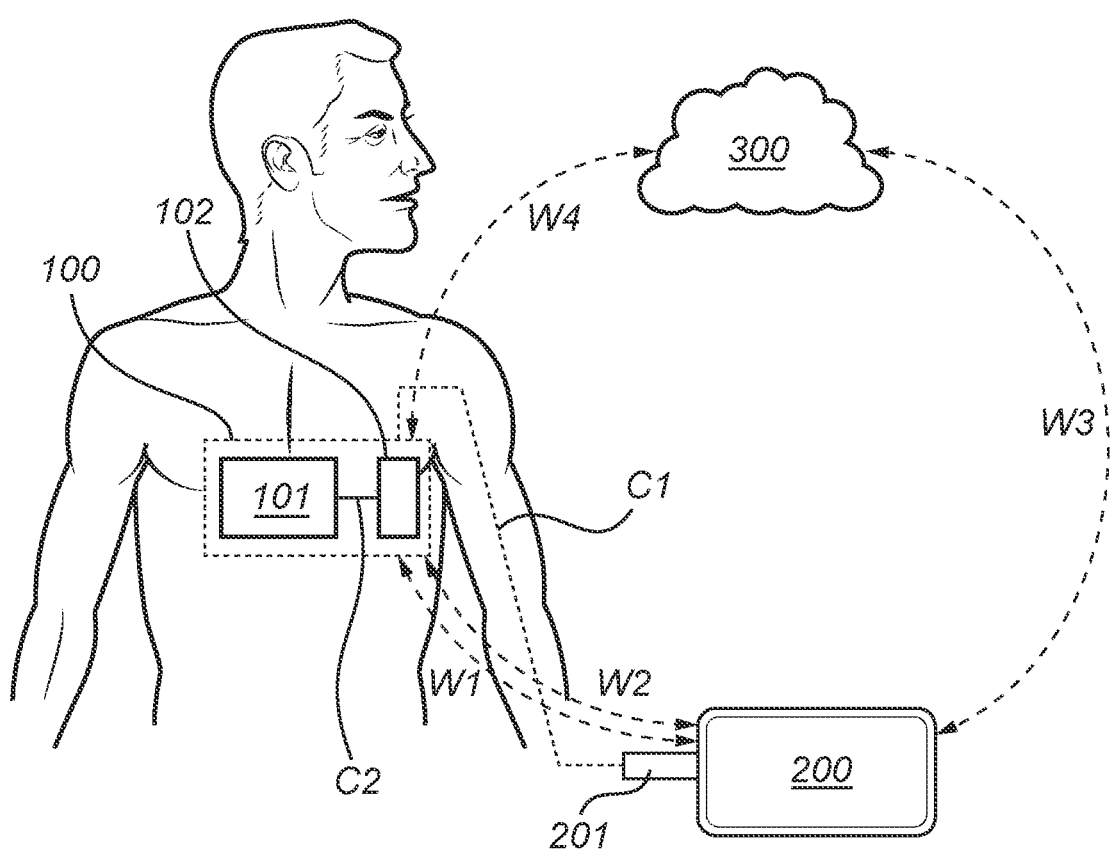
FIGS. 108A and 108B illustrate a system according to aspect 312SE.
Figure 108B:
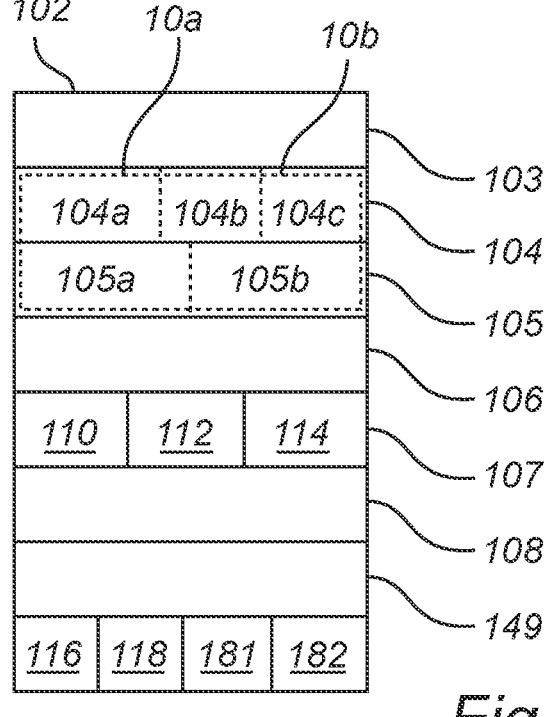
Figure 109:
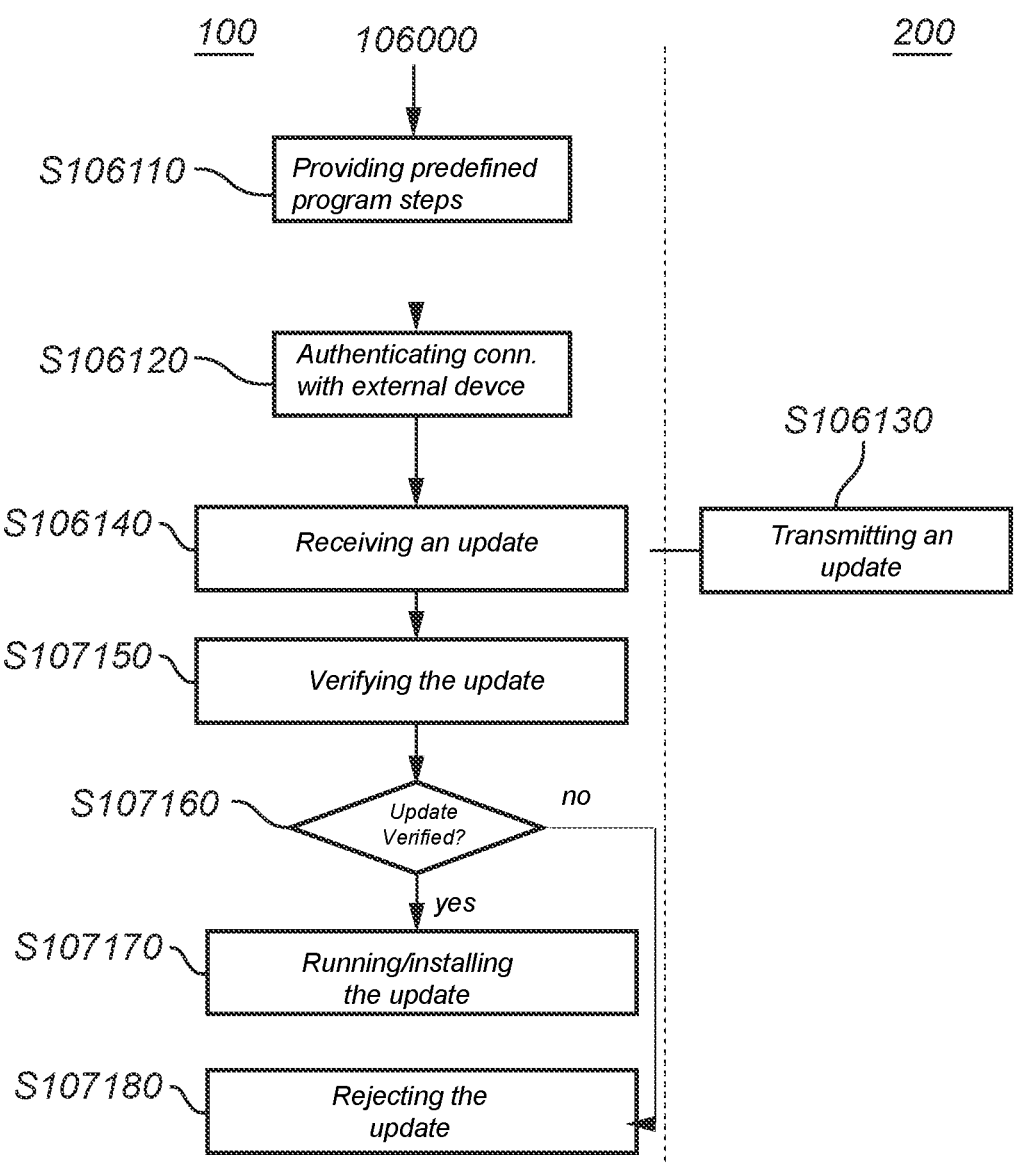
FIG. 109 illustrates a method according to aspect 312SE.

Aspect 312SE eHealth Programming Predefined Steps—Programming Via Predefined Steps—Embodiments of Aspect 312SE of the Disclosure In aspect 312SE, a method for communication between an external device 200 and an implant 100 is provided. FIGS. 108A-B and 109 shows embodiments of this aspect.

Generally, aspect 311SE defines a method, as shown in FIG. 109, and a system, as shown in FIGS. 108A-B. The system comprises an implant 100 an external device, which may be any of the implants 100 or external devices 200 described with reference to aspects one through twenty-six, further comprising the features described below.

As described above with reference to the general definition of features and the aspect 244SE, the implant may comprise a control program of the implant. The control program may be any software used for controlling the implant, and may be updatable, configurable, or replaceable. A system for updating or configuring a control program of the implant is now described with reference to FIGS. 108A-C.

The implant 100 may comprise an internal computing unit 106 configured to control a function of said implant 100, the internal computing unit 106 comprises an internal memory configured to store: i, a first control program 110 for controlling the internal computing unit, and ii, a second, configurable or updatable, with predefined program steps, control program 112 for controlling said function of said implant 100, and iii, a set of predefined program steps for updating the second control program 112. The internal computing unit 106 may further comprise or be connected to an internal communication unit 102, the internal communication unit being configured to communicate with an external device 200, wherein said internal computing unit 106 is configured to receive an update to the second control program 112 via said internal communication unit 102, and a verification function of, connected to, or transmitted to said internal computing unit 102, said verification function being configured to verify that the received update to the second control program 112 comprises program steps comprised in the set of predefined program steps. In this way, the updating or programming of the second control program may be performed using predefined program steps, which may decrease the risk that the new or updated control program is incorrect or comprises malicious software, such as a virus, spyware or a malware.

The predefined program steps may comprise setting a variable related to a pressure, a time, a minimum or maximum temperature, a current, a voltage, an intensity, a frequency, an amplitude of electrical stimulation, a feedback mode (sensorics or other), a post-operative mode or a normal mode, a catheter mode, a fibrotic tissue mode (for example semi-open), an time open after urination, a time open after urination before bed-time.

The verification function may be configured to reject the update in response to the update comprising program steps not comprised in the set of predefined program steps and/or be configured to allow the update in response to the update only comprising program steps comprised in the set of predefined program steps.

The internal computing unit may be configured to install the update in response to a positive verification, for example by a user using an external device, by a button or similarly pressed by a user, or by another external signal.

The authentication or verification of communications between the implant and an external device has been described above with reference to any of aspects one to eleven.

A corresponding method for programming an implant by an external device will now be described with reference to FIG. 109. The implant comprises an internal computing unit configured to control a function of said implant and an internal memory configured to store: a first control program for controlling the internal computing unit, a second, updatable or configurable, control program for controlling said function of said implant, and a set of predefined program steps for updating the second control program, the external device being configured to communicate with the implant via a first connection. The method comprises providing S106110, at the internal computing unit, a set of predefined program steps for updating the second control program; transmitting S106130, by the external device, an update comprising a subset of the predefined program steps over the first connection; receiving S106140, at the internal computing unit, the update, verifying S106150, by the internal computing unit, that the update comprise a subset of the predefined program steps, and upon verification S106160 of the instructions, running S106170 the update at the implant.

By verifying that an update to a control program for the implant is comprised in a set of predetermined program steps, the security may be improved. For example, this may lower the risk of malicious instructions being run at the implant, as such instructions would probably not be part of the predetermined program steps. Further, this decreases the risk that someone updating the control program would provide an update with an error that would be dangerous to the patient.

The predefined steps may, for example, comprise setting a variable related to a pressure, a time, a minimum or maximum temperature, a current, a voltage, an intensity, a frequency, an amplitude of electrical stimulation, a feedback, a post-operative mode or a normal mode, a catheter mode, a fibrotic tissue mode, an time open after urination, a time open after urination before bed-time.

The verifying S107150 may comprise rejecting S106180 the update in response to the update comprising program steps not comprised in the set of predefined program steps. By rejecting it is meant that the update is not run and/or not installed at the implant.

The verifying S170150 may comprise the verifying comprise allowing S106170 the update in response to the update only comprising program steps comprised in the set of predefined program steps. By allowing it is meant that the update is run and/or installed at the implant. The method may further comprise, upon verification, installing the update.

In an embodiment, the method further comprises authenticating S106120. S106125 the communication between the implant and the external device over a second connection. The authentication may be performed using any of the authentication methods described herein.

In some embodiments, the second connection is a wireless short-range connection. Alternatively, the second connection is an electrical connection using the patient's body as a conductor. Both of these options have been described with reference to C1-C3 and W1-W8 in other aspects of this description.

The method may further comprise or be combined with any embodiment of aspect 307SE.

Aspect 313SE eHealth Watchdog—Safety Reset
Function—Embodiments of the Twenty-Eighth
Aspect of the Disclosure According to aspect 313SE a method and a system for improved safety of the implant is provided. The safety reset function will now be described with reference to FIG. 110. In addition to or as an alternative to the reset function 116 described above with reference to the general definition of features, the implant may comprise another reset function, herein called the first reset function.

Figure 110:
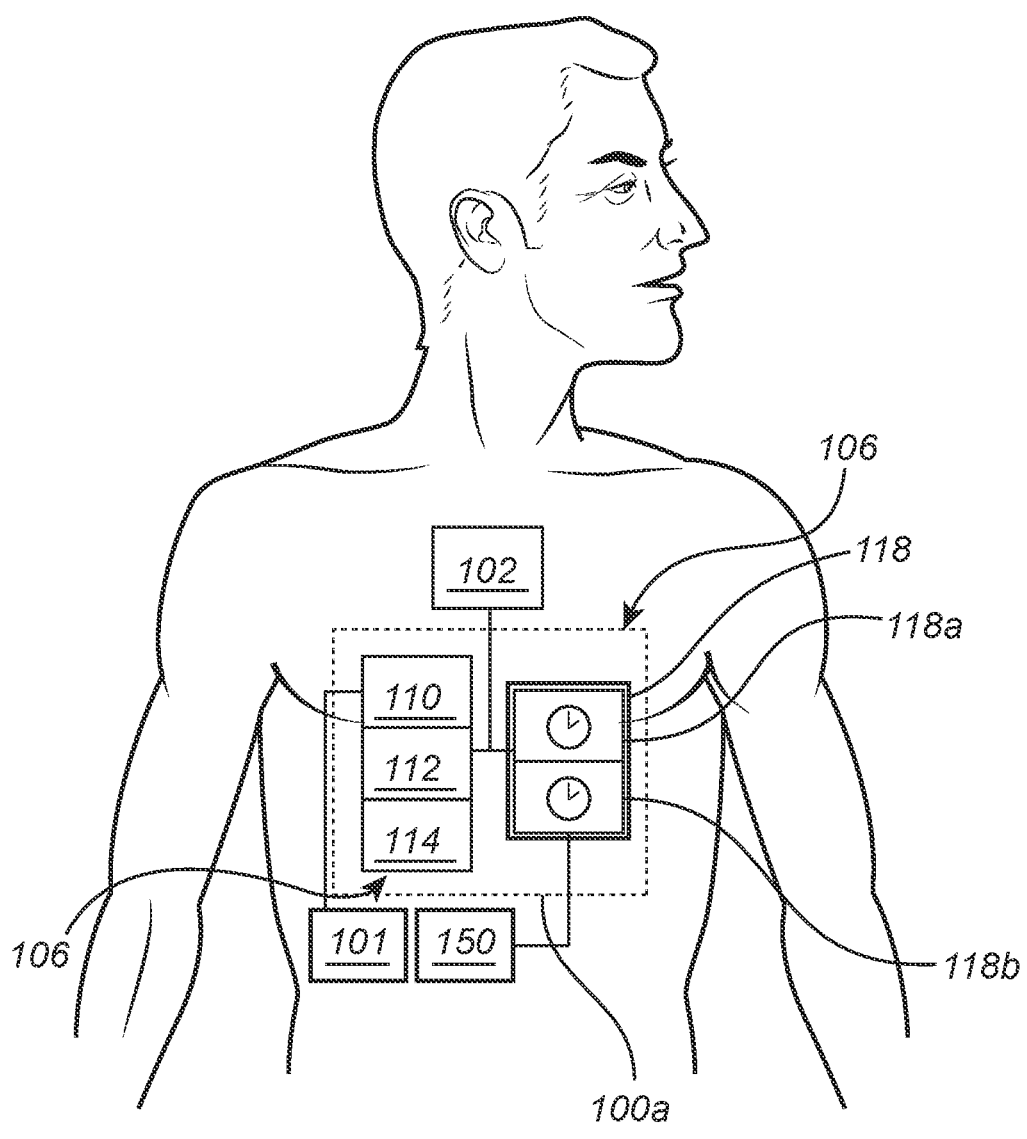
FIG. 110 illustrates a system according to aspect 313SE.

The implant shown in FIG. 110 comprises an internal processor 106 or an internal computing unit 106 (comprising an internal processor) having a second control program 112 for controlling a function of the implant, and a safety reset function 118. The safety reset function 118 may comprise a first reset function 118a, and optionally a second reset function 118a and/or optionally a third reset function. In this example, the internal processor 106 and the first reset function 118 are shown as separate from the communication unit 102 but may advantageously be comprised in the communication unit 102. The implant 100 and the external device 200 shown in FIG. 110 may further have any features or implement any method disclosed herein with reference to an implant 100 and an external device 200, in addition to the first reset function.

The first reset function 118a may be configured to restart or reset said second control program 112 in response to: i, a timer of the first reset function 118a has not been reset, or ii, a malfunction in the first control program.

The first reset function 118a may, for example, comprise a computer operating properly, COP, function connected to the internal computing unit 106.

The first reset function 118a may comprise a timer, and the first or the second control program 112 is configured to periodically reset the timer. If the time is not reset, i.e. if the timer times out, the first reset function 118a may be configured to request a status from the second control program 112, and in response to an absent or invalid response, restart or reset the second control program 112. Alternatively, in response to the timer timing out, the first reset function 118a may restart or reset the second control program 112.

The first reset function 118a, may alternatively, or in combination with the timer, be configured to monitor a status function of the second control program 112. In some examples, the first reset function 118a is configured to periodically request a status from a status function of the second control program 112, and in response to an invalid or absent response restart or reset the second control program 112.

The first reset function 118a may be configured to restart or reset the first or the second control program 112 using a second reset function 118b. In these embodiments, the first reset function 118a may be configured to reset a timer of the second reset function 118b in response to the timer of the first reset function 118a being reset, for example by the second control program 112. When the timer of the first reset function 118a times out, the first reset function 118a may be configured to send a corrective command to the second control program 112. If the corrective action is successful, the second control program 112 may be configured to reset the timer of the first reset function 118a, and the first reset function 118a may then reset the timer of the second reset function 118b. If the corrective action is not successful, the second control program 112 will not reset the timer of the first control program 118a, and the first control program 118a will thus not reset the timer of the second control program 118b. The timer of the second reset program 118b will thus eventually time out, and in response to the timer of the second reset program 118b timing out, the second reset program 118b may reset or restart the second control program 112. In this way, firstly, the first reset program 118a will try to correct the second control program 112, and in the correction is unsuccessful, secondly, the second reset function 118b will restart or reset the second control program 112. This may help avoid unnecessary restarts or resets.

In some examples, the reset or restart of the second control program 112 may be performed by invoking a reset function of the first control program 110, such as, for example, described above with reference to the reset function 116.

The safety function 118 may further comprise a third reset function connected to or comprised in the internal computing unit 106 and connected to the second reset function 118a. The third reset function may in an example be configured to trigger a corrective function for correcting the first 110 or second control program 112, and the second reset function is configured to restart the first 110 or second control program 112 sometime after the corrective function has been triggered. The corrective function may be a soft reset or a hard reset.

The second or third reset function may, for example, configured to invoke a hardware reset by triggering a hardware reset by activating an internal or external pulse generator which is configured to create a reset pulse. Alternatively, the second or third reset function may be implemented by software.

Figure 111:
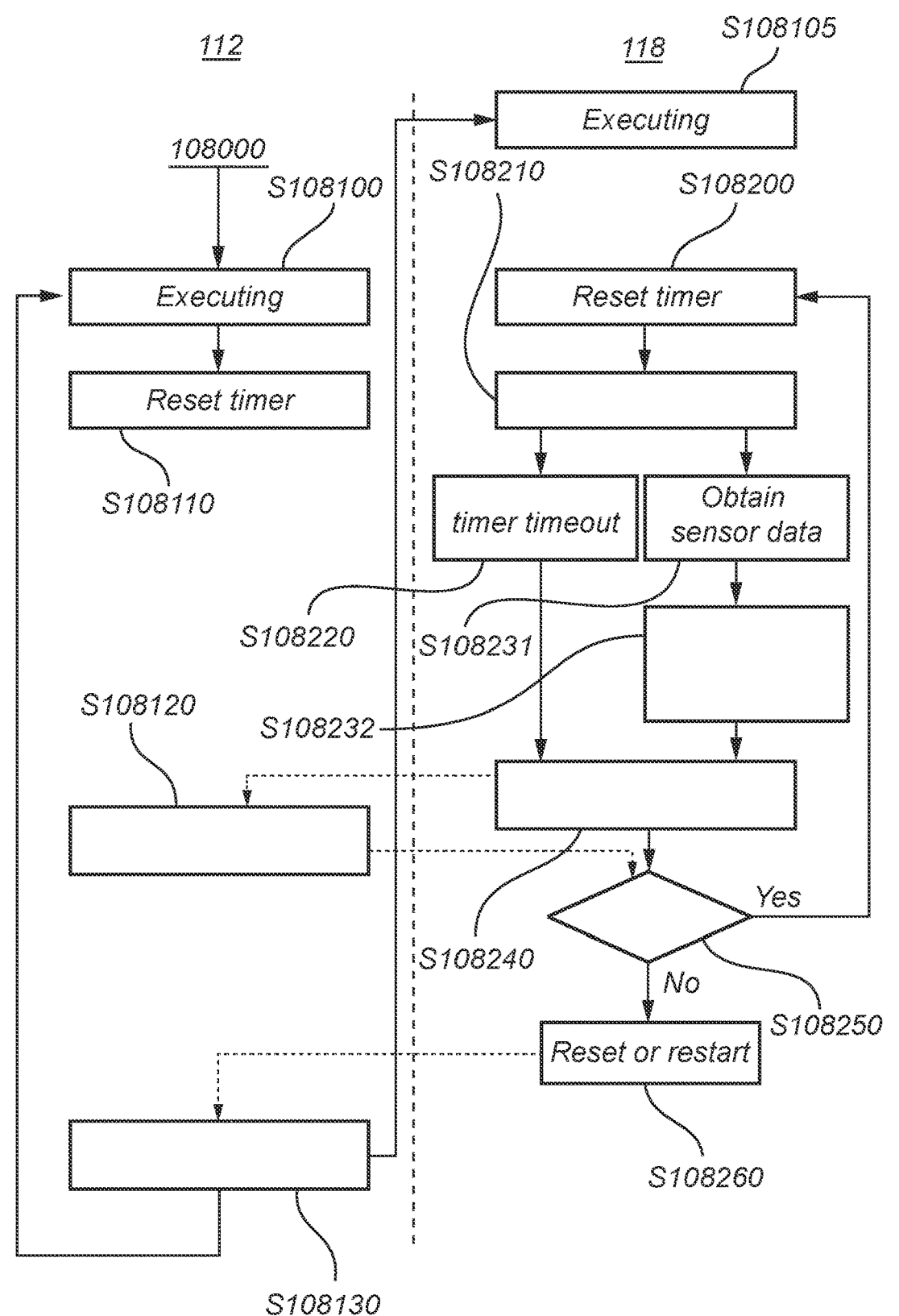
FIG. 111 illustrates a method according to aspect 313SE.

A corresponding method will now be described with reference to FIG. 111. The method 108000 for controlling a control program of an implant, when implanted in a patient, the implant comprising a processor for running the first control program, comprises: executing S108100 the first control program at the internal computing unit, executing S108105 a first reset function; resetting or restarting S108260 the first control program by the first reset function in response a detection S108250 of a malfunction in the first control program.

In some examples, the resetting or restarting of the first control program comprises triggering S108240 a corrective function for correcting the first control program.

The method 108100 may further comprise periodically resetting S108110, by the first control program, the first reset function, wherein the detecting S108210 of a malfunction comprises determining that the first reset function has not been reset for a predetermined period of time. In this example, the timer of the first control program may thus time out S108220.

Alternatively, or in combination, the method 108000 the detecting of a malfunction comprises obtaining S108231 data relating to the functioning of the first control program, for example by invoking a status function of the second control program or by obtaining measurement data relating to the functioning of the implant, detecting S108232 that a sensor measurement relating to a physiological parameter of the patient or a parameter of the implant being less than, exceeding or differing from a predetermined value. If it is determined that the obtained data indicates a malfunction, a corrective function S108120 of the second control program may be invoked S108240.

In some examples, the sensor measurement relates to a pressure in a part of the implant, to a pressure in a reservoir or a restriction device of the implant, a pressure in an organ of the patient's body. For example, the physiological parameter of the patient or a parameter of the implant may be a temperature.

In some examples, the reset function comprises invoking a first control program comprising a safety measure. The safety measure may, for example, be to turn off a restrictive function of the implant, such as a restriction device at a sphincter of the patient.

The method 108100 may further comprise monitoring a function of the implant or the first control program, and wherein the reset function is configured to in response to an incorrect or absent response for the monitoring program, reset or restart the first control program.

US 12,598,458 B2

325

Figure 112:
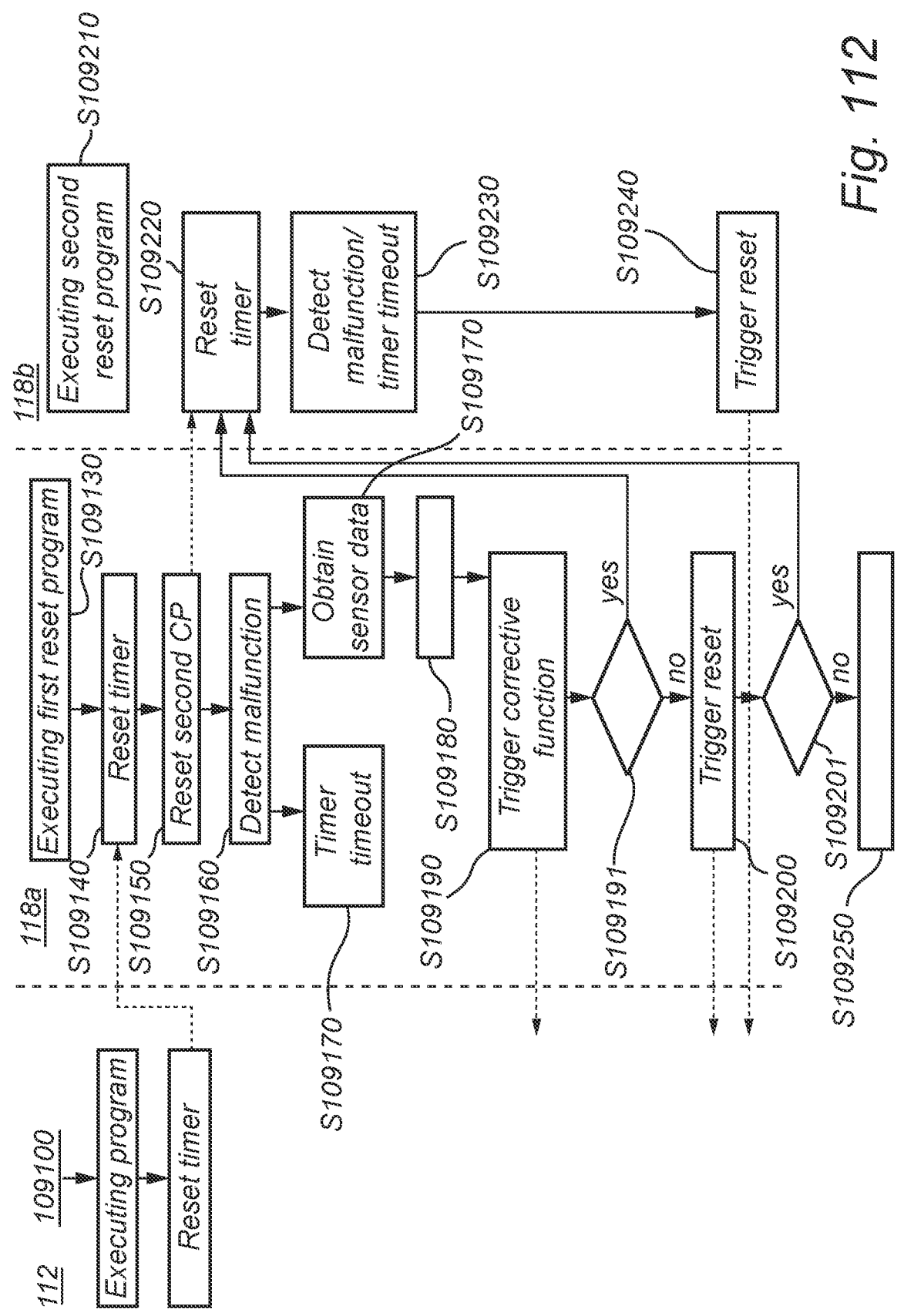
FIG. 112 illustrates a method according to aspect 313SE.

In some examples, the reset function 118 comprises, in addition to the first reset function 118a, a second reset function 118b. A method for a reset function having a first reset function and a second reset function will now be described with reference to FIG. 112.

The method comprises may, in relation to the first reset function, comprise the same steps as described above with reference to FIG. 111. The method may comprise executing S109130 a first reset program, resetting S109140 a timer of the first rest program by the second control program, and resetting S109150, by the first reset program, a timer of the second reset program, in response to the timer of the first reset program being reset.

The method may comprise detecting S109160 a malfunction in the second control program or in the implant, as described above with reference to FIG. 108, and in response to a detected malfunction, trigger S109190, by the first control program, a corrective function.

If the corrective function is successful, the second control program may reset S109120 the timer of the first reset program, and the first reset program may in turn reset the timer of the second reset program. Generally, the timer of the second reset function is longer that the timer for the first reset function.

If the corrective function is not successful, the first control program may be configured to trigger S109200 a reset function of the second control program S109200. This may, for example, be a soft (i.e. a software implemented) reset. If the reset function invocation is not successful, the first control program may wait S109250 for the timer of the second control program to detect S109230 that the malfunction is still present, and trigger S109240 a reset of the second control program 112. This reset may, for example, be a hard (i.e. a hardware implemented) reset.

The second reset program 118b may determine or detect the second control program 112 is malfunctioning by that the timer of the second reset program 118b has timed out or expired, or that the second control program 112 is malfunctioning, similarly to the detecting S109160 of the malfunction of the first reset program by the use of measurement data. In response to a detected malfunction the method may further comprise to trigger, by the second reset program 118a, a reset of the second control program 112.

The method may further comprise invoking a safety measure, wherein the safety measure comprises controlling a function of the implant.

Aspect 314SE eHealth Logging—Update
Confirmation—Embodiments of Aspect 314SE of
the Disclosure In aspect 314SE, a method updating a control program of an internal computing unit comprised in an implant is provided. FIGS. 114A-B and 113A-C shows embodiments of this aspect.

Figure 114A:
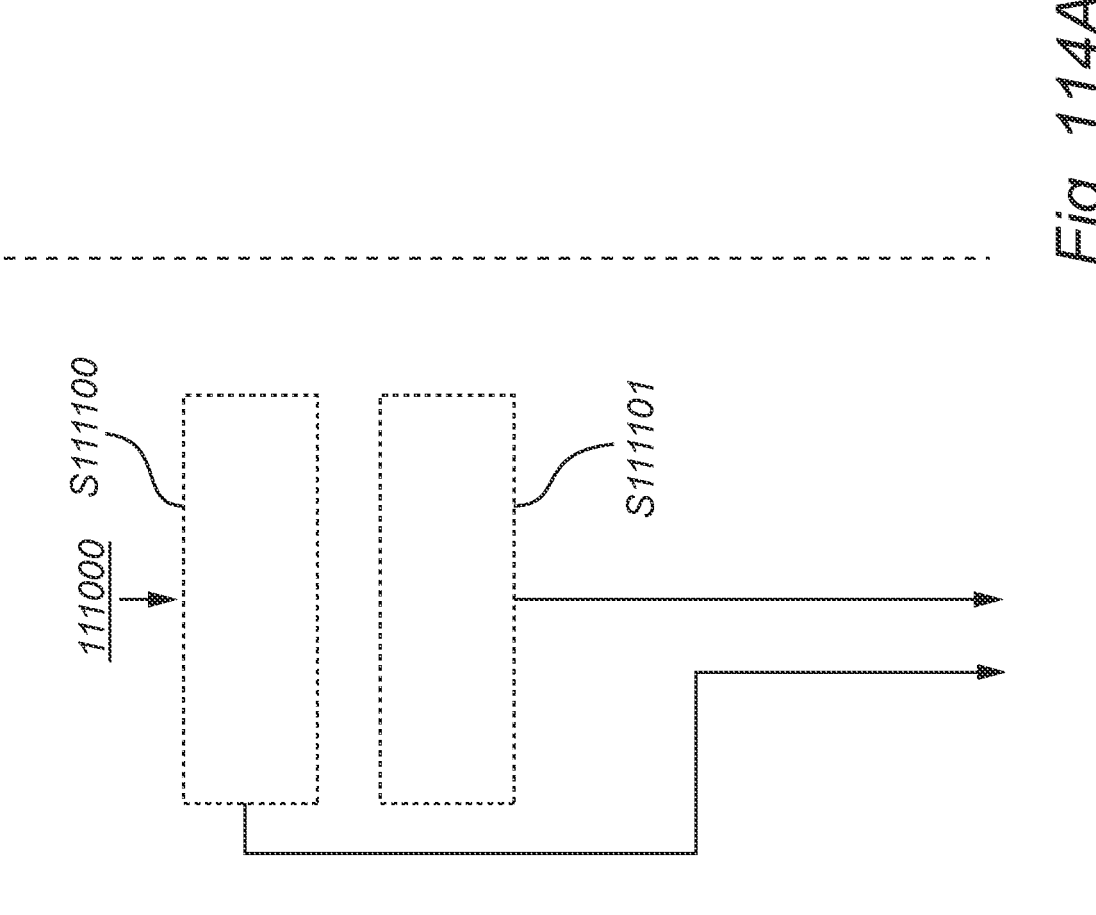
FIGS. 114A and 114B illustrates a method according to aspect 314SE.
Figure 114B:
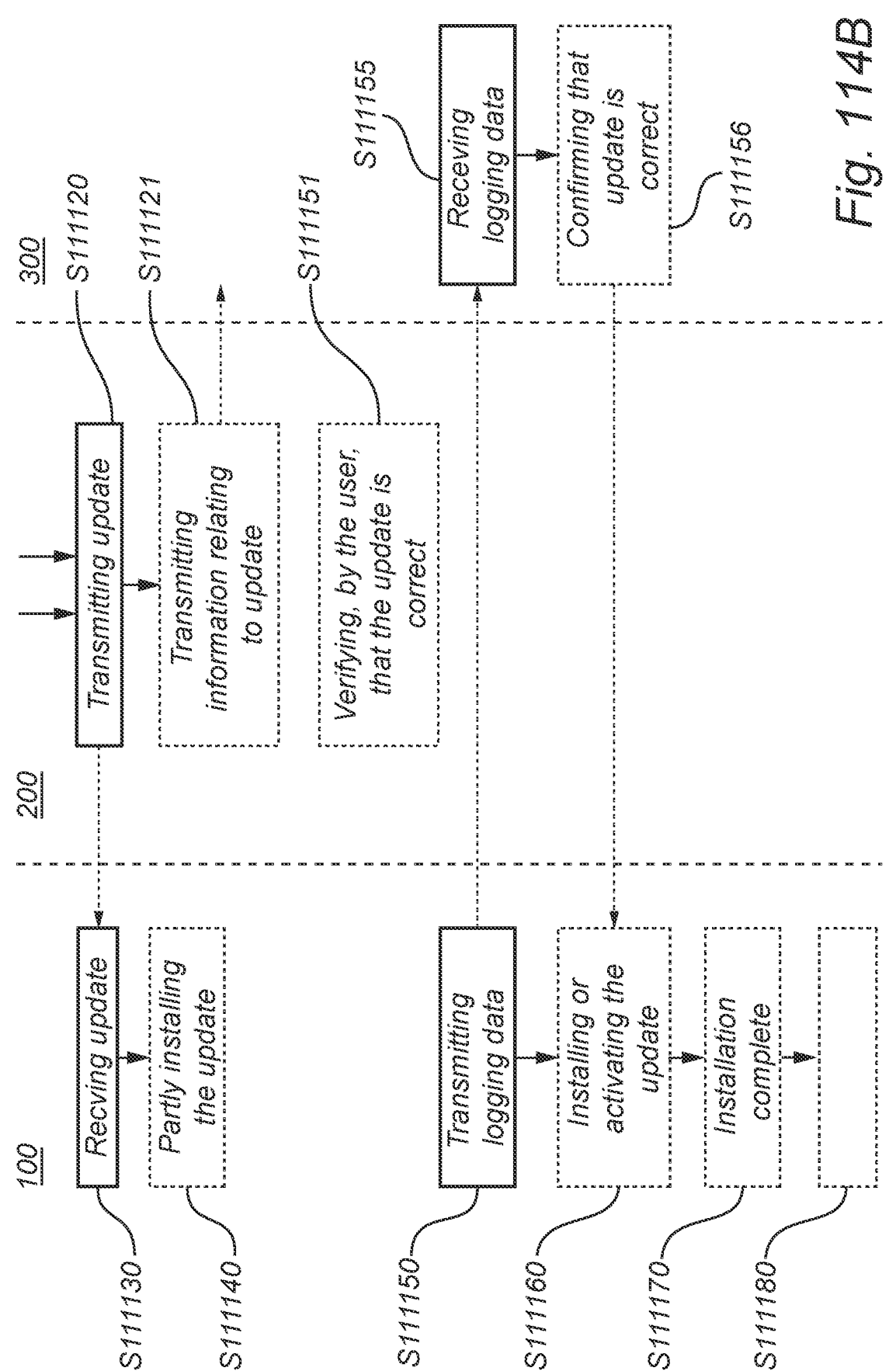

Generally, aspect 314SE defines a method, as shown in FIG. 114A-B, and a system, as shown in FIGS. 113A-C. The system generally comprises an implant 100, an external device 200 and a second external device 300, which may be any of the implants 100 or external devices 200, 300, 400 described with reference to aspects one through twenty-eight, as shown in FIGS. 110A-C.

When updating a control program of the internal computing unit, it may be beneficial to transmit a confirmation to a user or to an external device or system. Such a method is now described with reference to FIGS. 114A-B, with system reference to FIG. 113A-C. In FIGS. 114A-114B, optional method steps have been indicated with dashed lines.

The method 111000 for updating a control program 110/112/114 for an implant 100 according to any of the embodiments described with reference to aspects one to twenty-eight, wherein the implant is adapted for communication with a first external device and a second external device, which may comprise receiving S111130, by an internal computing unit or internal communication unit comprised in the implant 100, an update or configuration to the control program 110/112/114 from the first external device, wherein the update is received using a first communication channel W1/C1; installing S111140/S11160/S111170, by the internal computing unit, the update; and transmitting S111150, by the internal computing unit, logging data relating to the receipt of the update or configuration and/or logging data relating to an installation of the update to the second external device using the second communication channel W4; wherein the first and the second communication channels are different communication channels. By using a first and a second communication channels, in comparison to only using one, the security of the updating may be improved as any attempts to update the control program 110/112/114 will be logged via the second communication channel W4, and thus, increasing the chances of finding incorrect or malicious update attempts.

The update or configuration comprises a set of instructions for the control program, and may, for examples comprise a set of predefined program steps as described above with reference to aspect 312SE. The configuration or update may comprise a value for a predetermined parameter.

In some examples, the method further comprises confirming S111151. S1111156, by a user or by an external control unit, that the update or configuration is correct based on the received logging data.

The logging data may be related to the receipt of the update or configuration, and the internal computing unit is configured to install S111160 the update or configuration in response to receipt of a confirmation that the logging data relates to a correct set of instructions. In this way, the internal computing unit may receive S111130 data, transmit S11150 a logging entry relating to the receipt, and then install S111160 the data in response to a positive verification that the data should be installed.

In another example, or in combination with the one described above, the logging data is related to the installation or the update or configuration. In this example the logging data may be for information purposes only and not affect the installation, or the method may further comprise activating S111180 the installation in response to the confirmation that the update or configuration is correct.

If the update or configuration is transmitted to the internal computing unit in one or more steps, the verification as described above may be performed for each of the steps.

The method may further comprise, after transmitting the logging data to the second external device, verifying S111156 the update via a confirmation from the second external device via the second communication channel.

Figure 115:
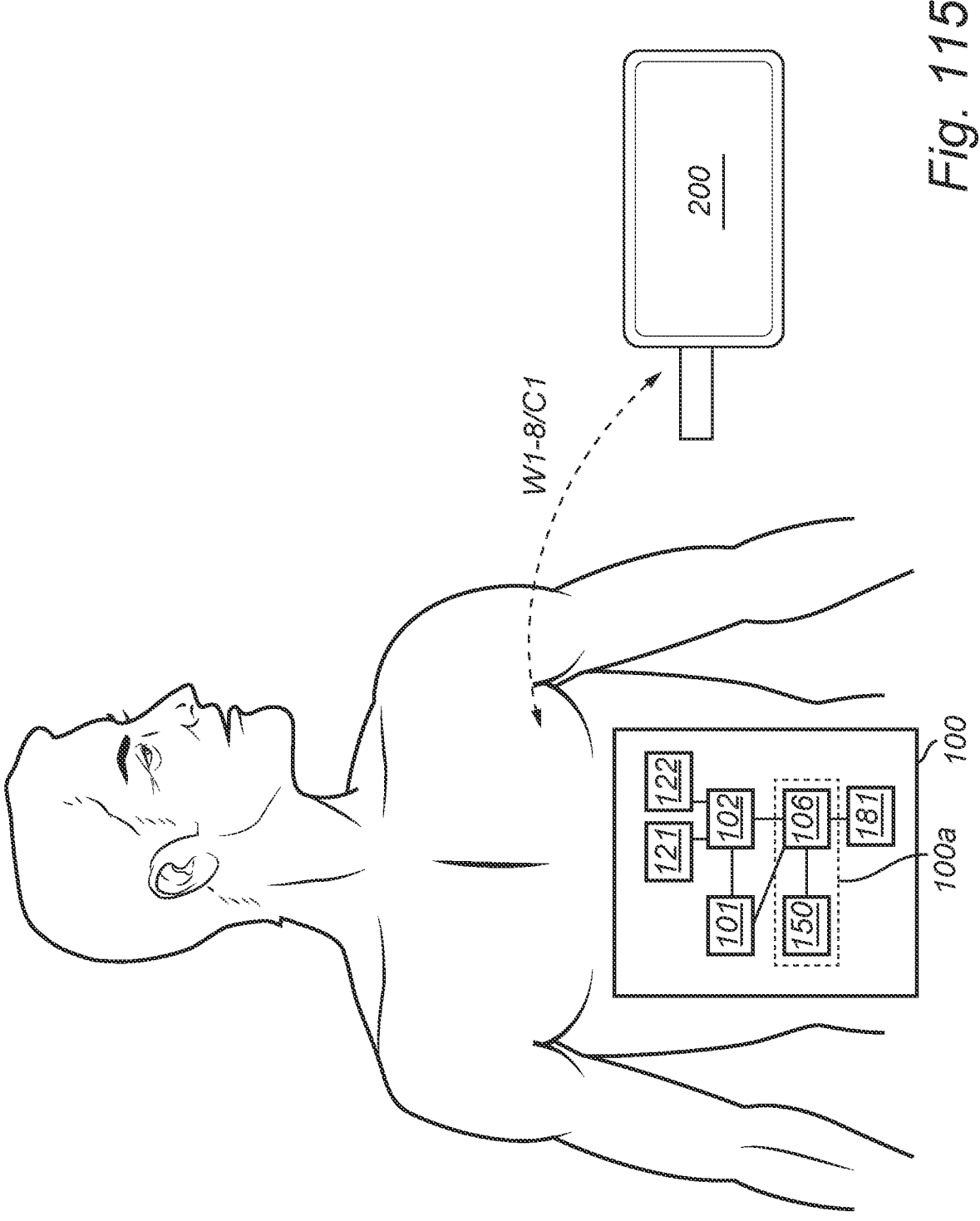
FIG. 115 illustrates a system according to aspect 315SE.
Figure 116:
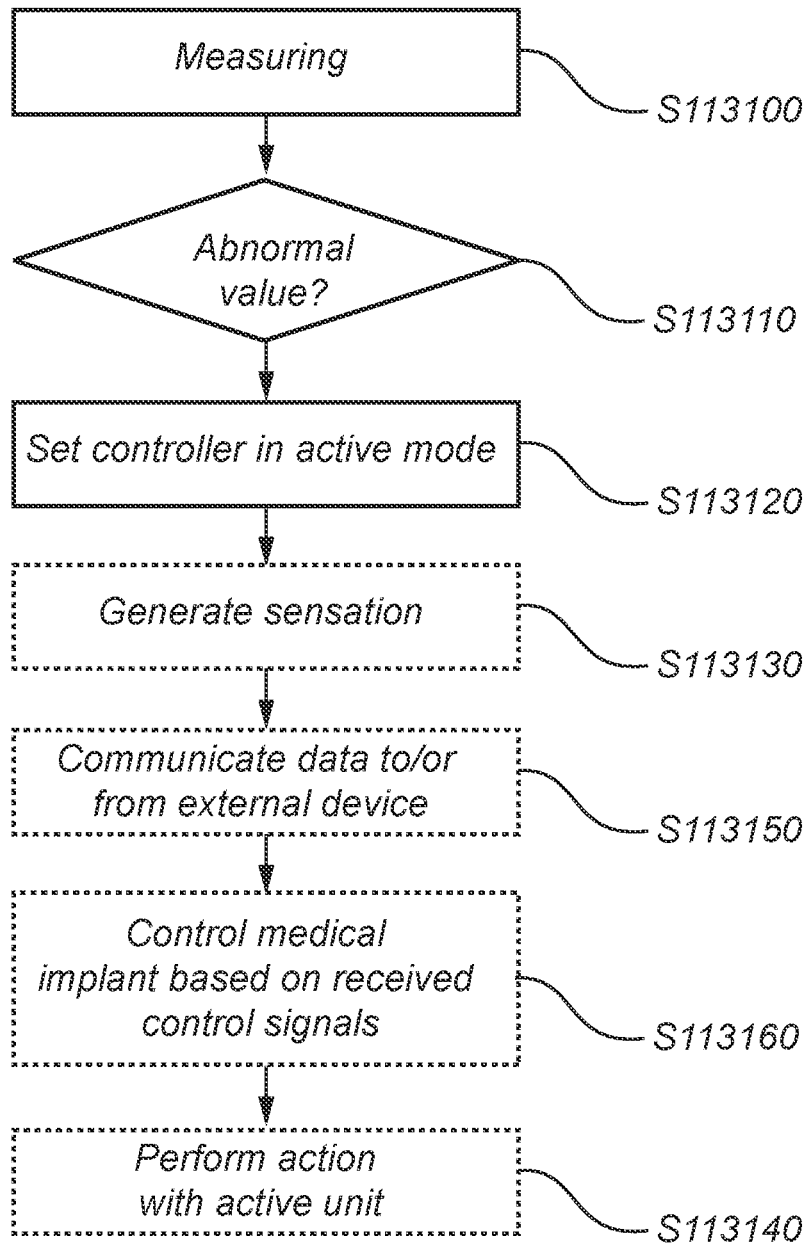
FIG. 116 illustrates a method according to aspect 315SE.

Aspect 315SE eHealth Sleeping Internal Control
Unit—Sleep Mode for Internal
Controller—Embodiments of Aspect 315SE of the
Disclosure In aspect 315SE, a method and a system for controlling an implant is provided. FIGS. 115 and 116 show embodiments of this aspect.

Generally, aspect 315SE defines a method, as shown in FIG. 116, and a system, as shown in FIG. 115. The system generally comprises an implant 100 and an external device 200, which may be any of the implants 100 or external devices 200, 300, 400 described with reference to aspects one through twenty-nine. The internal control unit 100a is in this example shown as separate from the communication unit 102 but may also beneficially be comprised in the communication unit 102, as for example shown in some aspects described herein.

As shown in FIG. 115, the internal control unit 100a comprises a processor 106, the processor having a sleep mode and an active mode, and a sensor 150, wherein the sensor 150 is configured to periodically measure a physical parameter of the patient, and wherein the internal control unit 100a is further configured to, in response to a sensor measurement preceding a predetermined value, setting the processing unit 106 in an active mode. That is, the internal control unit 100a may "wake up" or be set in an active mode in response to a measurement from, for example, the body. A physical parameter of the patient could for example be a local or systemic temperature, saturation/oxygenation, blood pressure or a parameter related to an ischemia marker such as lactate.

By sleeping mode, it is meant a mode with less battery consumption and/or processing power used in the processing unit 106, and by "active mode" it may be meant that the processing unit 106 is not restricted in its processing.

The sensor 150 may, for example, be a pressure sensor. The pressure sensor may be adapted to measure a pressure in an organ of a patient, a reservoir of the implant or a restriction device of the active unit 101. The sensor 150 may be an analog sensor or a digital sensor. i.e. a sensor 150 implemented in part in software. In some examples, the sensor is adapted to measure one or more of a battery or energy storage status of the implant and a temperature of the implant. In this way, the sensor 150 may periodically sense a pressure of the implant or of the patient and set the processing unit 106 in an active mode if the measured pressure is above a predetermined value, less than a predetermined value or outside of a defined range. Thus, less power. i.e. less of for example a battery or energy storage comprised in the implant, may be used, thereby prolonging the lifetime of the implant 100 or increasing the time between charging occasions of the implant 100.

In some examples, the processor 106, when in set in the active mode, may cause a sensation generator 181 connected to the implant, comprised in the implant or comprised in an external device 200, 300, to generate a sensation detectable by a sense of the patient. For example, the processor may cause the sensation generator to generate a sensation in response to a measure battery status, for example that the battery is above or below a predetermined level, that a measured pressure is above or below a predetermined level, or that another measured parameter has an abnormal value. i.e. less than or exceeding a predetermined threshold or outside of a predetermined interval. The sensation generator 181 has been described in further detail earlier in this description. In this way, the patient in which the implant is implanted may be informed of changes or other information regarding the implant.

The processing unit 106 may be configured to perform a corrective action for the active unit 101 in response to a measurement being below or above a predetermined level. Such a corrective action may, for example, be increasing or decreasing a pressure, increasing or decreasing electrical stimulation, increasing or decreasing power, or another action.

The internal control unit 100a may comprise or be connected to an internal communication unit 102 or a signal transmitter 120, and wherein the processing unit is configured to transmit data relating to the measurement via the internal communication unit 102 or the internal signal transmitter 120. The transmitted data may be received by an external device 200.

The external device 200 may have an external communication unit 290. The external device may comprise a signal provider 280 for providing a wake signal to the internal control unit. In some examples, the signal provider comprises a coil or magnet 281 for providing a magnetic wake signal.

The implant 100 may implement a corresponding method for controlling a medical implant when implanted in a patient, which will now be described with reference to FIG. 116. The method 113000 comprises measuring S113100, with a sensor of a controller connected to or comprised in the medical implant, a physiological parameter of the patient or a parameter of the medical implant, and, in response to S113110 a sensor measurement having a value outside of a predetermined interval, setting S113130, by the controller, a processor of the controller from a sleep mode to an active mode. The measuring S113100 may be carried out periodically. By "a value outside of a predetermined interval" it may be meant a measured value exceeding or being less than a predetermined value, or a measured value being outside a defined range or an interval determined by a control unit. The method may further comprise generating S113130, with a sensation generator as described above, a sensation detectable by the patient. In some examples, the generating comprises requesting, by the processor, the sensation generator to generate the sensation.

The method may further comprise to perform a S113150 medical intervention or an action with the active unit in response to a sensor measurement having a value outside of a predetermined interval, preferably after the processing unit has been set in the active mode.

The method 113000 may further comprise a step of communicating S113150 data to the external device. The data may, for example, be related to the measured value. In some examples, the external device may respond S113150 to the communicated data with a control signal. The method 113000 may further comprise the step of controlling S113160 the implant based on the received control signal.

Figure 117:
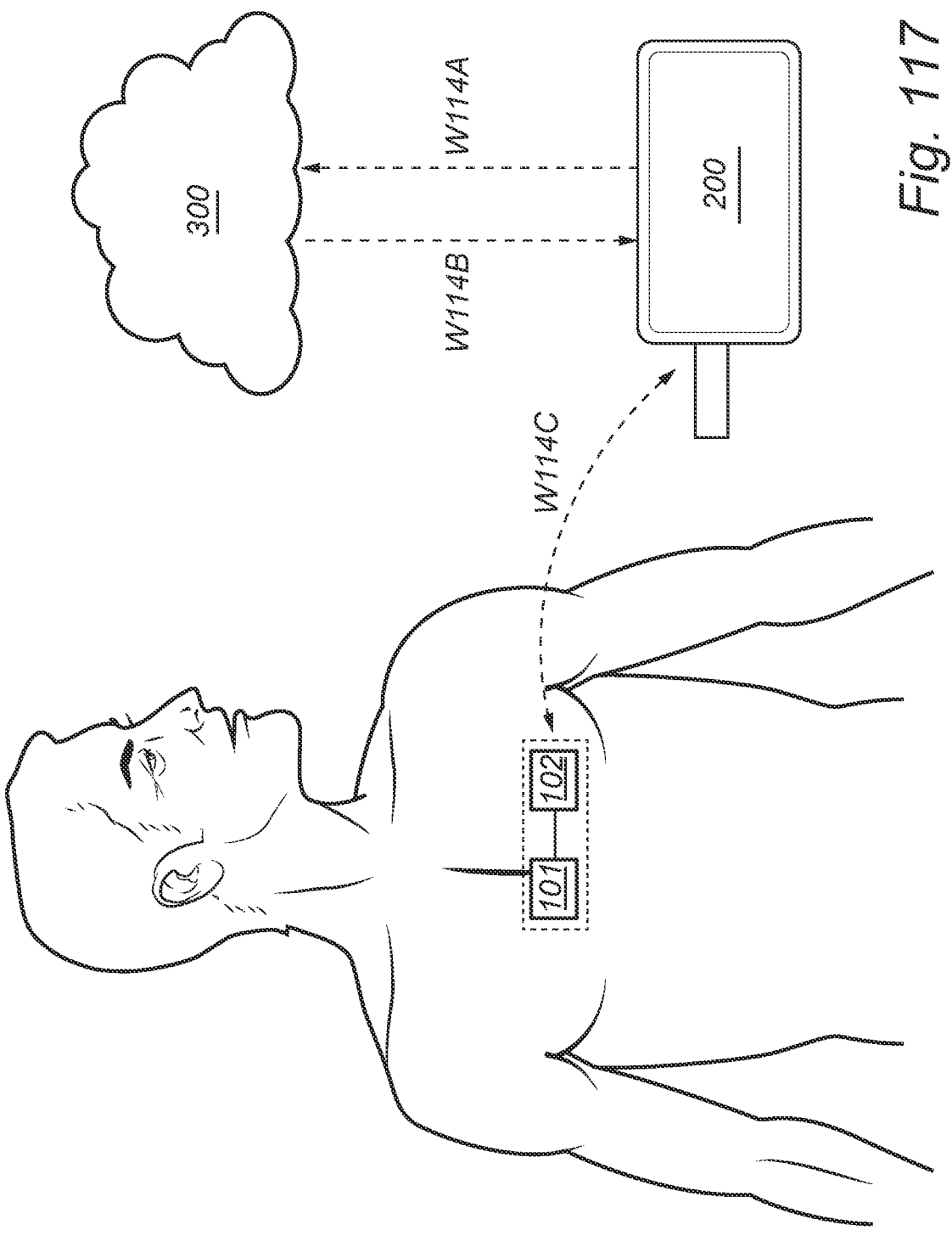
FIG. 117 illustrates a system according to aspect 316SE.
Figure 118:
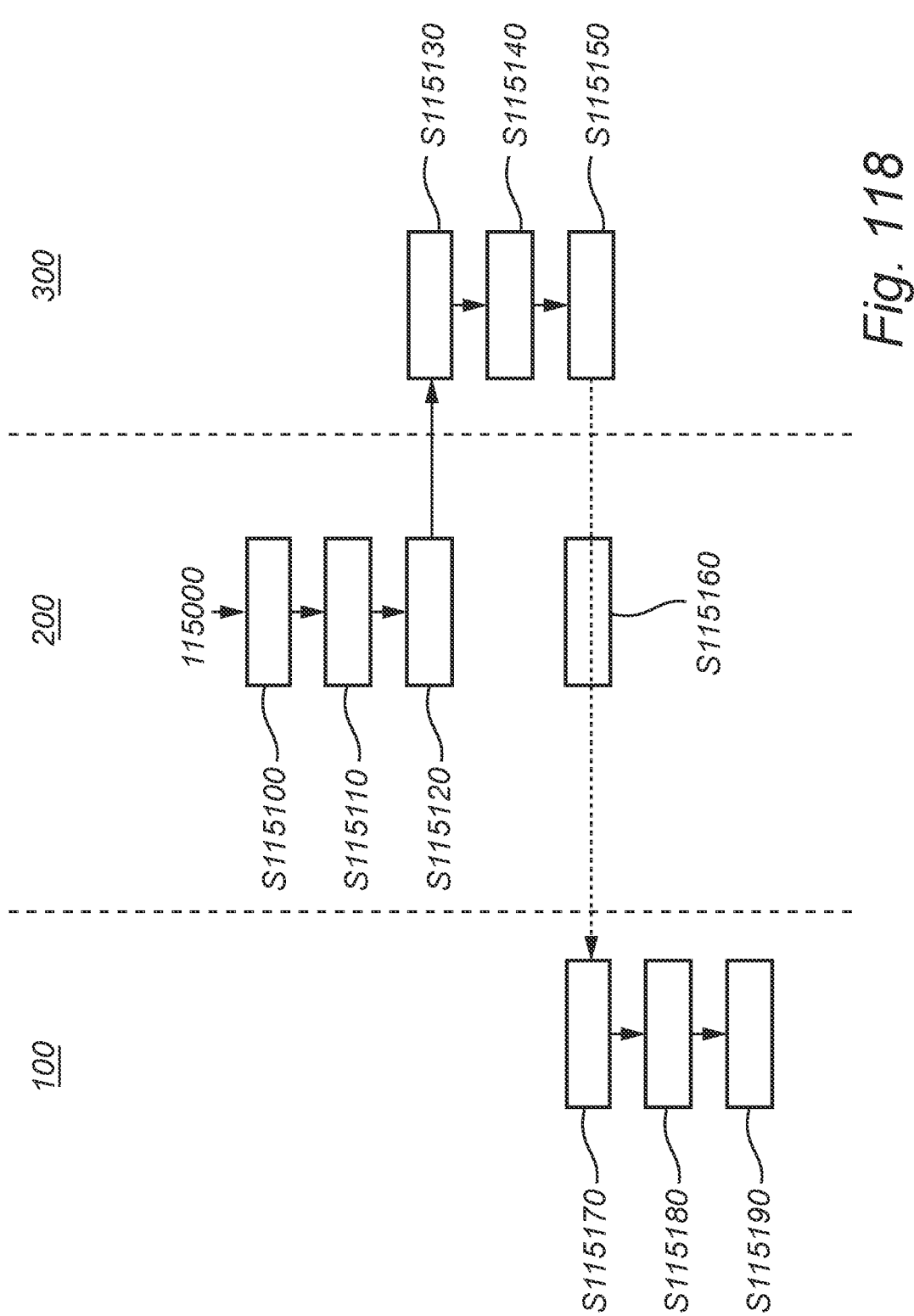
FIG. 118 illustrates a method according to aspect 316SE.

Aspect 316SE Relaying of Instructions—Relaying of Instructions—Embodiments of Aspect 316SE In aspect 316SE, a system, and a method for communication between an external device 200 and an implant 100 is provided. FIGS. 117 and 118 shows embodiments of this aspect.

Generally, aspect 316SE defines a system, as shown in FIG. 117 and a method shown in FIG. 118. The system shown in FIG. 117 is generally adapted to perform the method described with reference to FIG. 118. The implant 100 and the external devices 200, 300 may be any of the implants 100 or external devices 200, 300, 400 described with reference to aspects one through thirty, further comprising the features described below.

The system shown in FIG. 117 comprises an implant 100, a first external device 200, and a second external device 300. The implant comprises a communication unit 102 (which could also be called an internal control unit, or the communication unit 102 may be comprised in an internal control unit, in some examples the communication unit may comprise a processor) and an active unit 101. The communication unit 102 is adapted to receive an instruction from an external device 200 over the communication channel W1114C and run the instruction to control a function of the implant, such as a function of the active unit 101. The communication channel may be any type of communication channel, such as any of the wireless connection W1-W8 or the conductive connection C1-C3 described with reference to aspects 1 through thirty. For example, the wireless connection may comprise at least one of the following protocols:

Radio Frequency type protocol
    RFID type protocol
    WLAN type protocol
    Bluetooth type protocol
    BLE type protocol
    NFC type protocol
    3G/4G/5G type protocol
    GSM type protocol
    Bluetooth 5.

The first external device 200 is adapted to receive, such as through a user interface, or determine an instruction to be transmitted to the implant 100. The determination of the instruction may, for example, be based on received data from the implant 100, such as measurement data or data relating to a state of the implant, such as a battery status or a free memory status. The first external device 200 may be any type of device capable of transmitting information to the implant 100 and capable of determining or receiving an instruction to be transmitted to the implant 100. In a preferred embodiment, the first external device 200 is a handheld device, such as a smartphone, smartwatch, tablet etc. handled by the patient, having a user interface for receiving an instruction from a user, such as the patient or a caregiver.

The first external device 200 is further adapted to transmit the instruction to a second external device 300 via communication channel W114B. The second external device 300 is adapted to receive the instruction, encrypt the instruction using an encryption key, and then transmit the encrypted instruction to the implant 100. The implant 100 is configured to decrypt the received instruction. The decryption may be performed using a decryption key corresponding to the encryption key. The encryption key, the decryption key and methods for encryption/decryption and exchange of keys may be performed as described in the "general definition of features" or as described with reference to aspects two to nine or thirteen to fifteen. Further, there are many known methods for encrypting data which the skilled person would understand to be usable in this example.

The second external device may be any computing device capable of receiving, encrypting, and transmitting data as described above. For example, the second external device may be a network device, such as a network server, or it may be an encryption device communicatively coupled to the first external device.

The instruction may be a single instruction for running a specific function or method in the implant, a value for a parameter of the implant, or a set of sub-steps to be performed by a processor or computing unit comprised in the implant.

In one embodiment the instruction for controlling a function of the implant 100 is received at the first external device but transmitted to the implant via the second external device 300. By having a second external device encrypting the instruction before transmitting it to the implant, the instruction may be verified by the external device and the first external device may function so as to relay the instruction. In some alternatives, the second external device 300 may transmit the instruction directly to the implant 100. This may provide an increased security as the instruction sent to the implant may be verified by the second external device, which, for example, may be a proprietary device managed by the medical professional responsible for the implant. Further, by having the second medical device verifying and encrypting the instruction, the responsibility authenticity and/or correctness of the instruction lies with the second external device, which may be beneficial for regulatory purposes, as the first external device may not be considered as the instructor of the implant.

Further, the second external device 300 may verify that the instruction is correct before encrypting or signing and transmitting it to the implant 100. The second external device may, for example, verify that the instruction is correct by comparing the instruction with a predetermined set of instructions, and if the instruction is comprised in the predetermined set of instructions determine that the instruction is correct. If the instruction comprises a plurality of sub-steps, the second external device may determine that the instruction is correct if all the sub-steps are comprised in the predetermined set of instructions. If the instruction comprises a value for a parameter of the implant, the second external device may verify that the value is within a predetermined range for the parameter.

The second external device may be configured to reject the instruction, i.e. to not encrypt and transmit the instruction to the implant, if the verification of the instruction would fail. For example, the second external device determines that the instruction or any sub step of the instruction is not comprised in the predetermined set of instructions, or if a value for a parameter is not within a predetermined interval, the second external device may determine that the verification has failed.

In some embodiments, the implant may be configured to verify the instruction. The verification of the instruction may be performed in the same way as described with reference to the second external device above. If the verification is performed by comparing the instruction or any sub steps of the instruction with a predetermined set of instructions, the implant may comprise a predetermined set of instructions. The predetermined set of instructions may, for example, be stored in an internal memory of the implant. Similarly, the implant may store predetermined reference intervals for any parameter that can be set, and the implant may be configured to compare a received value for a parameter to such a predetermined reference interval. If the verification of the instruction would fail, the implant may be configured to reject the instruction, i.e. not run the instruction at the implant.

In an alternative to encrypting and decrypting the instruction, the instruction may be signed by the second external device using a cryptographic hash, and the implant may be configured to verify that the signature is correct before running the instruction.

A corresponding method will now be described with reference to FIG. 118. FIG. 118 shows a flowchart for a method for transmitting instructions from a first external device to an implant. The instruction may relate to a function of the implant, such as an instruction to run a function or method of the implant, or to set a value of a parameter of the implant.

The method comprises:

transmitting S115120 an instruction for the implant from the first external device 200 to a second external device 300, the instruction relating to a function of the implant 100.

encrypting S115140, at the second external device 300 and using a first encryption key, the instruction into an encrypted instruction, and transmitting S115150 the encrypted instruction from the second external device 300 to the implant 100.

decrypting S115170, at the implant, the instructions using a second encryption key corresponding to the first encryption key.

The instruction may be any type of instruction for controlling a function of the implant. For example, the instruction may be an instruction to run a function or method of the implant, an instruction comprising a plurality of sub steps to be run at the implant, or a value for a parameter at the implant. The first external device may, for example, receive the instruction from a user via a user interface displayed at or connected to the first external device. In another example, the first external device may determine the instruction in response to data received from the implant, such as measurement data, or from another external device. Thus, in some examples, the method may further comprise receiving S115100, at the first external device, an instruction to be transmitted to the implant. The method may further comprise displaying a user interface for receiving the instruction. In another example, the method comprises determining S115110, at the first external device, an instruction to be transmitted to the implant.

In some embodiments, the transmitting of the encrypted instruction from the second external device to the implant comprises transmitting S115150 the encrypted instruction from the second external device to the first external device, and transmitting S115160 the encrypted instruction from the first external device to the implant. In other words, the first external device may relay the encrypted instruction from the second external device to the implant, preferably without decrypting the instruction before transmitting it.

Additionally or alternatively, the transmitting of the encrypted instruction from the second external device to the implant comprises transmitting the encrypted instruction from the second external device to a third external device, and transmitting the encrypted instruction from the third external device to the implant. Accordingly, the third external device act as relay between the implant and the second external device wherein the third external device does not decrypt the instruction before transmitting it. Accordingly, in some embodiments the first external device is used for transmitting instructions to the second external device whereas the third external device is used for relaying the encrypted instruction from the second external device to the implant. For example, the first external device is an advanced user device such as a smartphone whereas the third external device is a simpler device or a proprietary relaying device which may be configured to essentially only act as a relaying device from the second external device to the implant. The third external device comprises a transmitter for wirelessly transmitting the encrypted instructions to the implant. Alternatively or additionally, the third external device is configured to be in conductive or capacitive connection with the implant and transmit the encrypted instruction to the implant. The third external device further comprises a receiver configured to receive the encrypted instructions from the second external device. The third external device communicates with the second external device using a wireless or wired communication channel.

In some embodiments the implant is configured to directly receive the encrypted instructions from the second external device, e.g. over a wireless communication channel such as a mobile network communication channel. To this end the implant comprise a receiver configured to receive the encrypted instructions transmitted from the second external device. The second external device may be a remote server or a cloud server.

The method may further comprise to, at the implant, running S115190 the instruction or performing the instruction. The running of the instruction may be performed by an internal computing unit or a processor comprised in the implant, and may, for example, cause the internal computing unit or processor to instruct an active unit of the implant to perform an action.

The method may further comprise verifying S115130, at the second external device, that the instructions are correct. The verifying may be performed as described above with reference to the system and FIG. 117.

The method may further comprise verifying S115180, at the implant, that the instructions are correct. The verifying may be performed as described above with reference to the system and FIG. 117.

The method may further comprise authenticating the connection between the first external device and the implant over which the encrypted instruction is to be transmitted. The authentication may be performed as described in any of aspects one through thirty.

Aspect 317SE Energy General
Microphone—Microphone Sensor—Embodiments
of Aspect 317SE of the Disclosure In aspect 317SE there is provided an implantable controller for controlling an implant based on registered microphone signals. Generally, aspect 316SE defines an implantable controller for controlling an energized implant, and a method for authenticating a method of authenticating an energized implant implanted in a patent.

Figures 18A, 18B, 18C:
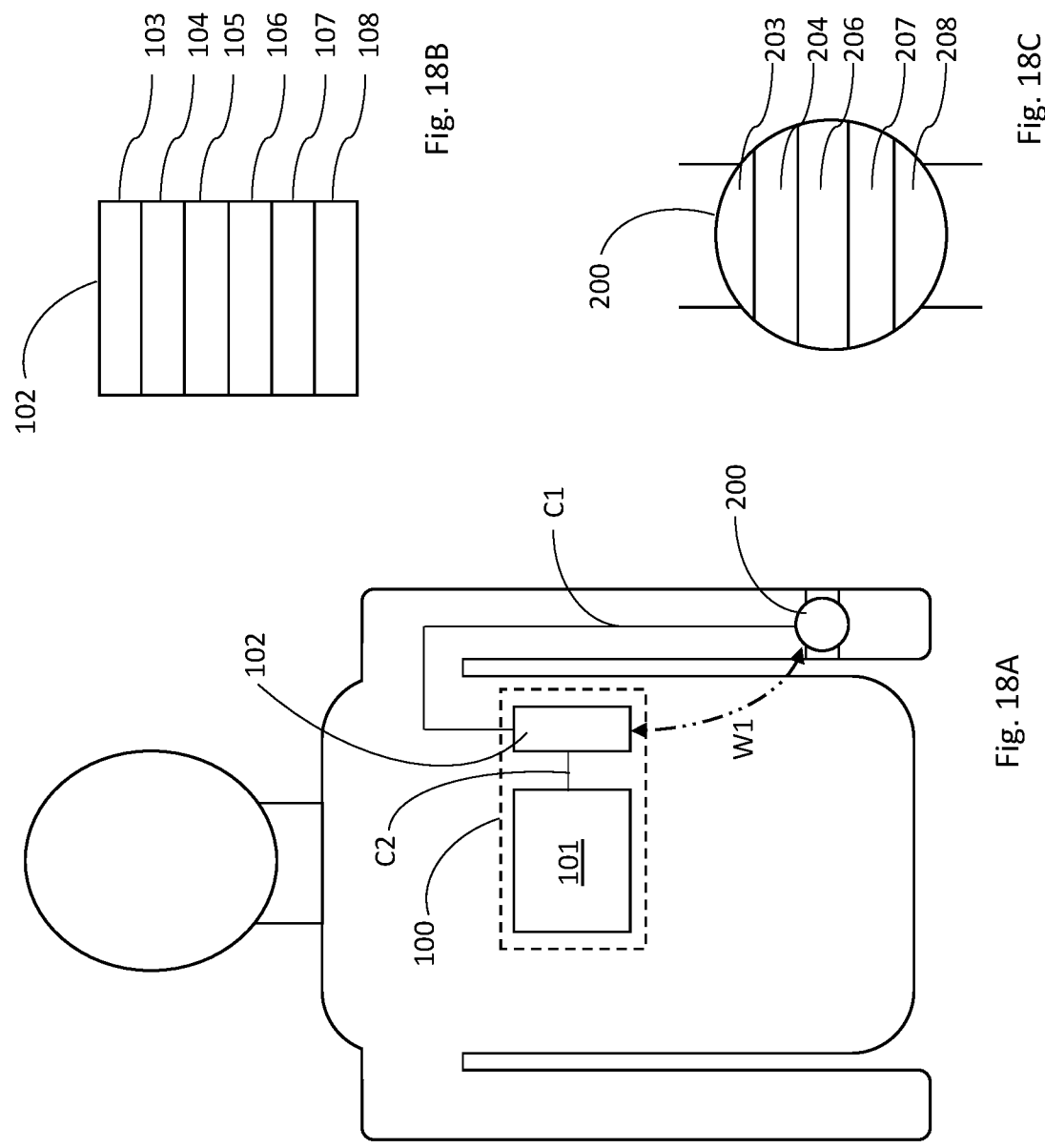
FIG. 18A illustrates a system comprising an implant, further illustrated in FIG. 18B, and an external device, further illustrated in FIG. 18C, all according to aspect 246SE.
Figure 19:
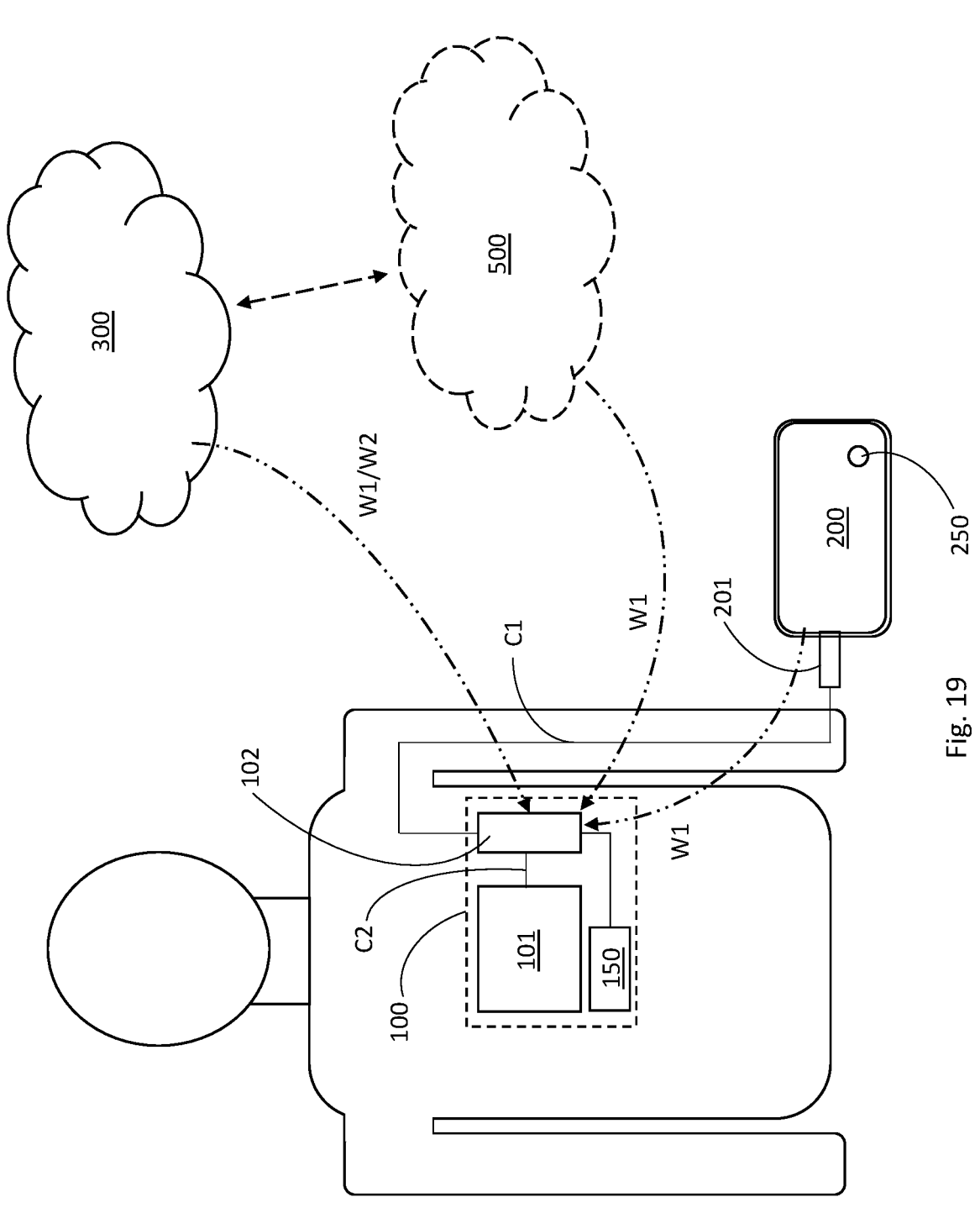
FIGS. 19-21 illustrate systems according to aspect 246SE comprising an implant in connection with an external device wherein either the implant or the external device is in connection with a second external device, third external device, or other external devices.
Figure 20:
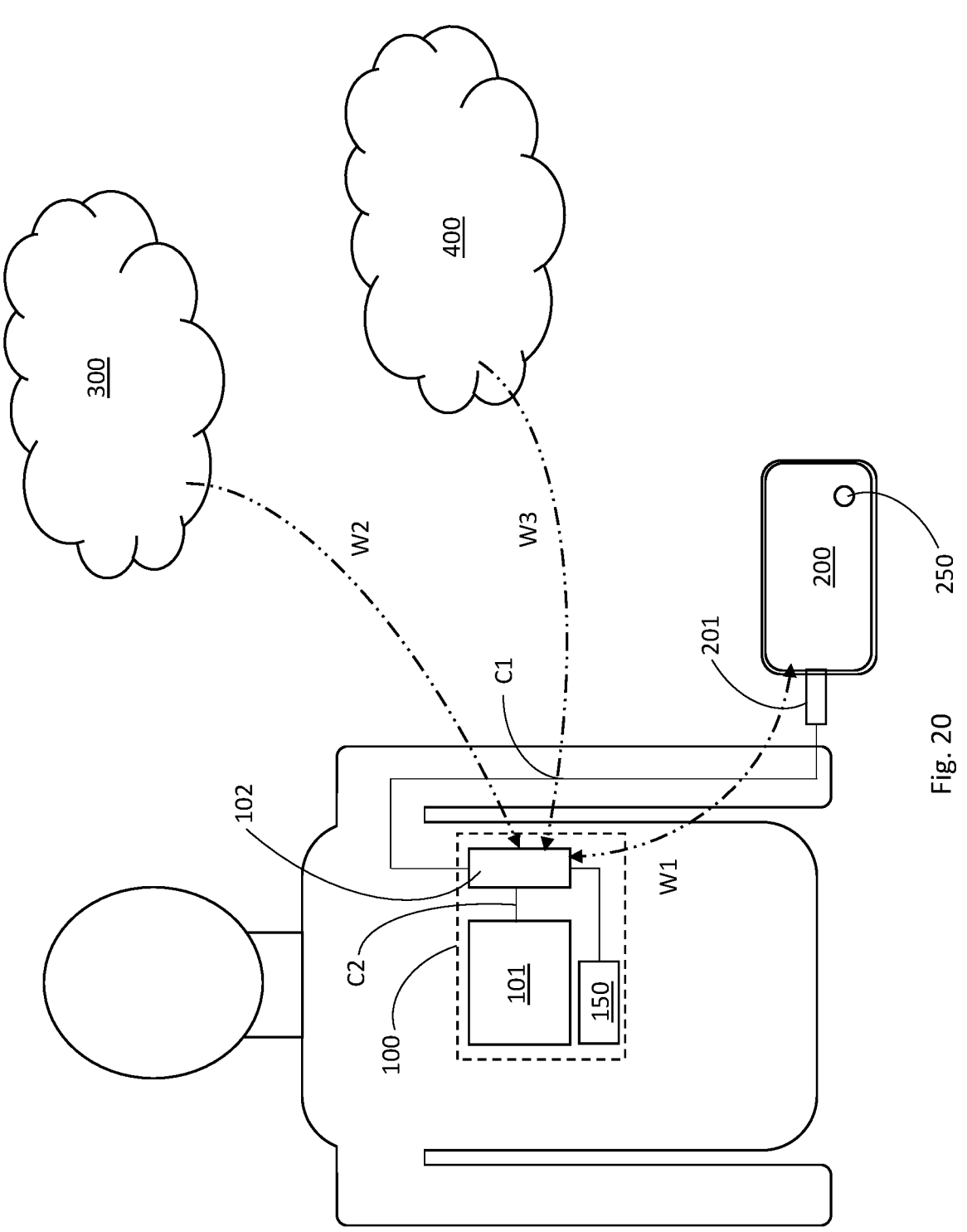
Figure 21:
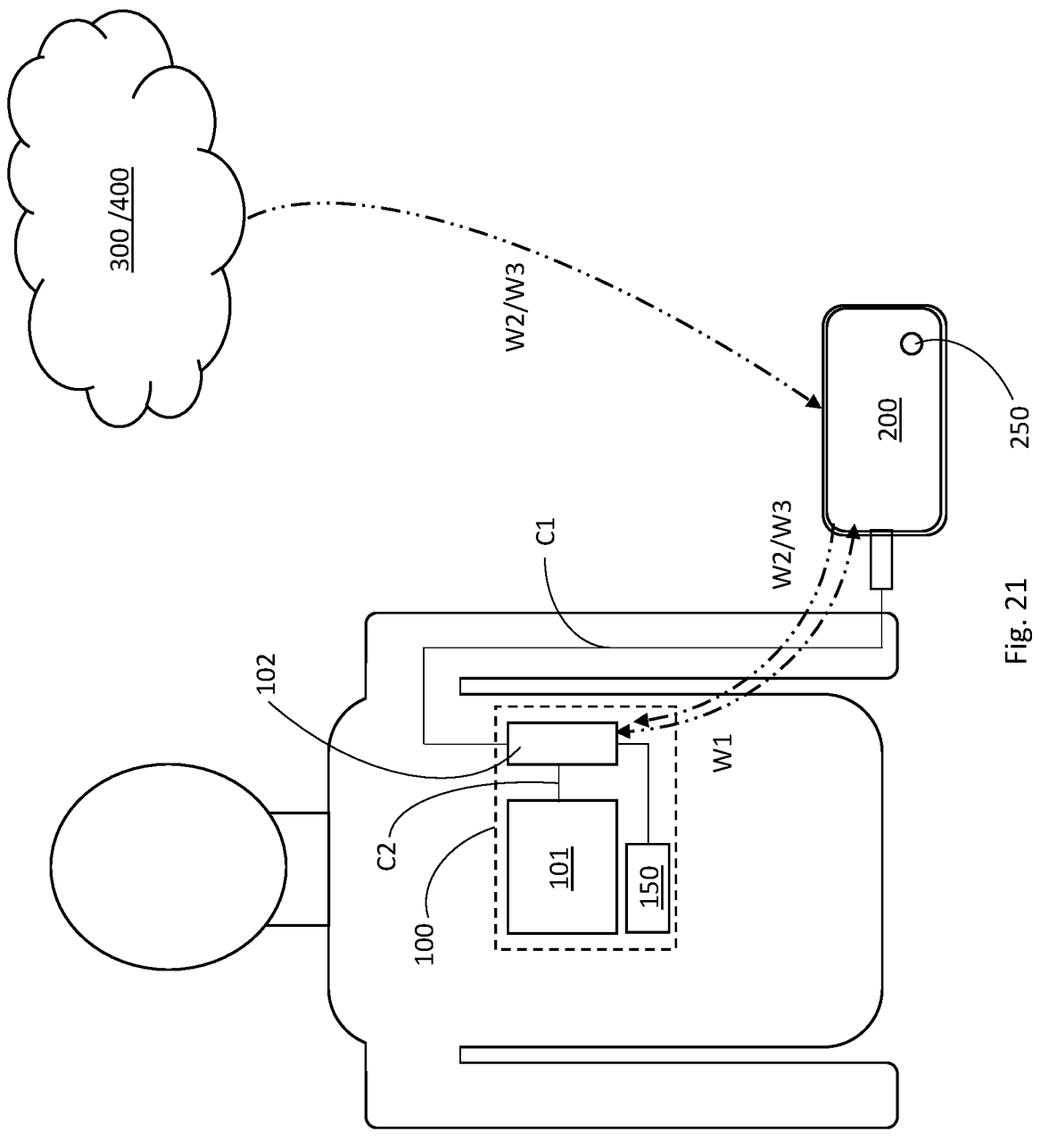

With reference to FIG. 18A. FIG. 18B and FIG. 19 there is provided a medical implant 100. The implantable controller may be connected to or comprised in the medical implant 100. The controller may comprise or be connected to a sensor 150 wherein the sensor 150 is at least one microphone sensor 150 configured to record acoustic signals. For instance, the controller may be configured to register a sound related to at least one of a bodily function of the patient and a function of the implant 100. The controller may further comprise or be in communication with a computing unit 106 wherein the computing unit 106 is configured to derive at least one of a pulse of the patient from the registered sound related to a bodily function, information related to the patient urinating from the registered sound related to a bodily function, information related to a bowel activity of the patient from the registered sound related to a bodily function, and information related to a functional status of the implant from the registered sound related to a function of the implant. To this end the computing unit 106 may be configured to perform signal processing on the registered sound (e.g. on a digital or analog signal representing the registered sound) so as to derive any of the above mentioned information related to a bodily function of the patient or a function of the implant 100. The signal processing may comprise filtering the registered sound signals of the microphone sensor 150.

The implantable controller may further comprise at least one implantable housing for scaling against fluid wherein the computing unit 106 and the microphone sensor 150 are placed inside of the housing. For instance, the implant 100 may comprise the controller and the microphone sensor 150 inside a implantable housing for scaling against fluid. Accordingly, at least the controller and the microphone sensor 150 does not come into contact with bodily fluids when implanted which ensures proper operation of the controller and the microphone sensor 150.

In some implementations, the computing unit 106 is configured to derive information related to the functional status of an operation device of the implant, from the registered sound related to a function of the implant. Accordingly, the computing unit 106 may be configured to derive information related to the functional status of at least one of: a motor, a pump and a transmission of the operation device of the implant from, the registered sound related to a function of the implant.

The controller may comprise a transceiver wherein the controller is configured to transmit a parameter derived from the sound registered by the at least one microphone sensor 150 using the transceiver. For example, the controller is provided externally of the implant 100 and transmits the derived parameter to the implant 100 or the controller is comprised in the implant 100 and the transceiver is a transceiver of a communication unit 102 of the implant 100 wherein communication unit 102 of the implant 100 is configured to transmit the parameter wirelessly or conductively to an external device 200 or wirelessly to a second external device 300.

Aspect 316SE further relates to a method of authenticating at least one of an energized implant implanted 100 in a patent, an external device 200 and a connection between the implant 100 and the external device. The method is performed in a system comprising the energized implant 100 and an external device 200, the energized implant 100 comprising at least one microphone sensor 150, and a transmitter, and the external device 200 comprising a receiver and a computing unit. The method comprising the steps of registering a sound related to at least one of a bodily function and a function of the implant 100, using the at least one microphone sensor 150, transmitting a signal derived from the registered sound, using the transmitter, receiving, in the external device, the signal derived from the registered sound, using the receiver, and comparing, in the external device 200, a parameter derived from the received signal with a reference parameter, using the computing unit. The registered sound may be related to the pulse of the patient. Based on the comparison at least one of an energized implant implanted 100 in a patent, an external device 200 and a connection between the implant 100 and the external device 200.

The aforementioned method is exemplified with further reference to FIG. 88 and FIG. 89. At S5602 a sound related to at least one of a bodily function and a function of the implant 100, using the at least one microphone sensor 150 is registered as a parameter. The method then goes to S5604b wherein a signal derived from the registered sound is transmitted to the external device 200 and compared to a reference parameter. Optionally, upon comparing the parameter derived from the received signal with a reference parameter at S5604b the method may go to S5605 involving authenticating at least one of an energized implant implanted 100 in a patent, an external device 200 and a connection between the implant 100 and the external device 200 on the basis of the comparison. For example, if the difference between the derived parameter and reference parameters is below a predetermined threshold or within an expected range of differences the energized implant 100 is authenticated. The method may further comprise the step of receiving at the receiver of the external device a parameter to be used as a reference parameter. For instance, the parameter may be received from a sensor external to the patient. Such as a pulse sensor, microphone or temperature sensor. In other words, aspect 317SE is similar to aspect 256SE wherein the sensed parameter is a registered sound.

Alternatively, the comparison of the parameter derived from the sound with the reference parameter may be performed by the computing unit 106 in the in the energized implant 100 as opposed to the in the computing unit of the external device 200. Accordingly, another method is provided wherein the method is a method of authenticating at least one of energized implant 100 implanted in a patent, an external device 200 and a connection between the implant 100 and the external device 200, performed in a system comprising the energized implant 100 and an external device 200, the energized implant 100 comprising at least one microphone, a receiver, and a computing unit 106, and the external device 200 comprising a transmitter. The method comprising the steps of registering a sound related to at least one of: a bodily function and a function of the implant 100, using the at least one microphone, deriving a parameter from the sound using the computing unit 106, receiving, in the energized implant 100, a reference parameter, from the external device 200, using the receiver, and comparing, in the energized implant 100, the parameter derived from the sound with the received reference parameter, using the computing unit 106. The registered sound may be related to a pulse of the patient wherein the reference parameter is related to the pulse of the patient and/or another bodily function of the patient. A sound related to at least one of a bodily function and a function of the implant 100, using the at least one microphone of the implant 100 is registered as a parameter at S5602. The method may then go to S5604 comprising receiving a reference parameter from the external device 200 at the implant 100 using the receiver of the implant 100 and comparing the parameter derived from the sound with the received reference parameter, using the computing unit 106 of the implant 100. The method may further comprise the step S5605 of authenticating the energized implant 100 and/or external device 200 and/or connection therebetween on the basis of the comparison performed in the computing unit 106 of the implant 100. For instance, if the comparison yields that the derived parameter and the reference parameter are similar the implant 100 may be authenticated. Additionally or alternatively, the method may further comprise receiving, at a receiver of the external device 200, a parameter to be used as reference parameter wherein the parameter is received form a sensor external to the patient. The sensor may be integrated with the external device 200 or provided separately from the external device.

The authentication of the external device is performed by the energized implant. i.e. the step of comparing two parameters for the purpose of authentication is performed by the computing unit of the energized implant.

The authentication of the communication may be performed by the energized implant or by the external device. i.e. the step of comparing two parameters for the purpose of authenticating the communication session may be performed by the computing unit of the energized implant or by the computing unit of the of the external device.

Aspect 318SE Energy Appetite Control
Microphone—Microphone Sensor for Appetite
Control—Embodiments of Aspect 318SE of the
Disclosure In aspect 318SE there is provided an implantable con-
troller for controlling an energized implant for stretching the
stomach wall of a patient to create satiety based on regis-
tered sound sensor signals. Generally, aspect 318SE defines
an implantable controller for controlling an energized
implant to create satiety, a system for controlling an ener-
gized implant for stretching the stomach wall of a patient to
create satiety and a method for controlling an energized
implant for stretching the stomach wall of a patient to create
satiety. With reference to FIG. 18A there is illustrated an
energized implant 100. The aforementioned implantable
controller may be comprised in the energized implant 100 or
provided externally and being configured to communicate
with energized implant 100. With further reference to FIG.
18B it is illustrated that the energized implant 100 may
further computing unit 106. The computing unit 106 may be
comprised in the controller.

With further reference to FIG. 19 it is illustrated that the
controller and/or implant 100 may comprise a sensor 150
wherein the sensor 150 in aspect 318SE is at least one
microphone sensor 150 configured to register a sound
related to the patient swallowing. The computing unit 106 is
configured to derive a parameter related to the patient
swallowing from the sound registered by the microphone
sensor 150. The computing unit 106 may be configured to
derive a parameter related to one or more of the size and/or
shape and/or viscosity of a swallowed contents. Additionally
or alternatively, the computing unit 106 is configured to
determine if a swallowed content is a liquid or a solid and/or
to determine an accumulated amount of swallowed content
over a time period. Accordingly, the stretching of the stom-
ach wall may be controlled depending on when and/or what
the patient is swallowing so as to e.g. create satiety when the
patient is eating or has eaten a predetermined threshold
amount of food.

For example, the computing unit 106 may be configured
to analyze acoustic properties of the registered sound so as
to derive a parameter according to the above. Wherein the
acoustic properties may comprise at least one of the fre-
quency content of the registered sound, the magnitude or
amplitude of the registered sound and the duration of the
registered sound.

In some implementations, the controller further comprises
and/or is in communication with a transmitter wherein the
controller is configured to transmit the parameter derived
from the sound registered by the at least one microphone
sensor 150 using the transmitter. The transmitter may be a
part of the communication unit 102 of an implant 100 which
comprises or is in communication with the controller. For
instance, the computing unit may be configured to transmit
the parameter derived from the registered sound to an
external device 200 using the transmitter. Additionally or
alternatively, the controller comprises and/or is on commu-
nication with a receiver wherein the controller is configured
to receive a signal from an external device. The receiver may
be a part of the communication unit 102 of an implant 100
which comprises or is in communication with the controller.
For instance, the computing unit 106 may be configured to
receive a control signal from an external device.

In some implementations the computing unit 106 is
further configured to generate a control signal for controlling
the energized implant 100 for stretching the stomach wall of a patient on the basis of at least one of the derived parameter
related to the patient swallowing, the signal received from
the external device 200, and a combination of the derived
parameter related to the patient swallowing and the signal
received from the external device 200. Accordingly, the
implant 100 may be controlled to stretch the stomach wall of
a patient so as to create satiety based on the derived
parameter related to the patient swallowing or the signal
received from the external device 200. That is, satiety may
be created based on the patient swallowing or the contents
which the patient swallows. Additionally or alternatively,
satiety is created based on a signal received from the
external device 200. For instance, the patient may input to
the external device 200 information associated with the
content which the patient is eating or the external device
may detect that the patient is eating wherein associated
information may be conveyed as a signal to the implantable
controller for controlling the stretching of the stomach wall.

Aspect 318SE further relates to a system for controlling
an energized implant 100 for stretching the stomach wall of
a patient to thereby create satiety, the system comprising an
implantable controller for controlling the energized implant
and an external device 200. The system further comprises at
least one microphone sensor 150 configured to register a
sound related to the patient swallowing, a computing unit
106 configured to derive a parameter related to the patient
swallowing from the registered sound, a transmitter config-
ured to transmit the derived parameter, a receiver configured
to receive control signals from the external device. Addi-
tionally, the system comprises the external device 200 which
comprises a receiver configured to receive a parameter
derived from a sound related to the patient swallowing, a
computing unit 106 configured to generate a control signal
on the basis of the received parameter, and a transmitter
configured to transmit the control signal to the implantable
controller for controlling the energized implant for stretch-
ing the stomach wall of a patient to thereby create satiety.

Accordingly, the external device 200 receives a derived
parameter and generates a control signal based on the
derived parameter, wherein the external device 200 trans-
mits control signal back to the implantable controller for
controlling the energized implant 100 according to gener-
ated control signals. The computing unit 106 in the external
device 200 may be configured to derive a parameter related
to the size and/or shape and/or viscosity of swallowed
contents and/or to determine if a swallowed content is a
liquid or a solid on the basis of the received parameter.

The computing unit 106 of the external device 200 may be
configured to determine an accumulated amount of swal-
lowed content over a time period and the computing unit
may further be configured to generate the control signal on
the basis of the accumulated amount of swallowed content
over a time period. For instance, for larger accumulated
amounts of swallowed contents the stretching of the stomach
wall is increased so as to increase the level of satiety.

Aspect 318SE further relates to a method in an implant-
able controller for controlling an energized implant 100 for
stretching the stomach wall of a patient to thereby create
satiety, when implanted in a patient, the implantable con-
troller comprises at least one microphone sensor 150 and a
computing unit 106. The method comprises the steps of
registering a sound related to the patient swallowing, using
the at least one microphone and deriving a parameter related
to the patient swallowing from the sound, using the com-
puting unit. Any structural features described in relation to
the at least one microphone, controller or computing unit,
may have the corresponding steps in this method. It is noted that aspect 318SE relates to all possible combinations of features recited in the embodiments, e.g. the method may comprise the step of controlling the energized implant 100 for stretching the stomach wall of a patient, using the computing unit, on the basis of at least one of the derived parameter related to the patient swallowing, the signal received from the external device, and a combination of the derived parameter related to the patient swallowing and the signal received from the external device 200.

Aspect 318SE further relates to a method of authenticating at least one of an implantable controller for controlling an energized implant 100 for stretching the stomach wall of a patient to create satiety, an external device 200, and a connection between the implant 100 and the externa device 200. The method is performed in a system comprising the energized implant 100 and an external device 200, the energized implant 100 comprising at least one microphone, and a transmitter, and the external device 200 comprising a receiver and a computing unit. The method comprises the steps of registering a sound related to the patient swallowing, using the at least one microphone 150, and transmitting a signal derived from the registered sound, using the transmitter, receiving, in the external device 200, the signal derived from the registered sound, using the receiver, and comparing, in the external device 200, a parameter derived from the received signal with a reference parameter, using the computing unit. With further reference to FIG. 88 and FIG. 89 the at least one microphone is used to register a sound related to the patient swallowing at S5602 and at S5604*b* the signal is transmitted to the external device 200 wherein the external device 200 compares a parameter derived from the received signal with a reference parameter at S5604. The method may optionally comprise the further step S5605 of authenticating the energized implant 100 on the basis of the comparison. For instance, if the difference between the parameter derived from the received signal and the reference parameter is below a predetermined threshold the at least one of the energized implant 100, external device 200 and connection between the energized implant 100 and external device 200 is authenticated.

Additionally or alternatively the method may further comprise receiving, at a receiver of the external device 200, a parameter to be used as reference parameter wherein the parameter may be received form a sensor external to the patient. The sensor may be integrated with the external device 200 or provided separately from the external device. The step of receiving the parameter from a sensor external to the patient may comprise receiving the parameter from a sensor configured to sense the patient swallowing. Wherein this external sensor is separate from the at least one microphone of the controller. The step of receiving a parameter to be used as reference parameter at the external device 200 may comprise receiving input from the patient. For instance, the patient may input to the external device 200 information indicating whether or not the patient is eating and optionally whether the food is fluid or solid. Accordingly, the implant 100, external device 200 or connection therebetween may be authenticated based on the at least one microphone of the controller determining that the patient is swallowing content corresponding to the reference parameter received at the external device 200.

Aspect 318SE relates at least partially to sensing that the patient is swallowing (e.g. the amount of the matter the patient is swallowing and whether the swallowed matter is fluid or solid) using at least one microphone sensor 150 implanted in the patient. It is understood that the registered sound which is associated with the patient swallowing may be used for device synchronization and/or authentication analogously to the parameters of aspect 248SE and 256SE. The patient swallowing may also be used as sensation in aspect 258SE.

The authentication of the external device is performed by the energized implant, i.e. the step of comparing two parameters for the purpose of authentication is performed by the computing unit of the energized implant.

The authentication of the communication may be performed by the energized implant or by the external device. i.e. the step of comparing two parameters for the purpose of authenticating the communication session may be performed by the computing unit of the energized implant or by the computing unit of the of the external device.

Aspects 396-403 Communication System

Figure 119A:
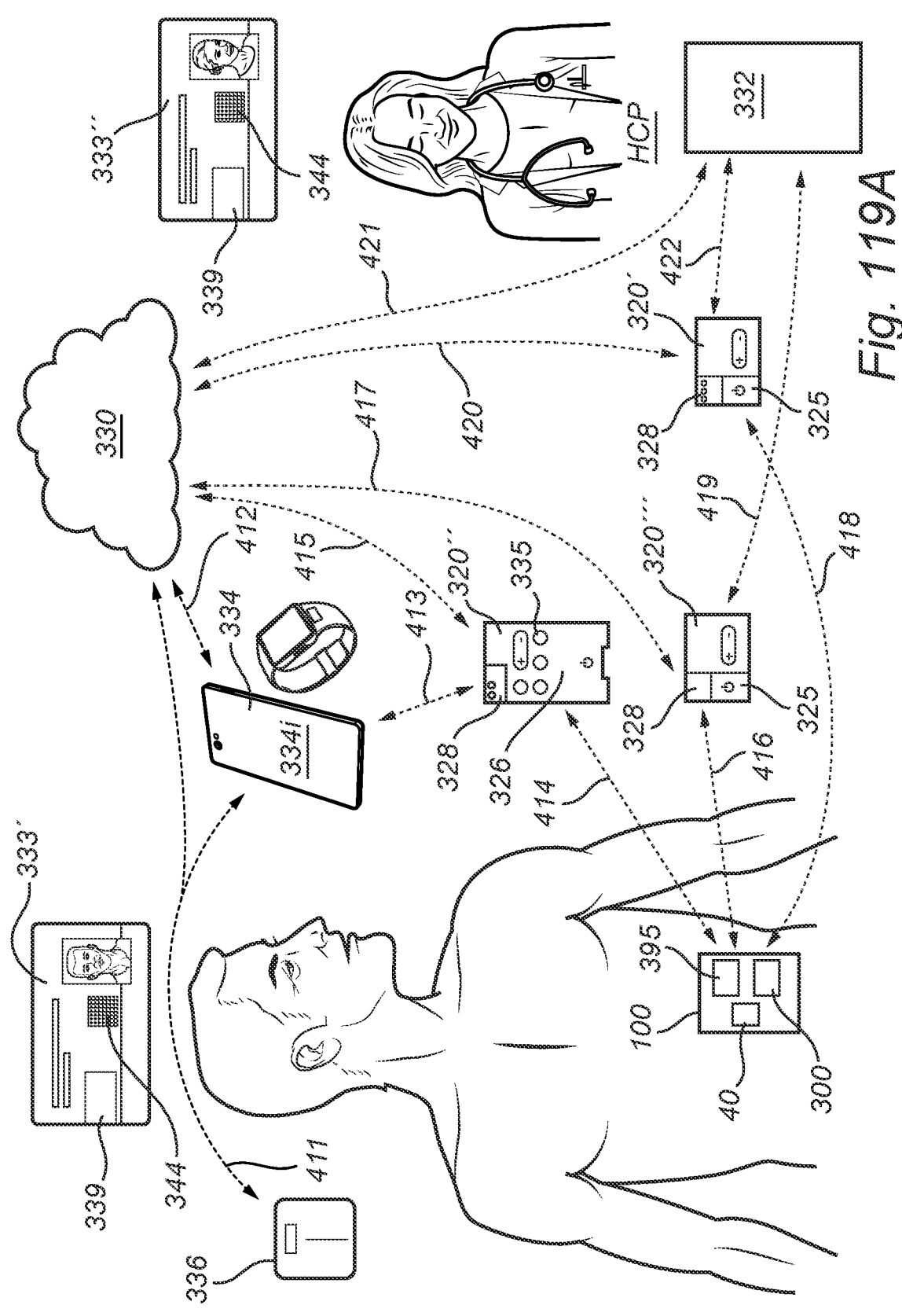
FIG. 119A, 119AA, 119B-119H shows embodiments and describes various functions of an implantable controller for controlling the implantable medical device/implant and a system for communication between different external devices.
Figure 119A:
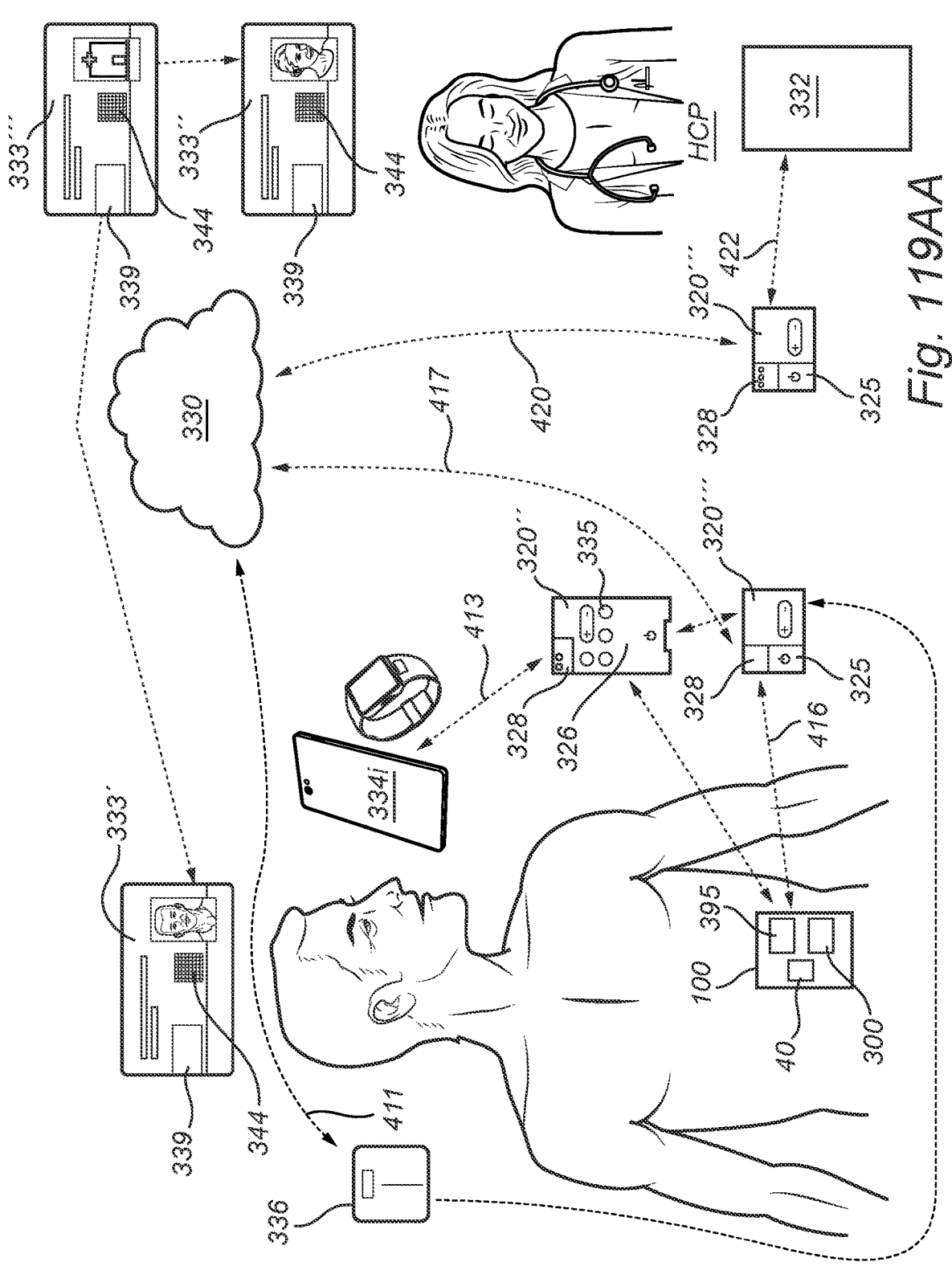

FIG. 119A and FIG. 119AA shows one embodiment of a system for charging, programming and communicating with the controller 300 of the implanted medical device 100. FIGS. 119A and 119AA further describes the communication and interaction between different external devices which may be devices held and operated by the patient, by the health care provider (HCP) or by the Dedicated Data Infrastructure (DDI), which is an infrastructure supplier for example by the manufacturer of the implanted medical device 100 or the external devices 320',320",320'''. The system of the embodiment of FIGS. 119A and 119AA comprises three external devices 320',320",320''' capable of communicating with the controller 300. The basic idea is to ensure the security of the communication with, and the operation of, the medical device 100 by having three external devices 320',320",320''' with different levels of authority. The lowest level of authority is given to the patient operated remote control 320". The remote control external device 320" is authorized to operate functions of the implanted medical device 100 via the implanted controller 300, on the basis of patient input. The remote control 320" is further authorized to fetch some necessary data from the controller 300. The remote control 320" is only capable of operating the controller 300 by communicating with the software currently running on the controller 300, with the currently settings of the software. The next level of authority is given to the Patient External Interrogation Device (P-EID) 320''', which is a charging and communication unit which is held by the patient but is partially remotely operated by the Health Care Provider (HCP) (Usually a medical doctor with the clinic providing the treatment with help of the implanted medical device 100). The P-EID 320''' is authorized to make setting changes by selecting pre-programmed steps of the software or hardware running on the controller 300 of the implanted medical device 100. The P-EID is remotely operated by the HCP, and receives input from the HCP, via the DDI. The highest level of authority is given to the HCP-EID 320' and its controller the HCP Dedicated Display Device (DDD). The HCP-EID 320' is a charging and communication unit which is held by the HCP physically at the clinic of the HCP. The HCP-EID 320' is authorized to freely alter or replace the software running on the controller 300, when the patient is physically in the clinic of the HCP. The HCP-EID 320' is controlled by the HCP DDD, which either acts on a "webview" portal from the HCP-EID or is a device closed down to any activities (which may include the absence of an internet connection) other than controlling and communicating with the HCP-EID. The webview portal does not necessarily mean internet based or HTML-protocol and the webview portal may be communicated over other communicating protocols such as Bluetooth or any other type of standard or proprietary protocol. The HCP DDD may also communicate with the HCP-EID over a local network or via Bluetooth or other standard or proprietary protocols.

Starting from the lowest level of authority, the patient remote control external device 320" comprises a wireless transceiver 328 for communicating with the implanted medical device 100. The remote control 320" is capable of controlling the operation of the implanted medical device 100 via the controller 300, by controlling pre-set functions of the implantable medical device 100, e.g. for operating an active portion of the implanted medical device 100 for performing the intended function of the implanted medical device 100. The remote control 320" is able communicate with implanted medical device 100 using any standard or proprietary protocol designed for the purpose. In the embodiment shown in FIGS. 119A and 119AA, the wireless transceiver 328 comprises a Bluetooth (BT) transceiver, and the remote control 320" is configured to communicate with implanted medical device 100 using BT. In an alternative configuration, the remote control 320" communicates with the implanted medical device 100 using a combination of Ultra-Wide Band (UWB) wireless communication and BT. The use of UWB technology enables positioning of the remote control 320" which can be used by the implanted medical device 100 as a way to establish that the remote control 320" is at a position which the implanted medical device 100 and/or the patient can acknowledge as being correct, e.g. in the direct proximity to the medical device 100 and/or the patient, such as within reach of the patient and/or within 1 or 2 meters of the implanted medical device 100.

UWB communication is performed by the generation of radio energy at specific time intervals and occupying a large bandwidth, thus enabling pulse-position or time modulation. The information can also be modulated on UWB signals (pulses) by encoding the polarity of the pulse, its amplitude and/or by using orthogonal pulses. A UWB radio system can be used to determine the "time of flight" of the transmission at various frequencies. This helps overcome multipath propagation, since some of the frequencies have a line-of-sight trajectory, while other indirect paths have longer delay. With a cooperative symmetric two-way metering technique, distances can be measured to high resolution and accuracy. UWB is useful for real-time location systems, and its precision capabilities and low power make it well-suited for radio-frequency-sensitive environments, such as health care environments.

In embodiments in which a combination of BT and UWB technology is used, the UWB technology may be used for location-based authentication of the remote control 320", whereas the communication and/or data transfer could take place using BT or any other way of communicating different from the UWB. The UWB signal could in some embodiments also be used as a wake-up signal for the controller 300, or for the BT transceiver, such that the BT transceiver in the implanted medical device 100 can be turned off when not in use, which eliminates the risk that the BT is intercepted, or that the controller 300 of the implanted medical device 100 is hacked by means of BT communication. In embodiments in which a BT (or alternatives)/UWB combination is used, the UWB connection may be used also for the transmission of data. In the alternative, the UWB connection could be used for the transmission of some portions of the data, such as sensitive portions of the data, or for the transmission of keys for the unlocking of encrypted communication sent over BT.

The remote control 320" comprises computing unit 326 which runs a software application for communicating with the implanted medical device 100. The computing unit 326 can receive input directly from control buttons 335 arranged on the remote control 320" or may receive input from a control interface 334*i* displayed on a patient display device 334 operated by the patient. In the embodiments in which the remote control 320" receives input from a control interface 334*i* displayed on the patient display device 334 operated by the patient, the remote control 320" transmits the control interface 334*i* in the form of a web-view portal. i.e. a remote interface that run in a sandbox environment on the patient's display device 334. A sandbox environment means that it runs on the display device 334 but only displays what is presented from the remote control and can only use a tightly controlled set of commands and resources, such as storage and memory space as well as network access, the ability to inspect the host system and read or write from other input devices connected to the display device 334 is extremely limited. Any action or command generated by the patient display device is like controlling a webpage. All acting software is located on the remote control that only displays its control interface onto the patient display unit. The computing unit 326 is further configured to encrypt the control interface before transmission to the patient display device 334, and encrypt the control commands before transmission to the implanted medical device 100. The computing unit 326 is further configured to transform the received user input into control commands for wireless transmission to the implantable medical device 100.

The patient's display device 334 could for example be a mobile phone, a tablet or a smart watch. In the embodiment shown in FIGS. 119A and 119AA, the patient's display device 334 communicates with the remote control 320" by means of BT. The control interface 334*i* in the form of a web-view portal is transmitted from the remote control 320" to the patient's display device 334 over BT. Control commands in the form of inputs from the patient to the control interface 334*i* is transmitted from the patient's display device 334 to the remote control 320", providing input to the remote control 320" equivalent to the input that may be provided using the control buttons 335. The control commands created in the patient's display device 334 is encrypted in the patient's display device 334 and transmitted to the remote control 320' using BT or any other communication protocol.

The remote control is normally not connected to the DDI or the Internet to increase security. In addition, the remote control 320" may in one embodiment have its own private key and in a specific embodiment the remote control 320" is activated by the patient's private key for a certain time period. This may activate the function of the patient's display device and the remote wed-view display portal supplied by the remote control to the patient's display device.

The patient's private key is supplied in a patient private key device compromising a smartcard that may be inserted or provided close to the remote control 320" to activate a permission to communicate with the implant 100 for a certain time period.

The patient's display device 334 may (in the case of the display device 334 being a mobile phone or tablet) comprise auxiliary radio transmitters for providing auxiliary radio connection, such as Wi-Fi or mobile connectivity (e.g. according to the 3G, 4G or 5G standards). The auxiliary radio connection(s) may have to be disconnected to enable communication with the remote control 320''. Disconnecting the auxiliary radio connections reduces the risk that the integrity of the control interface 334i displayed on the patient's display device 334 is compromised, or that the control interface 334i displayed on the patient's display device 334 is remote controlled by an unauthorized device.

In alternative embodiments, control commands are generated and encrypted by the patient's display device and transmitted to the DDI 330. The DDI 330 could either alter the created control commands to commands readable by the remote control 320'' before further encrypting the control commands for transmission to the remote control 320'' or could simply add an extra layer of encryption before transmitting the control commands to the remote control 320'', or could simply act as a router for relaying the control commands from the patients' display device 334 to the remote control 320''. It is also conceivable that the DDI 330 adds a layer of end-to-end encryption directed at the implanted medical device 100, such that only the implanted medical device 100 can decrypt the control commands to perform the commands intended by the patient. In the embodiments above, when the patient remote display device 334 is communicating with the DDI, the patient's display device 334 may be configured to only display and interact with a web-view portal provided by a section of the DDI and it is conceivable that the web-view portal is a view of a back-end provided on the DDI 330, and in such embodiments, the patient interacting with the control interface on the patient's display device 334 is equivalent to the patient interacting with an area of the DDI 330.

The patient's display device 334 could have a first and second application related to the implanted medical device 100. The first application is the control application displaying the control interface 334i for control of the implanted medical device 100, whereas the second application is a general application for providing the patient with general information of the status of the implanted medical device 100 or information from the DDI 330 or HCP, or for providing an interface for the patient to provide general input to the DDI 330 or HCP related to the general wellbeing of the patient, the lifestyle of the patient or related to general input from the patient concerning the function of the implanted medical device 100. The second application, which do not provide input to the remote control 320'' and/or the implanted medical device 100 thus handles data which is less sensitive. As such, the general application could be configured to function also when all auxiliary radio connections are activated, whereas switching to the control application which handles the more sensitive control commands and communication with the implanted medical device 100 could require that the auxiliary radio connections are temporarily de-activated. It is also conceivable that the control application is a sub-application running within the general application, in which case the activation of the control application as a sub-application in the general application could require the temporary de-activation of auxiliary radio connections. In the embodiment shown in FIG. 119A, access to the control application requires the use of the optical and/or NFC means of the hardware key 333' in combination with biometric input to the patient's display device, whereas accessing the general application only requires biometric input to the patient's display device and/or a pin code. In the alternative, a two-factor authentication solution, such as a digital key in combination with a pin code could be used for accessing the general application and/or the control application.

In general, a hardware key is needed to activate the patient display device 334 for certain time period to control the web-view portal of the remote control 320'', displaying the control interface 334i for control of the implanted medical device 100.

In the embodiments in which the patients display device 334 is configured to only display and interact with a web-view provided by another unit in the system, it is conceivable that the web-view portal is a view of a back-end provided on the DDI 330, and in such embodiments, the patient interacting with the control interface on the patient's display device is equivalent to the patient interacting with an area of the DDI 330.

Moving now to the P-EID 320'''. The P-EID 320''' is an external device used by the patient, patient external device, which communicates with, and charges, the implanted medical device 100. The P-EID 320''' can be remotely controlled by the HCP to read information from the implanted medical device 100. The P-EID 320''' controls the operation of the implanted medical device 100, control the charging of the medical device 100, and adjusts the settings on the controller 300 of the implanted medical device 100 by changing pre-defined pre-programed steps and/or by the selection of pre-defined parameters within a defined range., e.g. Just as the remote control 320'', the P-EID 320''' could be configured to communicate with the implanted medical device 100 using BT or UWB communication or any other proprietary or standard communication method. Since the device may be used for charging the implant, the charging signal and communication could be combined. Just as with the remote control 320'', it is also conceivable to use a combination of UWB wireless communication and BT for enabling positioning of the P-EID 320'' as a way to establish that the P-EID 320'' is at a position which the implanted medical device 100 and/or patient and/or HCP can acknowledge as being correct, e.g. in the direct proximity to the correct patient and/or the correct medical device 100. Just as for the remote control 320'', in embodiments in which a combination of BT and UWB technology is used, the UWB technology may be used for location-based authentication of the P-EID 320'', whereas the communication and/or data transfer could take place using BT. The P-EID 320'' comprises a wireless transmitter/transceiver 328 for communication and also comprises a wireless transmitter 325 configured for transferring energy wirelessly, which may be in the form of a magnetic field or any other signal such as electromagnetic, radio, light, sound or any other type of signal to transfer energy wirelessly to a wireless receiver 395 of the implanted medical device 100. The wireless receiver 395 of the implanted medical device 100 is configured to receive the energy in the form of the magnetic field and transform the energy into electric energy for storage in an implanted energy storage unit 40, and/or for consumption in an energy consuming part of the implanted medical device 100 (such as the operation device, controller 300 etc.). The magnetic field generated in the P-EID 320''' and received in the implanted medical device 100 is denoted charging signal. In addition to enabling the wireless transfer of energy from the P-EID 320''' to the implanted medical implant 100, the charging signal may also function as a means of communication. E.g., variations in the frequency of the transmission, and/or the amplitude of the signal may be uses as signaling means for enabling communication in one direction, from the P-EID 320''' to the implanted medical device 100, or in both directions between the P-EID 320''' and the implanted medical device 100. The charging signal in the embodiment shown in FIG. 119A is a signal in the range 10 65 kHz or 115-140 kHz. and the communication follow a proprietary communication signaling protocol. i.e., it is not based on an open standard. In alternative embodiments. BT could be combined with communication using the charging signal, or communication using the charging signal could be combined with an UWB signal. The energy signal could also be used as a carrying signal for the communication signal.

Just as for the remote control 320", the UWB signal could in some embodiments also be used as a wake-up signal for the controller 300, or for the BT transceiver, such that the BT transceiver in the implanted medical device 100 can be turned off when not in use, which eliminates the risk that the BT is intercepted, or that the controller 300 of the implanted medical device 100 is hacked by means of BT communication. In the alternative, the charging signal could be used as a wakeup signal for the BT, as the charging signal does not travel very far. Also, as a means of location-based authentication, the effect of the charging signal or the RSSI could be assessed by the controller 300 in the implanted medical device 100 to establish that the transmitter is within a defined range. In the BT/UWB combination, the UWB may be used also for transmission of data. In some embodiments, the UWB and/or the charging signal could be used for the transmission of some portions of the data, such as sensitive portions of the data, or for the transmission keys for unlocking encrypted communication sent by BT. Wake-up could be performed with any other signal.

UWB could also be used for waking up the charging signal transmission, to start the wireless transfer of energy or for initiating communication using the charging signal. As the signal for transferring energy has a very high effect in relation to normal radio communication signals, the signal for transferring energy cannot be active all the time, as this signal may be hazardous e.g., by generating heat.

The P-EID 320''' communicates with the HCP over the Internet by means of a secure communication, such as over a VPN. The communication between the HCP and the P-EID 320''' is preferably encrypted. Preferably, the communication is sent via the DDI, which may only be relying the information. The communication from the HCP to the implanted medical device 100 may be performed using an end-to-end encryption, in which case the communication cannot be decrypted by the P-EID 320'''. In such embodiments, the P-EID 320''' acts as a router, only passing on encrypted communication from the HCP to the controller 300 of the implanted medical device 100 (without full decryption). This solution further increases security as the keys for decrypting the information rests only with the HCP and with the implanted medical device 100, which reduces the risk that an unencrypted signal is intercepted by an unauthorized device. The P-EID 320''' may add own encryption or information, specifically for security reasons. The P-EID 320''' may hold its own private key and may be allowed to communicate with the implant 100 based on confirmation from the patient's private key, which may be provided as a smartcard to be inserted in a slot of the P-EID 320''' or hold in close proximity thereto to be read by the P-EID 320'''. These two keys will add a high level of security to the performed communication between the Implant 100 and the P-EID 320''' since the patient's hardware key in this example on the smartcard may activate and thereby allow the communication and action taken in relation to the implant. The P-EID 320''' may as previously described change the treatment setting of the implant by selecting pre-programmed steps of the treatment possibilities. Such pre-programmed treatment options may include for example to change:

at least one of the position, frequency and level of compression of an implanted heart compression device, the flow of an apparatus assisting the pump function of a heart of the patient, the flow of an apparatus assisting the pump function comprising a turbine bump placed within a patient's blood vessel for assisting the pump function of the heart, the function of an operable artificial heart valve, at least one of the function of, the valve opening pressure and time for closure of an operable artificial heart valve for increasing the blood flow to the coronary arteries. at least one of the functions of, the amount and/or concentration of a drug from an implantable drug delivery device, at least one of the injection site and frequency as well as amount of drug delivered by an implantable drug delivery device for injecting directly into a blood vessel and change the position of the injection site, all from within the patient's body, at least one of the injection site and frequency as well as amount of drug delivered by an implantable drug delivery device for injecting potency enhancing drugs into an erectile tissue of the patient, at least one of the level of constriction, pressure or position of a hydraulic, mechanic, and/or electric constriction implant, the volume of an operable volume filling device, the constriction of an operable gastric band, at least one of the level and time of stretching and when such stretching occur in relation to food intake of a patient for an operable implant for stretching the stomach wall of the patient for creating satiety, when an action should be taken relating to an implant configured to sense the amount of food intake based on number of times a patient swallows solid food, at least one of the size and shape of an operable cosmetic implant, at least one of the shape and size in the breast region of a patient of an operable cosmetic implant for adjustment, at least one of pressure, volume, sensor input or time of an implant controlling medical device for the emptying of a urinary bladder, at least one of the closing pressure, the time to close after urinating, how much extra pressure would be allowed at exercise of an implant hindering urinary leakage, at least one of the closing pressure, the time to close after revealing, how much extra pressure would be allowed at exercise of an implant hindering anal incontinence, parameters of an implant controlling the emptying of fecal matter, such as pressure, volume, pump or motor position etc., parameters of an implant monitoring an aneurysm, such as pressure, aneurysm expansion, volume, reservoir volume, etc., parameters of an implant for hindering the expansion of an aneurysm, such as pressure, aneurysm expansion, volume, reservoir volume, etc., parameters of an implant lubricating a joint, such as volume, reservoir volume, etc., parameters of an implant for affecting the blood flow to an erectile tissue of the patient, such as the level of constriction, pressure or position of a hydraulic, mechanic, and/or electric constriction implant, parameters of an implant for simulating the engorgement of an erectile tissue, such as the level of stimulation, frequency, or amplitude of an electrical stimulation, parameters of an implant with a reservoir for holding bodily fluids, such as volume, reservoir volume, etc., parameters of an implant storing and/or emptying a bodily reservoir or a surgically created reservoir, such as stimulation parameters in a peristaltic wave, stretch or bending sensors, reservoir volume, etc., parameters of an implant communicating with a database outside the body, such as key handshake, new key pairing, signal amplitude etc., parameters of an implant able to be programmed from outside the body, parameters of an implant able to be programmed from outside the body with a wireless signal, parameters of an implant treating impotence, such as pressure, amount of drug delivered, time for erection period etc., parameters of an implant controlling the flow of eggs in the uterine tube, such as the level of constriction, time period, position of a hydraulic, mechanic, and/or electric constriction implant, parameters of an implant controlling the flow of sperms in the uterine tube, such as the level of stimulation, frequency, or amplitude of an electrical stimulation, parameters of an implant controlling the flow of sperms in the vas deferens, such as the level of constriction, time period, position of a hydraulic, mechanic, and/or electric constriction implant, parameters of an implant for hindering the transportation of the sperm in the vas deferens, such as the level of constriction, time period, position of a hydraulic, mechanic, and/or electric constriction implant, parameters of an implant treating osteoarthritis, parameters of an implant performing a test of parameters inside the body, parameters of an implant controlling specific treatment parameters from inside the body, parameters of an implant controlling bodily parameters from inside the body, parameters of an implant controlling the blood pressure, parameters of an implant controlling the blood pressure by affecting the dilatation of the renal artery, such as heat and time period in relation to blood pressure, parameters of an implant controlling a drug treatment parameter, parameters of an implant controlling a parameter in the blood, parameters of an implant for adjusting or replacing any bone part of a body of the patient, parameters of an implant replacing an organ of the patient or part of an organ of the patient or the function thereof, parameters of a vascular treatment device, such as bending, expanding sensor, parameters of an implant adapted to move fluid inside the body of the patient, such as volume, pumping parameters, parameters of an implant configured to sense a parameter related to the patient swallowing, parameters of an implant configured to exercise a muscle with electrical or mechanical stimulation, such as stimulation parameters, amplitude frequency time period etc., parameters of an implant configured for emptying an intestine portion on command, such as electrical stimulation parameters, peristaltic wave adjustment etc., parameters of an operable implant configured to be invaginated in the stomach of the patient to reduce the volume of the stomach substantially more than the volume of the device, such as volume, parameters of an implant configured for emptying the urinary bladder from within the patient's body by compressing the bladder, such as pressure, volume and time parameters of an implant configured for draining fluid from within the patient's body.

parameters of an implant configured for the active lubrication of a joint with an added lubrication fluid, such as frequency and/or volume of the drug supplied, parameters of an implant configured for removing clots and particles from the patient's blood stream, parameters of an implant configured for elongating or straightening a bone in the patient, to reduce scoliosis, force, length etc., parameters of a device to stimulate the brain for a several position to a focused point, parameters of an artificial stomach replacing the function of the natural stomach, parameters of an implant configured for adjusting the position of a female's urinary tract or bladder neck, parameters of an implant configured for stimulating the ampulla vas deference and creating temporary constriction.

When the implanted medical device 100 is to be controlled and/or updated remotely by the HCP, via the P-EID 320''', a HCP Dedicated Device (DD) 332 displays an interface in which predefined program steps or setting values are presented to the HCP. The HCP provides input to the HCP DD 332 by selecting program steps, altering settings and/or values or by altering the order in which pre-defined program steps is to be executed. The instructions/parameters inputted into the HCP DD 332 for remote operation is in the embodiment shown in FIG. 119A routed to the P-EID 320''' via the DDI 330, which may or may not be able to decrypt/ read the instructions. The DDI 330 may store the instructions for a time period to later transfer the instructions in a package of created instructions to the P-EID 320'''. It is also conceivable that an additional layer of encryption is provided to the package by the DDI 330. The additional layer of encryption may be a layer of encryption to be decrypted by the P-EID 330, or a layer of encryption which may only be decrypted by the controller 300 of the implanted medical device 100, which reduces the risk that unencrypted instructions or packages are intercepted by unauthorized devices. The instructions/parameters are then provided to the P-EID 320'', which then loads the instructions/parameters into the during the next charging/energy transfer to the implanted medical device 100 using any of the signal transferring means (wireless or conductive) disclosed herein.

The Health Care Provider EID (HCP EID) 320' have the same features as the P-EID 320'' and can communicate with the implanted medical device 100 in the same alternative ways (and combinations of alternative ways) as the P-EID 320'''. However, in addition, the HCP EID 320' also enables the HCP to freely reprogram the controller 300 of the implanted medical device 100, including replacing the entire program code running in the controller 300. The idea is that the HCP EID 320' always remain with the HCP and as such, all updates to the program code or retrieval of data from the implanted medical device 100 using the HCP EID 320' is performed with the HCP and patient present (i.e. not remote). The physical presence of the HCP is an additional layer of security for these updates which may be critical to the function of the implanted medical device 100.

In the embodiment shown in FIG. 119A, the HCP communicates with the HCP EID 320' using a HCP Dedicated Display Device 332 (HCP DDD), which is a HCP display device comprising a control interface for controlling and communicating with the HCP EID 320'. As the HCP EID 320' always stays physically at the HCP's clinic, communication between the HCP EID 320' and HCP DDD 332 does not have to be sent over the Internet. Instead, the HCP DDD 332 and the HCP EID 320' can communicate using one or more of BT, a proprietary wireless communication channel, or a wired connection. The alteration to the programming is then sent to the implanted medical device 100 directly via the HCP EID 320'. Inputting into the HCP DDD 332 for direct operation by means of the HCP EID 320' is the same as inputting directly into the HCP EID 320', which then directly transfers the instructions into the implanted medical device 100.

In the embodiment shown in FIG. 119A, both the patient and the HCP has a combined hardware key 333',333". The combined keys 333',333" comprises a hardware component comprising a unique circuitry (providing the highest level of security), a wireless NFC-transmitter 339 for transmitting a specific code (providing mid-level security), and a printed QR-code 344 for optical recognition of the card (providing the lowest level of security). The HCP private key is supplied by a HCP private key device 333" adapted to be provided to the HCP EID external device via at least one of; a reading slot or comparable for the HCP private key device 333", an RFID communication or other close distance wireless activation communication to both the HCP EID 320' and the HCP DDD 332 if used. The HCP DDD 332 will be activated by such HCP private key device 333", which for example may comprise at least one of, a smartcard, a key-ring device, a watch an arm or wrist band a neckless or any shape device.

The HCP EID external device may comprise at least one of;

a reading slot or comparable for the HCP private key device.

an RFID communication and other close distance wireless activation communication means The HCP external device 320' may further comprise at least one wireless transceiver 328 configured for communication with a data infrastructure server. DDI, through a first network protocol.

A dedicated data infrastructure server, DDI, is in one embodiment adapted to receive commands from said HCP external device 320' and may be adapted to rely the received commands without opening said commands directed to the patient external device 320", the DDI 330 comprising one wireless transceiver configured for communication with said patient external device 320".

The patient EID external device 320" is in one embodiment adapted to receive the commands relayed by the DDI, and further adapted to send these commands to the implanted medical device 100, which is adapted to receive commands from the HCP. Health Care Provider, via the DDI 330 to change the pre-programmed treatment steps of the implanted medical device 100. The patient EID is adapted to be activated and authenticated and allowed to perform the commands by the patient providing a patient private key device 333'. The patient's private key device is in one embodiment adapted to be provided to the patient external device by the patient via at least one of; a reading slot or comparable for the patient private key device 333', an RFID communication or other close distance wireless activation communication.

The patient EID external device, in one or more embodiments, comprises at least one of;

a reading slot or comparable for the HCP private key device.

an RFID communication, or other close distance wireless activation communication The patient EID external device may in one or more embodiments comprise at least one wireless transceiver configured for communication with the implanted medical device through a second network protocol.

The patient's key 333' is in the embodiment shown in FIG. 119A in the form of a key card having an interface for communicating with the P-EID 320''', such that the key card could be inserted into a key card slot in the P-EID 320". The NFC-transmitter 339 and/or the printed QR-code 344 can be used as means for accessing the control interface 334i of the display device 334. In addition, the display device 334 may require a pin-code and/or a biometric input, such as face recognition or fingerprint recognition.

The HCP's key 333", in the embodiment shown in FIG. 119A is in the form of a key card having an interface for communicating with the HCP-EID 320', such that in one embodiment the key card could be inserted into a key card slot in the HCP-EID 320'. The NFC-transmitter 339 and/or the printed QR-code 344 can be used as means for accessing the control interface of the HCP DDD 332. In addition, the HCP DDD 332 may require a pin-code and/or a biometric input, such as face recognition or fingerprint recognition.

In alternative embodiments, it is however conceivable that the hardware key solution is replaced by a two-factor authentication solution, such as a digital key in combination with a PIN code or a biometric input (such as face recognition and/or fingerprint recognition). The key could also be a software key, holding similar advance key features, such as the Swedish Bank ID being a good example thereof.

In the embodiment shown in FIG. 119A, communication over the Internet takes place over a Dedicated Data Infrastructure (DDI) 330, running on a cloud service. The DDI 330 in this case handles communication between the HCP DDD 332 and the P-EID 320'''. however, the more likely scenario is that the HCP DDD 332 is closed down, such that only the necessary functions of the control application can function on the HCP DDD 332. In the closed down embodiment, the HCP DDD 332 is only able to give the necessary commands to HCP EID 320' to further update the pre-programmed treatment steps of the Implant 100 via the P-EID 320''' in direct contact, or more likely indirect contact via the DDI 332. If the patient is present locally, the HCP EID may communicate and act directly on the patient's implant. However, before anything is accepted by the implant, a patient private key device 333' has to be presented to the P EID 320''' or HCP EID 320' for maximum security.

The DDI 330 is logging information of the contact between the HCP and the remote control 320" via implant feedback data supplied from the implant to P-EID 320'''. Data generated between the HCP and the patient's display device 334, as well as between the HCP and auxiliary devices 336 (such as tools for following up the patient's treatments e.g. a scale in obesity treatment example or a blood pressure monitor in a blood pressure treatment example) are logged by the DDI 330. In some embodiments, although less likely, the HCP DDD 332 may also handle the communication between the patient's display device 334 and the remote control 320". In FIG. 119AA, the auxiliary devices 336 is connected to the P-EID as well and can thus provide input from the auxiliary devices 336 to the P-EID which can be used by the P-EID for altering the treatment or for follow up.

In all examples, the communication from the HCP to: the P-EID 320''', the remote control 320'', the patient's display device 334 and the auxiliary devices 336 may be performed using an end-to-end encryption. In embodiments with end-to-end encryption, the communication cannot be decrypted by the DDI 330. In such embodiments, the DDI 330 acts as a router, only passing on encrypted communication from the HCP to various devices. This solution further increases security as the keys for decrypting the information rests only with the HCP and with the device sending or receiving the communication, which reduces the risk that an unencrypted signal is intercepted by an unauthorized device. The P-EID 320''' may also only pass on encrypted information.

In addition to acting as an intermediary or router for communication, the DDI 330 collects data on the implanted medical device 100, on the treatment and on the patient. The data may be collected in an encrypted form, in an anonymized form or in an open form. The form of the collected data may depend on the sensitivity of the data or on the source from which the data is collected. In the embodiment shown in FIG. 119A, the DDI 330 sends a questionnaire to the patient's display device 334. The questionnaire could comprise questions to the patient related to the general health of the patient, related to the way of life of the patient, or related specifically to the treatment provided by the implanted medical device 100 (such as for example a visual analogue scale for measuring pain). The DDI 330 could compile and/or combine input from several sources and communicate the input to the HCP which could use the provided information to create instructions to the various devices to be sent back over the DDI 330. The data collection performed by the DDI 330 could also be in the form a log to make sure that all communication between the units in the system can be back traced. Logging the communication ensures that all alterations to software or the settings of the software, as well as the frequency and operation of the implanted medical device 100 can be followed. Following the communication enables the DDI 330 or the HCP to follow the treatment and react it something in the communication indicates that the treatment does not provide the intended results or if something appears to be wrong with any of the components in the system. If patient feedback from the patient display device 334 indicates that a new treatment step of the implant is needed, such information must be confirmed by direct contact between HCP and patient.

In the specific embodiment disclosed in FIG. 119A, the wireless connections between the different units are as follows. The wireless connection 411 between the auxiliary device 336 and the DDI 330 is based on WiFi or a mobile telecommunication regime or may be sent to the DDI 330 via the P-EID 320''' and the wireless connection 411 between the auxiliary device 336 and the patient's display device 334 is based on BT or any other communication pathway disclosed herein. The wireless connection 412 between the patient's display device 334 and the DDI 330 is based on WiFi or a mobile telecommunication regime. The wireless connection 413 between the patient's display device 334 and the remote control 320'' is based on BT or any other communication pathway disclosed herein. The wireless connection 414 between the patient remote control 320'' and the implanted medical device 100 is based on BT and UWB or any other communication pathway disclosed herein. The wireless connection 415 between the remote control 320'' and the DDI 330 is likely to not be used, and if present be based on WiFi or a mobile telecommunication regime. The wireless connection 416 between the P-EID 320''' and the implanted medical device 100 is based on BT. UWB and the charging signal or any other communication or energizing pathway disclosed herein. The wireless connection 417 between the P-EID 320''' and the DDI 330 is based on WiFi or a mobile telecommunication regime. The wireless connection 418 between the HCP-EID 320' and the implanted medical device 100 is based on at least one of the BT. UWB and the charging signal. The wireless connection 419 between the P-EID 320''' and the HCP DD 332 is based on BT or any other communication path disclosed herein. The wireless connection 420 between the HPC-EID 320' and the DDI 330 is based on WiFi or a mobile telecommunication regime. The wireless connection 421 between the HPC DD 332 and the DDI 330 is normally closed and not used and if so based on WiFi or a mobile telecommunication regime. The wireless connection 422 between the HCP-EID 320' and the HCP DD 332 is based on at least one of BT. UWB, local network or any other communication path disclosed herein.

The wireless connections specifically described in the embodiment shown in FIG. 119A may however be replaced or assisted by wireless connections based on radio frequency identification (RFID), near field communication (NFC), Bluetooth, Bluetooth low energy (BLE), or wireless local area network (WLAN). The mobile telecommunication regimes may for example be 1G, 2G, 3G, 4G, or 5G. The wireless connections may further be based on modulation techniques such as amplitude modulation (AM), frequency modulation (FM), phase modulation (PM), or quadrature amplitude modulation (QAM). The wireless connection may further feature technologies such as time-division multiple access (TDMA), frequency-division multiple access (FDMA), or code-division multiple access (CDMA). The wireless connection may also be based on infra-red (IR) communication. The wireless connection may feature radio frequencies in the high frequency band (HF), very-high frequency band (VHF), and the ultra-high frequency band (UHF) as well as essentially any other applicable band for electromagnetic wave communication. The wireless connection may also be based on ultrasound communication to name at least one example that does not rely on electromagnetic waves.

FIG. 119AA also discloses a master private key 333''' device that allow issuance of new private key device wherein the HCP or HCP admin have such master private key 333''' device adapted to be able to replace and pair a new patient private key 333' device or HCP private key device 333'' into the system, through the HCP EID external device 320''.

A system configured for changing pre-programmed treatment settings of an implantable medical device, when implanted in a patient, from a distant remote location in relation to the patient, the system comprising:

FIG. 119AA also discloses a scenario in which at least one health care provider. HCP, external device 320' is adapted to receive a command from the HCP to change said preprogrammed treatment settings of an implanted medical device 100, further adapted to be activated and authenticated and allowed to perform said command by the HCP providing a HCP private key device 333''. The HCP EID external device 320' further comprising at least one wireless transceiver 328 configured for communication with a patient EID external device 320''', through a first network protocol. The system comprises the patient EID external device 320''', the patient EID external 320''' device being adapted to receive command from said HCP external device 320', and to relay the received command without modifying said command to the implanted medical device 100. The patient EID external device 320''' comprising one wireless transceiver 328. The patient EID 320''' is adapted to send the command to the implanted medical device 100, to receive a command from the HCP to change said pre-programmed treatment settings of the implanted medical device 100, and further to be activated and authenticated and allowed to perform said command by the patient providing a patient private key 333' device comprising a patient private key.

Although wireless transfer is primarily described in the embodiment disclosed with reference to FIGS. 119A, 119AA the wireless communication between any of the external device may be substituted for wired communication. Also, some or all of the wireless communication between an external device and the implanted medical device 100 may be substituted for conductive communication using a portion of the human body as conductor.

Figure 119B:
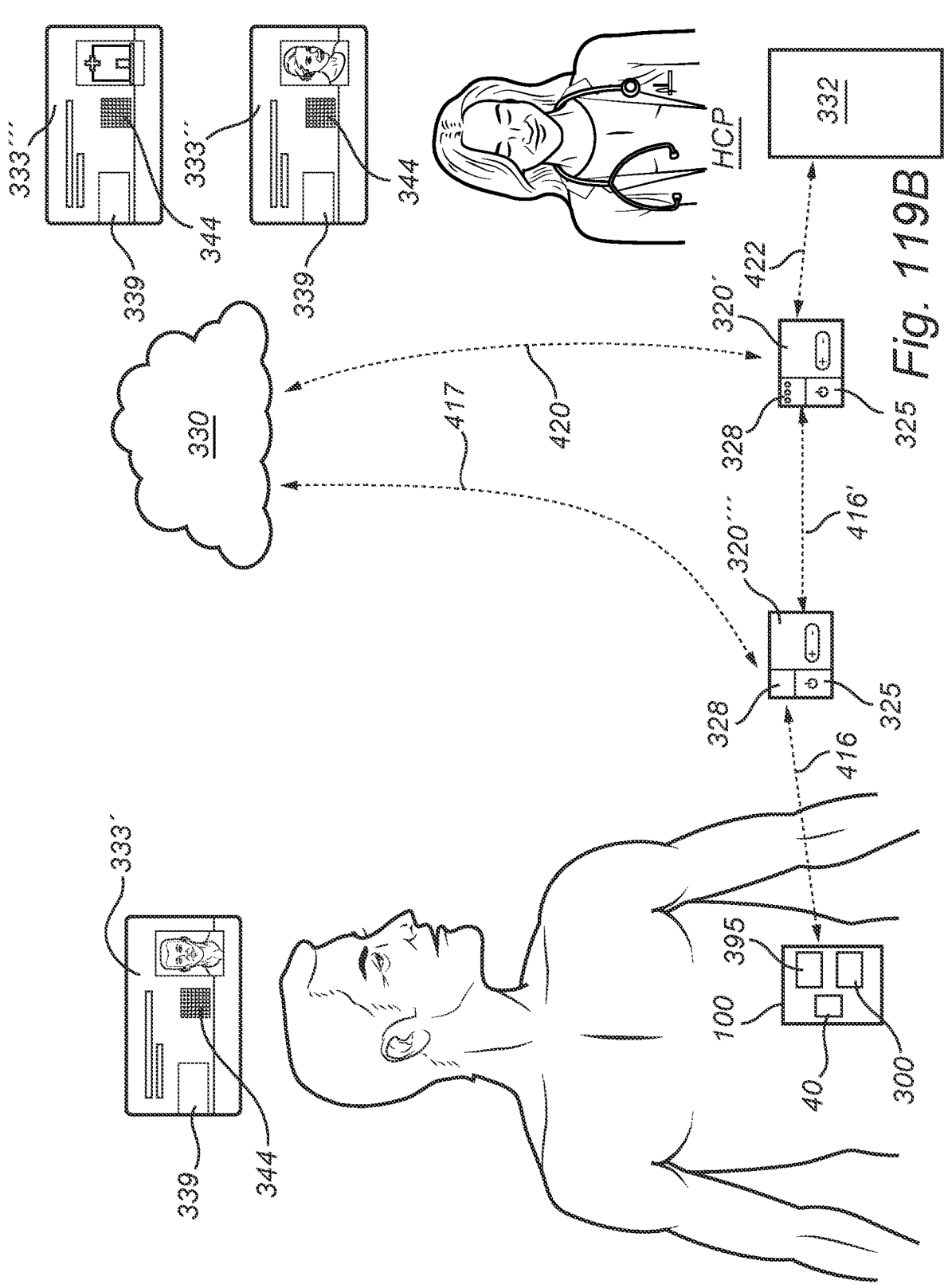

FIG. 119B shows a portion of FIG. 119A, in which some of the components have been omitted to outline a specific scenario. In the scenario outlined in FIG. 119B, the system is configured for changing pre-programmed treatment settings of an implantable medical device 100, when implanted in a patient, from a distant remote location in relation to the patient. The system if FIG. 119B comprises at least one HCP EID 320' external device adapted to receive commands from the HCP to change said pre-programmed treatment settings of an implanted medical device 100. The HCP EID 320' external device is further adapted to be activated and authenticated and allowed to perform said command by the HCP providing a HCP private key device 333" adapted to be provided to the HCP EID external device 320'. The private key device 333" is adapted to be provided to the HCP EID external device 320' via at least one of: a reading slot or comparable for the HCP private key device 333", and an RFID communication or other close distance wireless activation communication. The HCP EID external device 320' comprises at least one of: a reading slot or comparable for the HCP private key device 333", an RFID communication, and other close distance wireless activation communication or electrical direct contact. The HCP EID external device 320' further comprises at least one wireless transceiver 328 configured for communication with a dedicated data infrastructure server (DDI) 330, through a first network protocol. The system further comprises a dedicated data infrastructure server (DDI) 330, adapted to receive command from said HCP EID external device 320', adapted to relay the received commands without modifying said command to a patient EID external device 320'''. The dedicated data infrastructure server (DDI) 330 further comprises a wireless transceiver 328 configured for communication with said patient external device. The system further comprises a patient EID external device 320''' adapted to receive the command relayed by the dedicated data infrastructure server (DDI) 330 and further adapted to send commands to the implanted medical device 100 and further adapted to receive commands from the HCP EID external device 320' via the dedicated data infrastructure server (DDI) 330 to change said pre-programmed treatment settings of the implanted medical device 100. The patient EID external device 320''', and further adapted to be activated and authenticated and allowed to perform said command by the patient providing a patient private key device 333' adapted to be provided to the patient EID external device 320''' by the patient via at least one of: a reading slot or comparable for the patient private key device

333', an RFID communication or other close distance wireless activation communication or electrical direct contact. The patient EID external device 320''' further comprises at least one of: a reading slot or comparable for the HCP private key device, an RFID communication and other close distance wireless activation communication or electrical direct contact. The patient EID external device 320''' further comprises at least one wireless transceiver 328 configured for communication with the implanted medical device 100 through a second network protocol. The implanted medical device 100 is in turn configured to treat the patient or perform a bodily function.

FIG. 119B further shows a scenario in which the external system comprises a first external device in the form of the HCP EID external device 320' and a second external device in the form of patient EID external device 320'''. The HCP EID external device 320' and the patient EID external device 320''' have a wireless or wired connection 416' to each other and external system is configured for providing remote instructions to the implantable medical device 100. The HCP EID external device 320' or the patient EID external device 320''' is configured to, derive a checksum from the instructions that will be sent to the implant and electronically sign the instructions and the checksum using at least one of a patient private key device 333' or a HCP private key device 333'''. The HCP EID external device 320' or the patient EID external device 320''' is then configured to form a data packet from the instructions, the electronic signature and the checksum. In the embodiment shown in FIG. 19b, the patient EID external device 320''' comprises a wireless transmitter configured to wirelessly send the data packet to the implantable medical device 100. The HCP EID external device 320' or the patient EID external device 320''' may further be configured encrypt the data packet prior to transmission. If the HCP EID external device 320' creates and signed the instructions, the patient EID external device 320''' may be configured to transmit the data packet wirelessly to the implantable medical device without changing the data packet and/or without full decryption of the data packet. In the embodiment shown in FIG. 19b, the patient private key and the HCP private key are placed on a patient private key device 333' and a HCP private key device 333'''. However, the patient private key and the HCP private key may be placed directly on the HCP EID external device 320' or the patient EID external device 320'''. Either way, the patient private key and the HCP private key may be placed on the EIDs or the key devices by the manufacturers and may be placed on the EIDs or the key devices in the form of software or hardware. The key may be a non-extractable key.

In the example when the HCP EID external device 320' communicates directly with the patient EID external device 320''', the external system is configured to function without connection to the Internet which greatly reduces the risk that the system is hacked. As the system is not connected to the Internet, the system cannot depend on a synchronized time e.g. for time-out of log-in functionality. As such, the external system is configured to communicate with the implantable medical device 100 independently of time. The authentication and verification may thus be based entirely on the possession of keys. In an alternative embodiment, the log-in of signing functionality offered by the key devices 333", 333''' may be complemented or replaced by an input button on one or both of the HCP EID external device 320' or the patient EID external device 320''', configured to be used for verifying user presence. I.e., a user presses the input button on request from the HCP EID external device 320' or the patient EID external device 320''' and thereby verifies presence.

The implantable medical device 100 is in this embodiment configured to receive remote instructions from the external system by a wireless receiver configured to receive wirelessly transmitted data packets from the external system, i.e. the HCP EID external device 320' or the patient EID external device 320'''. The implantable medical device 100 is configured to: verify the electronic signature, and use a checksum provided in the data packet to verify the integrity of the instructions.

A verification query operation may further be built into the external system or between the external system and the implantable medical device 100. The verification query operation comprising: transmitting, from the HCP EID external device 320', the patient EID external device 320''', or the implantable medical device 100, a query comprising a computational challenge to at least one other of the HCP EID external device 320', the patient EID external device 320''', or the implantable medical device 100 and receiving, at the first or second external devices, a response based on the transmitted computational challenge, and verifying at the HCP EID external device 320', the patient EID external device 320''', or the implantable medical device 100, the received response. The verification query operation may be in the form of a proof of possession operation comprising: receiving a public key, the public key being associated with a private key, transmitting a computational challenge to the first or second key device, based on the public key received from the first or second key device, receiving a response from the first or second key device based on the possession of the private key in the first or second key device, and verifying that the response based on the possession of the private key matches the query based on a public key. The verification query operation may also be performed between one of the HCP EID external device 320' or the patient EID external device 320''' and one of the first and second key devices.

In an alternative authentication or verification method for providing remote instructions from the external system to the implantable medical device 100, the implantable medical device comprises a list of codes and the external system comprises a list of codes. The method comprising encrypting the instructions at the external system using a code from a position on the list of codes, wirelessly sending the encrypted instructions to the implantable medical device, and decrypting, at the implantable medical device, the instructions using a code from a position on the list of codes. The same authentication or verification method may be used for authentication or verification or s signature applied to a communication which may comprise at least one instruction.

The scenario described with reference to FIG. 119B may in alternative embodiments be complemented with additional units or communication connections, or combined with any of the scenarios described with reference to FIGS. 119C-119E.

Figure 119C:
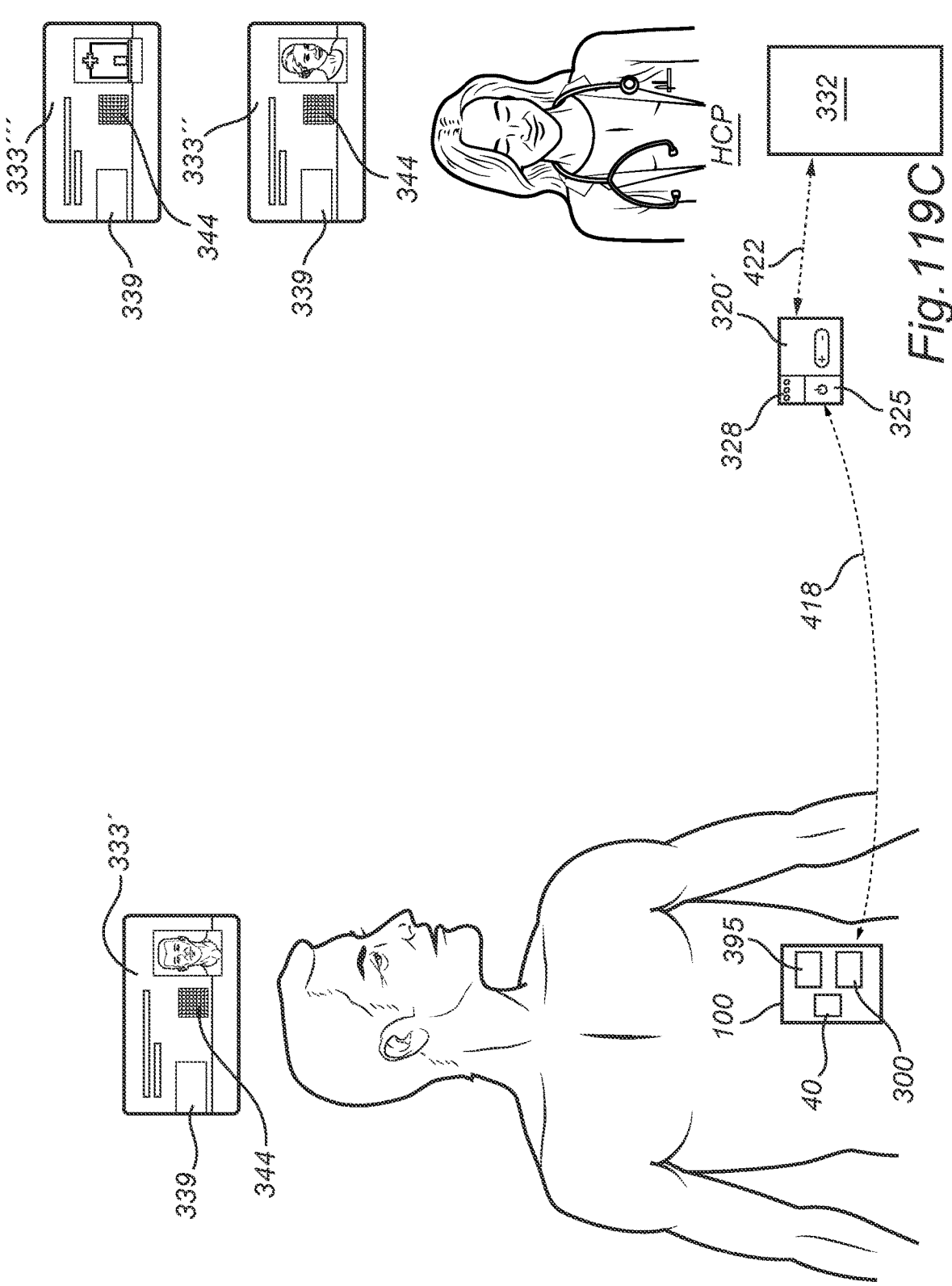

FIG. 119C shows a portion of FIG. 119A, in which some of the components have been omitted to outline a specific scenario. In the scenario outlined in FIG. 119C, system configured for changing pre-programmed treatment settings of an implantable medical device 100 is disclosed. The changing pre-programmed treatment settings are performed by a health care provider (HCP) in the physical presence of the patient. The system comprises at least one HCP EID external device 320' adapted to receive commands from the HCP, directly or indirectly, to change said pre-programmed treatment settings in steps of an implantable medical device 100, when implanted. The HCP EID external device 320' is further adapted to be activated, authenticated, and allowed to perform said command by the HCP providing a HCP private key device 333'' comprising a HCP private key. The HCP private key device in the embodiment of FIG. 119C, comprises at least one of: a smart card, a keyring device, a watch, an arm or wrist band, a necklace, and any shaped device. The HCP EID external device 320' is adapted to be involved in at least one of: receiving information from the implant 100, receiving information from a patient remote external device 336, actuating the implanted medical device 100, changing pre-programmed settings, and updating software of the implantable medical device 100, when implanted. The HCP EID external device 320' is adapted to be activated, authenticated, and allowed to perform said command also by the patient, the system comprises a patient private key device 333' comprising a patient private key. The patient private key device 333' comprising at least one of: a smart card, a keyring device, a watch, an arm or wrist band, a necklace, and any shaped device. The HCP private key 333'' and the patients private key are required for performing said actions by the HCP EID external device 320' to at least one of: receive information from the implant 100, to receive information from a patient remote external device 336, to actuate the implanted medical device 100, to change pre-programmed settings, and to update software of the implantable medical device 100, when the implantable medical device is implanted.

FIG. 19c also outlines a scenario in which the system is configured for changing pre-programmed treatment settings in steps of an implantable medical device, when implanted in a patient, by a health care provider. HCP, with the patient on remote on distance, the system comprising: at least one HCP EID external device 320' adapted to receive a command from the HCP direct or indirect, to change said pre-programmed treatment settings in steps of an implantable medical device, when implanted, wherein the HCP EID external device 320' is further adapted to be activated, authenticated, and allowed to perform said command by the HCP. The said action by the HCP EID external device 320' to change pre-programmed settings in the implant 100 and to update software of the implantable medical device 100, when the implantable medical device 100 is implanted, is adapted to be authenticated by a HCP private key device 333'' and a patient private key device 333'.

The scenario described with reference to FIG. 119C may in alternative embodiments be complemented with additional units or communication connections, or combined with any of the scenarios described with reference to FIG. 119B, or 119D-119E.

Figure 119D:
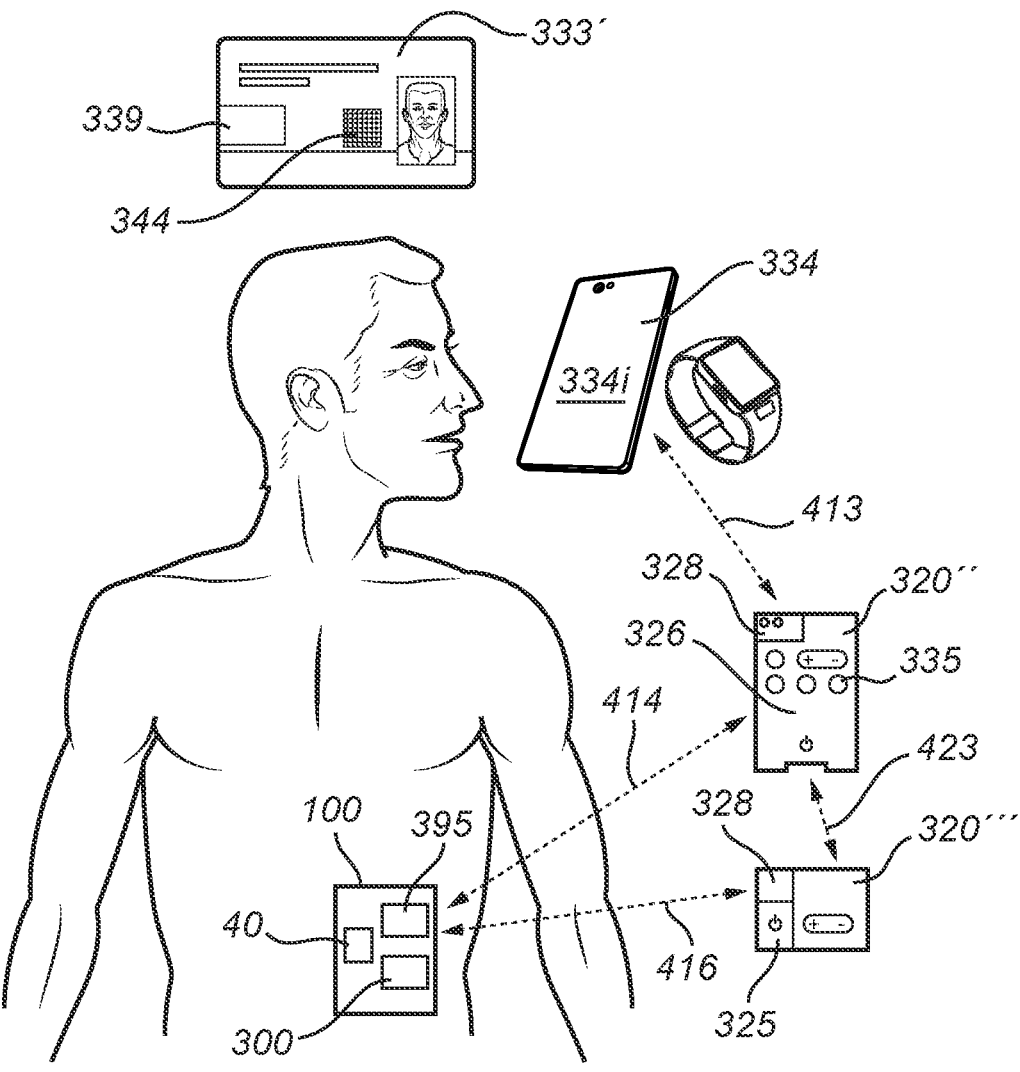

FIG. 119D shows a portion of FIG. 119A, in which some of the components have been omitted to outline a specific scenario. In the scenario outlined in FIG. 119D, a system configured to change pre-programmed and pre-selected treatment actions of an implantable medical device 100 by command from the patient is described. The system comprises an implantable medical device 100, a patient remote external device 320'', and a wireless transceiver 328 configured for communication with the implantable medical device 100, when the medical device is implanted, through a second network protocol. The system further comprises a remote display portal interface 334i configured to receive content delivered from the patient remote external device 320'' to expose buttons to express the will to actuate the functions of the implanted medical device 100 by the patient through the patient remote external device 320''. The remote external device 320" is further configured to present the display portal remotely on a patient display device 334 allowing the patient to actuate the functions of the implanted medical device 100 through the display portal of the patient remote external device 320" visualised on the patient display device 334. In FIG. 119D, a further wireless connection 423 between the patient remote external device 320" and the patient EID external device 320''' is provided. This further wireless connection 423 could be a wireless connection according to any one of the wireless signaling methods and protocols described herein, and the communication can be encrypted.

The scenario described with reference to FIG. 119D may in alternative embodiments be complemented with additional units or communication connections, or combined with any of the scenarios described with reference to FIG. 119B, 119C, or 119E.

Figure 119E:
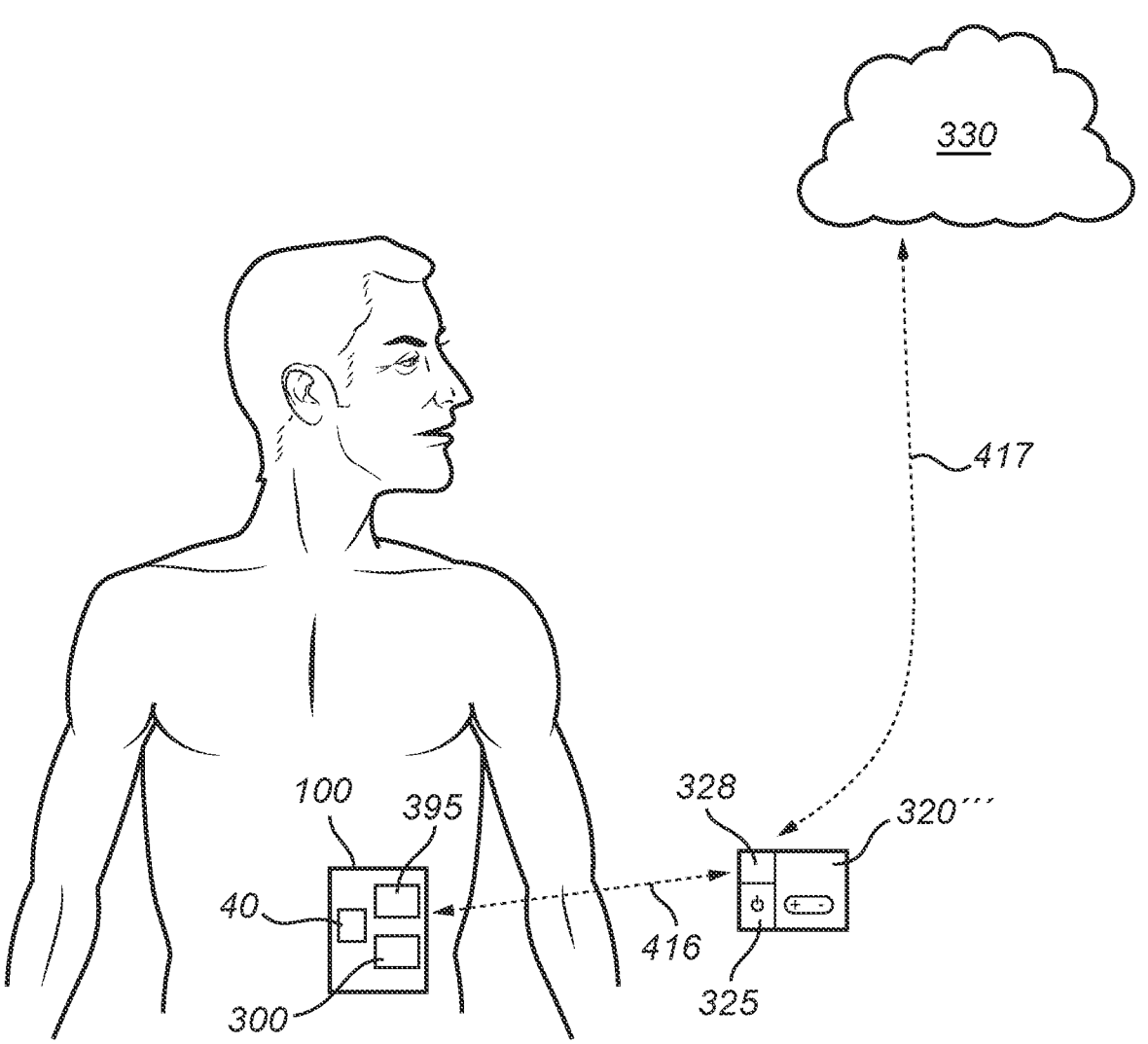

FIG. 119E shows a portion of FIG. 119A, in which some of the components have been omitted to outline a specific scenario. In the scenario outlined in FIG. 119E, a system configured for providing information from an implantable medical device 100, when implanted in a patient, from a distant remote location in relation to the patient is described. The system comprises at least one patient EID external device 320''' adapted to receive information from the implant 100, and adapted to send such information further on to a server or dedicated data infrastructure, DDI, 330. The patient EID external device 320''' is further adapted to be activated and authenticated and allowed to receive said information from the implanted medical device 100 by the patient providing a private key. The patient private key device comprises the private key adapted to be provided to the patient EID external device 320''' via at least one of; a reading slot or comparable for the patient private key device, an RFID communication or other close distance wireless activation communication or direct electrical connection. The patient EID external device 320''' comprises at least one of: a reading slot or comparable for the patient private key device, an RFID communication and other close distance wireless activation communication or direct electrical contact. The patient EID external device 320''' further comprises at least one wireless transceiver 328 configured for communication with the DDI 330, through a first network protocol.

The scenario described with reference to FIG. 119E may in alternative embodiments be complemented with additional units or communication connections, or combined with any of the scenarios described with reference to FIGS. 119B-119D.

Figure 119F:
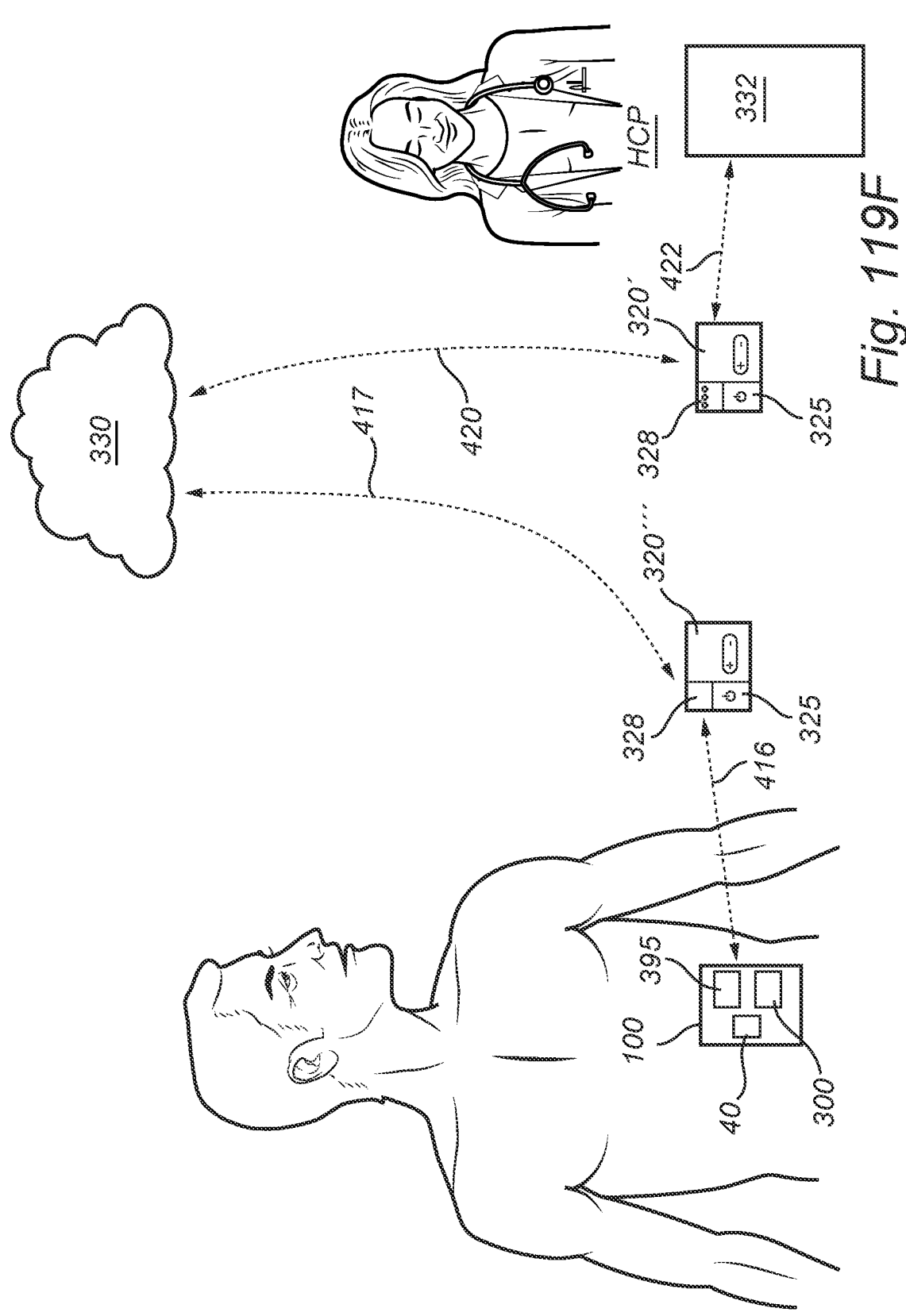

FIG. 119F shows a portion of FIG. 119A, in which some of the components have been omitted to outline a specific scenario. In the scenario outlined in FIG. 119F a system configured for changing pre-programmed treatment settings in steps of an implantable medical device 100, when implanted in a patient, by a health care provider, HCP, either in the physical presence of the patient or remotely with the patient on distance is described. The system comprising at least one HCP EID external device 320" adapted to receive a command directly or indirectly from the HCP to change said pre-programmed treatment settings in steps of the implantable medical device 100, when implanted, wherein the HCP EID external device 320' is further adapted to be activated, authenticated, and allowed to perform said command by the HCP providing a HCP private key device comprising a HCP private key, comprising at least one of: a smart card, a keyring device, a watch, a arm or wrist band, a necklace, and any shaped device. The system further comprises a patient private key device comprising a patient private key comprising at least one of: a smart card, a keyring device, a watch, a arm or wrist band, a necklace, and any shaped device. Both the HCP and patient private key is required for performing said action by the HCP EID external device 320' to change the pre-programmed settings in the implant 100 and to update software of the implantable medical device 100, when the implantable medical device 100 is implanted. The patient private key is adapted to activate, be authenticated, and allowed to perform said command provided by the HCP, either via the HCP EID external device or when the action is performed remotely via a patient EID external device 320'. In the embodiment shown in FIG. 119F, the communication is routed over the DDI server 330.

The scenario described with reference to FIG. 119F may in alternative embodiments be complemented with additional units or communication connections, or combined with any of the scenarios described with reference to FIGS. 119B-119E.

Figure 119G:
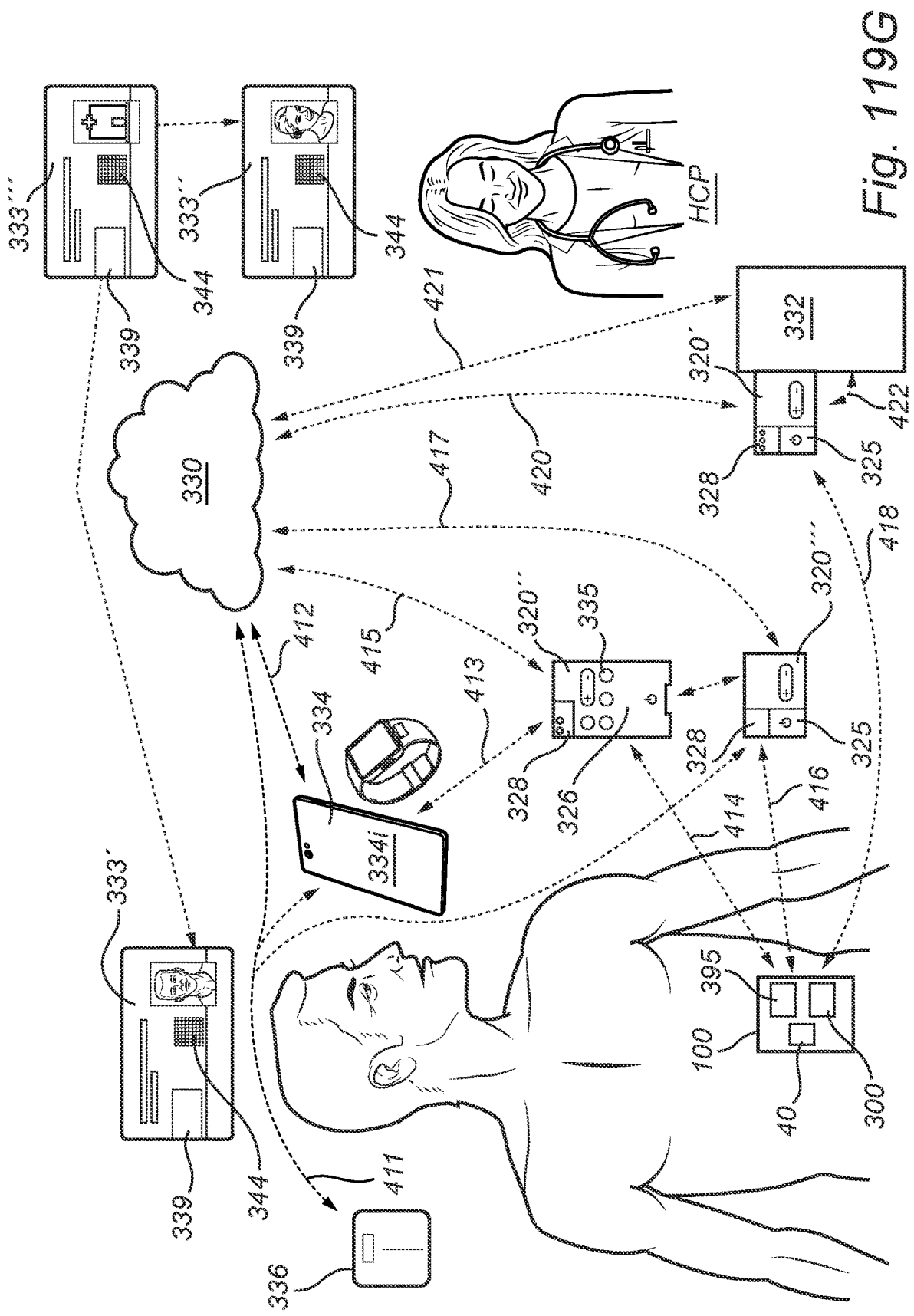

FIG. 119G shows an overview of an embodiment of the system, similar to that described with reference to FIG. 119AA, the difference being that the HCP EID and the HCP DDD are combined into a single device.

Figure 119H:
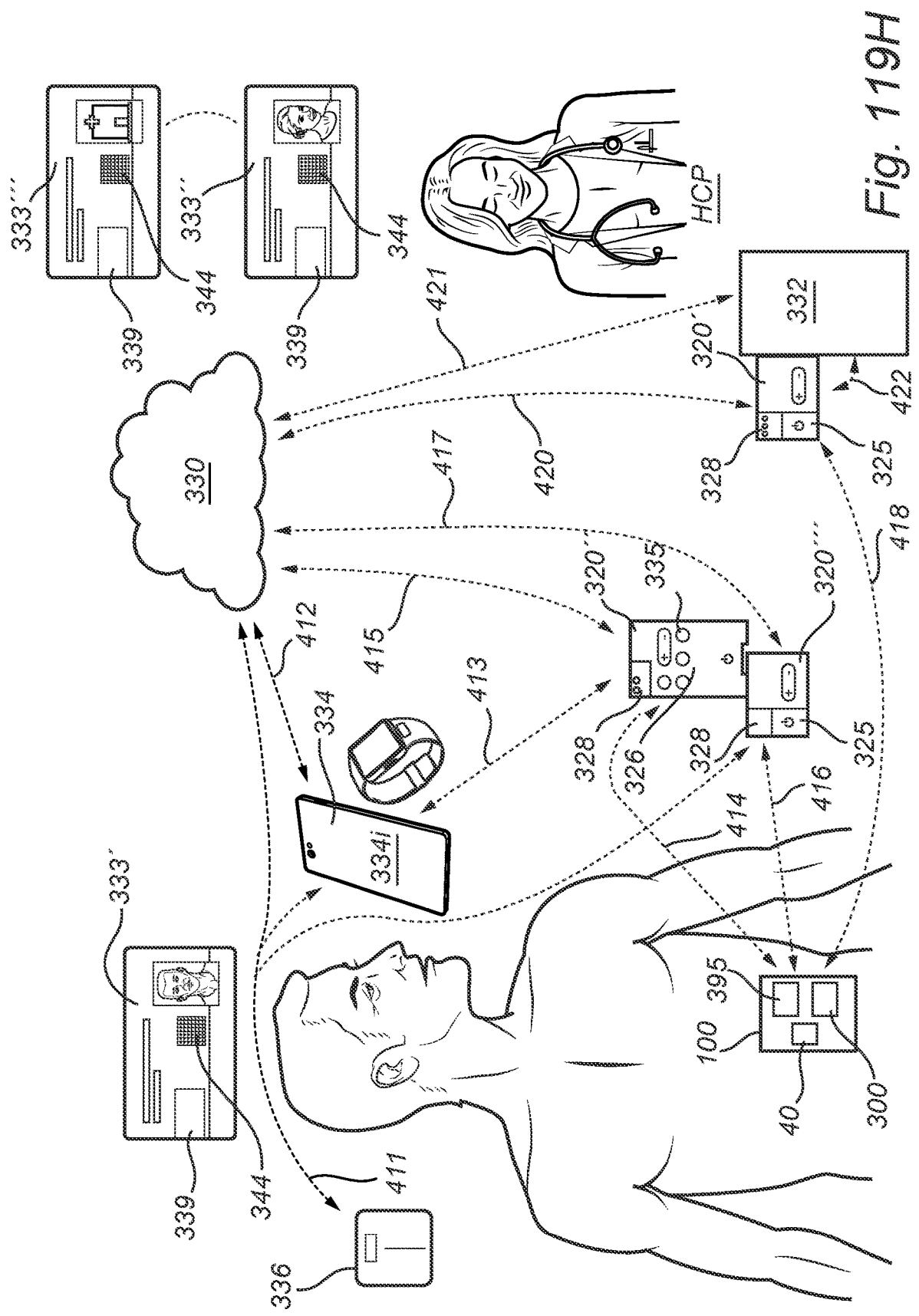

FIG. 119H shows an overview of an embodiment of the system, similar to that described with reference to FIG. 119AA, the difference being that the HCP EID 320''' and the HCP DDD 332 are combined into a single device and the P EID 320''' and the patient remote control external device 320" are combined into a single device.

One probable scenario/design of the communication system is for the purpose of changing pre-programmed treatment settings of an implantable medical device, when implanted in a patient, from a distant remote location in relation to the patient. The system comprises at least one health care provider. HCP, external device 320' adapted to receive a command from the HCP to change said pre-programmed treatment settings of an implanted medical device, further adapted to be activated and authenticated and allowed to perform said command by the HCP providing a HCP private key device 333" adapted to be provided to an HCP EID external device via at least one of; a reading slot or comparable for the HCP private key device, a RFID communication or other close distance wireless activation communication. The HCP EID external device comprising at least one of: a reading slot or comparable for the HCP private key device, a RFID communication, and other close distance wireless activation communication or electrical direct contact. The HCP EID external device further comprises at least one wireless transceiver configured for communication with a patient EID external device, through a first network protocol, wherein the system comprises the patient EID external device, the patient EID external device being adapted to receive command from said HCP external device, and to relay the received command without modifying said command to the implanted medical device. The patient EID external device comprising one wireless transceiver configured for communication with said patient external device. The patient EID is adapted to send the command to the implanted medical device, to receive a command from the HCP to change said pre-programmed treatment settings of the implanted medical device, and further to be activated and authenticated and allowed to perform said command by the patient providing a patient private key device comprising a patient private key.

In another scenario, the implantable medical device may be configured to transmit information. Such information may, for example, relate to a function of the implantable medical device, a parameter of the body of the patient, measurements, among others. In that scenario, the implantable medical device may be configured to only transmit such data in response to a received authentication. The authentication may be received from the patient EID, or from another external device. The implantable medical device may verify that the authenticated device is authorized to request data, for example through a cryptographic verification, which in some examples is based on a key stored at the implantable medical device.

The patient EID (alternatively patient external device) may provide the authentication based on a patient private key provided to the patient EID. The implantable medical device may in that scenario verify that the authentication is based on a patient private key associated with a patient that is authorized to request information from the implant. Based on a valid authorization, the implantable medical device may send data to the patient external device. The data may in some examples be encrypted, for example in any of the ways of encrypting data from the medical implant are described herein. The authorization may be a one-time authorization, an authorization for a predetermined time interval or an authorization that is valid until withdrawn. For example, the authorization may be provided once a day, or at the time of requesting the data from the implantable medical device.

While FIGS. 65F and 65FA-FH and the description thereof discloses different scenarios, also other combinations of authentication or authorization are conceivable. For example, for changing settings of an implantable medical device, it may be required that a health care provider provides an authentication for the changes using their HCP private key. In some examples, an authorization is necessary also from the patient by the patient providing a patient private key device in order for the changes to be accepted by the implantable medical implant. In some examples, the patient may delegate its authorization to the health care provider by using the patient private key.

In some cases, when both an authorization from the health care provider and the patient are required, the health care provider and the patient could be in the same location. To provide an authorization showing that both the health care provider and the patient are at the same location, either the HCP external device or the patient external device may be adapted to receive both the patient private key and the HCP private key in order to authorize a command or a change for the implantable medical implant. Alternatively, the HCP external device or the patient external device may be configured to communicate via a short range communications technology to verify that the other device is present and authenticated before sending the changes to the implantable medical device. This added security may be beneficial, for example, when the medical implant is re-programmed, or software of the implantable medical device is otherwise changed.

In other examples, both an authorization from a patient and from a health care provider may be required, but without the requirement that they are at the same location. In those examples, the authorization may be given using their respective external device. This may be beneficial, for example, when making changes to treatment settings or updating a software is considered to be low risk. Different programs comprised in the implantable medical implant may be considered to have a different risk level associated with them. A risk determination may be programmed into the implantable medical implant as conditions for accepting an update. If the implantable medical implant determines that an update fulfils the conditions, it may install it, otherwise, if the implantable medical implant determines that the conditions are not fulfilled, it may reject the update.

In some examples, it may be sufficient to only require an authorization from at least one of a health care provider and a patient. For example, changes associated with a lower risk, such as changing pre-programmed settings or treatment settings within pre-determined ranges, may be performed using only one authorization.

Although the different scenarios outlined in FIGS. 119B-119G are described with specific units and method of signaling, these scenarios may very well be combined with each other or complemented with additional units or communication connections.

Aspect 330SE eHealth General Communication Housing

As have been discussed before in this application, communication with a medical implant needs to be reliable and secure. For this purpose, it is desirable to have a standalone device as an external remote control (for example described as 320" in FIGS. 119A-119H) for the medical implant, such that no other programs or applications run on the same device which may disturb or corrupt the communication to the medical implant. However, the smartphone or tablet (for example described as 334 in FIGS. 119A-119H) has become an integrated part of everyday life for most people. This means that we almost always have our smartphones at hand. For this reason, it would have been convenient for the patient to communicate with the medical implant directly using the smartphone, such that no additional standalone device would have to be carried. However, as a lot of other applications are running on the smartphone, it does not fulfill the requirement of being a secure and reliable communication tool without interference from other communication. It is therefore desirable to split the tasks of providing secure communication between the external device and the implant from the task of communicating with the Internet and providing a familiar and intuitive user interface. For this purpose, and external device providing secure communication and tamperproof soft- and hardware, where the display device allows for intuitive and easy use is provided. In the embodiments described with reference to FIGS. 120-124 a device fulfilling these combinatory needs will be described in the form of a standalone remote control external device integrated in a housing unit 320" connectable to a smartphone or another display device 334, such as a smart watch or a tablet.

FIG. 120 shows the housing unit 320" in an elevated perspective view form the left, and FIG. 121 shows the housing unit 320" in a plain view from the left. In the embodiment shown in FIG. 120, the housing unit 320" has a rectangular shape with rounded edges, having a height 1521 which is more than 1.5 times the width 1522. The housing unit 320" comprises recess 1525 configured to receive a display device 334, in the form of a smartphone, configured to be fitted in the housing unit 320" for mechanically, disconnectably connecting the display device 334 to the housing unit 320". The boundaries of the recess 1525 in the housing unit 320" forms an edge 1528 configured to encircle the display device 334, when the display device 334 is inserted into the recess 1525. In the embodiment shown in FIG. 120, the recess 1525 has a depth 1526 configured to allow the display device 334 to be entirely inserted into the recess 1525. As such, the depth 1526 of the recess 1525 exceeds the depth 1531 of the display device 334. In the embodiment shown in FIGS. 120 and 121, the edge is relatively thin, and has a width 1527 which is in the range ⅛-1/100 of the width of the display device 334, as such, the housing unit 320" has a width in the range 1.02-1.25 times the width 1522 of the housing unit 320". In the same way, the housing unit 320" has a height 1521 in the range 1.01-1.25 times the height 1521 of the display device 334. In the embodiment shown in FIGS. 120-121, the edges 1528 are configured to clasp the display device 334 and thereby mechanically fixate the display device 334 in the housing unit 320". The minimum bounding box of the housing unit 320" and the display device 334 when mechanically connected, is no more than, 10% wider, 10% longer or 100% higher, than the minimum bounding box of the display device 334.

For creating a clasping fixation, the edges of the housing unit 320" is made from an clastic material crating a tension between the edge 1528 and the display device 334 holding the display device 334 in place. The clastic material could be an elastic polymer material, or a thin sheet of elastic metal. For the purpose of further fixating the display device 334 in the housing unit 320", the inner surface of the edges 1528 may optionally comprise a recess or protrusion (not shown) corresponding to a recess or protrusion of the outer surface of the display device 334. The edges 1528 may in the alterative comprise concave portions for creating a snap-lock clasping mechanical fixation between the housing unit 320" and the display device 334.

In the embodiment shown in FIGS. 120 and 121, the housing unit 320" functions as a remote control for communicating with an implanted medical device, including receiving information from, and providing instructions and updates to, the implanted medical device. Information could be information related to a state of the implanted medical device including any functional parameter of the implanted medical device or could be related to a state of the patient, including any physiological parameter pertaining to the body of the patient (further described on other sections of this disclosure). For the purpose of providing input to the implanted medical device and controlling and updating the functions of the housing unit 320", the housing unit 320" comprises a control interface comprising switches in the form of control buttons 335. The control buttons 335 are configured to be used when the external device is disconnected from the display device 334. The control interface further comprises a display 1505, which is a smaller and typically less sophisticated display 1505 than the display of the display device 334. In an alternative embodiment, the control buttons 335 and display 1505 are integrated into a single touch-responsive (touchscreen) display on which the control buttons may be displayed. In the embodiment shown in FIGS. 120 and 121, one of the control buttons 335 is a control button for activating the implanted medical device and another of the control buttons 335 is a control button for deactivating the implanted medical device. When the display device 334 is attached to the housing unit 320", the control buttons 335 and the display is covered by the display device 334 and are as such not in an operational state. In the embodiment shown in FIGS. 120 and 121, the housing unit 320" is configured to transmit information pertaining to the display of the user interface to the display device 334 and the display device 334 is configured to receive input pertaining to communication to or from the implantable medical device from the patient, and transmit signals based on the received input to the housing unit 320". The input may be a command to change the operational state of the implantable medical device. The display device 334 comprises a touch screen configured to display the user interface and receive the input from the patient. The display of the display device 334 may comprise one or more OLEDs or IPS LCDs elements. When the display device 334 is connected to the housing unit 320", the display device 334 is configured to display a control interface which is used to communicate with the housing unit 320". i.e. providing input to and receiving information from the housing unit 320". The input provided the housing unit 320" is then relayed to the implanted medical device— and in the same way information communicated from the implanted medical device to the housing unit 320" may be relayed or displayed on the display device 334. Having an external device comprising a combination of a housing unit 320" comprising the communication means for communicating with the implanted medical device and a display device 334 basically only functioning as and Input/Output device connected to the housing unit 320" makes it possible to have a secure communication between the housing unit 320" and the display device 334, which is out of reach from the Internet connection of the display device 334, which makes it much harder for an external attacker to get access to any of the vital communication portions of the housing unit 320". The communication between the housing unit and the display device 334 is very restricted and the only communication allowed from the display device 334 to the housing unit 320" is input from the patient or a healthcare professional, and authentication parameters created by an authentication application running on the display device 334. The authentication application running on the display device 334 could be a number-generating authenticator or a biometric authenticator for authenticating the patient or health care professional, and the authentication parameters could for example be parameters derived from a facial image or a fingerprint. In the opposite direction. i.e. from the housing unit 320" to the display device 334, the communication could be restricted to only communication needed for displaying information and/or a graphical user interface on the display device 334. The communication restrictions could for example be based on size of the communication packages or the frequency with which the communication takes place which reduces the risk that an un-authorized person makes multiple attempts to extract information from, or transit information in to, the hand-held device.

In the embodiment shown with reference to FIGS. 120 and 121, the housing unit 320" comprises a first communication unit providing a wireless connection 413 to the display device 334. The wireless connection 413 is in the embodiment shown in FIGS. 120 and 121 based on NFC, but could in alternative embodiment be based on Bluetooth or any other communication pathway disclosed herein. The housing unit 320" further comprises a second communication unit providing a wireless connection with the implanted medical device. The wireless communication between the housing unit 320" and the implanted medical device is in the embodiment shown in FIGS. 120 and 121 based on Bluetooth, but could in alternative embodiments be based on NFC or UWB or any other communication pathway disclosed herein.

As mentioned, in the embodiment shown in FIGS. 120 and 121, the wireless communication between the housing unit 320" and the display device 334 is based on NFC, while the wireless communication between the housing unit 320" and the is based on Bluetooth. As such, the first communication unit of the housing unit 320" is configured to communicate wirelessly with the display device 334' using a first communication frequency and the second communication unit of the housing unit 320" is configured to communicate wirelessly with the implantable medical device using a second different communication frequency. For this purpose, the first communication unit of the housing unit 320" comprises a first antenna configured for NFC-based wireless communication with the display device 334, and the second communication unit comprises a second antenna configured for Bluetooth-based wireless communication with the implantable medical device. The first and second antennae may be a wire-based antennae or a substrate-based antennae. As such, the first communication unit is configured to communicate wirelessly with the display device 334 on a first frequency and the second communication unit is configured to communicate wirelessly with the implantable medical device using a second different communication frequency. Also, first communication unit of the housing unit 320' is configured to communicate wirelessly with the display device 334 using a first communication protocol (the NFC-communication protocol), and the second communication unit is configured to communicate wirelessly with the implantable medical device using a second communication protocol (the Bluetooth communication protocol). The first and second communication protocols are different which adds an additional layer of security as security structures could be built into the electronics and/or software enabling the transfer from a first to a second communication protocol.

In an alternative embodiment, the second communication unit may be configured to communicate wirelessly with the implantable medical device using electromagnetic waves at a frequency below 100 kHz, or preferably at a frequency below 40 kHz. The second communication unit may thus be configured to communicate with the implantable medical device using "Very Low Frequency" communication (VLF). VLF signals have the ability to penetrate a titanium housing of the implant, such that the electronics of the implantable medical device can be completely encapsulated in a titanium housing. In yet further embodiments, the first and second communication units may be configured to communicate by means of an RFID type protocol, a WLAN type protocol, a BLE type protocol, a 3G/4G/5G type protocol, or a GSM type protocol.

In yet other alternative embodiments, it is conceivable that the mechanical connection between the housing unit 320" and the display device 334 comprises an electrical connection for creating a wire-based communication channel between the housing unit 320" and the display device 334. The electrical connection could also be configured to transfer electric energy from the display device 334 to the housing unit, such that the housing unit 320" may be powered or charged by the display device 334. A wired connection is even harder to access for a non-authorized entity than an NFC-based wireless connection, which further increases the security of the communication between the housing unit 320" and the display device 334.

In the embodiment shown with reference to FIGS. 120 and 121, the display device 334 comprises a first communication unit providing a wireless connection 413 to the housing unit 320" based on NFC. The display device 334 further comprises a second communication unit providing a wireless connection with a further external device and/or with the Internet. The second external device may be far away, for example at a hospital or a place where a medical professional practice. The wireless communication between the display device 334 and a further external device is in the embodiment shown in FIGS. 120 and 121 based on WiFi, but could in alternative embodiments be based on for example Bluetooth.

As mentioned, in the embodiment shown in FIGS. 120 and 121, the wireless communication between the display device 334 and the housing unit 320" is based on NFC, while the wireless communication between the display device and a further external unit is based on WiFi. As such, the first communication unit of the display device 334 is configured to communicate wirelessly with the housing unit 320" using a first communication frequency and the second communication unit of the display device 334 is configured to communicate wirelessly with a further external device using a second different communication frequency. For this purpose, the first communication unit of the display device 334 comprises a first antenna configured for NFC-based wireless communication with the housing unit 320", and the second communication unit comprises a second antenna configured for WiFi-based wireless communication with a further external device. The first and second antennae may be wire-based antennae or substrate-based antennae. As such, the first communication unit is configured to communicate wirelessly with the housing unit 320" on a first frequency and the second communication unit is configured to communicate wirelessly with the further external device using a second different communication frequency. Also, the first communication unit of the display device 334 is configured to communicate wirelessly with the housing unit 320" using a first communication protocol (the NFC communication protocol), and the second communication unit is configured to communicate wirelessly with the further external device using a second communication protocol (the WiFi communication protocol). The first and second communication protocols are different which adds an additional layer of security as security structures could be built into the electronics and/or software enabling the transfer from a first to a second communication protocol.

In alternative embodiments, the second communication unit of the display device 334 may be configured to communicate with the further external device by means of, a WLAN type protocol, or a 3G/4G/5G type protocol, or a GSM type protocol.

In the embodiment shown in FIGS. 120 and 121, the communication range of the first communication unit of the housing unit 320" is less than a communication range of the second communication unit of the housing unit 320', such that the communication distance between the housing unit 320" and the medical implant may be longer than the communication distance between the housing unit 320" and the display device 334. In the embodiment shown in FIGS. 120 and 121, the communication range of the first communication unit may be constrained to a length that is less than five times the longest dimension of the minimal bounding box of the display device 334, or more precisely constrained to a length that is less than three times the longest dimension of the minimal bounding box of the display device 334.

In the embodiment shown in FIGS. 120 and 121, communication between the housing unit 320" and the display device 334 is only enabled when the housing unit 320" is connected to the display device 334. I.e, at least one of the housing unit 320" and the display device 334 is configured to allow communication between the housing unit 320" and the display device 334 on the basis of the distance between the housing unit 320" and the display device 334. In the alternative, the housing unit 320" and/or the display device 334 may comprise a sensor configured to estimate whether the housing unit 320" is attached to the display device 334 or not, such as a mechanically activated switch or a photo resistive sensor which providing sensor input when the housing unit 320" and display device 334 are mechanically connected to each other. The signal from the at least one sensor then may be used to permit usage of the communication unit configured for communication with the display device 334.

In the embodiment shown in FIGS. 120 and 121, communication between the housing unit 320" and the implantable medical device is only enabled on the basis of a distance between the housing unit 320" and the implantable medical device. In the embodiment shown in FIGS. 120 and 121, the distance should be less than twenty times the longest dimension of the minimal bounding box of the display device, or more specifically less than ten times the longest dimension of the minimal bounding box of the display device. The distance between the housing unit 320" and the medical implant may be measured using electromagnetic waves, or acoustic waves. The process of measuring the distance may comprise triangulation.

In the embodiment shown in FIGS. 120 and 121, the second communication unit of the display device 334 need to be disabled to enable communication between the display device 334 and the housing unit 320", and further the second communication unit of the display device 334 needs to be disabled to enable communication between the housing unit 320" and the medical implant. Also, the second communication unit of the housing unit 320" needs to be disabled to enable communication between the housing unit 320" and the medical implant.

In the embodiment shown in FIGS. 120 and 121, the housing unit 320" further comprises an encryption unit configured to encrypt communication received from the display device 334 before transmitting the communication to the implanted medical device. The encryption unit may for example be based on one of the following algorithms: AES. Blowfish, DES, Kalyna, Serpent or Twofish. For the purpose for handling the communication. I/O and encryption, the housing unit 320" comprises a processor which could be a general-purpose microprocessor and/or an instruction set processor and/or related chips sets and/or special purpose microprocessors such as ASICs (Application Specific Integrated Circuit). The processor also comprise memory for storing instruction and/or data. The housing unit 320" may comprise a storage unit, such as a battery, for storing energy. The storage unit may be adapted to be charged by the display device 334, or another external device. In some examples, the charging is performed using reverse wireless charging. To that end, the housing unit 320" may comprise an energy receiver connected to the storage unit, the energy receiver being adapted to wirelessly receive energy from another device. The display device 334 may comprise a primary coil and the housing unit comprise a secondary coil connected to an energy storage of the housing unit, wherein the display device 334 is adapted to wirelessly charge the housing unit using the first coil, and wherein the housing unit is adapted to receive wirelessly transmitted energy through the second coil and store the energy in the storage unit. In one example, the wireless charging may be performed using the Qi standard for wireless charging.

FIGS. 122 and 123 shows an embodiment of the external unit similar to the embodiment described with reference to FIGS. 120 and 121. The difference being that in the embodiment of FIGS. 122 and 123, the housing unit 320" does not clasp the display device 334. Instead, the housing unit comprises two magnets 1510 for magnetically fixating the display device 334 to the housing unit 320". In alternative embodiments, it is equally conceivable that the external device comprises an intermediate portion, which is fixedly fixated to the housing unit for providing a detachable connection with the display device 334. In the alternative, the intermediate device could be fixedly fixated to the display device 334 and provide a detachable connection with the housing unit 320".

Figure 124:
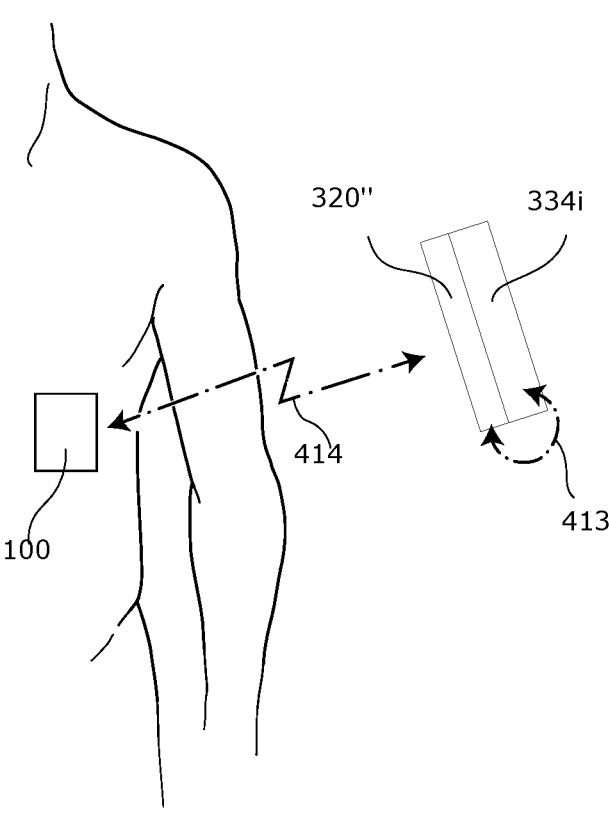
FIG. 124 shows a system overview of an external device comprising a housing unit and a display device in wireless communication with an implanted medical device.

FIG. 124 shows a system overview of the external device (which could be the external device of the embodiment described with reference to FIGS. 120 and 121, or of the embodiment described with reference to FIGS. 122 and 123). The housing unit 320" is connected to the display device 334. A wireless connection 413 is provided between the housing unit 320" and the display device 334, and a further wireless connection 413 is provided between the housing unit 320" and the implanted medical device 100, such that the housing unit can send instructions and updates to the implanted medical device 100, and receive information, parameters (such as sensor values) and alarms from the implanted medical device 100. The communication between the external device and the medical implant 100 is further described in other portions of this disclosure.

The implantable medical device 100 may be an active and/or operable implantable medical device 100 which may be an implantable medical device configured to exert a force on a body portion of the patient. The body portion of the patient may be a fluid carrying vessel, an organ, a joint, a membrane, a muscle, a bone or a nerve. The implantable medical device 100 may comprises an electrical motor and a controller for controlling the electrical motor and instructions transmitted to the implantable medical device 100 could be instructions pertaining to the control of the electrical motor. The controller may control, the velocity, the acceleration or the torque of the motor. The implantable medical device 100 could for example comprises at least one of: an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries, an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 447A, B, C
Data_Packet_Encryption-Implant, External, Method

An implantable medical device 100 configured to receive remote instructions from an external system will now be described with reference to FIGS. 119A-h. The implantable medical device 100 comprises a wireless receiver configured to receive wirelessly transmitted data packets from an external device 320', 320", 320''' and a computing unit configured to verify the electronic signature, and use a checksum provided in the data packet to verify the integrity of the instructions. The wireless receiver mat be part of a wireless transceiver. The computing unit may comprise a memory unit configured to store electronic signatures, and wherein the computing unit is configured to verify the electronic signature my comparing the electronic signature with the electronic signatures stored in the memory unit.

The computing unit may be configured to decrypt the data packet. The computing unit may be configured to use the checksum to verify that the bit stream making up the instructions is unchanged.

As an alternative, the date packet may be decrypted using the methods and/or systems described with reference to aspect 331.

In one example, the implantable medical device 100 comprises a control program configured to control at least one function of the implantable medical device. The computing unit may thus be configured to alter the control program on the basis of the received instructions.

The implantable medical device 100 may comprise an internal computing unit configured to run a control program for controlling a function of the implantable medical device 100, wherein the control program comprises at least one adjustable parameter affecting the control of the implantable medical device, and wherein the method of providing remote instructions comprises providing instructions for altering the at least one parameter for affecting the control of the implantable medical device.

The computing unit may comprise a memory unit configured to store parameter values. The implantable medical device may be configured to verify that the instructions for altering the at least one parameter will result in the at least one parameter being updated to a parameter value comprised in the set of stored parameter values. In some examples, the implantable medical device is configured to at least one of decrypting the data packet and verifying the electronic signature using a private key of the implantable medical device.

The private key may be provided in the implantable medical device by the manufacturer of the implantable medical device. In some examples, the private key is stored as hardware or software in the implantable medical device. The private key may be a non-extractable key. In some examples the private key is a physical unclonable function.

To further increase the security, the wireless receiver or wireless transceiver may be configured to be placed in an off-mode, in which no wireless communication can be received by the wireless transceiver, and wherein the set of rules comprises a rule stipulating that communication from the central unit is only accepted at the security module when the wireless transceiver is placed in the off-mode.

According to an embodiment, the implantable medical device is configured to perform a proof of possession operation comprising transmitting, from the implantable medical device to the external system, a query based on a public key associated with the private key of the external system, receiving, at the implantable medical device, a response based on the possession of the private key in the external system, and verifying that the response based on the possession of the private key matches the query based on a public key.

The implantable medical device may be configured to communicate with the external system independently of time, for example by using single use codes, as described in aspect 447D.

The implantable medical device may be configured to verify a first electronic signature made using at least one of a first key and a second key, and verifying a second electronic signature made using at least one of a first key and a second key. At least one of the first and second keys mat be a private key, and/or the first and second keys are different. In some examples, the first and second keys comprises at least one common element.

T the implantable medical device may be configured to verify a first electronic signature to allow communication from the external system to the implantable medical device, and verify a second electronic signature to allow an instruction received in the communication to alter the control program running on the implantable medical device. The first electronic signature may be an electronic signature linked to the user of the implantable medical device and the second electronic signature may be an electronic signature linked to a healthcare provider.

In some examples, only a portion of the private key is needed to at least one of: decrypt the data packet and verify the electronic signature.

In some examples, the implantable medical device trusts any external device holding the private key.

The implantable medical device may be configured to receive the data packet comprising at least one instruction signed by a private key of the external system, and a public key including information about which root have created the public key. In some examples, the implantable medical device is configured to accept communication from an external system based on at least one password being provided to the implantable medical device. The implantable medical device may be configured to accept communication from an external system based on two passwords being provided to the implantable medical device. For examples, the implantable medical device is configured to accept communication from an external system based on one patient password and one healthcare provider passwords being provided to the implantable medical device.

A corresponding external device 320', 320", 320''' will now be described with reference to FIGS. 119A-h. An external system or external device for providing remote instructions to an implantable medical device is shown. The external system, or any of the external devices therein 320', 320", 320", is configured to instructions to be transmitted to the implantable medical device, derive a checksum from the instructions, electronically sign the instructions and the checksum, form a data packet from the instructions, the electronic signature and the checksum, wherein the external system comprises a wireless transmitter configured to wirelessly send the data packet to the implantable medical device.

The external system, may comprise comprises a first external device 320' and a second external device 320", and wherein the first external device 320' is configured to transmit the data packet to the second external device 320", and wherein the second external device 320" is configured to transmit the data packet wirelessly to the implantable medical device 100 without changing the data packet.

Alternatively, the first external device 320' is configured to transmit the data packet to the second external device 320", and wherein the second external device 320" is configured to transmit the data packet wirelessly to the implantable medical device 100 without full decryption of the data packet.

The first external device 320' may be configured to send the data packet from the first external device 320' to the second external device 320" using a first network protocol the second external device 320" may send the data packet to the implantable medical device 100 using a second network protocol. In some examples, the first external device 320' is configured to send the data packet from the first external device 320' to the second external device 320" using wired communication and send the data packet from the second external device 320" to the implantable medical device 100 using wireless communication. If using wireless communication, the first external device 320' may be configured to wirelessly send the data packet from the first external device 320' to the second external device 320" using a first frequency band, and wirelessly send the data packet from the second external device 320" to the implantable medical device 100 using a second frequency band. In some examples, the first external device is configured to wirelessly send the data packet from the first external device to the second external device using a first wireless technology, and wirelessly send the data packet from the second external device to the implantable medical device using a second wireless technology.

The external system may be configured to transmit at least one instruction for altering the control program of the implantable medical device 100, to the implantable medical device 100, and/or the external system may be configured to provide at least one instruction to the implantable medical device 100 for altering at least one parameter for affecting the control of the implantable medical device 100. In some examples, the external system is configured to provide at least one instruction for updating at least one parameter of the control program to a parameter value comprised in a set of parameter values stored in the implantable medical device 100.

The external system may be configured to electronically sign the instructions at the external system using a key of the external system. Details of the key, and any use of a first and a second key, have been discussed above with reference to the implantable medical device 100.

The first external device may be configured to form the data packet and electronically sign the instruction using a first private key, and the second external device is configured to: receive the data packet from the first external device, verify that the first external device is a trusted transmitter, in response to the verification, electronically sign the data packet using a second private key, and transmit the data packet from the second external device to the medical implant. The checksum is configured to verify that no changes have been made to the bit stream forming the instructions.

The key may be placed on a key device external to the any of the external devices. In some examples, the key device comprises a wireless transmitter for wirelessly transmitting the at least one private key or a signal based on the private key, to the first external device. The key device may, for example, comprise at least one of: a key card, a wearable device and a handset.

The external device may be locker for an increased security. The external device may thus be unlocked by a user providing credentials to the external device. Such credentials may, for example, comprise a username, a password, a PIN-code, or any other credential.

An improved security may further be achieved by combining the embodiments described with reference to Aspects 447A-C with any of the methods disclosed in aspects 36, 307, 308, 399, 400, 401, and 402, which relate to methods for communicating instructions or updates to the implantable medical device using any of the external devices shown in FIGS. 119A-h. Aspects 447A-C may advantageously be combined with the use of single use codes, as will be described below with reference to aspect 447D.

Aspect 447D Single-Use_Codes_Encryption

A method of providing remote instructions from an external system to an implantable medical device, wherein the implantable medical device comprises a list of codes and the external system comprises a list of codes, will now be described with reference to FIGS. 119A-h. The method may be performed by the system(s) shown in FIGS. 119A-h. The method comprises encrypting the instructions at the external system or at an external device 320', 320", 320" using a code from a position on the list of codes, wirelessly sending the encrypted instructions to the implantable medical device 100, and decrypting, at the implantable medical device 100, the instructions using a code from a position on the list of codes.

The method may further comprise the steps of wirelessly sending position information from the external device 320', 320", 320'" to the implantable medical device 100, and using the information at the implantable medical device 100 for selecting the code from the list of codes.

The step of encrypting, at the external system or at the external device 320', 320", 320'", the instructions using a code from a position on the list of codes comprises selecting the code on a current position on the list of codes, wherein the method further comprises the step of updating the current position to a new current position after using the code.

The step of decrypting, at the implantable medical device 100, the instructions using a code from a position on the list of codes comprises selecting the code on a current position on the list of codes, wherein the method further comprises the step of updating the current position to a new current position after using the code.

The current position may comprise a number and wherein the step of updating the current position comprises updating the number to a sequential number.

The step of wirelessly sending the encrypted instructions to the implantable medical device 100 comprises sending the encrypted instructions from a first external device 320' to a second external device 320" and further wirelessly sending the encrypted instructions from the second external device 320" to the implantable medical device 100. The second external device may transmit the encrypted instructions without changing the encrypted instructions, and/or the encrypted instructions without full decryption.

The implantable medical device 100 may comprise a control program configured to control at least one function of the implantable medical device 100, and wherein the method further comprises altering the control program on the basis of the received instructions. The implantable medical device 100 may comprises internal computing unit configured to run a control program for controlling a function of the implantable medical device 100, wherein the control program comprises at least one adjustable parameter affecting the control of the implantable medical device 100, and wherein the method of providing remote instructions comprises providing instructions for altering the at least one parameter for affecting the control of the implantable medical device 100.

The implantable medical device 100 may comprise a set of stored parameter values, and wherein the method further comprises the step of verifying that the instructions for altering the at least one parameter will result in the at least one parameter being updated to a parameter value comprised in the set of stored parameter values.

In the same way as discussed above with reference to aspects 447A-C, the communication between the implantable medical device 100 and the first and/or second external device 320', 320", 320'" may be performed using wired or wireless technology, different protocols and/or different frequency bands.

The method may be combined with the security module as described with reference to aspect 331.

The step of electronically signing the instruction at the external system, may be performed and using keys as discussed with reference to Aspects 447A-C.

Aspect 454: Dual Remote Controls

Figure 125A:
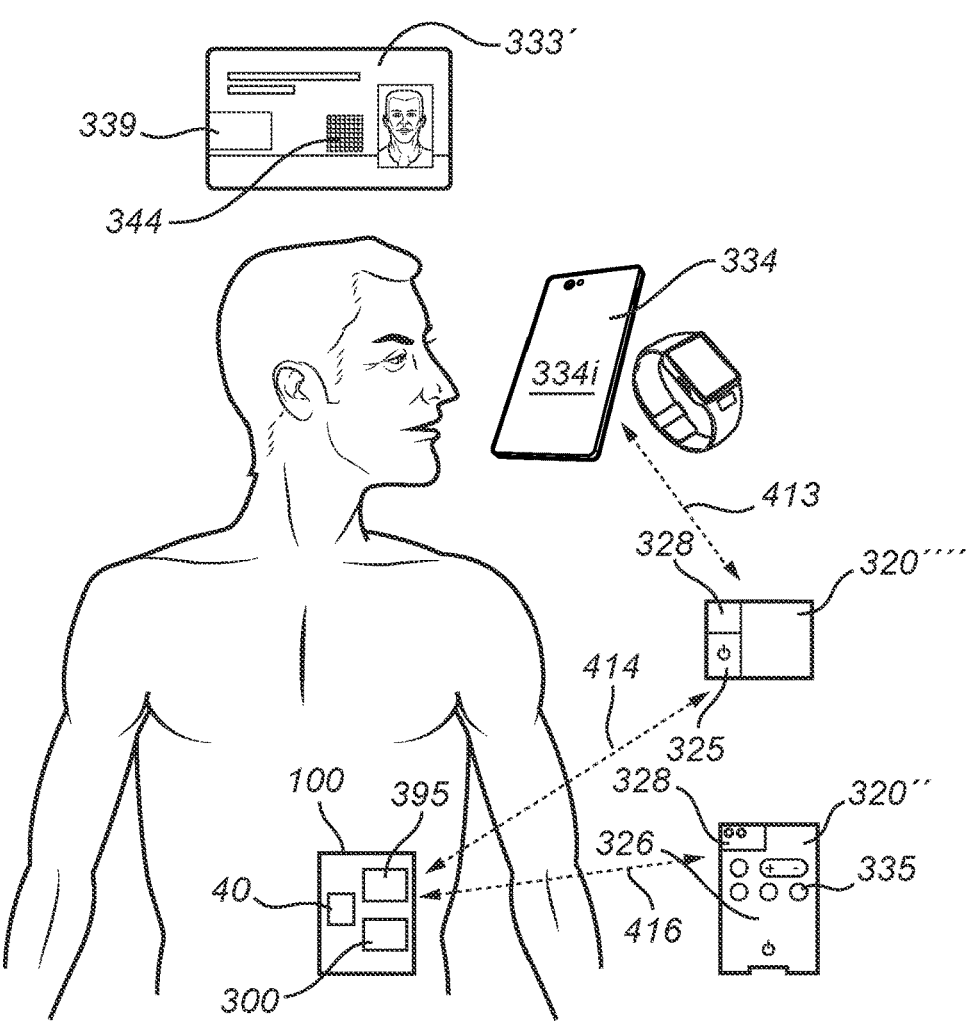
FIG. 125A shows a system having a first and a second remote control.

FIG. 125A shows one embodiment of a communication system for transmission of data to and/or from an implantable medical device 100. The communication system comprises an implantable medical implant, a first remote control 320", and a second remote control 320"". The first remote control 320" (also referred to as patient external device 320") is operable by a user and comprises a first wireless communication unit configured for wireless transmission of data to and/or from the implantable medical device 100. The second remote control 320"" is inoperable by a user (i.e. may not comprise any input means such as buttons, switches, or user interface to receive any input directly from a user) and comprises a second wireless communication unit configured for wireless transmission of control commands and/or data to and/or from the implantable medical device 100. The second remote control 320"" further comprises a third communication unit for communicating with a patient display device 334 (e.g. a smartphone, smartwatch, tablet, and/or the like).

By having two separate remote controls, the security of the implant may be improved, as there are two separate ways of controlling the implant. Thus, in case of a malfunction of either of the remote controls, the implant may still be controlled. Furthermore, this allows for the second remote control to be smaller or more compact since it is inoperable by the user other than through a patient display device or another external device. The second remote control may thus be smaller and potentially less expensive.

The first and second remote controls 320", 320"" each comprise a wireless transceiver 328 for communicating with the implantable medical device 100. The first and/or second remote control 320". 320"" is capable of controlling the operation of the implantable medical device 100 via the controller 300 (for controlling the implantable medical device and for communicating with devices external to the body of the patient and/or implantable sensors). The first and/or second remote control 320", 320" " may control the operation of the implantable medical device 100 by controlling pre-set functions of the implantable medical device 100, e.g. for operating an active portion of the implantable medical device 100 for performing the intended function of the implantable medical device 100.

The first and/or second remote control 320", 320"" is able to communicate with implantable medical device 100 using any standard or proprietary protocol designed for the purpose. At least one of the first remote control 320", the second remote control 320"", and the implantable medical device 100 may, e.g., comprise a Bluetooth (BT) transceiver. In particular, the wireless transceiver 328 may comprise a BT transceiver, and the and/or second remote control 320", 320"" may be configured to communicate with implantable medical device 100 using BT. In one embodiment, the first and/or second remote control 320", 320"" is configured to communicate with implantable medical device 100 using NFMI.

In an alternative configuration, the first and/or second remote control 320", 320"" may communicate with the implantable medical device 100 using a combination of Ultra-Wide Band (UWB) wireless communication, NFMI and/or BT. For example, at least one of first remote control 320", the second remote control 320"", and the implantable medical device 100 may comprise a UWB transceiver. The use of UWB technology enables positioning of the first and/or second remote control 320", 320"" which can be used by the implantable medical device 100 as a way to establish that the first and/or second remote control 320", 320"" is at a position which the implantable medical device 100 and/or the patient can acknowledge as being correct, e.g. in the direct proximity to the medical device 100 and/or the patient, such as within reach of the patient and/or within 1 or 2 meters of the implantable medical device 100.

When a combination of BT and UWB and/or NFMI technology is used, the UWB or NFMI technology may be used for location-based authentication of the first and/or second remote control 320", 320"", whereas the communication and/or data transfer could take place using BT or any other way of communicating different from the UWB or NFMI. The UWB or NFMI signal could in some embodiments also be used as a wake-up signal for the controller 300, or for the BT transceiver, such that the BT transceiver in the implantable medical device 100 can be turned off when not in use, which eliminates the risk that the BT is intercepted, or that the controller 300 of the implantable medical device 100 is hacked by means of BT communication. In embodiments in which a BT (or alternatives)/UWB combination is used, the UWB connection may be used also for the transmission of data. In the alternative, the UWB connection could be used for the transmission of some portions of the data, such as sensitive portions of the data, or for the transmission of keys for the unlocking of encrypted communication sent over BT.

The first remote control 320" may be configured to control functions of the implantable medical device 100 based on user input to the first remote control 320". In particular, the first remote control 320" may comprise an input device for receiving a first user input, wherein the first remote control 320" is configured to transmit the first user input to the implantable medical device 100. The first remote control 320" may comprise a computing unit 326 which runs a software application for communicating with the implantable medical device 100. The computing unit 326 may receive the first user input directly from control buttons 335 arranged on the first remote control 320". The computing unit 326 may be configured to encrypt control commands before transmission to the implantable medical device 100. The computing unit 326 is further configured to transform the received first user input into control commands for wireless transmission to the implantable medical device 100.

The second remote control 320"" may comprise a wireless transmitter 325 configured for transferring energy wirelessly. The energy may be in the form of a magnetic field or any other signal such as electromagnetic, radio, light, sound or any other type of signal to transfer energy wirelessly to a wireless receiver 395 of the implantable medical device 100. The wireless receiver 395 of the implantable medical device 100 is configured to receive the energy in the form of the magnetic field and transform the energy into electric energy for storage in an implantable energy storage unit 40 of the implantable medical device 100, and/or for consumption in an energy consuming part of the implantable medical device 100 (such as the operation device, controller 300 etc.). In other words, the implantable energy storage unit 40 may be adapted to be wirelessly charged. The first remote control may similarly comprise a wireless transmitter for transferring energy wirelessly to the implantable medical implant. The implantable energy storage unit 40 may particularly be connected to the wireless receiver 395 for receiving wireless energy from the first and/or second remote control 320", 320"".

In the embodiment shown in FIG. 125A, the second remote control 320"" is configured to communicate with a patient display device 334. Here, the patient display device 334 comprises the consumer electronics device. In particular, the second remote control 320"" is configured to receive a second user input from the patient display device 334 and to transmit the second user input to the implantable medical implant. The second remote control 320"" may receive the second user input from a control interface 334i displayed on the patient display device 334 operated by the patient.

The patient display device 334 may for example be a mobile phone, a tablet or a smart watch. The display device 334 may, for example, communicate with the second remote control 320"" by means of BT, but any wireless or wired communication means may be used. The control interface 334i, e.g. in the form of a web-view portal, may be transmitted from the second remote control 320"" to the patient display device 334 over BT. Control commands in the form of inputs from the patient to the control interface 334i are transmitted from the patient display device 334 to the second remote control 320"", providing input to the second remote control 320"" equivalent to the input that may be provided using the control buttons 335 or other input means of the first remote control 320". The control commands created in the patient display device 334 may be encrypted in the patient display device 334 and transmitted to the second remote control 320"" using BT or any other communication protocol.

The second remote control 320"" may be implemented and/or integrated in an accessory to the patient display device 334. The second remote control 320"" may, e.g., form part of a mobile phone case (i.e. smartphone case) for a mobile phone. Alternatively, the second remote control 320"" may be integrated in a case for a personal computer, or a body worn camera, or any other suitable type of external device as described herein. The case may for example be connected to the patient display device 334 (e.g. mobile phone) using a wire from the case and connected to the patient display device (e.g. a charging port).

The second remote control 320"" may not be connected to the DDI or the Internet, thereby increasing security. The second remote control 320"" may have a private key, in particular the second remote control 320"" may be activated by a private key 333' of the patient for a certain time period. This may activate the function of the patient display device 334 and the remote wed-view display portal supplied by the second remote control to the patient display device 334.

The patient's private key 333' may be supplied in a patient private key device comprising a smartcard that may be inserted or provided close to the first remote control 320" and/or close to the second remote control 320"" to activate a permission to communicate with the implantable medical device 100 for a certain time period. The patient's private key 333' is in the embodiment shown in FIG. 125A in the form of a key card having an interface for communicating with the first remote control 320", the second remote control 320"", and/or another device or control. The NFC-transmitter 339 and/or the printed QR-code 344 may be used as means for accessing the control interface 334i of the display device 334. In addition, the display device 334 may require a pin-code and/or a biometric input, such as face recognition or fingerprint recognition, for controlling the implantable medical implant.

The patient display device 334 may comprise auxiliary radio transmitters for providing auxiliary radio connection, such as Wi-Fi or mobile connectivity (e.g. according to the 3G, 4G or 5G standards). The auxiliary radio connection(s) may have to be disconnected to enable communication with the second remote control 320"". Disconnecting the auxiliary radio connections reduces the risk that the integrity of the control interface 334i displayed on the patient display device 334 is compromised, or that the control interface 334i displayed on the patient's display device 334 is remote controlled by an unauthorized device.

The data transmitted in the communication system may comprises a control command for the medical implant. Hence, real-time, remote management of patient care is provided and settings of the medical implant may be adjusted, e.g., based on the patient's current health status. Thus, invasive procedures may be averted while efficiency of healthcare delivery and patient comfort may be improved. Furthermore, more responsive and/or personalized health-care may be provided, as adjustments can be made promptly in response to changes in the patient's condition.

At least one of the first wireless communication unit of the first remote control 320" and the second wireless commu-nication unit of the second remote control 320"" may be configured to send and/or receive data using near-field magnetic induction (NFMI). Thus, enhanced security and reliability of the communication system may be provided. NFMI creates a private, secure communication link that is difficult to intercept or disrupt due to the magnetic field being spatially confined and thus less susceptible to inter-ference compared to traditional radio frequency communi-cation. Furthermore, NFMI penetrate materials such as water and body tissue, making it particularly suitable for communication with medical implants.

Further, at least one of the first wireless communication unit and the second wireless communication unit may com-prise a transmitter coil for modulating a magnetic field for transmitting the data. In turn, the implantable medical implant may comprise a receiving coil and an NFMI receiver connected to the receiving coil to receive the data. The transmitter coil(s), in conjunction with the receiving coil and NFMI receiver of the implantable medical implant, may provide efficient and reliable data transfer. The use of a magnetic field for data transmission, which is typically more energy-efficient than traditional radio frequency com-munication, may additionally reduce power consumption and thereby extend an operational period of the implantable medical implant.

The transmitter coil(s) may be configured to modulate a magnetic field, and the NFMI receiver may be adapted to measure the magnetic field in the receiving coil. A modu-lated magnetic field may enable the construction of specific signal patterns for the data transmission such that transmis-sion of complex data sets is enabled.

At least one of the first wireless communication unit and the second wireless communication unit may further be configured to wirelessly charge the implantable medical implant using NFMI. In particular, at least one of the first wireless communication unit and the second wireless com-munication unit may be, and/or act as, the wireless trans-mitter 325 configured for transferring energy wirelessly Similarly, the implantable medical implant may comprise a coil for receiving wireless energy for charging the implant via NFMI. The coil of the implantable medical implant may, e.g., form part of, or be, the wireless receiver 395.

The second and third communication units of the second control unit 320"" may be configured to transmit and/or receive data using different network protocols. In other words, the second and third communication units may be designed to send and/or receive data using separate and/or alternate networking standards. Thus, the communication system can communicate across a variety of network envi-ronments and conditions. A multi-protocol support may enhance interoperability of the second remote control 320"", allowing for communicate with a wide range of devices and systems (such as the patient display device 334 and the implantable medical device 100). Alternatively, or addition-ally, the second and third communication units may for the same reasons be configured to transmit and/or receive data using different frequency bands.

The standard, communication, and/or network protocols discussed herein may be any one or more from the list of: Radio Frequency type protocol, RFID type protocol, WLAN type protocol, Bluetooth type protocol. BLE type protocol. NFC type protocol, 3G/4G/5G type protocol, and GSM type protocol.

In an example, the second communication unit has a longer effective range than the third communication unit. In other words, the second communication unit may be able to communicate with a device (e.g., the implantable medical device 100) from a further distance than the distance at which the third communication unit is able to communicate with another device (e.g., the patient display device 334). For example, the second communication unit may use a network protocol with a longer effective range than the network protocol of the third communication unit.

In the specific embodiment disclosed in FIG. 125A, the wireless connections between the different units are as follows. The wireless connection 413 between the patient display device 334 and the second remote control 320"" is based on BT or any other communication protocol disclosed herein. The wireless connection 414 between the second remote control 320"" and the implantable medical device 100 is based on BT and UWB or any other communication protocol disclosed herein. The wireless connection 416 between the first remote control 320" and the implantable medical device 100 is based on BT. UWB, and the charging signal, or any other communication or energizing pathway disclosed herein.

The wireless connections specifically described in the embodiment shown in FIG. 125A may be replaced or assisted by wireless connections based on radio frequency identification (RFID), near field communication (NFC), Bluetooth, Bluetooth low energy (BLE), or wireless local area network (WLAN). The wireless connections may fur-ther be based on modulation techniques such as amplitude modulation (AM), frequency modulation (FM), phase modulation (PM), or quadrature amplitude modulation (QAM). The wireless connection may further feature tech-nologies such as time-division multiple access (TDMA), frequency-division multiple access (FDMA), or code-divi-sion multiple access (CDMA). The wireless connection may also be based on infra-red (IR) communication. The wireless connection may feature radio frequencies in the high fre-quency band (HF), very-high frequency band (VHF), and the ultra-high frequency band (UHF) as well as essentially any other applicable band for electromagnetic wave com-munication. The wireless connection may also be based on ultrasound communication to name at least one example that does not rely on electromagnetic waves.

Figure 125B:
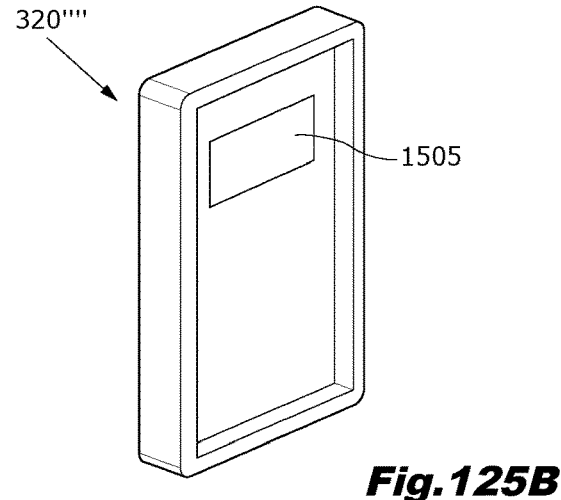
FIG. 125B shows the second remote control comprised in a housing unit.

An embodiment in which the second remote control 320"" is comprised in a housing is shown in FIG. 125B.

Aspect 453: Voice Control

FIG. 126A schematically shows a medical implant 10 when implanted in a patient 1. The medical implant com-prises a processor 1300 connected to a medical device 100, which may be comprised in the implant 100. The medical device may be any medical device or implant discussed herein, and may be configured to control or monitor a function of the body of a patient. The medical implant 10 may further comprise or be connected to a microphone 1369. The microphone 1369 may receive audio and transfer that audio to the processor 1300. The processor 1300 may thus receive audio via microphone 369.

The processor 1300 may have two modes of operation, a learning mode for learning voice commands and an operational mode for recognizing and transmitting voice commands to the medical device 110 or the medical implant 1100. The processor 1300 may be configured to, when in the learning mode, receive a first audio training phrase and creating a transfer function, the transfer function being based on the first audio training phrase, wherein the transfer function is configured to adjust the amplitude of at least one frequency of audio received at the medical device 110 for enhancing audio received at the medical implant 100 to facilitate detection of voice commands. To this end, the processor 1300 may comprise a transfer function unit 1370. The processor 1300 may be further adapted to receive a second audio training phrase, the second audio training phrase comprising a voice command, wherein the voice command comprises an instruction for the control of the medical implant 1100 and/or the medical device 110. The processor 300 may be further configured to use the transfer function for generating an enhanced second audio training phrase in the medical implant, and associating the enhanced second audio training phrase with the instruction for the control of the medical implant. Thus, the medical implant 110 has learned that the voice command comprised in the enhanced audio training phrase corresponds to the instruction.

In some examples, the audio training phrases are inputted into a transfer function unit 1370 for creating the transfer function. The processor may further comprise a learning unit 1371 for associating the enhanced second audio training phrase with the instruction for the control of the medical implant. The learning unit 1371 may, for example, comprise an algorithm based on machine learning for learning to associate the enhanced audio training phrase with the correct instruction for the medical device 1100. The voice commands, the instructions and any association between the voice commands may be stored in a memory unit 1373 comprised in or connected to the processor 1300.

The processor 1300 may be further adapted to receive audio input, process the audio input in order to determine an instruction and to transfer that instruction to the medical device 1100. In order to determine the instruction, the processor may use the transfer function 1370 to enhance the audio input and then determine the instruction associated with the enhanced audio input (as associated by the method described herein). The instruction may also be called a control command or a command. The instruction may be determined by and/or be transferred to the medical device 1100 via a command unit 1372 comprised in or connected to the processor 1300. The instruction may relate to a function of the medical device 1100 and may cause the medical device 1100 to perform an action, or it may relate to any other function of the medical implant 10, such as the processor 1300.

By learning voice commands, it may be meant that the processor associates an audio input with a control command for the medical device.

The processor 1300 may be further configured to, when in the operational mode, receive an audio command phrase for the medical device 1100 or implant 110. The processor 1300 may be further configured to apply a transfer function to create an enhanced audio command phrase. The transfer function may have been created as discussed above. The processor 1300 may determine a corresponding command for the medical based on the enhance audio command phrase, and send the command to the medical device 1100 or the medical implant 110. The medical device 1100 or implant 110 may then execute the command.

When the medical implant is implanted in the body, typically the medical implant stays in the same place in the body. Thus, it has been realized that any noise or distortion created by the body to audio commands may be substantially the same. By creating a transfer function based on a first audio training phase when the medical implant is implanted in the body, any noise created by the body or any distortions to the audio training phase caused by the body itself can be accounted for. The method thus accounts for that that the noise and distortions created by the body is substantially the same over time. Thus, the transfer function may account for those disturbances when enhancing any audio received by the medical implant. In this way, audio received by the medical implant may be enhanced, i.e., any known disturbances created by the body to the audio may be accounted for, before the medical implant does any further processing. Since the audio is enhanced before any training or processing, the process of recognizing which command for the medical implant the audio relates to may be simplified. That is, the processing power needed for recognizing voice commands may be reduced, which is advantageous in medical implants since the size of the implant may be decreased.

FIG. 125B shows a flow chart for a method for training a medical implant to recognize a voice command, according to some embodiments. The method 200 comprises receiving 210, by a medical implant, a first audio training phrase, when the medical implant is implanted in the body of the patient.

The method further comprises creating 220 a transfer function, the transfer function being based on the first audio training phrase, wherein the transfer function is configured to adjust the amplitude of at least one frequency of audio received at the medical device for enhancing audio received at the medical implant to facilitate detection of voice commands. Creating 220 a transfer function based on a first audio input phase when the implant has been implanted in a patient allows for specifically correcting the audio input phrase for noise and/or distortion caused by the patient's body specifically.

The creation of the transfer function may be based on training a machine learning model.

A purpose of the transfer function may be to adjust the audio input for distortions or noise specific to the body the implant has been implanted into. After the audio input has been adjusted, or enhanced, the audio input may be in a better condition for use in later steps of the method, such as for recognizing a command for the medical implant comprised in the audio input. In that way, there may be a two-step method for training the medical implant to recognize commands. Since the audio input has been adjusted or enhanced, the voice recognition of the command in the audio input may be easier, which may allow for using less processing power.

In some embodiments, the creating 220 a transfer function may further comprise to compare 221 the first audio training phrase with a stored audio phrase to determine a difference between them. Based on the difference, the transfer function may be created 222. In other words, the method may comprise creating a transfer function based on a difference between a stored audio phrase and the first audio phrase.

As an illustrative example only, the stored audio phrase may comprise a specific command or test phrase. When in a training session, a user of the implant or another person that the implant should be trained for, may speak the same specific command or test phrase. The command or test phrase may then be captured by the microphone of the implant, and transferred to the learning unit of the processor. The learning unit may then compare the received command or test phrase with the stored command or test phrase, and then, based on the difference(s), create a transfer function which takes the differences into account. The differences between the received command or test phrase and the stored command or test phrase may be indicative of a noise or distortion created by the body in which the implant has been implanted.

The method 200 may further comprise inputting 230 a second audio training phrase to the medical implant, the second audio training phrase comprising the voice command, the voice command comprising an instruction for the control of the medical implant.

The second audio training phrase may be used as input to the transfer function in order to create an enhanced audio training phrase. In this way, any noise or distortion created by the body may be alleviated by the transfer function, thus resulting in an enhanced audio training phrase. Thus, the method may further comprise using 240 the transfer function for generating an enhanced second audio training phrase in the medical implant.

The enhanced audio training phrase may then be associated 250 with the instruction for the control of the medical implant. That is, the method may comprise training a command unit to associate the second audio training phrase to a command for the medical device. The training may comprise training a machine learning model to associate enhanced audio training phrases with commands for the medical implant.

By first creating a transfer function, any following audio input may be enhanced by using the transfer function, and thus the associating of a second audio training phrase with a command may be simpler, i.e. less computationally intense, as the quality of the enhanced audio may be better that the originally audio received by the microphone of the implant. The method also allows for avoiding training the medical implant on distorted audio or audio with a lot of noise, thus improving the quality of the training.

FIG. 126C shows a flow chart for a method 300 for using voice commands to control a medical implant, according to some embodiments. In some examples, the voice commands have been learnt with the method described with reference to FIGS. 126A and 126B.

The method 300 comprises receiving 310 an audio command phrase for the medical device. The method further comprises applying 320 a transfer function to create an enhanced audio command phrase.

The method may further comprise to determine 320 a corresponding command for the medical based on the enhance audio command phrase, and send 340 the command to the medical device. The medical device may then execute 350 the command. By running the audio command phrase through the transfer function, the audio quality of the audio command phrase may be improved, thus allowing for an easier recognition of the corresponding command. This may make the recognition or determination of the command for the medical device less computationally intensive.

Aspect 457: Controlling Energy Transfer at the Implant

Any of the implantable medical implants described herein are configured to wirelessly receive energy for powering or charging the implantable medical implant. When transferring energy to an implantable medical implant it is important to adequately control the energy transfer. If the energy transferred or received at the medical implant is excessive, it may harm the patient. For example, if the position of external device relative to the receiving unit changes during energy transfer, the energy transferred may also increase or decrease drastically. This situation could cause severe problems since the implant cannot "consume" the suddenly very high amount of supplied energy. Unused excessive energy must be absorbed in some way, resulting in the generation of heat, which is highly undesirable as it may harm the patient. Hence, if excessive energy is transferred from external device the receiving unit, the temperature of the implant will increase, which may damage the surrounding tissue or otherwise have a negative effect on body functions. It is therefore highly desirable to always supply the right amount of energy to an implanted medical device during operation. Similarly, if too much energy is received by the implant, there may be temperature increases which may harm the patient. It has thus been realized that controlling the energy transfer at the medical implant may be advantageous.

An embodiment of a system for transferring energy to an implantable medical device will now be described with reference to FIGS. 113A-113C. Alternatively. "transferring energy" may be referred to as "charging". A corresponding a method for wireless energy transfer from an external energy source located outside the patient to an internal energy receiver 305 located inside the patient is also provided.

The system comprises an external energy source, or a charger, and an internal energy receiver 305. The external energy source may be comprised in any of the external devices, i.e. devices arranged outside of the body of a patient, described herein. The internal energy receiver 305 is connected to an implantable medical device 300 for supplying received energy thereto. Internal energy receiver 305 may be configured to determine an accumulated amount of received energy; determine a current change in the received energy, determine a control signal reflecting the accumulated received energy and the change in the received energy, and controlling the energy transfer based on the control signal. As an alternative, the determination of the control signal may be omitted, and the controlling may be performed based on the accumulated amount of energy and the current change.

By "controlling the energy transfer" it may be meant or include adjusting the energy transfer efficiency, controlling switches affecting the energy transfer, controlling a part of the internal energy receiver, controlling a part of the external energy source, turning the energy transfer off completely, or any other way of affecting the energy transfer.

In one embodiment the external energy source or the internal energy receiver 305 may comprise an energy transfer controller for controlling the energy transfer. The energy transfer controller may be configured to determine the rate of change of the received energy and/or the accumulated amount of received energy, and adjust the energy transfer based on the determined parameters.

Advantageously, the energy transfer may be controlled or adjusted by the internal energy receiver 305, as the internal energy receiver 305 is capable of directly determining how much energy is received in the internal energy receiver and faster determine if there is a risk to the patient or the medical implant. Thus, the internal energy receiver 305 may be configured to determine an accumulated amount of transferred energy is determined by the internal energy receiver 305. The internal energy receiver 305 may alternatively or in combination, be configured to determine a current change in the energy transfer. Further, the internal energy receiver 305 may be configured to determine a control signal for controlling the energy transfer. The control signal may be used in the internal energy receiver 305 for adjusting the receiving of energy, or it may be transmitted to the external energy source, and the external energy source may be configured to adjust the transmitted energy based on the control signal. That is, the controlling of the energy transfer may be performed by the internal energy receiver 305.

In some examples, the controlling of the energy transfer may be performed by the external energy source.

In some examples, the internal energy receiver 305 is configured to measure, via a measuring unit, an accumulated energy received a period of time and/or to measure a current change in energy received, and to control the energy received based on the accumulated energy and/or the current change. In some examples, this may be performed using a PID regulator, which will be described in the following.

In some examples, the controller comprised in the internal energy receiver comprises a PID regulator. Such a PID regulator may be used to control the difference between a received voltage and a desired voltage level. The PID regulator may control a switch to signal to selectively de-tune the receiving coil of the internal energy receiver. Alternatively, or in combination, the PID may regulate the switch to modulate the power signal. The PID regulator may respond quickly to changes in the power levels and provides increased control over the pulse width modulation of the power signal.

A PID regulator may be used for controlling any energy transfer as discussed herein.

Aspect Pulse Width Modulation (PWM)

In some embodiments, the energy is supplied from the primary coil to the secondary coil using energy pulses. The pulses are achieved using modulation techniques. For example, modulation (PWMT—Pulse width modulation technique) of the pulses may be created with a system that controls the power using a continuous square wave pulse signal with a constant frequency where the duty cycle of the pulses is varied or a system that controls power using a continuous square wave pulse train signal with both constant frequency and constant pulse with and thereby adjusting the duty cycle width of the train of pulses. The PWMT may be used to digitally vary the amount of power from the power amplifier that drives the transmitting coil. Thus, the amount of energy transferred from the primary coil to the secondary coil may be controlled.

In some examples, the energy is supplied using a pulse pattern. In those examples, the receiving unit 305 may be configured to receive transcutaneously transferred energy in pulses according to a pulse pattern, and the measurement unit may be configured to measure a parameter related to the pulse pattern. In some examples, the controller is configured to control the energy received (for example by a variable impedance or via switches as described below) in response to the pulse pattern deviating from a predefined pulse pattern.

In some examples, the energy transmitted may be varied by varying the width of the energy pulses and having constant frequency and constant amplitude. The pulse width is achieved with a modulation technique. (hereafter PWMT) (in the preferred embodiment many times per second), to control the amount of energy transferred from the external energy transmitting coil in the system to the implanted receiver. The PWMT is used to digitally vary the amount of power from a power amplifier that drives the transmitting coil. There are several different ways to achieve the PWMT to control the amount of output energy from the power amplifier to the transmitting coil. Generally, modulation of the pulse width may be created with a system that controls the power using a continuous square wave pulse signal with a constant frequency where the duty cycle of the pulses are varied or a system that controls power using a continuous square wave pulse train signal with both constant frequency and a constant pulse width and thereby adjusting the duty cycle width of the train of pulses. These two basic techniques as well as most modifications of them can be used to control the output power of the transmitting coil.

The transmission of wireless energy from the external energy transmitting device may be controlled by applying to the external energy transmitting device electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

Advantageously, the PWM embodiments described herein may be combined with any embodiment relating to controlling energy transfer to an implantable medical device, variable impedance, resonant circuit. NFMI, large coil, or any other implantable medical device being in any way configured to receive energy wirelessly, as described herein.

Aspect Variable Impedance

According to one embodiment described with reference to FIG. 113A-113C, the controller 300 of the implantable system 10 comprises a receiving unit 305 or energy receiver 305 comprising a coil 192 (specifically shown in FIG. 65B) configured for receiving transcutaneously transferred energy. The receiving unit 305 further comprises a measurement unit 194 configured to measure a parameter related to the energy received by the coil 192 and a variable impedance 193 electrically connected to the coil 192. The receiving unit 305 further comprises a switch 195a placed between the variable impedance 193 and the coil 192 for switching off the electrical connection between the variable impedance 193 and the coil 192. The controller 300 is configured to control the variable impedance 193 for varying the impedance and thereby tune the coil 192 based on the measured parameter. The controller 300 is further configured to control the switch 195a for switching off the electrical connection between the variable impedance 193 and the coil 192 in response to the measured parameter exceeding a threshold value. As such, the coil can be tuned or switched off to reduce the amount of received energy if the amount of received energy becomes excessive.

The controller 300 may further be configured to vary the variable impedance in response to the measured parameter exceeding a threshold value. By varying the variable impedance, the tuning of the coil may be varied, thus affecting the resonant frequency of the receiving coil. In this way, the efficiency of the reception of energy may be varied.

The measurement unit 194 is configured to measure a parameter related to the energy received by the coil 192 over a time period and/or measure a parameter related to a change in energy received by the coil 192 by for example measure the derivative of the received energy over time. The variable impedance 193 is in the embodiment shown in FIG. 65B' placed in series with the coil 192. In alternative embodiments it is however conceivable that the variable impedance is placed parallel to the coil 192.

The first switch 195a is placed at a first end portion 192a of the coil 192, and the receiving unit 305 further comprises a second switch 195b placed at a second end portion of the coil 192, such that the coil 192 can be completely disconnected from other portions of the implantable system 10. The receiving unit 305 is configured to receive transcutaneously transferred energy in pulses according to a pulse pattern. The measurement unit 194 is in the embodiment shown in FIG. 65B' configured to measure a parameter related to the pulse pattern. The controller 300 is configured to control the variable impedance in response to the pulse pattern deviating from a predefined pulse pattern. The controller 300 is configured to control the switch 195a for switching off the electrical connection between the variable impedance 193 and the coil 192 in response to the pulse pattern deviating from a predefined pulse pattern. The measurement unit is configured to measure a temperature in the implantable system 10 or in the body of the patient, and the controller 300 is configured to control the first and second switch 195a. 195b in response to the measured temperature.

The variable impedance 193 may comprise a resistor and a capacitor and/or a resistor and an inductor and/or an inductor and a capacitor. The variable impedance 193 may comprise a digitally tuned capacitor or a digital potentiometer. The variable impedance 193 may comprise a variable inductor. The first and second switch comprises a semiconductor, such as a MOSFET. The variation of the impedance is configured to lower the active power that is received by the receiving unit. As can be seen in FIG. 65B", the variable impedance 193, the first and second switch 195a. 195b and the measurement unit 194 are connected to the communication unit/controller 300 and the receiving unit 305 is connected to an energy storage unit 40 such that the energy storage unit 40 can store energy received by the receiving unit 305.

Aspect 459: Resonant Circuit

Figures 128A, 128B:
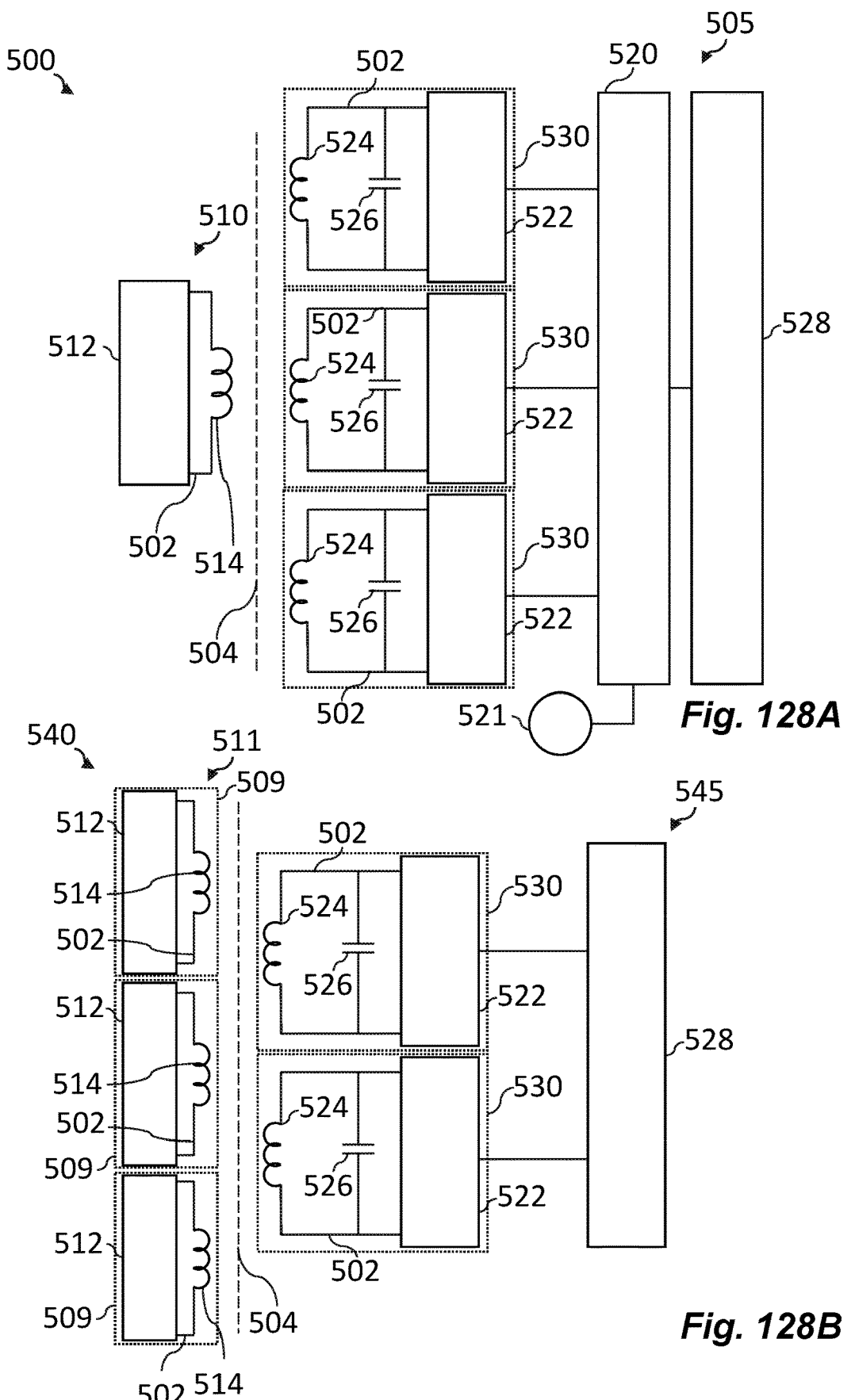
FIG. 128A-E illustrates implantable medical devices and external devices for transferring wireless energy to the implantable medical devices.

FIG. 128A schematically illustrates a system 500 comprising an external unit 510 and an implantable medical device 505. The external unit 510 is adapted to be arranged outside of a body. The implantable medical device 505 is adapted to be implanted into a body of a patient. The external unit 510 comprises a transmitting circuit 512, a transmitting coil 514 and electrical connections 502. The electrical connections 502 electrically connect the transmitting circuit 512 with the transmitting coil 514. The electrical connections 502 may, for example, be wires or any electrically conducting material, or they may be wireless electrical connections. The electrical connections 502 may have intrinsic electrical resistance.

The implantable medical device 505 comprises an energy consuming part 528. The implantable medical device 505 further comprises receiving units 530 for receiving transcutaneously transferred energy, wherein the receiving unit 530 is configured to transfer the received energy to the energy consuming part 528. In FIG. 128A, three receiving units 530 are illustrated. However, the medical device 505 may comprise any number of receiving units 530. The medical device 505 preferably comprises two or more receiving units 530.

Each receiving unit 530 comprises a receiving circuit 522, an impedance unit 526 and a receiving coil, or coil. 524, and electrical connections 502. The electrical connections 502 in the receiving unit 530 electrically connect the receiving circuit 522 to the impedance unit 526 and to the coil 524. Electrical connections 502 electrically connect the receiving unit 530 to the energy consuming part 528. The receiving unit 530 may be directly connected to the energy consuming part 528. The receiving unit 530 may be connected to intermediate circuits, wherein the intermediate circuits are connected to the energy consuming part 528. The intermediate circuits may process the output from the receiving unit 530 and prepare it for the energy consuming part 528. The intermediate circuit may comprise amplifiers, switches, filtering, modulators, other signal transformers, or a combination thereof. In FIG. 128A, the impedance units 526 are connected in parallel to the coil 524. The impedance units 526 and the respective coil 524 may instead be connected in series, partially in series and partially in parallel, or in any other way. In FIG. 128A, the impedance units 526 are capacitors. The impedance unit 526 may consist of inductors, capacitors, capacitors and resistances, inductors and resistances, or a mixture thereof. The impedance unit 526 may have a variable impedance.

The implantable medical device may further comprise a measurement unit 521 and a controller 520. The measurement unit 521 may be configured to measure a parameter related to energy transfer from the external unit 510 to the implantable medical device 505. The controller 520 may be configured to control the subcutaneously received energy to the energy consuming part 528. The controller 520 may be configured to control the subcutaneously received energy based on the parameter measured by the measurement unit 521. The controller 520 may control the impedance units 526. The controller 520 may control a variable impedance of the impedance unit 526.

The implantable medical device 505 and the external unit 510 are electrically coupled. The transmitting circuit 512 generates an alternating current in the transmitting coil 514. The alternating current of the transmitting coil 514 induces a current in the coil(s) 524. The receiving unit 530 is configured to receive transcutaneously transferred energy from the external unit 505 via the coil 524. One external unit 510 may transfer energy to many receiving units 530 having a respective coil 524.

The inductance of the coil 524 and the impedance of the corresponding impedance unit 526 contributes to a resonance frequency of the receiving unit 530. The inductance of the coils 524 and/or the impedance of the corresponding impedance unit 526 may differ in size between the respective receiving units 530. This may cause receiving units 530 to have different resonance frequencies in relation to each other. A variable impedance of the impedance unit 526 may allow the resonance frequencies of the receiving unit 530 to be tuned. The controller 520 may be able to tune the resonance frequency of each of the receiving units 530 individually by controlling the respective impedance unit 526. The receiving unit 530 may transfer different amounts of energy to the energy consuming device 528 depending on the frequency of an alternating magnetic field generated by the external device 510 and the resonance frequency of the receiving unit 530. By having different resonance frequencies for receiving units 530, a better energy transfer efficiency of the implantable medical device 505 may be obtained. Each receiving unit 530 may be designed to, or be fined tuned to, have the resonance frequency adapted to different frequencies of the external unit 510. By having different resonance frequencies of the receiving units 530, different external units 510 may be used, which is illustrated in FIG. 128B.

FIG. 128B schematically illustrates a system 540 comprising a second external unit 511 and an implantable medical device 545. The second external unit 511 comprises several transmitting units 509, wherein each transmitting unit 509 is similar to the external unit 510 illustrated in FIG. 128A, described above. The implantable medical device 545 illustrated in FIG. 128B comprises an energy consuming part 528 and receiving units 530. The energy consuming part 528 of FIG. 128B is similar to the energy consuming part 528 of FIG. 128A, described above. The receiving units 530 of FIG. 128B are similar to the receiving units 530 of FIG. 128A, described above. The implantable medical device 545 of FIG. 128B may further comprise a measurement unit and/or a controller similar to the measurement unit 521 and the controller 520 of FIG. 128A, described above.

FIG. 128B illustrates an implantable medical device 545 comprising two receiving units 530. As mentioned above, there may be any number of receiving units 530 in the implantable medical device 545. As mentioned above, the receiving units 530 are connected to the energy consuming part 528, directly or via an intermediate circuit. The receiving units 530 are adapted to receive transcutaneously transferred energy from the external device 511. The external device 511 is adapted to transmit energy to the receiving unit 530 via the transmitting units 509 in the external device 511.

The external unit 511 of FIG. 128B illustrates several transmitting units 509. The transmitting units 509 may all be comprised in one device, in separate devices, or a combination thereof. Each transmitting unit 509 may be adapted to send energy on a separate frequency. The transmitting units 509 illustrated in FIG. 128B may be configured to transmit different frequencies. A transmitting unit 509 may be comprised in any external device or remote control described herein, a charging device, such as a smartphone, a qi charger, wireless charging pad, any device comprising a coil configured to send out energy, or any device configured to produce an oscillating a magnetic field. Each receiving unit 530 may be adapted to receive energy from a different transmitting unit 509 by having its resonance frequency configured to match the frequency of the transmitting unit 509. The transmitting units 509 could transmit sequentially, simultaneously, or have one or more transmissions partially overlap.

An advantage of multiple transmitting units 509 is that a better energy transfer efficiency of the implantable medical device 545 may be obtained. Each receiving unit 530 may be tuned to receive energy of a specific frequency of a corresponding transmitting unit 509, so that the receiving units 530 could be charged by their respective transmitting unit 509. Each receiving unit 530 may receive a respective transmitted energy sequentially, simultaneously, and/or independently of the other receiving units 530. An advantageous transmitted energy for a receiving unit 530 may be energy with the frequency of the resonance frequency of the respective receiving unit 530, energy with a frequency within a symmetric or nonsymmetric range around the resonance frequency of the respective receiving unit 530, or energy with a frequency that is at an offset from the resonance frequency of the respective receiving unit 530.

Each receiving unit 530 comprises a coil 524 and a resonance frequency. The resonance frequency is a function of the coil 524. Instead of a coil 524 and one resonance frequency, a part of a coil 524 may contribute to a resonance frequency, meaning that a coil 524 may have several resonance frequencies. This is illustrated in FIG. 128C.

Figures 128C, 128D, 128E:
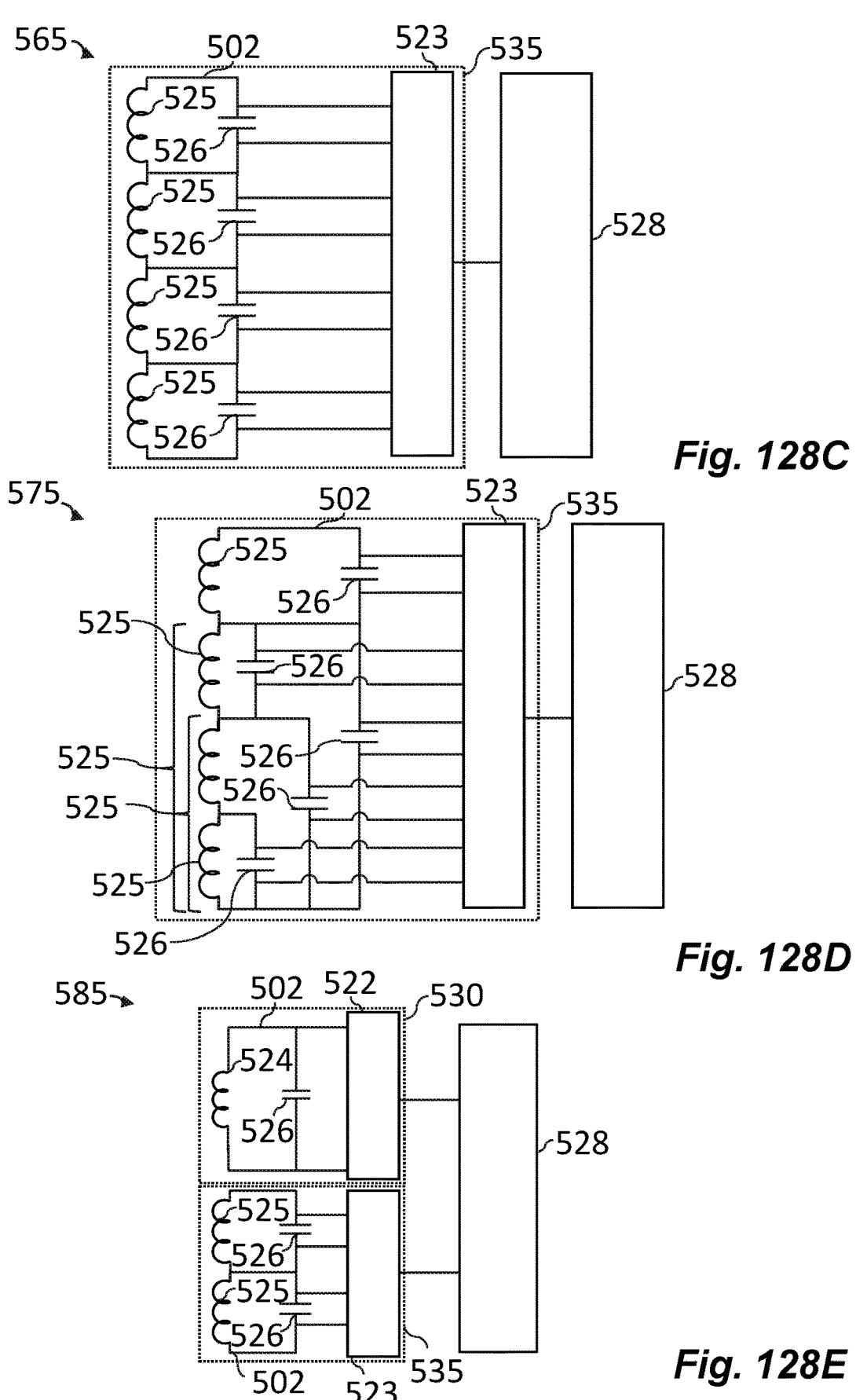

FIG. 128C schematically illustrates an implantable medical device 565. The implantable medical device 565 is adapted to be implanted into a body of a patient. The implantable medical device 565 comprises an energy consuming part 528, similar to the energy consuming parts of FIGS. 128C and 128B, described above. The implantable medical device 565 of FIG. 128C may further comprise a measurement unit and/or a controller similar to the measurement unit 521 and the controller 520 of FIG. 128A, described above. The medical device 565 may be configured to receive energy from an external unit, such as the external unit 510 of FIG. 128A and/or the external unit 511 of FIG. 128B.

The implantable medical device 565 further comprises a receiving unit 535 for receiving transcutaneously transferred energy, wherein the receiving unit 535 is configured to transfer the received energy to the energy consuming part 528. The receiving unit 535 comprises a receiving circuit 523. The receiving unit 535 comprises a receiver coil, wherein the receiver coil comprises a coil with one or more center taps, a multitude of coils in parallel, or a combination thereof. Center taps do not have to be positioned in the center of a coil. Parts of a receiver coil are coil portions 525. The receiving unit 535 of FIG. 128C further comprises impedance units 526, similar to the impedance units 526 of FIG. 128A, described above. The receiving unit 535 of FIG. 128C further comprises electrical connections 502, similar to the electrical connections 502 of FIG. 128A, described above. The electrical connections 502 connect the receiving unit 535 to the energy consuming part 528. As mentioned for the receiving unit 530 of FIG. 128A, the receiving unit 535 of FIG. 128C may be connected directly to the energy consuming part 528 or connected first to intermediate circuits, wherein the intermediate circuits are connected to the energy consuming part 528. Intermediate circuits may be the same as described for FIG. 128A above.

The electrical connections 502 in the receiving unit 535 connect the receiving circuit 523 to the impedance units 526 and the coil portions 525 so that each impedance unit 526 is connected to a respective coil portion 525. The impedance unit 526 and the respective coil portions 525 form a receiving portion. The receiving portions may be seen as akin to the receiving units 530 of FIG. 128A, described above. FIG. 128C illustrates each impedance unit 526 being connected in parallel to the respective coil portion 525. The impedance unit 526 may be connected in series, or partially in series and partially in parallel, with the respective coil portion 525. The receiving circuit 523 is connected in parallel to the impedance unit 526. The receiving circuit 523 may be connected in parallel to a portion of the impedance unit 526. The receiving circuit 523 may be connected in series with the entire, or a portion of the, impedance unit 526.

The inductance of the coil portion 525 and the impedance of the corresponding impedance unit 526 contribute to a resonance frequency of the corresponding receiving portion. The inductance of the coil portions 525 and/or the impedance of the corresponding impedance unit 526 may differ in size between the respective receiving portions. This may cause receiving portions to have different resonance frequencies in relation to each other. A variable impedance of the impedance unit 526 may be individually controlled by a controller to change the resonance frequencies of the respective receiving portions. Each receiving portion may transfer different amounts of energy to the energy consuming device 528 depending on the resonance frequency of the receiving portion and the frequency of the transcutaneous transferred energy. By having different resonance frequencies of the receiving portions, a better energy transfer efficiency of the implantable medical device 565 may be obtained. Consecutive, sequential, or independent charging may be performed, where each receiving portion receives energy of different frequencies. Each receiving portion may have a resonance frequency adapted to different transcutaneously transferred energy frequencies, from one or more external units.

Advantages of having coil portions 525 include that it may reduce the required amount of coils and the amount of material needed. FIG. 128C illustrates sequential coil portions 525, where the coil portions 525 are adjacent but not overlapping. Coil portions 525 may overlap, be separate, or be partially overlapping segments of the receiving coil. This is illustrated in FIG. 128D.

FIG. 128D illustrates an implantable medical device 575. The implantable medical device 575 comprises an energy consuming part 528, a receiving circuit 523, and impedance units 526, similar to the energy consuming part 528, receiving circuit 523, and impedance units 526 of FIG. 128C, respectively. The implantable medical device of FIG. 128D may further comprise a measurement unit and/or a controller similar to the measurement unit 521 and the controller 520 of FIG. 128A, described above. Similar to the receiving unit 530 of FIG. 128A, the receiving unit 575 of FIG. 128D may be connected directly to the energy consuming part 528 or connected first to intermediate circuits, wherein the intermediate circuits are connected to the energy consuming part 528. Intermediate circuits may be the same as described for FIG. 128A above. The medical device 575 of FIG. 128D may be configured to receive energy from an external unit, such as the external unit 510 of FIG. 128A and/or the external unit 511 of FIG. 128B.

The implantable medical device 575 further comprises coil portions 525, similar to the coil portions 525 of FIG. 128C, described above. FIG. 128D illustrates coil portions 525 that are overlapping with each other. Each coil portion 525 is connected to the respective impedance unit 526, as mentioned for the coil portions 525 and the impedance units 526 of FIG. 128C. An advantage of having overlapping coil portions 525 is that shorter or fewer coils may be used. Overlapping coil portions allow for larger inductances of the coil portions for a set receiver coil. Overlapping coil portions allows for a better energy transfer efficiency.

FIG. 128E illustrates an implantable medical device 585. The implantable medical device 585 comprises an energy consuming part 528, similar to the energy consuming part 528 of any of FIGS. 128A-128D. The implantable medical device 585 of FIG. 128E further comprise a first receiving unit 530, similar to the receiving unit 530 of FIGS. 128A and 128B. The implantable medical device 585 of FIG. 128E further comprise a second receiving unit 535, similar to the receiving unit 535 of any of FIGS. 128C and 128D. The first receiving unit 530 and the second receiving unit 535 are electrically connected to the energy consuming part 528 by electrical connections 502. As mentioned for the receiving unit 530 of FIG. 128A, the receiving unit 585 of FIG. 128E may be connected directly to the energy consuming part 528 or connected first to intermediate circuits, wherein the intermediate circuits are connected to the energy consuming part 528. Intermediate circuits may be the same as described for FIG. 128A above.

FIG. 128E illustrates a implantable medical device 585 comprising one first receiving unit 530 and one second receiving unit 535. The implantable medical device 585 may comprise more than one first receiving unit 530. The implantable medical device 585 may comprise more than one second receiving unit 535. A mix of first receiving units 530 and second receiving units 535 may allow the implantable medical device 585 to be compact and customizable. The implantable medical device 585 may comprise more than one second receiving unit 535 and no first receiving units 530.

The implantable medical device 585 of FIG. 128E may further comprise a measurement unit and/or a controller similar to the measurement unit 521 and the controller 520 of FIG. 128A. The medical device 585 may be configured to receive energy from an external unit, such as the external unit 510 of FIG. 128A and/or the external unit 511 of FIG. 128B.

In some examples, a coil comprised in the receiving unit 530 may comprise a plurality of windings. The plurality of windings may be connected to a respective variable impedance (as described above). An internal controller may control each of the variable impedances individually, thus providing for adjusting the resonant frequency of each of the windings separately. For examples, the secondary coil may comprise a first and a second winding, each connected to a respective variable impedance.

Aspect Large Coil

A system for wirelessly charging an implantable medical implant, when implanted in a body of a patient is provided. The system comprises an internal energy receiver comprising a secondary coil, the internal energy receiver being connected to the implantable medical implant and an external energy transmitter comprising a primary coil for wirelessly transmitting energy to the internal energy receiver via the secondary coil. The diameter of the primary coil is larger than a diameter of the secondary coil.

According to embodiments described with reference to FIG. 113A-113C, the controller 300 of the implantable system 10 comprises a receiving unit 305 or internal energy receiver 305 comprising a secondary coil 192 (specifically shown in FIG. 65B) configured for receiving transcutaneously transferred energy. The implantable system may receive the energy from an external device (also called an external energy transmitter), the external device being arranged outside of the body of the patient. The external device may comprise a primary coil for inducing a current in the coil 192 of the energy receiver 304 for wirelessly transfer energy to the receiving unit 305.

According to some embodiments, the primary coil is larger than the coil 192. By having the primary coil being larger than the secondary coil 192, the energy transmission may be improved. By having a diameter of the primary coil being larger than a diameter of the secondary coil, the wireless charging may be improved. For example, in previous wireless charging solution, there is a need for a great precision of arrangement of the secondary coil in relation to the primary coil. By having a larger diameter of the secondary coil, the need for precision may be reduced. Furthermore, having a larger primary coil wirelessly transmitting energy to a small secondary coil may provide for an improved energy transfer efficiency.

The implantable medical device may further comprise an internal controller connected to the internal energy receiver, for controlling the amount of energy received by the internal energy receiver. In some examples, the internal energy receiver further comprises a measurement unit for measuring a parameter related to the implantable medical implant or the body of the patient. The controller may be configured to measure the accumulated energy received by the internal energy receiver over a period of time and to measure a current change in energy received, and to control the energy received based on the accumulated energy and the current change. In some examples, the controlled comprises a Proportional-Integral-Derivative, PID, regulator for controlling the received energy.

The implantable medical device may comprise a variable impedance and/or a switch as described above.

With regards to the primary coil, the diameter of the primary coil may be more than 0.5 cm, more than 10 cm, more than 15 cm, more than 20 cm, more than 30 cm, or more than 50 cm. Alternatively, or in combination, the area of the primary coil is more than 0.5 cm2, more than 2 cm2, more than 10 cm2, more than 100 cm2, more than 300 cm2, more than 500 cm2, or more than 800 cm2.

Advantageously, any of the embodiments relating to wireless charging, for example, controlling energy transfer, PID regulation, variable impedance, large coil, and emergency backup function, among others, may be combined with any embodiment related to energy transfer described herein, for example Aspects 432, 433, 434, for an increased energy transfer safety mechanism. All of these aspects may further be combined with any type of implantable medical device or medical implant as described herein.

Aspect Emergency Backup Function

Another risk associated with an energized implantable medical device is that the implantable medical device's battery or energy storage is depleted and thus unable to energize the implantable medical device. Further, there is a risk that the internal energy receiver malfunctions, also resulting in a malfunction of the powering of the implantable medical device.

Thus, there is provided a safety mechanism that may be advantageously combined with any embodiment or aspect relating to an energized implantable medical implant described herein.

Figure 127:
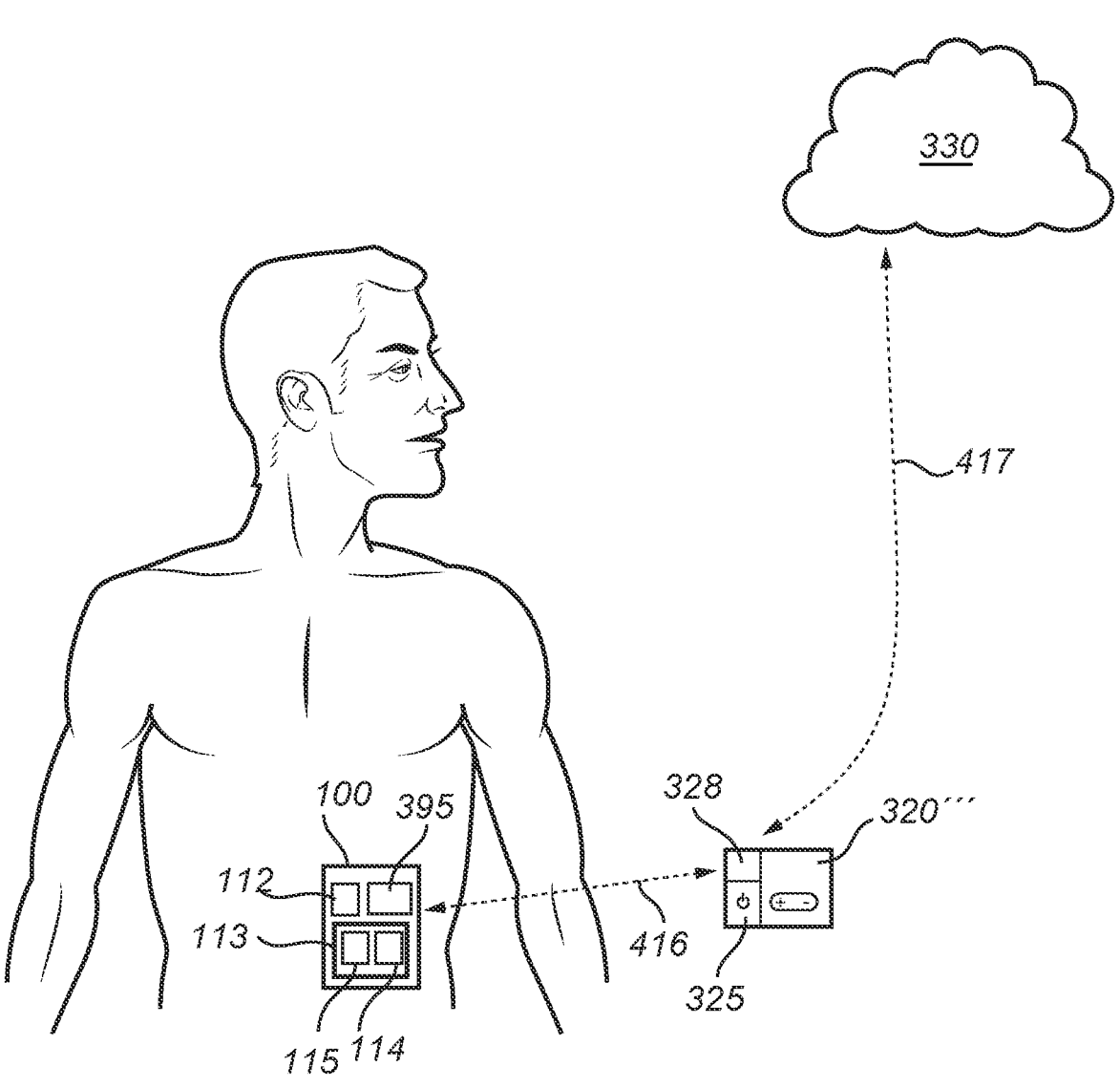
FIG. 127 shows a schematic illustration of an implantable medical device having a backup system.

FIG. 127 shows a schematic illustration of an implantable medical device 100. The implantable medical device 100 may have an active portion 112 and an internal energy receiver 395. The active portion 112 may, for example, be configured to treat, monitor or perform a function of a body of a patient. The implantable medical implant 100 may comprise or be connected to a backup system 113, the backup system 113 being adapted to perform a backup function related to the active portion 112 of the implantable medical device 100.

In some examples, the backup function relates to switching a function of the active portion 112 off. The backup function may be any function relating to the function of the active portion, such as, but not limited to: opening an artificial sphincter, stopping a stretching a stomach portion, or stopping a stimulation of tissue. In some examples, the backup system is configured to reverse a function of the medical devices. For example, if the implanted medical device is used to constrict the urethra of a patient having urinary incontinence, the user must naturally be capable of opening said constriction, in order to perform urination, even if the implantable medical device 100 is malfunctioning.

The backup system 113 may, for example, comprise a backup energy receiver 114 to receive energy from an external device (such as any of the external devices or remote controls described herein), or to perform a function of the active portion. The backup energy receiver 114 may be adapted to receive wirelessly transferred energy from an external device (which may also be referred to as an external energy transmitter). To this end, the backup energy receiver may comprise a second secondary coil for receiving such energy. For example, in a case where the implantable medical device 100 malfunctions, an external device may wirelessly transfer energy to the backup energy receiver. The backup energy receiver 114 may receive the wirelessly transferred energy and the received energy may be used by the backup system 113 to perform the backup function.

In some examples, the function of the backup system 113 is to transfer the energy received via the backup energy receiver 114 for powering the medical device 100, or it may be used to charge a battery or accumulator of the medical device 100.

In some examples, the backup system 113 may use a battery or energy storage used by the active portion 112.

The backup function may be triggered by an external device 320′″. The external device may be any external device or remote control as described herein. The external device 320′″ may be adapted to wirelessly transfer energy to the backup system, and/or be configured to trigger the backup function of the backup system 113. The backup function may thus comprise an backup internal communications unit 115 for receiving a command from the external device, and be configured to execute the received command.

In some examples, the backup function may be triggered by an error detected by a measuring unit or a controller comprised in the medical implant. Such an error may, for example, be detected by a pressure being too high or too low, a temperature being too high or low, a battery charge status being too low, a measurement value deviating from a predetermined interval, or something else.

In other examples, a malfunction of the implantable medical device 100 may relate to the programming of the implantable medical device. In that case, the backup function of the backup system may be to re-program the malfunctioning program of the implantable medical device 100. The reprogramming may be performed using any of the methods described herein.

In some examples, the backup energy receiver 114 comprises a passive or active RFID circuit adapted to be powered by the external device. In some examples, the backup energy receiver 114 comprises an NFMI energy receiver adapted to receive energy from the external device. The backup energy receiver 114 and the backup internal communication unit 115 may in some examples be comprised in the same unit, for example, in the cases where energy transmission and wireless communication may be performed using the same hardware.

Aspect 456: NFMI Communication and Wireless Energy Transfer

Any one of the medical devices described herein which utilize wireless communication in any way may be comprised in a system for communicating information from or to an implantable medical device, wherein the implantable medical device is implanted in a body of a patient. The system may comprise an internal communications unit comprised in or connected to the implantable medical device, and an external communications unit, wherein the internal communications unit and the external communications units are configured to send or receive data using near-field magnetic induction.

NFMI is a short-range wireless technology that communicates using a tightly coupled magnetic field. By the term NFMI it may be meant a short range wireless physical layer using low-power and non-propagating magnetic field. NFMI systems are designed to contain transmission energy within the localized magnetic field, and the magnetic field energy resonates around the communication system, but does not radiate into free space. The power density of near-field transmissions is restrictive and attenuates or rolls off at a rate proportional to the inverse of the range to the sixth power (1/r6) or −60 dB per decade. Thus, NFMI in the typical use only has a reach of around 1.5 to 2 meters.

NFMI signal can penetrate through human body tissue with low absorption rate. For example, the specific absorption rate (SAR) may be 100 times lower than Bluetooth. It has been realized that NFMI has a communication range through body tissue of for example 50 cm, which thus makes it advantageous to use for medical implants, as compared to RF communication which is disturbed by passing though body tissue. Thus, NFMI allows for communication with implants implanted also implanted deeper in the body.

Since NFMI has such a short rage, the possibility of an adversary to eavesdrop on communication with an implant, or to hack an implant form a distance is greatly reduced, as any adversary must be very close to the implant.

Figure 129:
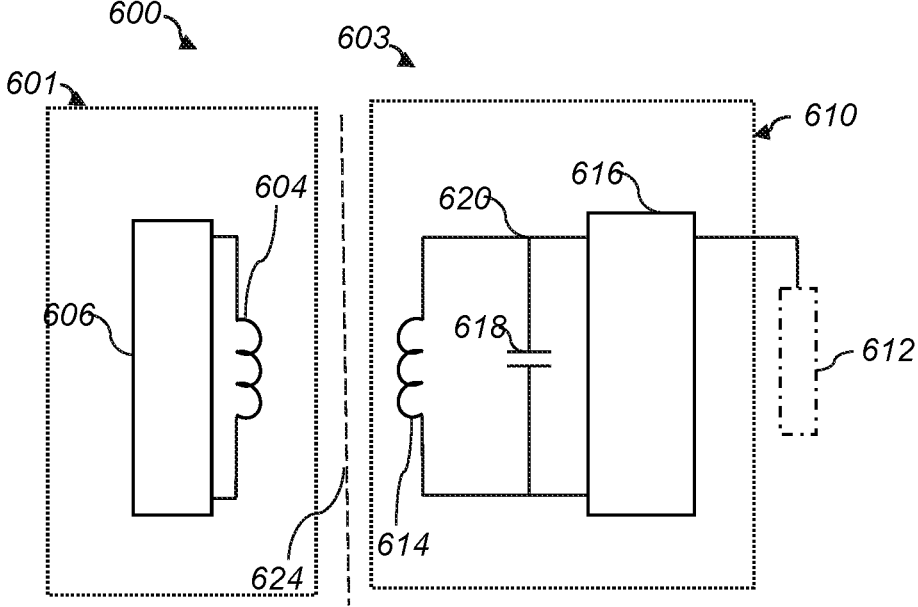
FIG. 129 illustrates an implantable medical device and an external device configured to transmit data using near-field magnetic induction.

FIG. 129 shows an example of a system 600 using NFMI communication between an external communications unit 601 and an implantable medical device 603. The communications unit 602 is configured to communicate with the implantable medical device 603 through the skin 624 of the patient using NFMI communication. The implantable medical device comprises an internal communications unit 610 (which may alternatively be referred to as a receiving unit 305 in other embodiments) and an active portion 612. The active portion 612 may be configured to monitor, treat or perform a function of a body of a patient, and may be any medical device or medical implant described herein. The communications unit 601 may be comprised in any external device described herein.

The external communications unit 601 comprises an external coil 604 connected to an external NFMI transceiver 606. The external NFMI transceiver 606 which may comprise an NFMI transmitter chip. The external coil 604 and the external NFMI transceiver are configured to modulate a magnetic field for sending data and/or energy to the implantable medical device 603. The external NFMI may further comprise a capacitor for tuning.

In turn, the internal communications unit 610 may comprise an internal coil 614 and an internal NFMI transceiver 616. To receive data, the magnetic field modulated by the external coil 604 induces a voltage on the internal coil 614, which may be measured by the internal NFMI transceiver 616 and be decoded at the internal NFMI transceiver or at another part of the implantable medical device 603. The NFMI transceiver 616 may comprise an NFMI receiver chip. The NFMI receiver chip may comprise a tunable resistor and capacitor tank. Both of the tunable capacitance and resistance may vary within a certain range to automatically compensate the detuning of NFMI antennas.

It will be appreciated that a similar method may be used for sending data from the implantable medical device via the internal communications unit 616 to the communications unit 601 via the external communications unit 606. In that examples, the internal communications unit may comprise an NFMI transmitter chip similar to the NFMI transmitter chip comprised in the external device, and the external NFMI transceiver may comprise an NFMI receiver chip similar to the NFMI receiver chip comprised in the internal NFMI transceiver, connected to a respective coil for transmitting and/or receiving data.

Modulation schemes such as amplitude modulation, phase modulation and frequency modulation typically used in RF communications may be used in NFMI communication.

In some embodiments, the active portion is not a pacemaker, hearing aid or a neurostimulation implant.

The internal communications unit is adapted to be implanted at a tissue depth of at least 8 or 10 cm. For example, the internal communications unit may be adapted to be implanted in an abdomen of a patient.

Thus, any internal wireless communication unit comprised in an implant described herein may use NFMI to communicate with an external device. For example, for transmitting data, receiving data, receiving new programming or changes to the software of the implant and/or receiving control commands. The short rage of NFMI and the tissue depth at which NFMI may be used, makes it advantageous to use for any communication between an external device, such as a patient EID 320'', a patient remote device 320''', a HCP EID, a HCP remote device, and an implantable medical device.

While the communications security between an implant and an external device is improved by the use of NFMI (as compared to RF communication), the information security may advantageously be combined with any encryption, data integrity checks or the like described herein.

For example, the internal communications unit may be configured to encrypt any data to be transmitted to the external communications unit, and the external communications unit may be configured to receive the data transmitted from the internal communications unit. In some examples, the external communications unit may be further configured to transmit that data to a server.

In a more specific example, NFMI may be used for wireless communication between an implant and a patient external interrogation device, patient EID, as described herein.

In some examples the external communications unit is configured to transmit a control command to the internal communications unit, and the internal communications unit is configured to transmit the control command to the implantable medical device. The control command may cause the implantable medical device to perform an action. The internal communications unit may, for example, be configured to transmit data, the data relating to a function of the implantable medical device or a measurement obtained by the implant.

The magnetic field may in addition to or as an alternative be used for charging or powering the medical implant. The use of NFMI for changing is an alternative or addition to any wireless charging of a medical implant described herein. In those cases, the internal communications unit is configured to store the received energy in a battery or similar, or to directly forward the received energy to the active portion 612 or another energy consuming part of the implantable medical device 603.

Using NFMI for charging a medical implant also has the advantage, compared to previous methods of charging an implant, that it is not heavily affected by passing through body tissue. For example, with the use of NFMI for charging, an implant at a tissue depth of 8 and up to 13 cm or more may be charged. This allows for practically charging an implant in almost any part of a body.

Advantageously, the NFMI communication system disclosed herein may be combined with any of aspects 250, 252, 255 and 284, and any of the embodiments described herein relating to wireless energy transfer using a coil.

According to one example, the system further comprises a second internal communications unit and a second external communications unit, wherein the second internal communications unit is adapted to receive and transmit data using a short range communications technology, and the second external communications unit is adapted to receive and transmit data using a short range communications technology, the short range communications technology having a shorter maximum range than NFMI. In one example, the short range communications technology is NFC, and the second internal communication unit comprises an NFC transceiver and the second external communication unit comprises an interrogation device for transmitting data to and from the RFID transceiver. By having these second internal and external communications unit, the implant may require a second authentication based on that the external communication unit is close to the implant, for example close enough to interrogate the NCF transceiver. Thus, it may be verified that the second external communication device is indeed close to the patient's body.

Legend

The following legend lists references used in some of the figures, description, and claims. Note that the same feature may have several labels or terms associated with it. The labels and terms in this legend are not to be seen as limiting and other nomenclature may be used in within this document in relation to specific references. The meanings of the labels and terms herein should chiefly be considered with reference to the definitions within this document and only secondarily with external uses and meanings. The references are primarily in the form of reference numerals. References for method steps are excluded from this legend.

C1-C3 Electrical/conductive/wired connection/communication 1-5

W1-W6 Wireless connection/communication 1-6

WS Wake signal

100 Implant

100*a* Internal control unit

101 Active unit

102 Communication unit

103 Wired transceiver/first transceiver/internal wired transceiver/first internal transceiver/internal transceiver/transceiver/wired transmitter 10*a* First power supply 10*b* Second power supply 104 Energy storage/Internal energy storage/internal energy source 104*a* First energy storage/first internal energy storage 104*b* Second energy storage/second internal energy storage 104*c* Energy source indicator 105 Energy receiver 105*a* First energy receiver 105*b* Second energy receiver 106 Computing unit/internal computing unit/processing unit/control unit 107 Memory/internal memory 108 Wireless transceiver/transceiver/internal wireless transceiver/transceiver/wireless receiver 1091 Wireless receiver/first wireless receiver 1092 Second wireless receiver 110 Control program/first control program 112 Second control program 114 Third control program 116 Reset function 118 Computer operating properly (COP) timer 119 Energy provider 120 Energy source 121 Frequency detector 1281 First communication system 1282 Second communication system 149 Feedback unit/internal feedback unit 150 Internal sensor/sensor/first sensor/at least one sensor 160 Internal clock 171 Implantable sensor/at least one sensor 172 Implantable manual receiver 173 Implantable switch 181 Sensation generator 182 Internal encryption unit/encryptor 183 Motor 200 External device 201 Conductive member/conduction member/electrical conduction element 203 Second wired transceiver/wired transceiver/external wired transceiver/first external transmitter/transceiver 204 Energy storage/external energy storage 205 Energy transmitter 206 Computing unit/external computing unit 207 Memory/external memory 208 Wireless transceiver/external wireless transceiver/wireless transmitter/transceiver/wireless receiver 2081 First wireless transceiver 2082 Second wireless transceiver 209 External encryption unit 210 External feedback unit 220 Verification unit 222 Fingerprint reader 250 External sensor/sensor/second sensor 260 External clock 270 Instruction provider 274 Remote control 280 Signal provider 281 Coil or magnet 290 External communication unit 300 Second external device/Controller 40 Energy storage unit 320' Health Care Provider Patient External Interrogation Device 320" Remote control 320''' Patient External Interrogation Device 325 Energy transmitter 326 Computing unit 328 Wireless transceiver 330 Dedicated Data Infrastructure 332 Health Care Provider Dedicated Device 333 Hardware key 334 Display device 334 Control interface 335 Control buttons 336 Auxiliary device 339 NFC-transmitter 344 QR-code 395 Wireless receiver 411-421 Wireless connections 400 Third external device 500 Another external device (being the generator of the second key)

550 Sensor

57 Vascular portion

58 Needle operating device

59 Intestinal portion

60 Cardiac portion

US 12,598,458 B2

393

61
Pulmonary portion
Urinary portion
62
800 At least one point (where destructive/constructive interference occurs)
801 First point/first transmitter
802 Second point/second transmitter
811 First slit
812 Second slit Numbered Aspects In the following, exemplifying numbered aspects are provided and numbered, with Arabic numerals, in groups according to their aspect. The numbered aspects are not to be seen as limiting the scope of the invention, which is defined by the appended claims. The reference numerals in the different numbered aspects are to be seen only as examples of elements in the appended drawings which correspond to elements described in the numbered aspects.

All aspects or part of aspects in the different aspects herein could be combined with any and/or all other aspects or parts thereof in any order, thus comprising; aspects or parts thereof in the same aspect in any order or combined with any and/or all aspects or parts thereof in any different aspect in any order. The connection herein between the aspects and any of its aspects or parts thereof are just examples and they are intended to be combined with each other in any combination or order. The aspects or parts thereof may therefore be connected to each other in any order of connection between the aspects or parts thereof.

Thus, all the different aspects or parts thereof could be combined with each other in any combination. Any and/or all aspects or parts thereof in one aspect could be combined with any and/or all aspects or parts thereof in any and/or all other aspects, aspect(s) or parts thereof, described elsewhere in any order or combination.

Aspect 309B eHealth Broadcasting Data

1. An implant comprising:
at least one sensor for sensing at least one physiological parameter of the patient or a functional parameter of the implant to obtain a sensed parameter, and
a communication unit configured to broadcast data;
wherein the sensor is configured to periodically sense the parameter and wherein the communication unit is configured to broadcast the data relating to the sensed parameter in response to at least one of
the sensed parameter being above a predetermined threshold,
the sensed parameter being below a predetermined threshold,
the sensed parameter being outside of a predetermined range,
a predetermined point in time,
an expiry of a time period,
a predetermined event, or
a use of the implant, wherein
the implant comprises an implantable energized medical device configured to be held in position by a tissue portion of a patient, the medical device comprising:
a first portion configured to be placed on a first side of the tissue portion, the first portion having a first cross-sectional area in a first plane and comprising a first surface configured to face a first tissue surface of the first side of the tissue portion,
a second portion configured to be placed on a second side of the tissue portion, the second side opposing the first side, the second portion having a second cross-sectional area in a second plane and comprising a second surface configured to engage a second tissue surface of the second side of the tissue portion, and
a connecting portion configured to be placed through a hole in the tissue portion extending between the first and second sides of the tissue portion, the connecting portion having a third cross-sectional area in a third plane and a fourth cross-sectional area in a fourth plane and a third surface configured to engage the first tissue surface of the first side of the tissue portion,
wherein the connecting portion is configured to connect the first portion to the second portion, wherein:
the first, second, third and fourth planes are parallel to each other,
the third cross-sectional area is smaller than the first, second and fourth cross-sectional areas, such that the first portion, second portion and connecting portion are prevented from travelling through the hole in the tissue portion in a direction perpendicular to the first, second and third planes, and
the first portion is detachably connected to at least one of the connecting portion and the second portion.
2. An implant comprising:
at least one sensor for sensing at least one physiological parameter of the patient or a functional parameter of the implant to obtain a sensed parameter, and
a communication unit configured to broadcast data;
wherein the sensor is configured to periodically sense the parameter and wherein the communication unit is configured to broadcast the data relating to the sensed parameter in response to at least one of
the sensed parameter being above a predetermined threshold,
the sensed parameter being below a predetermined threshold,
the sensed parameter being outside of a predetermined range,
a predetermined point in time,
an expiry of a time period,
a predetermined event, or
a use of the implant, wherein
the implant comprises a system for treating a patient having a disorder related to the patient's intestine, the system comprises
an artificial intestine section adapted to being implanted inside a patient's body, along with an accumulator for accumulating energy, the artificial intestine section has a first open end portion and a second open end portion in flow communication with one another, wherein at least the first open end is adapted to being connected to a surgically created opening in the patient's intestine, and
the accumulator is adapted to be charged wirelessly with energy and to be arranged so as to supply energy directly or indirectly to at least one energy consuming part of said artificial intestine section.
3. An implant comprising:
at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an artificial flow control device implantable in the patient's body and adapted to control flow of the intestinal contents from said reservoir the artificial flow control device comprises at least one pump adapted to act on said intestinal wall so as to reduce the reservoir's volume in order to empty the reservoir.

4. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an infusion device comprising an infusion needle and a drive unit coupled to the infusion needle and arranged for advancing the tip end of the infusion needle to penetrate fibrosis when the device is implanted in the patient's body, wherein at least the infusion needle and the drive unit are sized and formed for implantation in the patient's body.

5. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises a drug delivery device for injecting a drug into a patient's body such as stimulation of penis erection wherein the drug is injected into the patient's body into at least one of both a right and left corpus cavernosum, two deep arteries of the right and left corpus cavernosum, muscle tissue regulating blood flow through the right and left corpus cavernosum, and tissue in close proximity to the left and right corpus cavernosum, wherein the drug delivery device comprises a catheter adapted to be implanted outside the corpora cavernosa in close proximity thereto so as to supply the drugs through the catheter or the catheter may be adapted to be implanted in at least one of the corpora cavernosa so as to supply the drugs directly into the corpus cavernosum through the catheter.

6. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an implantable lubrication device comprising:

a reservoir that stores a lubricating fluid and, a fluid connection that introduces the stored lubricating fluid into a damaged joint when the lubrication device is implanted in a patient's body, wherein the lubricating device is configured to be completely implanted into the patient's body such that a damaged joint can post-operatively be lubricated from within the patient's body, and wherein the operative supply of lubricating fluid to the damaged joint is controlled continuously, intermittently, periodically or depending on a physical parameter of the patient, such as a fluid level within the joint.

An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time,
an expiry of a time period,
a predetermined event, or
a use of the implant, wherein
the implant comprises a device for bone adjustment in a mammal, comprising
two or more anchoring devices for attaching to a bone in said mammal,
an adjustment device for exerting force on said anchoring devices to adjust the distance between or orientation of at least two of said anchoring devices,
wherein
said anchoring devices and said adjustment device are implanted intramedullary in said mammal and wherein said adjustment device is constructed to postoperatively adjust said distance, and
the adjustment is a lengthening of a bone, a healing of a fracture, a changing of a bone angle, a reshaping of a bone, a compression of a bone, a torsion of a bone, or a combination thereof.

7. An implant comprising:
at least one sensor for sensing at least one physiological parameter of the patient or a functional parameter of the implant to obtain a sensed parameter, and
a communication unit configured to broadcast data;
wherein the sensor is configured to periodically sense the parameter and wherein the communication unit is configured to broadcast the data relating to the sensed parameter in response to at least one of
the sensed parameter being above a predetermined threshold,
the sensed parameter being below a predetermined threshold,
the sensed parameter being outside of a predetermined range,
a predetermined point in time,
an expiry of a time period,
a predetermined event, or
a use of the implant, wherein
the implant comprises an implantable drain adapted to move body fluid or a hydraulic reservoir with hydraulic treatment fluid to move hydraulic fluid, from one part of the body to another part of the body, a fluid movement device that which is completely implanted and which does not have any mechanical structure penetrating through the skin of the patient is obtained.

8. An implant comprising:
at least one sensor for sensing at least one physiological parameter of the patient or a functional parameter of the implant to obtain a sensed parameter, and
a communication unit configured to broadcast data;
wherein the sensor is configured to periodically sense the parameter and wherein the communication unit is configured to broadcast the data relating to the sensed parameter in response to at least one of
the sensed parameter being above a predetermined threshold,
the sensed parameter being below a predetermined threshold,
the sensed parameter being outside of a predetermined range,
a predetermined point in time,
an expiry of a time period,
a predetermined event, or
a use of the implant, wherein the implant comprises an apparatus for drainage of a body fluid or movement of hydraulic treatment fluid in a human or mammal patient comprising
a fluid movement device for pumping hydraulic treatment fluid or body fluid, the fluid movement device being powered by an energy source and powered by an electrical or a hydraulic motor
at least one connecting tube connected to the fluid movement device so that the fluid movement device and the tube form a drainage or hydraulic arrangement
wherein the hydraulic arrangement is adapted to be implanted inside the body of the patient, and placed so that the tube interconnects one part of the body with another part of the body and where fluid movement device is adapted to suck body fluid from the one part of the body via the tube to the other part of the body.

9. An implant comprising:
at least one sensor for sensing at least one physiological parameter of the patient or a functional parameter of the implant to obtain a sensed parameter, and
a communication unit configured to broadcast data;
wherein the sensor is configured to periodically sense the parameter and wherein the communication unit is configured to broadcast the data relating to the sensed parameter in response to at least one of
the sensed parameter being above a predetermined threshold,
the sensed parameter being below a predetermined threshold,
the sensed parameter being outside of a predetermined range,
a predetermined point in time,
an expiry of a time period,
a predetermined event, or
a use of the implant, wherein
the implant comprises an implantable device for improving the pump function of the heart of a human patient by applying an external force on the heart muscle, said device comprising
at least one heart contacting organ, periodically exerting force onto the heart following the heart contractions and adding force thereto,
a drive unit to create kinetic movement to be used by the heart contacting organ,
a fixation device adapted to be mounted in a stable position to human bone allowing said drive unit and kinetic movement to get necessary contra force,
wherein said drive unit further comprises a respiration movement compensator for compensating for the respiratory movement of the heart in relation to the stable bone position, and said drive unit is adapted to allow a movement to compensate for the respiratory movement in relation between said heart contacting organ and said bone.

10. An implant comprising:
at least one sensor for sensing at least one physiological parameter of the patient or a functional parameter of the implant to obtain a sensed parameter, and
a communication unit configured to broadcast data;
wherein the sensor is configured to periodically sense the parameter and wherein the communication unit is configured to broadcast the data relating to the sensed parameter in response to at least one of
the sensed parameter being above a predetermined threshold,
the sensed parameter being below a predetermined threshold, the sensed parameter being outside of a predetermined range, a predetermined point in time, an expiry of a time period, a predetermined event, or a use of the implant, wherein the implant comprises a male sexual impotence treatment prosthesis apparatus, comprising an operable prosthesis implantable in the cavities of the corpora cavernosa of an impotent patient to provide erect penile condition, when the prosthesis is operated, characterised by an energy transmission device for wireless transmission of energy from outside the patient's body to inside the patient's body for use in connection with the operation of the prosthesis, when the prosthesis is implanted.

11. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises a device for treatment or monitoring of an aneurysm, comprising an implantable member adapted to hold fluid, the member being adapted to be placed in connection with a blood vessel having the aneurysm and to exercise a pressure on the aneurysm, a control unit adapted to control pressure adjustments of the implantable member.

12. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an implantable blood clot removal device for removing blood clots from the vascular system of a patient comprising:

a blood flow passageway to be connected to the patient's vascular system to allow circulation of the patient's blood through the blood flow passageway, a filter provided in the blood flow passageway for collecting blood clots occurring in the blood flowing through the blood flow passageway, and a cleaning device for moving blood clots collected by the filter out of the blood flow passageway.

13. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an implantable apparatus for treating urinary retention of a mammal patient comprising:

an implantable powered member adapted exert a force from the outside on a selected part of the urinary bladder in order to discharge urine from the urinary bladder, and a control device for controlling the operation of the powered member.

14. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises a breast implant system comprises a plurality of chambers including one or more first fluid chambers and one or more second fluid chambers, wherein:

at least the first fluid chamber is to be implanted in the human body to form part of a breast implant, the second fluid chambers is implanted to form part of the breast implant or implanted inside the patient's body remote from the breast implant, the first fluid chamber is interconnected with the second fluid chamber, such that fluid can be exchanged between the first and second fluid chambers, so as to change their respective fluid content.

401

15. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an apparatus for treating obesity and/or reflux comprising at least one volume filling device adapted to be at least substantially invaginated by a stomach wall portion of the patient, wherein the volume filling device is adapted to be placed outside of the stomach wall with the outer surface of the volume filling device resting against the outside of the stomach wall, such that the volume of the food cavity is reduced in size by a volume substantially exceeding the volume of the volume filling device.

16. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises a system for treating a female patient to avoid or promote pregnancy comprising a restriction device adapted to postoperatively restrict and release an oviduct of the patient.

17. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range,

a predetermined point in time, an expiry of a time period, a predetermined event, or a use of the implant, wherein the implant comprises an apparatus for controlling a flow of sperms in a uterine tube of a female patient, the apparatus comprising: an implantable constriction device for constricting at least one portion of the uterine tube wall to at least partly constrict the uterine tube to influence the flow of sperms in the uterine tube.

18. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an implantable medical device for lubrication of a synovial joint having a joint cavity, the implantable device comprising a solid lubricant and a feeding device, wherein said feeding device is adapted to feed said solid lubricant into the joint cavity for lubricating the synovial joint.

19. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an artificial valve for implantation in a mammal body, in or adjacent to a mammal blood vessel, the artificial valve comprises a casing and an opening and closing mechanism, at least part of the opening and closing mechanism comprises a first moving part adapted to make an opening and a closing movement relative to the casing, the movements comprising movements to assume an open and a closed position for opening and closing, respectively, the blood flow through said blood vessel.

20. An implant comprising:

at least one sensor for sensing at least one physiological parameter of the patient or a functional parameter of the implant to obtain a sensed parameter, and a communication unit configured to broadcast data;

wherein the sensor is configured to periodically sense the parameter and wherein the communication unit is configured to broadcast the data relating to the sensed parameter in response to at least one of the sensed parameter being above a predetermined threshold, the sensed parameter being below a predetermined threshold, the sensed parameter being outside of a predetermined range, a predetermined point in time, an expiry of a time period, a predetermined event, or a use of the implant, wherein the implant comprises an apparatus adapted to control the flow of fluids and/or other bodily matter in a lumen that is formed by the tissue wall of a bodily organ, the apparatus comprising an implantable constriction device for constricting a portion of the tissue wall to influence the flow in the lumen, a stimulation device for stimulating the wall portion of the tissue wall, and a control device for controlling the stimulation device to stimulate the wall portion as the constriction device constricts the wall portion to cause contraction of the wall portion to further influence the flow in the lumen.

22. The implant according to any one of aspect 1-21, wherein the communication unit is configured to broadcast the information using a short to mid-range transmitting protocol.

23. The implant according to any one of aspect 1-21, wherein the information is broadcasted using at least one of: Radio Frequency type protocol, RFID type protocol, WLAN type protocol, Bluetooth type protocol, BLE type protocol, NFC type protocol, 3G/4G/5G type protocol, GSM type protocol.

24. The implant according to any one of aspect 1-21, wherein the implant further comprises a control unit connected to the sensor and to the communication unit, wherein the control unit is configured to anonymize the information.

25. The implant according to any one of aspect 1-21, wherein the implant further comprises a control unit connected to the sensor and to the communication unit, wherein the control unit is configured to encrypt the information.

26. The implant according to any one of aspect 1-21, wherein the communication unit further is configured to broadcast the information periodically.

27. The implant according to any one of aspect 1-21, further comprising a control unit configured to cause the communication unit to broadcast the information in response to a second parameter being above a predetermined threshold.

28. The implant according to any one of aspect 1-21, wherein the sensed parameter is at least one of a temperature, a pulse, a glucose level, an activity of an organ, or an acceleration.

29. The implant according to any one of aspect 1-21, further comprising an implantable energy source and an energy source indicator, wherein the energy source indicator is configured to indicate a functional status of the implantable energy source.

30. The implant according to aspect 29, wherein the functional status indicates at least one of charge level and temperature of the implantable energy source.

31. The implant according to any one of aspect 1-21, wherein the functional parameter is a parameter relating to the internal control unit.

Aspect 310C eHealth Double Encryption, Aspects 1-30

1. A system comprising:

an implant comprising:

a communication unit configured to transmit data from the body of the patient to an external device, and an encryption unit for encrypting the data to be transmitted, and an external device configured to receive the data transmitted by the communication unit, authenticate, encrypt or authenticate and encrypt the received data using a first key and transmit the encrypted received data to a third device.

2. The system according to aspect 1, wherein the encryption unit is configured to encrypt the data to be transmitted using a second key.

3. The system according to any of aspects 1 or 2, wherein the first key or the second key is implant specific information, a secret key associated with the external device, an identifier of the implant or an identifier of the communication unit.

4. The system according to any of the preceding aspects, wherein the second key is a key transmitted by the external device to the internal device.

5. The system according to any of aspects 1-3, wherein the second key is a combined key comprising a third key received by the implant form the external device.

6. The system according to any preceding aspect, wherein the first key is a combined key comprising a fourth key, wherein the fourth key is received by the external device from a verification unit connected to or comprised in the external device.

7. The system according to any preceding aspect, wherein the verification unit is configured to receive authentication input from a user, for authenticating the communication between the implant and the external device.

8. The system according to aspect 7, wherein the authentication input is a code.

9. The system according to aspect 7, wherein the authentication input is based on a biometric technique selected from the list of: a fingerprint, a palm vein structure, image recognition, face recognition, iris recognition, a retinal scan, a hand geometry, and genome comparison.

10. The system according to aspect 9, wherein the verification unit is configured to receive a fingerprint from a fingerprint reader.

11. A system according to any preceding aspect, wherein the information is broadcasted using a short to mid-range transmitting protocol.

12. A system according to any preceding aspect, wherein the information is transmitted using at least one of: Radio Frequency type protocol, RFID type protocol, WLAN type protocol, Bluetooth type protocol, BLE type protocol, NFC type protocol, 3G/4G/5G type protocol, GSM type protocol, Bluetooth 5.

13. A system according to any preceding aspect, wherein the internal device comprises a first conductive member and the external device comprises a second conductive member, wherein the first and the second conductive members are configured to transmit the data using the body as a conductor.

14. A system according to any preceding aspect, wherein the communication unit is configured to encrypt the data before transmitting the data.

15. A system according to aspect 6 wherein the external device is configured to decrypt the received data and encrypt it before transmitting the data to the third device.

16. A system according to any preceding aspect, wherein the external device is configured to transmit a request for data to the communication unit, and the communication unit is configured to in response to a request for data transmit the data to the external device.

17. A system according to any preceding aspect, wherein the communication unit further is configured to broadcast the information periodically.

18. A system according to any preceding aspect, further comprising an internal control unit configured to cause the communication unit to broadcast the information in response to a second parameter being above a predetermined threshold.

19. A method for encrypted communication between an implant, when implanted in a patient's body, and an external device, the method comprising:
  encrypting, by the implant, data relating to the implant or the operation thereof;
  transmitting, by a first communication unit comprised in the implant, the data;
  receiving, by a second communication unit comprised the external device, the data;
  encrypting, by the external device, the data using an encryption key to obtain encrypted data; and
  transmitting the encrypted data to a third external device.

20. The method according to aspect 19, wherein the encrypting, by the implant, comprises encrypting the data using a second key.

21. The method according to aspects 19 or 20, wherein the first or the second key is implant specific information, a secret key associated with the external device, an identifier of the implant or an identifier of the communication unit.

22. The method according to any of aspects 19-21, wherein the second key is a key transmitted by the external device to the internal device.

23. The method according to any of aspects 19-22, wherein the second key is a combined key comprising a third key; and the method further comprises:
  receiving, at the implant via a conductive member or wirelessly, the third key from the external device.

24. The method according to any of aspects 19-23 further comprising:
  receiving, at the external device, a fourth key from a verification unit connected to or comprised in the external device,
  wherein the verification unit is configured to receive authentication input from a user, for authenticating the communication between the implant and the external device, and
  wherein the first key is a combined key comprising a fourth key.

25. The method according to ay of aspects 19-24, wherein the authentication input is a code.

26. The method according to aspect 25, wherein the authentication input is based on a biometric technique selected from the list of: a fingerprint, a palm vein structure, image recognition, face recognition, iris recognition, a retinal scan, a hand geometry, and genome comparison.

27. The method according to aspect 25, wherein the verification unit is configured to receive a fingerprint from a fingerprint reader.

28. A computer program product comprising a computer-readable storage medium with instructions adapted to carry out the method of any one of aspects 19-28 and/or with instructions adapted to carry out an action in any of the system aspects 1-19, when executed by a computing unit in an external device having processing capability.

29. A computer program product comprising a computer-readable storage medium with instructions adapted to carry out the method of any one of aspects 19-27 and/or with instructions adapted to carry out an action in any of the system aspects 1-19, when executed by a computing unit in the implant having processing capability.

30. The implant according to any one of the following, alone or in any combination; system aspects 1-19, with ability to perform method aspects 19-28, and ability to use program product aspects 28-29, comprising an internal control unit adapted to be involved in at least a part of the actions performed by the implant in at least a part of any one of the aspects 1-29 above.

31. A system according to aspect 1-30 of Aspect 310SE comprising:
  a second key placed in the implant adapted to authenticate, encrypt or authenticate and encrypt the data before being transmitted using the second key and transmit the encrypted received data to the external device.

32. A system according to aspect 31 of Aspect 310SE wherein at least one of the following:
  a) the second key is a software key;
  b) the second key is a hardware key;
  c) the first key is a software key; and
  d) the first key is a hardware key.

33. A system according to aspect 31-32 of Aspect 310SE, wherein the third device is adapted to authenticate the implant, the external device, or the implant and the external device, and decrypt the received data using a third key.

34. A system according to aspect 31-33 of Aspect 310SE, wherein the third key comprises at least one of the following:
  a) a software key; and
  b) a hardware key.

35. A system according to aspect 31-34 of Aspect 310SE, wherein the third device comprises: a storage unit adapted to store the received data.

Aspect 310D eHealth Double Decryption Circuits,
Aspects 1-12

1. A system comprising:
an implant adapted to be implanted in a human or mammal comprising:
a communication unit configured to receive data from an external device, wherein the communication unit is controlled by a first chip, a first circuit, or a first chip and a first circuit,
a decryption unit for decrypting the data received, controlled by a second chip, a second circuit, or a second chip and a second circuit adapted to not be directly in contact with the external device,
a narrow secure communication tunnel between the first chip, a first circuit, or a first chip and a first circuit, and the second chip, a second circuit, or a second chip and a second circuit, wherein the communication unit is adapted to only communicate with the decryption unit via the narrow secure communication tunnel, and wherein the decryption unit is adapted to authenticate the original generator of the received data and authenticate that the data has not been tampered with.

2. A system according to aspect 1 of Aspect 310D, wherein the decryption unit is adapted to decrypt the received data and use the decrypted data after the decryption unit has authenticated the original generator of the received data and authenticated that the information has not been tampered with.

3. A system according to aspect 1-2 of Aspect 310D, wherein the implant comprises preprogrammed steps of action, wherein use of the decrypted data comprises instructions to select any one of the pre-programmed steps of actions of the implant.

4. A system according to aspect 1-3 of Aspect 310D, wherein use of the decrypted data comprises reprogramming part of a software of the implant to reprogram and add selectable preprogrammed steps of actions of the implant.

5. A system according to aspect 1-4 of Aspect 310D, wherein use of the decrypted data comprises reprogramming part of the implant software to change any one of usable information and actions of the implant.

6. A system according to aspect 1-5 of Aspect 310D, wherein the implant is adapted to receive data from the external device wherein the data is authenticated, encrypted or authenticated and encrypted before received.

7. A system according to aspect 1-6 of Aspect 310D, wherein a third device is adapted to authenticate, encrypt or authenticate and encrypt the data and adapted to transmit the information to the external device, wherein the external device is adapted to transmit the information to the implant untouched, relaying the information from the third device.

8. A system according to aspect 1-7 of Aspect 310D, wherein the implant is adapted to authenticate, decrypt or authenticate and decrypt the received data using a first key.

9. A system according to aspect 1-8 of Aspect 310D, wherein the external device is adapted to authenticate, encrypt, or authenticate and encrypt the transmitted data before transmitting the data, using a second key.

10. A system according to aspect 1-9 of Aspect 310D, wherein the third device is adapted to authenticate, encrypt, or authenticate and encrypt the transmitted data before transmitting the data, using a third key.

11. A system according to aspect 8-10 of Aspect 310D wherein at least one of the following:
    a) the third key is a software key;
    b) the third key is a hardware key;
    c) the second key is a software key;
    d) the second key is a hardware key;
    e) the first key is a software key; and
    f) the first key is a hardware key.

12. A system according to aspect 1-11 of Aspect 310D, wherein the decryption unit comprises a storage unit comprising information comprising at least one of authenticating information and key related information related to at least one of the external device and the third device, wherein the decryption unit is adapted to compare stored information with received data related to at least one of authentication and decryption.

Aspect 311C eHealth Data Integrity

1. A method for evaluating a functional parameter of an implant implanted in a patient, the implant comprising a processor, a sensor for measuring the functional parameter, and an internal communication unit, the method comprising:

measuring, using the sensor, the functional parameter to obtain measurement data,
establishing a connection between the internal communication unit and an external device, a third device, an external device relaying the data from a third device unchanged, or an external device and a third device configured to receive data from the implant,
determining, by the processor, a cryptographic hash or a metadata relating to the measurement data and adapted to be used by the external device to verify the integrity of the received data, and
transmitting the cryptographic hash or metadata, and
transmitting, from the communication unit, the measurement data.

2. The method according to aspect 1, further comprising, at the external device,
receiving the transmitted cryptographic hash or metadata,
receiving the measurement data, and
verifying the integrity of the measurement data with the cryptographic hash, metadata or information relating to the functional parameter.

3. The method according to any of aspects 1-2, wherein the cryptographic hash or metadata comprises a cryptographic hash, and wherein the verifying the integrity of the measurement data comprises:
calculating a second cryptographic hash for the received measurement data using a same cryptographic hash algorithm as the processor, and
determining that the measurement data has been correctly received based on that the cryptographic hash and the second cryptographic hash are equal.

4. The method according to aspect 3, wherein the cryptographic hash algorithm comprises one of: MD5, SHA1, or SHA 256.

5. The method according to any of aspects 3-4, wherein the cryptographic hash is a signature obtained by using a private key of the implant, and wherein the verifying, by the external device, comprises verifying the signature using a public key corresponding to the private key.

6. The method according to any of aspects 2-5, wherein the cryptographic hash or metadata comprises a metadata, and wherein the verifying the integrity of the data comprises:
obtaining a second metadata for the received measurement data relating to the functional parameter, and
determining that the data has been correctly received based on that metadata and the second metadata are equal.

7. The method according to aspect 5, wherein the metadata comprises: a length of the data, a timestamp, or a sensor measurement.

8. The method according to any preceding aspect, further comprising, at the external device, evaluating the measurement data relating to the functional parameter.

9. The method according to any preceding aspect, wherein the sensor is a pressure sensor, an electrical sensor, a clock, a temperature sensor, a motion sensor, an optical sensor, a sonic sensor, an ultrasonic sensor.

10. The method according to any preceding aspect, wherein the functional parameter is at least one of a temperature, a pressure, a battery status indicator, a time period length, or a pressure at a sphincter.

11. The method according to any preceding aspect, further comprising, at the external device, to determining, based on the evaluating, that the implant is functioning correctly.

12. The method according to any preceding aspect, further comprising, at the external device, determining based on the evaluating that the implant is not functioning correctly.

13. The method according to aspect 12, further comprising sending, from the external device, a corrective command to the implant, receiving the corrective command at the implant, and correcting the functioning of the implant according to the corrective command.

14. The method according to any aspect, wherein the transmitting of the measurement data is transmitted in a plurality of data packets, wherein the cryptographic mash or metadata comprises a plurality of cryptographic hashes or metadata each corresponding to a respective data packet, and wherein the transmitting of each the cryptographic hashes or metadata is performed for each of the corresponding data packets.

15. The method according to any preceding aspect, wherein the method is for evaluating a pressure at a sphincter of the patient.

16. A method of communicating instructions from an external device to an implant implanted in a patient, the method comprising:

establishing a first connection between the external device and the implant, establishing a second connection between a second external device and the implant, transmitting, from the external device, a first set of instructions to the implant over the first connection, transmitting, from the second external device, a first cryptographic hash or metadata corresponding to the first set of instructions to the implant, at the implant, verifying the integrity of the first set of instructions and the first cryptographic hash, based on the first cryptographic hash.

17. The method according to aspect 16, wherein the verifying of the integrity of the first set of instructions comprises a cyclic redundancy check.

18. The method according to any of aspects 16-17, wherein the cryptographic hash or metadata comprises a cryptographic hash, and wherein the verifying the integrity of the first set of instructions comprises:

calculating a second cryptographic hash for the received first set of instructions using a same cryptographic hash algorithm as the processor, and determining that the first set of instructions has been correctly received based on that the cryptographic hash and the second cryptographic hash are equal.

19. The method according to aspect 18, wherein the cryptographic hash algorithm comprises at least one of MD5, SHA1, or SHA 256.

20. The method according to any of aspects 16-17, wherein the cryptographic hash is a signature obtained by using a private key of the implant, and wherein the verifying comprises verifying the signature using a public key corresponding to the private key.

21. The method according to any of aspect 17-20, wherein the cryptographic hash or metadata comprises a metadata, and wherein the verifying the integrity of the data comprises:

obtaining a second metadata for the received first set of instructions, and determining that the first set of instructions has been correctly received based on that metadata and the second metadata are equal.

22. The method according to aspect 21, wherein the metadata comprises at least one of: a length of the data, and a timestamp.

32. The method according to any one of the preceding aspects, wherein the external device is separate from the second external device.

33. The method according to any one of the preceding aspects, wherein communication using the second connection is performed using a different protocol than a protocol used for communication using the first communication channel.

34. The method according to any one of the preceding aspects, wherein the first connection is a wireless connection and the second connection is an electrical connection.

35. The method according to aspect 34, wherein the second connection is an electrical connection using the patient's body as a conductor.

36. The method according to any preceding aspect, further comprising:

transmitting, by the implant, information relating to the received first set of instructions, receiving, by the external device, the information, and verifying, by the external device, that the information corresponds to the first set of instructions sent by the external device.

37. The method according to aspect 36, wherein the information comprises a length of the first set of instructions.

38. The method according to any preceding aspect, further comprising:

at the implant, verifying the authenticity of the first set of instructions by i. calculating a second cryptographic hash for the first set of instructions, ii. comparing the second cryptographic hash with the first cryptographic hash, iii. determining that the first set of instructions are authentic based on that the second cryptographic hash is equal to the first cryptographic hash upon verification of the authenticity of the first set of instructions, storing them at the implant.

39. The method according to any preceding aspect, wherein the first set of instructions comprises a cryptographic hash corresponding to a previous set of instructions.

40. The method according to any preceding aspect, further comprising:

measuring, by the implant using a first sensor, a parameter relating to the body of the patient to obtain a first measurement, measuring, by the external device using a second sensor, the parameter relating to the body of the patient to obtain a second measurement, wherein the first set of instructions comprises the second measurement relating to the body of the patient, and wherein the verification of the authenticity of the first set of instructions comprises comparing the first and the second measurements.

41. The method according to aspect 40, wherein the first and second parameters relate to a pulse of the patient, a respiration rate of the patient, a temperature of the patient, a sound of the patient, or a physical movement of the patient.

42. The method according to aspect 40 or 41, wherein the measured parameter by the external device is provided with a timestamp, and the measured parameter measured by the implant is provided with a timestamp, wherein the comparison of the parameter measured at the implant to the parameter measured by the external device comprises comparing the timestamp of the measured parameter received from the implant to the timestamp of the measured parameter by the external device.

43. A system for communication instructions, the system comprising:

an implant adapted to be implanted in a patient, the implant comprising an active unit, an internal communication unit and an internal controller, an external device comprising an external communication unit configured to transmit a first set of instructions to the internal communication unit over a first communications connection, a second external device comprising a third communication unit configured to transmit a first cryptographic hash to the internal communication unit, wherein the internal controller is configured to receive, via the internal communication unit, the first set of instructions and the first cryptographic hash and verify the integrity of the first set of instructions based on the first cryptographic hash.

44. The system according to aspect 43, wherein the internal controller is configured to verify the integrity of the first set of instructions using a cyclic redundancy check.

45. The system according to any of aspects 43-44, wherein the cryptographic hash or metadata comprises a cryptographic hash, and wherein the internal controller is configured to verifying the integrity of the first set of instructions by:

calculating a second cryptographic hash for the received first set of instructions using a same cryptographic hash algorithm as the processor, and determining that the first set of instructions has been correctly received based on that the cryptographic hash and the second cryptographic hash are equal.

46. The system according to aspect 45, wherein the cryptographic hash algorithm comprises one of:

47. The system according to any of aspects 45-46, wherein the cryptographic hash is a signature obtained by using a private key of the implant, and wherein the internal controller is configured to verifying the first set of instructions by the signature using a public key corresponding to the private key.

48. The system according to any of aspects 45-47, wherein the cryptographic hash or metadata comprises a metadata, and wherein the internal controller is configured to verifying the integrity of the data by:

obtaining a second metadata for the received first set of instructions, and determining that the first set of instructions has been correctly received based on that metadata and the second metadata are equal.

49. The method according to aspect 48, wherein the metadata comprises: a length of the data, a timestamp, . . . .

50. The system according to any of aspects 43-49, wherein the external device is separate from the second external device.

51. The system according to any of aspects 43-50, wherein the internal controller is configured to communicate with the second external device using a different protocol than a protocol used for communication with the external device.

52. The system according to any of aspects 43-51, wherein the internal communication unit comprises a wireless transceiver for communication with the external device, and a conductive member for communicating with the second external device, wherein the second external device comprises a second conductive member.

53. The system according to aspect 52, wherein the communication between the internal communication unit and the second external device is performed using the patient's body as a conductor.

54. The system according to any of aspects 43-53, wherein the internal controller is configured to transmit information relating to the received first set of instructions to the external device, and the external device is configured to confirm that the information relates to the first set of instructions transmitted by the external device.

55. The system according to any of aspects 43-54, wherein the internal controller is configured to:

calculating a second cryptographic hash for the first set of instructions, comparing the second cryptographic hash with the first cryptographic hash, determining that the first set of instructions are authentic based on that the second cryptographic hash is equal to the first cryptographic hash, and upon verification of the authenticity of the first set of instructions, storing them at the implant.

56. The system according to any of aspects 43-55, wherein the external device is configured to transmit the first set of instructions, and wherein the first set of instructions comprises a cryptographic hash corresponding to a previous set of instructions.

57. The system according to any of aspects 43-56, wherein the internal controller is connected to or comprising a first sensor adapted to obtain a measurement of a parameter relating to the body of the patient.

the external device is connected to or comprising a second sensor adapted to obtain a measurement of the parameter relating to the body of the patient, wherein the first set of instructions comprises the second measurement, and wherein the internal controller is configured to verify the authenticity of the first set of instructions at least based on a comparison of the first and second measurements.

58. The system according to aspect 57, wherein the first and second parameters relate to a pulse of the patient, a respiration rate of the patient, a temperature of the patient, a sound of the patient, or a physical movement of the patient.

59. The system according to any of aspects 57-58, wherein the measured parameter by the external device is provided with a timestamp, and the measured parameter measured by the implant is provided with a timestamp, wherein the comparison of the parameter measured at the implant to the parameter measured by the external device comprises comparing the timestamp of the measured parameter received from the implant to the timestamp of the measured parameter by the external device.

60. A computer program product comprising a computer-readable storage medium with instructions adapted to carry out the method of any one of aspects 1-42 and/or with instructions adapted to carry out an action in any of the system aspects 53-59, when executed by a computing unit in an external device having processing capability.

61. A computer program product comprising a computer-readable storage medium with instructions adapted to carry out the method of any one of aspects 1-42 and/or with instructions adapted to carry out an action in any of the system aspects 53-59, when executed by a computing unit in the implant having processing capability.

62. The implant according to any one of the following, alone or in any combination; system aspects 43-59, with ability to perform method aspects 1-42, and ability to use program product aspects 60-61, comprising an internal control unit adapted to be involved in at least a part of the actions performed by the implant in at least a part of any one of the aspects 1-61 above.

Aspect 311D eHealth Data Integrity

1. A system for communicating with an implant when implanted in a mammal or patient, the implant comprising a processor, and an internal communication unit, the implant is adapted to communicate with a third device directly and indirectly being external to the body, wherein
    the internal communication unit is adapted to receive data from the third device directly and indirectly, wherein the data is adapted to include a cryptographic hash or a metadata relating to the data adapted to be used by the internal communication unit to verify the authentication, unhampering of, or authentication and unhampering of the received data, wherein
    the cryptographic hash or metadata is compared to the storage unit comprising such hash or data stored.
2. The method according to aspect 1, further comprising, at the external device,
    receiving the transmitted cryptographic hash or metadata,
    receiving the measurement data, and
    verifying the integrity of the measurement data with the cryptographic hash, metadata or information relating to the functional parameter.
3. The method according to any of aspects 1-2, wherein the cryptographic hash or metadata comprises a cryptographic hash, and wherein the verifying the integrity of the measurement data comprises:
    calculating a second cryptographic hash for the received measurement data using a same cryptographic hash algorithm as the processor, and
    determining that the measurement data has been correctly received based on that the cryptographic hash and the second cryptographic hash are equal.
4. The method according to aspect 3, wherein the cryptographic hash algorithm comprises one of: MD5, SHA1, or SHA 256.
5. The method according to any of aspects 3-4, wherein the cryptographic hash is a signature obtained by using a private key of the implant, and wherein the verifying, by the external device, comprises verifying the signature using a public key corresponding to the private key.
6. The method according to any of aspects 2-5, wherein the cryptographic hash or metadata comprises a metadata, and wherein the verifying the integrity of the data comprises:
    obtaining a second metadata for the received measurement data relating to the functional parameter, and
    determining that the data has been correctly received based on that metadata and the second metadata are equal.
7. The method according to aspect 5, wherein the metadata comprises: a length of the data, a timestamp, or a sensor measurement.
8. The method according to any preceding aspect, further comprising, at the external device, evaluating the measurement data relating to the functional parameter.
9. The method according to any preceding aspect, wherein the sensor is a pressure sensor, an electrical sensor, a clock, a temperature sensor, a motion sensor, an optical sensor, a sonic sensor, an ultrasonic sensor.

10. The method according to any preceding aspect, wherein the functional parameter is at least one of a temperature, a pressure, a battery status indicator, a time period length, or a pressure at a sphincter.
11. The method according to any preceding aspect, further comprising, at the external device, to determining, based on the evaluating, that the implant is functioning correctly.
12. The method according to any preceding aspect, further comprising, at the external device, determining based on the evaluating that the implant is not functioning correctly.
13. The method according to aspect 12, further comprising
    sending, from the external device, a corrective command to the implant,
    receiving the corrective command at the implant, and
    correcting the functioning of the implant according to the corrective command.
14. The method according to any aspect,
    wherein the transmitting of the measurement data is transmitted in a plurality of data packets,
    wherein the cryptographic mash or metadata comprises a plurality of cryptographic hashes or metadata each corresponding to a respective data packet, and
    wherein the transmitting of each the cryptographic hashes or metadata is performed for each of the corresponding data packets.
15. The method according to any preceding aspect, wherein the method is for evaluating a pressure at a sphincter of the patient.
16. A method of communicating instructions from an external device to an implant implanted in a patient, the method comprising:
    establishing a first connection between the external device and the implant,
    establishing a second connection between a second external device and the implant,
    transmitting, from the external device, a first set of instructions to the implant over the first connection,
    transmitting, from the second external device, a first cryptographic hash or metadata corresponding to the first set of instructions to the implant,
    at the implant, verifying the integrity of the first set of instructions and the first cryptographic hash, based on the first cryptographic hash.
17. The method according to aspect 16, wherein the verifying of the integrity of the first set of instructions comprises a cyclic redundancy check.
18. The method according to any of aspects 16-17, wherein the cryptographic hash or metadata comprises a cryptographic hash, and wherein the verifying the integrity of the first set of instructions comprises:
    calculating a second cryptographic hash for the received first set of instructions using a same cryptographic hash algorithm as the processor, and
    determining that the first set of instructions has been correctly received based on that the cryptographic hash and the second cryptographic hash are equal.
19. The method according to aspect 18, wherein the cryptographic hash algorithm comprises at least one of MD5, SHA1, or SHA 256.
20. The method according to any of aspects 16-17, wherein the cryptographic hash is a signature obtained by using a private key of the implant, and wherein the verifying comprises verifying the signature using a public key corresponding to the private key.

21. The method according to any of aspect 17-20, wherein the cryptographic hash or metadata comprises a metadata, and wherein the verifying the integrity of the data comprises:

obtaining a second metadata for the received first set of instructions, and determining that the first set of instructions has been correctly received based on that metadata and the second metadata are equal.

22. The method according to aspect 21, wherein the metadata comprises at least one of: a length of the data, and a timestamp.

32. The method according to any one of the preceding aspects, wherein the external device is separate from the second external device.

33. The method according to any one of the preceding aspects, wherein communication using the second connection is performed using a different protocol than a protocol used for communication using the first communication channel.

34. The method according to any one of the preceding aspects, wherein the first connection is a wireless connection and the second connection is an electrical connection.

35. The method according to aspect 34, wherein the second connection is an electrical connection using the patient's body as a conductor.

36. The method according to any preceding aspect, further comprising:

transmitting, by the implant, information relating to the received first set of instructions, receiving, by the external device, the information, and verifying, by the external device, that the information corresponds to the first set of instructions sent by the external device.

37. The method according to aspect 36, wherein the information comprises a length of the first set of instructions.

38. The method according to any preceding aspect, further comprising:

at the implant, verifying the authenticity of the first set of instructions by i. calculating a second cryptographic hash for the first set of instructions, ii. comparing the second cryptographic hash with the first cryptographic hash.

iii. determining that the first set of instructions are authentic based on that the second cryptographic hash is equal to the first cryptographic hash upon verification of the authenticity of the first set of instructions, storing them at the implant.

39. The method according to any preceding aspect, wherein the first set of instructions comprises a cryptographic hash corresponding to a previous set of instructions.

40. The method according to any preceding aspect, further comprising:

measuring, by the implant using a first sensor, a parameter relating to the body of the patient to obtain a first measurement.

measuring, by the external device using a second sensor, the parameter relating to the body of the patient to obtain a second measurement, wherein the first set of instructions comprises the second measurement relating to the body of the patient, and wherein the verification of the authenticity of the first set of instructions comprises comparing the first and the second measurements.

41. The method according to aspect 40, wherein the first and second parameters relate to a pulse of the patient, a respiration rate of the patient, a temperature of the patient, a sound of the patient, or a physical movement of the patient.

42. The method according to aspect 40 or 41, wherein the measured parameter by the external device is provided with a timestamp, and the measured parameter measured by the implant is provided with a timestamp, wherein the comparison of the parameter measured at the implant to the parameter measured by the external device comprises comparing the timestamp of the measured parameter received from the implant to the timestamp of the measured parameter by the external device.

43. A system for communication instructions, the system comprising:

an implant adapted to be implanted in a patient, the implant comprising an active unit, an internal communication unit and an internal controller, an external device comprising an external communication unit configured to transmit a first set of instructions to the internal communication unit over a first communications connection, a second external device comprising a third communication unit configured to transmit a first cryptographic hash to the internal communication unit, wherein the internal controller is configured to receive, via the internal communication unit, the first set of instructions and the first cryptographic hash and verify the integrity of the first set of instructions based on the first cryptographic hash.

44. The system according to aspect 43, wherein the internal controller is configured to verify the integrity of the first set of instructions using a cyclic redundancy check.

45. The system according to any of aspects 43-44, wherein the cryptographic hash or metadata comprises a cryptographic hash, and wherein the internal controller is configured to verifying the integrity of the first set of instructions by:

calculating a second cryptographic hash for the received first set of instructions using a same cryptographic hash algorithm as the processor, and determining that the first set of instructions has been correctly received based on that the cryptographic hash and the second cryptographic hash are equal.

46. The system according to aspect 45, wherein the cryptographic hash algorithm comprises one of:

47. The system according to any of aspects 45-46, wherein the cryptographic hash is a signature obtained by using a private key of the implant, and wherein the internal controller is configured to verifying the first set of instructions by the signature using a public key corresponding to the private key.

48. The system according to any of aspects 45-47, wherein the cryptographic hash or metadata comprises a metadata, and wherein the internal controller is configured to verifying the integrity of the data by:

obtaining a second metadata for the received first set of instructions, and determining that the first set of instructions has been correctly received based on that metadata and the second metadata are equal.

49. The method according to aspect 48, wherein the metadata comprises: a length of the data, a timestamp, . . . .

50. The system according to any of aspects 43-49, wherein the external device is separate from the second external device.

51. The system according to any of aspects 43-50, wherein the internal controller is configured to communicate with the second external device using a different protocol than a protocol used for communication with the external device.

52. The system according to any of aspects 43-51, wherein the internal communication unit comprises a wireless transceiver for communication with the external device, and a conductive member for communicating with the second external device, wherein the second external device comprises a second conductive member.

53. The system according to aspect 52, wherein the communication between the internal communication unit and the second external device is performed using the patient's body as a conductor.

54. The system according to any of aspects 43-53, wherein the internal controller is configured to transmit information relating to the received first set of instructions to the external device, and the external device is configured to confirm that the information relates to the first set of instructions transmitted by the external device.

55. The system according to any of aspects 43-54, wherein the internal controller is configured to:
    calculating a second cryptographic hash for the first set of instructions,
    comparing the second cryptographic hash with the first cryptographic hash,
    determining that the first set of instructions are authentic based on that the second cryptographic hash is equal to the first cryptographic hash, and
    upon verification of the authenticity of the first set of instructions, storing them at the implant.

56. The system according to any of aspects 43-55, wherein the external device is configured to transmit the first set of instructions, and wherein the first set of instructions comprises a cryptographic hash corresponding to a previous set of instructions.

57. The system according to any of aspects 43-56, wherein
    the internal controller is connected to or comprising a first sensor adapted to obtain a measurement of a parameter relating to the body of the patient,
    the external device is connected to or comprising a second sensor adapted to obtain a measurement of the parameter relating to the body of the patient,
    wherein the first set of instructions comprises the second measurement, and wherein the internal controller is configured to verify the authenticity of the first set of instructions at least based on a comparison of the first and second measurements.

58. The system according to aspect 57, wherein the first and second parameters relate to a pulse of the patient, a respiration rate of the patient, a temperature of the patient, a sound of the patient, or a physical movement of the patient.

59. The system according to any of aspects 57-58, wherein the measured parameter by the external device is provided with a timestamp, and the measured parameter measured by the implant is provided with a timestamp, wherein the comparison of the parameter measured at the implant to the parameter measured by the external device comprises comparing the timestamp of the measured parameter received from the implant to the timestamp of the measured parameter by the external device.

60. A computer program product comprising a computer-readable storage medium with instructions adapted to carry out the method of any one of aspects 1-42 and/or with instructions adapted to carry out an action in any of the system aspects 53-59, when executed by a computing unit in an external device having processing capability.

61. A computer program product comprising a computer-readable storage medium with instructions adapted to carry out the method of any one of aspects 1-42 and/or with instructions adapted to carry out an action in any of the system aspects 53-59, when executed by a computing unit in the implant having processing capability.

62. The implant according to any one of the following, alone or in any combination; system aspects 43-59, with ability to perform method aspects 1-42, and ability to use program product aspects 60-61, comprising an internal control unit adapted to be involved in at least a part of the actions performed by the implant in at least a part of any one of the aspects 1-61 above.

Aspect 312C eHealth Programming Predefined
Steps, Aspects 1-46

1. An implant comprising:
an internal computing unit configured to control a function of said implant, said internal computing unit comprises an internal memory configured to store:
    i. a first control program for controlling the internal computing unit, and
    ii. a second, configurable or updatable or selectable, predefined program steps, control program for controlling said function of said implant,
    iii. a set of predefined program steps for updating and selecting predefined program steps of the second control program,
an internal communication unit connected to said internal computing unit and configured to communicate with an external device, a third device, or an external device receiving a data from a third device, wherein said internal computing unit is configured to receive an update and selection of preprogrammed steps to the second control program via said internal communication unit, and
a verification unit or function of, connected to, or transmitted to said internal computing unit, said verification function being configured to verify that the received update and selection of preprogrammed steps to the second control program comprises program steps comprised in the set of predefined program steps.

2. The implant according to any preceding aspect, wherein the predefined program steps comprise setting a variable related to a pressure, a time, a minimum or maximum temperature, a current, a voltage, an intensity, a frequency, an amplitude of electrical stimulation, a feedback, a post-operative mode or a normal mode, a catheter mode, a fibrotic tissue mode, an time open after urination, a time open after urination before bed-time.

3. The implant according to any preceding aspect, wherein the verification function is configured to reject the update in response to the update comprising program steps not comprised in the set of predefined program steps.

4. The implant according to any preceding aspect, wherein the verification function is configured to allow the update in response to the update only comprising program steps comprised in the set of predefined program steps.

5. The implant according to aspect 1, wherein the internal communication unit is configured to communicate with the external device via a first wireless connection for receiving the update to the second control program, and a second connection for performing an authentication of the communication with the external device.

6. The implant according to aspect 5, wherein the second connection is a wireless short-range connection.

7. The implant according to aspect 5 or 6, wherein the authentication second connection is an electrical connection using the patient's body as a conductor 8. The implant according to any preceding aspect, wherein the internal computing unit is further configured to, upon verification, installing the update.

9. The implant according to any preceding aspect, wherein the internal computing unit has a sleep mode and an active mode, and the implant further comprises a sensor configured to detect a wake signal, and wherein the implant is configured to in response to a detected wake signal set the internal computing unit to the active mode.

10. The implant according to aspect 9, wherein sensor is configured to detect an acoustic signal as wake signal or wherein the sensor is configured to detect a magnetic signal as the wake signal 11. The implant according to any of aspects 9-10, wherein
the sensor is configured to detect the received signal strength of a signal; and
the implant is further configured to set the internal computing unit to the active mode in response to the sensor detecting a signal exceeding a threshold signal strength.

12. The implant according to any of aspects 9-11, further comprising a second internal computing unit, and wherein the implant is configured to set the internal computing unit to the active mode via the second internal computing unit.

13. The implant according to any of aspects 9-12, wherein the internal computing unit in the sleep mode is substantially without power, and wherein setting the internal computing unit in the active mode comprises providing the internal computing unit with power.

14. The implant according to aspect 13, wherein the implant comprises an energy controller for controlling the power supplied to the internal computing unit.

15. The implant according to aspect 14, wherein the sensor is configured to provide the energy controller with a second wake signal in response to detecting the wake signal, and wherein the energy controller is configured to set the computing unit in the active mode in response to the second wake signal.

16. The implant according to any preceding aspect, wherein
the sensor is configured to detect the received signal strength of a signal; and
the internal control unit is further configured to set the internal computing unit to the active mode in response to the sensor detecting a signal exceeding a threshold signal strength.

17. The implant according to any preceding aspect, wherein
the wake signal comprises a predetermined signal pattern; and
the implant is further configured to set the processing unit to the active mode in response to the sensor detecting the predetermined signal pattern.

18. The implant according to any preceding aspect, wherein the sensor is a hall effect sensor, a fluxgate sensor, an ultra-sensitive magnetic field sensor or a magneto-resistive sensor.

19. The implant according to any preceding aspect, wherein the sensor comprises a third coil having an iron core.

20. The implant according to any preceding aspect, wherein the sensor is comprised in the internal communication unit.

21. The implant according to any preceding aspect, further comprising a frequency detector, communicatively coupled to the internal computing unit and configured to detect a frequency for data communication between the internal communication unit and an external device configured to transmit a frequency indicator signal.

22. The implant according to aspect 21, wherein the frequency detector comprises an antenna.

23. The implant according to any preceding aspect, wherein the internal communication unit comprises a coil or a high-sensitivity magnetic field detector for communicating with the external device.

24. The implant according to any preceding aspect, further comprising:
a sensation generator configured to generate a sensation detectable by a sense of the patient, the sensation generator being communicatively coupled to the internal control unit and being configured to, upon request, generate the sensation when the implant is implanted in the patient.

25. The implant according to aspect 24, wherein the sensation generator is configured to receive the request from the internal control unit of the implant.

26. The implant according to any of aspects 24-25, wherein the sensation generator is configured to create the sensation or sensation components by at least one of:
a vibration of the sensation generator; producing a sound; providing a photonic signal; providing a light signal; providing an electric signal; and a heat signal.

27. The implant according to any of aspects 24-26, wherein the sensation generator is configured to be implanted in the patient.

28. The implant according to any of aspects 24-27, wherein the sensation generator is configured to be worn in contact with the skin of the patient.

29. the implant according to any of aspects 24-27, the sensation generator is configured generate the sensation without being in physical contact with the patient.

30. A method for programming an implant by an external device, implant comprising an internal computing unit configured to control a function of said implant and an internal memory configured to store: a first control program for controlling the internal computing unit, a second, updatable or configurable, control program for controlling said function of said implant, and a set of predefined program steps for updating the second control program, the external device being configured to communicate with the implant via a first connection, comprising:
providing, at the internal computing unit, a set of predefined program steps for updating the second control program;
transmitting, by the external device, an update comprising a subset of the predefined program steps over the first connection;
receiving, at the internal computing unit, the update,
verifying, by the internal computing unit, that the update comprises a subset of the predefined program steps, and
upon verification of the instructions, running the update at the implant.

31. The method according to aspect 30, wherein the predefined program steps comprise setting a variable related to a pressure, a time, a minimum or maximum temperature, a current, a voltage, an intensity, a frequency, an amplitude of electrical stimulation, a feedback, a post-operative mode or a normal mode, a catheter mode, a fibrotic tissue mode, an time open after urination, a time open after urination before bed-time.

32. The method according to any of aspects 30-31, wherein the verifying comprises rejecting the update in response to the update comprising program steps not comprised in the set of predefined program steps.

33. The method according to any of aspects 30-32, wherein the verifying comprises allowing the update in response to the update only comprising program steps comprised in the set of predefined program steps.

34. The method according to any of aspects 30-33, further comprising:

authenticating the communication between the implant and the external device over a second connection.

35. The method according to any of aspects 30-34, wherein the second connection is a wireless short-range connection.

36. The method according to any of aspects 34-35, wherein the second connection is an electrical connection using the patient's body as a conductor.

37. The method according to any of aspects 30-36, further comprising, upon verification, installing the update.

38. The method according to any of aspects 30-36, further comprising:

monitoring for signals by a sensor connected to the internal computing unit;

providing, from a signal provider comprised in the external control unit, a wake signal;

setting, by the internal computing unit and in response to a detected wake signal, a mode of a portion of the internal control unit from a sleep mode to an active mode.

39. The method according to aspect 38, wherein the portion of the internal computing unit is the first control program or the second control program.

40. The method according to any of aspects 38-39, further comprising detecting, using a frequency detector, a frequency for the first communication channel between a first communication unit and a second communication unit, the first communication unit being associated with the internal control unit and the second communication unit being associated with the external device, wherein the frequency detector is communicatively coupled to the internal computing unit.

41. The method according to aspect 40, further comprising:

determining, using the frequency detector, the frequency for the first communication channel.

42. The method according to aspect 40, further comprising:

generating, using a sensation generator communicatively coupled to the internal control unit, a sensation detectable by a sense of the patient in response to verifying the update, in response to running the update or in response to the update being installed at the implant.

43. The method according to aspect 42, wherein the generating comprises at least one of: providing a vibration of the sensation generator; producing a sound; providing a photonic signal; providing a light signal; providing an electric signal; and providing a heat signal.

44. A computer program product comprising a computer-readable storage medium with instructions adapted to carry out the method of any one of aspects 30-43 and/or with instructions adapted to carry out an action in any of the implant aspects 1-29, when executed by a computing unit in an external device having processing capability.

45. A computer program product comprising a computer-readable storage medium with instructions adapted to carry out the method of any one of aspects 30-43 and/or with instructions adapted to carry out an action in any of the implant aspects 1-29, when executed by a computing unit in the implant having processing capability.

46. The implant according to any one of the following, alone or in any combination; implant aspects 1-29, with ability to perform method aspects 30-43, and ability to use program product aspects 44-45, comprising an internal control unit adapted to be involved in at least a part of the actions performed by the implant in at least a part of any one of the aspects 1-45 above.

Aspect 312D eHealth Reprogramming of the
Preprogrammed Steps, Aspects 1

1. An implant comprising:
an internal computing unit configured to control a function of said implant, said internal computing unit comprises an internal memory configured to store:
i. a first control program for controlling the internal computing unit, and
ii. a second, configurable or updatable or programmable, of predefined program steps, control program for controlling said function of said implant,
iii. a set of predefined program steps for selecting predefined program steps of the second control program,
an internal communication unit connected to said internal computing unit and configured to communicate with an external device, a third device, or an external device receiving a data from a third device, wherein said internal computing unit is configured to receive an update and change to reprogram the preprogrammed steps of the second control program via said internal communication unit, and
a verification unit or function of, connected to, or transmitted to said internal computing unit, said verification unit or function being configured to verify that the received update and reprograming with change of the preprogrammed steps to the second control program, comprises program steps comprised in the set of program limitation stored in the internal memory.

2. The implant according to any preceding aspect, wherein the predefined program steps comprise setting a variable related to a pressure, a time, a minimum or maximum temperature, a current, a voltage, an intensity, a frequency, an amplitude of electrical stimulation, a feedback, a post-operative mode or a normal mode, a catheter mode, a fibrotic tissue mode, an time open after urination, a time open after urination before bed-time.

3. The implant according to any preceding aspect, wherein the verification function is configured to reject the update in response to the update comprising program steps not comprised in the set of predefined program steps.

4. The implant according to any preceding aspect, wherein the verification function is configured to allow the update in response to the update only comprising program steps comprised in the set of predefined program steps.

5. The implant according to aspect 1, wherein the internal communication unit is configured to communicate with the external device via a first wireless connection for receiving the update to the second control program, and a second connection for performing an authentication of the communication with the external device.

6. The implant according to aspect 5, wherein the second connection is a wireless short-range connection.

7. The implant according to aspect 5 or 6, wherein the authentication second connection is an electrical connection using the patient's body as a conductor

8. The implant according to any preceding aspect, wherein the internal computing unit is further configured to, upon verification, installing the update.

9. The implant according to any preceding aspect, wherein the internal computing unit has a sleep mode and an active mode, and the implant further comprises a sensor configured to detect a wake signal, and wherein the implant is configured to in response to a detected wake signal set the internal computing unit to the active mode.

10. The implant according to aspect 9, wherein sensor is configured to detect an acoustic signal as wake signal or wherein the sensor is configured to detect a magnetic signal as the wake signal 11. The implant according to any of aspects 9-10, wherein
   the sensor is configured to detect the received signal strength of a signal; and
   the implant is further configured to set the internal computing unit to the active mode in response to the sensor detecting a signal exceeding a threshold signal strength.

12. The implant according to any of aspects 9-11, further comprising a second internal computing unit, and wherein the implant is configured to set the internal computing unit to the active mode via the second internal computing unit.

13. The implant according to any of aspects 9-12, wherein the internal computing unit in the sleep mode is substantially without power, and wherein setting the internal computing unit in the active mode comprises providing the internal computing unit with power.

14. The implant according to aspect 13, wherein the implant comprises an energy controller for controlling the power supplied to the internal computing unit.

15. The implant according to aspect 14, wherein the sensor is configured to provide the energy controller with a second wake signal in response to detecting the wake signal, and wherein the energy controller is configured to set the computing unit in the active mode in response to the second wake signal.

16. The implant according to any preceding aspect, wherein
   the sensor is configured to detect the received signal strength of a signal; and
   the internal control unit is further configured to set the internal computing unit to the active mode in response to the sensor detecting a signal exceeding a threshold signal strength.

17. The implant according to any preceding aspect, wherein
   the wake signal comprises a predetermined signal pattern; and
   the implant is further configured to set the processing unit to the active mode in response to the sensor detecting the predetermined signal pattern.

18. The implant according to any preceding aspect, wherein the sensor is a hall effect sensor, a fluxgate sensor, an ultra-sensitive magnetic field sensor or a magneto-resistive sensor.

19. The implant according to any preceding aspect, wherein the sensor comprises a third coil having an iron core.

20. The implant according to any preceding aspect, wherein the sensor is comprised in the internal communication unit.

21. The implant according to any preceding aspect, further comprising a frequency detector, communicatively coupled to the internal computing unit and configured to detect a frequency for data communication between the internal communication unit and an external device configured to transmit a frequency indicator signal.

22. The implant according to aspect 21, wherein the frequency detector comprises an antenna.

23. The implant according to any preceding aspect, wherein the internal communication unit comprises a coil or a high-sensitivity magnetic field detector for communicating with the external device.

24. The implant according to any preceding aspect, further comprising:
   a sensation generator configured to generate a sensation detectable by a sense of the patient, the sensation generator being communicatively coupled to the internal control unit and being configured to, upon request, generate the sensation when the implant is implanted in the patient.

25. The implant according to aspect 24, wherein the sensation generator is configured to receive the request from the internal control unit of the implant.

26. The implant according to any of aspects 24-25, wherein the sensation generator is configured to create the sensation or sensation components by at least one of:
   a vibration of the sensation generator; producing a sound; providing a photonic signal; providing a light signal; providing an electric signal; and a heat signal.

27. The implant according to any of aspects 24-26, wherein the sensation generator is configured to be implanted in the patient.

28. The implant according to any of aspects 24-27, wherein the sensation generator is configured to be worn in contact with the skin of the patient.

29. the implant according to any of aspects 24-27, the sensation generator is configured generate the sensation without being in physical contact with the patient.

30. A method for programming an implant by an external device, implant comprising an internal computing unit configured to control a function of said implant and an internal memory configured to store: a first control program for controlling the internal computing unit, a second, updatable or configurable, control program for controlling said function of said implant, and a set of predefined program steps for updating the second control program, the external device being configured to communicate with the implant via a first connection, comprising:
   providing, at the internal computing unit, a set of predefined program steps for updating the second control program;
   transmitting, by the external device, an update comprising a subset of the predefined program steps over the first connection;
   receiving, at the internal computing unit, the update,
   verifying, by the internal computing unit, that the update comprises a subset of the predefined program steps, and
   upon verification of the instructions, running the update at the implant.

31. The method according to aspect 30, wherein the predefined program steps comprise setting a variable related to a pressure, a time, a minimum or maximum temperature, a current, a voltage, an intensity, a frequency, an amplitude of electrical stimulation, a feedback, a post-operative mode or a normal mode, a catheter mode, a fibrotic tissue mode, an time open after urination, a time open after urination before bed-time.

32. The method according to any of aspects 30-31, wherein the verifying comprises rejecting the update in response to the update comprising program steps not comprised in the set of predefined program steps.

33. The method according to any of aspects 30-32, wherein the verifying comprises allowing the update in response to the update only comprising program steps comprised in the set of predefined program steps.

34. The method according to any of aspects 30-33, further comprising:
authenticating the communication between the implant and the external device over a second connection.

35. The method according to any of aspects 30-34, wherein the second connection is a wireless short-range connection.

36. The method according to any of aspects 34-35, wherein the second connection is an electrical connection using the patient's body as a conductor.

37. The method according to any of aspects 30-36, further comprising, upon verification, installing the update.

38. The method according to any of aspects 30-36, further comprising:
monitoring for signals by a sensor connected to the internal computing unit;
providing, from a signal provider comprised in the external control unit, a wake signal;
setting, by the internal computing unit and in response to a detected wake signal, a mode of a portion of the internal control unit from a sleep mode to an active mode.

39. The method according to aspect 38, wherein the portion of the internal computing unit is the first control program or the second control program.

40. The method according to any of aspects 38-39, further comprising
detecting, using a frequency detector, a frequency for the first communication channel between a first communication unit and a second communication unit, the first communication unit being associated with the internal control unit and the second communication unit being associated with the external device,
wherein the frequency detector is communicatively coupled to the internal computing unit.

41. The method according to aspect 40, further comprising:
determining, using the frequency detector, the frequency for the first communication channel.

42. The method according to aspect 40, further comprising:
generating, using a sensation generator communicatively coupled to the internal control unit, a sensation detectable by a sense of the patient in response to verifying the update, in response to running the update or in response to the update being installed at the implant.

43. The method according to aspect 42, wherein the generating comprises at least one of: providing a vibration of the sensation generator; producing a sound; providing a photonic signal; providing a light signal; providing an electric signal; and providing a heat signal.

44. A computer program product comprising a computer-readable storage medium with instructions adapted to carry out the method of any one of aspects 30-43 and/or with instructions adapted to carry out an action in any of the implant aspects 1-29, when executed by a computing unit in an external device having processing capability.

45. A computer program product comprising a computer-readable storage medium with instructions adapted to carry out the method of any one of aspects 30-43 and/or with instructions adapted to carry out an action in any of the implant aspects 1-29, when executed by a computing unit in the implant having processing capability.

46. The implant according to any one of the following, alone or in any combination; implant aspects 1-29, with ability to perform method aspects 30-43, and ability to use program product aspects 44-45, comprising an internal control unit adapted to be involved in at least a part of the actions performed by the implant in at least a part of any one of the aspects 1-45 above.

Aspect 313B eHealth Watchdog

1. A system comprising an implant comprising:
an internal processor comprising:
a first control program for controlling a function of the implant, and
a first reset function, said first reset function being configured to restart or reset said first control program in response to:
a timer of the first reset function has not been reset, or
a malfunction in the first control program
the system further comprising
an implantable energized medical device configured to be held in position by a tissue portion of a patient, the medical device comprising:
a first portion configured to be placed on a first side of the tissue portion, the first portion having a first cross-sectional area in a first plane and comprising a first surface configured to face a first tissue surface of the first side of the tissue portion,
a second portion configured to be placed on a second side of the tissue portion, the second side opposing the first side, the second portion having a second cross-sectional area in a second plane and comprising a second surface configured to engage a second tissue surface of the second side of the tissue portion, and
a connecting portion configured to be placed through a hole in the tissue portion extending between the first and second sides of the tissue portion, the connecting portion having a third cross-sectional area in a third plane and a fourth cross-sectional area in a fourth plane and a third surface configured to engage the first tissue surface of the first side of the tissue portion,
wherein the connecting portion is configured to connect the first portion to the second portion, wherein:
the first, second, third and fourth planes are parallel to each other,
the third cross-sectional area is smaller than the first, second and fourth cross-sectional areas, such that the first portion, second portion and connecting portion are prevented from travelling through the hole in the tissue portion in a direction perpendicular to the first, second and third planes, and
the first portion is detachably connected to at least one of the connecting portion and the second portion.

2. A system comprising an implant comprising:
an internal processor comprising:
a first control program for controlling a function of the implant, and
a first reset function, said first reset function being configured to restart or reset said first control program in response to:
a timer of the first reset function has not been reset, or
a malfunction in the first control program
the system further comprising
a system for treating a patient having a disorder related to the patient's intestine, the system comprises an artificial intestine section adapted to being implanted inside a patient's body, along with an accumulator for accumulating energy, the artificial intestine section has a first open end portion and a second open end portion in flow communication with one another, wherein at least the first open end portion and possibly also the second open end portion is adapted to being connected to a surgically created opening in the patient's intestine, and the accumulator is adapted to be charged wirelessly with energy and to be arranged so as to supply energy directly or indirectly to at least one energy consuming part of said artificial intestine section.

3. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising a system that acts on an intestinal reservoir formed from surgically modified intestine that has been cut along a mutual contact line of laterally adjacent sections of a bent portion of intestine and connected so that the resulting upper and lower halves of the intestine form an intestinal wall of the reservoir, the system comprises an artificial flow control device implantable in the patient's body and adapted to control flow of the intestinal contents from said reservoir the artificial flow control device comprises at least one pump adapted to act on said intestinal wall so as to reduce the reservoir's volume in order to empty the reservoir.

4. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an infusion device comprising an infusion needle and a drive unit coupled to the infusion needle and arranged for advancing the tip end of the infusion needle to penetrate fibrosis when the device is implanted in the patient's body, wherein at least the infusion needle and the drive unit are sized and formed for implantation in the patient's body.

5. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising a drug delivery device for injecting a drug into a patient's body such as stimulation of penis erection wherein the drug is injected into the patient's body into at least one of both a right and left corpus cavernosum, two deep arteries of the right and left corpus cavernosum, muscle tissue regulating blood flow through the right and left corpus cavernosum, and tissue in close proximity to the left and right corpus cavernosum, wherein the drug delivery device comprises a catheter adapted to be implanted outside the corpora cavernosa in close proximity thereto so as to supply the drugs through the catheter or the catheter may be adapted to be implanted in at least one of the corpora cavernosa so as to supply the drugs directly into the corpus cavernosum through the catheter.

6. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an implantable lubrication device comprising:

a reservoir that stores a lubricating fluid and, a fluid connection that introduces the stored lubricating fluid into a damaged joint when the lubrication device is implanted in a patient's body.

wherein the lubricating device is configured to be completely implanted into the patient's body such that a damaged joint can post-operatively be lubricated from within the patient's body, and wherein the operative supply of lubricating fluid to the damaged joint is controlled continuously, intermittently, periodically or depending on a physical parameter of the patient, such as a fluid level within the joint.

7. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising a device for bone adjustment in a mammal, comprising two or more anchoring devices for attaching to a bone in said mammal, an adjustment device for exerting force on said anchoring devices to adjust the distance between or orientation of at least two of said anchoring devices, wherein said anchoring devices and said adjustment device are implanted intramedullary in said mammal and wherein said adjustment device is constructed to postoperatively adjust said distance, and the adjustment is a lengthening of a bone, a healing of a fracture, a changing of a bone angle, a reshaping of a bone, a compression of a bone, a torsion of a bone, or a combination thereof.

8. A system comprising an implant comprising:
an internal processor comprising:
a first control program for controlling a function of the
implant, and
a first reset function, said first reset function being
configured to restart or reset said first control pro-
gram in response to:
a timer of the first reset function has not been reset, or
a malfunction in the first control program
the system further comprising
an implantable drain adapted to move body fluid or a
hydraulic reservoir with hydraulic treatment fluid to
move hydraulic fluid, from one part of the body to
another part of the body, a fluid movement device that
which is completely implanted and which does not
have any mechanical structure penetrating through the
skin of the patient is obtained.
9. A system comprising an implant comprising:
an internal processor comprising:
a first control program for controlling a function of the
implant, and
a first reset function, said first reset function being
configured to restart or reset said first control pro-
gram in response to:
a timer of the first reset function has not been reset, or
a malfunction in the first control program
the system further comprising
apparatus for drainage of a body fluid or movement of
hydraulic treatment fluid in a human or mammal patient
comprising
a fluid movement device for pumping hydraulic treatment
fluid or body fluid, the fluid movement device being
powered by an energy source and powered by an
electrical or a hydraulic motor
at least one connecting tube connected to the fluid move-
ment device so that the fluid movement device and the
tube form a drainage or hydraulic arrangement
wherein the hydraulic arrangement is adapted to be
implanted inside the body of the patient, and placed so
that the tube interconnects one part of the body with
another part of the body and where fluid movement
device is adapted to suck body fluid from the one part
of the body via the tube to the other part of the body.
10. A system comprising an implant comprising:
an internal processor comprising:
a first control program for controlling a function of the
implant, and
a first reset function, said first reset function being
configured to restart or reset said first control pro-
gram in response to:
a timer of the first reset function has not been reset, or
a malfunction in the first control program
the system further comprising
an implantable device for improving the pump function of
the heart of a human patient by applying an external
force on the heart muscle, said device comprising
at least one heart contacting organ, periodically exerting
force onto the heart following the heart contractions
and adding force thereto,
a drive unit to create kinetic movement to be used by the
heart contacting organ,
a fixation device adapted to be mounted in a stable
position to human bone allowing said drive unit and
kinetic movement to get necessary contra force,
wherein said drive unit further comprises a respiration
movement compensator for compensating for the respi-
ratory movement of the heart in relation to the stable bone position, and said drive unit is adapted to allow a
movement to compensate for the respiratory movement
in relation between said heart contacting organ and said
bone.
11. A system comprising an implant comprising:
an internal processor comprising:
a first control program for controlling a function of the
implant, and
a first reset function, said first reset function being
configured to restart or reset said first control pro-
gram in response to:
a timer of the first reset function has not been reset, or
a malfunction in the first control program
the system further comprising
a male sexual impotence treatment prosthesis apparatus,
comprising
an operable prosthesis implantable in the cavities of the
corpora cavernosa of an impotent patient to provide
erect penile condition, when the prosthesis is operated,
wherein an energy transmission device for wireless trans-
mission of energy from outside the patient's body to
inside the patient's body for use in connection with the
operation of the prosthesis, when the prosthesis is
implanted.
12. A system comprising an implant comprising:
an internal processor comprising:
a first control program for controlling a function of the
implant, and
a first reset function, said first reset function being
configured to restart or reset said first control pro-
gram in response to:
a timer of the first reset function has not been reset, or
a malfunction in the first control program
the system further comprising
a device for treatment or monitoring of an aneurysm,
comprising
an implantable member adapted to hold fluid, the member
being adapted to be placed in connection with a blood
vessel having the aneurysm and to exercise a pressure
on the aneurysm, wherein the controller functions as a
control unit adapted to control pressure adjustments of
the implantable member.
13. A system comprising an implant comprising:
an internal processor comprising:
a first control program for controlling a function of the
implant, and
a first reset function, said first reset function being
configured to restart or reset said first control pro-
gram in response to:
a timer of the first reset function has not been reset, or
a malfunction in the first control program
the system further comprising
an implantable blood clot removal device for removing
blood clots from the vascular system of a patient
comprising:
a blood flow passageway to be connected to the patient's
vascular system to allow circulation of the patient's
blood through the blood flow passageway,
a filter provided in the blood flow passageway for col-
lecting blood clots occurring in the blood flowing
through the blood flow passageway, and
a cleaning device for moving blood clots collected by the
filter out of the blood flow passageway.
14. A system comprising an implant comprising:
an internal processor comprising:
a first control program for controlling a function of the
implant, and a first reset function, said first reset function being configured to restart or reset said first control program in response to:

a timer of the first reset function has not been reset, or a malfunction in the first control program the system further comprising an implantable apparatus for treating urinary retention of a mammal patient comprising:

an implantable powered member adapted exert a force from the outside on a selected part of the urinary bladder in order to discharge urine from the urinary bladder, and a control device for controlling the operation of the powered member.

15. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising a breast implant system comprises a plurality of chambers including one or more first fluid chambers and one or more second fluid chambers, wherein:

at least the first fluid chamber is to be implanted in the human body to form part of a breast implant, the second fluid chambers is implanted to form part of the breast implant or implanted inside the patient's body remote from the breast implant, the first fluid chamber is interconnected with the second fluid chamber, such that fluid can be exchanged between the first and second fluid chambers, so as to change their respective fluid content.

16. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an apparatus for treating obesity and/or reflux comprising at least one volume filling device adapted to be at least substantially invaginated by a stomach wall portion of the patient, wherein the volume filling device is adapted to be placed outside of the stomach wall with the outer surface of the volume filling device resting against the outside of the stomach wall, such that the volume of the food cavity is reduced in size by a volume substantially exceeding the volume of the volume filling device.

17. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising a system for treating a female patient to avoid or promote pregnancy comprising a restriction device adapted to postoperatively restrict and release an oviduct of the patient.

18. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an apparatus for controlling a flow of sperms in an uterine tube of a female patient, the apparatus comprising: an implantable constriction device for constricting at least one portion of the uterine tube wall to at least partly constrict the uterine tube to influence the flow of sperms in the uterine tube.

19. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an implantable medical device for lubrication of a synovial joint having a joint cavity, the implantable device comprising a solid lubricant and a feeding device, wherein said feeding device is adapted to feed said solid lubricant into the joint cavity for lubricating the synovial joint.

20. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an artificial valve for implantation in a mammal body, in or adjacent to a mammal blood vessel, the artificial valve comprises a casing and an opening and closing mechanism, at least part of the opening and closing mechanism comprises a first moving part adapted to make an opening and a closing movement relative to the casing, the movements comprising movements to assume an open and a closed position for opening and closing, respectively, the blood flow through said blood vessel.

21. A system comprising an implant comprising:

an internal processor comprising:

a first control program for controlling a function of the implant, and a first reset function, said first reset function being configured to restart or reset said first control program in response to:

a timer of the first reset function has not been reset, or a malfunction in the first control program the system further comprising an apparatus adapted to control the flow of fluids and/or other bodily matter in a lumen that is formed by the tissue wall of a bodily organ, the apparatus comprising an implantable constriction device for constricting a portion of the tissue wall to influence the flow in the lumen, a stimulation device for stimulating the wall portion of the tissue wall, and a control device for controlling the stimulation device to stimulate the wall portion as the constriction device constricts the wall portion to cause contraction of the wall portion to further influence the flow in the lumen.

22. The system according to anyone of aspect 1-21, wherein the first control program comprises a second reset function for resetting the timer of the first reset function.

23. The system according to anyone of aspect 1-21, wherein the first reset function comprises a timer and the second reset function is configured to reset the timer.

24. The system according to anyone of aspect 1-21, wherein the reset function comprises a first reset function and a second reset function, wherein the first reset function is configured to trigger a corrective function for correcting the first control program, and wherein the second reset function is configured to restart the first control program after the corrective function has been triggered.

25. The system according to anyone of aspect 1-21, wherein the first or second reset function is configured to invoke a hardware reset by activating an internal or external pulse generator which is configured to create a reset pulse for the internal computing unit or the first control program.

26. The system according to anyone of aspect 1-21, wherein the internal computing unit is configured to have an active mode and a sleep mode, and wherein the first reset function is configured to have an active mode and a sleep mode corresponding to the active mode and the sleep mode of the internal computing unit.

27. The system according to anyone of aspect 1-21, further comprising a sensor for measuring a physiological parameter of the patient or a parameter of the implant, and wherein the sensor is configured to invoke the reset function in response to the parameter being above or below a pre-determined value.

28. The system according to anyone of aspect 1-21, wherein the sensor is a pressure sensor adapted to measure a pressure in a part of the implant.

29. The system according to anyone of aspect 1-21, wherein the pressure sensor is configured to measure a pressure in a reservoir or a restriction device of the implant.

30. The system according to anyone of aspect 1-21, wherein the sensor is a pressure sensor adapted to measure a pressure in an organ of the patient's body.

31. The system according to anyone of aspect 1-21, wherein the reset function is configured to be invoked by an electrical reset pulse, and wherein the sensor is adapted to invoke the reset function by activating an internal or external pulse generator which is configured to create a reset pulse for the reset function.

32. The system according to anyone of aspect 1-21, wherein the physiological parameter of the patient or a parameter of the implant is a temperature.

32. The system according to anyone of aspect 1-21, wherein the reset function comprises invoking a second control program comprising a safety measure.

33. The system according to anyone of aspect 1-21, wherein the safety measure comprises controlling a function of the implant.

34. The system according to anyone of aspect 1-21, wherein the internal computing unit is configured to invoke the reset function periodically.

35. The system according to anyone of aspect 1-21, wherein periodically comprises every 24 hours.

36. The system according to anyone of aspect 1-21, wherein the internal computing unit further comprises a monitoring function for monitoring a function of the implant or the first control program, and wherein the reset function is configured to in response to an incorrect or absent response for the monitoring program, reset or restart the first control program.

37. The system according to anyone of aspect 1-21.

wherein the internal computing unit has an active mode and a sleep mode, the sleep mode having a lower energy consumption than the active mode, and wherein the implant further comprises an internal control unit connected to the internal computing unit and adapted to control the mode of the internal computing unit.

38. The system according to anyone of aspect 1-21.

wherein the implant further comprises a second sensor for measuring a physiological parameter of the patient or a parameter of the implant, the second sensor being connected to the internal control unit, and wherein, in response to a sensor measurement differing from, exceeding or being less than a predetermined value, setting the internal computing unit in the active mode.

39. The system according to anyone of aspect 1-21, wherein the sensor is configured to measure the physical parameter periodically.

40. The system according to anyone of aspect 1-21, wherein the sensor and the second sensor is the same sensor.

Aspect 316C eHealth Relay Instructions, Aspects 1-25

1. A method for transmitting an instruction from a first external device to an implant, comprising:

transmitting an instruction for the implant from the first external device to a second external device, the instruction relating to a function of the implant, encrypting, at the first external device and using a first encryption key, the instruction into an encrypted instruction, and transmitting the encrypted instruction from the first external device to the second external device, wherein the second external device is relaying the instruction without decrypting the instruction to the implant, decrypting, at the implant, the instructions using a second authentication, encryption, or authentication and encryption key corresponding or relating to the first encryption key.

2. The method according to aspect 1, wherein the transmitting of the encrypted instruction from the second external device to the implant comprises:

transmitting the encrypted instruction from the second external device to the first external device, and transmitting the encrypted instruction from the first external device to the implant.

3. The method according to aspect 1, wherein the transmitting of the encrypted instruction from the second external device to the implant comprises:

transmitting the encrypted instruction from the second external device to a third external device, and transmitting the encrypted instruction from the third external device to the implant.

4. The method according to any preceding aspect, wherein the second external device is an encryption device communicatively coupled to the first external device, and wherein the communication of the instruction between the second external device and the implant is relayed through the first external device.

5. The method according to any preceding aspect, further comprising, at the implant, running the instruction.

6. The method according to any preceding aspect, further comprising receiving, at the first external device, the instruction.

7. The method according to aspect 6, further comprising displaying, at the external device, a user interface for receiving the instruction.

8. The method according to aspect 7, wherein the implant comprises a set of a predefined program steps, and wherein the method further comprises verifying, by the implant, that the received instruction is comprised in the predefined program steps.

9. The method according to aspect 8, wherein the verifying comprises rejecting the instruction in response to the instruction not being comprised in the set of predefined program steps.

10. The method according to any of aspects 8-9, wherein the verifying comprises allowing the instruction in response to the instruction being comprised in the set of predefined program steps.

11. The method according to any preceding aspect, wherein the first external device and the implant are configured to communicate over a wireless connection.

12. The method according to aspect 11, wherein the wireless connection comprises at least one of the following protocols: Radio Frequency type protocol, RFID type protocol, WLAN type protocol, Bluetooth type protocol, BLE type protocol, NFC type protocol, 3G/4G/5G type protocol, GSM type protocol, Bluetooth 5.

13. The method according to any preceding aspect, wherein the transmitting of data between the first external device and the second external device is performed a wireless connection.

14. The method according to any preceding aspect, further comprising authenticating the connection between the first external device and the implant over which the encrypted instruction is to be transmitted.

15. The method according to any preceding aspect, wherein the implant comprises an internal control unit for controlling a function of the implant, and wherein the internal control unit is configured to run the instruction.

16. A system for transmitting an instruction from a first external device to an implant, comprising:

an implant implanted in a human patient, the implant comprising an internal control unit configured to control a function of the implant and configured to receive an instruction from an external device;

a first external device configured to receive or determine an instruction to be transmitted to the implant, and to transmit the instruction to a second external device; and a second external device configured to receive the instruction transmitted from the first external device, encrypt the instruction, and transmit the encrypted instruction to the implant.

wherein the implant is configured to received and decrypt the instruction.

17. The system according to aspect 16, wherein the second external device is configured to transmit the encrypted instruction by transmitting the encrypted instruction to the first external device, and wherein the first external device is configured to transmit the encrypted instruction to the implant.

18. The system according to aspect 16, wherein the second external device is configured to transmit the encrypted instruction by transmitting the encrypted instruction to a third external device, and wherein the third external device is configured to transmit the encrypted instruction to the implant.

19. The system according to any of aspects 16-18, wherein the second external device is an encryption device communicatively coupled to the first external device, and wherein any communication between the implant and the second external device is relayed through the first external device.

20. The system according to any one of aspects 16-19, wherein the internal control unit is configured to run the decrypted instruction for controlling a function of the implant.

21. The system according to any one of aspects 16-20, wherein the first external device is configured to display a user interface for receiving the instruction.

22. The system according to any one of aspects 16-21, wherein the implant comprises a set of a predefined program steps, and wherein the implant is configured to verify that the received instruction is comprised in the predefined program steps.

23. The system according to aspect 22, wherein the implant is configured to reject the instruction in response to the instruction not being comprised in the set of predefined program steps.

24. The system according to any of aspects 21-22, wherein the implant is configured to allow the instruction in response to the instruction being comprised in the set of predefined program steps.

25. The system according to any of aspects 16-24, wherein the first external device and the implant are configured to communicate over a wireless connection.

26. A computer program product comprising a computer-readable storage medium with instructions adapted to carry out the method of any one of aspects 1-15 and/or with instructions adapted to carry out an action in any of the system aspects 16-25, when executed by a computing unit in an external device having processing capability.

27. A computer program product comprising a computer-readable storage medium with instructions adapted to carry out the method of any one of aspects 1-15 and/or with instructions adapted to carry out an action in any of the system aspects 16-25, when executed by a computing unit in the implant having processing capability.

Aspect 317C Energy General Microphone, Aspects 1-19

1. An implantable controller for controlling an energized implant, when implanted in a patient, the controller comprises:

a computing unit, at least one microphone, at least one accelerometer, or at least one microphone and at least one accelerometer, wherein the at least one microphone, at least one accelerometer, or at least one microphone and at least one accelerometer is configured to register a sound, a vibration or a movement related to at least one of: a bodily function, and a function of the implant.

2. The implantable controller according to aspect 1, wherein the implantable controller further comprises at least one implantable housing for sealing against fluid, and wherein the computing unit and the microphone are placed inside of the housing.

3. The implantable controller according to any one of aspects 1 and 2, wherein the computing unit is configured to derive a pulse of the patient from the registered sound related to a bodily function.

4. The implantable controller according to any one of aspects 1 and 2, wherein the computing unit is configured to derive information related to the patient urinating from the registered sound related to a bodily function.

5. The implantable controller according to any one of aspects 1 and 2, wherein the computing unit is configured to derive information related to a bowel activity of the patient from the registered sound related to a bodily function.

6. The implantable controller according to any one of aspects 1 and 2, wherein the computing unit is configured to derive information related to a functional status of the implant from the registered sound related to a function of the implant.

7. The implantable controller according to aspect 6, wherein the computing unit is configured to derive information related to the functional status of an operation device of the implant, from the registered sound related to a function of the implant.

8. The implantable controller according to aspect 7, wherein the computing unit is configured to derive information related to the functional status of at least one of: a motor, a pump and a transmission of the operation device of the implant from, the registered sound related to a function of the implant.

9. The implantable controller according to any one of the preceding aspects, further comprising a transceiver, and wherein the controller is configured to transmit a parameter derived from the sound registered by the at least one microphone using the transceiver.

10. A method of authenticating at least one of an energized implant implanted in a patent, an external device, and a connection between the energized implant and the external device performed in a system comprising the energized implant and the external device, the energized implant comprising at least one microphone, and a transmitter, and the external device comprising a receiver and a computing unit, the method comprising:

registering a sound related to at least one of: a bodily function and a function of the implant, using the at least one microphone, transmitting a signal derived from the registered sound, using the transmitter, receiving, in the external device, the signal derived from the registered sound, using the receiver, and comparing, in the external device, a parameter derived from the received signal with a reference parameter, using the computing unit.

11. The method according to aspect 9, further comprising the step of authenticating at least one of:

the energized implant, the external device, and the connection between the energized implant and the external device the energized implant on the basis of the comparison.

12. The method according to any one of aspects 10 and 11, further comprising receiving, at the receiver of the external device, a parameter to be used as reference parameter.

13. The method according to aspect 12, wherein the step of receiving a parameter to be used as reference parameter comprises receiving the parameter from a sensor external to the patient.

14. The method according to any one of aspects 10-13, wherein the registered sound is related to a pulse of the patient, and wherein the reference parameter is related to the pulse of the patient.

15. A method of authenticating at least one of an energized implant implanted in a patent, an external device, and a connection between the energized implant and the external device, performed in a system comprising the energized implant and the external device, the energized implant comprising at least one microphone, a receiver, and a computing unit, and the external device comprising a transmitter, the method comprising:

registering a sound related to at least one of: a bodily function and a function of the implant, using the at least one microphone, deriving a parameter from the sound using the computing unit, receiving, in the energized implant, a reference parameter, from the external device, using the receiver, and comparing, in the energized implant, the parameter derived from the sound with the received reference parameter, using the computing unit.

16. The method according to aspect 15, further comprising the step of authenticating at least one of: the energized implant, the external device, and the connection between the energized implant and the external device on the basis of the comparison.

17. The method according to any one of aspects 15 and 16, further comprising receiving, at a receiver of the external device, a parameter to be used as reference parameter.

18. The method according to aspect 17, wherein the step of receiving a parameter to be used as reference parameter comprises receiving the parameter from a sensor external to the patient.

19. The method according to any one of aspects 15-18, wherein the registered sound is related to a pulse of the patient, and wherein the reference parameter is related to the pulse of the patient.

Aspect
384SE—eHealth_General_Communication_Dual,
Aspects 1-24

1. An external device configured for communication with an implantable medical device when implanted in a patient, the external device comprising:

at least one first wireless transceiver configured for communication with the implantable medical device using a first network protocol, for determining a distance between the external device and the implantable medical device, and at least one second wireless transceiver configured for communication with the implantable medical device using a second network protocol, for transferring data between the external device and the implantable medical device.

2. The external device according to aspect 1, wherein the first wireless transceiver comprises an UWB transceiver.

3. The external device according to aspect 1, wherein the first wireless transceiver is configured for transcutaneous energy transfer for at least one of:

powering an energy consuming component of the implantable medical device, and charging an implantable energy storage unit.

4. The external device according to any one of the preceding aspects, wherein the second network protocol is a standard network protocol.

5. The external device according to any one of the preceding aspects, wherein the second wireless transceiver comprises a Bluetooth transceiver.

6. The external device according to any one of the preceding aspects, wherein the external device is further configured to communicate with a second external device using said at least one wireless transceiver.

7. The external device according to any one of the preceding aspects, wherein the external device is configured for determining a distance between the external device and the implantable medical device by determining the RSSI.

8. The external device according to any one of aspects 4-7, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

9. The external device according to any one of the preceding aspects, wherein a communication range of the first network protocol is less than a communication range of the second network protocol.

10. The external device according to any one of the preceding aspects, wherein a frequency band of the first network protocol differs from a frequency band of the second network protocol.

11. The external device according to any one of the preceding aspects, wherein the external device is configured to authenticate the implantable medical device if the determined distance between the external device and the implantable medical device is less than a predetermined threshold value.

12. The external device according to aspect 11, wherein the external device is configured to allow the transfer of data between the external device and the implantable medical device after the implantable medical device has been authenticated.

13. The external device according to any one of the preceding aspects, wherein the external device is one from the list of: a wearable external device, and a handset.

14. An implantable medical device configured for communication with an external device, the implantable medical device comprising:

at least one first wireless transceiver configured for communication with the external device using a first network protocol, for determining a distance between the external device and the implantable medical device, and at least one second wireless transceiver configured for communication with the external device using a second network protocol, for transferring data between the external device and the implantable medical device.

15. The implantable medical device according to aspect 14, wherein the first wireless transceiver comprises an UWB transceiver.

16. The implantable medical device according to aspect 14, wherein the first wireless transceiver is configured for transcutaneous energy transfer for at least one of:

powering an energy consuming component of the implantable medical device, and charging an implantable energy storage unit.

17. The implantable medical device according to any one of aspects 14-16, wherein the second network protocol is a standard network protocol.

18. The implantable medical device according to any one of aspects 14-17, wherein the second wireless transceiver comprises a Bluetooth transceiver.

19. The implantable medical device according to any one of aspects 14-18, wherein the implantable medical device is further configured to communicate with a second external device using said at least one wireless transceiver.

20. The implantable medical device according to any one of aspects 14-19, wherein the implantable medical device is configured for determining a distance between the external device and the implantable medical device by determining the RSSI.

21. The implantable medical device according to any one of aspects 14-20, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

22. The implantable medical device according to any one of the aspects 14-21, wherein a communication range of the first network protocol is less than a communication range of the second network protocol.

23. The implantable medical device according to any one of aspects 14-22, wherein a frequency band of the first network protocol differs from a frequency band of the second network protocol.

24. The implantable medical device according to any one of aspects 14-23, wherein the implantable medical device is configured to authenticate the external device if the determined distance between the external device and the implantable medical device is less than a predetermined threshold value.

25. The implantable medical device according to aspect 24, wherein the implantable medical device is configured to allow the transfer of data between the implantable medical device and the external device after the external device has been authenticated.

26. The implantable medical device according to any one of aspects 14-25, wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

27. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

28. The system according to anyone of the preceding aspects, wherein the patient remote external device and the patient EID external device are an integrated unit.

29. The system according to anyone of the preceding aspects, wherein the HCP dedicated device and the HCP EID external device are an integrated unit.

30. The system according to anyone of the preceding aspects, comprising a measurement device or sensor adapted to deliver a measurement to at least one of the DDI, patent EID external device and a patient display device.

31. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

Aspect 385SE—eHealth_General_General_Remote Display Portal, Aspects 1-35

1. A patient external device configured for communication with an implantable medical device when implanted in a patient, the patient external device comprising:

a wireless communication unit configured for wireless transmission of control commands to the implantable medical device and configured for wireless communication with a patient display device, and a computing unit configured for running a control software for creating the control commands for the operation of the implantable medical device, wherein the computing unit is configured to:

transmit a control interface as a remote display portal to a patient display device configured to display the control interface to a user, receive user input from the patient display device, and transform the user input into the control commands for wireless transmission to the implantable medical device.

2. The patient external device according to aspect 1, wherein the wireless communication unit comprises a wireless transceiver for:

wireless transmission of control commands to the implantable medical device, and wireless transmission of the control interface as the remote display portal to the patient display device.

3. The patient external device according to aspect 1, wherein the wireless communication unit comprises:

a first wireless transceiver for wireless transmission of control commands to the implantable medical device, and a second wireless transceiver for wireless transmission of the control interface to the patient display device.

4. The patient external device according to any one of the preceding aspects, wherein the wireless communication unit is configured for wireless communication with the patient display device using a standard network protocol.

5. The patient external device according to any one of the preceding aspects, wherein the wireless communication unit is configured for wireless communication with the implantable medical device using a proprietary network protocol.

6. The patient external device according to any one of the preceding aspects, wherein the wireless communication unit comprises a Bluetooth transceiver.

7. The patient external device according to aspect 6, wherein at least one of the first and second wireless transceiver comprises a Bluetooth transceiver.

8. The patient external device according to any one of aspects 1-5, wherein the wireless communication unit comprises a UWB transceiver.

9. The patient external device according to aspect 8, wherein at least one of the first and second wireless transceiver comprises a UWB transceiver.

10. The patient external device according to aspect 1, wherein the wireless communication unit comprises:

at least one first wireless transceiver configured for communication with the implantable medical device using a first network protocol, for determining a distance between the patient external device and the implantable medical device, and at least one second wireless transceiver configured for communication with the implantable medical device using a second network protocol, for transferring data between the patient external device and the implantable medical device.

11. The patient external device according to aspect 3, wherein the first wireless transceiver is configured for transcutaneous energy transfer for at least one of:

powering an energy consuming component of the implantable medical device, and charging an implantable energy storage unit.

12. The patient external device according to aspect 4, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

13. The patient external device according to any one of aspects 3-12, wherein a communication range of the first wireless transceiver is less than a communication range of the second wireless transceiver.

14. The patient external device according to any one of the preceding aspects, wherein at least one of:

the patient external device is configured to authenticate the implantable medical device if a distance between the patient external device and the implantable medical device is less than a predetermined threshold value, the patient external device is configured to be authenticated by the implantable medical device if a distance between the patient external device and the implantable medical device is less than a predetermined threshold value, the patient external device is configured to authenticate the patient display device if a distance between the patient external device and the patient display device is less than a predetermined threshold value, and the patient external device is configured to be authenticated by the implantable medical device if a distance between the patient external device and the patient display device is less than a predetermined threshold value.

15. The patient external device according to aspect 14, wherein the patient external device is configured to allow the transfer of data between at least one of:

the patient external device and the implantable medical device, and the patient external device and the patient display device, on the basis of the authentication.

16. The communication system according to any one of the preceding aspects, wherein the computing unit is configured to encrypt at least one of the control interface and the control commands.

17. The implantable medical device according to any one of preceding aspects, wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

18. A patient display device for communication with a patient remote external device for communication with an implantable medical device, the patient display device comprising:

a wireless communication unit configured for wirelessly receiving an implant control interface as a remote display portal from the patient remote external device and configured for wirelessly transmitting implant control user input to the patient remote external device, a display for displaying the received implant control interface, and an input device for receiving implant control input from the user.

19. The patient display device according to aspect 18 wherein the patient display device further comprises an auxiliary wireless communication unit, and wherein the auxiliary wireless communication unit is configured to be disabled to enable at least one of:

wirelessly receiving the implant control interface as the remote display portal from the patient remote external device, and wirelessly transmitting implant control user input to the patient remote external device.

20. The patient display device according to any one of aspects 18-19, wherein the wireless communication unit is configured for wireless communication with the patient remote external device using a standard network protocol.

21. The patient display device according to any one of aspects 18-20, wherein the wireless communication unit is configured for wireless communication with the patient remote external device using a proprietary network protocol.

22. The patient display device according to any one of aspects 18-20, wherein the wireless communication unit comprises a Bluetooth transceiver.

23. The patient display device according to any one of aspects 18-22, wherein the wireless communication unit comprises a UWB transceiver.

24. The patient display device according to aspect 20, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

25. The patient display device according to aspect 19, wherein a communication range of the wireless communication unit is less than a communication range of the auxiliary wireless communication unit.

26. The patient display device according to any one of aspects 18-25, wherein at least one of:

the patient display device is configured to authenticate the patient remote external device if a distance between the patient display device and the patient remote external device is less than a predetermined threshold value, and the patient display device is configured to be authenticated by the patient remote external device if a distance between the patient display device and the patient remote external device is less than a predetermined threshold value.

27. The patient display device according to aspect 26, wherein the patient display device is configured to allow the transfer of data between the patient display device and the patient remote external device on the basis of the authentication.

28. The patient display device according to any one of the preceding aspects, wherein the patient display device is a wearable external device or a handset.

29. A communication system for enabling communication between a patient display device and an implantable medical device, when implanted, the communication system comprising:

a patient display device, a server, and a patient remote external device, wherein:

the patient display device comprises:

a wireless communication unit configured for wirelessly receiving an implant control interface as a remote display portal being provided by the patient remote external device, the wireless communication unit further being configured for wirelessly transmitting implant control user input to the server, destined for the patient remote external device, a display for displaying the received remote display portal, and an input device for receiving implant control input from the user, the patient remote external device comprising:

a wireless communication unit configured for wireless transmission of control commands to the implantable medical device, and a computing unit configured for:

running a control software for creating the control commands for the operation of the implantable medical device, transmitting a control interface to the patient display device, receiving implant control user input generated at the patient display device, from the server, and transforming the user input into the control commands for wireless transmission to the implantable medical device.

30. The communication system according to aspect 29, wherein the computing unit is configured to encrypt at least one of the control interface and the control commands.

31. The communication system according to any one of aspects 29 and 30, wherein the patient display device is configured to encrypt the user input.

32. The communication system according to any one of aspects 29-31, wherein the server is configured to encrypt at least one of the user input received from the patient display device and the control interface received from the patient remote external device.

33. The communication system according to aspect 29, wherein the computing unit is configured to encrypt the control interface and the patient display device is configured to decrypt the encrypted control interface.

34. The communication system according to aspect 33, wherein the server is configured to act as a router, transferring the encrypted control interface from the patient remote external device to the patient display device without decryption.

35. The communication system or patient display device according to any one of the preceding aspects, wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

36. The communication system according to any one of the preceding aspects, further comprising a server comprising:

a wireless communication unit configured for wirelessly receiving an implant control interface received from the patient remote external device and wirelessly transmitting the implant control interface as a remote display portal to the patient display device, the wireless communication unit further being configured for wirelessly receiving implant control user input from a patient EID external device and wirelessly transmitting the implant control user input to the patient display device.

37. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

38. The system according to anyone of the preceding aspects, wherein the patient remote external device and the patient EID external device are an integrated unit.

39. The system according to anyone of the preceding aspects, wherein the HCP dedicated device and the HCP EID external device are an integrated unit.

40. The system according to anyone of the preceding aspects, comprising a measurement device or sensor adapted to deliver a measurement to at least one of the DDI, patient EID external device and a patient display device.

41. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

Aspect
386SE—eHealth_General_General_App_in_App,
Aspects 1-43

1. A patient display device for communication with a patient external device for communication with an implantable medical device, when implanted, the patient display device comprising:

a wireless communication unit, a display, and an input device for receiving implant control input from the user, wherein the patient display device is configured to:

run a first application for wireless communication with a server and/or DDI, and run a second application for wireless communication with the patient external device for transmission of the implant control input to a remote display portal of the patient external device for the communication with the implantable medical device, wherein the second application is configured to be accessed through the first application.

2. The patient display device according to aspect 1, wherein the first log-in is a PIN-based log-in.

3. The patient display device according to aspect 1, wherein at least one of the first and second log-in is a log-in based on a biometric input or a hardware key.

4. The patient display device according to any one of aspects 1-3, wherein the patient display device further comprises an auxiliary wireless communication unit, and wherein the auxiliary wireless communication unit is configured to be disabled to enable wireless communication with the patient external device.

5. The patient display device according to any one of aspects 1-4, wherein the patient display device is configured to wirelessly receive an implant control interface as a remote display portal from the patient external device to be displayed on the display.

6. The patient display device according to any one of aspects 1-5, wherein the wireless communication unit is configured for wireless communication with the patient external device using a standard network protocol.

7. The patient display device according to any one of aspects 1-5, wherein the wireless communication unit is configured for wireless communication with the patient external device using a proprietary network protocol.

8. The patient display device according to any one of aspects 1-5, wherein the wireless communication unit is configured for wireless communication with the patient external device using a first network protocol and with the server using a second network protocol.

9. The patient display device according to any one of aspects 1-5, wherein the wireless communication unit is configured for wireless communication with the patient external device using a first frequency band and with the server using a second frequency band.

10. The patient display device according to any one of aspects 1-9, wherein the wireless communication unit comprises a Bluetooth transceiver.

11. The patient display device according to any one of aspects 1-10, wherein the wireless communication unit comprises a UWB transceiver.

12. The patient display device according to aspect 6, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

13. The patient display device according to aspect 4, wherein a communication range of the wireless communication unit is less than a communication range of the auxiliary wireless communication unit.

14. The patient display device according to any one of aspects 1-13, wherein the wireless communication unit comprises a first wireless transceiver for communication with the patient external device and a second wireless transceiver for communication with the server.

15. The patient display device according to aspect 14, wherein the second wireless transceiver is configured to be disabled to enable wireless communication using the first wireless transceiver.

16. The patient display device according to any one of aspects 1-15, wherein at least one of:

the patient display device is configured to authenticate the patient external device if a distance between the patient display device and the patient external device is less than a predetermined threshold value, and the patient display device is configured to be authenticated by the patient external device if a distance between the patient display device and the patient external device is less than a predetermined threshold value.

17. The patient display device according to aspect 16, wherein the patient display device is configured to allow the transfer of data between the patient display device and the patient external device on the basis of the authentication.

18. The patient display device according to any one of the preceding aspects, wherein the patient display device is a wearable external device or a handset.

19. The patient display device according to any one of the preceding aspects, wherein the second application is configured to receive data related to a parameter of the implanted medical device.

20. The patient display device according to aspect 19, wherein the second application is configured to receive data related to a sensor value received from the implanted medical device.

21. The patient display device according to aspect 19, wherein the second application is configured to receive data related to a parameter related to at least one of:

a battery status,
a temperature,
a time, and
an error.

22. The patient display device according to any one of the preceding aspects, wherein the patient display device is configured to encrypt the user input.

23. The patient display device according to aspect 22, wherein the display is configured to encrypt the user input for decryption by the implantable medical device.

24. The patient display device according to any one of the preceding aspects, wherein the patient display device is configured to decrypt the control interface received from the patient external device, for displaying the control interface on the display.

25. The patient display device according to any one of the preceding aspects, wherein at least one of the first and second application is configured to receive data from an auxiliary external device and present the received data to the user.

26. The patient display device according to aspect 25, wherein at least one of the first and second application is configured to receive data from an auxiliary external device comprising a scale for determining the weight of the user.

27. The patient display device according to aspect 26, wherein at least one of the first and second application is configured to receive data related to the weight of the user from an auxiliary external device comprising a scale.

28. The patient display device according to aspect 27, wherein the patient display device is configured to:

wirelessly transmit the data related to the weight of the user to the patient external device, or wirelessly transmit an instruction derived from the data related to the weight of the user, or wirelessly transmit an instruction derived from a combination of the data related to the weight of the user and the implant control input received from the user.

29. A communication system for enabling communication between a patient display device and an implantable medical device, when implanted, the communication system comprising:

a patient display device,
a server or DDI, and
a patient remote external device, wherein:
the patient display device comprises:
a wireless communication unit configured for wirelessly receiving an implant control interface as a remote display portal from the patient remote external device, the wireless communication unit further being configured for wirelessly transmitting implant control user input to the patient remote external device, a display for displaying the received implant control interface as a remote display portal, and an input device for receiving implant control input from the user, wherein the patient display device is configured:
to run a first application for wireless communication with the server, and
to run a second application for wireless communication with the patient remote external device for transmission of the implant control input to the remote display portal of the patient remote external device for the communication with the implantable medical device, and wherein the patient remote external device comprises a wireless communication unit configured for wireless transmission of control commands based on the implant control input to the implantable medical device and configured for wireless communication with the patient display device.

30. The communication system according to aspect 29, wherein the patient display device comprises a first log-in function and a second log-in function, and wherein the first log-in function gives the user access to the first application and wherein the first and second log-in function in combination gives the user access to the second application.

31. The communication system according to any one of aspects 29 and 30, wherein the second application is configured to receive data related to a parameter of the implanted medical device.

32. The communication system according to aspect 31, wherein the second application is configured to receive data related to a sensor value received from the implanted medical device.

33. The communication system according to aspect 31, wherein the second application is configured to receive data related to a parameter related to at least one of:

a battery status,
a temperature,
a time, or
an error.

34. The communication system according to any one of aspects 29-33, wherein the patient display device is configured to encrypt the user input.

35. The communication system according to aspect 34, wherein the display is configured to encrypt the user input for decryption by the implantable medical device.

36. The communication system according to aspect 35, wherein the patient remote external device is configured to act as a router, transferring the encrypted user input from the patient display device to the implantable medical device without decryption.

37. The communication system according to any one of aspects 29-36, wherein the patient remote external device is configured to encrypt at least one of the control interface and the control commands.

38. The communication system according to any one of aspects 29-37, wherein the patient remote external device is configured to encrypt the control interface and wherein the patient display device is configured to decrypt the encrypted control interface.

39. A computer program product configured to run in a patient display device comprising a wireless communication unit, a display for displaying the received implant control interface as a remote display portal, and an input device for receiving implant control input from a user, the computer program product comprising:

a first application for communication with a server or DDI, a second application for communication with an patient remote external device for transmission of the implant control input via the remote display portal of the patient remote external device for the communication with an implantable medical device, wherein the second application is configured to be accessed through the first application.

a first log-in function using at least one of a password, pincode, fingerprint, or face recognition, and a second log-in function within the first application, using a private key from the user to authenticate for a defined time period a second hardware key of the patient remote external device, wherein the first log-in function gives the user access to the first application and the first and second log-in function in combination gives the user access to the second application.

40. The computer program product according to aspect 39, wherein the second application is configured to receive data related to a parameter of the implanted medical device.

41. The computer program product according to aspect 40, wherein the second application is configured to receive data related to a sensor value received from the implanted medical device.

42. The computer program product according to aspect 40, wherein the second application is configured to receive data related to a parameter related to at least one of:

a battery status, a temperature, a time, or an error.

43. The communication system, patient display device or computer program product according to any one of the preceding aspects, wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

44. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

45. The system according to anyone of the preceding aspects, wherein the patient remote external device and the patient EID external device are an integrated unit.

46. The system according to anyone of the preceding aspects, wherein the HCP dedicated device and the HCP EID external device are an integrated unit.

47. The system according to anyone of the preceding aspects, comprising a measurement device or sensor adapted to deliver a measurement to at least one of the DDI, patent EID external device and a patient display device.

48. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

49. A patient display device for communication with a patient external device for communication with the implantable medical device of any of aspects 1-28 of aspect 386SE, wherein the patient display device comprises a first log-in function and a second log-in function, and wherein the first log-in function gives the user access to the first application and wherein the first and second log-in function in combination gives the user access to the second application.

50 A patient display device for communication with a patient external device for communication with the implantable medical device of any of aspects 1-28 of aspect 386SE, wherein the first log-in function is configured to use at least one of a password, pin code, fingerprint, voice and face recognition, and a second log-in function within the first application is configured to use a private key from the user to authenticate, for a defined time period, a second hardware key of the patient external device.

51. A patient display device for communication with a patient external device for communication with an implantable medical device, when implanted, the patient display device comprising:

a wireless communication unit, a display, and an input device for receiving implant control input from the user, wherein the patient display device is configured to:

run a first application for wireless communication with a server and/or DDI, and run a second application for wireless communication with the patient external device for transmission of the implant control input to a remote display portal of the patient external device for the communication with the implantable medical device, wherein the second application is configured to be accessed through the first application.

52. A patient display device for communication with a patient external device for communication with the implantable medical device of any of aspects 1-28 of aspect 386SE, wherein the patient display device comprises a first log-in function and a second log-in function, and wherein the first log-in function gives the user access to the first application and wherein the first and second log-in function in combination gives the user access to the second application.

Aspect
387SE—eHealth_General_Encryption_End-to-End,
Aspects 1-28

1. A communication system for enabling communication between a patient display device, a patient external device, a server and an implantable medical device, the communication system comprising:

a server, a patient external device, and an implantable medical device, wherein a patient display device is adapted to co-operate with at least one of the patient external device and the server and further adapted to use:

a wireless communication unit for wirelessly communicating with at least one of the patient external device and the server, a display, and an input device for receiving input from the user, wherein the patient external device comprises a wireless communication unit configured for wireless transmission of control commands to the implantable medical device and configured for wireless communication with at least one of the patient display device and the server, wherein the server comprises a wireless communication unit configured for wireless communication with at least one of the patient display device and the patient external device, wherein the implantable medical device comprises a wireless communication unit configured for wireless communication with the patient external device, wherein the implantable medical device comprises an encryption unit and is configured to: encrypt data destined for the server, transmit the data to the server via at least one of the patient external device and a second external device or patient EID, wherein at least one of the patient external device and the patient EID, wherein the implantable medical device comprises an encryption unit and is configured to: encrypt data destined for the patient display device, transmit the data to the patient display device via the patient external device, wherein the patient external device acts as a router transferring the data without full decryption, or wherein the server comprises an encryption unit and is configured to: encrypt data destined for the implantable medical device, transmit the data to the implantable medical device via the patient external device or patient EID, wherein the patient external device or patient EID acts as a router transferring the data authenticated and with or without full decryption, or wherein the server comprises an encryption unit and is configured to: encrypt data destined for the implantable medical device, transmit the data to the implantable medical device via the patient display device and the patient external device, wherein the patient display device and the patient external device acts as a router transferring the data with or without full decryption, or wherein the patient display device comprises an encryption unit and is configured to: encrypt data destined for the implantable medical device, transmit the data to the implantable medical device via the patient external device, wherein the patient external device acts as a router transferring the data with or without full decryption, or wherein the patient display device comprises an encryption unit and is configured to: encrypt data destined for the implantable medical device, transmit the data to the implantable medical device via the server and the patient external device or patient EID, wherein the server and the patient external device or the patient EID acts as a router transferring the data with or without full decryption.

2. The communication system according to aspect 1, wherein the patient display device is configured to wirelessly receive an implant control interface from the patient external device to be displayed on the display.

3. The communication system according to any one of aspects 1-2, wherein at least two of: the wireless communication unit of the server, the wireless communication unit of the patient display device, the wireless communication unit of the patient external device, and the wireless communication unit of the implantable medical device, is configured for wireless communication using a standard network protocol.

4. The communication system according to any one of aspects 1-2, wherein at least two of:

the wireless communication unit of the server, the wireless communication unit of the patient display device, the wireless communication unit of the patient external device, and the wireless communication unit of the implantable medical device, is configured for wireless communication using a proprietary network protocol.

5. The communication system according to any one of aspects 1-4, wherein the wireless communication unit of the patient external device is configured to:

use a first network protocol for communication with the implantable medical device and use a second network protocol for communication with the server, or use a first network protocol for communication with the implantable medical device and use a second network protocol for communication with the patient display device.

6. The communication system according to any one of aspects 1-5, wherein the wireless communication unit of the patient external device is configured to:

use a first frequency band for communication with the implantable medical device and use a second frequency band for communication with the server, or use a first frequency band for communication with the implantable medical device and use a second frequency band for communication with the patient display device.

7. The communication system according to any one of aspects 1-6, wherein the wireless communication unit of the patient display device is configured to use a first network protocol for communication with the patient external device and use a second network protocol for communication with the server.

8. The communication system according to any one of aspects 1-7, wherein the wireless communication unit of the patient display device is configured to use a first frequency band for communication with the patient external device and use a second frequency band for communication with the server.

9. The communication system according to any one of aspects 1-8, wherein the wireless communication unit of the server is configured to use a first network protocol for communication with the patient external device and use a second network protocol for communication with the patient display device.

10. The communication system according to any one of aspects 1-9, wherein the wireless communication unit of the server is configured to use a first frequency band for communication with the patient external device and use a second frequency band for communication with the patient display device.

11. The communication system according to any one of aspects 1-10, wherein the wireless communication unit of at least one of the server, the patient display device, the patient external device, and the implantable medical device comprises a Bluetooth transceiver.

12. The communication system according to any one of aspects 1-11, wherein the wireless communication unit of at least one of the server, the patient display device, the patient external device, and the implantable medical device comprises a UWB transceiver.

13. The communication system according to aspect 3, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

14. The communication system according to any one of the preceding aspects, wherein the wireless communication unit of the patient external device comprises a first wireless transceiver for wireless communication with the implantable medical device, and a second wireless transceiver for wireless communication with the server, and wherein the second wireless transceiver has a longer effective range than the first wireless transceiver.

15. The communication system according to any one of the preceding aspects, wherein the wireless communication unit of the patient external device comprises a first wireless transceiver for wireless communication with the implantable medical device, and a second wireless transceiver for wireless communication with the patient display device, and wherein the second wireless transceiver has a longer effective range than the first wireless transceiver.

16. The communication system according to any one of the preceding aspects, wherein the wireless communication unit of the patient display device comprises a first wireless transceiver for wireless communication with the patient external device, and a second wireless transceiver for wireless communication with the server, and wherein the second wireless transceiver has a longer effective range than the first wireless transceiver.

17. The communication system according to any one of aspect 14-17, wherein the second wireless transceiver has an effective range being one of: 2 times, 4 times, 8 times 20 times, 50 times or 100 times longer than the first wireless transceiver.

18. The communication system according to any one of aspects 14-17, wherein the second wireless transceiver is configured to be disabled to enable wireless communication using the first wireless transceiver.

19. The communication system according to any one of the preceding aspects, wherein at least one of:

the patient display device is configured to authenticate the patient external device if a distance between the patient display device and the patient external device is less than a predetermined threshold value, the patient display device is configured to be authenticated by the patient external device if a distance between the patient display device and the patient external device is less than a predetermined threshold value, the patient display device is configured to authenticate the implantable medical device if a distance between the patient display device and the implantable medical device is less than a predetermined threshold value, the patient display device is configured to be authenticated by the implantable medical device if a distance between the patient display device and the implantable medical device is less than a predetermined threshold value, the patient external device is configured to authenticate the patient display device if a distance between the patient external device and the patient display device is less than a predetermined threshold value, the patient external device is configured to be authenticated by the patient display device if a distance between the patient external device and the patient display device is less than a predetermined threshold value, the patient external device is configured to authenticate the implantable medical device if a distance between the patient external device and the implantable medical device is less than a predetermined threshold value, and the patient external device is configured to be authenticated by the implantable medical device if a distance between the patient external device and the implantable medical device is less than a predetermined threshold value.

20. The communication system according to aspect 19, wherein the patient display device is configured to allow the transfer of data between the patient display device and the patient external device on the basis of the authentication.

21. The communication system according to aspect 19, wherein the patient external device is configured to allow the transfer of data between the patient display device and the patient external device on the basis of the authentication.

22. The communication system according to aspect 19, wherein the patient external device is configured to allow the transfer of data between the patient external device and the implantable medical device on the basis of the authentication.

23. The communication system according to any one of the preceding aspects, wherein the patient display device is a wearable patient external device or a handset.

24. The communication system according to any one of the preceding aspects, wherein the data encrypted by the implantable medical device is related to at least one of: a battery status, a temperature, a time, or an error.

25. A server for use in the communication system according to any one of aspects 1-24.

26. A patient display device for use in the communication system according to any one of aspects 1-24.

27. A patient external device for use in the communication system according to any one of aspects 1-24.

28. An implantable medical device for use in the communication system according to any one of aspects 1-24.

29. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

30. The system according to anyone of the preceding aspects, wherein the patient remote external device and the patient EID external device are an integrated unit.

31. The system according to anyone of the preceding aspects, wherein the HCP dedicated device and the HCP EID external device are an integrated unit.

32. The system according to anyone of the preceding aspects, comprising a measurement device or sensor adapted to deliver a measurement to at least one of the DDI, patent EID external device and a patient display device.

33. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

Aspect
387B—eHealth_General_Encryption_End-to-End

1. A communication system for communication of data to or from an implantable medical device, the communication system comprising:
an implantable medical device,
a server,
a patient external device comprising:
a first wireless communication unit configured for wireless transmission of control commands or data to or from the implantable medical device, and
a second wireless communication unit for wireless communication with the server,
a patient display device adapted to communicate with at least one of the patient external device and the server,
wherein the implantable medical device comprises an encryption unit and is configured to:
encrypt data destined for the server,
transmit the data to the server via at least one of the patient external device.

2. A communication system for enabling communication to or from an implantable medical device, the communication system comprising:
a server,
a patient external device comprising:
a first wireless communication unit configured for wireless transmission of control commands or data to or from the implantable medical device, and

a second wireless communication unit for wireless communication with the server, an implantable medical device, a patient display device adapted to communicate with at least one of the patient external device and the server, wherein the implantable medical device comprises an encryption unit and is configured to:

encrypt data destined for the patient display device, transmit the data to the patient display device via the patient external device, wherein the patient external device acts as a router transferring the data without full decryption.

3. A communication system for enabling communication to or from an implantable medical device, the communication system comprising:

a server, a patient external device comprising:

a first wireless communication unit configured for wireless transmission of control commands or data to or from the implantable medical device, and a second wireless communication unit for wireless communication with the server, an implantable medical device, a patient display device adapted to communicate with at least one of the patient external device and the server, wherein the server comprises an encryption unit and is configured to:

encrypt data destined for the implantable medical device, transmit the data to the implantable medical device via the patient external device, wherein the patient external device acts as a router transferring the data without full decryption.

4. A communication system for enabling communication to or from an implantable medical device, the communication system comprising:

a server, a patient external device comprising:

a first wireless communication unit configured for wireless transmission of control commands or data to or from the implantable medical device, and a second wireless communication unit for wireless communication with the server, an implantable medical device, a patient display device adapted to communicate with at least one of the patient external device and the server, wherein the patient display device comprises an encryption unit and is configured to: encrypt data destined for the implantable medical device, transmit the data to the implantable medical device via the patient external device, wherein the patient external device acts as a router transferring the data with or without full decryption.

5. A communication system for enabling communication to or from a implantable medical device, the communication system comprising:

a server, a patient external device comprising:

a first wireless communication unit configured for wireless transmission of control commands or data to or from the implantable medical device, and a second wireless communication unit for wireless communication with the server, an implantable medical device, a patient display device adapted to communicate with at least one of the patient external device and the server,

wherein the patient display device comprises an encryption unit and is configured to:

encrypt data destined for the implantable medical device, transmit the data to the implantable medical device via the server and/or the patient external device, wherein the server and/or the patient external device acts as a router transferring the data with or without full decryption.

6. The communication system according to any one of the preceding embodiments, further comprising:

a display connected to the patient display device, and an input device for receiving input from the user, the input device being connected to the patient display device.

wherein the patient display device is configured to receive an implant control interface from the patient external device to be displayed on the display, and wherein the patient display device is configured to transmit any control input received form the input device to the patient external device.

7. The communication system according to any one of the preceding embodiments, wherein at least two of:

the server, the patient display device, the patient external device, and the implantable medical device, are configured for wireless communication using a standard network protocol.

8. The communication system according to any one of the preceding embodiments, wherein at least two of: the server, the patient display device, the patient external device, and the implantable medical device, are configured for wireless communication using a proprietary network protocol.

9. The communication system according to any one of the preceding embodiments, wherein the patient external device is configured to:

use a first network protocol for communication with the implantable medical device and use a second network protocol for communication with the server, or use a first network protocol for communication with the implantable medical device and use a second network protocol for communication with the patient display device.

6. The communication system according to any one of the preceding embodiments, wherein the patient external device is configured to:

use a first frequency band for communication with the implantable medical device and use a second frequency band for communication with the server, or use a first frequency band for communication with the implantable medical device and use a second frequency band for communication with the patient display device.

10. The communication system according to any one of the preceding embodiments, wherein the patient display device is configured to use a first network protocol for communication with the patient external device and use a second network protocol for communication with the server.

11. The communication system according to any one of the preceding embodiments, wherein the patient display device is configured to use a first frequency band for communication with the patient external device and use a second frequency band for communication with the server.

12. The communication system according to any one of the preceding embodiments, wherein at least one of the patient display device, the patient external device, and the implantable medical device comprises a Bluetooth transceiver.

13. The communication system according to any one of the preceding embodiments, wherein at least one the patient display device, the patient external device, and the implantable medical device comprises a UWB transceiver.

14. The communication system according to embodiment 3, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

15. The communication system according to any one of the preceding embodiments, wherein the patient external device comprises a first wireless transceiver for wireless communication with the implantable medical device, and a second wireless transceiver for wireless communication with the server, and wherein the second wireless transceiver has a longer effective range than the first wireless transceiver.

16. The communication system according to any one of the preceding embodiments, wherein the patient external device comprises a first wireless transceiver for wireless communication with the implantable medical device, and a second wireless transceiver for wireless communication with the patient display device, and wherein the second wireless transceiver has a longer effective range than the first wireless transceiver.

17. The communication system according to any one of the preceding embodiments, wherein the patient display device comprises a first wireless transceiver for wireless communication with the patient external device, and a second wireless transceiver for wireless communication with the server, and wherein the second wireless transceiver has a longer effective range than the first wireless transceiver.

18. The communication system according to any one of embodiment 15-17, wherein the second wireless transceiver has an effective range being one of: 2 times, 4 times, 8 times 20 times, 50 times or 100 times longer than the first wireless transceiver.

19. The communication system according to any one of embodiments 15-17, wherein the second wireless transceiver is configured to be disabled while the first wireless transceiver is enabled.

20. The communication system according to any one of the preceding embodiments, wherein the patient display device is configured to allow the transfer of data between the patient display device and the patient external device based on that a distance between the patient display device and the patient external device is less than a predetermined threshold value.

21. The communication system according to any one of the preceding embodiments, wherein the patient external device is configured to allow the transfer of data between the patient display device and the patient external device based on that a distance between the patient display device and the patient external device is less than a predetermined threshold value.

22. The communication system according to any one of the preceding embodiments, wherein the patient external device is configured to allow the transfer of data between the patient external device and the implantable medical device based on that a distance between the patient display device and the patient external device is less than a predetermined threshold value.

23. The communication system according to any one of the preceding embodiments, wherein the patient display device is a wearable patient display device or a handset.

24. The communication system according to any one of the preceding embodiments, wherein the implantable medical device is configured to transmit encrypted data related to at least one of: a battery status, a temperature, a time, or an error.

25. A server for use in the communication system according to any one of embodiments 1-24.

26. A patient display device for use in the communication system according to any one of embodiments 1-24.

27. A patient external device for use in the communication system according to any one of embodiments 1-24.

28. An implantable medical device for use in the communication system according to any one of embodiments 1-24.

29. The communication system according to any one of the preceding embodiments, wherein at least one of:

The server comprises or is adapted to receive a health care provider private key for encrypting and/or decrypting data, the patient display device comprises or is adapted to receive a patient display private key for encrypting and/or decrypting data, the patient external device comprises or is adapted to receive a patient private key for encrypting and/or decrypting data, and the implantable medical device comprises a medical device private key for encrypting or decrypting data.

30. The communication system according to embodiment 29, wherein at least one of the health care provider private key, patient display private key, the patient private key, the medical device private key comprises a hardware or a software key.

Aspect
396SE—eHealth_General_Communication_Dual

1. A system configured for changing pre-programmed treatment settings of an implantable medical device, when implanted in a patient, from a distant remote location in relation to the patient, the system comprising:

at least one health care provider, HCP, EID external device, and a HCP private key device, wherein the HCP EID external device is adapted to receive a command from the HCP to change said pre-programmed treatment settings of an implanted medical device, and further adapted to be activated and authenticated and allowed to perform said command by the HCP providing the HCP private key device, wherein the HCP private key device is adapted to be provided to the HCP EID external device via at least one of: a reading slot or comparable for the HCP private key device, and a RFID communication or other close distance wireless activation communication;

wherein said HCP EID external device comprises at least one of:

a reading slot or comparable for the HCP private key device, a RFID communication, and other close distance wireless activation communication or electrical direct contact;

wherein said HCP EID external device further comprises at least one wireless transceiver configured for communication with a data infrastructure server, DDI, through a first network protocol, wherein said system further comprises:

a data infrastructure server, DDI, adapted to receive command from said HCP EID external device and to relay the received command without modifying said command to a patient EID external device, wherein the DDI comprises one wireless transceiver configured for communication with said patient external device, and a patient EID external device adapted to receive the command from the HCP EID relayed by the DDI, further adapted to send this command to the implanted medical device, said command adapted to change said pre-programmed treatment settings of the implanted medical device, and further adapted to be activated and authenticated and allowed to perform said command by the implant, wherein the implanted medical device is configured to treat the patient or perform a bodily function.

2. The system configured for changing pre-programmed treatment settings of an implantable medical device according to aspect 1, wherein the patient providing a patient private key device adapted to be provided to the patient EID external device by the patient via at least one of: a reading slot or comparable for the patient private key device, a RFID communication or other close distance wireless activation communication or electrical direct contact, wherein said patient EID external device comprises at least one of:

a reading slot or comparable for the HCP private key device, a RFID communication, and other close distance wireless activation communication or electrical direct contact.

3. The system configured for changing pre-programmed treatment settings of an implantable medical device according to aspect 1-2, wherein the wherein said patient EID external device further comprises at least one wireless transceiver configured for communication with the implanted medical device through a second network protocol.

4. The system according to aspect 1-3, wherein at least one of the patient private key device or HCP private key device comprises a hardware key.

5. The system according to any preceding aspect, wherein the private key device is at least one of, a smartcard, a key-ring device, a watch an arm or wrist band a neckless or any shaped device.

6. The system according to any of the preceding aspects, wherein at least two of:

the HCP EID external device, the patient EID external device, the HCP private key device, the patient private key device, and the DDI is configured for wireless communication using a standard network protocol.

7. The system according to any of the preceding aspects, wherein at least two of:

the HCP EID external device, the patient EID external device, the HCP private key device, the patient private key device, and the DDI is configured for wireless communication using a proprietary network protocol.

8. The system according to any of the preceding aspects, wherein the patient EID external device is configured to use a first network protocol for communication with the implantable medical device and use a second network protocol for communication with the DDI.

9. The system according to any of the preceding aspects, wherein the patient EID external device is configured to use a first frequency band for communication with the implantable medical device and use a second frequency band for communication with the DDI.

10. The system according to any of the preceding aspects, wherein the DDI is configured to use a first frequency band for communication with the patient EID external device and a second frequency band for communication with the patient private key device.

11. The system according to any of the preceding aspects, wherein at least one of the HCP EID external device, the patient EID external device, the HCP private key device, the patient private key device and the DDI comprises a Bluetooth transceiver.

12. The system according to any of the preceding aspects, wherein at least one of the HCP EID external device, the patient EID external device, the HCP private key device, the patient private key device and the DDI comprises a UWB transceiver.

13. The system according to aspect 4, wherein the standard network protocol is one from the list of:

Radio Frequency type protocol, RFID type protocol, WLAN type protocol, Bluetooth type protocol, BLE type protocol, NFC type protocol, 3G/4G/5G type protocol, and GSM type protocol.

14. The system according to any of the preceding aspects, wherein the patient EID external device comprises a first wireless transceiver for wireless communication with the implantable medical device, and a second wireless transceiver for wireless communication with the DDI, and wherein the second wireless transceiver has longer effective range than the first wireless transceiver.

15. The system according to any of the preceding aspects, wherein the patient private key device comprises a first wireless transceiver for wireless communication with the HCP EID external device, and a second wireless transceiver for wireless communication with the DDI, and wherein the second wireless transceiver has longer effective range than the first wireless transceiver.

16. The system according to aspects 12 or 13, wherein the second wireless transceiver has an effective range being one of: 2 times, 4 times, 8 time, 20 times, 50 times or 100 times longer than the effective range of the first wireless transceiver.

17. The system according to any of aspects 12-14, wherein the second wireless transceiver is configured to be disabled to enable wireless communication using the first wireless transceiver.

18. The system according to any of the preceding aspects, wherein the patient EID external device is configured to allow transfer of data between the EID external device and the implantable medical device on the basis of an authentication of the patient EID external device.

19. The system according to any of the preceding aspects, wherein the patient EID external device is a wearable patient external device or a handset.

20. The system according to any of the preceding aspects, wherein the data encrypted by the implantable medical device is related to at least one of: a battery status, a temperature, a time, or an error.

21. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

22. The system according to anyone of the preceding aspects, wherein the patient remote external device and the patient EID external device are an integrated unit.

23. The system according to anyone of the preceding aspects, wherein the HCP dedicated device and the HCP EID external device are an integrated unit.

24. The system according to anyone of the preceding aspects, comprising a measurement device or sensor adapted to deliver a measurement to at least one of the DDI, patent EID external device and a patient display device.

25. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

26. A system configured for changing pre-programmed treatment settings of an implantable medical device according to aspect 1-25, wherein the HCP, HCP EID, or HCP via HCP EID are adapted to be providing changed pre-programmed settings of an implant of a human or mammal to:
a communication unit configured to receive such changed pre-programmed settings in an authenticated file, wherein the communication unit is controlled by a first chip, a first circuit, or a first chip and a first circuit, adapted to further provide the authenticated file to:
an decryption unit for decrypting the file received, controlled by a second chip, a second circuit, or a second chip and a second circuit adapted to not be directly in contact with any external device, adapted to be received via:
a narrow secure communication tunnel between the first chip, a first circuit, or a first chip and a first circuit, and the second chip, a second circuit, or a second chip and a second circuit, wherein the communication unit is adapted to only communicate with the decryption unit via the narrow secure communication tunnel, and wherein the decryption unit is adapted to authenticate the HCP provider of the authenticated file and that the data of the file has not been tampered with.

27. A system according to aspect 1-26, wherein the authenticated file is adapted to be received indirect by the decryption unit adapted to decrypt the received data and use the decrypted data after the decryption unit has authenticated the HCP, HCP EID, or HCP and HCP EID as originator of the received data of the authenticated file and that the file or data has not been tampered with.

28. A system according to aspect 1-27, wherein the authenticated file comprises instruction about selected programmed settings of steps of action, wherein use of the decrypted data of the authenticated file comprises instructions to select anyone of the pre-programmed settings of steps of actions of the implant.

29. A system according to aspect 1-28, wherein the implant is adapted to authenticate, decrypt or authenticate and decrypt the received data using a first key.

30. A system according to aspect 1-29, wherein the HCP private key, patient private key, or HCP private key and patient private key comprising a hardware key.

31. A system according to aspect 1-30, wherein the HCP private key, patient private key, or HCP private key and patient private key comprising an advanced software key.

32. A system according to aspect 1-31, wherein authenticated file is adapted to be received by a storage unit of the decryption unit comprising at least one of authenticating information and key related information, related to the HCP, HCP EID or HCP and HCP EID, wherein the decryption unit is adapted to compare stored information with received authenticated file data related to at least one of authentication and decryption.

Aspect 396B eHealth_Implant Programming_Dual_Remote

1. A system configured for changing pre-programmed treatment settings of an implantable medical device, when implanted in a patient, from a remote location in relation to the patient, the system comprising:
a health care provider, HCP, external device, adapted to receive a HCP private key from a HCP private key device,
a patient external device, adapted to receive a patient private key from a patient private key device;
a server,
wherein:
the HCP external device is adapted to receive a user command to change said pre-programmed treatment settings, the HCP external device being configured to authorize said command via the HCP private key device and transmit said command and authorization to the server;
the server is adapted to receive said command and authorization from the HCP external device and to relay the received command and authorization to the patient external device, and
the patient external device is adapted to receive the command and authorization, and further adapted to send said command to the implanted medical device upon a provided authorization from the patient private key device and a positive verification of the authorization.

2. The system according to embodiment 1, wherein the patient private key is provided to the patient external device via at least one of: a reading slot for a patient private key device, a RFID communication or other close distance wireless activation communication or electrical direct contact.

3. The system according to embodiment 1-2, wherein the wherein said patient external device further comprises at least one wireless transceiver configured for communication with the implanted medical device through a second network protocol different from the network protocol for communicating with the server.

4. The system according to embodiment 1-3, wherein at least one of the patient private key device or HCP private key device comprises a hardware key.

5. The system according to any preceding embodiment, wherein the private key device is at least one of, a smartcard, a key-ring device, a watch, an arm or wrist band, a neckless.

6. The system according to any of the preceding embodiments, wherein at least two of:
the HCP external device, the patient external device, the HCP private key device, the patient private key device, and the server, are configured for wireless communication using a standard network protocol.

7. The system according to any of the preceding embodiments, wherein at least two of:
the HCP external device, the patient external device, the HCP private key device, the patient private key device, and the server, are configured for wireless communication using a proprietary network protocol.

8. The system according to any of the preceding embodiments, wherein the patient external device is configured to use a first network protocol for communication with the server.

9. The system according to any of the preceding embodiments, wherein the patient external device is configured to use a first frequency band for communication with the implantable medical device and use a second frequency band for communication with the server.

10. The system according to any of the preceding embodiments, wherein the server is configured to use a first frequency band for communication with the patient external device and a second frequency band for communication with the HCP external device.

11. The system according to any of the preceding embodiments, wherein at least one of the HCP external device, the patient external device, the HCP private key device, the patient private key device and the server comprises a Bluetooth transceiver.

12. The system according to any of the preceding embodiments, wherein at least one of the HCP external device, the patient external device, the HCP private key device, the patient private key device and the server comprises a UWB transceiver.

13. The system according to embodiment 4, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

14. The system according to any of the preceding embodiments, wherein the patient external device comprises a first wireless transceiver for wireless communication with the implantable medical device, and a second wireless transceiver for wireless communication with the server, and wherein the second wireless transceiver has longer effective range than the first wireless transceiver.

15. The system according to any of the preceding embodiments, wherein the implantable medical device is configured to transmit data related to at least one of: a battery status, a temperature, a time, or an error.

16. The system according to any one of the preceding embodiments, wherein the implantable medical device comprises a measurement device or sensor, and wherein the medical device is adapted to transmit measurements from the measurement device or sensor to the patient external device.

17. The system according to any one of embodiments 1-16, wherein the medical device comprises:
    a communication unit comprising a first chip, a first circuit, or a first chip and a first circuit, for receiving encrypted data from the external device,
    a decryption unit for decrypting the encrypted data, the decryption unit comprising a second chip, a second circuit, or a second chip and a second circuit,
    a narrow secure communication tunnel between the first chip, a first circuit, or a first chip and a first circuit, and the second chip, a second circuit, or a second chip and a second circuit.

18. A system according to embodiment 17, wherein the communication unit is adapted to verify the integrity and authenticity of the encrypted data, verify that the encrypted data originates from the DDI or the HCP EID, and in response to positive verifications, transmit the encrypted data to the decryption unit.

19. A system according to embodiment 17-18, wherein the encrypted data comprises an instruction about selected programmed settings of steps of action.

20. A system according to embodiment 1-19, wherein the implant is adapted to authenticate, decrypt or authenticate and decrypt the received data using a first key.

Aspect
397SE—eHealth_General_Communication_Dual

1. A system configured for changing pre-programmed treatment settings of an implantable medical device, when implanted in a patient, by a health care provider, HCP, in the physical presence of the patient, the system comprising:
    at least one HCP EID external device adapted to receive a command from the HCP, directly or indirectly, to change said pre-programmed treatment settings in steps of an implantable medical device, when implanted, wherein the HCP EID external device is further adapted to be activated, authenticated, and allowed to perform said command by the HCP providing a HCP private key device comprising a HCP private key,
    wherein the HCP private key device comprises at least one of: a smart card, a keyring device.
    a watch, a arm or wrist band, a necklace, and any shaped device;
    wherein the HCP EID external device is adapted to be involved in at least one of: receiving information from the implant, receiving information from a patient EID, receiving information direct or indirect from a remote external device, actuating the implanted medical device, changing pre-programmed settings, and updating software of the implantable medical device, when implanted.
    wherein the HCP EID external device is adapted to be activated, authenticated, and allowed to perform said command also by the patient,
    wherein the system further comprises:
    a patient private key device comprising a patient private key, the patient private key device comprising at least one of:
    a smart card, a keyring device, a watch, a arm or wrist band, a necklace, and any shaped device;
    wherein the HCP private key and the patient private key are required for performing said actions by the HCP EID external device to at least one of: receive information from the implant, to receive information direct or indirect from a patient remote external device, to actuate the implanted medical device, to change pre-programmed settings, and to update software of the implantable medical device, when the implantable medical device is implanted.

2. The system according to aspect 1, wherein the HCP EID external device further comprises a wireless transceiver configured for communication with the implanted medical device through a second network protocol.

3. The system according to aspect 1 or 2, wherein the HCP private key device is adapted to be provided to the at least one HCP external device via at least one of;
    a reading slot or comparable for the HCP private key device,
    a RFID communication, and
    a close distance wireless activation communication unit, or electrical direct contact.

4. The system according to anyone of the preceding aspects, wherein the HCP EID external device comprises at least one of:

reading slot or comparable for the HCP private key device, a RFID communication and a close distance wireless activation communication unit, or electrical direct contact.

5. The system according to any of the preceding aspects, wherein the HCP EID external device is adapted to receive a command from a HCP dedicated device to change said pre-programmed treatment steps of the implantable medical device, when implanted, wherein the HCP dedicated device is further adapted to be activated, authenticated, and allowed to perform said command by the HCP providing their private key.

6. The system according to any of the preceding aspects, wherein at least two of:

the HCP EID external device, the patient EID external device, the HCP private key device, and the patient private key device, are configured for wireless communication using a standard network protocol.

7. The system according to any of the preceding aspects, wherein at least two of:

the HCP EID external device, the patient EID external device, the HCP private key device, and the patient private key device, are configured for wireless communication using a proprietary network protocol.

8. The system according to any of the preceding aspects, wherein the patient EID external device is configured to use a first network protocol for communication with the implantable medical device and use a second network protocol for communication with the patient private key device.

9. The system according to any of the preceding aspects, wherein the patient EID external device is configured to use a first frequency band for communication with the implantable medical device and use a second frequency band for communication with the patient private key device.

10. The system according to any of the preceding aspects, wherein at least one of the HCP EID external device, the patient EID external device, the HCP private key device, and the patient private key device comprises a Bluetooth transceiver.

11. The system according to any of the preceding aspects, wherein at least one of the HCP EID external device, the patient EID external device, the HCP private key device, and the patient private key device comprises a UWB transceiver.

12. The system according to aspect 6, wherein the standard network protocol is one from the list of:

Radio Frequency type protocol, RFID type protocol, WLAN type protocol, Bluetooth type protocol, BLE type protocol, NFC type protocol, 3G/4G/5G type protocol, and GSM type protocol.

13. The system according to any of the preceding aspects, wherein the patient EID external device comprises a first wireless transceiver for wireless communication with the implantable medical device, and a second wireless transceiver for wireless communication with the patient private key device, and wherein the second wireless transceiver has longer effective range than the first wireless transceiver.

14. The system according to aspect 13, wherein the second wireless transceiver has an effective range being one of: 2 times, 4 times, 8 time, 20 times, 50 times or 100 times longer than the effective range of the first wireless transceiver.

15. The system according to aspects 13 or 14, wherein the second wireless transceiver is configured to be disabled to enable wireless communication using the first wireless transceiver.

16. The system according to any of the preceding aspects, wherein the patient EID external device is configured to allow transfer of data between the EID external device and the implantable medical device on the basis of an authentication of the patient EID external device.

17. The system according to any of the preceding aspects, wherein the patient EID external device is a wearable patient external device or a handset.

18. The system according to any of the preceding aspects, wherein the data encrypted by the implantable medical device is related to at least one of: a battery status, a temperature, a time, or an error.

19. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

20. The system according to anyone of the preceding aspects, wherein the patient remote external device and the patient EID external device are an integrated unit.

21. The system according to anyone of the preceding aspects, wherein the HCP dedicated device and the HCP EID external device are an integrated unit.

22. The system according to anyone of the preceding aspects, comprising a measurement device or sensor adapted to deliver a measurement to at least one of the DDI, patent EID external device and a patient display device.

23. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

24. A system configured for changing pre-programmed treatment settings of an implantable medical device according to aspect 1-23, wherein the HCP private key and the patient private key are required in the same location normally at the Hospital to activate the HCP EID external device for performing at least one of the actions by the HCP EID external device to at least one of: to change pre-programmed settings, and to update software of the implantable medical device, when the implantable medical device is implanted.

Aspect 397B Implant Programming_Dual_Local

1. A system for updating software of an implantable medical device, when implanted in a patient, by a health care provider, HCP, the system comprising:

a health care provider, HCP, external device, adapted to receive a HCP private key from a HCP private key device, a patient external device adapted to receive a patient private key from a patient private key device;

a server, wherein:

the HCP external device is adapted to receive a user command to change said pre-programmed treatment settings, the HCP external device being configured to authorize said user command by receiving the HCP private key device and via the patient private key device, and to transmit said user command and authorization to the server, the server is adapted to receive said command from the HCP external device and to relay the received command to the patient external device, and the patient eternal device is adapted to receive the user command and to send said user command to the implanted medical device based on the HCP external device authorization.

2. The system according to embodiment 1, wherein the HCP external device further comprises a wireless transceiver configured for communication with the implanted medical device through a second network protocol.

3. The system according to embodiment 1 or 2, wherein the HCP external device comprises at least one of:

a reading slot or comparable for the HCP private key device, a RFID communication means, and a close distance wireless activation communication unit, or electrical direct contact, for receiving the HCP private key from the HCP private key device or for receiving a patient private key from the patient private key device.

4. The system according to any of the preceding embodiments, wherein the HCP external device is adapted to receive a command from a user to change said software of the implantable medical device.

5. The system according to any of the preceding embodiments, wherein at least two of:

the HCP external device, the patient external device, the HCP private key device, and the patient private key device, are configured for wireless communication using a standard network protocol.

6. The system according to any of the preceding embodiments, wherein at least two of:

the HCP EID external device, the patient external device, the HCP private key device, and the patient private key device, are configured for wireless communication using a proprietary network protocol.

7. The system according to any of the preceding embodiments, wherein the patient external device is configured to use a first network protocol for communication with the implantable medical device and use a second network protocol for communication with the patient private key device.

8. The system according to any of the preceding embodiments, wherein the patient external device is configured to use a first frequency band for communication with the implantable medical device and use a second frequency band for communication with the server.

9. The system according to any of the preceding embodiments, wherein at least one of the HCP external device, the patient EID external device, the HCP private key device, and the patient private key device comprises a Bluetooth transceiver.

10. The system according to any of the preceding embodiments, wherein at least one of the HCP external device, the patient external device, the HCP private key device, and the patient private key device comprises a UWB transceiver.

11. The system according to embodiment 5, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

12. The system according to any of the preceding embodiments, wherein the patient external device comprises a first wireless transceiver for wireless communication with the implantable medical device, and a second wireless transceiver for wireless communication with the server, and wherein the second wireless transceiver has longer effective range than the first wireless transceiver.

13. The system according to any of the preceding embodiments, wherein the patient external device is a wearable external device or a handset.

14. The system according to any of the preceding embodiments, wherein the implantable medical device is adapted to transmit data to the patient external device, the data being comprising at least one of: a battery status, a temperature, a time, or an error.

15. The system according to anyone of the preceding embodiments, wherein the implantable medical device comprises a measurement device or sensor.

16. The system according to any one of the preceding embodiments, wherein the patient EID is adapted to send said command to the implantable medical device in response to the HCP external device and the patient external device being within a pre-determined distance, or in response to the HCP external device and the patient external device being connected to each other, or in response to receiving the HCP private key.

Aspect
398SE—eHealth_General_Communication_Dual

1. A system configured to change pre-programmed and pre-selected treatment actions of an implantable medical device, when implanted in a patient, by command from the patient, the system comprising:

an implantable medical device, a patient remote external device, comprising a wireless transceiver configured for communication with the implantable medical device, when the medical device is implanted, and a remote display portal configured to receive content delivered from the patient remote external device to expose buttons to express the will to actuate the functions of the implanted medical device by the patient through the patient remote external device, and further configured to present the display portal remotely on a patient display device allowing the patient to actuate the functions of the implanted medical device through the display portal of the patient remote external device visualised on the patient display device.

2. The system according to aspect 1, wherein the wireless transceiver, the remote display portal, and the remote display portal are comprised in the patient remote external device.

3. The system according to aspects 1 or 2, further comprising the patient display device comprising:

a supporting application, a display which hosts the Remote Display Portal, and a patient display device private key.

4. The system according to aspect 3, wherein the remote display portal is capable of generating a command to be signed by the patient display device private key.

5 The system according to anyone of the preceding aspects, wherein the patient remote external device is adapted to accept input from the patient via said patient display device through its remote display portal.

6. The system according to anyone of the preceding aspects, wherein the patient remote external device comprises a graphical user interface arranged on a touch-responsive display exposing buttons to express actuation functions of the implanted medical device.

7. The system according to anyone of the preceding aspects, configured to allow the patient to actuate the implant at home through the patient remote external device by means of an authorization granted by a patient private key.

8. The system according to aspect 7, wherein the patient private key comprises at least one of:

a smart card, a keyring device, a watch, a arm or wrist band, a necklace, and any shaped device.

9. The system according to anyone of the preceding aspects, configured to allow the patient to actuate the implantable medical device, when implanted, at home through the patient remote external device, using an authorization granted by the patient private key.

10. The system according to anyone of the preceding aspects, wherein the system further comprises a patient EID external device comprising at least one of:

a reading slot or comparable for the patient private key device.

a RFID communication, and a close distance wireless activation communication, or electrical direct contact.

11. The system according to anyone of the preceding aspects, wherein the patient EID external device is adapted to be synchronised with the patient remote external device.

12. The system according to anyone of the preceding aspects, wherein said patient EID external device further comprises at least one of:

a wireless transceiver configured for communication with the patient, a remote external device, and a wired connector for communication with the patient remote external device.

13. The system according to anyone of the preceding aspects, wherein the patient EID external device is adapted to generate an authorization to be signed by the patient private key to be installed into at least one of:

the patient remote external device through the patient EID external device, and the implantable medical device.

14. The system according to anyone of the preceding aspect, comprising a patient display device comprising a supporting application capable of displaying the remote display portal with content delivered from the patient remote external device.

15. The system according to aspect 14, wherein said remote display portal and patient remote external device are adapted to expose buttons to express the will to actuate the functions of the implanted medical device by the patient through the patient remote external device.

16. The system according to aspect 14 or 15, wherein the patient display device comprises at least one of:

a display which hosts the remote display portal, and a patient display device private key.

17. The system according to any of aspects 14-16, wherein said remote display portal is capable of generating a command to be signed by the patient private key.

18. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

19. The system according to anyone of the preceding aspects, wherein the patient remote external device and the patient EID external device are an integrated unit.

20. The system according to anyone of the preceding aspects, wherein the HCP dedicated device and the HCP EID external device are an integrated unit.

21. The system according to anyone of the preceding aspects, comprising a measurement device or sensor adapted to deliver a measurement to at least one of the DDI, patent EID external device and a patient display device.

22. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

Aspect 398B eHealth_Pre-Programmed Steps_Patient Remote Control

1. A system for changing pre-programmed steps or pre-selected treatment actions of an implantable medical device, when implanted in a patient, the system comprising:

an implantable medical device, a patient external device, comprising a wireless transceiver for communication with the implantable medical device, and a patient display device configured to receive a control interface from the patient external device for receiving user input for actuating a function of the implanted medical device and transmitting the user input to the patient remote external device, wherein the patient external device is configured to receive the user input form the patient display device, generate a command for the implantable medical device based on the user input, cryptographically sign the command and transmit the command to the implantable medical device.

2. The system according to embodiment 1, wherein the wireless transceiver and the patient display device are comprised in the patient external device.

3. The system according to embodiments 1 or 2, wherein the patient display device comprises a patient display device private key.

4. The system according to embodiment 3, wherein the patient display device is configured to generate a command signed by the patient display device private key.

5. The system according to anyone of the preceding embodiments, wherein the patient external device comprises a graphical user interface arranged on a touch-responsive display exposing buttons to invoke functions of the implanted medical device.

6. The system according to embodiment 7, wherein the patient private key comprises at least one of: a smart card, a keyring device, a watch, an arm or wrist band, a necklace.

7. The system according to anyone of the preceding embodiments, wherein the patient external device is configured to receive the patient private key for authorizing and in response to receiving the patient private key, transmit a the command to the implantable medical device.

8. The system according to anyone of the preceding embodiments, wherein patient external device comprises at least one of: a reading slot, a RFID communication, and a close distance wireless activation communication, or electrical direct contact, for receiving the patient private key from the patient private key device.

9. The system according to anyone of the preceding embodiments, wherein the patient external device is adapted to generate an authorization for the command to be signed by the patient private key to be installed into at least one of: the patient external device, and the implantable medical device.

14. The system according to anyone of the preceding embodiment, wherein the patient display device comprises a supporting application capable of displaying the a display portal with content delivered from the patient external device.

15. The system according to embodiment 14, wherein said display portal and patient remote external device are adapted to expose buttons to actuate the functions of the implanted medical device by the patient through the patient remote external device.

16. The system according to embodiment 14 or 15, wherein the patient display device comprises a display for displaying the display portal.

17. The system according to any of embodiments 14-16, wherein said display portal is capable of generating a command to be signed by the patient private key.

18. The system according to any of the preceding embodiments, comprising a master private key device configured to allow issuance of new patient private key device, the master private key device adapted to be able to create a new patient private key for a patient private key device.

Aspect 399SE—eHealth_General_Implant Information

1. A system configured for providing information from an implantable medical device, when implanted in a patient, to a distant remote location in relation to the patient, the system comprising:

at least one patient EID external device 320''' adapted to receive information from the implant, adapted to send such information further on to a server or dedicated data infrastructure, DDI, 330, further adapted to be activated and authenticated and allowed to receive said information by the implanted medical device by the patient providing a private key, a patient private key device comprising the private key adapted to be provided to the patient EID external device via at least one of: a reading slot or comparable for the patient private key device, a RFID communication or other close distance wireless activation communication or direct electrical connection, wherein said patient EID external device comprises at least one of;

a reading slot or comparable for the patient private key device, an RFID communication, and other close distance wireless activation communication or direct electrical contact;

wherein said patient EID external device further comprises at least one wireless transceiver configured for communication with the DDI, through a first network protocol.

2. The system according to aspect 1, wherein the at least one patient EID external device 320''' is adapted to receive information from the implant, through a second network protocol.

3. The system according to aspects 1 or 2, comprising the DDI, wherein the DDI is adapted to receive information from said patient EID external device, and wherein the DDI comprises a wireless transceiver configured for communication with said patient EID external device.

4. The system according to anyone of the preceding aspects, wherein the patient EID external device is adapted to receive a command relayed by the DDI, to further send the command to the implanted medical device to change said pre-programmed treatment settings of the implanted medical device, and further adapted to be activated and authenticated and allowed to perform said command by the patient providing the patient private key.

5. The system according to anyone of the preceding aspects, wherein the patient private key device is adapted to provide the patient private key to the patient EID external device by the patient via at least one of; a reading slot or comparable for the patient private key device, an RFID communication or other close distance wireless activation communication, or electrical direct contact.

6. The system according to anyone of the preceding aspects, said patient EID external device comprising at least one of:

a reading slot or comparable for the HCP private key device.

a RFID communication, and other close distance wireless activation communication, or direct electrical contact.

7. The system according to anyone of the preceding aspects, said patient EID external device further comprising at least one wireless transceiver configured for communication with the implanted medical device through a second network protocol.

8. The system according to anyone of the preceding aspects, comprising the implantable medical device adapted to, when implanted, treat the patient or perform a bodily function.

9. The system according to anyone of the preceding aspect, wherein the patient private key comprises at least one of: a smart card, a keyring device, a watch, an arm band or wrist band, a necklace, and any shaped device.

10. The system according to any of the preceding aspects, wherein at least two of:

the patient EID external device, the IDD, and the patient private key device, are configured for wireless communication using a standard network protocol.

11. The system according to any of the preceding aspects, wherein at least two of:

the patient EID external device, the IDD, and the patient private key device, are configured for wireless communication using a proprietary network protocol.

12. The system according to any of the preceding aspects, wherein the patient EID external device is configured to use a first network protocol for communication with the implantable medical device and use a second network protocol for communication with the patient private key device.

13. The system according to any of the preceding aspects, wherein the patient EID external device is configured to use a first frequency band for communication with the implantable medical device and use a second frequency band for communication with the patient private key device.

14. The system according to any of the preceding aspects, wherein at least one of the patient EID external device, the patient private key device and the IDD comprises a Bluetooth transceiver.

15. The system according to any of the preceding aspects, wherein at least one of the patient EID external device, the patient private key device and the IDD comprises a UWB transceiver.

16. The system according to aspect 10, wherein the standard network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

17. The system according to any of the preceding aspects, wherein the patient EID external device comprises a first wireless transceiver for wireless communication with the implantable medical device, and a second wireless transceiver for wireless communication with the patient private key device, and wherein the second wireless transceiver has longer effective range than the first wireless transceiver.

18. The system according to aspect 17, wherein the second wireless transceiver has an effective range being one of: 2 times, 4 times, 8 time, 20 times, 50 times or 100 times longer than the effective range of the first wireless transceiver.

19. The system according to aspects 17 or 18, wherein the second wireless transceiver is configured to be disabled to enable wireless communication using the first wireless transceiver.

20. The system according to any of the preceding aspects, wherein the patient EID external device is a wearable patient external device or a handset.

21. The system according to any of the preceding aspects, wherein the data encrypted by the implantable medical device is related to at least one of: a battery status, a temperature, a time, or an error.

22. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

23. The system according to anyone of the preceding aspects, wherein the patient remote external device and the patient EID external device are an integrated unit.

24. The system according to anyone of the preceding aspects, wherein the HCP dedicated device and the HCP EID external device are an integrated unit.

25. The system according to anyone of the preceding aspects, comprising a measurement device or sensor adapted to deliver a measurement to at least one of the DDI, patient EID external device and a patient display device.

26. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

Aspect 399B eHealth_Communication_Information from Implant_Remote

1. A system for transmitting information from an implantable medical device, when implanted in a patient, the system comprising:
   an implantable medical device;
   a patient external device (320''') adapted to provide an authorization to the implantable medical device for the patient external device to receive information from the implantable medical device, the authorization being based on the patient external device receiving a patient private key, the patient external device being further configured to send the information to a server (330), a patient private key device comprising the patient private key adapted to be provided to the patient external device.

2. The system according to embodiment 1, wherein the patient external device comprises at least one of: a reading slot, a RFID communication or other close distance wireless communication, or direct electrical connection, for receiving the patient private key device.

3. The system according to embodiment 1 or 2, wherein the authorization is valid for a predetermined period of time, or wherein the authorization is provided at the time of sending the information.

4. The system according to any one of the preceding embodiments, wherein the authorization is provided during charging of the patient external device.

5. The system according to any one of the preceding embodiments, wherein the authorization is provided using a magnetic field, near-field magnetic induction, an electrical field, ultrasound or light, and wherein the implantable medical device comprises a receiver for a magnetic field, an electrical field, ultrasound or light.

5. The system according to any one of the preceding embodiments, wherein the patient external device 320''' is adapted to encrypt the information before sending the information to the server.

6. The system according to any one of the preceding embodiments, wherein the implantable medical device is configured to encrypt the data before sending it to the patient external device.

7. The system according to any one of the preceding embodiments, wherein the patient external device is adapted to transmit information to the server using a first network protocol and receive information from the implant using a second network protocol.

8. The system according to anyone of the preceding embodiments, comprising the implantable medical device, the implantable medical device being adapted to treat the patient or perform a bodily function.

9. The system according to anyone of the preceding embodiment, wherein the patient private key device comprises at least one of: a smart card, a keyring device, a watch, an arm band or wrist band, a necklace.

10. The system according to any of the preceding embodiments, wherein at least two of: the patient external device, the server, and the patient private key device, are configured for wireless communication using a standard network protocol.

11. The system according to any of the preceding embodiments, wherein at least two of: the patient external device, the server, and the patient private key device, are configured for wireless communication using a proprietary network protocol.

12. The system according to any of the preceding embodiments, wherein the patient external device is configured to use a first network protocol for communication with the implantable medical device and use a second network protocol for communication with the patient private key device or the server.

13. The system according to any of the preceding embodiments, wherein the patient external device is configured to use a first frequency band for communication with the implantable medical device and use a second frequency band for communication with the patient private key device or the server.

14. The system according to any of the preceding embodiments, wherein at least one of the patient external device, the patient private key device and the server comprises a Bluetooth transceiver.

15. The system according to any of the preceding embodiments, wherein at least one of the patient external device, the patient private key device and the server comprises a UWB transceiver.

16. The system according to embodiment 6, wherein the standard network protocol is one from the list of: Radio Frequency type protocol. RFID type protocol. WLAN type protocol. Bluetooth type protocol, BLE type protocol. NFC type protocol, 3G/4G/5G type protocol, and GSM type protocol.

17. The system according to any of the preceding embodiments, wherein the patient external device comprises a first wireless transceiver for wireless communication with the implantable medical device, and a second wireless transceiver for wireless communication with the patient private key device or the server, and wherein the second wireless transceiver has longer effective range than the first wireless transceiver.

18. The system according to embodiment 13, wherein the second wireless transceiver has an effective range being one of: 2 times, 4 times, 8 times, 20 times, 50 times or 100 times longer than the effective range of the first wireless transceiver.

19. The system according to embodiments 17 or 18, wherein the second wireless transceiver is configured to be disabled to enable wireless communication using the first wireless transceiver.

20. The system according to any of the preceding embodiments, wherein the patient external device is a wearable patient external device or a handset.

21. The system according to any of the preceding embodiments, wherein the data encrypted by the implantable medical device is related to at least one of:
a battery status,
a temperature,
a time, or
an error.

22. The system according to any of the preceding embodiments, comprising a master private key device configured to issue of a new private key device and configured to replace and pair a new patient private key device or HCP private key device into the system, through the HCP external device.

23. The system according to anyone of the preceding embodiments, comprising a measurement device or sensor adapted to deliver a measurement to at least one of the server, patent external device and a patient display device.

Aspect 399BSE—eHealth_General_Implant Information

1. A system configured for providing information to an implantable medical device, when implanted in a patient, from a distant remote location in relation to the patient, the system comprising:
at least one patient EID external device 320''' adapted to transmit information to the implant, further adapted to be activated and authenticated and allowed to transmit said information to the implanted medical device by the patient providing a private key,
a patient private key device comprising the private key adapted to be provided to the patient EID external device via at least one of: a reading slot or comparable for the patient private key device, a RFID communication or other close distance wireless activation communication or direct electrical connection, wherein said patient EID external device comprises at least one of;
a reading slot or comparable for the patient private key device,
an RFID communication, and
other close distance wireless activation communication or direct electrical contact;
wherein said patient EID external device further comprises at least one wireless transceiver configured for communication of log information about the transmitted information with a server or DDI, through a first network protocol.

Aspect 399CSE—eHealth_General_Implant Information

1. A system configured for providing information to an implantable medical device, when implanted in a patient, from a distant remote location in relation to the patient, the system comprising:
at least one patient EID external device 320''' adapted to charge the implant, with energy, further adapted to be activated and authenticated and allowed to charge the implanted medical device by the patient providing a private key,
a patient private key device comprising the private key adapted to be provided to the patient EID external device via at least one of: a reading slot or comparable for the patient private key device, a RFID communication or other close distance wireless activation communication or direct electrical connection,
wherein said patient EID external device comprises at least one of;
a reading slot or comparable for the patient private key device,
an RFID communication, and
other close distance wireless activation communication or direct electrical contact;
wherein said patient EID external device further comprises at least one wireless transceiver configured for communication of log information relating to such charging or implant feedback with a server or DDI, through a first network protocol.

Aspect 400SE—eHealth_General_System, DDI Inactivation of Remote or Private Key 1. A system comprising,
an implantable medical device adapted to, when implanted in a patient, to communicate with an external device, the external device comprising at least one of a patient remote external device or a patient EID external device, the system further comprising:
the patient EID external device adapted to communicate with and send commands to the implantable medical device when implanted, to change pre-programmed settings,
a patient private key device comprising a patient private key, adapted to activate and authenticate and allow to perform said command by the patient EID external device, wherein said private key is adapted to be provided to the external device via at least one of: a reading slot or comparable for the HCP private key device, an RFID communication or other close distance wireless activation communication, or direct electrical contact, and a data infrastructure server, DDI, adapted to send commands to the patient EID external device for further transport to the implanted medical device, to inactivate the authority and authenticating function of the patient private key.

2. The system according to aspect 1, wherein the at least one patient remote external device comprises a patient remote external device private key, wherein the DDI via the patient EID external device is able to inactivate the authority and authenticating function of the patient remote external device, thereby inactivating the patient remote external device.

2. The system according to aspect 1 or 2, wherein said patient EID external device comprises at least one wireless transceiver configured for communication with the DDI via a first network protocol.

3. The system according to anyone of the preceding aspects, comprising the DDI, wherein the DDI is adapted to receive command from a HCP EID external device, and to send the received command to the patient EID external device, wherein the DDI comprises a wireless transceiver configured for communication with said patient external device.

4. The system according to anyone of the preceding aspects, wherein the patient EID external device is adapted to receive the command from the DDI, wherein the command originates from a health care provider, HCP, and wherein the patient EID is adapted to inactivate the patient private key and to send the command to the implanted medical device.

5. The system according to anyone of the preceding aspects, wherein the patient EID external device is adapted to receive the command from the DDI, wherein the command originates from a health care provider, HCP, wherein the patient EID external device is adapted to receive the command from the HCP via the DDI to inactivate the patient remote external device comprising a patient remote external device private key, and wherein the patient EID external device is further adapted to send this command to the implanted medical device.

6. The system according to anyone of the preceding aspects, wherein the patient EID external device further comprises at least one wireless transceiver configured for communication with the implanted medical device through a second network protocol.

7. The system according to aspect any preceding aspect, wherein at least one of the patient private key and a patient remote external device private key comprises a hardware key.

8. The system according to any preceding aspect, wherein the private key device is at least one of, a smartcard, a key-ring device, a watch an arm or wrist band a neckless or any shaped device.

9. The system according to any preceding aspect, wherein at least two of:
the patient remote external device,
the patient EID external device,
the patient private key device, and
the DDI,
are configured for wireless communication using a standard network protocol.

10. The system according to any preceding aspect, wherein at least two of:
the patient remote external device,
the patient EID external device,
the patient private key device, and
the DDI, are configured for wireless communication using a proprietary network protocol.

11. The system according to any of the preceding aspects, wherein the patient EID external device is configured to use a first network protocol for communication with the implantable medical device and use a second network protocol for communication with the patient private key device.

12. The system according to any of the preceding aspects, wherein the patient EID external device is configured to use a first frequency band for communication with the implantable medical device and use a second frequency band for communication with the patient private key device.

13. The system according to any of the preceding aspects, wherein at least one of the patient remote external device, the patient EID external device, the patient private key device, and the DDI, comprise a Bluetooth transceiver.

14. The system according to any of the preceding aspects, wherein at least one of the patient remote external device, the patient EID external device, the patient private key device, and the DDI, comprise an UWB transceiver.

15. The system according to aspect 9, wherein the standard network protocol is one from the list of:
Radio Frequency type protocol,
RFID type protocol,
WLAN type protocol,
Bluetooth type protocol,
BLE type protocol,
NFC type protocol,
3G/4G/5G type protocol, and
GSM type protocol.

16. The system according to any of the preceding aspects, patient EID external device comprises a first wireless transceiver for wireless communication with the implantable medical device, and a second wireless transceiver for wireless communication with the patient private key device, and wherein the second wireless transceiver has longer effective range than the first wireless transceiver.

17. The system according to aspect 16, wherein the second wireless transceiver has an effective range being one of: 2 times, 4 times, 8 time, 20 times, 50 times or 100 times longer than the effective range of the first wireless transceiver.

18. The system according to aspects 16 or 17, wherein the second wireless transceiver is configured to be disabled to enable wireless communication using the first wireless transceiver.

19. The system according to any of the preceding aspects, wherein the patient EID external device is a wearable patient external device or a handset.

20. The system according to any of the preceding aspects, wherein the data encrypted by the implantable medical device is related to at least one of:
a battery status,
a temperature,
a time, or
an error.

21. The system according to any of the preceding aspects, comprising a master private key device configured to allow issuance of new private key device, wherein the HCP or HCP admin have such master private key device adapted to be able to replace and pair a new patient private key device or HCP private key device into the system, through the HCP EID external device.

22. The system according to anyone of the preceding aspects, wherein the patient remote external device and the patient EID external device are an integrated unit.

23. The system according to anyone of the preceding aspects, wherein the HCP dedicated device and the HCP EID external device are an integrated unit.

24. The system according to anyone of the preceding aspects, comprising a measurement device or sensor adapted to deliver a measurement to at least one of the DDI, patient EID external device and a patient display device.

25. The system according to anyone of the preceding aspects, comprising a food sensor, adapted to measure at least if the patient swallows solid food or is drinking fluid, wherein said food sensor is connected to the control unit of a medical device to cause an action to stretch the stomach after a determined amount of food intake.

Aspect 400B eHealth_Communication_Inactivation of Key

1. A system comprising:
an implantable medical device;
an external device adapted to communicate with the implantable medical device.
a private key device comprising a private key, wherein said private key is adapted to be provided to the external device via at least one of: a reading slot, an RFID communication or other close distance wireless activation communication, or direct electrical contact, and
a data infrastructure server, DDI, adapted to send commands to the external device for relaying to the implanted medical device, to inactivate the authority and authenticating function of the patient private key.

2. The system according to embodiment 1, wherein the system further comprises a second patient external device, wherein the DDI via the patient external device is able to inactivate the authority and authenticating function of the second patient external device, thereby inactivating the second patient remote external device.

3. The system according to embodiment 1 or 2, wherein said external device comprises at least one wireless transceiver configured for communication with the DDI via a first network protocol.

4. The system according to anyone of the preceding embodiments, wherein the DDI is adapted to receive command from a health care provider, HCP, external device, and to send the received command to the patient external device.

5. The system according to anyone of the preceding embodiments, wherein the external device further comprises at least one wireless transceiver configured for communication with the implanted medical device through a second network protocol.

6. The system according to embodiment any preceding embodiment, wherein the patient private key device comprises a hardware key.

7. The system according to any preceding embodiment, wherein the private key device is at least one of: a smartcard, a key-ring device, a watch an arm or wrist band a neckless or any shaped device.

8. The system according to any preceding embodiment, wherein at least two of: the external device, the HCP external device, the patient private key device, and the DDI, are configured for wireless communication using a standard network protocol.

9. The system according to any preceding embodiment, wherein at least two of: the external device, the HCP external device, the patient private key device, and the DDI, are configured for wireless communication using a proprietary network protocol.

10. The system according to any of the preceding embodiments, wherein the external device is configured to use a first network protocol for communication with the implantable medical device and use a second network protocol for communication with the patient private key device.

11. The system according to any of the preceding embodiments, wherein the external device is configured to use a first frequency band for communication with the implantable medical device and use a second frequency band for communication with the patient private key device.

12. The system according to any of the preceding embodiments, wherein at least one of the patient remote external device, the external device, the patient private key device, and the DDI, comprise a Bluetooth transceiver.

13. The system according to any of the preceding embodiments, wherein at least one of the external device, the HCP external device, the patient private key device, and the DDI, comprise an UWB transceiver or an NFMI transceiver.

14. The system according to embodiment 7, wherein the standard network protocol is one from the list of: Radio Frequency type protocol, RFID type protocol, WLAN type protocol, Bluetooth type protocol, BLE type protocol, NFC type protocol, 3G/4G/5G type protocol, NFMI type protocol and GSM type protocol.

15. The system according to any of the preceding embodiments, external device comprises a first wireless transceiver for wireless communication with the implantable medical device, and a second wireless transceiver for wireless communication with the patient private key device or the DDI, and wherein the second wireless transceiver has longer effective range than the first wireless transceiver.

16. The system according to embodiment 15, wherein the second wireless transceiver has an effective range being one of: 2 times, 4 times, 8 time, 20 times, 50 times or 100 times longer than the effective range of the first wireless transceiver.

17. The system according to embodiments 15 or 16, wherein the second wireless transceiver is configured to be disabled to enable wireless communication using the first wireless transceiver.

18. The system according to any of the preceding embodiments, wherein the external device is a wearable patient external device or a handset.

19. The system according to any of the preceding embodiments, comprising a master private key device configured to allow issuance of new private key device, and adapted to be able to replace and pair a new patient private key device or HCP private key device into the system, through the HCP EID external device.

Aspect 401SE—eHealth_General_Patient_at Hospital

1. A system configured for changing pre-programmed treatment settings in steps of an implantable medical device, when implanted in a patient, by a health care provider, HCP, either in the physical presence of the patient or remotely with the patient on distance, the system comprising:
at least one HCP EID external device adapted to receive a command directly or indirectly from the HCP to change said pre-programmed treatment settings in steps of the implantable medical device, when implanted, wherein the HCP EID external device is further adapted to be activated, authenticated, and allowed to perform said command by the HCP providing:

a HCP private key device comprising a HCP private key, comprising at least one of:

a smart card, a keyring device, a watch, a arm or wrist band, a necklace, and any shaped device;

wherein the system further comprises:

a patient private key device comprising a patient private key, comprising at least one of:

a smart card, a keyring device, a watch, a arm or wrist band, a necklace, and any shaped device;

wherein both the HCP and patient private key is required for performing said action by the HCP EID external device to change the pre-programmed settings in the implant and to update software of the implantable medical device, when the implantable medical device is implanted, and wherein the patient private key is adapted to activate, be authenticated, and allowed to perform said command provided by the HCP, either via the HCP EID external device or when the action is performed remotely via a patient EID external device.

2. The system according to anyone of the preceding aspects, comprising a master private key device that allow issuance of new private key device wherein the HCP or HCP admin have such master private key device adapted to be able to replace and pair a new patient private key device or HCP private key device into the system, through the HCP EID external device.

3. The system according to anyone of the preceding aspects, wherein the patient remote external device and the patient EID external device are an integrated unit.

4. The system according to anyone of the preceding aspects, wherein the HCP dedicated device and the HCP EID external device are an integrated unit.

5. The system according to anyone of the preceding aspects, further comprising a measurement device or sensor adapted to deliver a measurement to at least one of the DDI, patent EID external device and a patient display device.

6. The system according to anyone of the preceding aspects, further comprising a food sensor adapted to measure at least if the patient swallows solid food or is drinking fluid, wherein said food sensor is configured to be connected to the control unit of a medical device to cause an action to stretch the stomach after a determined amount of food intake.

7. The system according to any preceding aspect, wherein the HCP EID external device further comprises a wireless transceiver configured for communication with the implanted medical device through a second network protocol.

8. The system according to aspect any preceding aspect, wherein the HCP private key device is adapted to be provided to the at least one HCP external device via at least one of;

a reading slot or comparable for the HCP private key device.

a RFID communication, and a close distance wireless activation communication unit, or electrical direct contact.

9. The system according to anyone of the preceding aspects, wherein the HCP EID external device comprises at least one of:

reading slot or comparable for the HCP private key device.

a RFID communication, and a close distance wireless activation communication unit, or electrical direct contact.

10. The system according to any of the preceding aspects, wherein the HCP EID external device is adapted to receive a command from an HCP dedicated device to change said pre-programmed treatment steps of the implantable medical device, when implanted, wherein the HCP dedicated device is further adapted to be activated, authenticated, and allowed to perform said command by the HCP providing their private key.

11. The system according to any of the preceding aspects, wherein the HCP EID external device and the HCP private key device are configured for wireless communication using a standard network protocol.

12. The system according to any of the preceding aspects, wherein the HCP EID external device and the HCP private key device are configured for wireless communication using a proprietary network protocol.

13. The system according to any of the preceding aspects, wherein the HCP EID external device is configured to use a first network protocol for communication with the implantable medical device and use a second network protocol for communication with the HCP private key device.

14. The system according to any of the preceding aspects, wherein the HPC EID external device is configured to use a first frequency band for communication with the implantable medical device and use a second frequency band for communication with the HCP private key device.

15. The system according to any of the preceding aspects, wherein at least one of the HCP EID external device and the HCP private key device comprises a Bluetooth transceiver.

16. The system according to any of the preceding aspects, wherein at least one of the HCP EID external device and the HCP private key device comprises a UWB transceiver.

Aspect 402SE—eHealth_General_EID and DDI

1. A system configured for changing pre-programmed treatment settings in steps of an implantable medical device, when implanted in a patient, by a health care provider, HCP, with the patient on remote on distance, the system comprising:

at least one HCP EID external device adapted to receive a command from the HCP direct or indirect, to change said pre-programmed treatment settings in steps of an implantable medical device, when implanted, wherein the HCP EID external device is further adapted to be activated, authenticated, and allowed to perform said command by the HCP;

wherein said action by the HCP EID external device to change pre-programmed settings in the implant and to update software of the implantable medical device, when the implantable medical device is implanted, is adapted to be authenticated by a HCP private key device and a patient private key device.

2. The system according to aspect 1, comprising the HCP private key device comprising a HCP private key, comprising at least one of:

a smart card, a keyring device, a watch, a arm or wrist band, a necklace, and any shaped device.

3. The system according to anyone of the preceding aspects, comprising:

the patient private key device comprising a patient private key, comprising at least one of:

a smart card, a keyring device, a watch, a arm or wrist band, a necklace, and any shaped device.

5. The system according to anyone of the preceding aspects, wherein the patient private key is adapted to activate, be authenticated, and allowed to perform said command provided by the HCP, either via the HCP EID external device or when the action is performed remotely via a patient EID external device.

6. The system according to anyone of the preceding aspects, further comprising a dedicated data infrastructure, DDI, the patient EID external device, and the HCP EID external device, wherein the communication between the patient EID external device and the HCP EID external device is performed via the DDI.

7. The system according to anyone of the preceding aspects, comprising a master private key device that allows issuance of new private key device wherein the HCP or HCP admin have such master private key device adapted to be able to replace and pair a new patient private key device or HCP private key device into the system.

8. The system according to anyone of the preceding aspects, wherein the patient remote external device and the patient EID external device are an integrated unit.

10. The system according to anyone of the preceding aspects, wherein the HCP dedicated device and the HCP EID external device are an integrated unit.

11. The system according to anyone of the preceding aspects, further comprising a measurement device or sensor adapted to deliver a measurement to at least one of the DDI, patent EID external device and patient display device.

12. The system according to anyone of the preceding aspects, comprising a food sensor, adapted to measure at least if the patient swallow solid food or is drinking fluid, wherein said food sensor is connected to the control unit of a medical device to cause an action to stretch the stomach after a determined amount of food intake.

13. The system according to any preceding aspect, wherein the HCP EID external device further comprises a wireless transceiver configured for communication with the implanted medical device through a second network protocol.

14. The system according to aspect any preceding aspect, wherein the HCP private key device is adapted to be provided to the at least one HCP external device via at least one of:

a reading slot or comparable for the HCP private key device, a RFID communication, and a close distance wireless activation communication unit, or electrical direct contact.

15. The system according to anyone of the preceding aspects, wherein the HCP EID external device comprises at least one of:

reading slot or comparable for the HCP private key device, a RFID communication, and a close distance wireless activation communication unit, or electrical direct contact.

16. The system according to any of the preceding aspects, wherein the HCP EID external device is adapted to receive a command from an HCP dedicated device to change said pre-programmed treatment steps of the implantable medical device, when implanted, wherein the HCP dedicated device is further adapted to be activated, authenticated, and allowed to perform said command by the HCP providing their private key.

17. The system according to any of the preceding aspects, wherein the HCP EID external device and the HCP private key device are configured for wireless communication using a standard network protocol.

18. The system according to any of the preceding aspects, wherein the HCP EID external device and the HCP private key device are configured for wireless communication using a proprietary network protocol.

19. The system according to any of the preceding aspects, wherein the HCP EID external device is configured to use a first network protocol for communication with the implantable medical device and use a second network protocol for communication with the HCP private key device.

20. The system according to any of the preceding aspects, wherein the HPC EID external device is configured to use a first frequency band for communication with the implantable medical device and use a second frequency band for communication with the HCP private key device.

21. The system according to any of the preceding aspects, wherein at least one of the HCP EID external device and the HCP private key device comprises a Bluetooth transceiver.

22. The system according to any of the preceding aspects, wherein at least one of the HCP EID external device and the HCP private key device comprises a UWB transceiver.

Aspect 403SE—eHealth_General

1. A system configured for changing pre-programmed treatment settings of an implantable medical device, when implanted in a patient, from a distant remote location in relation to the patient, the system comprising:

at least one health care provider, HCP, external device adapted to receive a command from the HCP to change said pre-programmed treatment settings of an implanted medical device, further adapted to be activated and authenticated and allowed to perform said command by the HCP providing, a HCP private key device adapted to be provided to an HCP EID external device via at least one of; a reading slot or comparable for the HCP private key device, a RFID communication or other close distance wireless activation communication, wherein the HCP EID external device comprising at least one of;

a reading slot or comparable for the HCP private key device, a RFID communication, and other close distance wireless activation communication or electrical direct contact, wherein the HCP EID external device further comprising at least one wireless transceiver configured for communication with a patient EID external device, through a first network protocol, wherein the system comprises the patient EID external device, the patient EID external device being adapted to receive command from said HCP external device, and to relay the received command without modifying said command to the implanted medical device, wherein the patient EID external device comprising one wireless transceiver configured for communication with said patient external device, wherein the patient EID is adapted to send the command to the implanted medical device, to receive a command from the HCP to change said pre-programmed treatment settings of the implanted medical device, and further to be activated and authenticated and allowed to perform said command by the patient providing a patient private key device comprising a patient private key.

2. The system according to aspect 1, wherein at least one of the patient private key device or HCP private key device comprises a hardware key.

3. The system according to aspect 1 or 2, wherein the private key device is at least one of, a smartcard, a key-ring device, a watch an arm or wrist band a neckless or any shaped device.

4. The system according to anyone of the preceding aspects, comprising a master private key device that allow issuance of new private key device wherein the HCP or HCP admin have such master private key device adapted to be able to replace and pair a new patient private key device or HCP private key device into the system, through the HCP EID external device.

5. The system according to anyone of the preceding aspects, wherein the patient remote external device and the patient EID external device is an integrated unit.

6. The system according to anyone of the preceding aspects, wherein the HCP dedicated device and the HCP EID external device are an integrated unit.

7. The system according to anyone of the preceding aspects, comprising a measurement device or sensor adapted to deliver a measurement to at least one of the DDI, patent EID external device and a patient display device.

8. The system according to anyone of the preceding aspects, comprising a food sensor, adapted to measure at least if the patient swallow solid food or is drinking fluid, wherein said food sensor is connected to the control unit of a medical device to cause an action to stretch the stomach after a determined amount of food intake.

9. The system according to any preceding aspect, wherein the HCP EID external device further comprises a wireless transceiver configured for communication with the implanted medical device through a second network protocol.

10. The system according to aspect any preceding aspect, wherein the HCP private key device is adapted to be provided to the at least one HCP external device via at least one of;

a reading slot or comparable for the HCP private key device, a RFID communication, and a close distance wireless activation communication unit, or electrical direct contact.

11. The system according to anyone of the preceding aspects, wherein the HCP EID external device comprises at least one of:

reading slot or comparable for the HCP private key device.

a RFID communication, and a close distance wireless activation communication unit, or electrical direct contact.

12. The system according to any of the preceding aspects, wherein the HCP EID external device is adapted to receive a command from an HCP dedicated device to change said pre-programmed treatment steps of the implantable medical device, when implanted, wherein the HCP dedicated device is further adapted to be activated, authenticated, and allowed to perform said command by the HCP providing their private key.

13. The system according to any of the preceding aspects, wherein the HCP EID external device and the HCP private key device are configured for wireless communication using a standard network protocol.

14. The system according to any of the preceding aspects, wherein the HCP EID external device and the HCP private key device are configured for wireless communication using a proprietary network protocol.

15. The system according to any of the preceding aspects, wherein the HCP EID external device is configured to use a first network protocol for communication with the implantable medical device and use a second network protocol for communication with the HCP private key device.

16. The system according to any of the preceding aspects, wherein the HPC EID external device is configured to use a first frequency band for communication with the implantable medical device and use a second frequency band for communication with the HCP private key device.

18. The system according to any of the preceding aspects, wherein at least one of the HCP EID external device and the HCP private key device comprises a Bluetooth transceiver.

19. The system according to any of the preceding aspects, wherein at least one of the HCP EID external device and the HCP private key device comprises a UWB transceiver.

Aspect 330SE eHealth General Communication Housing

1. An external device configured for communication with an implantable medical device implanted in a patient, the external device comprising:

a display device, a housing unit configured to mechanically, disconnectably connect to the display device, the housing unit comprising:

a first communication unit for receiving communication from the display device, and a second communication unit for wirelessly transmitting communication to the implantable medical device.

2. The external device according to aspect 1, wherein the external device comprises a handheld electronic device.

3. The external device according to any one of aspects 1 and 2, wherein the external device is configured for communicating with the implantable medical device for changing an operational state of the implantable medical device.

4. The external device according to any one of the preceding aspects, wherein the first communication unit is a wireless communication unit for wireless communication with the display device.

5. The external device according to aspect 4, wherein:

the first communication unit is configured to communicate wirelessly with the display device using a first communication frequency, the second communication unit is configured to communicate wirelessly with the implantable medical device (10) using a second communication frequency, and the first and second communication frequencies are different.

6. The external device according to any one of the preceding aspects, wherein the second communication unit is configured to communicate wirelessly with the implantable medical device (10) using electromagnetic waves at a frequency below 100 KHz.

7. The external device according to any one of the preceding aspects, wherein the second communication unit is configured to communicate wirelessly with the implantable medical device (10) using electromagnetic waves at a frequency below 40 KHz.

8. The external device according to any one of aspects 4-7, wherein the first communication unit is configured to communicate wirelessly with the display device using electromagnetic waves at a frequency above 100 KHz.

9. The external device according to any one of preceding aspects, wherein:

the first communication unit is configured to communicate with the display device using a first communication protocol.

the second communication unit is configured to communicate wirelessly with the implantable medical device (10) using a second communication protocol, and the first and second communication protocols are different.

10. The external device according to any one of aspects 3-9, wherein the housing unit comprises:

a first antenna configured for wireless communication with the display device, and a second antenna configured for wireless communication with the implantable medical device (10).

11. The external device according to any one of aspects 1-3, wherein the first communication unit is a wire-based communication unit for wire-based communication with the display device.

12. The external device according to any one of preceding aspects, wherein the display device comprises:

a first communication unit for communication with the housing unit, and a second communication unit for wireless communication with a second external device.

13. The external device according to aspect 12, wherein the second communication unit of the display device is configured for communicating with the second external device over the Internet.

14. The external device according to any one of aspects 12 and 13, wherein the first communication unit of the display device is a wireless communication unit for wireless communication with the housing unit.

15. The external device according to aspect 14, wherein:

the first communication unit of the display device is configured to communicate wirelessly with the housing unit using a first communication frequency, the second communication unit of the display device is configured to communicate wirelessly with the second external device using a second communication frequency, and the first and second communication frequencies are different.

16. The external device according to any one of aspects 14 and 15, wherein:

the first communication unit of the display device is configured to communicate wirelessly with the housing unit using a first communication protocol, the second communication unit of the display device is configured to communicate wirelessly with the second external device using a second communication protocol, and the first and second communication protocols are different.

17. The external device according to any one of aspects 14-16, wherein the display device comprises:

a first antenna configured for wireless communication with the housing, and a second antenna configured for wireless communication with the second external device.

18. The external device according to any one of aspects 12-13, wherein the first communication unit is a wire-based communication unit for wire-based communication with the housing unit.

19. The external device according to any one of the preceding aspects, wherein the display device is configured to display a user interface to the patient.

20. The external device according to any one of the preceding aspects, wherein the housing unit is configured to transmit information pertaining to the display of the user interface to the display device.

21. The external device according to any one of aspects 19 and 20, wherein the display device is configured to:

receive input pertaining to communication to or from the implantable medical device from the patient, and transmit communication based on the received input to the housing unit.

22. The external device according to any one of aspects 19-21, wherein the display device comprises a touch screen configured to display the user interface and receive the input from the patient.

23. The external device according to any one of the preceding aspects, wherein the housing unit is configured to display a user interface to the patient.

24. The external device according to any one of the preceding aspects, wherein the first communication unit of the housing unit is configured to receive communication from the implantable medical device pertaining to input from the patient, and wirelessly transmit communication based on the received input to the implantable medical device, using the second communication unit.

25. The external device according to any one of the preceding aspects, wherein the second communication unit of the housing unit is configured for wireless communication with the implantable medical device using a standard network protocol.

26. The external device according to aspect 25, wherein the standard network protocol is selected from a list comprising:

RFID type protocol,

WLAN type protocol,

Bluetooth type protocol,

BLE type protocol,

NFC type protocol,

3G/4G/5G type protocol, and

GSM type protocol.

27. The external device according to aspect 25, wherein the second communication unit of the housing unit comprises a Bluetooth transceiver.

27. The external device according to any one of the preceding aspects, wherein the second communication unit of the housing unit is configured for wireless communication with the implantable medical device using a proprietary network protocol.

28. The external device according to any one of aspects 25-27, wherein the second communication unit of the housing unit comprises a UWB transceiver.

29. The external device according to any one of aspects 4-28, wherein the first communication unit of the housing unit is configured for wireless communication with the display device using a standard network protocol.

30. The external device according to aspect 29, wherein the standard network protocol is an NFC type protocol.

31. The external device according to any one of aspects 4-28, wherein the first communication unit of the housing unit is configured for wireless communication with the display device using a proprietary network protocol.

32. The external device according to any one of aspects 4-31, wherein a communication range of the first communication unit of the housing unit is less than a communication range of the second communication unit of the housing unit.

33. The external device according to any one of aspects 14-32, wherein a communication range of the first communication unit of the display device is less than a communication range of the second communication unit of the display device.

34. The external device according to any one of the preceding aspects, wherein at least one of the housing unit and the display device is configured allow communication between the housing unit and the display device on the basis of a distance between the housing unit and the display device.

35. The external device according to any one of the preceding aspects, wherein at least one of the housing unit and the display device is configured allow communication between the housing unit and the display device on the basis of the housing unit being mechanically connected to the display device.

36. The external device according to any one of the preceding aspects, wherein the housing unit is configured allow communication between the housing unit and the implantable medical device on the basis of a distance between the housing unit and the implantable medical device.

37. The external device according to any one of the preceding aspects, wherein the housing unit further comprises an encryption unit configured to encrypt communication received from the display device.

38. The external device according to aspect 37, wherein the housing unit is further adapted to transmit the encrypted communication, using the second communication unit, to the implantable medical device.

39. The external device according to any one of aspects 14-38, wherein the second communication unit of the display device is configured to be disabled to enable at least one of:

communication between the display device and the housing unit, and communication between the housing unit and the implantable medical device.

40. The external device according to any one of the preceding aspects, wherein the display device is a wearable device or a handset.

41. The external device according to aspect 40, wherein the housing unit comprises a case for the wearable device or handset.

42. The external device according to any one of the preceding aspects, wherein the implantable medical device is an implantable medical device configured to exert a force on a body portion of the patient.

43. The external device according to any one of the preceding aspects, wherein the implantable medical device comprises an electrical motor and a controller (300) for controlling the electrical motor.

44. The external device according to any one of aspects 1-41 wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

45. A housing unit configured for communication with an implantable medical device (10) when implanted in a patient, the housing unit being configured to mechanically, disconnectably connect to a display device and comprising:

a first communication unit for receiving communication from the display device, and a second communication unit for wirelessly transmitting communication to the implantable medical device.

46. The housing unit according to aspect 45, wherein display device is a wearable device or a handset and the housing unit comprises a case for the wearable device or handset.

47. The housing unit according to any one of aspects 45-46, wherein the first communication unit is a wireless communication unit for wireless communication with the display device.

48. The housing unit according to aspect 47, wherein:

the first communication unit is configured to communicate wirelessly with the display device using a first communication frequency, the second communication unit is configured to communicate wirelessly with the implantable medical device using a second communication frequency, and the first and second communication frequencies are different.

49. The housing unit according to any one of aspects 45-48, wherein the second communication unit is configured to communicate wirelessly with the implantable medical device (10) using electromagnetic waves at a frequency below 100 KHz.

50. The housing unit according to any one of aspects 45-49, wherein the second communication unit is configured to communicate wirelessly with the implantable medical device using electromagnetic waves at a frequency below 40 kHz.

51. The housing unit according to any one of aspects 47-50, wherein the first communication unit is configured to communicate wirelessly with the display device using electromagnetic waves at a frequency above 100 KHz.

52. The housing unit according to any one of aspects 45-51, wherein:

the first communication unit is configured to communicate wirelessly with the display device using a first communication protocol, the second communication unit is configured to communicate wirelessly with the implantable medical device using a second communication protocol, and the first and second communication protocols are different.

53. The housing unit according to any one of aspects 47-52, wherein the housing unit comprises:

a first antenna configured for wireless communication with the display device, and a second antenna configured for wireless communication with the implantable medical device (10).

54. The housing unit according to any one of aspects 45-46, wherein the first communication unit is a wire-based communication unit for wire-based communication with the display device.

55. The housing unit according to any one of aspects 45-54, wherein the housing unit is configured to transmit information pertaining to the display of a user interface to the display device.

56. The housing unit according to any one of aspects 45-55, wherein the housing unit is configured to receive patient input from the display device.

57. The housing unit according to any one of aspects 45-56, wherein the housing unit is configured to display a user interface to the patient.

58. The housing unit according to any one of aspects 45-57, wherein the second communication unit is configured for wireless communication with the implantable medical device using a standard network protocol.

59. The housing unit according to aspect 58, wherein the standard network protocol is one selected from a list comprising:

RFID type protocol,

WLAN type protocol,

Bluetooth type protocol,

BLE type protocol,

NFC type protocol,

3G/4G/5G type protocol, and

GSM type protocol.

60. The housing unit according to aspect 58, wherein the second communication unit comprises a Bluetooth transceiver.

61. The housing unit according to any one of aspects 45-57, wherein the second communication unit is configured for wireless communication with the implantable medical device using a proprietary network protocol.

62. The housing unit according to any one of aspects 58-61, wherein the second communication unit of the housing unit comprises a UWB transceiver.

63. The housing unit according to any one of aspects 47-62, wherein the first communication unit of the housing unit is configured for wireless communication with the display device using a standard network protocol.

64. The housing unit according to aspect 63, wherein the standard network protocol is an NFC type protocol.

65. The housing unit according to any one of aspects 47-62, wherein the first communication unit of the housing unit is configured for wireless communication with the display device using a proprietary network protocol.

66. The housing unit according to any one of aspects 47-65, wherein a communication range of the first communication unit is less than a communication range of the second communication unit.

67. The housing unit according to any one of aspects 45-66, wherein the housing unit is configured allow communication between the housing unit and the display device on the basis of a distance between the housing unit and the display device.

68. The housing unit according to any one of aspects 45-67, wherein the housing unit is configured allow communication between the housing unit and the display device on the basis of the housing unit being mechanically connected to the display device.

69. The housing unit according to any one of aspects 45-68, wherein the housing unit is configured allow communication between the housing unit and the implantable medical device on the basis of a distance between the housing unit and the implantable medical device.

70. The housing unit according to any one of aspects 45-69, wherein the housing unit further comprises an encryption unit configured to encrypt communication received from the display device.

71. The housing unit according to aspect 70, wherein the housing unit is further adapted to transmit the encrypted communication, using the second communication unit, to the implantable medical device.

72. The housing unit according to aspects 45-71, wherein the minimum bounding box of the housing unit and the display device when mechanically connected, is no more than: 10% wider, 10% longer or 100% higher, than the minimum bounding box of the display device.

73. The housing unit according to aspects 45-72, wherein the housing unit comprises one or more switches configured to, when the housing is not mechanically connected to the display device, be used by the patient.

74. The housing unit according to aspect 73, wherein the switches are at least partly covered by the display device, when the display device is mechanically connected to the housing unit.

75. The housing unit according to any one of aspects 45-74, wherein at least a part of the housing unit is configured to bend to mechanically connect to the display device.

76. The housing unit according to any one of aspects 45-75, wherein at least a part of the housing unit is configured to covers at least one side of the display device.

77. The housing unit according to any one of aspects 45-76, wherein the housing unit is configured to clasp the display device.

78. The housing unit according to any one of aspects 45-76, wherein the housing unit is configured to mechanically connect to the display unit by an attachment device mechanically connected to the housing unit and to the display device.

79. The housing unit according to any one of aspects 45-76, wherein the housing unit comprises a magnet for magnetically attaching the housing unit to the display device.

80. The housing unit according to any one of aspects 45-79, wherein the housing unit is configured to communi-cate with an implantable medical device configured to exert a force on a body portion of the patient.

81. The external device according to any one of aspects 45-80, wherein the housing unit is configured to communi-cate with an implantable medical device comprising an electrical motor and a controller (300) for controlling the electrical motor.

82. The external device according to any one of aspects 45-81, wherein the housing unit is configured to communi-cate with an implantable medical device comprising at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 331SE eHealth General Security Module

1. An implantable controller for an implantable medical device, the implantable controller comprises:

a wireless transceiver for communicating wirelessly with an external device, a security module, and a central unit configured to be in communication with the wireless transceiver, the security module and the implantable medical device:

the wireless transceiver is configured to receive communication from the external device including at least one instruction to the implantable medical device, and transmit the received communication to the central unit, the central unit is configured to send secure communication to the security module, derived from the received communication from the external device, and the security module is configured to at least one of:

decrypt at least a portion of the secure communication, and verify the authenticity of the secure communication, and the security module is configured to transmit a response communication to the central unit, and the central unit is configured to communicate the at least one instruction to the implantable medical device, the at least one instruction being based on:

the response communication, or a combination of the response communication and the received communication from the external device.

2. The implantable controller according to aspect 1, wherein the security module comprises a set of rules for accepting communication from the central unit.

3. The implantable controller according to aspect 2, wherein the wireless transceiver is configured to be placed in an off-mode, in which no wireless communication can be transmitted or received by the wireless transceiver, and wherein the set of rules comprises a rule stipulating that communication from the central unit is only accepted when the wireless transceiver is placed in the off-mode.

4. The implantable controller according to aspect 4, wherein the set of rules comprises a rule stipulating that communication from the central unit is only accepted when the wireless transceiver has been placed in the off-mode for a specific time period.

5. The implantable controller according to any one of the preceding aspects wherein the central unit is configured to verify a digital signature of the received communication from the external device.

6. The implantable controller according to aspect 4, wherein the set of rules comprises a rule stipulating that communication from the central unit is only accepted when the digital signature of the received communication has been verified by the central unit.

7. The implantable controller according to any one of the preceding aspects, wherein the central unit is configured to verify the size of the received communication from the external device.

8. The implantable controller according to aspect 7, wherein the set of rules comprises a rule stipulating that communication from the central unit is only accepted when the size of the received communication has been verified by the central unit.

9. The implantable controller according to any one of the preceding aspects, wherein:

the wireless transceiver is configured to receive a message from the external device being encrypted with at least a first and second layer of encryption.

the central unit is configured to decrypt a first layer of decryption and transmit at least a portion of the message comprising the second layer of encryption to the security model, and the security module is configured to decrypt the second layer of encryption and transmit a response communication to the central unit based on the portion of the message decrypted by the security module.

10. The implantable controller according to aspect 9, wherein the central unit is configured to decrypt a portion of the message comprising a digital signature, such that the digital signature can be verified by the central unit.

11. The implantable controller according to aspect 9, wherein the central unit is configured to decrypt a portion of the message comprising message size information, such that the message size can be verified by the central unit.

12. The implantable controller according to aspect 9, wherein the central unit is configured to decrypt a first and second portion of the message, and wherein the first portion comprises a checksum for verifying the authenticity of the second portion.

13. The implantable controller according to any one of aspects 9-12, wherein the response communication transmitted from the security module comprises a checksum, and wherein the central unit is configured to verify the authenticity of at least a portion of the message decrypted by the central unit using the received checksum.

14. The implantable controller according to aspect 4, wherein the set of rules comprises a rule related to the rate of data transfer between the central unit and the security module.

15. The implantable controller according to any one of aspects 9-14, wherein the security module is configured to decrypt a portion of the message comprising a digital signature, encrypted with the second layer of encryption, such that the digital signature can be verified by the security module.

16. The implantable controller according to any one of aspects 4-15, wherein the central unit is only capable of decrypting a portion of the receive communication from the external device when the wireless transceiver is placed in the off-mode.

17. The implantable controller according to any one of aspects 4-16, wherein the central unit is only capable of communicating the at least one instruction to the implantable medical device when the wireless transceiver is placed in the off-mode.

18. The implantable controller according to any one of the preceding aspects, wherein the implantable controller is configured to:

receive, using the wireless transceiver, a message from the external device comprising a first un-encrypted portion and a second encrypted portion, decrypt the encrypted portion, and use the decrypted portion to verify the authenticity of the un-encrypted portion.

19. The implantable controller according to aspect 18, wherein the central unit is configured to:

transmit the encrypted portion to the security module, receive a response communication from the security module, based on information contained in the encrypted portion being decrypted by the security module, and use the response communication to verify the authenticity of the un-encrypted portion.

20. The implantable controller according to any one of aspects 18-19, wherein the un-encrypted portion comprises at least a portion of the at least one instruction to the implantable medical device.

21. The implantable controller according to any one of the preceding aspects, wherein the implantable controller is configured to:

receive, using the wireless transceiver, a message from the external device comprising information related to at least one of: a physiological parameter of the patient and a physical parameter of the implanted medical device, and use the received information to verify the authenticity of the message.

22. The implantable controller according to aspect 21, wherein the physiological parameter of the patient comprises at least one of: a temperature, a heart rate and a saturation value.

23. The implantable controller according to aspect 21, wherein the physical parameter of the implanted medical device comprises at least one of: a current setting or value of the implanted medical device, a prior instruction sent to the implanted medical device or an ID of the implanted medical device.

24. The implantable controller according to any one of aspects 21-23, wherein the portion of the message comprising the information is encrypted, and wherein the central unit is configured to transmit the encrypted portion to the security module and receive a response communication from the security module, based on the information having been decrypted by the security module.

25. The implantable controller according to any one of the preceding aspects, wherein the security module comprises a hardware security module comprising at least one hardware-based key.

26. The implantable controller according to aspect 25, wherein the hardware-based key corresponds to a hardware-based key in the external device.

27. The implantable controller according to aspect 25, wherein the hardware-based key corresponds to a hardware-based key on a key-card connectable to the external device.

28. The implantable controller according to any one of the preceding aspects, wherein the security module comprises a software security module comprising at least one software-based key.

29. The implantable controller according to aspect 28, wherein the software-based key corresponds to a software-based key in the external device.

30. The implantable controller according to aspect 28, wherein the software-based key corresponds to a software-based key on a key-card connectable to the external device.

31. The implantable controller according to any one of the preceding aspects, wherein the security module comprises a combination of a software-based key and a hardware-based key.

32. The implantable controller according to any one of the preceding aspects, wherein the security module comprises at least one cryptoprocessor.

33. The implantable controller according to any one of the preceding aspects, wherein the wireless transceiver is configured to receive communication from a handheld external device.

34. The implantable controller according to any one of the preceding aspects, wherein the at least one instruction to the implantable medical device comprises an instruction for changing an operational state of the implantable medical device.

35. The implantable controller according to any one of the preceding aspects, wherein the wireless transceiver is configured to communicate wirelessly with the external device using electromagnetic waves at a frequency below 100 KHz.

36. The implantable controller according to aspect 35, wherein the wireless transceiver is configured to communicate wirelessly with the external device using electromagnetic waves at a frequency below 40 KHz.

37. The implantable controller according to any one of the preceding aspects, wherein:

the wireless transceiver is configured to communicate wirelessly with the external device using a first communication protocol, the central unit is configured to communicate with the security module using a second communication protocol, and the first and second communication protocols are different.

38. The implantable controller according to any one of preceding aspects, wherein the wireless transceiver is configured to communicate wirelessly with the external device using a standard network protocol.

39. The implantable controller according to aspect 38, wherein the standard network protocol is selected from a list comprising:

RFID type protocol,

WLAN type protocol,

Bluetooth type protocol,

BLE type protocol,

NFC type protocol,

3G/4G/5G type protocol, and

GSM type protocol.

40. The implantable controller according to any one of aspects 1-37, wherein the wireless transceiver is configured to communicate wirelessly with the external device using a proprietary network protocol.

41. The implantable controller according to any one of aspects 1-40, wherein the wireless transceiver comprises a UWB transceiver.

42. The external device according to any one of the preceding aspects, wherein the security module and the central unit are comprised in a controller.

43. The external device according to aspect 42, wherein the wireless transceiver is comprised in the controller.

44. The external device according to any one of the preceding aspects, wherein the implantable medical device is an implantable medical device configured to exert a force on a body portion of the patient.

45. The external device according to any one of the preceding aspects, wherein the implantable medical device comprises an electrical motor and wherein the controller is configured for controlling the electrical motor.

46. The external device according to any one of aspects 1-43 wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant,

506 an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 331B eHealth General Security Module

1. An implantable controller for an implantable medical device, the implantable controller comprises:

a wireless transceiver for communicating wirelessly with an external device, a security module, and a central unit configured to be in communication with the wireless transceiver and the security module.

wherein:

the wireless transceiver is configured to receive data from the external device including at least one instruction to the implantable medical device, and transmit the received communication to the central unit, the central unit is configured to send the data to the security module, derived from the received communication from the external device, and the security module is configured to:

decrypt at least a portion of the data or verify the authenticity of the data, and communicate the at least one instruction to the implantable medical device based on a successful decryption or verification of the secure communication.

2. The implantable controller according to embodiment 1, wherein the security module comprises a set of rules for accepting communication from the central unit.

3. The implantable controller according to embodiment 2, wherein the wireless transceiver is configured to be placed in an off-mode, in which no wireless communication can be transmitted or received by the wireless transceiver, and wherein the set of rules comprises a rule stipulating that data from the central unit is only accepted by the security module when the wireless transceiver is placed in the off-mode.

4. The implantable controller according to embodiment 3, wherein the set of rules comprises a rule stipulating that data from the central unit is only accepted when the wireless transceiver has been placed in the off-mode for a specific time period.

5. The implantable controller according to any one of the preceding embodiments wherein the central unit is configured to verify a digital signature of the received data from the external device and on a positive verification send the received data to the security module.

6. The implantable controller according to embodiment 4, wherein the set of rules comprises a rule stipulating that data from the central unit is only accepted when the digital signature of the received communication has been verified by the central unit.

7. The implantable controller according to any one of the preceding embodiments, wherein the central unit is configured to verify the size of the received data from the external device.

8. The implantable controller according to embodiment 7, wherein the set of rules comprises a rule stipulating that data from the central unit is only accepted when the size of the received data has been verified by the central unit.

9. The implantable controller according to any one of the preceding embodiments, wherein:

the wireless transceiver is configured to receive data from the external device being encrypted with at least a first and second layer of encryption, the central unit is configured to decrypt a first layer of decryption of the data to obtain a first decrypted data, and transmit the first decrypted data comprising the second layer of encryption to the security model, and the security module is configured to decrypt the second layer of encryption of the first decrypted data and transmit the at least one instruction to the implantable medical.

10. The implantable controller according to embodiment 9, wherein the central unit is configured to decrypt a portion of the data comprising a digital signature, such that the digital signature can be verified by the central unit.

11. The implantable controller according to embodiment 9, wherein the central unit is configured to decrypt a portion of the data comprising message size information, such that the data size can be verified by the central unit.

12. The implantable controller according to embodiment 9, wherein the central unit is configured to decrypt a first and second portion of the data, and wherein the first portion comprises a checksum for verifying the authenticity of the second portion.

13. The implantable controller according to embodiment 4, wherein the set of rules comprises a rule related to the rate of data transfer between the central unit and the security module.

14. The implantable controller according to any one of embodiments 9-13, wherein the security module is configured to decrypt a portion of the data comprising a digital signature, encrypted with the second layer of encryption, such that the digital signature can be verified by the security module.

15. The implantable controller according to any one of embodiments 4-14, wherein the central unit is only able to decrypt a portion of the data received from the external device when the wireless transceiver is placed in the off-mode.

16. The implantable controller according to any one of embodiments 4-15, wherein the security unit is only able to communicate the at least one instruction to the implantable medical device when the wireless transceiver is placed in the off-mode.

17. The implantable controller according to any one of the preceding embodiments, wherein the implantable controller is configured to:

receive, using the wireless transceiver, a message from the external device comprising a first un-encrypted portion and a second encrypted portion, decrypt the encrypted portion, and use the decrypted portion to verify the authenticity of the un-encrypted portion.

18. The implantable controller according to any one of embodiment 17, wherein the un-encrypted portion comprises at least a portion of the at least one instruction to the implantable medical device.

19. The implantable controller according to any one of the preceding embodiments, wherein the implantable controller is configured to:

receive, using the wireless transceiver, a message from the external device comprising information related to at least one of: a physiological parameter of the patient and a physical parameter of the implanted medical device, and use the received information to verify the authenticity of the message.

20. The implantable controller according to embodiment 19, wherein the physiological parameter of the patient comprises at least one of: a temperature, a heart rate and a saturation value.

21. The implantable controller according to embodiment 19, wherein the physical parameter of the implanted medical device comprises at least one of: a current setting or value of the implanted medical device, a prior instruction sent to the implanted medical device or an ID of the implanted medical device.

22. The implantable controller according to any one of embodiments 19-21, wherein the portion of the message comprising the information is encrypted, and wherein the central unit is configured to transmit the encrypted portion to the security module.

23. The implantable controller according to any one of the preceding embodiments, wherein the security module comprises a hardware security module comprising at least one hardware-based key.

24. The implantable controller according to embodiment 23, wherein the hardware-based key corresponds to a hardware-based key in the external device.

25. The implantable controller according to embodiment 23, wherein the hardware-based key corresponds to a hardware-based key on a key-card connectable to the external device.

26. The implantable controller according to any one of the preceding embodiments, wherein the security module comprises a software security module comprising at least one software-based key.

27. The implantable controller according to embodiment 26, wherein the software-based key corresponds to a software-based key in the external device.

28. The implantable controller according to embodiment 26, wherein the software-based key corresponds to a software-based key on a key-card connectable to the external device.

29. The implantable controller according to any one of the preceding embodiments, wherein the security module comprises a combination of a software-based key and a hardware-based key.

30. The implantable controller according to any one of the preceding embodiments, wherein the security module comprises at least one crypto processor.

31. The implantable controller according to any one of the preceding embodiments, wherein the wireless transceiver is configured to receive communication from a handheld external device.

32. The implantable controller according to any one of the preceding embodiments, wherein the at least one instruction to the implantable medical device comprises an instruction for changing an operational state of the implantable medical device.

33. The implantable controller according to any one of the preceding embodiments, wherein the wireless transceiver is configured to communicate wirelessly with the external device using electromagnetic waves at a frequency below 100 KHz.

34. The implantable controller according to embodiment 33, wherein the wireless transceiver is configured to communicate wirelessly with the external device using electromagnetic waves at a frequency below 40 KHz.

35. The implantable controller according to any one of the preceding embodiments, wherein:

the wireless transceiver is configured to communicate wirelessly with the external device using a first communication protocol.

the central unit is configured to communicate with the security module using a second communication protocol, and the first and second communication protocols are different.

36. The implantable controller according to any one of the preceding embodiments, wherein the wireless transceiver is configured to communicate wirelessly with the external device using a standard network protocol.

37. The implantable controller according to embodiment 36, wherein the standard network protocol is selected from a list comprising:

RFID type protocol,

WLAN type protocol,

Bluetooth type protocol,

BLE type protocol,

NFC type protocol,

3G/4G/5G type protocol, and

GSM type protocol.

38. The implantable controller according to any one of embodiments 1-35, wherein the wireless transceiver is configured to communicate wirelessly with the external device using a proprietary network protocol.

39. The implantable controller according to any one of embodiments 1-38, wherein the wireless transceiver comprises a UWB transceiver.

40. The implantable controller according to any one of the preceding embodiments, wherein the security module and the central unit are comprised in a controller.

41. The implantable controller according to any one of the preceding embodiments, wherein the central module and the security module are implemented in a respective processor on a chip.

42. The implantable controller according to embodiment 40 or 41, wherein the wireless transceiver is comprised in the controller.

43. The implantable controller according to any one of the preceding embodiments, wherein the implantable medical device is an implantable medical device configured to exert a force on a body portion of the patient.

44. The implantable controller according to any one of the preceding embodiments, wherein the implantable medical device comprises an electrical motor and wherein the controller is configured for controlling the electrical motor.

45. The implantable controller according to any one of embodiments 1-44 wherein the implantable medical device comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 432SE eHealth_Variable_Impedance_1

1. An implantable medical device comprising a receiving unit comprising:

at least one coil configured for receiving transcutaneously transferred energy, a measurement unit configured to measure a parameter related to the energy received by the coil, a variable impedance electrically connected to the coil, a switch placed between the variable impedance and the coil for switching off the electrical connection between the variable impedance and the coil, and a controller configured to:

control the variable impedance for varying the impedance and thereby tune the coil based on the measured parameter, and control the switch for switching off the electrical connection between the variable impedance and the coil in response to the measured parameter exceeding a threshold value.

2. The implantable medical device according to aspect 1, wherein the controller is configured to vary the variable impedance in response to the measured parameter exceeding a threshold value.

3. The implantable medical device according to any one of aspects 1 and 2, wherein the measurement unit is configured to measure a parameter related to the energy received by the coil over a time period.

4. The implantable medical device according to any one of the preceding aspects, wherein the measurement unit is configured to measure a parameter related to a change in energy received by the coil.

5. The implantable medical device according to any one of the preceding aspects, wherein the first switch is placed at a first end portion of the coil, and wherein the implantable medical device further comprises a second switch placed at a second end portion of the coil, such that the coil can be completely disconnected from other portions of the implantable medical device.

6. The implantable medical device according to any one of the preceding aspects, wherein the receiving unit is configured to receive transcutaneously transferred energy in pulses according to a pulse pattern, and wherein the measurement unit is configured to measure a parameter related to the pulse pattern.

7. The implantable medical device according to aspect 6, wherein the controller is configured to control the variable impedance in response to the pulse pattern deviating from a predefined pulse pattern.

8. The implantable medical device according to aspect 6, wherein the controller is configured to control the switch for switching off the electrical connection between the variable impedance and the coil in response to the pulse pattern deviating from a predefined pulse pattern.

9. The implantable medical device according to any one of the preceding aspects, wherein the measurement unit is configured to measure a temperature in the implantable medical device or in the body of the patient, and wherein the controller is configured to control the first and second switch in response to the measured temperature.

10. The implantable medical device according to any one of the preceding aspects, wherein the variable impedance comprises a resistor and a capacitor.

11. The implantable medical device according to any one of the preceding aspects, wherein the variable impedance comprises a resistor and an inductor.

12. The implantable medical device according to any one of the preceding aspects, wherein the variable impedance comprises an inductor and a capacitor.

13. The implantable medical device according to any one of the preceding aspects, wherein the variable impedance comprises a digitally tuned capacitor.

14. The implantable medical device according to any one of the preceding aspects, wherein the variable impedance comprises a digital potentiometer.

15. The implantable medical device according to any one of the preceding aspects, wherein the variable impedance comprises a variable inductor.

16. The implantable medical device according to any one of the preceding aspects, wherein the variation of the impedance is configured to lower the active power that is received by the receiving unit.

17. The implantable medical device according to any one of the preceding aspects, wherein the variable impedance is placed in series with the coil.

18. The implantable medical device according to any one of aspects 1-16, wherein the variable impedance is placed parallel to the coil.

19. The implantable medical device according to any one of the preceding aspects, further comprising an energy storage unit connected to the receiving unit, and wherein the energy storage unit is configured for storing energy received by the receiving unit.

20. The implantable medical device according to any one of the preceding aspects, further comprising an energy consuming part.

21. The implantable medical device according to aspect 20, wherein the energy consuming part of the implantable medical device is configured to exert a force on a body portion of the patient.

22. The implantable medical device according to aspect 20, wherein the energy consuming part of the implantable medical device comprises an electrical motor and wherein the controller is configured for controlling the electrical motor.

23. The implantable medical device according to aspect 20, wherein the energy consuming part comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 433SE eHealth_Variable_Impedance_2

1. An implantable medical device comprising a receiving unit comprising:

at least one coil configured for receiving transcutaneously transferred energy, a measurement unit configured to measure a parameter related to the energy received by the coil, a first switch is placed at a first end portion of the coil, a second switch placed at a second end portion of the coil, such that the coil can be completely disconnected from other portions of the implantable medical device, and a controller configured to control the first and second switch for completely disconnecting the coil from other portions of the implantable medical device on the basis of the measured parameter.

2. The implantable medical device according to aspect 1, wherein the controller is configured to control the first and second switch in response to the measured parameter exceeding a threshold value.

3. The implantable medical device according to any one of aspects 1 and 2, wherein the measurement unit is configured to measure a parameter related to the energy received by the coil over a time period.

4. The implantable medical device according to any one of the preceding aspects, wherein the measurement unit is configured to measure a parameter related to a change in energy received by the coil.

5. The implantable medical device according to any one of the preceding aspects, wherein the receiving unit is configured to receive transcutaneously transferred energy in pulses according to a pulse pattern, and wherein the measurement unit is configured to measure a parameter related to the pulse pattern.

6. The implantable medical device according to aspect 5, wherein the controller is configured to control the first and second switch in response to the pulse pattern deviating from a predefined pulse pattern.

7. The implantable medical device according to any one of the preceding aspects, wherein the measurement unit is configured to measure a temperature in the implantable medical device or in the body of the patient, and wherein the controller is configured to control the first and second switch in response to the measured temperature.

8. The implantable medical device according to any one of the preceding aspects, further comprising an energy storage unit connected to the receiving unit, and wherein the energy storage unit is configured for storing energy received by the receiving unit.

9. The implantable medical device according to any one of the preceding aspects, further comprising an energy consuming part.

10. The implantable medical device according to aspect 9, wherein the energy consuming part of the implantable medical device is configured to exert a force on a body portion of the patient.

11. The implantable medical device according to aspect 9, wherein the energy consuming part of the implantable medical device comprises an electrical motor and wherein the controller is configured for controlling the electrical motor.

12. The implantable medical device according to aspect 9, wherein the energy consuming part comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 434SE eHealth_Variable_Impedance_3

1. An implantable medical device comprising a receiving unit comprising:

at least one coil configured for receiving transcutaneously transferred energy, a measurement unit configured to measure a parameter related to the energy received by the coil, and a controller, wherein:

the receiving unit is configured to receive transcutaneously transferred energy in pulses according to a pulse pattern, and the measurement unit is configured to measure a parameter related to the pulse pattern, and the controller is configured to control the receiving unit in response to the pulse pattern of the received energy deviating from a predetermined pulse pattern.

2. The implantable medical device according to aspect 1, further comprising at least one switch placed in series with the coil for switching of the coil, wherein the controller is configured to control the switch to switch of the coil in response to the pulse pattern of the received energy deviating from a predetermined pulse pattern.

3. The implantable medical device according to aspect 1, further comprising a variable impedance electrically connected to the coil, for varying the impedance and thereby tuning the coil, and wherein the controller is configured to control the variable impedance in response to the pulse pattern of the received energy deviating from a predetermined pulse pattern.

4. The implantable medical device according to any one of the preceding aspects, wherein the measurement unit is configured to measure a parameter related to the energy received by the coil over a time period.

5. The implantable medical device according to any one of the preceding aspects, wherein the measurement unit is configured to measure a parameter related to a change in energy received by the coil.

6. The implantable medical device according to any one of the preceding aspects, wherein the measurement unit is configured to measure a temperature in the implantable medical device or in the body of the patient, and wherein the controller is configured to control the first and second switch in response to the measured temperature.

7 The implantable medical device according to any one of the preceding aspects, wherein the first switch is placed at a first end portion of the coil, and wherein the implantable medical device further comprises a second switch placed at a second end portion of the coil, such that the coil can be completely disconnected from other portions of the implantable medical device.

8. The implantable medical device according to aspect 3, wherein the variable impedance comprises a resistor and a capacitor.

9. The implantable medical device according to aspect 3, wherein the variable impedance comprises a resistor and an inductor.

10. The implantable medical device according to aspect 3, wherein the variable impedance comprises an inductor and a capacitor.

11. The implantable medical device according to aspect 3, wherein the variable impedance comprises a digitally tuned capacitor.

12. The implantable medical device according to aspect 3, wherein the variable impedance comprises a digital potentiometer.

13. The implantable medical device according to aspect 3, wherein the variable impedance comprises a variable inductor.

14. The implantable medical device according to any one of aspects 3-12, wherein the variation of the impedance is configured to lower the active power that is received by the receiving unit.

15. The implantable medical device according to any one of aspects 3-13, wherein the variable impedance is placed in series with the coil.

16. The implantable medical device according to any one of aspects 3-13, wherein the variable impedance is placed parallel to the coil.

17. The implantable medical device according to any one of the preceding aspects, further comprising an energy storage unit connected to the receiving unit, and wherein the energy storage unit is configured for storing energy received by the receiving unit.

18. The implantable medical device according to any one of the preceding aspects, further comprising an energy consuming part.

19. The implantable medical device according to aspect 18, wherein the energy consuming part of the implantable medical device is configured to exert a force on a body portion of the patient.

20. The implantable medical device according to aspect 18, wherein the energy consuming part of the implantable medical device comprises an electrical motor and wherein the controller is configured for controlling the electrical motor.

21. The implantable medical device according to aspect 18, wherein the energy consuming part comprises at least one of:

an external heart compression device, an apparatus assisting the pump function of a heart of the patient, an apparatus assisting the pump function comprising a turbine bump placed within a patient's blood vessel for assisting the pump function of the heart, an operable artificial heart valve, an operable artificial heart valve for increasing the blood flow to the coronary arteries.

an implantable drug delivery device, an implantable drug delivery device for injecting directly into a blood vessel and change the position of the injection site, all from within the patient's body, an implantable drug delivery device for injecting potency enhancing drugs into an erectile tissue of the patient, a hydraulic, mechanic, and/or electric constriction implant, an operable volume filling device, an operable gastric band, an operable implant for stretching the stomach wall of the patient for creating satiety, an implant configured to sense the frequency of the patient ingesting food, an operable cosmetic implant, an operable cosmetic implant for adjust the shape and/or size in the breast region of a patient, an implant controlling medical device for the emptying of a urinary bladder, an implant hindering urinary leakage, an implant hindering anal incontinence, an implant controlling the emptying of fecal matter, an implant monitoring an aneurysm, an implant for hindering the expansion of an aneurysm, an implant lubricating a joint, an implant for affecting the blood flow to an erectile tissue of the patient, an implant for simulating the engorgement of an erectile tissue, an implant with a reservoir for holding bodily fluids, an implant storing and/or emptying a bodily reservoir or a surgically created reservoir, an implant communicating with a database outside the body, an implant able to be programmed from outside the body, an implant able to be programmed from outside the body with a wireless signal, an implant treating impotence, an implant controlling the flow of eggs in the uterine tube, an implant controlling the flow of sperms in the uterine tube, an implant controlling the flow of sperms in the vas deferens, an implant for hindering the transportation of the sperm in the vas deferens, an implant treating osteoarthritis, an implant performing a test of parameters inside the body, an implant controlling specific treatment parameters from inside the body, an implant controlling bodily parameters from inside the body, an implant controlling the blood pressure, an implant controlling the blood pressure by affecting the dilatation of the renal artery, an implant controlling a drug treatment parameter, an implant controlling a parameter in the blood, an implant for adjusting or replacing any bone part of a body of the patient, an implant replacing an organ of the patient or part of an organ of the patient or the function thereof, a vascular treatment device, an implant adapted to move fluid inside the body of the patient, an implant configured to sense a parameter related to the patient swallowing, an implant configured to exercise a muscle with electrical or mechanical stimulation, an implant configured for emptying an intestine portion on command, an operable implant configured to be invaginated in the stomach of the patient to reduce the volume of the stomach substantially more than the volume of the device, an implant configured for emptying the urinary bladder from within the patient's body by compressing the bladder, an implant configured for draining fluid from within the patient's body, an implant configured for the active lubrication of a joint with an added lubrication fluid, an implant configured for removing clots and particles from the patient's blood stream, an implant configured for elongating or straightening a bone in the patient, to reduce scoliosis, a device to stimulate the brain for a several position to a focused point, an artificial stomach replacing the function of the natural stomach, an implant configured for adjusting the position of a female's urinary tract or bladder neck, an implant configured for stimulating the ampulla vas deference and creating temporary constriction.

Aspect 447 Data_Packet_Encryption—External Device

1. An external system for providing remote instructions to an implantable medical device, the external system being configured to:

provide instructions to be transmitted to the implantable medical device, derive a checksum from the instructions, electronically sign the instructions and the checksum, form a data packet from the instructions, the electronic signature and the checksum, wherein the external system comprises a wireless transmitter configured to wirelessly send the data packet to the implantable medical device.

2. The external system according to aspect 1, wherein the external system is further configured to encrypt the data packet at the external system.

3. The external system according to any one of aspects 1 and 2, wherein the wireless transmitter is part of a wireless transceiver comprised in the external system.

4. The external system according to any one of the preceding aspects, wherein the external system comprises a first external device and a second external device, and wherein the first external device is configured to transmit the data packet to the second external device, and wherein the second external device is configured to transmit the data packet wirelessly to the implantable medical device without changing the data packet.

5. The external system according to any one of the preceding aspects, wherein the external system comprises a first external device and a second external device, and wherein the first external device is configured to transmit the data packet to the second external device, and wherein the second external device is configured to transmit the data packet wirelessly to the implantable medical device without full decryption of the data packet.

6. The external system according to any one of the preceding aspects, wherein the external system is configured to transmit at least one instruction for altering the control program of the implantable medical device, to the implantable medical device.

7. The external system according to any one of the preceding aspects, wherein the external system is configured to provide at least one instruction to the implantable medical device for altering at least one parameter for affecting the control of the implantable medical device.

8. The external system according to aspect 7, wherein the external system is configured to provide at least one instruction for updating at least one parameter of the control program to a parameter value comprised in a set of parameter values stored in the implantable medical device.

9. The external system according to any one of the preceding aspects, wherein the first external device is configured to send the data packet from the first external device to the second external device using a first network protocol and send the data packet from the second external device to the implantable medical device using a second network protocol.

10. The external system according to any one of the preceding aspects, wherein the first external device is configured to send the data packet from the first external device to the second external device using wired communication and send the data packet from the second external device to the implantable medical device using wireless communication.

11. The external system according to any one of aspects 1-9, wherein the first external device is configured to wirelessly send the data packet from the first external device to the second external device using a first network protocol, and wirelessly send the data packet from the second external device to the implantable medical device using a second network protocol.

12. The external system according to any one of aspects 1-9 or 11, wherein the first external device is configured to wirelessly send the data packet from the first external device to the second external device using a first frequency band, and wirelessly send the data packet from the second external device to the implantable medical device using a second frequency band.

13. The external system according to any one of the preceding aspects, wherein the first external device is configured to wirelessly send the data packet from the first external device to the second external device using a first wireless technology, and wirelessly send the data packet from the second external device to the implantable medical device using a second wireless technology.

14. The external system according to any one of the preceding aspects, wherein the external system is configured to electronically sign the instructions at the external system using a key of the external system.

15. The external system according to aspect 14, wherein the key is a non-extractable key.

16. The external system according to any one of aspects 14 and 15, wherein the second external device is configured to perform a proof of possession operation comprising the steps of:

transmitting, form the first external device to the second external device, a query based on a public key associated with the private of the external system, receiving, at the second external device, a response based on the possession of the private key in the first external device, and verifying that the response based on the possession of the private key matches the query based on a public key.

17. The external system according to any one of the preceding aspects, wherein:

the first external device is configured to form the data packet and electronically sign the instruction using a first private key, and the second external device is configured to:

receive the data packet from the first external device, verify that the first external device is a trusted transmitter, in response to the verification, electronically sign the data packet using a second private key, and transmit the data packet from the second external device to the medical implant.

18. The external system according to any one of the preceding aspects, wherein the checksum is configured to verify that no changes have been made to the bit stream forming the instructions.

19. The external system according to any one of the preceding aspects, wherein the first external device is configured to at least one of: electronically sign the instructions and encrypt the data packet using a key placed on a key device external to the first external device.

20. The external system according to any one of the preceding aspects, wherein the external system further comprises a key device configured to hold at least one private key.

21. The external system according to aspect 20, wherein the key device comprises a wireless transmitter for wirelessly transmitting the at least one private key or a signal based on the private key, to the first external device.

22. The external system according to any one of the preceding aspects, wherein the second external device is configured to at least one of: electronically sign the instructions and encrypt the data packet using a key placed on a key device external to the second external device.

23. The external system according to any one of aspects 14-22, wherein the external system further comprises a second key device configured to hold at least one second private key.

24. The external system according to aspect 23, wherein the second key device comprises a wireless transmitter for wirelessly transmitting the at least one private key or a signal based on the private key to the second external device.

25. The external system according to aspect 14, further comprising a second key device comprising a wireless transmitter for wirelessly transmitting at least one second private key or a signal based on the second private key to the first external device.

26. The external system according to any one of aspects 14-25, wherein at least one of the key device and the second key device comprises at least one of: a key card, a wearable device and a handset.

27. The external system according to any one of the preceding aspects, wherein the first external device is configured to be unlocked by user credentials provided to the first external device.

28. The external system according to aspect 27, wherein the first external device is configured to be unlocked by user credentials comprising a username and a password.

29. The external system according to aspect 28, wherein the first external device is configured to be unlocked by user credentials comprising a PIN-code.

30. The external system according to any one of aspects 27-29, wherein the first external device is configured to verify the user credentials by comparing the user credentials with user credentials stored in the first external device.

31. The external system according to aspect 30, wherein the first external device is configured to verify the user credentials by comparing the user credentials with user credentials stored in the first external device by the manufacturer of the first external device.

32. The external system according to any one of aspects 27-31, wherein the first external device is configured verify the user credentials by comparing the user credentials with user credentials stored as hardware or software in the first external device.

33. The external system according to any one of aspects 27-32, wherein the first external device is configured verify the user credentials by communicating with a remote server.

34. The external system according to any one of the preceding aspects, wherein the second external device is configured to be unlocked by user credentials provided to the second external device.

35. The external system according to aspect 34, wherein the first external device is configured to be unlocked by user credentials comprising a username and a password.

36. The external system according to aspect 34, wherein the first external device is configured to be unlocked by user credentials comprising a PIN-code.

37. The external system according to aspect 36, wherein the second external device is configured to verify the user credentials by comparing the user credentials with user credentials stored in the second external device.

38. The external system according to aspect 37, wherein the second external device is configured to verify the user credentials by comparing the user credentials with user credentials stored in the second external device by the manufacturer of the second external device.

39. The external system according to any one of aspects 37 and 38, wherein the second external device is configured verify the user credentials by comparing the user credentials with user credentials stored as hardware or software in the second external device.

40. The external system according to any one of aspects 37-39, wherein the second external device is configured verify the user credentials by communicating with a remote server.

41. The external system according to any one of the preceding aspects, wherein the external system is configured to function without connection to the Internet.

42. The external system according to any one of the preceding aspects, wherein the external system is configured to communicate with the implantable medical device independently of time.

43. The external system according to any one of the preceding aspects 14-42, wherein the first and second private keys are different.

44. The external system according to aspect 43, wherein the first and second private keys comprises at least one common element.

45. The external system according to any one of aspects 14-44, wherein at least one first and second external device are configured to be unlocked by at least one of the first and second private key.

46. The external system according to any one of the preceding aspects, wherein the external system comprises a central server, and wherein the central server is configured to form a data packet from the instructions, the electronic signature and the checksum and further configured to provide the formed data packet to the first external device.

47. The external system according to aspect 46, wherein the central server can be accessed by at least one healthcare professional, such that the healthcare professional can provide input to the central server for forming the instructions to be sent to the implantable medical device.

48. The external system according to aspect 46, wherein the central server can be accessed by at least one patient, such that the patient can provide input to the central server for verifying at least one of: the authenticity of the healthcare professional and the correctness of the instructions.

49. The external system according to aspect 48, wherein the healthcare provider can electronically sign the instructions at the central server.

50. The external system according to any one of aspects 48 and 49, wherein the patient can electronically sign the instructions at the central server.

51. The external system according to any one of aspects 46-50, wherein the central server is configured to verify the authenticity of the first and second key and electronically sign the instructions using the first and second key.

52. The external system according to any one of the preceding aspects, wherein the second key is a user key, and wherein the external system is configured to use the second key for at least one of:

approving that communication is transmitted to the implantable medical device, and approving that a healthcare provider prepares an instruction to the implantable medical device.

53. The external system according to aspect 52, wherein the approval step can be performed by first or second external device.

54. The external system according to any one of aspects 14-53, wherein the first key is required to create an instruction to the implantable medical device and the second key is required to transmit the created instruction to the implantable medical device.

55. The external system according to any one of aspects 2-54, wherein at least one of the first and second external device comprises an input button configured to be used for verifying user presence.

56. The external system according to aspect 55, wherein the input button con be configured to replace at least one of:

input of at least one key to at least one of the first and second external device, and input of credentials into at least one of the first and second external device.

56. The external system according to aspect 55, wherein the input button is configured to replace the second key.

57. The external system according to any one of the preceding aspects, wherein the external system is configured to transmit the data packet to the implantable medical device, and wherein the data packet comprises:

at least one instruction signed by a first key and a public key including information about which root have created the public key.

58. The external system according to any one of aspects 2-57, wherein at least one of the first and second external device is configured to enable communication with the implantable medical device based on at least one password being provided to at least one of the first and second external device.

59. The external system according to aspect 58, wherein at least one of the first and second external device is configured to enable communication with the implantable medical device based on two passwords being provided to at least one of the first and second external device.

60. The external system according to aspect 59, wherein at least one of the first and second external device is configured to enable communication with the implantable medical device based on one patient password and one healthcare provider passwords being provided to at least one of the first and second external device.

61. The external system according to any one of the preceding aspects, wherein at least one of the first and second external devices are configured to perform a verification query operation with at least one of the first and second key device, the verification query operation comprising:

transmitting, from the first or second external devices, a query comprising a computational challenge to at least one of the first and second key device, receiving, at the first or second external devices, a response based on the transmitted computational challenge, and verifying, at the first or second external devices, the received response.

62. The external system according to aspect 61, wherein at least one of the first and second external devices are configured to perform a verification query operation in the form of a proof of possession operation comprising:

receiving a public key of at least one of the first and second key devices, the public key being associated with a private key of the first or second key device.

transmitting, from at least one of the first and second external devices, a computational challenge to the first or second key device, based on the public key received from the first or second key device.

receiving a response from the first or second key device based on the possession of the private key in the first or second key device, and verifying that the response based on the possession of the private key matches the query based on a public key.

63. A medical system comprising the external system according to any one of the preceding aspects and an implantable medical device.

64. The medical system according to aspect 63, wherein the implantable medical device comprises an implantable energized medical device configured to be held in position by a tissue portion of a patient, the medical device comprising:

a first portion configured to be placed on a first side of the tissue portion, the first portion having a first cross-sectional area in a first plane and comprising a first surface configured to face a first tissue surface of the first side of the tissue portion, a second portion configured to be placed on a second side of the tissue portion, the second side opposing the first side, the second portion having a second cross-sectional area in a second plane and comprising a second surface configured to engage a second tissue surface of the second side of the tissue portion, and a connecting portion configured to be placed through a hole in the tissue portion extending between the first and second sides of the tissue portion, the connecting portion having a third cross-sectional area in a third plane and a fourth cross-sectional area in a fourth plane and a third surface configured to engage the first tissue surface of the first side of the tissue portion, wherein the connecting portion is configured to connect the first portion to the second portion, wherein:

the first, second, third and fourth planes are parallel to each other, the third cross-sectional area is smaller than the first, second and fourth cross-sectional areas, such that the first portion, second portion and connecting portion are prevented from travelling through the hole in the tissue portion in a direction perpendicular to the first, second and third planes, and the first portion is detachably connected to at least one of the connecting portion and the second portion.

65. The medical system according to aspect 63, wherein the implantable medical device comprises a system for treating a patient having a disorder related to the patient's intestine, the system comprises an artificial intestine section adapted to being implanted inside a patient's body, along with an accumulator for accumulating energy, the artificial intestine section has a first open end portion and a second open end portion in flow communication with one another, wherein at least the first open end portion and possibly also the second open end portion is adapted to being connected to a surgically created opening in the patient's intestine, and the accumulator is adapted to be charged wirelessly with energy and to be arranged so as to supply energy directly or indirectly to at least one energy consuming part of said artificial intestine section.

66. The medical system according to aspect 63, wherein the implantable medical device comprises an artificial flow control device implantable in the patient's body and adapted to control flow of the intestinal contents from said reservoir the artificial flow control device comprises at least one pump adapted to act on said intestinal wall so as to reduce the reservoir's volume in order to empty the reservoir.

67. The medical system according to aspect 63, wherein the implantable medical device comprises an infusion device comprising an infusion needle and a drive unit coupled to the infusion needle and arranged for advancing the tip end of the infusion needle to penetrate fibrosis when the device is implanted in the patient's body, wherein at least the infusion needle and the drive unit are sized and formed for implantation in the patient's body.

68. The medical system according to aspect 63, wherein the implantable medical device comprises a drug delivery device for injecting a drug into a patient's body such as stimulation of penis erection wherein the drug is injected into the patient's body into at least one of both a right and left corpus cavernosum, two deep arteries of the right and left corpus cavernosum, muscle tissue regulating blood flow through the right and left corpus cavernosum, and tissue in close proximity to the left and right corpus cavernosum, wherein the drug delivery device comprises a catheter adapted to be implanted outside the corpora cavernosa in close proximity thereto so as to supply the drugs through the catheter or the catheter may be adapted to be implanted in at least one of the corpora cavernosa so as to supply the drugs directly into the corpus cavernosum through the catheter.

69. The medical system according to aspect 63, wherein the implantable medical device comprises an implantable lubrication device comprising:

a reservoir that stores a lubricating fluid and, a fluid connection that introduces the stored lubricating fluid into a damaged joint when the lubrication device is implanted in a patient's body.

wherein the lubricating device is configured to be completely implanted into the patient's body such that a damaged joint can post-operatively be lubricated from within the patient's body, and wherein the operative supply of lubricating fluid to the damaged joint is controlled continuously, intermittently, periodically or depending on a physical parameter of the patient, such as a fluid level within the joint.

70. The medical system according to aspect 63, wherein the implantable medical device comprises a device for bone adjustment in a mammal, comprising two or more anchoring devices for attaching to a bone in said mammal, an adjustment device for exerting force on said anchoring devices to adjust the distance between or orientation of at least two of said anchoring devices, wherein said anchoring devices and said adjustment device are implanted intramedullary in said mammal and wherein said adjustment device is constructed to postoperatively adjust said distance, and the adjustment is a lengthening of a bone, a healing of a fracture, a changing of a bone angle, a reshaping of a bone, a compression of a bone, a torsion of a bone, or a combination thereof.

71. The medical system according to aspect 63, wherein the implantable medical device comprises an implantable drain adapted to move body fluid or a hydraulic reservoir with hydraulic treatment fluid to move hydraulic fluid, from one part of the body to another part of the body, a fluid movement device that which is completely implanted and which does not have any mechanical structure penetrating through the skin of the patient is obtained.

72. The medical system according to aspect 63, wherein the implantable medical device comprises a fluid movement device for pumping hydraulic treatment fluid or body fluid, the fluid movement device being powered by an energy source and powered by an electrical or a hydraulic motor at least one connecting tube connected to the fluid movement device so that the fluid movement device and the tube form a drainage or hydraulic arrangement wherein the hydraulic arrangement is adapted to be implanted inside the body of the patient, and placed so that the tube interconnects one part of the body with another part of the body and where fluid movement device is adapted to suck body fluid from the one part of the body via the tube to the other part of the body.

73. The medical system according to aspect 63, wherein the implantable medical device comprises an implantable device for improving the pump function of the heart of a human patient by applying an external force on the heart muscle, said device comprising at least one heart contacting organ, periodically exerting force onto the heart following the heart contractions and adding force thereto, a drive unit to create kinetic movement to be used by the heart contacting organ, a fixation device adapted to be mounted in a stable position to human bone allowing said drive unit and kinetic movement to get necessary contra force, wherein said drive unit further comprises a respiration movement compensator for compensating for the respiratory movement of the heart in relation to the stable bone position, and said drive unit is adapted to allow a movement to compensate for the respiratory movement in relation between said heart contacting organ and said bone.

74. The medical system according to aspect 63, wherein the implantable medical device comprises a male sexual impotence treatment prosthesis apparatus, comprising an operable prosthesis implantable in the cavities of the corpora cavernosa of an impotent patient to provide erect penile condition, when the prosthesis is operated, wherein an energy transmission device for wireless transmission of energy from outside the patient's body to inside the patient's body for use in connection with the operation of the prosthesis, when the prosthesis is implanted.

75. The medical system according to aspect 63, wherein the implantable medical device comprises a device for treatment or monitoring of an aneurysm, comprising an implantable member adapted to hold fluid, the member being adapted to be placed in connection with a blood vessel having the aneurysm and to exercise a pressure on the aneurysm, wherein the controller functions as a control unit adapted to control pressure adjustments of the implantable member.

76. The medical system according to aspect 63, wherein the implantable medical device comprises an implantable blood clot removal device for removing blood clots from the vascular system of a patient comprising:

a blood flow passageway to be connected to the patient's vascular system to allow circulation of the patient's blood through the blood flow passageway.

a filter provided in the blood flow passageway for collecting blood clots occurring in the blood flowing through the blood flow passageway, and a cleaning device for moving blood clots collected by the filter out of the blood flow passageway.

77. The medical system according to aspect 63, wherein the implantable medical device comprises an implantable apparatus for treating urinary retention of a mammal patient comprising:

an implantable powered member adapted exert a force from the outside on a selected part of the urinary bladder in order to discharge urine from the urinary bladder, and a control device for controlling the operation of the powered member.

78. The medical system according to aspect 63, wherein the implantable medical device comprises a breast implant system comprises a plurality of chambers including one or more first fluid chambers and one or more second fluid chambers, wherein:

at least the first fluid chamber is to be implanted in the human body to form part of a breast implant, the second fluid chambers is implanted to form part of the breast implant or implanted inside the patient's body remote from the breast implant.

the first fluid chamber is interconnected with the second fluid chamber, such that fluid can be exchanged between the first and second fluid chambers, so as to change their respective fluid content.

79. The medical system according to aspect 63, wherein the implantable medical device comprises an apparatus for treating obesity and/or reflux comprising at least one volume filling device adapted to be at least substantially invaginated by a stomach wall portion of the patient, wherein the volume filling device is adapted to be placed outside of the stomach wall with the outer surface of the volume filling device resting against the outside of the stomach wall, such that the volume of the food cavity is reduced in size by a volume substantially exceeding the volume of the volume filling device.

80. The medical system according to aspect 63, wherein the implantable medical device comprises a system for treating a female patient to avoid or promote pregnancy comprising a restriction device adapted to postoperatively restrict and release an oviduct of the patient.

81. The medical system according to aspect 63, wherein the implantable medical device comprises an apparatus for controlling a flow of sperms in an uterine tube of a female patient, the apparatus comprising: an implantable constriction device for constricting at least one portion of the uterine tube wall to at least partly constrict the uterine tube to influence the flow of sperms in the uterine tube.

82. The medical system according to aspect 63, wherein the implantable medical device comprises an implantable medical device for lubrication of a synovial joint having a joint cavity, the implantable device comprising a solid lubricant and a feeding device, wherein said feeding device is adapted to feed said solid lubricant into the joint cavity for lubricating the synovial joint.

83. The medical system according to aspect 63, wherein the implantable medical device comprises an artificial valve for implantation in a mammal body, in or adjacent to a mammal blood vessel, the artificial valve comprises a casing and an opening and closing mechanism, at least part of the opening and closing mechanism comprises a first moving part adapted to make an opening and a closing movement relative to the casing, the movements comprising movements to assume an open and a closed position for opening and closing, respectively, the blood flow through said blood vessel.

84. The medical system according to aspect 63, wherein the implantable medical device comprises an apparatus adapted to control the flow of fluids and/or other bodily matter in a lumen that is formed by the tissue wall of a bodily organ, the apparatus comprising an implantable constriction device for constricting a portion of the tissue wall to influence the flow in the lumen, a stimulation device for stimulating the wall portion of the tissue wall, and a control device for controlling the stimulation device to stimulate the wall portion as the constriction device constricts the wall portion to cause contraction of the wall portion to further influence the flow in the lumen.

Aspect 447B Data_Packet_Encryption-Implant

1. A implantable medical device configured to receive remote instructions from an external system, the implantable medical device comprising:

a wireless receiver configured to receive wirelessly transmitted data packets from the external system, a computing unit configured to:

verify the electronic signature, and use a checksum provided in the data packet to verify the integrity of the instructions.

2. The implantable medical device according to aspect 1, wherein the computing unit is configured to decrypt the data packet.

3. The implantable medical device according to any one of aspects 1 and 2, wherein the computing unit is configured to use the checksum to verify that the bit stream making up the instructions is unchanged.

4. The implantable medical device according to any one of aspects 1 and 2, wherein the wireless receiver is part of a wireless transceiver.

5. The implantable medical device according to any one of aspects 1-4, wherein the computing unit comprises a memory unit configured to store electronic signatures, and wherein the computing unit is configured to verify the electronic signature my comparing the electronic signature with the electronic signatures stored in the memory unit.

6. The implantable medical device according to any one of the preceding aspects, wherein the implantable medical device comprises a control program configured to control at least one function of the implantable medical device, and wherein computing unit is configured to alter the control program on the basis of the received instructions.

7. The implantable medical device according to any one of the preceding aspects, wherein the implantable medical device comprises an internal computing unit configured to run a control program for controlling a function of the implantable medical device, wherein the control program comprises at least one adjustable parameter affecting the control of the implantable medical device, and wherein the method of providing remote instructions comprises providing instructions for altering the at least one parameter for affecting the control of the implantable medical device.

8. The implantable medical device according to aspect 7, wherein the computing unit comprises a memory unit configured to store parameter values, and wherein the method further comprises the step of verifying that the instructions for altering the at least one parameter will result in the at least one parameter being updated to a parameter value comprised in the set of stored parameter values.

9. The implantable medical device according to any one of the preceding aspects, wherein the implantable medical device comprises a central unit, comprising at least one of a wireless receiver and a wireless transceiver, and a security module connected to the central unit, wherein the implantable medical device is configured to transfer the data packet from the central unit to the security module and wherein the security module is configured to performing at least a portion of at least one of the decryption and the signature verification.

10. The implantable medical device according to aspect 9, wherein the security module comprises a set of rules for accepting communication from the central unit, and wherein the security module is configured to verify compliance with the set of rules.

11. The implantable medical device according to aspect 10, wherein wireless receiver or wireless transceiver is configured to be placed in an off-mode, in which no wireless communication can be received by the wireless transceiver, and wherein the set of rules comprises a rule stipulating that communication from the central unit is only accepted at the security module when the wireless transceiver is placed in the off-mode.

12. The implantable medical device according to any one of the preceding aspects, wherein the implantable medical device is configured to at least one of decrypting the data packet and verifying the electronic signature using a private key of the implantable medical device.

13. The implantable medical device according to any one of aspects 10-12, wherein the private key is a non-extractable key.

14. The implantable medical device according to any one of aspects 10-13, wherein the implantable medical device is configured to perform a proof of possession operation comprising:

transmitting, from the implantable medical device to the external system, a query based on a public key associated with the private key of the external system, receiving, at the implantable medical device, a response based on the possession of the private key in the external system, and verifying that the response based on the possession of the private key matches the query based on a public key.

15. The implantable medical device according to any one of the preceding aspects, wherein the implantable medical device is configured to communicate with the external system independently of time.

16. The implantable medical device according to any one of the preceding aspects, wherein the private key is provided in the implantable medical device by the manufacturer of the implantable medical device.

17. The implantable medical device according to aspect 16, wherein the private key is stored as hardware or software in the implantable medical device.

18. The implantable medical device according to any one of the preceding aspects 12-17, wherein the implantable medical device is configured to:

verify a first electronic signature made using at least one of a first key and a second key, and verifying a second electronic signature made using at least one of a first key and a second key.

19. The implantable medical device according to aspect 18, wherein at least one of the first and second keys is a private key.

20. The implantable medical device according to aspect 18, wherein the first and second keys are different.

21. The implantable medical device according to aspect 20, wherein the first and second keys comprises at least one common element.

22. The implantable medical device according to any one of aspects 18-21, wherein the implantable medical device is configured to:

verify a first electronic signature to allow communication from the external system to the implantable medical device, and verify a second electronic signature to allow an instruction received in the communication to alter the control program running on the implantable medical device.

23. The implantable medical device according to aspect 22, wherein the first electronic signature is an electronic signature linked to the user of the implantable medical device and the second electronic signature is an electronic signature linked to a healthcare provider.

24. The implantable medical device according to any one of aspects 12-23, wherein only a portion of the private key is needed to at least one of: decrypt the data packet and verify the electronic signature.

25. The implantable medical device according to any one of aspects 12-23, wherein the implantable medical device trusts any external device holding the private key.

26. The implantable medical device according to any one of the preceding aspects, wherein the implantable medical device is configured to receive the data packet comprising:

at least one instruction signed by a private key of the external system, and a public key including information about which root have created the public key.

27. The implantable medical device according to any one of the preceding aspects, wherein the implantable medical device is configured to accept communication from an external system based on at least one password being provided to the implantable medical device.

28. The implantable medical device according to aspect 27, wherein the implantable medical device is configured to accept communication from an external system based on two passwords being provided to the implantable medical device.

29. The implantable medical device according to aspect 28, wherein the implantable medical device is configured to accept communication from an external system based on one patient password and one healthcare provider passwords being provided to the implantable medical device.

30. The implantable medical device according to any one of the preceding aspects, wherein the implantable medical device comprises an implantable energized medical device configured to be held in position by a tissue portion of a patient, the medical device comprising:

a first portion configured to be placed on a first side of the tissue portion, the first portion having a first cross-sectional area in a first plane and comprising a first surface configured to face a first tissue surface of the first side of the tissue portion, a second portion configured to be placed on a second side of the tissue portion, the second side opposing the first side, the second portion having a second cross-sectional area in a second plane and comprising a second surface configured to engage a second tissue surface of the second side of the tissue portion, and a connecting portion configured to be placed through a hole in the tissue portion extending between the first and second sides of the tissue portion, the connecting portion having a third cross-sectional area in a third plane and a fourth cross-sectional area in a fourth plane and a third surface configured to engage the first tissue surface of the first side of the tissue portion, wherein the connecting portion is configured to connect the first portion to the second portion, wherein:

the first, second, third and fourth planes are parallel to each other, the third cross-sectional area is smaller than the first, second and fourth cross-sectional areas, such that the first portion, second portion and connecting portion are prevented from travelling through the hole in the tissue portion in a direction perpendicular to the first, second and third planes, and the first portion is detachably connected to at least one of the connecting portion and the second portion.

31. The implantable medical device according to any one of the preceding aspects, wherein the implantable medical device comprises a system for treating a patient having a disorder related to the patient's intestine, the system comprises an artificial intestine section adapted to being implanted inside a patient's body, along with an accumulator for accumulating energy, the artificial intestine section has a first open end portion and a second open end portion in flow communication with one another, wherein at least the first open end portion and possibly also the second open end portion is adapted to being connected to a surgically created opening in the patient's intestine, and the accumulator is adapted to be charged wirelessly with energy and to be arranged so as to supply energy directly or indirectly to at least one energy consuming part of said artificial intestine section.

32. The implantable medical device according to any one of the preceding aspects, wherein the implantable medical device comprises an artificial flow control device implantable in the patient's body and adapted to control flow of the intestinal contents from said reservoir the artificial flow control device comprises at least one pump adapted to act on said intestinal wall so as to reduce the reservoir's volume in order to empty the reservoir.

33. The implantable medical device according to any one of the preceding aspects, wherein the implantable medical device comprises an infusion device comprising an infusion needle and a drive unit coupled to the infusion needle and arranged for advancing the tip end of the infusion needle to penetrate fibrosis when the device is implanted in the patient's body, wherein at least the infusion needle and the drive unit are sized and formed for implantation in the patient's body.

34. The implantable medical device according to any one of the preceding aspects, wherein the implantable medical device comprises a drug delivery device for injecting a drug into a patient's body such as stimulation of penis erection wherein the drug is injected into the patient's body into at least one of both a right and left corpus cavernosum, two deep arteries of the right and left corpus cavernosum, muscle tissue regulating blood flow through the right and left corpus cavernosum, and tissue in close proximity to the left and right corpus cavernosum, wherein the drug delivery device comprises a catheter adapted to be implanted outside the corpora cavernosa in close proximity thereto so as to supply the drugs through the catheter or the catheter may be adapted to be implanted in at least one of the corpora cavernosa so as to supply the drugs directly into the corpus cavernosum through the catheter.

35. The implantable medical device according to any one of the preceding aspects, wherein the implantable medical device comprises an implantable lubrication device comprising:

a reservoir that stores a lubricating fluid and, a fluid connection that introduces the stored lubricating fluid into a damaged joint when the lubrication device is implanted in a patient's body.

wherein the lubricating device is configured to be completely implanted into the patient's body such that a damaged joint can post-operatively be lubricated from within the patient's body.

and wherein the operative supply of lubricating fluid to the damaged joint is controlled continuously, intermittently, periodically or depending on a physical parameter of the patient, such as a fluid level within the joint.

36. The implantable medical device according to any one of the preceding aspects, wherein the implantable medical device comprises a device for bone adjustment in a mammal, comprising two or more anchoring devices for attaching to a bone in said mammal, an adjustment device for exerting force on said anchoring devices to adjust the distance between or orientation of at least two of said anchoring devices.

wherein said anchoring devices and said adjustment device are implanted intramedullary in said mammal and wherein said adjustment device is constructed to postoperatively adjust said distance, and the adjustment is a lengthening of a bone, a healing of a fracture, a changing of a bone angle, a reshaping of a bone, a compression of a bone, a torsion of a bone, or a combination thereof.

37. The implantable medical device according to any one of the preceding aspects, wherein the implantable medical device comprises an implantable drain adapted to move body fluid or a hydraulic reservoir with hydraulic treatment fluid to move hydraulic fluid, from one part of the body to another part of the body, a fluid movement device that which is completely implanted and which does not have any mechanical structure penetrating through the skin of the patient is obtained.

38. The implantable medical device according to any one of the preceding aspects, wherein the implantable medical device comprises a fluid movement device for pumping hydraulic treatment fluid or body fluid, the fluid movement device being powered by an energy source and powered by an electrical or a hydraulic motor at least one connecting tube connected to the fluid movement device so that the fluid movement device and the tube form a drainage or hydraulic arrangement wherein the hydraulic arrangement is adapted to be implanted inside the body of the patient, and placed so that the tube interconnects one part of the body with another part of the body and where fluid movement device is adapted to suck body fluid from the one part of the body via the tube to the other part of the body.

39. The implantable medical device according to any one of the preceding aspects, wherein the implantable medical device comprises an implantable device for improving the pump function of the heart of a human patient by applying an external force on the heart muscle, said device comprising at least one heart contacting organ, periodically exerting force onto the heart following the heart contractions and adding force thereto, a drive unit to create kinetic movement to be used by the heart contacting organ, a fixation device adapted to be mounted in a stable position to human bone allowing said drive unit and kinetic movement to get necessary contra force, wherein said drive unit further comprises a respiration movement compensator for compensating for the respiratory movement of the heart in relation to the stable bone position, and said drive unit is adapted to allow a movement to compensate for the respiratory movement in relation between said heart contacting organ and said bone.

40. The implantable medical device according to any one of the preceding aspects, wherein the implantable medical device comprises a male sexual impotence treatment prosthesis apparatus, comprising an operable prosthesis implantable in the cavities of the corpora cavernosa of an impotent patient to provide erect penile condition, when the prosthesis is operated, wherein an energy transmission device for wireless transmission of energy from outside the patient's body to inside the patient's body for use in connection with the operation of the prosthesis, when the prosthesis is implanted.

41. The implantable medical device according to any one of the preceding aspects, wherein the implantable medical device comprises a device for treatment or monitoring of an aneurysm, comprising an implantable member adapted to hold fluid, the member being adapted to be placed in connection with a blood vessel having the aneurysm and to exercise a pressure on the aneurysm, wherein the controller functions as a control unit adapted to control pressure adjustments of the implantable member.

42. The implantable medical device according to any one of the preceding aspects, wherein the implantable medical device comprises an implantable blood clot removal device for removing blood clots from the vascular system of a patient comprising:

a blood flow passageway to be connected to the patient's vascular system to allow circulation of the patient's blood through the blood flow passageway, a filter provided in the blood flow passageway for collecting blood clots occurring in the blood flowing through the blood flow passageway, and a cleaning device for moving blood clots collected by the filter out of the blood flow passageway.

43. The implantable medical device according to any one of the preceding aspects, wherein the implantable medical device comprises an implantable apparatus for treating urinary retention of a mammal patient comprising:

an implantable powered member adapted exert a force from the outside on a selected part of the urinary bladder in order to discharge urine from the urinary bladder, and a control device for controlling the operation of the powered member.

44. The implantable medical device according to any one of the preceding aspects, wherein the implantable medical device comprises a breast implant system comprises a plurality of chambers including one or more first fluid chambers and one or more second fluid chambers, wherein:

at least the first fluid chamber is to be implanted in the human body to form part of a breast implant, the second fluid chambers is implanted to form part of the breast implant or implanted inside the patient's body remote from the breast implant.

the first fluid chamber is interconnected with the second fluid chamber, such that fluid can be exchanged between the first and second fluid chambers, so as to change their respective fluid content.

45. The implantable medical device according to any one of the preceding aspects, wherein the implantable medical device comprises an apparatus for treating obesity and/or reflux comprising at least one volume filling device adapted to be at least substantially invaginated by a stomach wall portion of the patient, wherein the volume filling device is adapted to be placed outside of the stomach wall with the outer surface of the volume filling device resting against the outside of the stomach wall, such that the volume of the food cavity is reduced in size by a volume substantially exceeding the volume of the volume filling device.

46. The implantable medical device according to any one of the preceding aspects, wherein the implantable medical device comprises a system for treating a female patient to avoid or promote pregnancy comprising a restriction device adapted to postoperatively restrict and release an oviduct of the patient.

47. The implantable medical device according to any one of the preceding aspects, wherein the implantable medical device comprises an apparatus for controlling a flow of sperms in an uterine tube of a female patient, the apparatus comprising: an implantable constriction device for constricting at least one portion of the uterine tube wall to at least partly constrict the uterine tube to influence the flow of sperms in the uterine tube.

48. The medical system according to aspect 47, wherein the implantable medical device comprises an implantable medical device for lubrication of a synovial joint having a joint cavity, the implantable device comprising a solid lubricant and a feeding device, wherein said feeding device is adapted to feed said solid lubricant into the joint cavity for lubricating the synovial joint.

49. The implantable medical device according to any one of the preceding aspects, wherein the implantable medical device comprises an artificial valve for implantation in a mammal body, in or adjacent to a mammal blood vessel, the artificial valve comprises a casing and an opening and closing mechanism, at least part of the opening and closing mechanism comprises a first moving part adapted to make an opening and a closing movement relative to the casing, the movements comprising movements to assume an open and a closed position for opening and closing, respectively, the blood flow through said blood vessel.

50. The implantable medical device according to any one of the preceding aspects, wherein the implantable medical device comprises an apparatus adapted to control the flow of fluids and/or other bodily matter in a lumen that is formed by the tissue wall of a bodily organ, the apparatus comprising an implantable constriction device for constricting a portion of the tissue wall to influence the flow in the lumen, a stimulation device for stimulating the wall portion of the tissue wall, and a control device for controlling the stimulation device to stimulate the wall portion as the constriction device constricts the wall portion to cause contraction of the wall portion to further influence the flow in the lumen.

Aspect 447C Data_Packet_Encryption-Method

1. A method of providing remote instructions from an external system to an implantable medical device, the method comprising:

deriving a checksum, at the external system, from the instructions to be sent to the implantable medical device.

electronically signing the instructions and the checksum, at the external system, wherein: the instructions, the checksum and the electronic signature form a data packet, wirelessly sending the data packet to the implantable medical device, verifying the electronic signature, and using the checksum to verify the integrity of the instructions.

2. The method according to aspect 1, further comprising the steps of encrypting the data packet at the external system using a private key of the external system, and decrypting, at the implantable medical device, the data packet using a private key of the implantable medical device.

3. The method according to any one of aspects 1 and 2, wherein the step of verifying the electronic signature comprises comparing the electronic signature with electronic signatures stored in the implantable medical device.

4. The method according to any one of aspects 1-3, wherein the step of wirelessly sending the data packet to the implantable medical device comprises sending the data packet from a first external device to a second external device using wired communication and wirelessly sending the data packet from the second external device to the implantable medical device.

5. The method according to any one of aspects 1-4, wherein the step of wirelessly sending the data packet to the implantable medical device comprises sending the data packet from a first external device to a second external device and further wirelessly sending the data packet from the second external device to the implantable medical device, and wherein the second external device transmits the data packet without changing the data packet.

6. The method according to any one of aspects 1-5, wherein the step of wirelessly sending the data packet to the implantable medical device comprises sending the data packet from a first external device to a second external device and further wirelessly sending the data packet from the second external device to the implantable medical device, and wherein the second external device transmits the data packet without full decryption.

7. The method according to any one of the preceding aspects, wherein the implantable medical device comprises a control program configured to control at least one function of the implantable medical device, and wherein the method further comprises altering the control program on the basis of the received instructions.

8. The method according to any one of the preceding aspects, wherein the implantable medical device comprises an internal computing unit configured to run a control program for controlling a function of the implantable medical device, wherein the control program comprises at least one adjustable parameter affecting the control of the implantable medical device, and wherein the method of providing remote instructions comprises providing instructions for altering the at least one parameter for affecting the control of the implantable medical device.

9. The method according to aspect 8, wherein the implantable medical device comprises a set of stored parameter values, and wherein the method further comprises the step of verifying that the instructions for altering the at least one parameter will result in the at least one parameter being updated to a parameter value comprised in the set of stored parameter values.

10. The method according to any one of the preceding aspects, wherein the step of wirelessly sending the data packet to the implantable medical device comprises:

wirelessly sending the data packet from a first external device to a second external device using a first network protocol, and wirelessly sending the data packet from the second external device to the implantable medical device using a second network protocol.

11. The method according to any one of the preceding aspects, wherein the step of wirelessly sending the data packet to the implantable medical device comprises:

wirelessly sending the data packet from a first external device to a second external device using a first frequency band, and wirelessly sending the data packet from the second external device to the implantable medical device using a second frequency band.

12. The method according to any one of the preceding aspects, wherein the step of wirelessly sending the data packet to the implantable medical device comprises:

wirelessly sending the data packet from a first external device to a second external device using a first wireless technology, and wirelessly sending the data packet from the second external device to the implantable medical device using a second wireless technology, wherein the first wireless technology has an effective range being one of: 2 times, 4 times, 8 times 20 times, 50 times or 100 times longer than the first wireless technology.

13. The method according to any one of the preceding aspects, wherein the implantable medical device comprises a central unit, comprising a wireless transceiver, and a security module connected to the central unit, wherein the step of decrypting, at the implantable medical device, the data packet, comprises transferring the data packet from the central unit to the security module, and performing at least a portion of the decryption in the security module.

14. The method according to aspect 13, wherein the security module comprises a set of rules for accepting communication from the central unit, and wherein the step of transferring the data packet from the receiving unit of the implant to the security module comprises verifying compliance with the set of rules.

15. The method according to aspect 14, wherein wireless transceiver is configured to be placed in an off-mode, in which no wireless communication can be received by the wireless transceiver, and wherein the set of rules comprises a rule stipulating that communication from the central unit is only accepted at the security module when the wireless transceiver is placed in the off-mode.

16. The method according to any one of the preceding aspects, wherein the step of electronically signing the instructions at the external system comprises electronically signing the instructions at the external system using a private key of the external system.

17. The method according to aspect 16, wherein the private key is a non-extractable key.

18. The method according to any one of aspects 16 and 17, wherein the step of verifying the electronic signature comprises performing a proof of possession operation comprising the steps of:

transmitting, form the medical device to the external system, a query based on a public key associated with the private of the external system, receiving, at the medical device, a response based on the possession of the private key in the external system, and verifying that the response based on the possession of the private key matches the query based on a public key.

19. The method according to any one of the preceding aspects, wherein the step of forming the data packet is performed at a first external device, and wherein the step of electronically signing the instructions comprises electronically signing the instruction using a first private key, and wherein the method further comprises:

transmitting the data packet from the first external device to a second external device, verifying, at the second external device, that the transmitter is a trusted transmitter, in response to the verification, electronically signing the data packet using a second private key, and transmitting the data packet from the second external device to the medical implant, and verifying, at the medical implant, the electronic signatures generated using the first and second private keys.

using the checksum to verify the integrity of the instructions.

20. The method according to any one of the preceding aspects, wherein the step of electronically signing the instructions and the checksum, at the external system, comprising signing the instructions and the checksum with the use of a key placed on a key device separate from at least one of the first and second external device.

21. The method according to any one of the preceding aspects, wherein the step of electronically signing the instructions and the checksum, at the external system, comprising signing the instructions and the checksum with the use of a key placed on a key device comprising a wireless transmitter for wirelessly transmitting the at least one private key to at least one of the first and second external device.

22. The method according to any one of aspects 20 and 21, wherein the step of electronically signing the instructions and the checksum, at the external system, further comprises signing the instructions and the checksum with the use of a second key placed on the key device or on a second key device, separate from at least one of the first and second external device.

23. The method according to any one of aspects 21 and 22, wherein at least one of the key device and the second key device comprises at least one of: a key card, a wearable device and a handset.

24. The method according to any one of the preceding aspects, further comprising the step of unlocking at least one of the first and second external device using user credentials provided to the first and/or second external device.

25. The method according to aspect 24, wherein the step of unlocking at least one of the first and second external devices comprises unlocking at least one of the first and second external devices using a username and a password.

26. The method according to aspect 24, wherein the step of unlocking at least one of the first and second external devices comprises unlocking at least one of the first and second external devices using a PIN-code.

27. The method according to aspect 24, wherein the step of unlocking at least one of the first and second external devices comprises verifying, at the at least one first or second external devices, the user credentials by comparing the user credentials with user credentials stored in at least one of the first and second external devices.

28. The method according to aspect 24, wherein the step of unlocking at least one of the first and second external devices comprises verifying, at the at least one first or second external devices, the user credentials by comparing the user credentials with user credentials stored in at least one of the first and second external devices by the manufacturer of at least one of the first and second external devices.

29. The method according to any one of aspects 24-28, wherein the step of unlocking at least one of the first and second external devices comprises verifying, at the at least one first or second external devices, the user credentials by comparing the user credentials with user credentials stored as hardware or software in at least one of the first and second external devices.

30. The method according to any one of aspects 24-29, wherein the step of unlocking at least one of the first and second external devices comprises verifying, at the at least one first or second external devices, the user credentials by communicating with a remote server.

31. The method according to any one of the preceding aspects, wherein the method is performed without connection to the Internet.

32. The method according to any one of the preceding aspects, wherein the method is configured to be performed independently of time.

33. The method according to any one of the preceding aspects, wherein the first and second keys are different.

34. The method according to any one of the preceding aspects, wherein at least one of the first and second keys are private.

35. The method according to aspect 34, wherein the first and second private keys comprises at least one common element.

36. The method according to any one of aspects 4-35, comprising unlocking at least one of the first and second external devices using at least one of the first and second private key.

37. The method according to any one of the preceding aspects, wherein the step of electronically signing the instructions and the checksum is performed at a central server of the external system.

38. The method according to aspect 37, further comprising:

the central server being accessed by at least one healthcare professional, and the healthcare professional providing input to the central server for forming the instructions to be sent to the implantable medical device.

39. The method according to aspect 37, further comprising the central server being accessed by at least one patient, such that the patient can provide input to the central server for verifying at least one of: the authenticity of the healthcare professional and the correctness of the instructions.

40. The method according to aspect 38, further comprising the healthcare electronically signing the instructions at the central server.

41. The method according to aspect 38, further comprising the patient electronically signing the instructions at the central server.

42. The method according to any one of aspects 37-41, further comprising the steps of:

verifying the authenticity of the first and second key at the central server, and electronically sign the instructions using the first and second key.

42. The method according to any one of the preceding aspects, wherein the second key is a user key, and wherein the method comprises the steps of using the second key for at least one of:

approving that communication is transmitted to the implantable medical device, and approving that a healthcare provider prepares an instruction to the implantable medical device.

43. The method according to aspect 42, wherein the approval step can be performed by first or second external device.

44. The method according to any one of aspects 4-43, wherein the first key is required to create an instruction to the implantable medical device and the second key is required to transmit the created instruction to the implantable medical device.

45. The method according to any one of aspects 4-44, wherein at least one of the first and second external device comprises an input button, and wherein the method further comprises the step of pressing the button for verifying user presence.

46. The method according to aspect 45, wherein the input button is placed on the second external device.

47. The method according to any one of the preceding aspects, wherein the trental of the data packet comprises transmittal of:

at least one instruction signed by a first key, and a public key including information about which root have created the public key.

48. The method according to any one of aspects 4-47, further comprising enabling communication between the implantable medical device and at least one of the first and second medical device based on at least one password being provided to at least one of the first and second external device.

49. The method according to any one of aspects 4-47, further comprising enabling communication between the implantable medical device and at least one of the first and second medical device based on two passwords being provided to at least one of the first and second external device.

50. The method according to aspect 49, wherein the first password is a patient password and the second password is a healthcare provider passwords.

51. The method according to any one of the preceding aspects, further comprising at least one of the first and second external devices performing a verification query operation with at least one of the first and second key devices, the verification query operation comprising:

transmitting, from the first or second external devices, a query comprising a computational challenge to at least one of the first and second key device, receiving, at the first or second external devices, a response based on the transmitted computational challenge, and verifying, at the first or second external devices, the received response.

52. The method according to aspect 51, wherein the verification query operation is in the form of a proof of possession operation comprising:

receiving a public key of at least one of the first and second key devices, the public key being associated with a private key of the first or second key device, transmitting, from at least one of the first and second external devices, a computational challenge to the first or second key device, based on the public key received from the first or second key device, receiving a response from the first or second key device based on the possession of the private key in the first or second key device, and verifying that the response based on the possession of the private key matches the query based on a public key.

Aspect 447D Single-Use_Codes_Encryption

1. A method of providing remote instructions from an external system to an implantable medical device, wherein the implantable medical device comprises a list of codes and the external system comprises a list of codes, the method comprising:

encrypting the instructions at the external system using a code from a position on the list of codes, wirelessly sending the encrypted instructions to the implantable medical device, and decrypting, at the implantable medical device, the instructions using a code from a position on the list of codes.

2. The method according to aspect 1, further comprising the steps of:

wirelessly sending position information from the external device to the implantable medical device, and using the information at the implantable medical device for selecting the code from the list of codes.

3. The method according to aspect 1, wherein the step of encrypting, at the external system, the instructions using a code from a position on the list of codes comprises selecting the code on a current position on the list of codes, wherein the method further comprises the step of updating the current position to a new current position after using the code.

4. The method according to any one of aspects 1 and 3, wherein the step of decrypting, at the implantable medical device, the instructions using a code from a position on the list of codes comprises selecting the code on a current position on the list of codes, wherein the method further comprises the step of updating the current position to a new current position after using the code.

5. The method according to any one of aspects 3 and 4, wherein the current position comprises a number and wherein the step of updating the current position comprises updating the number to a sequential number.

6. The method according to any one of aspects 1-5, wherein the step of wirelessly sending the encrypted instructions to the implantable medical device comprises sending the encrypted instructions from a first external device to a second external device and further wirelessly sending the encrypted instructions from the second external device to the implantable medical device, and wherein the second external device transmits the encrypted instructions without changing the encrypted instructions.

7. The method according to any one of aspects 1-6, wherein the step of wirelessly sending the encrypted instructions to the implantable medical device comprises sending the encrypted instructions from a first external device to a second external device and further wirelessly sending the encrypted instructions from the second external device to the implantable medical device, and wherein the second external device transmits the encrypted instructions without full decryption.

8. The method according to any one of the preceding aspects, wherein the implantable medical device comprises a control program configured to control at least one function of the implantable medical device, and wherein the method further comprises altering the control program on the basis of the received instructions.

9. The method according to any one of the preceding aspects, wherein the implantable medical device comprises an internal computing unit configured to run a control program for controlling a function of the implantable medical device, wherein the control program comprises at least one adjustable parameter affecting the control of the implantable medical device, and wherein the method of providing remote instructions comprises providing instructions for altering the at least one parameter for affecting the control of the implantable medical device.

10. The method according to aspect 9, wherein the implantable medical device comprises a set of stored parameter values, and wherein the method further comprises the step of verifying that the instructions for altering the at least one parameter will result in the at least one parameter being updated to a parameter value comprised in the set of stored parameter values.

11. The method according to any one of the preceding aspects, wherein the step of wirelessly sending the encrypted instructions to the implantable medical device comprises:
wirelessly sending the encrypted instructions from a first external device to a second external device using a first network protocol, and
wirelessly sending the encrypted instructions from the second external device to the implantable medical device using a second network protocol.

11. The method according to any one of the preceding aspects, wherein the step of wirelessly sending the encrypted instructions to the implantable medical device comprises:
wirelessly sending the encrypted instructions from a first external device to a second external device using a first frequency band, and
wirelessly sending the encrypted instructions from the second external device to the implantable medical device using a second frequency band.

12. The method according to any one of the preceding aspects, wherein the step of wirelessly sending the encrypted instructions to the implantable medical device comprises:
wirelessly sending the encrypted instructions from a first external device to a second external device using a first wireless technology, and
wirelessly sending the encrypted instructions from the second external device to the implantable medical device using a second wireless technology, wherein the first wireless technology has an effective range being one of: 2 times, 4 times, 8 times 20 times, 50 times or 100 times longer than the first wireless technology.

13. The method according to any one of the preceding aspects, wherein the implantable medical device comprises a central unit, comprising a wireless transceiver, and a security module connected to the central unit, wherein the step of decrypting, at the implantable medical device, the encrypted instructions, comprises transferring the encrypted instructions from the central unit to the security module, and performing at least a portion of the decryption in the security module.

14. The method according to aspect 13, wherein the security module comprises a set of rules for accepting communication from the central unit, and wherein the step of transferring the encrypted instructions from the receiving unit of the implant to the security module comprises verifying compliance with the set of rules.

15. The method according to aspect 14, wherein wireless transceiver is configured to be placed in an off-mode, in which no wireless communication can be received by the wireless transceiver, and wherein the set of rules comprises a rule stipulating that communication from the central unit is only accepted at the security module when the wireless transceiver is placed in the off-mode.

16. The method according to any one of the preceding aspects, wherein the step of electronically signing the instructions at the external system comprises electronically signing the instructions at the external system using a private key of the external system.

17. The method according to aspect 16, wherein the private key is a non-extractable key.

18. The method according to any one of the preceding aspects, wherein the step of wirelessly sending the encrypted instructions to the implantable medical device comprises:
wirelessly sending the encrypted instructions from a first external device to a second external device using a first wireless technology, and
wirelessly sending the encrypted instructions from the second external device to the implantable medical device using a second wireless technology, wherein the first wireless technology has an effective range being one of: 2 times, 4 times, 8 times 20 times, 50 times or 100 times longer than the first wireless technology.

Aspect 454 Dual Remote Controls

1. A communication system for transmission of data to or from an implantable medical device, the communication system comprising:
an implantable medical implant;
a first remote control comprising a first wireless communication unit configured for wireless transmission of data to or from the implantable medical device, the first remote control being operable by a user; and
a second remote control comprising a second wireless communication unit configured for wireless transmission of control commands or data to or from the implantable medical device, and a third communication unit for communicating with a patient display device, the second remote control being inoperable by a user.

2. The communication system according to embodiment 1, wherein the first remote control comprises an input device for receiving a first user input, and wherein the first remote control is configured to transmit the first user input to the implantable medical device.

3. The communication system according to any one of the preceding embodiments, wherein the second remote control is configured to receive second user input from the patient display device and to transmit the second user input to the implantable medical implant.

4. The communication system according to any one of the preceding embodiments, wherein the data comprises a control command for the medical implant.

5. The communication system according to any one of the preceding embodiments, wherein at least one of the first wireless communication unit and the second wireless communication unit is configured to send or receive data using near-field magnetic induction.

6. The communication system according to embodiment 5, wherein at least one of the first wireless communication unit and the second wireless communication unit comprises a transmitter coil for modulating a magnetic field for transmitting the data, and wherein the implantable medical implant comprises a receiving coil and an NFMI receiver connected to the receiving coil to receive the data.

7. The communication system according to embodiment 6, wherein the transmitter coil is configured to modulate a magnetic field, and the NFMI receiver is adapted to measure the magnetic field in the receiving coil.

8. The communication system according to any one of the preceding embodiments, wherein at least one of the first wireless communication unit and the second wireless communication unit is configured to wirelessly charge the medical implant using near-field magnetic induction.

9. The communication system according to embodiment 9, wherein the medical implant comprises a coil for receiving wireless energy for charging the implant via near-field magnetic induction.

10. The communication system according to any one of the preceding embodiments, wherein the second and third communication units are configured to transmit and/or receive data using different network protocols.

11. The communication system according to any one of the preceding embodiments, wherein the second and third communication units are configured to transmit and/or receive data using different frequency bands.

12. The communication system according to any one of the preceding embodiments, wherein at least one of the first remote control, the second remote control and the implantable medical device comprises a Bluetooth transceiver.

13. The communication system according to any one of the preceding embodiments, wherein at least one of first remote control, the second remote control and the implantable medical device comprises a UWB transceiver.

14. The communication system according to embodiment 10, wherein the network protocol is one from the list of: Radio Frequency type protocol, RFID type protocol, WLAN type protocol, Bluetooth type protocol, BLE type protocol, NFC type protocol, 3G/4G/5G type protocol, and GSM type protocol.

15. The communication system according to any one of the preceding embodiments, wherein the second communication unit has a longer effective range than the third communication unit.

16. The communication system according to any one of the preceding embodiments, wherein the second remote control is configured to communicate with a consumer electronics device.

17. The communication system according to embodiment 16, wherein the patient display device comprises the consumer electronics device.

18. The communication system according to any one of the preceding embodiments, wherein the first remote control is configured to control functions of the implantable medical device based on user input to the first remote control.

Aspect 457 Controlling Energy Transfer Accumulated/PID

1. A method for wireless energy transfer from an external energy source located outside the patient to an internal energy receiver located inside the patient, the internal energy receiver being connected to an implantable medical device for supplying received energy thereto, the method comprising:

determining an accumulated amount of received energy over a time period;

determining a current change in the received energy;

determining a control signal reflecting the accumulated received energy and the change in the transferred or received energy;

controlling the energy transfer based on the control signal.

2. The method according to embodiment 1, wherein determining an accumulated amount of received energy is determined by the internal energy receiver.

3. The method according to any one of the preceding embodiments, wherein determining a current change is performed by the internal energy receiver.

4. The method according to any one of the preceding embodiments, wherein the internal energy received comprises a PID regulator for controlling the energy transfer.

5. The method according to embodiment 4, wherein the PID regulator is implemented in a microcontroller.

6. The method according to any one of the preceding embodiments, wherein determining a control signal is performed by the internal energy receiver.

7. The method according to embodiment 6, wherein the control signal is transmitted to the external energy source, and wherein the external energy source is configured to adjust the transmitted energy based on the control signal.

8. The method according to any one of the preceding embodiments, wherein controlling the energy transfer is controlled by the internal energy receiver.

9. The method according to any one of the preceding embodiments, wherein controlling the energy transfer is performed by the external energy source.

10. The method according to any one of the preceding embodiments, wherein controlling the energy transfer comprises adjusting the energy transfer efficiency.

11. The method according any one of the preceding embodiments, wherein the external device comprises a transmitter coil for modulating a magnetic field for transmitting data or transmitting energy, and wherein the implantable medical implant comprises a receiving coil and an NFMI receiver connected to the receiving coil to receive the data or the energy.

12. The method according to any one of the preceding embodiments, wherein at least one of the first wireless communication unit and the second wireless communication unit is configured to wirelessly charge the medical implant using near-field magnetic induction.

13. The method according to embodiment 9, wherein the medical implant comprises a coil for receiving wireless energy for charging the implant via near-field magnetic induction.

14. The method according to any one of the preceding embodiments, further comprising: receiving energy in pulses according to a pulse pattern, and measuring the received pulse pattern.

15. The method according to embodiment 15, further comprising: determining that the pulse pattern deviates from a predefined pulse pattern, and controlling the energy transfer based on the determination.

16. The method according to any one of the preceding embodiments, further comprising: measuring a temperature in the implantable medical device or in the body of the patient, and controlling the energy transfer in response to the measured temperature.

17. The method according to any one of the preceding embodiments, wherein the implantable medical device comprises at least one coil connected to a variable impedance, the method further comprising controlling the energy transfer by controlling the variable impedance.

18. The method according to any one of the preceding embodiments, wherein the implantable medical device comprises at least one coil having a plurality of windings, wherein the plurality of windings each are connected to a respective variable impedance, the method further comprising controlling the energy transfer by controlling the respective variable impedance individually.

Aspect 453 Voice Control

1. A method of teaching a voice-controlled medical implant to recognize a voice command, the method comprising:

inputting a first audio training phrase to the medical implant, when the medical implant is implanted in the body of the patient, creating a transfer function, the transfer function being based on the first audio training phrase, wherein the transfer function is configured to adjust the amplitude of at least one frequency of audio received at the medical device for enhancing audio received at the medical implant to facilitate detection of voice commands, inputting a second audio training phrase to the medical implant, the second audio training phrase comprising the voice command, the voice command comprising an instruction for the control of the medical implant, using the transfer function for generating an enhanced second audio training phrase in the medical implant, and associating the enhanced second audio training phrase with the instruction for the control of the medical implant.

2. The method according to embodiment 1, wherein adjusting the amplitude comprises at least one of: filtering, cancelling and amplifying the at least one frequency.

3. The method according to any one of the preceding embodiments, wherein at least one of the first and second audio training phrase is a spoken audio training phrase.

4. The method according to embodiment 3, wherein the spoken audio training phrase is spoken by the patient the implant is implanted in.

5. The method according to any one of the preceding embodiments, wherein the first audio training phrase comprises the at least one voice command related to an instruction for the control of the medical implant.

6. The method according to any one of the preceding embodiments, wherein the first and second audio training phrases is the same voice command.

7. The method according to any one of the preceding embodiments, wherein the first and second audio training phrases are different.

8. The method according to any one of the preceding embodiments, wherein creating the transfer function comprises amplifying frequencies muffled by the location of the medical implant in the body of the patient.

9. The method according to any one of the preceding embodiments, wherein creating the transfer function comprises filtering or cancelling noise generated by the body.

10. The method according to any one of the preceding embodiments, wherein the medical implant is configured to receive voice commands related to an instruction for control of the medical implant.

11. The method according to any one of the preceding embodiments, wherein the voice command relates to at least one of:

performing a function of the medical device;

using a sensor to measure a parameter relating to a condition of the patient or a condition of the medial implant;

sending or receiving data from the medical implant.

12. A method of using a voice command to control a medical implant, wherein the method comprises:

receiving an audio command phrase for the medical device;

applying a transfer function to create an enhanced audio command phrase;

determining a corresponding command for the medical based on the enhance audio command phrase; and sending the command to the medical device.

13. The method according to embodiment 12, further comprising executing, by the medical device, the command.

Aspect Large Coil

1. A system for wirelessly charging an implantable medical implant, when implanted in a body of a patient, the system comprising:

an internal energy receiver comprising a secondary coil, the internal energy receiver being connected to the implantable medical implant;

an external energy transmitter comprising a primary coil for wirelessly transmitting energy to the internal energy receiver via the secondary coil;

wherein a diameter of the primary coil is larger than a diameter of the secondary coil.

2. The system according to any one of the preceding embodiments, wherein the system further comprises:

an internal controller connected to the internal energy receiver, for controlling the amount of energy received by the internal energy receiver.

3. The system according to any one of the preceding embodiments, wherein the internal energy receiver further comprises a measurement unit for measuring a parameter related to the implantable medical implant or the body of the patient.

4. The system according to any one of the preceding embodiments, wherein the controller is configured to measure the accumulated energy received by the internal energy receiver over a period of time and to measure a current change in energy received, and to control the energy received based on the accumulated energy and the current change.

5. The system according to any one of the preceding embodiments, wherein the controlled comprises a Proportional-Integral-Derivative, PID, regulator for controlling the received energy.

6. The system according to any one of the preceding embodiments, wherein the internal energy received comprises a variable impedance.

7. The system according to embodiment 6, when depending on any one of embodiments 2-5, wherein the internal energy receiver is configured to control the resonant frequency by controlling the variable impedance.

8. The system according to embodiment 7, wherein the controller is configured to vary the variable impedance in response to a measured parameter deviating from a predetermined interval or exceeding a threshold value.

9. The system according to embodiment 7, wherein the parameter relates to the energy received by the coil over a time period.

10. The system according to embodiment 8 or 9, wherein the measurement unit is configured to measure a parameter related to a change in energy received by the coil.

11. The system according to embodiment 3-10, wherein the receiving unit is configured to receive transferred energy in pulses according to a pulse pattern, and wherein the measurement unit is configured to measure a parameter related to the pulse pattern.

12. The system according to embodiment 3-10, wherein the receiving unit is configured to receive transferred energy in pulses according to a pulse pattern, and wherein the measurement unit is configured to measure a parameter related to the pulse pattern.

13. The system according to embodiment 3-11, wherein the controller is configured to control the variable impedance in response to the pulse pattern deviating from a predefined pulse pattern.

14. The system according to embodiment 6-13, wherein:
the variable impedance comprises a resistor and a capacitor,
the variable impedance comprises a resistor and an inductor,
the variable impedance comprises an inductor and a capacitor,
the variable impedance comprises a digitally tuned capacitor,
the variable impedance comprises a digital potentiometer, or
the variable impedance comprises a variable inductor.

15. The system according any one of the preceding embodiments, wherein the diameter of the primary coil is more than 0.5 cm.

16. The system according to embodiment 15, wherein the diameter of the primary coil is more than 10 cm.

17. The system according to embodiment 16, wherein the diameter of the primary coil is more than 15 cm.

18. The system according to embodiment 17, wherein the diameter of the primary coil is more than 20 cm.

19. The system according to embodiment 18, wherein the diameter of the primary coil is more than 30 cm.

20. The system according to embodiment 19, wherein the diameter of the primary coil is more than 50 cm.

21. The system according to any one of embodiments 1-15, wherein the area of the primary coil is more than 0.5 cm2.

22. The system according to embodiment 21, wherein the area of the primary coil is more than 2 cm2.

23. The system according to embodiment 22, wherein the area of the primary coil is more than 10 cm2.

24. The system according to embodiment 23, wherein the area of the primary coil is more than 100 cm2.

25. The system according to embodiment 24, wherein the area of the primary coil is more than 300 cm2.

26. The system according to embodiment 25, wherein the area of the primary coil is more than 500 cm2.

27. The system according to embodiment 26, wherein the area of the primary coil is more than 800 cm2.

Aspect 456 NFMI Communication and Energy Transfer

1. A system for communication with an implantable medical device, when implanted in a body of a patient, comprising:

an internal communications unit, connected to or comprised in the implantable medical device;
an external communications unit,
wherein the internal communications unit and the external communications unit are configured to communicate using near field magnetic induction.

2. The system according to embodiment 1, wherein:
the internal communication unit comprises an internal NFMI receiver and an internal coil connected to the internal NFMI receiver, the internal NFMI receiver being configured to measure an induced voltage in the internal coil,
the external communications unit comprises an external NFMI transmitter and an external coil connected to the external NFMI transmitter, and
the external coil and the external NFMI transmitter are configured to modulate a magnetic field for sending data to the implantable medical device 603 via the internal coil.

3. The system according to embodiment 2, wherein the external NFMI transmitter further comprises a capacitor for tuning the external coil and the external NFMI transmitter.

4. The system according to embodiment 3, wherein the internal NFMI receiver comprises a tunable resistor and capacitor tank for turning the internal coil and the internal NFMI receiver.

5. The system according to any one of the preceding embodiments, wherein:
the internal communication unit comprises an internal NFMI transmitter and an internal coil connected to the internal NFMI transmitter,
the external communications unit comprises an external NFMI receiver and an external coil connected to the external NFMI receiver, the external NFMI receiver being configured to measure an induced voltage in the external coil,
the internal coil and the internal NFMI transmitter are configured to modulate a magnetic field for sending data to the external communications unit via the external coil.

6. The system according to embodiment 5, wherein the internal NFMI transmitter further comprises a capacitor for tuning the internal coil and the internal NFMI receiver.

7. The system according to embodiment 5 or 6, wherein the external NFMI receiver comprises a tunable resistor and capacitor tank for turning the external NFMI receiver and the external coil.

8. The system according to any one of the preceding embodiments, wherein the implantable medical device comprises an active portion configured to monitor, treat or perform a function of a body of a patient.

9. The system according to embodiment 8, wherein the active portion is not a pacemaker, hearing aid or a neurostimulation implant.

10. The system according to any one of the preceding embodiments, wherein the internal communications unit is adapted to be implanted at a tissue depth of at least 8 cm or at least 15 cm.

11. The system according to any one of the preceding embodiments, wherein the internal communications unit is adapted to be implanted in an abdomen of a patient.

12. The system according to any one of the preceding embodiments, wherein the external communications unit is configured to communicate with another external device.

13. The system according to any one of the preceding embodiments, wherein the internal communications unit is configured to encrypt data before transmitting it to the external communications unit.

14. The system according to embodiment 13, wherein the external communications unit is configured to relay the encrypted data to the another external device without decrypting it.

Aspect 459 Resonant Circuit

1. An implantable medical device adapted to receive transcutaneously and wirelessly transmitted energy, the implantable medical device comprising:
   an energy consuming part,
   a first energy receiving unit, comprising a first coil configured for receiving transcutaneously transferred energy, and a first impedance unit electrically connected to the first coil, the receiving unit being configured to transfer the received energy to the energy consuming part
   a second energy receiving unit, comprising a second coil configured for receiving transcutaneously transferred energy and a second impedance unit electrically connected to the second coil, the receiving unit being configured to transfer the received energy to the energy consuming part,
   a measurement unit configured to measure a parameter related to energy transfer, and
   a controller configured to control the subcutaneously received energy based on the parameter by controlling the first or the second impedance unit.

2. The implantable medical device according to embodiment 1, wherein the first energy receiving unit has a first resonant frequency based on the inductance of the first coil and the impedance of the first impedance unit, and the second energy receiving unit has a second resonant frequency based on the inductance of the second coil and the impedance of second impedance unit.

3. The implantable medical device according to embodiment 2, wherein the first receiving unit has a resonant frequency different from the resonant frequency of the second receiving unit.

4. The implantable medical device according to any preceding embodiment, wherein the first and second impedance units are connected in parallel to the respective coil.

5. An implantable medical device adapted to receive transcutaneously and wirelessly transmitted energy, the implantable medical device comprising:
   an energy consuming part.
   a receiving unit configured for receiving transcutaneously transferred energy and transferring the received energy to the energy consuming part, comprising:
   a first coil portion and a second coil portion, and
   a first impedance unit and a second impedance unit, wherein the first impedance unit is connected to the first coil portion and the second impedance unit is connected to the second coil portion,
   a measurement unit configured to measure a parameter related to energy transfer, and
   a controller configured to control the subcutaneously received energy based on the parameter by controlling the first or the second impedance unit.

6. The implantable medical device according to embodiment 5, wherein the first coil portion and the second coil portion are at least one of: portions of the same coil, or portions or different coils connected in series.

7. The implantable medical device according to embodiment 5 or 6, wherein the first coil portion and the second coil portion have the same inductance, or the first coil portion has a different inductance than the second coil portion.

8. The implantable medical device according to any one of embodiments 5-7, wherein the first impedance is connected in parallel to the first coil portion and the second impedance is connected in parallel to the second coil portion.

9. The implantable medical device according to any one of embodiments 5-8, wherein one of the first coil portion and the second coil portion are overlapping the other of the first coil portion and the second coil portion, or the first coil portion and the second coil portion are not overlapping with the other of the first coil portion and the second coil portion.

10. The implantable medical device according to any one of embodiments 5-9, wherein the first coil portion and the first impedance unit has a first resonance frequency, and the second coil portion and the second impedance unit has a second resonance frequency.

11. The implantable medical device according to embodiment 10, wherein the first resonance frequency is different from the second resonance frequency.

12. The implantable medical device according to any preceding embodiment, wherein the first or second impedance unit is a capacitor.

13. The implantable medical device according to any preceding embodiment, wherein the first impedance unit and the second impedance unit have different impedances.

14. An implantable medical device comprising:
   an energy consuming part,
   a first receiving unit comprising:
   a first coil configured for receiving transcutaneously transferred energy and transferring the received energy to the energy consuming part,
   a first impedance electrically connected to the coil,
   a second receiving unit comprising:
   a second coil portion and a third coil portion configured for receiving transcutaneously transferred energy and transferring the received energy to the energy consuming part, and
   a second impedance unit and a third impedance unit, wherein the second impedance unit is connected to the second coil portion and the third impedance unit is connected to the third coil portion,
   a measurement unit configured to measure a parameter related to energy transfer, and
   a controller configured to control the subcutaneously received energy based on the parameter by controlling the first, the second or the third impedance unit.

The invention claimed is:

1. A communication system for enabling communication between an implantable medical device, a patient external device, and a user display device, the communication system comprising:
   the implantable medical device comprising a wireless communication unit configured for wireless communication with the patient external device, and an encryption unit configured to encrypt data destined for the user display device,
   the patient external device comprising at least one wireless communication unit, and
   the user display device comprising a display for displaying information to a user, a decryption unit, and a wireless communication unit for wireless communication with the patient external device, wherein:
   the at least one wireless communication unit of the patient external device enables wireless transmission of the encrypted data from the implantable medical device and wireless transmission of the encrypted data to the user display device, the patient external device is configured to act as a router transferring the encrypted data from the implantable medical device to the user display device without full decryption, and the user display device is configured to decrypt the encrypted data using the decryption unit and display information to the user based on the decrypted data.

2. The communication system according to claim 1, wherein the user display device is configured to wirelessly receive an implant control interface from the patient external device to be displayed on the display.

3. The communication system according to claim 1, wherein at least two of:

the wireless communication unit of the user display device, the wireless communication unit of the patient external device, or the wireless communication unit of the implantable medical device, are configured for wireless communication using a standard network protocol.

4. The communication system according to claim 1, wherein at least two of:

the wireless communication unit of the user display device, the wireless communication unit of the patient external device, or the wireless communication unit of the implantable medical device, are configured for wireless communication using a proprietary network protocol.

5. The communication system according to claim 1, wherein the wireless communication unit of the patient external device is configured to:

use a first network protocol for communication with the implantable medical device and use a second network protocol for communication with the user display device.

6. The communication system according to claim 1, wherein the wireless communication unit of the patient external device is configured to:

use a first frequency band for communication with the implantable medical device and use a second frequency band for communication with the user display device.

7. The communication system according to claim 1, wherein the wireless communication unit of at least one of the user display device, the patient external device, and the implantable medical device comprises a Bluetooth transceiver.

8. The communication system according to claim 1, wherein the wireless communication unit of at least one of the user display device, the patient external device, and the implantable medical device comprises a UWB transceiver.

9. The communication system according to claim 1, wherein the wireless communication unit of the patient external device comprises a first wireless transceiver for wireless communication with the implantable medical device, and a second wireless transceiver for wireless communication with the user display device, and wherein the second wireless transceiver has a longer effective range than the first wireless transceiver.

10. The communication system according to claim 1, wherein at least one of:

the user display device is configured to authenticate the patient external device if a distance between the user display device and the patient external device is less than a predetermined threshold value, the user display device is configured to be authenticated by the patient external device if a distance between the user display device and the patient external device is less than a predetermined threshold value, the user display device is configured to authenticate the implantable medical device if a distance between the user display device and the implantable medical device is less than a predetermined threshold value, the user display device is configured to be authenticated by the implantable medical device if a distance between the user display device and the implantable medical device is less than a predetermined threshold value, the patient external device is configured to authenticate the user display device if a distance between the patient external device and the user display device is less than a predetermined threshold value, the patient external device is configured to be authenticated by the user display device if a distance between the patient external device and the user display device is less than a predetermined threshold value, the patient external device is configured to authenticate the implantable medical device if a distance between the patient external device and the implantable medical device is less than a predetermined threshold value, or the patient external device is configured to be authenticated by the implantable medical device if a distance between the patient external device and the implantable medical device is less than a predetermined threshold value.

11. A communication system for enabling communication between a user display device, a patient external device and an implantable medical device, the communication system comprising:

the user display device comprising a display and an input device for receiving input from a user, and a wireless communication unit configured for wireless communication with the patient external device, and an encryption unit configured to encrypt data destined for the implantable medical device, the patient external device comprising at least one wireless communication unit configured for wireless transmission to the implantable medical device, the implantable medical device comprising a decryption unit and a wireless communication unit configured for wireless communication with the patient external device, wherein the at least one communication unit of the patient external device enables wireless transmission of the encrypted data from the user display device and wireless transmission of the encrypted data to the implantable medical device, the patient external device is configured to act as a router transferring the encrypted data from the user display device to the implantable medical device without full decryption, and the implantable medical device is configured to decrypt the decrypted data using the decryption unit.

12. The communication system according to claim 11, wherein the user display device is configured to wirelessly receive an implant control interface from the patient external device to be displayed on the display.

13. The communication system according to claim 12, wherein the input device comprises the implant control interface, such that input can be provided to the input device using the implant control interface.

14. The communication system according to claim 11, wherein at least two of:

the wireless communication unit of the user display device, the wireless communication unit of the patient external device, and the wireless communication unit of the implantable medical device, are configured for wireless communication using a standard network protocol.

15. The communication system according to claim 11, wherein at least two of:

the wireless communication unit of the user display device, the wireless communication unit of the patient external device, or the wireless communication unit of the implantable medical device, are configured for wireless communication using a proprietary network protocol.

16. The communication system according to claim 11, wherein the wireless communication unit of the patient external device is configured to:

use a first frequency band for communication with the implantable medical device and use a second frequency band for communication with the user display device.

17. The communication system according to claim 11, wherein the wireless communication unit of at least one of the user display device, the patient external device, and the implantable medical device comprises a Bluetooth transceiver.

18. The communication system according to claim 11, wherein the wireless communication unit of at least one of the user display device, the patient external device, and the implantable medical device comprises a UWB transceiver.

19. The communication system according to claim 11, wherein the wireless communication unit of the patient external device comprises a first wireless transceiver for wireless communication with the implantable medical device, and a second wireless transceiver for wireless communication with the user display device, and wherein the second wireless transceiver has a longer effective range than the first wireless transceiver.

20. The communication system according to claim 11, wherein at least one of:

the user display device is configured to authenticate the patient external device if a distance between the user display device and the patient external device is less than a predetermined threshold value, the user display device is configured to be authenticated by the patient external device if a distance between the user display device and the patient external device is less than a predetermined threshold value, the user display device is configured to authenticate the implantable medical device if a distance between the user display device and the implantable medical device is less than a predetermined threshold value, the user display device is configured to be authenticated by the implantable medical device if a distance between the user display device and the implantable medical device is less than a predetermined threshold value, the patient external device is configured to authenticate the user display device if a distance between the patient external device and the user display device is less than a predetermined threshold value, the patient external device is configured to be authenticated by the user display device if a distance between the patient external device and the user display device is less than a predetermined threshold value, the patient external device is configured to authenticate the implantable medical device if a distance between the patient external device and the implantable medical device is less than a predetermined threshold value, and the patient external device is configured to be authenticated by the implantable medical device if a distance between the patient external device and the implantable medical device is less than a predetermined threshold value.

* * * * *